US009919064B2

(12) United States Patent
Cesati et al.

(10) Patent No.: US 9,919,064 B2
(45) Date of Patent: *Mar. 20, 2018

(54) COMPOSITIONS, METHODS, AND SYSTEMS FOR THE SYNTHESIS AND USE OF IMAGING AGENTS

(71) Applicant: Lantheus Medical Imaging, Inc., North Billerica, MA (US)

(72) Inventors: Richard R. Cesati, Pepperell, MA (US); Heike S. Radeke, South Grafton, MA (US); Suresh K. Pandey, East Brunswick, NJ (US); Ajay Purohit, Sudbury, MA (US); Simon P. Robinson, Stow, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/359,675

(22) Filed: Nov. 23, 2016

(65) Prior Publication Data

US 2017/0202984 A1    Jul. 20, 2017

Related U.S. Application Data

(63) Continuation of application No. 14/420,810, filed as application No. PCT/US2013/054268 on Aug. 9, 2013, now Pat. No. 9,713,651.

(60) Provisional application No. 61/794,277, filed on Mar. 15, 2013, provisional application No. 61/682,185, filed on Aug. 10, 2012.

(51) Int. Cl.
| *A61K 51/04* | (2006.01) |
| *C07D 401/12* | (2006.01) |
| *C07D 237/16* | (2006.01) |
| *A61K 49/00* | (2006.01) |
| *C07B 59/00* | (2006.01) |
| *C07D 403/12* | (2006.01) |
| *C07F 7/08* | (2006.01) |
| *B01J 19/24* | (2006.01) |

(52) U.S. Cl.
CPC ...... *A61K 51/0459* (2013.01); *A61K 49/0004* (2013.01); *B01J 19/24* (2013.01); *C07B 59/002* (2013.01); *C07D 237/16* (2013.01); *C07D 401/12* (2013.01); *C07D 403/12* (2013.01); *C07F 7/0812* (2013.01); *B01J 2219/24* (2013.01); *C07B 2200/05* (2013.01)

(58) Field of Classification Search
CPC ...... A61K 49/00; A61K 51/04; C07D 401/12; C07D 403/12
See application file for complete search history.

(56) References Cited

U.S. PATENT DOCUMENTS

| 3,359,103 A | 12/1967 | Becker et al. |
| 4,783,462 A | 11/1988 | Mutsukado et al. |
| 4,874,861 A | 10/1989 | Ogura et al. |
| 4,910,201 A | 3/1990 | Kawamura et al. |
| 5,087,440 A | 2/1992 | Cacheris et al. |
| 5,088,499 A | 2/1992 | Unger |
| 5,093,105 A | 3/1992 | Flanagan et al. |
| 5,098,900 A | 3/1992 | Mutsukado et al. |
| 5,155,215 A | 10/1992 | Ranney |
| 5,169,848 A | 12/1992 | Bettarini et al. |
| 5,169,942 A | 12/1992 | Johnson |
| 5,228,446 A | 7/1993 | Unger et al. |
| 5,281,704 A | 1/1994 | Love et al. |
| 5,306,482 A | 4/1994 | Tartaglia et al. |
| 5,377,681 A | 1/1995 | Drane |
| 5,384,113 A | 1/1995 | Deutsch et al. |
| 5,393,512 A | 2/1995 | Vanderheyden et al. |
| 5,412,148 A | 5/1995 | Keana |
| 5,417,959 A | 5/1995 | Wallace |
| 5,436,325 A | 7/1995 | Johnson et al. |
| 5,520,904 A | 5/1996 | Nosco et al. |
| 5,547,656 A | 8/1996 | Unger |
| 5,567,411 A | 10/1996 | Keana et al. |
| 5,585,112 A | 12/1996 | Unger et al. |
| 5,587,491 A | 12/1996 | Hoye et al. |
| 5,679,810 A | 10/1997 | Love et al. |

(Continued)

FOREIGN PATENT DOCUMENTS

| CN | 101555232 A | 10/2009 |
| CN | 102336741 | * 7/2011 |

(Continued)

OTHER PUBLICATIONS

Supplementary European Search Report for EP05756378.5, dated Jul. 17, 2009.
Extended European Search Report for EP10176056.9, dated Apr. 8, 2013.
International Search Report and Written Opinion for PCT/US05/014459, dated Oct. 21, 2005.
International Preliminary Report on Patentability for PCT/US05/014459, datd Nov. 1, 2006.
Examination Report for AU2005214898, dated Jun. 25, 2009.
Supplementary Extended European Search Report for EP05723066.6, dated Dec. 5, 2008.
International Search Report and Written Opinion for PCT/US05/004687, dated Nov. 17, 2005.
International Preliminary Report on Patentability for PCT/US05/004687, dated Aug. 14, 2006.

(Continued)

*Primary Examiner* — Michael G Hartley
*Assistant Examiner* — Jagadishwar R Samala
(74) *Attorney, Agent, or Firm* — Wolf, Greenfield & Sacks, P.C.

(57) ABSTRACT

The present invention provides compounds with imaging moieties for imaging a subject. The present invention also relates to systems, compositions, and methods for the synthesis and use of imaging agents, or precursors thereof. An imaging agent precursor may be converted to an imaging agent using the methods described herein. In some cases, a composition or plurality of imaging agents is enriched in $^{18}$F. In some cases, an imaging agent may be used to image an area of interest in a subject, including, but not limited to, the heart, cardiovascular system, cardiac vessels, brain, and other organs.

10 Claims, 10 Drawing Sheets

(56) References Cited

U.S. PATENT DOCUMENTS

| | | | |
|---|---|---|---|
| 5,760,191 | A | 6/1998 | Snow et al. |
| 5,801,228 | A | 9/1998 | Hollister et al. |
| 5,804,161 | A | 9/1998 | Long et al. |
| 5,811,073 | A | 9/1998 | Kassis et al. |
| 5,827,073 | A | 10/1998 | Leuscher et al. |
| 5,846,517 | A | 12/1998 | Unger |
| 5,961,955 | A | 10/1999 | Shochat et al. |
| 6,056,939 | A | 5/2000 | Desreux et al. |
| 6,066,309 | A | 5/2000 | Zamora et al. |
| 6,241,964 | B1 | 6/2001 | Burns et al. |
| 6,565,889 | B2 | 5/2003 | Zasadzinski et al. |
| 7,112,318 | B2 | 9/2006 | Madar et al. |
| 7,344,702 | B2 | 3/2008 | Casebier et al. |
| 7,410,998 | B2 | 8/2008 | Nicolaou et al. |
| 7,485,283 | B2 | 2/2009 | Radeke et al. |
| 7,824,659 | B2 | 11/2010 | Casebier et al. |
| 7,847,092 | B2 | 12/2010 | Moon et al. |
| 7,871,623 | B2 | 1/2011 | Biswal et al. |
| 7,927,616 | B2 | 4/2011 | Yamashita |
| 8,226,929 | B2 | 7/2012 | Casebier et al. |
| 8,263,042 | B2 | 9/2012 | Radeke et al. |
| 8,936,777 | B2 | 1/2015 | Cesati et al. |
| 9,029,295 | B2 | 5/2015 | Kuragano et al. |
| 9,161,997 | B2 | 10/2015 | Casebier et al. |
| 9,408,927 | B2 | 8/2016 | Robinson et al. |
| 9,550,000 | B2 | 1/2017 | Robinson et al. |
| 9,603,951 | B2 | 3/2017 | Lazewatsky et al. |
| 9,713,651 | B2 | 7/2017 | Robinson et al. |
| 9,718,786 | B2 | 8/2017 | Casebier et al. |
| 2003/0044354 | A1 | 3/2003 | Carpenter et al. |
| 2003/0124054 | A1 | 7/2003 | Toyohara et al. |
| 2004/0033197 | A1 | 2/2004 | Madar et al. |
| 2004/0034239 | A1 | 2/2004 | Nicolaou et al. |
| 2004/0142872 | A1 | 7/2004 | Poduslo et al. |
| 2004/0142972 | A1 | 7/2004 | Edgar et al. |
| 2005/0020594 | A1 | 1/2005 | Hepperle et al. |
| 2005/0129612 | A1 | 6/2005 | Zaczek et al. |
| 2005/0191238 | A1 | 9/2005 | Casebier et al. |
| 2005/0244332 | A1 | 11/2005 | Radeke et al. |
| 2006/0083681 | A1 | 4/2006 | Purohit et al. |
| 2007/0036716 | A1 | 2/2007 | Casebier et al. |
| 2007/0082879 | A1 | 4/2007 | Goodman |
| 2007/0258887 | A1 | 11/2007 | Tamagnan et al. |
| 2009/0104118 | A1 | 4/2009 | Radeke et al. |
| 2009/0297442 | A1 | 12/2009 | Hemstad |
| 2010/0236958 | A1 | 9/2010 | Veggeland et al. |
| 2010/0322855 | A1 | 12/2010 | Chong et al. |
| 2011/0091374 | A1 | 4/2011 | Robinson et al. |
| 2012/0237445 | A1 | 9/2012 | Castner et al. |
| 2012/0276006 | A1 | 11/2012 | Casebier et al. |
| 2013/0028837 | A1 | 1/2013 | Radeke et al. |
| 2013/0064769 | A1 | 3/2013 | Cesati, III et al. |
| 2013/0101508 | A9 | 4/2013 | Castner et al. |
| 2014/0328756 | A1 | 11/2014 | Cesati, III et al. |
| 2015/0165074 | A1 | 6/2015 | Lazewatsky et al. |
| 2015/0196672 | A1 | 7/2015 | Cesati et al. |
| 2015/0246143 | A1 | 9/2015 | El Fakhri et al. |
| 2016/0130235 | A1 | 5/2016 | Casebier et al. |
| 2016/0361448 | A1 | 12/2016 | Robinson et al. |

FOREIGN PATENT DOCUMENTS

| | | |
|---|---|---|
| CN | 102336741 A | 2/2012 |
| DE | 4446880 A1 | 7/1996 |
| EP | 0 169 375 A2 | 1/1986 |
| EP | 0 186 817 A1 | 7/1986 |
| EP | 0 111 415 B1 | 4/1990 |
| EP | 0 393 641 A2 | 10/1990 |
| EP | 0 627 424 A1 | 12/1994 |
| EP | 0 665 223 A1 | 8/1995 |
| EP | 0 727 225 A2 | 8/1996 |
| EP | 1 741 703 A1 | 1/2007 |
| EP | 2 103 653 A1 | 9/2009 |
| JP | S60-004173 A | 1/1985 |
| JP | S61-017570 A | 1/1986 |
| JP | S61-130275 A | 6/1986 |
| JP | 61-267560 A | 11/1986 |
| JP | S61-260018 A | 11/1986 |
| JP | S62-5967 A | 1/1987 |
| JP | S62-123176 A | 6/1987 |
| JP | S63-159372 A | 7/1988 |
| JP | S63-159373 A | 7/1988 |
| JP | S63-159374 A | 7/1988 |
| JP | H02-088507 A | 3/1990 |
| JP | H02-279676 A | 11/1990 |
| JP | H03-220177 A | 9/1991 |
| JP | H04-235975 A | 8/1992 |
| JP | H07-252236 A | 10/1995 |
| JP | 2007-112725 A | 5/2007 |
| JP | 2011-507893 A | 3/2011 |
| JP | 2011-516592 A | 5/2011 |
| JP | 2012-149044 A | 8/2012 |
| WO | WO 91/14460 A1 | 10/1991 |
| WO | WO 92/17215 A1 | 10/1992 |
| WO | WO 94/12479 A1 | 6/1994 |
| WO | WO 94/22496 A1 | 10/1994 |
| WO | WO 95/11901 A1 | 5/1995 |
| WO | WO 95/33757 A1 | 12/1995 |
| WO | WO 00/078283 A1 | 12/2000 |
| WO | WO 02/20008 A1 | 3/2002 |
| WO | WO 03/002157 A1 | 1/2003 |
| WO | WO 03/065882 A2 | 8/2003 |
| WO | WO 03/082350 A2 | 10/2003 |
| WO | WO 03/086476 A1 | 10/2003 |
| WO | WO 04/056400 A1 | 7/2004 |
| WO | WO 2005/009393 A2 | 2/2005 |
| WO | WO 2005/012319 A1 | 2/2005 |
| WO | WO 2005/079391 A2 | 9/2005 |
| WO | WO 2005/082425 A1 | 9/2005 |
| WO | WO 2005/103265 A1 | 11/2005 |
| WO | WO 2005/105159 A2 | 11/2005 |
| WO | WO 2007/021858 A2 | 2/2007 |
| WO | WO 2007/066119 A2 | 6/2007 |
| WO | WO 2008/022979 A1 | 2/2008 |
| WO | WO 2008/081852 A1 | 7/2008 |
| WO | WO 2009/054653 A2 | 4/2009 |
| WO | WO 2009/086041 A1 | 7/2009 |
| WO | WO 2009/103478 A1 | 8/2009 |
| WO | WO 2009/108376 A2 | 9/2009 |
| WO | WO 2009/110984 A2 | 9/2009 |
| WO | WO 2009/127544 A1 | 10/2009 |
| WO | WO 2010/104818 A1 | 9/2010 |
| WO | WO 2010/120368 A2 | 10/2010 |
| WO | WO 2011/006610 A1 | 1/2011 |
| WO | WO 2011/097649 A2 | 8/2011 |
| WO | WO 2013/058774 A2 | 4/2013 |
| WO | WO 2014/026079 A2 | 2/2014 |

OTHER PUBLICATIONS

International Search Report and Written Opinion for PCT/US2006/031231, dated Mar. 15, 2007.

International Preliminary Report on Patentability for PCT/US2006/031231, dated Feb. 21, 2008.

Extended European Search Report for EP09716528.6, dated Mar. 14, 2013.

International Search Report and Written Opinion for PCT/US2009/001247, dated Oct. 21, 2009.

International Preliminary Report on Patentability for PCT/US2009/001247, dated Sep. 10, 2010.

International Search Report and Written Opinion for PCT/US2009/001296, dated Sep. 30, 2009.

International Preliminary Report on Patentability for PCT/US2009/001296, dated Sep. 10, 2010.

International Search Report and Written Opinion for PCT/US2010/001120, dated Dec. 28, 2010.

International Preliminary Report on Patentablitiy for PCT/US2010/001120, dated Oct. 27, 2011.

Office Action for CN201180016758.9, dated Jun. 26, 2014.

Extended European Search Report for EP11740546.4, dated Jun. 25, 2013.

(56) References Cited

OTHER PUBLICATIONS

International Search Report and Written Opinion for PCT/US2011/024109, dated Oct. 24, 2011.
International Preliminary Report on Patentability for PCT/US2011/024109, dated Aug. 23, 2012.
International Search Report and Written Opinion for PCT/US2011/057358, dated May 9, 2012.
International Preliminary Report on Patentability for PCT/US2011/057358 dated May 1, 2014.
Partial Supplementary European Search Report for EP13828042.5 dated Dec. 16, 2015.
Extended European Search Report for EP13828042.5, dated Sep. 5, 2016.
International Search Report and Written Opinion for PCT/US2013/054268, dated Apr. 1, 2014.
International Preliminary Report on Patentability for PCT/US2013/054268 dated Feb. 19, 2015.
Alpert et al., Single-scan rest/stress imaging 18F-labeled flow tracers. Medical Physics. 2012;39(11):6609-20.
Amino et al., Metabolism of 4-Ethoxy-2-methyl-5-morpholino-3 (2H)-pyridazinone (M73101), a New Antiinflammatory Agent. III. Absorption, Distribution, Excretion and Metabolism of 3H-M73101 in Rats and Excretion of M73101 from Dog Kidney. J Pharmaceutical Soc Japan. Nov. 25, 1979;99(11):1091-101.
Anagnostopoulos et al., Assessment of myocardial perfusion and viability by Positron Emission Tomography. International Journal of Cardiology. 2013;167:1737-49.
Andrews et al., High specific activity tritiation of the pyridazin-3-one histamine H3 receptor inverse agonist CEP-27088. Appl Radiat Isot. Mar. 2012;70(3):512-4. doi:10.1016/j.apradiso.2011.11.061. Epub Dec. 7, 2011.
Bateman et al., Diagnostic accuracy of rest/stress ECG-gated Rb-82 myocardial perfusion PET: comparison with ECG-gated Tc-99m sestamibi SPECT. J Nucl Cardiol. Jan.-Feb. 2006;13(1):24-33.
Batra et al., Derivatives of 5,6-diphenylpyridazin-3-one: synthetic antimitotic agents which interact with plant and mammalian tubulin at a new drug-binding site. Cancer Res. Apr. 1986;46(4 Pt 2):1889-93.
Beanlands et al., Diagnosis and prognosis of coronary artery disease: PET is superior to SPECT: Pro. Journal of Nuclear Cardiology. 2010;17: 683-95.
Beller, Quantification of myocardial blood flow with PET: Ready for clinical application. Journal of Nuclear Cardiology. 2012;19(5):877-878.
Bengel et al., Cardiac Positron Emission Tomography. Journal of the American College of Cardiology. 2009; 54: 1-15.
Bergmann et al., Noninvasive quantitation of myocardial blood flow in human subjects with oxygen-15-labeled water and positron emission tomography. J Am Coll Cardiol. Sep. 1989;14(3):639-52.
Berman D.S., Germano.G, Slomka, P.J., (2012). Improvement in PET myocardial perfusion image quality and quantification with Flurpiridaz F 18. Journal of Nuclear Cardiology 19(1): S38-45.
Berman et al., (2010) Comparison of 18F-BMS747158 and 82Rb PET vs SPECT for detection of myocardial ischemia. Journal of Nuclear Cardiology 17(4): 743. Abstract #31.17.
Berman et al., Flurpiridaz F-18 PET versus Tc-99m SPECT for myocardial perfusion imaging. Cardiology. 2013;125, Supplement 2:27.
Berman et al., Phase II Safety and Clinical Comparison with Single-Photon Emission Computed Tomography Myocardial Perfusion Imaging for Detection of Coronary Artery Disease. Journal of the American College of Cardiology. 2013;61(4):469-77.
Boogers et al., The role of nuclear imaging in the failing heart: Myocardial blood flow, sympathetic innervation, and future applications. Heart Failure Reviews. 2011. 16(4): 411-423.
Bousquet, J.-C. et al., "Gd-DOTA: Characterization of a New Paramagnetic Complex," Radiology, vol. 166, No. 3, pp. 693-698 (1988).
Brown, M. et al., "Delineation of myocardial oxygen utilization with carbon—11-labeled acetate," Circulation, vol. 76, No. 3, pp. 687-696 (1987).
Cao et al., Synthesis and antifeedant activity of new oxadiazolyl 3(2H)-pyridazinones. J Agric Food Chem. Jan. 1, 2003;51(1):152-5.
Case et al., Automatic registration of F-18 labeled BMS-747158 stress and rest myocardial perfusion images using 6D cross-correlation optimization. Journal of Nuclear Medicine. 2010; 51(Supplement 2): 1687.
Case et al., Imaging properties of F-18 labeled myocardial perfusion PET agent, BMS747158: dosage, acquisition time and scanner type. Journal of Nuclear Medicine. 2009;50 (Supplement 2): 418. 2 pages.
Case et al., Impact of image filtering, BMI, and gender on optimal dosage acquisition time product using a novel PET myocardial perfusion tracer: F-18 labeled Flurpiridaz. Journal of Nuclear Cardiology. 2011;18(4): 769-770. Asbtract #14.32.
Case et al., Independence of myocardial functional parameters (LVEF, EDV, and ESV) across a large range of acquisition times and measured from a novel F-18 radiotracer, Flurpiridaz F-18. Journal of Nuclear Cardiology. 2010;17(4 Supplement 1): 725-726. Abstract #9.15.
Case et al., Iterative technique for optimizing injected tracer dosage and acquisition time for F-18 labeled myocardial perfusion tracer Flurpiridaz F-18. Journal of Nuclear Cardiology. 2010;17(4): 726. Abstract # 9.17.
Chary et al., Reductive cleavage of acetals/ketals. Synthetic Communications. 1999;29(8):1257-1261.
Cherednichenko et al., NADH oxidase activity of rat cardiac sarcoplasmic reticulum regulates calcium-induced calcium release. Biophys J. Jan. 2004;86(1-Part 2of 2, suppl):241a.
Clark et al., The present role of nuclear cardiology in clinical practice. Q J Nucl Med Mol Imaging. Mar. 2005;49(1):43-58.
Clark, Fluoride ion as a base in organic synthesis. Chem. Rev. 1980; 80(5):429-52.
Crane et al., Use of a tritiated (3H) analog of flurpiridaz F18 to characterize the pharmacokinetics, metabolism and excretion in normal human subjects. AAAPS. (2011) Abstract.
Di Carli et al., Cardiac PET/CT for the evaluation of known or suspected coronary artery disease. Radiographics. Sep.-Oct. 2011;31(5):1239-54. doi: 10.1148/rg.315115056.
Di Carli et al., Cardiac PET-CT. J Thorac Imaging. Feb. 2007;22(1):101-6.
Di Carli et al., Clinical myocardial perfusion PET/CT. J Nucl Med. May 2007;48(5):783-93.
Dilsizian et al., Journey in Evolution of Nuclear Cardiology: Will There Be Another Quantum Leap with the F-18-Labeled Myocardial Perfusion Tracers? Journal of the American College of Cardiology: Cardiovascular Imaging. 2012;5(12): 1269-84.
El-Apasery et al., Novel Routes to Biologically Active Enaminones, Dienoic Acid Amides, Arylazonicotinates and Dihydropyridazines under Microwave Irradiation. J Pure and Applied Chem. 2011;1(3):69-83.
El-Sayed et al., Synthesis and antibacterial activity of some glucosyl- and ribosyl-pyridazin-3-ones. Nucleosides Nucleotides Nucleic Acids. Mar. 2009;28(3):184-92. doi:10.1080/15257770902831011.
Esposti, Inhibitors of NADH—ubiquinone reductase: an overview. Biochimica et Biophysica Acta, vol. 1364, pp. 222-235 (1998).
Fukumoto et al., Detection of ischemic neuronal damage with [18F]BMS-747158-02, a mitochondrial complex-1 positron emission tomography ligand: Small animal PET study in rat brain. Synapse. 2012;66(10): 909-917.
Gaemperli et al., PET and PET/CT in cardiovascular disease. Annals of the New York Academy of Sciences. 2011;1228:109-36.
Garcia et al., What should we expect from cardiac PET? J Nucl Med. Jun. 1993;34(6):978-80.
Garcia, Quantitative Nuclear Cardiology: We are almost there! Journal of Nuclear Cardiology. 2012;19(3):424-437.
Garrison et al., Reaction mechanisms in the radiolysis of peptides, polypeptides, and proteins. Chem Rev. 1987;87:381-98.

(56) References Cited

OTHER PUBLICATIONS

Gewirtz, PET measurement of adenosine stimulated absolute myocardial blood flow for physiological assessment of the coronary circulation. Journal of Nuclear Cardiology. 2012;19(2):347-354.

Ghesani et al., Role of F-18 FDG positron emission tomography (PET) in the assessment of myocardial viability. Echocardiography. Feb. 2005;22(2):165-77.

Glover et al., Journey to find the ideal PET flow tracer for clinical use: are we there yet? J Nucl Cardiol. Nov.-Dec. 2007;14(6):765-8.

Glover et al., Comparison between 201Tl and 99mTc sestamibi uptake during adenosine-induced vasodilation as a function of coronary stenosis severity. Circulation. Feb. 1, 1995;91(3):813-20.

Glover et al., Myocardial 99mTc-tetrofosmin uptake during adenosine-induced vasodilatation with either a critical or mild coronary stenosis: comparison with 201Tl and regional myocardial blood flow. Circulation. Oct. 7, 1997;96(7):2332-8.

Glover et al., Myocardial kinetics of Tc-MIBI in canine myocardium after dipyridamole. Circulation. Feb. 1990;81(2):628-37.

Gout et al., Sulfasalazine, a potent suppressor of lymphoma growth by inhibition of the xc cystine transporter: a new action for an old drug. Leukemia, vol. 15, pp. 1633-1640 (2001).

Gropler, PET Radiotracers of the Cardiovascular System. PET Clinic 4. 2009: p. 69-87.

Han et al., Total Synthesis of 34-hydroxyasimicin and Its Photoactive Derivative for Affinity Labeling of the Mitochondrial Complex I. Chemistry—A European Journal, vol. 10, No. 9, pp. 2149-2158 (2004).

Harada et al., Development of novel PET probes, [18F]BCPP-EF, [18F]BCPP-BF, and [11C]BCPP-EM for mitochondrial complex 1 imaging in the living brain. J Labelled Comp Radiopharm. Sep. 2013;56(11):553-61. doi:10.1002/jlcr.3056. Epub Jul. 30, 2013.

Heller, Practical issues regarding the incorporation of PET into a busy SPECT practice. Journal of Nuclear Cardiology. 2012;19, SUPPL.1:S12-S18.

Higgins et al., [3H]dihydrorotenone binding to NADH: ubiquinone reductase (complex I) of the electron transport chain: an autoradiographic study. J Neurosci. Jun. 15, 1996;16(12):3807-16.

Higuchi et al., A new 18F-labeled myocardial PET tracer: myocardial uptake after permanent and transient coronary occlusion in rats. J Nucl Med. Oct. 2008;49(10):1715-22. Epub Sep. 15, 2008.

Higuchi et al., A Novel [F-18] labeled PET Tracer for the Characterization of Coronary Artery Disease: Preliminary Evaluation in a Coronary Occlusion Rat Model Circulation. 2007;116:II_658 Abstract #2947.

Hsu et al., Cardiac phantom simulation of dose injection parameters for one-day rest/stress myocardial perfusion tracer. Journal of Nuclear Medicine. 2010;51(Supplement 2): 320.

Hsu et al., Remote camera qualification (RCQ) of PET and PET/CT scanners for BMS747158 F18 myocardial perfusion phase 3 clinical trial using a standardized phantom procedure. J Nucl Med. 2011;52 (Supplement 1):54.

Huang et al., Evaluation of absolute mbf at rest and stress with Flurpiridaz F-18 injection PET in normal subjects and patients with coronary artery disease (CAD) and in two types of scanners. Journal of Nuclear Cardiology. 2011;18(4): 783-784. Abstract #26.19.

Huang et al., Rabbit myocardial 82Rb kinetics and a compartmental model for blood flow estimation. Am J Physiol. Apr. 1989;256(4 Pt 2):H1156-64.

Huang et al., Streamlined quantification of absolute MBF at rest and stress with flurpiridaz F-18 injection PET in normal subjects and patients with coronary artery disease (CAD). J Nucl Med. 2011;52 (Supplement 1):1114.

Huisman et al., First Preclinical Study of a New F-18 Labeled PET Tracer for Myocardial Perfusion Imaging Circulation. 2007;116:II_718 Abstract # 3193.

Huisman et al., Initial characterization of an 18F-labeled myocardial perfusion tracer. J Nucl Med. Apr. 2008;49(4):630-6. Epub Mar. 14, 2008.

Igarashi et al., Summary of toxicology studies with Pyridaben. J Peticide Sci. 1994;19:Technical Information.

Jiang et al., Mimicry of annonaceous acetogenins: Enantioselective syntheiss of a (4R)-hydroxy analogue having potent antitumor activity. J. Org. Chem., vol. 67, No. 10, pp. 3404-3408 (2002).

Kadrmas et al., Single-scan dual-tracer FLT+FDG PET tumor characterization. Physics in Medicine and Biology. 2013;58:429-49.

Kagan et al., Comparison of flurpiridaz F 18 and FDG for assessment of left ventricular tissue mass following myocardial infarction in rats. Journal of Nuclear Medicine;2011:52( Supp.1):1097.

Kagan et al., LMI1195 and flurpiridaz F 18 PET imaging in evaluation of time-course changes in mismatch of cardiac denervated and perfusion defect areas following acute myocardial infarction. Journal of Nuclear Medicine. 2012;53, Supplement. 1:84.

Kann et al., Mitochondria and neuronal activity. Am J Physiol Cell Physiol. Feb. 2007;292(2):C641-57. Epub Nov. 8, 2006.

Knapp et al., Availability of rhenium-188 from the alumina-based tungsten-188/rhenium-188 generator for preparation of rhenium-188-labeled radiopharmaceuticals for cancer treatment. Anticancer Res. May-Jun. 1997;17(3B):1783-95.

Knuuti et al., Imaging highlights from the European Society of Cardiology, American Society of Nuclear Cardiology, and Heart Failure Society of America. Journal of the American College of Cardiology Imaging. 2008;1: 119-28.

Krivokapich et al., 13N Ammonia Myocardial Imaging at Rest and With Exercise in Normal Volunteers, Quantification of Absolute Myocardial Perfusion With Dynamic Positron Emission Tomography. Circulation, vol. 80, No. 5, pp. 1328-1337 (1989).

Kroemer, Mitochondria in cancer. Oncogene. Aug. 7, 2006;25(34):4630-2.

Lan et al., Non-invasive imaging modalities for the diagnosis of coronary artery disease: The present and the future. Tzu Chi Medical Journal. 2013, 7 pages.

Latli et al., Photoaffinity radioligand for NADH:ubiquinone oxidoreductase: [S-C3H2](trifluoromethyl)diazirinyl-pyridaben. J. Labelled Compounds Radiopharm. 1998;41(3):191-9.

Lazewatsky et al., Development of a method for the determination of dose ratio and minimum inter-injection interval for a one-day rest-stress protocol with BMS747158 PET myocardial perfusion agent. Journal of Nuclear Medicine. 2010;51(Supplement 2):600.

Lazewatsky et al., Dosimetry of BMS747158, a novel 18F labeled tracer for myocardial perfusion imaging, in nonhuman primates at rest. J Nucl Med. 2008;49(Supplement 1):15p.

Lazewatsky et al., Relative defect radioactivity and perceived defect severity are proportional with flurpiridaz F18 PET myocardial perfusion imaging. J Nucl Med. 2011;52 (Supplement 1):1115.

Le Guludec et al., Present and future of clinical cardiovascular PET imaging in Europe—a position statement by the European Council of Nuclear Cardiology (ECNC). European Journal of Nuclear Medicine and Molecular Imaging. 2008; 35: 1709-24.

Lee et al., Potential and practical adrenomedullary PET radiopharmaceuticals as an alternative to m-iodobenzylguanidine: m-(omega-[18F]fluoroalltyl)benzylguanidines. Bioconjug Chem. Jan.-Feb. 2004;15(1):104-11.

Lindell et al., The design and synthesis of novel inhibitors of NADH: ubiquinone oxidoreductase. Bioorganic & Medicinal Chemistry Letters, vol. 14, pp. 511-514 (2004).

Liu et al., Integrin avb3 directed radiopharmaceuticals for tumor imaging. Drugs of the Future, vol. 28, No. 6, pp. 551-564 (2003).

Maddahi et al., Cardiac PET perfusion tracers: current status and future directions. Semin Nucl Med. Sep. 2014;44(5):333-43. doi:10.1053/j.semnuclmed.2014.06.011.

Maddahi et al., Comparison of F-18 labeled BMS747158 PET and Tc-99m labeled spect myocardial perfusion imaging for detection and evaluation of coronary artery disease. Journal of the American College of Cardiology. 2010;55(10A): E616.

Maddahi et al., Comparison of flurpiridaz F 18 PET injection and Tc-99m labeled SPECT myocardial perfusion imaging for identifying severity and extent of stress induced myocardial ischemia in phase 2 clinical trials. J Nucl Med. 2011;52 (Supplement 1):444.

Maddahi et al., F-18 labeled BMS747158 PET myocardial perfusion imaging identifies more severe and extensive stress induced myocardial ischemia than Tc-99m Sestamibi SPECT. Journal of Nuclear Medicine. 2010;51(Supplement 2): 1739.

(56) References Cited

OTHER PUBLICATIONS

Maddahi et al., First human study of of BMS747158, a novel F-18 labeled tracer for myocardial perfusion imaging. J Nucl Med. 2008;49:70P.

Maddahi et al., Human safety, dosimetry, biodistribution, and rest-stress myocardial imaging characteristics of the new F-18 labeled BMS747158 myocardial perfusion PET tracer. European Heart Journal. 2009;11(Supplement): S89. Abstract #432.

Maddahi et al., Phase 1 Human safety, dosimetry, Biodistribution and rest/stress myocardial imaging characteristics of F18 Labeled BMS 747158. (2009) Journal of the American College of Cardiology 53(10): A297. Abstract #1054-263.

Maddahi et al., Phase 2 clinical comparison of flurpiridaz F 18 injection PET and SPECT myocardial perfusion imaging for diagnosis of coronary artery disease. J Nucl Med. 2011;52 (Supplement 1):59.

Maddahi et al., Phase 2 safety and clinical comparison of flurpiridaz F18 injection PET and SPECT myocardial perfusion imaging for diagnosis of coronary artery disease. European Heart Journal Supplements. 2011;13( Supplement A ): A45. Abstract # 197.

Maddahi et al., Phase I, First-in-Human Study of BMS747158, a Novel 18F-Labeled Tracer for Myocardial Perfusion PET: Dosimetry, Biodistribution, Safety, and Imaging Characteristics After a Single Injection at Rest. J Nucl Med. 2011;52: 1490-9.

Maddahi et al., Preliminary results of absolute quantification of rest and stress myocardial blood flow with Flurpridaz F-18 PET in normal and coronary artery disease patients in a single-center study. Journal of Nuclear Cardiology. 2010;17(4): 743. Abstract # 31.18.

Maddahi et al., Protocols for same day rest-stress PET imaging with the new F-18 labeled BMS747158 myocardial perfusion tracer. European Heart Journal. 2009;11(Supp B): S89. Abstract #433.

Maddahi et al., Same day rest-stress protocols for PET imaging with the new F-18 labeled BMS747158 myocardial perfusion tracer. Journal of Nuclear Medicine. 2009;50(Supplement 2): 1173.

Maddahi, Properties of an ideal PET perfusion tracer: New PET tracer cases and data. Journal of Nuclear Cardiology. 2012;19(Supplement 1): S30-37.

Magerstadt et al., Gd(DOTA): An Alternative to Gd(DTPA) as a T1,2 Relaxation Agent for NMR Imaging of Spectroscopy. Magnetic Resonance in Medicine, vol. 3, pp. 808-812 (1986).

Marshall et al., Kinetic Analysis of a 125I-iodorotenone as a deposited myocardial flow tracer: Comparison with 99mTc-sestamibi. Journal of Nuclear Medicine, vol. 42, No. 2, pp. 272-281 (2001).

Marshall et al., Kinetic Analysis of a 18F-fluorodihydrorotenone as a deposited myocardial flow tracer: Comparison with 291TL. Journal of Nuclear Medicine, vol. 45, No. 11, pp. 1950-1959 (2004).

Martarello et al., Synthesis and evaluation of a new fluorine-18 labeled rotenoid as a potential pet probe of mitochondrial complex I activity. Journal of Labelled Compounds and Radiopharmaceuticals, vol. 42, No. 11, pp. 1039-1051 (1999).

Miller et al., Synthesis of 11C, 18F, 15O, and 13N radiolabels for positron emission tomography. Angew Chem Int Ed Engl. 2008;47(47):8998-9033.

Mistry et al., Toxicological evaluation of BMS-747158, a PET myocardial perfusion imaging agent. The Toxicologist. 2008;102:476.

Miyoshi et al., Essential structural factors of annonaceous acetogenenins as potent inhibitors of mitochondrial complex I. Biochimica et Biophysica Acta, vol. 1365, No. 3, pp. 443-452 (1998).

Miyoshi, Structure-activity relationships of some complex I inhibitors. Biochim Biophys Acta. May 6, 1998;1364(2):236-44.

Mizuno et al., NT-702, a selective phosphodiesterase 3 inhibitor, dilates rabbit spinal arterioles via endothelium-dependent and endothelium-independent mechanisms. J Physiol Sci. Aug. 2008;58(4):229-37. doi:10.2170/physiolsci.RP003808. Epub Jun. 18, 2008.

Mou et al., Preparation and biodistribution of [18F]FP2OP as myocardial perfusion imaging agent for positron emission tomography. Bioorg Med Chem. Feb. 2010;18(3):1312-20. Epub Dec. 26, 2009.

Mou et al., Synthesis and preliminary evaluation of 18F-labeled pyridaben analogues for myocardial perfusion imaging with PET. J Nucl Med. Mar. 2012;53(3):472-9. doi: 10.2967/jnumed.111.088096. Epub Feb. 2, 2012.

Mukherjee, Fluorinated benzamide neuroleptics--2. Synthesis and radiosynthesis of (S)-N-[(1-ethyl-2-pyrrolidinyl)methyl]-5-(3-[18F]fluoropropyl)-3- substituted-2-methoxybenzamides. Int J Rad Appl Instrum A. 1991;42(8):713-21.

Murthy et al., Non-invasive quantification of coronary vascular dysfunction for diagnosis and management of coronary artery disease. Journal of Nuclear Cardiology. 2012;19(5):1060-1072.

Nakanishi et al., Acetogenins as selective inhibitors of the human ovarian 1A9 tumor cell line. Journal of Medicinal Chemistry, vol. 46, No. 15, pp. 3185-3188 (2003).

Nakazato et al., CFR and FFR assessment with PET and CTA: Strengths and limitations. Current Cardiology Reports. 2014;16(5):484-94.

Nakazato et al., Myocardial perfusion imaging with PET. Imaging in Medicine. 2013;5(1):35-46.

Nekolla et al., Assessment of imaging properties of a new F-18 labelled flow tracer in a pig model. J Am Coll Cardiol. 2008;51:A170.

Nekolla et al., Evaluation of a new myocardial PET tracer 18F-BMS-747158-02 (18F-BMS): Comparison to 13N ammonia and validation with microspheres. J Nucl Med. 2008; 49 (Supplement 1):29P.

Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.

Nekolla et al., Model free quantification of myocardial flow reserve with flurpiridaz F 18: Validation with microspheres in a pig model. European Heart Journal. 2011;13, SUPPL.A:A94. No. 420.

Nekolla et al., Novel F-18 Labeled PET Myocardial Perfusion Tracers: Bench to Bedside. Current Cardiology Reports. 2011;13: 145-150.

Nicolaou et al., Combinatorial synthesis of novel and potent inhibitors of NADH: ubiquinone oxidoreductase. Chem Biol. Dec. 2000;7(12):979-92.

Ohira et al., Current and Future Clinical Applications of Cardiac Positron Emission Tomography. Circulation Journal. 2013; 77(4) :836-48.

Okun et al., Three classes of inhibitors share a common binding domain in mitochondrial complex I (NADH:ubiquinone oxidoreductase). J Biol Chem. Jan. 29, 1999;274(5):2625-30.

Paterson et al., Imaging Heart Failure; Current and Future Applications. Canadian Journal of Cardiology. 2013;29:317-28.

Paterson et al., Radionuclide ventriculography assessment of synchrony and entropy: Compariosn of SPECT and planar techniques. European Heart Journal. 2011;13(Supplement A):A93-94. No. 419.

Pauwels et al., Fluorine-18-radiolabeled pharmaceuticals for imaging with positron emission tomography, excluding [18F]-fluorodeoxyglucose. Drugs of the Future. 2002;27:655-67.

Pike, PET radiotracers: crossing the blood-brain barrier and surviving metabolism. Trends Pharmacol Sci. Aug. 2009;30(8):431-40. doi: 10.1016/j.tips.2009.05.005. Epub Jul. 16, 2009.

Purohit et al., Quinazoline derivatives as MC-I inhibitors: evaluation of myocardial uptake using Positron Emission Tomography in rat and non-human primate. Bioorg Med Chem Lett. Sep. 1, 2007;17(17):4882-5. Epub Jun. 14, 2007.

Purohit et al., Synthesis and biological evaluation of pyridazinone analogues as potential cardiac positron emission tomography tracers. J Med Chem. May 22, 2008;51(10):2954-70. Epub Apr. 19, 2008.

Radeke et al., Synthesis and biological evaluation of the mitochondrial complex 1 inhibitor 2-[4-(4-fluorobutyl)benzylsulfanyl]-3-methylchromene-4-one as a potential

(56) References Cited

OTHER PUBLICATIONS cardiac positron emission tomography tracer. J Med Chem. Sep. 6, 2007;50(18):4304-15. Epub Aug. 15, 2007.
Rahmim et al., Towards quantitative myocardial perfusion PET in the clinic. Journal of the American College of Radiology. 2014;11(4):429-32.
Ramsay et al., Interaction of 1-methyl-4-phenylpyridinium ion (MPP+) and its analogs with the rotenone/piericidin binding site of NADH dehydrogenase. J Neurochem. Apr. 1995;56(4):1184-90.
Ravert et al., Radiosynthesis of 3-[18F]fluoropropyl and 4-[18F]fluorobenzyl triarylphosphonium ions. J Lab Comp Radiopharm. 2004;47(8):469-76.
Rimoldi, Assessing the activity of cardiac sympathetic innervations with a novel PET tracer. European Journal of Nuclear Medicine and Molecular Imaging. 2012;39(12):1901-3.
Rischpler et al., Advances in PET myocardial perfusion imaging: F-18 labeled tracers. Annals of Nuclear Medicine. 2012;26(1):1-6.
Ritchie et al., Guidelines for clinical use of cardiac radionuclide imaging. Report of the American College of Cardiology/American Heart Association Task Force on Assessment of Diagnostic and Therapeutic Cardiovascular Procedures (Committee on Radionuclide Imaging), developed in collaboration with the American Society of Nuclear Cardiology. J Am Coll Cardiol. Feb. 1995;25(2):521-47.
Rubin et al., The cell biology of the blood-brain barrier. Annu Rev Neurosci. 1999;22:11-28.
Runge et al., MR Imaging of Rat Brain Glioma: Gd-DTPA versus Gd-DOTA. Radiology, vol. 166, No. 3, pp. 835-838 (1988).
Santi et al., Toxicology of rotenone. Farmaco Sci. Apr. 1965;20:270-9.
Saraste et al., PET: Is myocardial flow quantification a clinical reality? Journal of Nuclear Cardiology. 2012;19(5):1044-1059.
Schelbert et al., N-13 ammonia as an indicator of myocardial blood flow. Circulation. Jun. 1981;63(6):1259-72.
Schuler et al., Functional coupling of PSST and ND1 subunits in NADH: ubiquinone oxidoreductase established by photoaffinity labeling. Biochimica et Biophysica Acta, vol. 1506, pp. 79-87 (2001).
Schuler et al., The insecticide target in the PSST subunit of complex I. Pest Manag Sci. Oct. 2001;57(10):932-40.
Schyler, PET tracers and radiochemistry. Ann Acad Med Singapore. Mar. 2004;33(2):146-54.
Shaw et al., From adequate evidence to optimal evidence. JACC: Cardiovascular Imaging. 2012;5(12):1292-1293.
Sherif et al., Evaluation of a novel (18)F-labeled positron-emission tomography perfusion tracer for the assessment of myocardial infarct size in rats. Circulation: Cardiovascular Imaging. Mar. 2009;2(2):77-84.
Sherif et al., Evaluation of the novel PET perfusion tracer 18F BMS747158-02 for measurement of myocardial infarct size in a rat model. J Nucl Med. 2008; 49 (Supplement 1):186P.
Sherif et al., Reply: Simplified Quantification of Myocardial Flow Reserve with 18F-Flurpiridaz: Validation with Microspheres in a Pig Model. Journal of Nuclear Medicine. 2011;52(11):1835-1836.
Sherif et al., Simplified quantification of myocardial flow reserve with flurpiridaz F-18: Validation with Microspheres in a pig model. Journal of Nuclear Medicine. 2011;52: 617-624.
Singh et al., A versatile route to 2-alkyl-/aryl-amino-3-formyl and heter-annelated-chromosones, through a facile nucleophilic substitution at C2 in 2-(N-methylanilino)-3-formylchromones. Tetrahedron. 2002;58(12):2471-80.
Sirion et al., An efficient F-18 labeling method for PET study: Huisgen 1,3-dipolar cycloaddition of bioactive substances and F-18-labeled compounds. Tetrahedron Letters. Jun. 4, 2007;48(23):3953-7.
Slomka et al., Multicenter development of normal perfusion and function limits for stress and rest flurpiridaz F-18 Cardiac PET. Journal of Nuclear Cardiology. 2010;17(4): 725. Abstract #9.14.

Soderquist et al., Reductive cleavage of acetals and ketals with 9-borabicyclo[3.3.1]nonane†. Org Process Res Dev. 2006;10(5):1076-9.
Strauss et al., Society of Nuclear Medicine Procedure Guideline for Myocardial Perfusion Imaging. Soc. Nucl Med Pro Guide Man. Jun. 2002:9-17.
Strauss, Editorial Viewpoint: Myocardial Imaging for Mitochondrial Membrane Potential. Journal of the American College of Cardiology: Cardiovascular Imaging. 2012;5(3):293-96.
Takalkar et al., Cardiac assessment with PET. PET Clinics. 2011; 6(3): 313-326.
Talpade et al., In vivo labeling of mitochondrial complex I (NADH:ubiquinone oxidoreductase) in rat brain using [(3)H]dihydrorotenone. J Neurochem. Dec. 2000;75(6):2611-21.
Tamarappoo et al., Comparison of myocardial stress perfusion defect assessment using 99mTc Sestamibi SPECT vs 18F-BMS747158 PET. Journal of Nuclear Cardiology. 2010;17(4): 742. Abstract #31.14.
Tang et al., Automated commercial synthesis system for preparation of O-(2-[18F]fluoroethyl)-L-tyrosine by direct nucleophilic displacement on a resin column. J. Label Compd Radiopharm 2003; 46:661-668.
Tsukada et al., Novel PET Probes 18F-BCPP-EF and 18F-BCPP-BF for Mitochondrial Complex I: A PET Study in Comparison with 18F-BMS-747158-02 in Rat Brain. Journal of Nuclear Medicine. 2014;55:473-80.
Udelson, Advances in myocardial perfusion imaging. Journal of Nuclear Cardiology. 2012;19, SUPPL. 1:S1-S2.
Ueno et al., Comparison of the inhibitory action of natural rotenone and its stereoisomers with various NADH-ubiquinone reductases. Eur J Biochem. Oct. 1, 1994;225(1):411-7.
Ueno et al., Structural factors of rotenone required for inhibition of various NADH-ubiquinone oxidoreductases. Biochim Biophys Acta. Sep. 30, 1996;1276(3):195-202.
Unger, Pesticide synthesis handbook. Technology and Engineering. 1996:523-4. Google books result.
Vallabhajosula, Guest Editorial: New PET Radiopharmaceuticals as Molecular Imaging Probes. Seminars in Nuclear Medicine. 2011:244-5.
Vanbrocklin et al., (F-18)fluorodihydrorotenone: Synthesis and evaluation of a mitochondrial electron transport chain (ETC) complex I probe for PET. Journal of Nuclear Medicine, vol. 35, No. 5 Suppl., p. 73P (1994).
Vanbrocklin et al., Fluorine-18 labeled dihydrorotenone analogs: preparation and evaluation of PET mitochondrial probes. Journal of Labelled Compounds and Radiopharmaceuticals, Symposium abstracts (continue in part IV). 1994; 35:217-19.
Vanbrocklin et al., Mitochondrial avid radioprobes. Preparation and evaluation of 7"(Z)[125I]iodorotenone and 7"(Z)-[125I]iodorotenol. Nucl Med Biol. Jan. 2007;34(1):109-16. Epub Nov. 28, 2006.
Volkov et al., Interaction of Acetals and Ortho-Ethers With Triisobutylaluminum. Zhurnal Organicheskoi KHIMII. Dec. 31, 1986; 22(8):1787-1788.
Von Schulthess et al., Clinical positron emission tomography/magnetic resonance imaging applications. Seminars in Nuclear Medicine. 2013;43(1):3-10.
Walker, The NADH: ubiquinone oxidoreductase (complex I) of respiratory chains. Quarterly Review of Biophysics, vol. 25, No. 3, pp. 253-324 (1992).
Wallace, A mitochondrial paradigm of metabolic and degenerative diseases, aging, and cancer: a dawn for evolutionary medicine. Annu Rev Genet. 2005;39:359-407.
Wang et al., Insights into amyloid-beta-induced mitochondrial dysfunction in Alzheimer disease. Free Radic Biol Med. Dec. 15, 2007;43(12):1569-73. Epub Sep. 21, 2007.
Wells et al., Comparison of attenuation, dual-energy window, and model-based scatter correction of low-count SPECT to 82Rb PET/CT quantified myocardial perfusion scores. Journal of Nuclear Cardiology. Published online: Jun. 5, 2013. 12 pages.

(56) References Cited

OTHER PUBLICATIONS

Woo et al., Automatic 3D registration of dynamic stress and rest (82)Rb and flurpiridaz F 18 myocardial perfusion PET data for patient motion detection and correction. Medical Physics. 2011;38(11): 6313-26.

Wood et al., Fenazaquin Acaricide Specific Binding Sites in NADH: Ubiquinone Oxidoreductase and Apparently the ATP Synthase Stalk. Pest Biochem Phys. Feb. 1996;54(2):135-45.

Yalamanchili et al., Mechanism of uptake and retention of F-18 BMS-747158-02 in cardiomyocytes: a novel PET myocardial imaging agent. J Nucl Cardiol. Nov.-Dec. 2007;14(6):782-8. Epub Oct. 22, 2007.

Yu et al., [18F]-RP1012: A Novel Myocardial Perfusion Imaging Agent for use with positron emission tomography (PET). Circulation Supplmement 2, 112(17), II-761, Abstract #3546, 2005.

Yu et al., A novel cardiac PET imaging agent. International Hospital Equipment and Solutions. 2009; 35(4):14-5.

Yu et al., Assessment of 18F-labeled mitochondrial complex I inhibitors as PET myocardial perfusion imaging agents in rats, rabbits, and primates. Eur J Nucl Med Mol Imaging. Jan. 2009;36(1):63-72. Epub Aug. 21, 2008.

Yu et al., BMS-747158-02: a novel PET myocardial perfusion imaging agent. Journal of Nuclear Cardiology, vol. 14. No. 6, pp. 789-98 (2007).

Yu et al., Cardiac imaging and safety evaluation of BMS747158, a novel PET myocardial perfusion imaging agent, in chronic myocardial compromised rabbits. J Nuclear Cardiology. 2010;17(4):631-6.

Yu et al., Cardiac imaging and uptake of BMS747158-02 under various experimental conditions. J Nucl Med. 2008; 49 (Supplement 1):187P.

Yu et al., Effects of Food Intake and Anesthetic on Cardiac Imaging and Uptake of BMS-747158-02 in Comparison with FDS. Journal Nuclear Cardiology. Sep.-Oct. 2009;16(5):763-8.

Yu et al., Evaluation of LMI1195, a Novel 18F-Labeled Cardiac Neuronal PET Imaging Agent, in Cells and Animal Models. Circulation: Cardiovascular Imaging 2011 4: 435-443.

Yu et al., In-vivo Assessment of Mitochondrial Complex-1 Inhibitors as Myocardial Perfusion Imaging Agents (MPIA). Circulation Supplement 2, 112 (17), II-474, Abstract #2283, 2005.

Yu et al., LMI119 PET imaging in evaluation of regional cardiac sympathetic denervation and its potential role in antiarrhythmic drug treatment. European Journal of Nuclear Medicine and Molecular Imaging. 2012;39(12):1910-1919.

Yu et al., Myocardial Perfusion Imaging with 18F-Chromone Based MC-1 Inhibitors. Molecular Imaging. 2006;5(3):372-3. Abstract ID: 642 Poster board space:105.

Yu et al., The next generation of cardiac positron emission tomography imaging agents: discovery of flurpiridaz f-18 for detection of coronary disease. Seminars Nucl Med. Jul. 2011;41(4):305-13.

Yu et al., Value of flurpiridaz F 18 myocardial SUV analysis in clinical assessment of intermediate to severe coronary stenosis. Journal of Nuclear Cardiology. 2013;20,Supplement 1: S44-S45.

Ziadi et al., The clinical utility of assessing myocardial blood flow using positron emission tomography. Journal of Nuclear Cardiology. 2010; 17:571-581.

* cited by examiner

Heart
Liver 5-10 min          50-60 min
Time after injection (min)

Heart
Liver 5-10 min          50-60 min
Time after injection (min)

5-10 min    50-60 min
Time after injection (min)

5-10 min    50-60 min
Time after injectio(min)

60-65 min after injection

Time after injection (min)

Time after injection (min)

Heart
Liver 5-10 min    50-60 min
Time after injection (min)

Heart
Liver

COMPOSITIONS, METHODS, AND SYSTEMS FOR THE SYNTHESIS AND USE OF IMAGING AGENTS

RELATED APPLICATIONS

The present application is a continuation of U.S. application Ser. No. 14/420,810, filed on Feb. 10, 2015, which is a national stage filing under 35 U.S.C. § 371 of International Application No. PCT/US2013/054268, filed on Aug. 9, 2013, which claims priority under 35 U.S.C. § 119(e) to U.S. provisional patent applications, U.S. Ser. No. 61/682,185, filed Aug. 10, 2012, and U.S. Ser. No. 61/794,277, filed Mar. 15, 2013, each of which is incorporated herein by reference

FIELD OF THE INVENTION

The present invention relates to compounds useful as imaging agents, compositions thereof, methods for the synthesis and use thereof, and precursors thereto.

BACKGROUND OF THE INVENTION

Mitochondria are membrane-enclosed organelles distributed through the cytosol of most eukaryotic cells. Mitochondria are especially concentrated in myocardial tissue.

Mitochondrial complex 1 ("MC-1") is a membrane-bound protein complex of 46 dissimilar subunits. This enzyme complex is one of three energy-transducing complexes that constitute the respiratory chain in mammalian mitochondria. This NADH-ubiquinone oxidoreductase is the point of entry for the majority of electrons that traverse the respiratory chain, eventually resulting in the reduction of oxygen to water (*Q. Rev. Biophys.* 1992, 25, 253-324). Examples of inhibitors of MC-1 include deguelin, piericidin A, ubicidin-3, rolliniastatin-1, rolliniastatin-2 (bullatacin), capsaicin, pyridaben, fenpyroximate, amytal, MPP+, quinolines, and quinolones (*BBA* 1998, 1364, 222-235). Studies have shown that interrupting the normal function of mitochondria could advantageously concentrate certain compounds in the mitochondria, and hence in the mitochondria-rich myocardial tissue. Compounds that include an imaging moiety (e.g., $^{18}$F) can be useful in determining such a build-up of compounds, thereby providing valuable diagnostic markers for myocardial perfusion imaging. In addition, such compounds may find application for the diagnosis of coronary artery disease (CAD).

CAD is a major cause of death in modern industrialized countries, and it has been found previously that assessments of regional myocardial perfusion at rest and during stress (exercise or pharmacologic coronary vasodilation) are valuable for noninvasive diagnosis of CAD. While myocardial perfusion imaging (MPI) with Positron Emission Tomography (PET) has been shown to be superior in some embodiments as compared to single photon emission computed tomography (SPECT), widespread clinical use of PET MPI has been limited by the previously available PET myocardial perfusion tracers.

Several PET blood flow tracers, such as rubidium-82 ($^{82}$Rb) chloride, nitrogen-13 ($^{13}$N) ammonia, and oxygen-15 ($^{15}$O) water, have been developed and validated for assessment of myocardial perfusion. $^{13}$N and $^{15}$O are cyclotron-produced isotopes with short half-lives. Therefore, their use is limited to facilities with an on-site cyclotron. Although $^{82}$Rb is a generator-produced tracer, its short half-life, the high cost of the generator, and the inability to perform studies in conjunction with treadmill exercise have made this tracer impractical for widespread use. Tracers that comprise $^{18}$F have, however, found application as imaging agents.

SUMMARY OF THE INVENTION

The present invention provides, in a broad sense, compounds, and compositions thereof, that are useful as imaging agents or imaging agent precursors, kits thereof, methods of use thereof, and methods of synthesizing the provided compounds.

In some embodiments, a compound is provided comprising the structure:

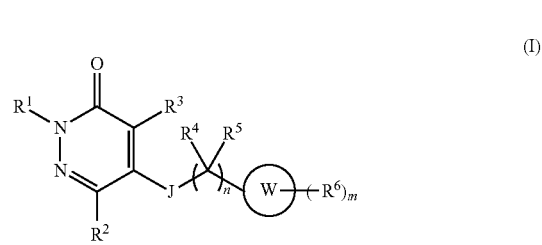

(I)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N($R^7$), S, O, C(=O), C(=O)O, OC(=O), C(=O)N($R^7$), N($R^7$)C(=O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

W is heteroaryl, naphthyl, heterocyclyl or aryl;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^9$)$_3$, —O$R^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound; and provided that when W is aryl, a) $R^3$ is not halo, alkyl or haloalkyl, or b) at least one $R^6$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$.

In some embodiments, a compound is provided comprising the structure:

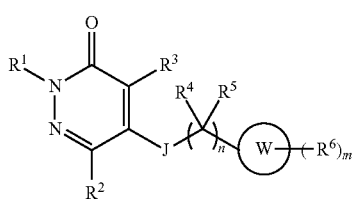

(II)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(=O), C(=O)O, OC(=O), C(=O)N(R$^7$), N(R$^7$)C(=O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

W is heteroaryl, naphthyl, or heterocyclyl;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^{9'}$)$_3$, —OR$^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

In some embodiments, a compound is provided comprising the structure:

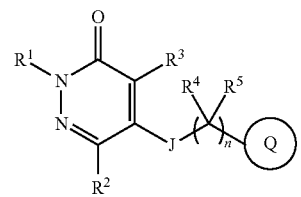

(III)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(=O), C(=O)O, OC(=O), C(=O)N(R$^7$), N(R$^7$)C(=O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

Q has the structure:

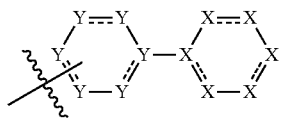

wherein each Y and each X is independently selected from the group consisting of C, C($R^6$), C($R^6$)$_2$, N, N$R^7$, O, and S, provided at least one Y is not C or C($R^6$), optionally, wherein one X and/or one Y is absent;

each ====== is independently a single or double bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

In some embodiments, a compound is provided comprising the structure:

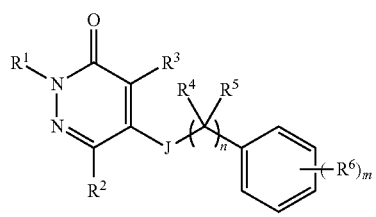

(IV)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, unsubstituted alkyl or alkyl optionally substituted with a moiety other than a halogen, heteroalkyl optionally substituted, alkoxy optionally substituted, alkoxyalkyl optionally substituted, aryl optionally substituted, heteroaryl optionally substituted, —CN, and —NO$_2$;

J is selected from the group consisting of N($R^7$), S, O, C(=O), C(=O)O, OC(=O), C(=O)N($R^7$), N($R^7$)C(=O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

m is 0, 1, 2, 3, 4, or 5;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

In some embodiments, a compound is provided comprising the structure:

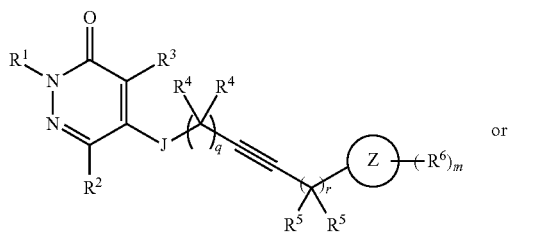

(V)

or

-continued

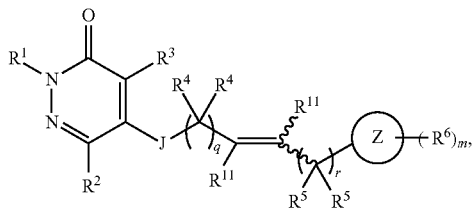
(VI)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —$NO_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —$NO_2$, and an imaging moiety;

J is selected from the group consisting of N($R^7$), S, O, C(=O), C(=O)O, OC(=O), C(=O)N($R^7$), N($R^7$)C(=O), $CH_2O$, and a bond;

each $R^4$, $R^5$, and $R^{11}$ is independently selected from the group consisting of hydrogen, alkyl optionally substituted, and an imaging moiety, or optionally any two of $R^4$ or any two of $R^5$ are joined together to form a ring;

q, and r are each independently 0, 1, 2, or 3;

Z is selected from the group consisting of aryl, heteroaryl, heterocyclyl, and a bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —$NO_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

In some embodiments, a compound is provided comprising the structure:

(VII)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, —$NO_2$, haloalkyl, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —$NO_2$, and an imaging moiety;

J is selected from the group consisting of N($R^7$), S, O, C(=O), C(=O)O, OC(=O), C(=O)N($R^7$), N($R^7$)C(=O), and —$CH_2O$;

each $R^4$ and $R^5$ is independently selected from the group consisting of hydrogen, alkyl optionally substituted, and an imaging moiety, or optionally any two of $R^4$ and $R^5$ are joined together to form a ring;

n is 1, 2, or 3;

Z is selected from the group consisting of aryl, heteroaryl, heterocyclyl, and a bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —$NO_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halo, and an imaging moiety; and each R$^{9'}$ is independently selected from the group consisting of halo, alkyl optionally substituted, aryl optionally substituted, and an imaging moiety, provided that at least one imaging moiety is present in the compound.

In some embodiments, a compound is provided comprising the structure:

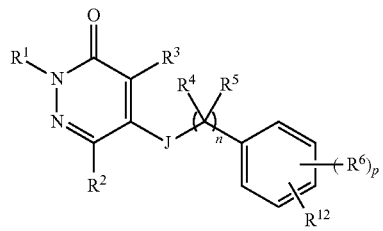

(VIII)

or a pharmaceutically acceptable salt thereof, wherein:

R$^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R$^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

R$^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(=O), C(=O)O, OC(=O), C(=O)N(R$^7$), N(R$^7$)C(=O), CH$_2$O, and a bond;

R$^4$ and R$^5$ are each independently selected from the group consisting of hydrogen, alkyl optionally substituted, and an imaging moiety, or optionally any two of R$^4$ and R$^5$ are joined together to form a ring;

n is 0, 1, 2, or 3;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^{9'}$)$_3$, —OR$^8$, and an imaging moiety;

p is 0, 1, 2, 3, or 4;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring; and each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

R$^{12}$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$;

each R$^9$ is independently selected from the group consisting of hydrogen, alkyl optionally substituted, aryl optionally substituted, haloalkyl, halo, and an imaging moiety; and each R$^{9'}$ is independently selected from the group consisting of halo, alkyl optionally substituted, aryl optionally substituted, and an imaging moiety, provided that at least one imaging moiety is present in the compound.

In some embodiments, a compound is provided comprising the structure:

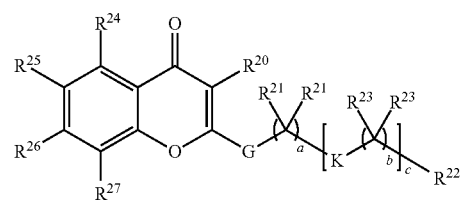

(IX)

or a pharmaceutically acceptable salt thereof, wherein:

R$^{20}$ is selected from the group consisting of hydrogen, heteroalkyl optionally substituted, alkoxy optionally substituted, alkoxyalkyl optionally substituted, aryl optionally substituted, heteroaryl optionally substituted, halo, haloalkyl, —CN, and —NO$_2$;

each R$^{21}$ and R$^{23}$ is independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two R$^{21}$ or any two R$^{23}$ may be joined together to form a ring;

R$^{22}$ is selected from the group consisting of hydrogen, alkyl optionally substituted, heteroalkyl optionally substituted, alkoxyalkyl optionally substituted, halo, haloalkyl, —OR$^{28}$, —Si(R$^9$)$_3$, —B(R$^{9'}$)$_3$, and an imaging moiety;

R$^{24}$, R$^{25}$, R$^{26}$, and R$^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring; and each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety;

each $R^{9'}$ is independently selected from the group consisting of halo, alkyl optionally substituted, aryl optionally substituted, and an imaging moiety, $R^{28}$ is selected from the group consisting of hydrogen, alkyl optionally substituted, and heteroalkyl optionally substituted;

G is O, S, or $NR^{28}$;

a is 0, 1, 2, 3, or 4;

each K is independently arylene, heteroarylene, alkenylene, or alkynylene, each optionally substituted;

each b is independently 0, 1, 2, 3, or 4; and c is 1 or 2, provided at least one imaging moiety is present in the compound.

In some embodiments, a compound is provided comprising the structure:

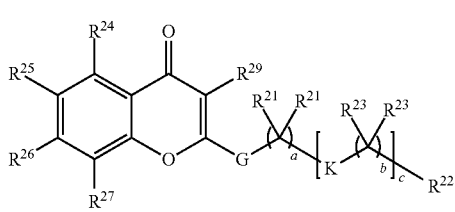

(X)

or a pharmaceutically acceptable salt thereof, wherein:

each $R^{21}$ and $R^{23}$ is independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two $R^{21}$ or any two $R^{23}$ may be joined together to form a ring;

$R^{22}$ is selected from the group consisting of hydrogen, alkyl optionally substituted, heteroalkyl optionally substituted, alkoxyalkyl optionally substituted, halo, haloalkyl, $-OR^{28}$, $-Si(R^9)_3$, $-B(R^{9'})_3$, and an imaging moiety;

$R^{24}$, $R^{25}$, $R^{26}$, and $R^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, $-NO_2$, $-OH$, $-C(=O)R^8$, $-C(=O)OR^8$, $-OC(=O)R^8$, $-C(=O)N(R^7)_2$, $-N(R^7)C(=O)R^8$, $-CN$, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring; and each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety;

each $R^{9'}$ is independently selected from the group consisting of halo, alkyl optionally substituted, aryl optionally substituted, and an imaging moiety, $R^{28}$ is selected from the group consisting of hydrogen, alkyl optionally substituted, and heteroalkyl optionally substituted;

$R^{29}$ is selected from the group consisting of hydrogen, alkyl optionally substituted, heteroalkyl optionally substituted, aryl optionally substituted, heteroaryl optionally substituted, halo, haloalkyl, $-CN$, $-NO_2$, and an imaging moiety;

G is O, S, or $NR^{28}$;

a is 0, 1, 2, 3, or 4;

each K is independently arylene, heteroarylene, alkenylene, or alkynylene, each optionally substituted, provided at least one K is alkenylene, or alkynylene;

each b is independently 0, 1, 2, 3, or 4; and c is 1 or 2, provided at least one imaging moiety is present in the compound.

In some embodiments, the compounds provided above are imaging agents. In some embodiments, a pharmaceutical composition is provided comprising a compound described above and optionally a pharmaceutically acceptable excipient. In some embodiments, a sterile aqueous solution is provided comprising a compound as described above. In some embodiments, use of a compound as described above as an imaging agent is provided. In some embodiments, use of a compound as described above in myocardial perfusion imaging is provided. In some embodiments, use of a compound as described above in the manufacture of a medicament for detecting, imaging or monitoring myocardial perfusion is provided. In some embodiments, a method of imaging a portion of a subject is provided comprising administering to the subject a compound as described above and acquiring at least one image of a portion of the subject. In some embodiments, a method of imaging a portion of a subject is provided comprising administering to a subject a compound as described above, detecting radiation emitted by the compound, and forming an image therefrom. In some embodiments, a diagnostic kit is provided comprising one or more vials containing a precursor to a compound as described above and optionally other components. In some embodiments, a method of imaging myocardial perfusion is provided comprising administering to a patient a compound as described above and scanning the patient using diagnostic imaging. In some embodiments, a method of detecting myocardial perfusion is provided comprising administering to a patient a compound as described above and scanning the patient using diagnostic imaging. In some embodiments, a method of monitoring myocardial perfusion is provided comprising administering to a patient a compound as described above and scanning the patient using diagnostic imaging. In some embodiments, precursors to the compounds described above are provided. In some embodiments, the at least one imaging agent is replaced with at least one leaving group.

In some embodiments, a cassette for the preparation of an imaging agent is provided comprising the components arranged as shown in FIG. 17.

In some embodiments, an apparatus for synthesizing an imaging agent comprising a linear arrangement of a plurality of stopcock manifolds arranged in the order:

1) luer connections (2) to gas inlet and [$^{18}$O]H$_2$O recovery;
2) anion exchange cartridge—column eluting solution;
3) spike connection for acetonitrile;
4) empty syringe;
5) reservoir with solution of imaging agent precursor;
6) reaction vessel;
7) outlet to HPLC;
8) syringe with solution of a stabilizing agent;
9) inlet from HPLC;
10) ethanol reservoir;
11) syringe with solution of a stabilizing agent;
12) syringe with water;
13) final product vial;
14) empty syringe; and
15) reaction vessel and exhaust.

In some embodiments, an apparatus for synthesizing an imaging agent comprising a linear arrangement of a plurality of stopcock manifolds arranged in the order:

1) luer connections (2) to gas inlet and [$^{18}$O]H$_2$O recovery;
2) anion exchange cartridge—column eluting solution;
3) reservoir with solution of imaging agent precursor;
4) empty syringe;
5) spike connection for acetonitrile;
6) reaction vessel;
7) outlet to HPLC;
8) syringe with solution of a stabilizing agent;
9) inlet from HPLC;
10) ethanol reservoir;
11) syringe with solution of a stabilizing agent;
12) syringe with water;
13) final product vial;
14) empty syringe; and
15) reaction vessel and exhaust.

In some embodiments, an apparatus for synthesizing an imaging agent comprising a linear arrangement of a plurality of stopcock manifolds arranged in the order:

1) luer connections (2) to gas inlet and [$^{18}$O]H$_2$O recovery;
2) anion exchange cartridge—column eluting solution;
3) reservoir with solution of imaging agent precursor;
4) empty syringe;
5) spike connection for acetonitrile;
6) reaction vessel;
7) outlet to HPLC;
8) syringe with solution of a stabilizing agent;
9) inlet from HPLC;
10) ethanol reservoir;
11) final product vial;
12) syringe with water;
13) syringe with solution of a stabilizing agent
14) empty syringe; and
15) reaction vessel and exhaust.

In some embodiments, an apparatus for synthesizing an imaging agent comprising a linear arrangement of a plurality of stopcock manifolds arranged in the order:

1) luer connections (2) to gas inlet and [$^{18}$O]H$_2$O recovery;
2) anion exchange cartridge—column eluting solution;
3) spike connection for acetonitrile;
4) empty syringe;
5) reservoir with solution of imaging agent precursor;
6) reaction vessel;
7) outlet to HPLC;
8) syringe with solution of a stabilizing agent;
9) inlet from HPLC;
10) ethanol reservoir;
11) final product vial;
12) syringe with water;
13) syringe with solution of a stabilizing agent;
14) empty syringe; and
15) reaction vessel and exhaust.

Figure 1:
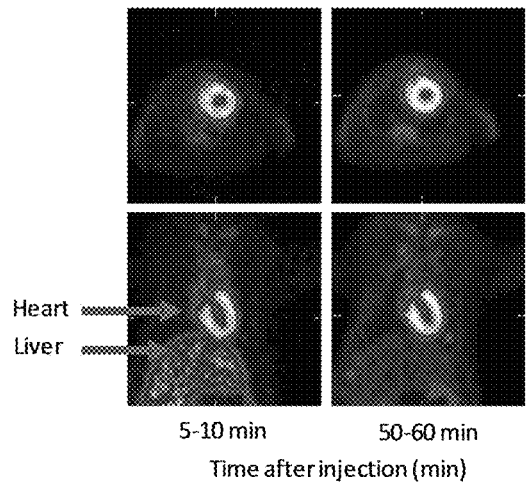
FIGS. 1-15 show representative images of non-limiting compounds in rat.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION OF CERTAIN EMBODIMENTS OF THE INVENTION

The present invention provides compounds, compositions thereof, systems comprising such compounds, reagents, cassettes, methods, kits, and apparatuses for the synthesis and/or use of the compounds as imaging agents and precursors thereof. The imaging agents of the present invention may be used to image an area of interest in a subject, including, but not limited to, the heart, a portion of the heart, the cardiovascular system, cardiac vessels, brain, and other organs. In some embodiments, the imaging agent comprises an imaging moiety, wherein the imaging moiety is selected from the group consisting of $^{11}$C, $^{13}$N, $^{18}$F, $^{76}$Br, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, and $^{68}$Ga. In certain embodiments, the imaging agent comprises $^{18}$F as the imaging moiety. In certain embodiments, the area of the subject being imaged is imaged by positron emission tomography (PET).

In some embodiments, the present invention provides methods of imaging, including methods of imaging of a subject that includes administering a composition or formulation (e.g., that comprises an imaging agent as described herein) to the subject by injection, infusion, or any other known method of administration, and imaging a region of the subject that is of interest. Regions of interest may include, but are not limited to, the heart, cardiovascular system, cardiac vessels, blood vessels (e.g., arteries, veins), brain, and other organs. Regions of interest may also include tumors or regions of the subject's body that may include a tumor. A parameter of interest, such as blood flow, cardiac wall motion, or perfusion, can be imaged and detected using methods and/or systems described herein. An event of interest can be imaged and detected and/or other information may be determined using methods and/or systems of the disclosure. In some embodiments, methods for evaluating perfusion, including myocardial perfusion, are provided.

Imaging Agents

In one aspect, the invention provides compounds useful as imaging agents for imaging an area of interest of a subject. In some embodiments, the imaging agent comprises an imaging moiety, wherein the imaging moiety is selected from the group consisting of $^{11}$C, $^{13}$N, $^{18}$F, $^{76}$Br, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, and $^{68}$Ga. In certain embodiments, the imaging agent is labeled with $^{18}$F and is useful in PET imaging. In some embodiments, a compound is provided comprising the structure:

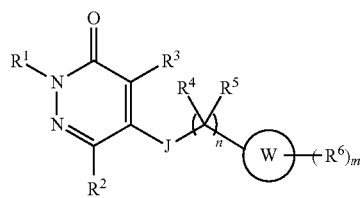

(I)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(═O), C(═O)O, OC(═O), C(═O)N(R$^7$), N(R$^7$)C(═O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

W is heteroaryl, naphthyl, heterocyclyl or aryl;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(═O)R$^8$, —C(═O)OR$^8$, —OC(═O)R$^8$, —C(═O)N(R$^7$)$_2$, —N(R$^7$)C(═O)R$^8$, —CN, —Si(R$^9$)$_3$, —B(R$^{9'}$)$_3$, —OR$^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound; and provided that when W is aryl, a) R$^3$ is not halo, alkyl, or haloalkyl, or b) at least one R$^6$ is selected from the group consisting of alkynyl optionally substituted, alkenyl optionally substituted, alkyl substituted with —CN, alkyl substituted with —C(═O)OR$^8$, alkyl substituted with —C(═O)R$^8$, alkyl substituted with —N(R$^7$)$_2$, —CN, —NO$_2$, —N(R$^7$)$_2$, —C(═O)OR$^8$, —OC(═O)R$^8$, —C(═O)R$^8$, —C(═O)N(R$^7$)$_2$, and —N(R$^7$)C(═O)R$^8$.

In some embodiments, a compound is provided comprising the structure:

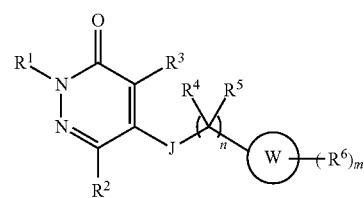

(II)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R⁷), S, O, C(=O), C(=O)O, OC(=O), C(=O)N(R⁷), N(R⁷)C(=O), CH₂O, and a bond;

R⁴ and R⁵ are each independently selected from the group consisting of hydrogen, alkyl optionally substituted, and an imaging moiety, or optionally any two of R⁴ and R⁵ are joined together to form a ring;

n is 0, 1, 2, or 3;

W is heteroaryl, naphthyl, or heterocyclyl;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹)₃, —OR⁸, and an imaging moiety;

m is 0, 1, 2, 3, 4, 5, 6, or 7;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R⁹ is independently selected from the group consisting of hydrogen, alkyl optionally substituted, aryl optionally substituted, haloalkyl, halo, and an imaging moiety; and each R⁹' is independently selected from the group consisting of halo, alkyl optionally substituted, aryl optionally substituted, and an imaging moiety, provided that at least one imaging moiety is present in the compound.

In some embodiments, for a compound of Formula (I), W is aryl. In some embodiments, for a compound of Formula (I), W is a 5-membered or 6-membered aryl group.

The following description of W groups may be used in connection with a compound of Formula (I) or (II), or as noted herein. In some embodiments, W is heteroaryl. In some embodiments, W is five-membered heteroaryl. In some embodiments, W is six-membered heteroaryl. In some embodiments, W is moncyclic heteroaryl. In some embodiments, W is bicyclic heteroaryl. In some embodiments, W is tricyclic heteroaryl. In some embodiments, W is naphthyl. In some embodiments, W is heterocyclyl. In some embodiments, W is:

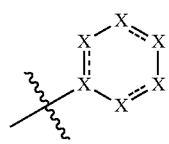

wherein each X is independently selected from the group consisting of C, C(R⁶), C(R⁶)₂, N, NR⁷, O, and S; and wherein each ===== is independently a single or double bond, provided at least one X is not C or C(R⁶). In some embodiments, at least one X is N. In some embodiments, at least one X is N(R⁷). In some embodiments, at least one X is O. In some embodiments, at least one X is S. In some embodiments, W is:

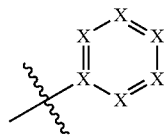

wherein each X is independently C, C(R⁶) or N, provided at least one X is not C or C(R⁶). In some embodiments, W is:

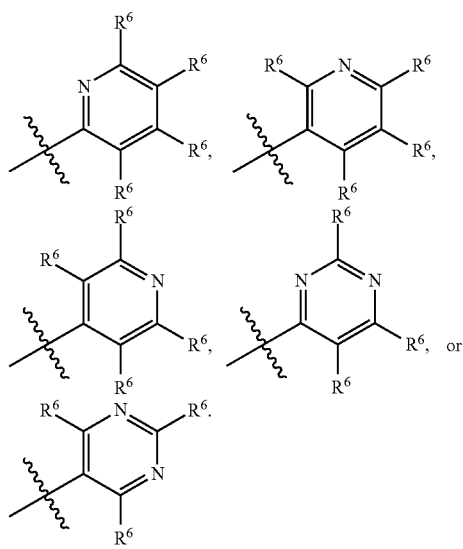

In some embodiments, W is:

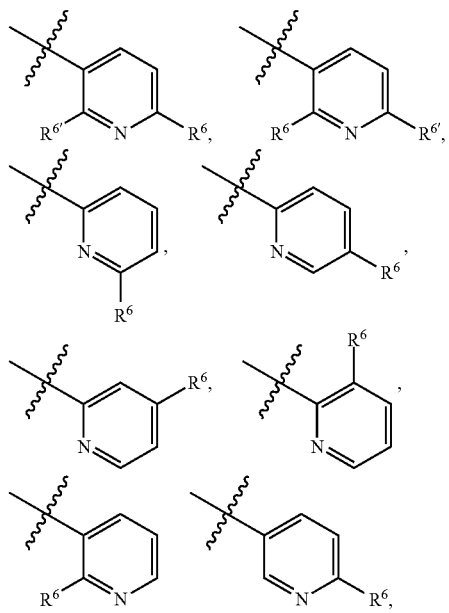

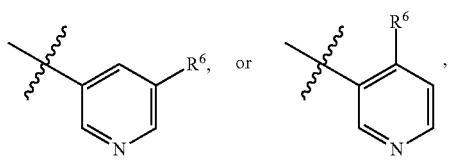

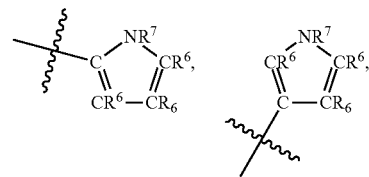

wherein R[6'] is halo or hydrogen. In some embodiments, R[6'] is fluoro, chloro, bromo, or hydrogen. In some embodiments, R[6] is —O(CH$_2$)$_j$I$_m$, wherein I$_m$ is an imaging moiety and j is 1, 2, 3, 4, 5, or 6. In some embodiments, R[6] is —(CH$_2$)$_j$O(CH$_2$)$_j$I$_m$ I$_m$ is an imaging moiety and wherein each j is independently 1, 2, 3, 4, 5, or 6. In some cases, I$_m$ is [18]F. In some embodiments, W is:

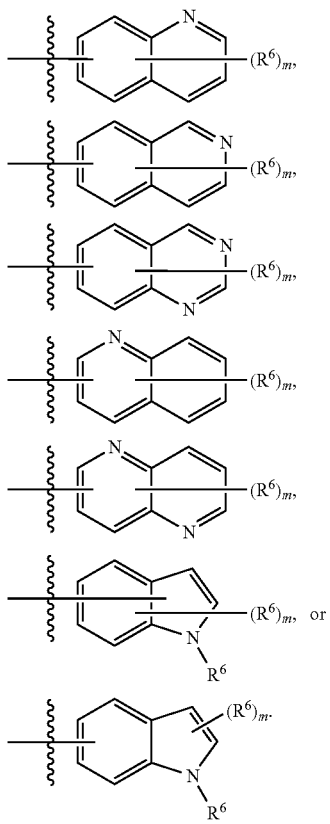

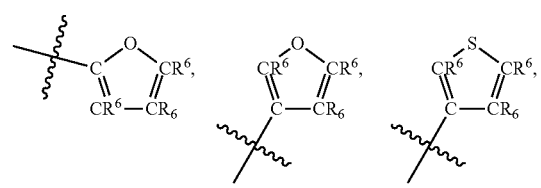

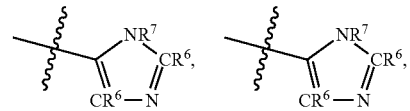

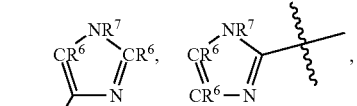

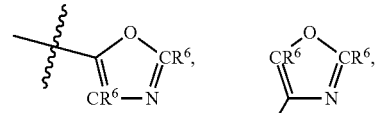

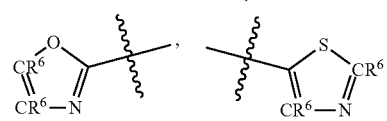

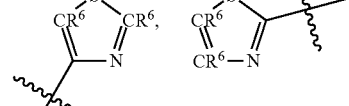

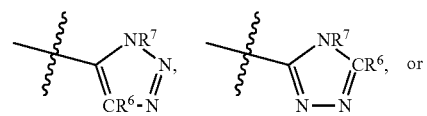

In some embodiments, W is:

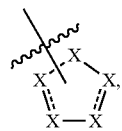

wherein each X is independently selected from the group consisting of C, C(R[6]), C(R[6])$_2$, N, NR[7], O, and S; and each ═══ is independently a single or double bond, provided at least one X is not C or C(R[6]). In some embodiments, W is selected from the group consisting of:

For a compound of Formula (I) or (II), each of the W groups described herein may be combined with any R[1], R[2], R[3], R[4], R[5], R[6], R[7], R[8], R[9], J, m, and n, or combinations thereof, as described herein.

In some embodiments, a compound is provided comprising the structure:

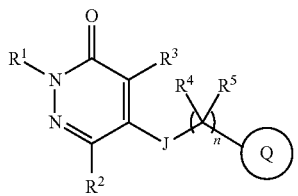

(III)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —$NO_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —$NO_2$, and an imaging moiety;

J is selected from the group consisting of $N(R^7)$, S, O, C(=O), C(=O)O, OC(=O), C(=O)$N(R^7)$, $N(R^7)$C(=O), $CH_2O$, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

Q has the structure:

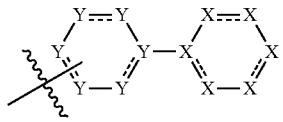

each Y and each X is independently selected from the group consisting of C, $C(R^6)$, $C(R^6)_2$, N, $NR^7$, O, and S, provided at least one Y is not C or $C(R^6)$, and optionally, wherein one Y and/or one X may be absent;

each ====== is independently a single or double bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —$N(R^7)_2$, —$NO_2$, —OH, —C(=O)$R^8$, —C(=O)$OR^8$, —OC(=O)$R^8$, —C(=O)$N(R^7)_2$, —$N(R^7)$C(=O)$R^8$, —CN, —$Si(R^9)_3$, —$B(R^{9'})_3$, —$OR^8$, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

The following description of Q groups may be used in connection with a compound of Formula (III), or as noted herein. In some embodiments, Q has the structure:

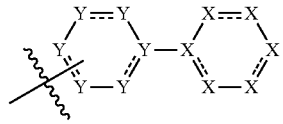

wherein each Y and each X is independently selected from the group consisting of C, $C(R^6)$, $C(R^6)_2$, N, $NR^7$, O, and S, provided at least one Y is not C or $C(R^6)$. In some embodiments, one Y and/or one X may be absent. In some embodiments, one Y is absent. In some embodiments, one X is absent. In some embodiments, one Y and one X are absent. In some embodiments, one Y is absent and one Y is N. In some embodiments, one Y is absent and one Y is $NR^7$. In some embodiments, one Y is absent and one Y is O. In some embodiments, one Y is absent and one Y is S. In some embodiments, one X is absent and one X is N. In some embodiments, one X is absent and one X is $NR^7$. In some embodiments, one X is absent and one X is O. In some embodiments, one X is absent and one X is S. In some embodiments, for Q, at least one Y is $NR^7$. In some embodiments, for Q, at least one of each of X and Y is $NR^7$. In some embodiments, for Q, at least one Y is N. In some embodiments, for Q, at least one of each of X and Y is N. In some embodiments, for Q, at least one Y is O. In some embodiments, for Q, at least one Y is S. In some embodiments, for Q, each X is C or $C(R^6)$. In some embodiments, for Q, at least one X is not C or $C(R^6)$. In some embodiments, for Q, at least two Y are not C or $C(R^6)$. In some embodiments, for Q, at least one of each of X and Y is not C or $C(R^6)$. In some embodiments, for Q, at least two X are not C or $C(R^6)$. In some embodiments, Q is:

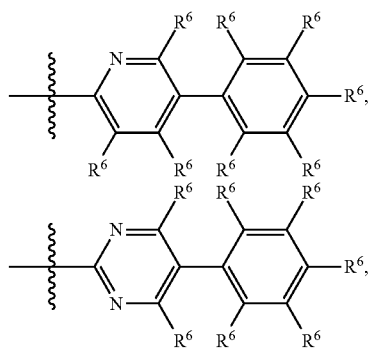

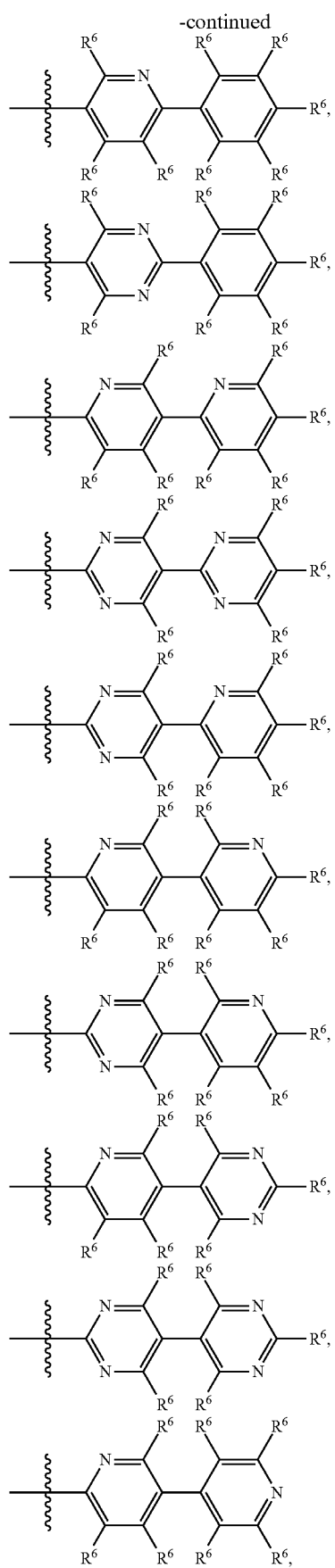
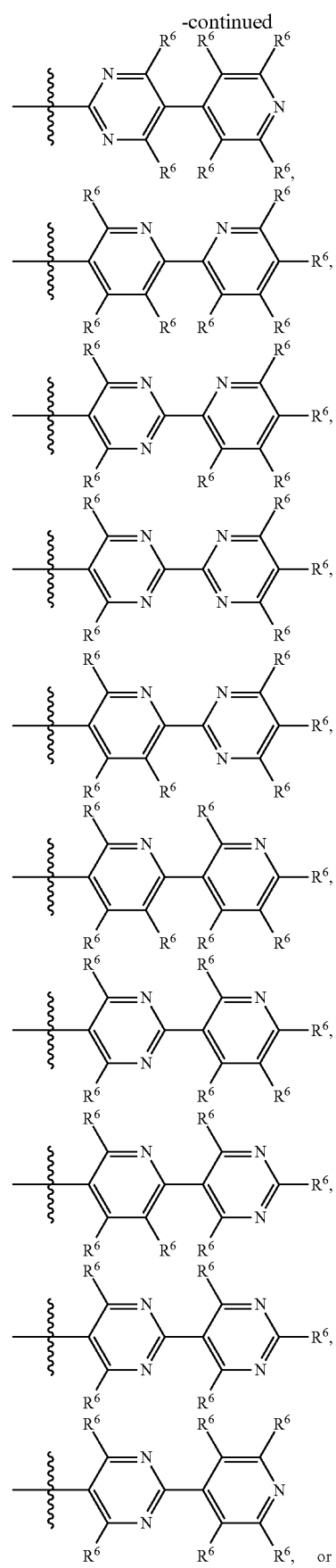

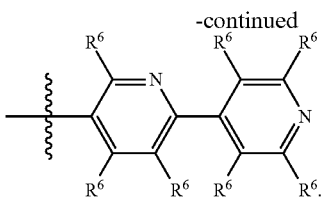

For a compound of Formula (III), each of the Q groups described herein may be combined with any R¹, R², R³, R⁴, R⁵, R⁶, R⁷, R⁸, R⁹, J, and n, or combinations thereof, as described herein.

In some embodiments, a compound is provided comprising the structure:

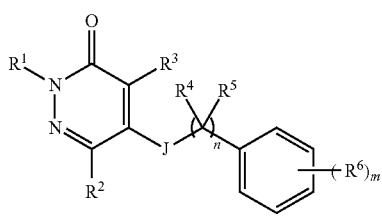

or a pharmaceutically acceptable salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and an imaging moiety;

R³ is selected from the group consisting of hydrogen, unsubstituted alkyl or alkyl optionally substituted with a moiety other than a halogen, heteroalkyl optionally substituted, alkoxy optionally substituted, alkoxyalkyl optionally substituted, aryl optionally substituted, heteroaryl optionally substituted, —CN, and —NO₂;

J is selected from the group consisting of N(R⁷), S, O, C(=O), C(=O)O, OC(=O), C(=O)N(R⁷), N(R⁷)C(=O), CH₂O, and a bond;

R⁴ and R⁵ are each independently selected from the group consisting of hydrogen, alkyl optionally substituted, and an imaging moiety, or optionally any two of R⁴ and R⁵ are joined together to form a ring;

n is 0, 1, 2, or 3;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹')₃, —OR⁸, and an imaging moiety;

m is 0, 1, 2, 3, 4, or 5;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R⁹ is independently selected from the group consisting of hydrogen, alkyl optionally substituted, aryl optionally substituted, haloalkyl, halo, and an imaging moiety; and each R⁹' is independently selected from the group consisting of halo, alkyl optionally substituted, aryl optionally substituted, and an imaging moiety, provided that at least one imaging moiety is present in the compound.

In some embodiments, a compound is provided comprising the structure:

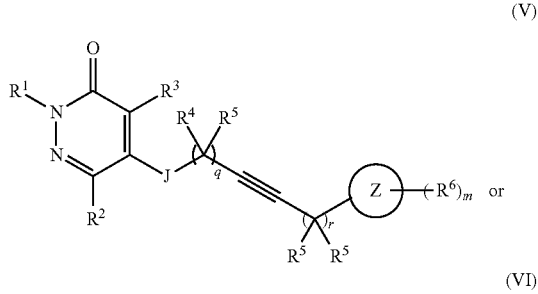

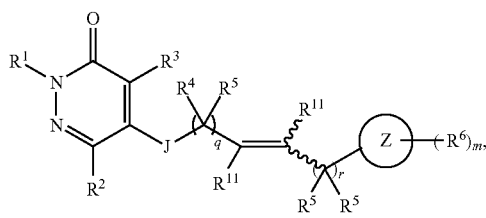

or a pharmaceutically acceptable salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and an imaging moiety;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO₂, and an imaging moiety;

J is selected from the group consisting of N(R⁷), S, O, C(=O), C(=O)O, OC(=O), C(=O)N(R⁷), N(R⁷)C(=O), CH₂O, and a bond;

each R⁴, R⁵, and R¹¹ is independently selected from the group consisting of hydrogen, alkyl optionally substituted, and an imaging moiety, or optionally any two of R⁴ or any two of R⁵ are joined together to form a ring;

q, and r are each independently 0, 1, 2, or 3;

Z is selected from the group consisting of aryl, heteroaryl, heterocyclyl, and a bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound. In some embodiments, In some embodiments, a compound is provided comprising the structure:

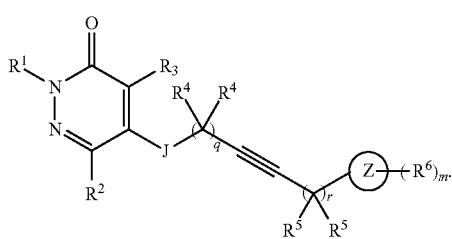
(V)

In some embodiments, a compound is provided comprising the structure:

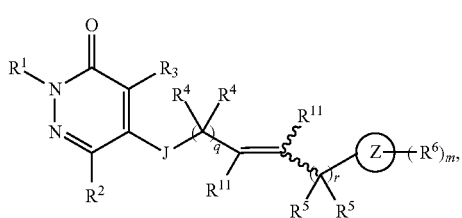
(VI)

In some embodiments, a compound is provided comprising the structure:

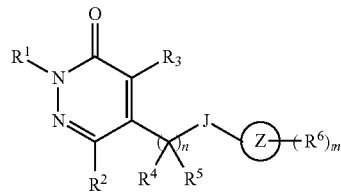
(VII)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, —NO$_2$, haloalkyl, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N($R^7$), S, O, C(=O), C(=O)O, OC(=O), C(=O)N($R^7$)$_2$, N($R^7$)C(=O), and —CH$_2$O;

each $R^4$ and $R^5$ is independently selected from the group consisting of hydrogen, alkyl optionally substituted, and an imaging moiety, or optionally any two of $R^4$ or any two of $R^5$ are joined together to form a ring;

n is 1, 2, or 3;

Z is selected from the group consisting of aryl, heteroaryl, heterocyclyl, and a bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

The following description of Z groups may be used in connection with a compound of Formula (V), (VI), or (VII). In some embodiments, Z is aryl. In some embodiments, Z is phenyl. In some embodiments, Z is naphthyl. In some embodiments, Z is heteroaryl. In some embodiments, Z is five-membered heteroaryl. In some embodiments, Z is six-membered heteroaryl. In some embodiments, Z is moncyclic heteroaryl. In some embodiments, Z is bicyclic heteroaryl. In some embodiments, Z is tricyclic heteroaryl. In some embodiments, Z is heterocyclyl. In some embodiments, Z is:

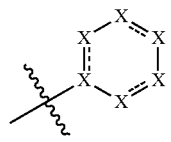

wherein each X is independently selected from the group consisting of C, C($R^6$), C($R^6$)$_2$, N, N$R^7$, O, and S; and wherein each ====== is independently a single or double bond. In some embodiments, at least one X is not C or C($R^6$). In some embodiments, at least one X is N. In some embodiments, at least one X is N($R^7$). In some embodiments, at least one X is O. In some embodiments, at least one X is S. In some embodiments, Z is:

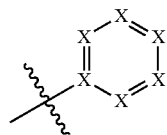

wherein each X is independently C, C($R^6$), or N. In some embodiments, at least one X is not C or C($R^6$). In some embodiments, at least one X is N. In some embodiments, Z is:

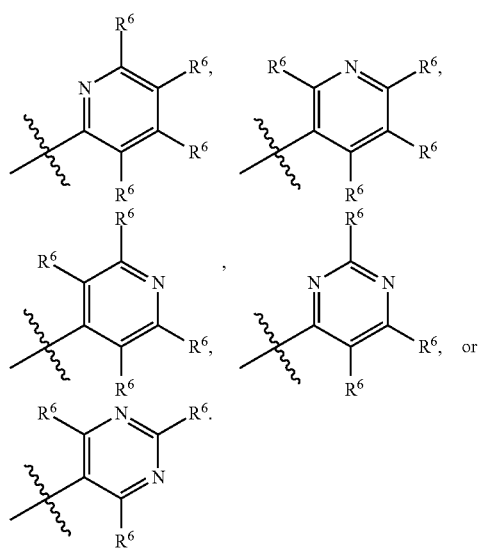

In some embodiments, Z is:

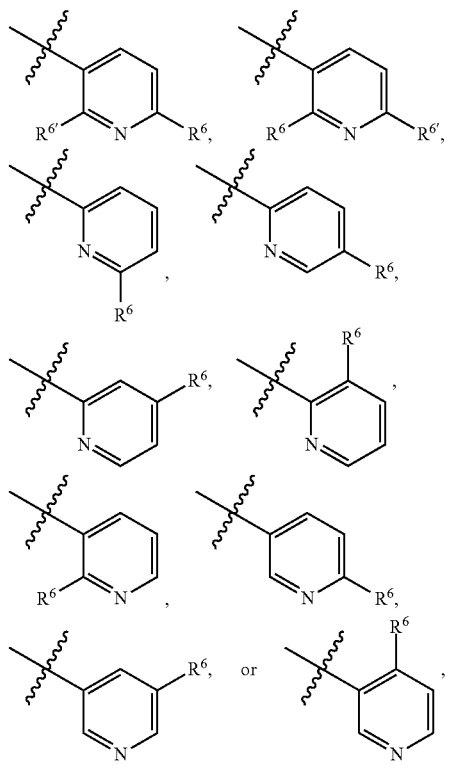

wherein $R^{6'}$ is halo or hydrogen. In some embodiments, $R^{6'}$ is fluoro, chloro, bromo, or hydrogen. In some embodiments, $R^6$ is —O(CH$_2$)$_j$I$_m$; wherein I$_m$ is an imaging moiety and j is 1, 2, 3, 4, 5, or 6. In some embodiments, $R^6$ is —(CH$_2$)$_j$O(CH$_2$)$_j$I$_m$; wherein I$_m$ is an imaging moiety and each j is independently 1, 2, 3, 4, 5, or 6. In some embodiments, Z is:

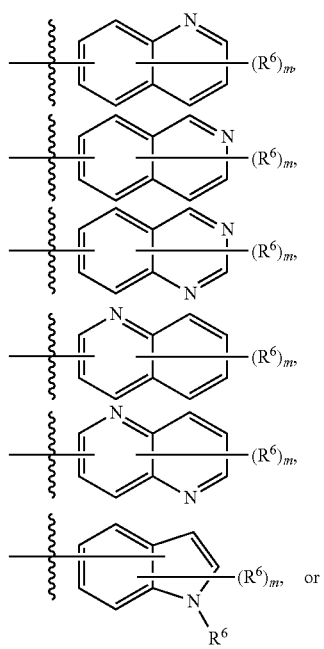

-continued

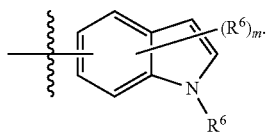

In some embodiments, Z is:

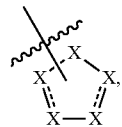

each X is independently selected from the group consisting of C, C(R$^6$), C(R$^6$)$_2$, N, NR$^7$, O, and S; and each ------ is independently a single or double bond. In some embodiments, at least one X is not C or C(R$^6$). In some embodiments, at least one X is N. In some embodiments, at least one X is N(R$^7$). In some embodiments, at least one X is O. In some embodiments, at least one X is S. In some embodiments, Z is selected from the group consisting of:

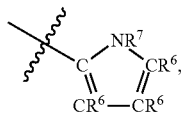 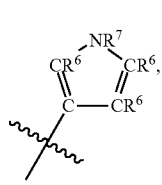

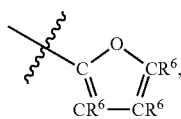 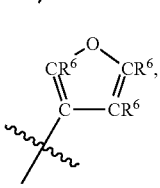

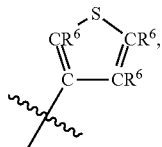 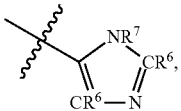

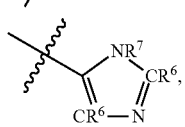 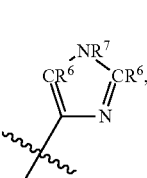

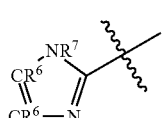 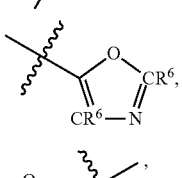

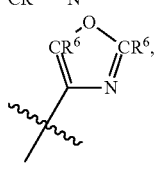 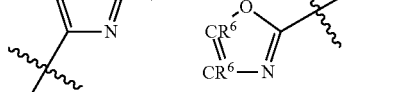

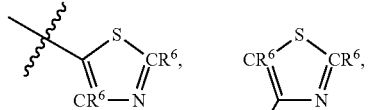

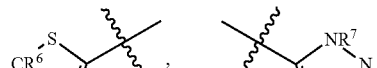

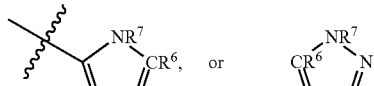

In some embodiments, Z is:

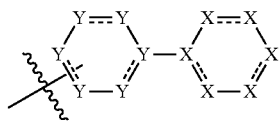

each Y is independently selected from the group consisting of C, C(R$^6$), C(R$^6$)$_2$, N, NR$^7$, O, and S; and each ------ is independently a single or double bond, optionally, wherein one X and/or one Y is absent. In some embodiments, one Y and/or one X may be absent. In some embodiments, one Y is absent. In some embodiments, one X is absent. In some embodiments, one Y and one X are absent. In some embodiments, one Y is absent and one Y is N. In some embodiments, one Y is absent and one Y is NR$^7$. In some embodiments, one Y is absent and one Y is O. In some embodiments, one Y is absent and one Y is S. In some embodiments, one X is absent and one X is N. In some embodiments, one X is absent and one X is NR$^7$. In some embodiments, one X is absent and one X is O. In some embodiments, one X is absent and one X is S. In some embodiments, for Z, at least one Y is NR$^7$. In some embodiments, for Z, at least one of each of X and Y is NR$^7$. In some embodiments, for Z, at least one Y is N. In some embodiments, for Z, at least one of each of X and Y is N. In some embodiments, for Z, at least one Y is O. In some embodiments, for Z, at least one Y is S. In some embodiments, for Z, each X is C or C(R$^6$). In some embodiments, for Z, at least one X is not C or C(R$^6$). In some embodiments, for Z, at least two Y are not C or C(R$^6$). In some embodiments, for Z, at least one of each of X and Y is not C or C(R$^6$). In some embodiments, for Z, at least two X are not C or C(R$^6$). In some embodiments, Z is:

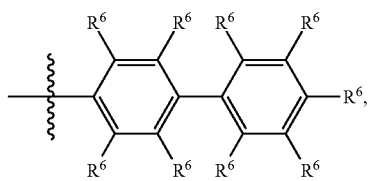

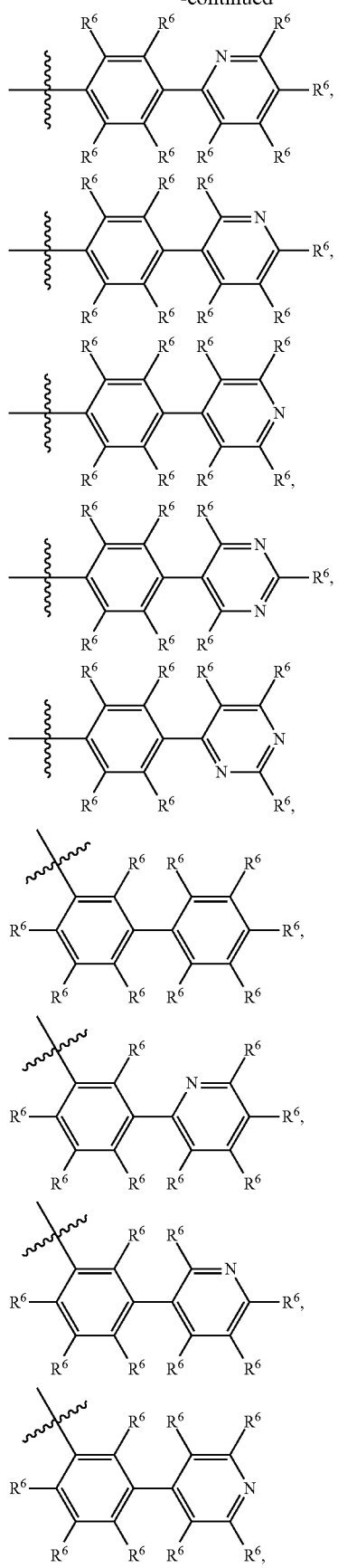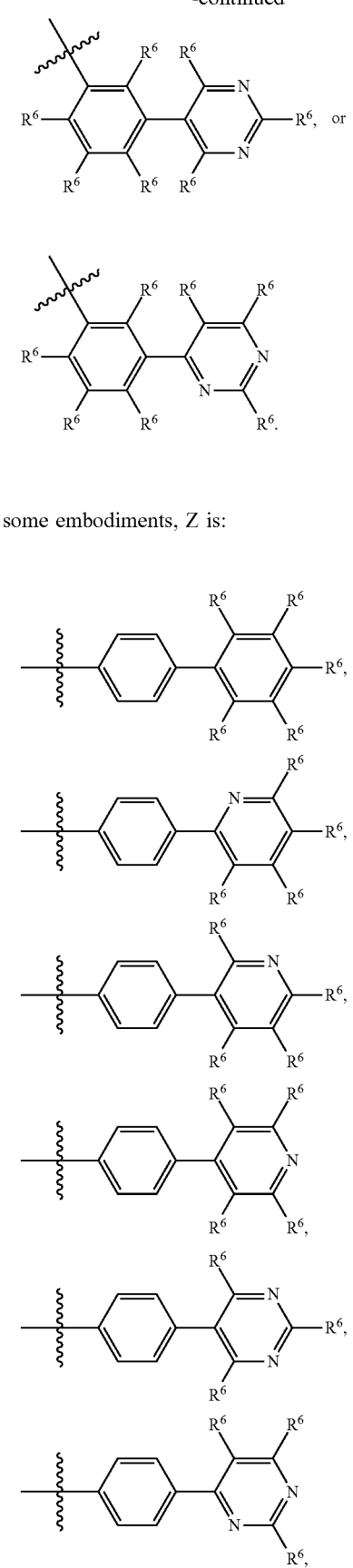
In some embodiments, Z is:

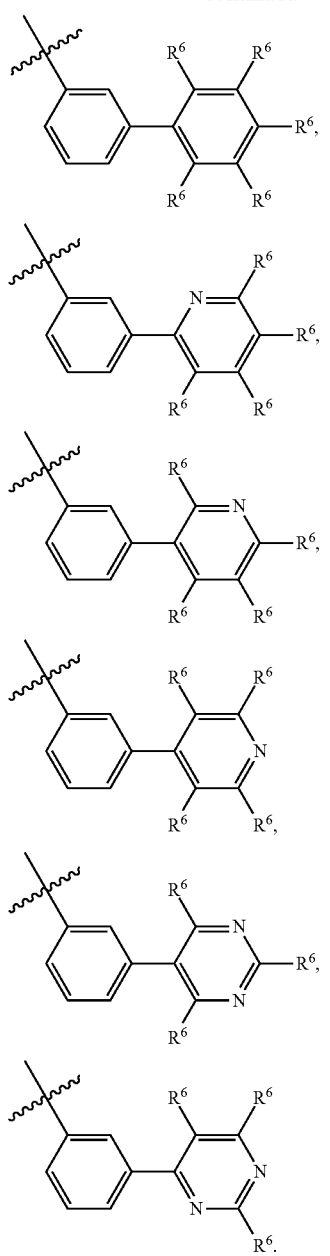
In some embodiments, Z is:
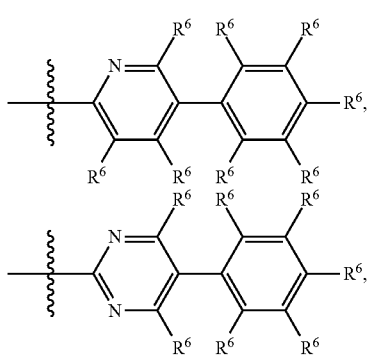
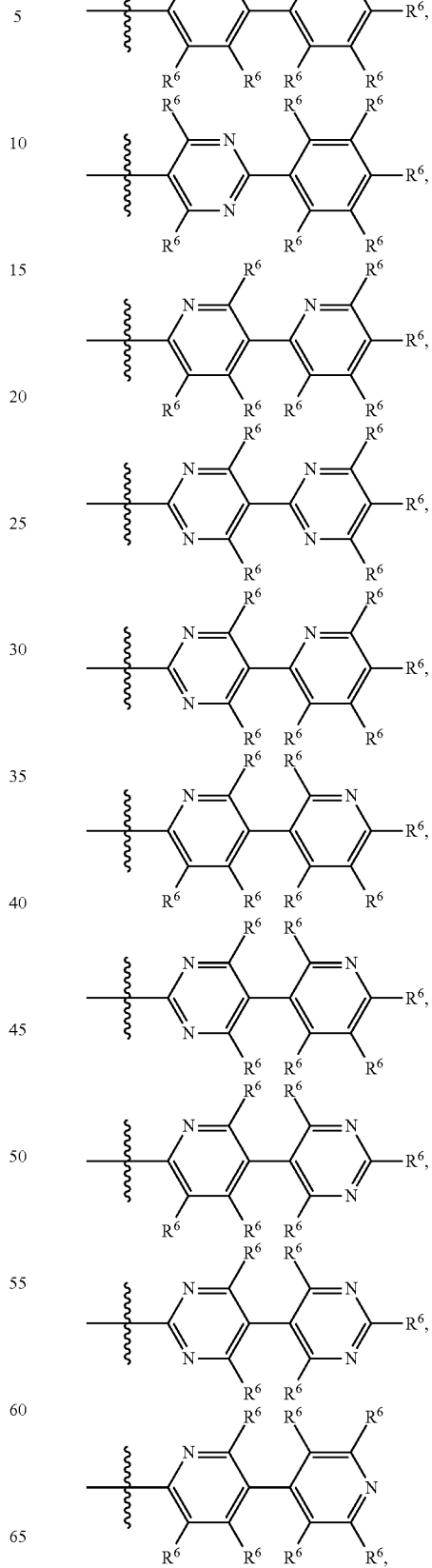

-continued

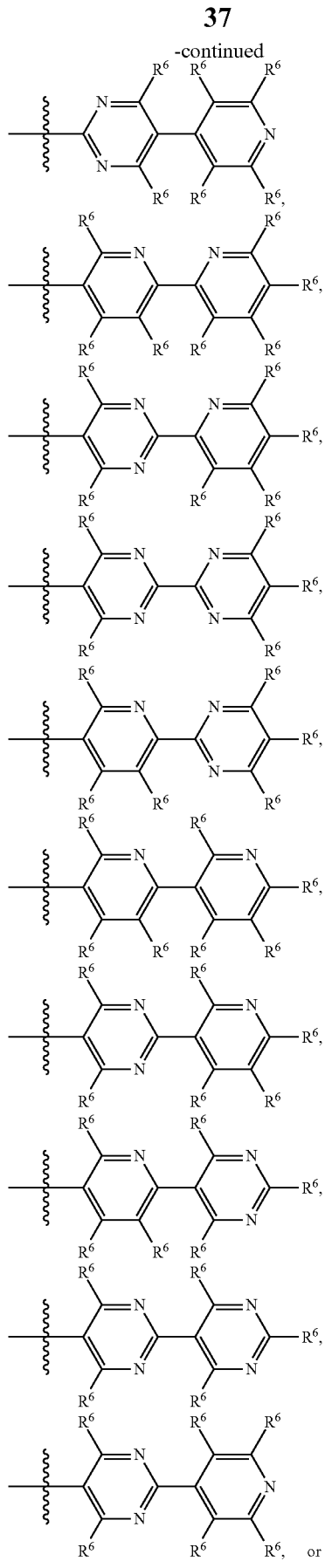

-continued

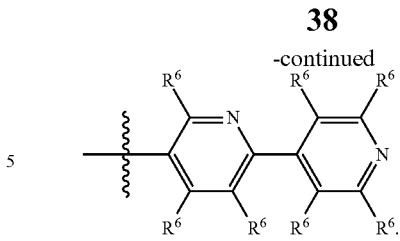

For a compound of Formula (V) or (VI), each of the Z groups described herein may be combined with any $R^1$, $R^2$, $R^3$, $R^4$, $R^5$, $R^6$, $R^7$, $R^8$, $R^9$, $R^{11}$, J, m, q, and r, or combinations thereof, as described herein. For a compound of Formula (VII), each of the Z groups described herein may be combined with any $R^1$, $R^2$, $R^3$, $R^4$, $R^5$, $R^6$, $R^7$, $R^8$, $R^9$, J, n, and m, or combinations thereof, as described herein.

In some embodiments, a compound is provided comprising the structure:

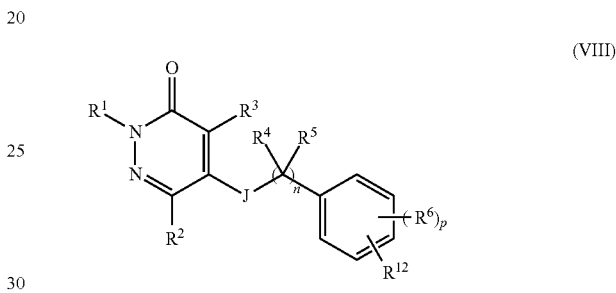

(VIII)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-NO_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-CN$, $-NO_2$, and an imaging moiety;

J is selected from the group consisting of consisting of $N(R^7)$, S, O, $C(=O)$, $C(=O)O$, $OC(=O)$, $C(=O)N(R^7)$, $N(R^7)C(=O)$, $CH_2O$, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, $-N(R^7)_2$, $-NO_2$, $-OH$, $-C(=O)R^8$, $-C(=O)OR^8$, $-OC(=O)R^8$, $-C(=O)N(R^7)_2$, $-N(R^7)C(=O)R^8$, $-CN$, $-Si(R^9)_3$, $-B(R^{9'})_3$, $-OR^8$, and an imaging moiety;

p is 0, 1, 2, 3, or 4;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

$R^{12}$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$;

each $R^9$ is independently selected from the group consisting of hydrogen, alkyl optionally substituted, aryl optionally substituted, haloalkyl, halo, and an imaging moiety; and each $R^{9'}$ is independently selected from the group consisting of halo, alkyl optionally substituted, aryl optionally substituted, and an imaging moiety, provided that at least one imaging moiety is present in the compound.

The following description of $R^1$ groups may be used in connection with a compound of Formula (I), (II), (III), (IV), (V), (VI), (VII), or (VIII). In some embodiments, $R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety. In some embodiments, $R^1$ is hydrogen. In some embodiments, $R^1$ is alkyl optionally substituted. In some embodiments, $R^1$ is unsubstituted alkyl. In some embodiments, $R^1$ is methyl, ethyl, n-propyl, i-propyl, n-butyl, i-butyl, or t-butyl. In some embodiments, $R^1$ is t-butyl. In some embodiments, $R^1$ is heteroalkyl optionally substituted. In some embodiments, $R^1$ is unsubstituted heteroalkyl. In some embodiments, $R^1$ is —[C(R')$_2$]$_j$OH, wherein j is 1, 2, 3, 4, 5, or 6, and each $R^1$ is the same or different and is hydrogen or alkyl optionally substituted. In some embodiments, $R^1$ is —C(CH$_3$)$_2$CH$_2$OH. In some embodiments, $R^1$ is alkoxy optionally substituted. In some embodiments, $R^1$ is alkoxyalkyl optionally substituted. In some embodiments, $R^1$ is aryl optionally substituted. In some embodiments, $R^1$ is unsubstituted aryl. In some embodiments, $R^1$ is phenyl optionally substituted. In some embodiments, $R^1$ is unsubstituted phenyl. In some embodiments, $R^1$ is cycloalkyl optionally substituted. In some embodiments, $R^1$ is unsubstituted cycloalkyl. In some embodiments, $R^1$ is cyclohexyl optionally substituted. In some embodiments, $R^1$ is unsubstituted cyclohexyl. In some embodiments, $R^1$ is cyclopentyl optionally substituted. In some embodiments, $R^1$ is unsubstituted cyclopentyl. For a compound of Formula (I) or (II) each of the $R^1$ groups described herein may be combined with any $R^2$, $R^3$, $R^4$, $R^5$, $R^6$, $R^7$, $R^8$, $R^9$, $R^{9'}$, J, W, m, and n, or combinations thereof, as described herein. For a compound of Formula (III), each of the $R^1$ groups described herein may be combined with any $R^2$, $R^3$, $R^4$, $R^5$, $R^6$, $R^7$, $R^8$, $R^9$, $R^{9'}$, J, Q, and n, or combinations thereof, as described herein. For a compound of Formula (IV), each of the $R^1$ groups described herein may be combined with any $R^2$, $R^3$, $R^4$, $R^5$, $R^6$, $R^7$, $R^8$, $R^9$, $R^{9'}$, J, m, and n, or combinations thereof, as described herein. For a compound of Formula (V) or (VI), each of the $R^1$ groups described herein may be combined with any $R^2$, $R^3$, $R^4$, $R^5$, $R^6$, $R^7$, $R^8$, $R^9$, $R^{9'}$, R11, J, Z, m, q, and r, or combinations thereof, as described herein. For a compound of Formula (VII), each of the $R^1$ groups described herein may be combined with any $R^2$, $R^3$, $R^4$, $R^5$, $R^6$, $R^7$, $R^8$, $R^9$, $R^{9'}$, J, Z, n, and m, or combinations thereof, as described herein. For a compound of Formula (VIII), each of the $R^1$ groups described herein may be combined with any $R^2$, $R^3$, $R^4$, $R^5$, $R^6$, $R^7$, $R^8$, $R^9$, $R^{9'}$, R12, J, p, and n, or combinations thereof, as described herein.

The following description of $R^2$ groups may be used in connection with a compound of Formula (I), (II), (III), (IV), (V), (VI), (VII), or (VIII). In some embodiments, $R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety. In some embodiments, $R^2$ is hydrogen. In some embodiments, $R^2$ is alkyl optionally substituted. In some embodiments, $R^2$ is unsubstituted alkyl. In some embodiments, $R^2$ is methyl, ethyl, n-propyl, i-propyl, n-butyl, i-butyl, or t-butyl. In some embodiments, $R^2$ is aryl optionally substituted. In some embodiments, $R^2$ is unsubstituted aryl. In some embodiments, $R^2$ is phenyl optionally substituted. In some embodiments, $R^2$ is unsubstituted phenyl. In some embodiments, $R^2$ is cycloalkyl optionally substituted. In some embodiments, $R^2$ is unsubstituted cycloalkyl. In some embodiments, $R^2$ is cyclohexyl optionally substituted. In some embodiments, $R^2$ is unsubstituted cyclohexyl. Each of the $R^2$ groups described herein may be combined with any $R^1$, $R^3$, $R^4$, $R^5$, $R^6$, $R^{12}$, J, Q, W, and/or m, or combinations thereof, as described herein. For a compound of Formula (I) or (II), each of the $R^2$ groups described herein may be combined with any $R^1$, $R^3$, $R^4$, $R^5$, $R^6$, $R^7$, $R^8$, $R^9$, $R^{9'}$, J, W, m, and n, or combinations thereof, as described herein. For a compound of Formula (III), each of the $R^2$ groups described herein may be combined with any $R^1$, $R^3$, $R^4$, $R^5$, $R^6$, $R^7$, $R^8$, $R^9$, $R^{9'}$, J, Q, and n, or combinations thereof, as described herein. For a compound of Formula (IV), each of the $R^2$ groups described herein may be combined with any $R^1$, $R^3$, $R^4$, $R^5$, $R^6$, $R^7$, $R^8$, $R^9$, $R^{9'}$, J, m, and n, or combinations thereof, as described herein. For a compound of Formula (V) or (VI), each of the $R^2$ groups described herein may be combined with any $R^1$, $R^3$, $R^4$, $R^5$, $R^6$, $R^7$, $R^8$, $R^9$, $R^{9'}$, $R^{11}$, J, Z, m, q, and r, or combinations thereof, as described herein. For a compound of Formula (VII), each of the $R^2$ groups described herein may be combined with any $R^1$, $R^3$, $R^4$, $R^5$, $R^6$, $R^7$, $R^8$, $R^9$, $R^{9'}$, J, Z, n, and m, or combinations thereof, as described herein. For a compound of Formula (VIII), each of the $R^2$ groups described herein may be combined with any $R^1$, $R^3$, $R^4$, $R^5$, $R^6$, $R^7$, $R^8$, $R^9$, $R^{9'}$, $R^{12}$, J, p, and n, or combinations thereof, as described herein.

The following description of $R^3$ groups may be used in connection with a compound of Formula (I), (II), (IV), (V), (VI), (VII), or (VIII). In some embodiments, $R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety. In some embodiments, $R^3$ is H. In some embodiments, $R^3$ is alkyl optionally substituted. In some embodiments, $R^3$ is alkyl optionally substituted with a moiety other than a halogen. In some embodiments, $R^3$ is unsubstituted alkyl. In some embodiments, $R^3$ is methyl, ethyl, n-propyl, i-propyl, n-butyl, i-butyl, or t-butyl. In some embodiments, $R^3$ is methyl. In some embodiments, $R^3$ is i-propyl. In some embodiments, $R^3$ is —CN. In some embodiments, $R^3$ is —NO$_2$. In some embodiments, $R^3$ is heteroalkyl optionally substituted. In some embodiments, $R^3$ is unsubstituted heteroalkyl. In some embodiments, $R^3$ is aryl optionally substituted. In some embodiments, $R^3$ is unsubstituted aryl. In some embodiments, $R^3$ is phenyl optionally substituted. In some embodiments, $R^3$ is unsubstituted phenyl. In some embodiments, $R^3$ is halo. In some embodiments, $R^3$ is F. In some embodiments, $R^3$ is $^{18}$F. In some embodiments, $R^3$ is Cl. In some embodiments, $R^3$ is Br. In some embodiments, $R^3$ is I. In some embodiments, $R^3$ is not halo. In some embodiments, $R^3$ is not halo, haloalkyl optionally substituted, or an imaging moiety. In some embodiments, $R^3$ is not haloalkyl optionally substituted. In some embodiments, $R^3$ is an imaging moiety. In some embodiments $R^3$ is not an imaging moiety. Each of the $R^3$ groups described herein may be combined with any $R^1$, $R^2$, $R^4$, $R^5$, $R^6$, $R^{12}$, J, Q, W, and/or m, or combinations thereof, as described herein. For a compound of Formula (I) or (II), each of the $R^3$ groups described herein may be combined with any $R^1$, $R^2$, $R^4$, $R^5$, $R^6$, $R^7$, $R^8$, $R^9$, $R^{9'}$, J, W, m, and n, or combinations thereof, as described herein. For a compound of Formula (IV), each of the $R^3$ groups described herein may be combined with any $R^1$, $R^2$, $R^4$, $R^5$, $R^6$, $R^7$, $R^8$, $R^9$, $R^{9'}$, J, m, and n, or combinations thereof, as described herein. For a compound of Formula (V) or (VI), each of the $R^3$ groups described herein may be combined with any $R^1$, $R^2$, $R^4$, $R^5$, $R^6$, $R^7$, $R^8$, $R^9$, $R^{9'}$, $R^{11}$, J, Z, m, q, and r, or combinations thereof, as described herein. For a compound of Formula (VII), each of the $R^3$ groups described herein may be combined with any $R^1$, $R^2$, $R^4$, $R^5$, $R^6$, $R^7$, $R^8$, $R^9$, $R^{9'}$, J, Z, n, and m, or combinations thereof, as described herein. For a compound of Formula (VIII), each of the $R^3$ groups described herein may be combined with any $R^1$, $R^2$, $R^4$, $R^5$, $R^6$, $R^7$, $R^8$, $R^9$, $R^{9'}$, $R^{12}$, J, p, and n, or combinations thereof, as described herein.

The following description of $R^3$ groups may be used in connection with a compound of Formula (III). In some embodiments, $R^3$ is selected from the group consisting of hydrogen, unsubstituted alkyl or alkyl optionally substituted with a moiety other than a halogen, heteroalkyl optionally substituted, alkoxy optionally substituted, alkoxyalkyl optionally substituted, aryl optionally substituted, heteroaryl optionally substituted, —CN, and —NO$_2$. In some embodiments, $R^3$ is alkyl optionally substituted with a moiety other than a halogen. In some embodiments, $R^3$ is unsubstituted alkyl. In some embodiments, $R^3$ is methyl, ethyl, n-propyl, i-propyl, n-butyl, i-butyl, or t-butyl. In some embodiments, $R^3$ is methyl. In some embodiments, $R^3$ is i-propyl. In some embodiments, $R^3$ is —CN. In some embodiments, $R^3$ is —NO$_2$. In some embodiments, $R^3$ is heteroalkyl optionally substituted. In some embodiments, $R^3$ is unsubstituted heteroalkyl. In some embodiments, $R^3$ is aryl optionally substituted. In some embodiments, $R^3$ is unsubstituted aryl. In some embodiments, $R^3$ is phenyl optionally substituted. In some embodiments, $R^3$ is unsubstituted phenyl. For a compound of Formula (III), each of the $R^3$ groups described herein may be combined with any $R^1$, $R^2$, $R^4$, $R^5$, $R^6$, $R^7$, $R^8$, $R^9$, $R^{9'}$, J, Q, and n, or combinations thereof, as described herein.

The following description of $R^4$ and $R^5$ groups may be used in connection with a compound of Formula (I), (II), (III), (IV), (V), (VI), (VII), or (VIII). In some embodiments, $R^4$ and $R^5$ are each independently selected from the group consisting of hydrogen, alkyl optionally substituted, and an imaging moiety, or optionally any two of $R^4$ and $R^5$ are joined together to form a ring. In some embodiments, any two of $R^4$ and $R^5$ may be joined together to form a ring. In some cases, the ring formed may comprise a total of 4, 5, 6, 7, 8, or more, atoms. In some cases, the ring comprises 5 or 6 atoms. In some embodiments, each of $R^4$ and $R^5$ is H. In some embodiments, at least one $R^4$ and $R^5$ is $^2$H. In some embodiments, each of $R^4$ and $R^5$ is $^2$H. In some embodiments, each of $R^4$ and $R^5$ is H or alkyl optionally substituted. In some embodiments, each of $R^4$ and $R^5$ is H or unsubstituted alkyl. In some embodiments, at least one $R^4$ or $R^5$ is not H. For a compound of Formula (I) or (II), each of the $R^4$ and/or $R^5$ groups described herein may be combined with any $R^1$, $R^2$, $R^3$, $R^6$, $R^7$, $R^8$, $R^9$, $R^{9'}$, J, W, m, and n, or combinations thereof, as described herein. For a compound of Formula (III), each of the $R^4$ and/or $R^5$ groups described herein may be combined with any $R^1$, $R^2$, $R^3$, $R^6$, $R^7$, $R^8$, $R^9$, $R^{9'}$, J, Q, and n, or combinations thereof, as described herein. For a compound of Formula (IV), each of the $R^4$ and/or $R^5$ groups described herein may be combined with any $R^1$, $R^2$, $R^3$, $R^6$, $R^7$, $R^8$, $R^9$, $R^{9'}$, J, m, and n, or combinations thereof, as described herein. For a compound of Formula (V) or (VI), each of the $R^4$ and/or $R^5$ groups described herein may be combined with any $R^1$, $R^2$, $R^3$, $R^6$, $R^7$, $R^8$, $R^9$, $R^{9'}$, $R^{11}$, J, Z, m, q, and r, or combinations thereof, as described herein. For a compound of Formula (VII), each of the $R^4$ and/or $R^5$ groups described herein may be combined with any $R^1$, $R^2$, $R^3$, $R^6$, $R^7$, $R^8$, $R^9$, $R^{9'}$, J, Z, n, and m, or combinations thereof, as described herein. For a compound of Formula (VIII), each of the $R^4$ and/or $R^5$ groups described herein may be combined with any $R^1$, $R^2$, $R^3$, $R^6$, $R^7$, $R^8$, $R^9$, $R^{9'}$, $R^{12}$, J, p, and n, or combinations thereof, as described herein.

The following description of $R^4$, $R^5$, and $R^{11}$ groups may be used in connection with a compound of Formula (VI). In some embodiments, $R^4$, $R^5$, and $R^{11}$ are each independently selected from the group consisting of hydrogen, alkyl optionally substituted, and an imaging moiety, or optionally any two of $R^4$, $R^5$, and $R^{11}$ are joined together to form a ring. In some embodiments, any two of $R^4$, $R^5$, and $R^1$ may be joined together to form a ring. In some cases, the ring formed may comprise a total of 4, 5, 6, 7, 8, or more, atoms. In some cases, the ring comprises 5 or 6 atoms. In some embodiments, each of $R^4$, $R^5$, and $R^{11}$ is H. In some embodiments, at least one $R^4$, $R^5$, and $R^{11}$ is $^2$H. In some embodiments, each of $R^4$, $R^5$, and $R^{11}$ is $^2$H. In some embodiments, each of $R^4$, $R^5$, and $R^{11}$ is H or alkyl optionally substituted. In some embodiments, each of $R^4$, $R^5$, and $R^{11}$ is H or unsubstituted alkyl. In some embodiments, at least one $R^4$, $R^5$, and $R^{11}$ is not H. For a compound of Formula (VI), each of the $R^4$, $R^5$, and/or $R^{11}$ groups described herein may be combined with any $R^1$, $R^2$, $R^3$, $R^6$, $R^7$, $R^8$, $R^9$, $R^{9'}$, J, Z, m, q, and r, or combinations thereof, as described herein.

The following description of $R^{12}$ groups may be used in connection with a compound of Formula (VIII). In some embodiments, $R^{12}$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$, wherein each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring; and each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety. In some embodiments, any two of $R^7$ may be joined together to form a ring. In some cases, the ring formed may comprise a total of 4, 5, 6, 7, 8, or more, atoms. In some cases, the ring comprises 5 or 6 atoms. In some embodiments, $R^{12}$ is alkynyl optionally substituted. In some embodiments, $R^{12}$ is unsubstituted alkynyl. In some embodiments, $R^{12}$ is alkenyl optionally substituted. In some embodiments, $R^{12}$ is unsubstituted alkenyl. In some embodiments, $R^{12}$ is alkyl substituted with —C(=O)OR$^8$. In some embodiments, $R^{12}$ is alkyl substituted with —C(=O)R$^8$. In some embodiments, $R^{12}$ is alkyl substituted with —N(R$^7$)$_2$. In some embodiments, $R^{12}$ is —CN. In some embodiments, $R^{12}$ is —NO$_2$. In some embodiments, $R^{12}$ is —N(R$^7$)$_2$. In some embodiments, $R^{12}$ is —C(=O)OR$^8$. In some embodiments, $R^{12}$ is —OC(=O)R$^8$. In some embodiments, $R^{12}$ is —C(=O)R$^8$. In some embodiments, $R^{12}$ is —C(=O)N(R$^7$)$_2$. In some embodiments, $R^{12}$ is —N(R$^7$)C(=O)R$^8$. In some embodiments, $R^{12}$ is —NO$_2$, —C(=O)(CH$_2$)$_u$I$_m$, —C(=O)O(CH$_2$)$_u$I$_m$, —C≡C(CH$_2$)$_u$I$_m$, or —Si(alkyl)$_2$I$_m$, wherein I$_m$ is an imaging moiety and u is 1, 2, 3, 4, 5, or 6. For a compound of Formula (VIII), each of the $R^{12}$ groups described herein may be combined with any $R^1$, $R^2$, $R^3$, $R^4$, $R^5$, $R^6$, $R^7$, $R^8$, $R^9$, $R^{9'}$, J, p, and n, or combinations thereof, as described herein.

The following description of J groups may be used in connection with a compound of Formula (I), (II), (III), (IV), (V), (VI), (VII), or (VIII). In some embodiments, J is selected from the group consisting of N(R$^7$), S, O, C(=O), C(=O)O, OC(=O), C(=O)N(R$^7$), N(R$^7$)C(=O), CH$_2$O, and a bond, wherein each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring. In some embodiments, any two of $R^7$ may be joined together to form a ring. In some cases, the ring formed may comprise a total of 4, 5, 6, 7, 8, or more, atoms. In some cases, the ring comprises 5 or 6 atoms. In some embodiments, J is a bond. In some embodiments, J is O. In some embodiments, J is S. In some embodiments, J is N(R$^7$). In some embodiments, J is C(=O). In some embodiments, J is C(=O)O. In some embodiments, J is OC(=O). In some embodiments, J is —CH$_2$O. In some embodiments, J is N(R$^7$) or C(=O)N(R$^7$) and any two $R^7$ are joined together to form a ring. In some cases, the ring formed may comprise a total of 4, 5, 6, 7, 8, or more, atoms. In some cases, the ring comprises 5 or 6 atoms. For a compound of Formula (I) or (II), each of the J groups described herein may be combined with any $R^1$, $R^2$, $R^3$, $R^4$, $R^5$, $R^6$, $R^7$, $R^8$, $R^9$, $R^{9'}$, W, m, and n, or combinations thereof, as described herein. For a compound of Formula (III), each of the J groups described herein may be combined with any $R^1$, $R^2$, $R^3$, $R^4$, $R^5$, $R^6$, $R^7$, $R^8$, $R^9$, $R^{9'}$, Q, and n, or combinations thereof, as described herein. For a compound of Formula (IV), each of the J groups described herein may be combined with any $R^1$, $R^2$, $R^3$, $R^4$, $R^5$, $R^6$, $R^7$, $R^8$, $R^9$, $R^{9'}$, m, and n, or combinations thereof, as described herein. For a compound of Formula (V) or (VI), each of the J groups described herein may be combined with any $R^1$, $R^2$, $R^3$, $R^4$, $R^5$, $R^6$, $R^7$, $R^8$, $R^9$, $R^{9'}$, R$^{11}$, Z, m, q, and r, or combinations thereof, as described herein. For a compound of Formula (VIII), each of the J groups described herein may be combined with any $R^1$, $R^2$, $R^3$, $R^4$, $R^5$, $R^6$, $R^7$, $R^8$, $R^9$, $R^{9'}$, R$^{12}$, p, and n, or combinations thereof, as described herein.

The following description of J and n groups may be used in connection with a compound of Formula (I), (II), (III), (IV), or (VIII). In some embodiments, n is 0. In some embodiments, n is 1. In some embodiments, n is 2. In some embodiments, n is 3. In some embodiments, J is O and n is 0. In some embodiments, J is O, and n is 1. In some embodiments, J is O, and n is 2. In some embodiments, J is O and n is 3. In some embodiments, J is S and n is 0. In some embodiments, J is S, and n is 1. In some embodiments, J is S, and n is 2. In some embodiments, J is S and n is 3. Each of the J groups and/or n groups described herein may be combined with any $R^1$, $R^2$, $R^3$, $R^4$, $R^5$, $R^6$, $R^{12}$, Q, W, and/or m, or combinations thereof, as described herein. For a compound of Formula (I) or (II), each of the J and/or n groups described herein may be combined with any $R^1$, $R^2$, $R^3$, $R^4$, $R^5$, $R^6$, $R^7$, $R^8$, $R^9$, $R^{9'}$, W, and m, or combinations thereof, as described herein. For a compound of Formula (III), each of the J and/or n groups described herein may be combined with any $R^1$, $R^2$, $R^3$, $R^4$, $R^5$, $R^6$, $R^7$, $R^8$, $R^9$, $R^{9'}$, and Q, or combinations thereof, as described herein. For a compound of Formula (IV), each of the J and/or n groups described herein may be combined with any $R^1$, $R^2$, $R^3$, $R^4$, $R^5$, $R^6$, $R^7$, $R^8$, $R^9$, $R^{9'}$, and m, or combinations thereof, as described herein. For a compound of Formula (VIII), each of the J and/or n groups described herein may be combined with any $R^1$, $R^2$, $R^3$, $R^4$, $R^5$, $R^6$, $R^7$, $R^8$, $R^9$, $R^{9'}$, $R^{12}$, and p, or combinations thereof, as described herein.

The following description of J, q, and/or r groups may be used in connection with a compound of Formula (V) or (VI). In some embodiments, q is 0. In some embodiments, q is 1. In some embodiments, q is 2. In some embodiments, q is 3. In some embodiments, r is 0. In some embodiments, r is 1. In some embodiments, r is 2. In some embodiments, r is 3. In some embodiments, q and r are each 0. In some embodiments, q and r are each 1. In some embodiments, J is O and q and r are each 0. In some embodiments, J is O and q and r are each 1. In some embodiments, J is O and q and r are each 2. In some embodiments, J is O and q and r are each 3. In some embodiments, J is S and q and r are each 0. In some embodiments, J is S and q and r are each 1. In some embodiments, J is S and q and r are each 2. In some embodiments, J is S and q and r are each 3. In some embodiments, J is O, q is 0, and r is 0, 1, 2, or 3. In some embodiments, J is O, q is 1, and r is 0, 1, 2, or 3. In some embodiments, J is O, q is 2, and r is 0, 1, 2, or 3. In some embodiments, J is O, q is 3, and r is 0, 1, 2, or 3. For a compound of Formula (V) or (VI), each of the J, q, and/or r groups described herein may be combined with any $R^1$, $R^2$, $R^3$, $R^4$, $R^5$, $R^6$, $R^7$, $R^8$, $R^9$, $R^{9'}$, R11, Z, and m, or combinations thereof, as described herein.

The following description of J and n groups may be used in connection with a compound of Formula (VII). In some embodiments, n is 1. In some embodiments, n is 2. In some embodiments, n is 3. In some embodiments, J is O, and n is 1. In some embodiments, J is O, and n is 2. In some embodiments, J is O and n is 3. In some embodiments, J is S, and n is 1. In some embodiments, J is S, and n is 2. In some embodiments, J is S and n is 3. For a compound of Formula (VII), each of the J and/or n groups described herein may be combined with any $R^1$, $R^2$, $R^3$, $R^4$, $R^5$, $R^6$, $R^7$, $R^8$, $R^9$, $R^{9'}$, Z, and m, or combinations thereof, as described herein.

In some embodiments, for a compound of Formula (I), (II), (III), (IV), (V), (VI), (VII) or (VIII), the compound comprises a single imaging moiety. In some embodiments, for a compound of Formula (I), (II), (III), (IV) or (VII), the at least one imaging moiety is present in $R^1$, $R^2$, $R^3$, $R^4$, $R^5$, $R^6$, $R^7$, $R^8$, or $R^9$. In some embodiments, for a compound of Formula (VIII), the at least one imaging moiety is present in $R^1$, $R^3$, $R^4$, $R^5$, $R^6$, $R^7$, $R^8$, $R^9$ or $R^{12}$. In some embodiments, for a compound of Formula (V) or (VI), the at least one imaging moiety is present in $R^1$, $R^2$, $R^3$, $R^4$, $R^5$, $R^6$, $R^7$, $R^8$, $R^9$ or $R^{11}$. In some embodiments, for a compound of Formula (I), (II), (III), (IV), (V), (VI), (VII) or (VIII), the at least one imaging moiety is present in $R^1$, $R^2$, $R^3$, $R^4$, $R^5$, or $R^6$. In some embodiments, for a compound of Formula (I), (II), (III), (IV), (V), (VI), (VII), or (VIII), the at least one imaging moiety is present in $R^6$. As will be understood by those of ordinary skill in the art, when referring to an imaging moiety, the imaging moiety "is present" in a group in embodiments wherein 1) the imaging moiety is the group (e.g., $R^6$ is an imaging moiety) or b) the group comprises the imaging moiety (e.g., $R^6$ is substituted with an imaging moiety). In some embodiments, for a compound of Formula (I), (II), (III), (IV), (V), (VI) or (VII), $R^1$, $R^2$, $R^3$, $R^4$, $R^5$, or $R^6$ comprises the at least one imaging moiety. In some embodiments, for a compound of Formula (VIII), $R^1$, $R^2$, $R^3$, $R^4$, $R^5$, $R^6$, or $R^{12}$ comprises the at least one imaging moiety. In some embodiments, for a compound of Formula (I), (II), (III), (IV), (V), (VI), (VII), or (VIII), at least one $R^6$ is substituted with the at least one imaging moiety. In some embodiments, for a compound of Formula (I), (II), (IV), or (VII), $R^1$, $R^2$, $R^3$, $R^4$, $R^5$, or $R^6$ is the at least one imaging moiety. In some embodiments, for a compound of Formula (III), $R^1$, $R^2$, $R^4$, $R^5$, or $R^6$ is the at least one imaging moiety. In some embodiments, for a compound of Formula (V) or (VI), $R^1$, $R^2$, $R^3$, $R^4$, $R^5$, $R^6$, or $R^1$ is the at least one imaging moiety. In some embodiments, for a compound of Formula (VIII), $R^1$, $R^3$, $R^4$, $R^5$, $R^6$, or $R^{12}$ is the at least one imaging moiety. In some embodiments, for a compound of Formula (I), (II), (IV), or (VII), $R^1$, $R^2$, $R^3$, $R^4$, $R^5$, or $R^6$ is not an imaging moiety. In some embodiments, for a compound of Formula (III), $R^1$, $R^2$, $R^4$, $R^5$, or $R^6$ is not an imaging moiety. In some embodiments, for a compound of Formula (V) or (VI), $R^1$, $R^2$, $R^3$, $R^4$, $R^5$, $R^6$, or $R^1$ is not an imaging moiety. In some embodiments, for a compound of Formula (VIII), $R^1$, $R^3$, $R^4$, $R^5$, $R^6$, or $R^{12}$ is not an imaging moiety. In some embodiments, for a compound of Formula (I), (II), (III), (IV), (V), (VI), (VII), or (VIII), at least one $R^6$ is an imaging moiety. For a compound of Formula (I) or (II), each of the placements of the imaging moieties described herein may be combined with any $R^1$, $R^2$, $R^3$, $R^4$, $R^5$, $R^6$, $R^7$, $R^8$, $R^9$, $R^{9'}$, J, W, m, and n, or combinations thereof, as described herein. For a compound of Formula (III), each of the placements of the imaging moieties described herein may be combined with any $R^1$, $R^2$, $R^3$, $R^4$, $R^5$, $R^6$, $R^7$, $R^8$, $R^9$, $R^{9'}$, Q, J, and n, or combinations thereof, as described herein. For a compound of Formula (IV), each of the placements of the imaging moieties described herein may be combined with any $R^1$, $R^2$, $R^3$, $R^4$, $R^5$, $R^6$, $R^7$, $R^8$, $R^9$, $R^{9'}$, J, n, and m, or combinations thereof, as described herein. For a compound of Formula (V) or (VI), each of the placements of the imaging moieties described herein may be combined with any $R^1$, $R^2$, $R^3$, $R^4$, $R^5$, $R^6$, $R^7$, $R^8$, $R^9$, $R^{9'}$, R11, J, Z, m, q, and r, or combinations thereof, as described herein. For a compound of Formula (VII), each of the placements of the imaging moieties described herein may be combined with any $R^1$, $R^2$, $R^3$, $R^4$, $R^5$, $R^6$, $R^7$, $R^8$, $R^9$, $R^{9'}$, J, Z, n, and m, or combinations thereof, as described herein.

For a compound of Formula (VIII), each of the placements of the imaging moieties described herein may be combined with any $R^1$, $R^2$, $R^3$, $R^4$, $R^5$, $R^6$, $R^7$, $R^8$, $R^9$, $R^{9'}$, R12, J, p, and n, or combinations thereof, as described herein.

The following description of the imaging moiety may be used in connection with a compound of Formula (I), (II), (III), (IV), (V), (VI), (VII), or (VIII). In some embodiments, the at least one imaging moiety is selected from the group consisting of $^{11}C$, $^{13}N$, $^{18}F$, $^{76}Br$, $^{89}Zr$, $^{123}I$, $^{124}I$, $^{125}I$, $^{131}I$, $^{99m}Tc$, $^{95}Tc$, $^{111}In$, $^{62}Cu$, $^{64}Cu$, $^{67}Ga$, and $^{68}Ga$. In some embodiments, the at least one imaging moiety is $^{18}F$. Imaging moieties are described in more detail herein.

The following description of $R^6$ groups may be used in connection with a compound of Formula (I), (II), (III), (IV), (V), (VI), (VII), or (VIII). In some embodiments, for a compound of Formula (I), (II), (III), (IV), (V), (VI), (VII), or (VIII), all but one $R^6$ is H. That is, all $R^6$ are H and one $R^6$ is not H. In some cases, the one $R^6$ which is not H is substituted with the at least one imaging moiety. In some cases, the one $R^6$ which is not H is the at least one imaging moiety. In some embodiments, for a compound of Formula (I), (II), (III), (IV), (V), (VI), (VII), or (VIII), at least one $R^6$ is alkyl optionally substituted, alkoxy optionally substituted, or alkoxyalkyl optionally substituted, each substituted with an imaging moiety. In some embodiments, for a compound of Formula (I), (II), (III), (IV), (V), (VI), (VII), or (VIII), at least one $R^6$ is —$(CH_2)_j I_m$; wherein $I_m$ is an imaging moiety and j is 1, 2, 3, 4, 5, or 6. In some cases, at least one $R^6$ is —$(CH_2)I_m$, —$(CH_2)_2 I_m$, —$(CH_2)_3 I_m$, —$(CH_2)_4 I_m$, —$(CH_2)_5 I_m$, —$(CH_2)_6 I_m$, —$(CH_2)_7 I_m$, —$(CH_2)_8 I_m$, —$(CH_2)_9 I_m$, or —$(CH_2)_{10} I_m$. In some cases, at least one $R^6$ is —$(CH_2)^{18}F$, —$(CH_2)_2 {}^{18}F$, —$(CH_2)_3 {}^{18}F$, —$(CH_2)_4 {}^{18}F$, —$(CH_2)_5 {}^{18}F$, —$(CH_2)_6 {}^{18}F$, —$(CH_2)_7 {}^{18}F$, —$(CH_2)_8 {}^{18}F$, —$(CH_2)_9 {}^{18}F$, or —$(CH_2)_{10} {}^{18}F$. In some embodiments, at least one $R^6$ is —$O(CH_2)_j I_m$; wherein $I_m$ is an imaging moiety and j is 1, 2, 3, 4, 5, or 6. In some cases, at least one $R^6$ is —$O(CH_2)_5 I_m$, —$O(CH_2)_6 I_m$, —$O(CH_2)_7 I_m$, —$O(CH_2)_8 I_m$, —$O(CH_2)_9 I_m$, or —$O(CH_2)_{10} I_m$. In some cases, at least one $R^6$ is —$O(CH_2)^{18}F$, —$O(CH_2)_2 {}^{18}F$, —$O(CH_2)_3 {}^{18}F$, —$O(CH_2)_4 {}^{18}F$, —$O(CH_2)_5 {}^{18}F$, —$O(CH_2)_6 {}^{18}F$, —$O(CH_2)_7 {}^{18}F$, —$O(CH_2)_8 {}^{18}F$, —$O(CH_2)_9 {}^{18}F$, or —$O(CH_2)_{10} {}^{18}F$. In some embodiments, at least one $R^6$ is —$(CH_2)_j O(CH_2)_j I_m$; wherein $I_m$ is an imaging moiety and each j is independently 1, 2, 3, 4, 5, or 6. In some embodiments, at least one $R^6$ is —$(CH_2) O(CH_2)_j I_m$; wherein $I_m$ is an imaging moiety and each j is independently 1, 2, 3, 4, 5, or 6. In some cases, at least one $R^6$ is —$CH_2 O(CH_2) I_m$, —$CH_2 O(CH_2)_2 I_m$, —$CH_2 O(CH_2)_3 I_m$, —$CH_2 O(CH_2)_4 I_m$, —$CH_2 O(CH_2)_5 I_m$, —$CH_2 O(CH_2)_6 I_m$, —$CH_2 O(CH_2)_7 I_m$, —$CH_2 O(CH_2)_8 I_m$, —$CH_2 O(CH_2)_9 I_m$, or —$CH_2 O(CH_2)_{10} I_m$. In some cases, at least one $R^6$ is —$CH_2 O(CH_2)^{18}F$, —$CH_2 O(CH_2)_2 {}^{18}F$, —$CH_2 O(CH_2)_3 {}^{18}F$, —$CH_2 O(CH_2)_4 {}^{18}F$, —$CH_2 O(CH_2)_5 {}^{18}F$, —$CH_2 O(CH_2)_6 {}^{18}F$, —$CH_2 O(CH_2)_7 {}^{18}F$, —$CH_2 O(CH_2)_8 {}^{18}F$, —$CH_2 O(CH_2)_9 {}^{18}F$, or —$CH_2 O(CH_2)_{10} {}^{18}F$. In some embodiments, at least one $R^6$ is —C≡C—$(CH_2)_j I_m$; wherein $I_m$ is an imaging moiety and j is 1, 2, 3, 4, 5, or 6. In some embodiments, at least one $R^6$ is —$[(CH_2)_j O]_j (CH_2)_j I_m$; wherein $I_m$ is an imaging moiety and each j is independently 1, 2, 3, 4, 5, or 6. In some embodiments, at least one $R^6$ is —$O[(CH_2)_j O]_j (CH_2)_j I_m$; wherein $I_m$ is an imaging moiety and each j is independently 1, 2, 3, 4, 5, or 6. In some embodiments, at least one $R^6$ is optionally substituted alkyl substituted with an imaging moiety. In some embodiments, at least one $R^6$ is —C(=O)O(CH$_2$)$_j$I$_m$; wherein I$_m$ is an imaging moiety and j is 1, 2, 3, 4, 5, or 6. In some embodiments, at least one $R^6$ is —C(=O)(CH$_2$)$_j$I$_m$; wherein I$_m$ is an imaging moiety and j is 1, 2, 3, 4, 5, or 6. In some embodiments, at least one $R^6$ is —(CH$_2$)$_j$NH(CH$_2$)$_j$I$_m$; wherein I$_m$ is an imaging moiety and each j is independently 1, 2, 3, 4, 5, or 6. In some embodiments, at least one $R^6$ is Si(R$^9$)$_2$ I$_m$, wherein each $R^9$ is alkyl optionally substituted and wherein I$_m$ is an imaging moiety. In some embodiments, at least one $R^6$ is B(R$^{9'}$)$_2$ In, wherein each $R^{9'}$ is alkyl optionally substituted and wherein I$_m$ is an imaging moiety. In some embodiments, at least one $R^6$ is selected from the group consisting of —C≡C—CH$_2$CH$_2$CH$_2$I$_m$, —C≡C—CH$_2$CH$_2$I$_m$, —C≡C—CH$_2$I$_m$, —CH$_2$I$_m$, —(CH$_2$)$_2$I$_m$, —(CH$_2$)$_3$I$_m$, —(CH$_2$)$_4$I$_m$, —(CH$_2$)$_5$I$_m$, —(CH$_2$)$_6$I$_m$, —OCH$_2$I$_m$, —O(CH$_2$)$_2$I$_m$, —O(CH$_2$)$_3$I$_m$, —O(CH$_2$)$_4$I$_m$, —O(CH$_2$)$_5$I$_m$, —O(CH$_2$)$_6$I$_m$, —CH$_2$O(CH$_2$)$_2$I$_m$, —CH(CH$_3$)O(CH$_2$)$_2$I$_m$, —CH$_2$O(CH$_2$)$_3$I$_m$, —CD$_2$O(CH$_2$)$_2$I$_m$, —(CH$_2$)$_2$O(CH$_2$)$_2$I$_m$, —CHBrC(CH$_3$)$_2$I$_m$, —CHClC(CH$_3$)$_2$I$_m$, —CHFC(CH$_3$)$_2$I$_m$, —C(=O)OCH$_2$I$_m$, —C(=O)O(CH$_2$)$_2$I$_m$, —C(=O)O(CH$_2$)$_3$I$_m$, —CH$_2$NH(CH$_2$)$_2$I$_m$, —CH$_2$NHCH$_2$I$_m$, —CH$_2$O(CH$_2$)$_2$O(CH$_2$)$_2$I$_m$, —CH$_2$O(CH$_2$)$_2$O(CH$_2$)$_2$I$_m$, —O(CH$_2$)$_2$O(CH$_2$)$_2$I$_m$, —C(=O)(CH$_2$)$_2$I$_m$, and —C(=O)(CH$_2$)$_3$I$_m$. In some embodiments, I$_m$ is $^{18}$F. In some embodiments, at least one $R^6$ is selected from the group consisting of:

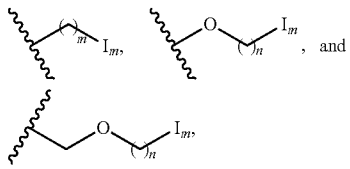

wherein m and n is an integer between 1 and 6, inclusive, and I$_m$ is an imaging moiety. In some embodiments, at least one $R^6$ is selected from the group consisting of:

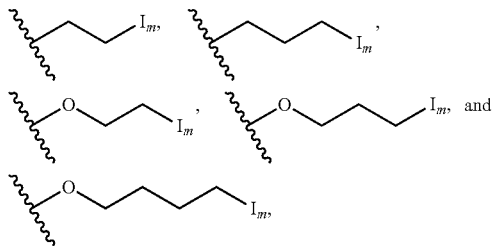

wherein I$_m$ is an imaging moiety. In some embodiments, at least one $R^6$ is selected from the group consisting of:

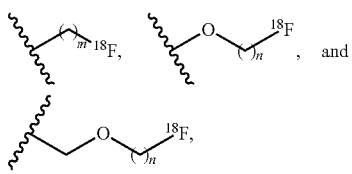

wherein m and n is an integer between 1 and 6, inclusive. In some embodiments, at least one $R^6$ is selected from the group consisting of:

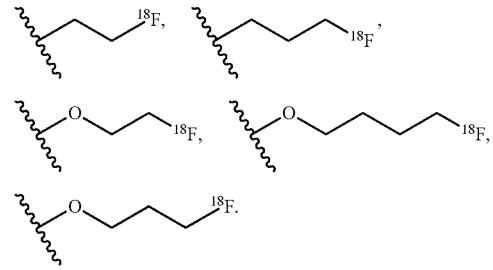

In some embodiments, for a compound of Formula (I), (II), (III), (IV), (V), (VI), (VII), or (VIII), at least one $R^6$ is optionally substituted with at least one $^2$H. In some embodiments, at least one $R^6$ is Si(R$^9$)$_3$. In some embodiments, at least one $R^6$ is B(R$^{9'}$)$_3$. In some embodiments, at least one $R^6$ is —NO$_2$. In some embodiments, at least one $R^6$ is halo. In some embodiments, at least one $R^6$ is Cl. In some embodiments, at least one $R^6$ is Br. In some embodiments, at least one $R^6$ is F. For a compound of Formula (I) or (II), each of the $R^6$ groups described herein may be combined with any $R^1$, $R^2$, $R^3$, $R^4$, $R^5$, $R^7$, $R^8$, $R^9$, $R^{9'}$, J, W, m, and n, or combinations thereof, as described herein. For a compound of Formula (III), each of the $R^6$ groups described herein may be combined with any $R^1$, $R^2$, $R^3$, $R^4$, $R^5$, $R^7$, $R^8$, $R^9$, $R^{9'}$, Q, J, and n, or combinations thereof, as described herein. For a compound of Formula (IV), each of the $R^6$ groups described herein may be combined with any $R^1$, $R^2$, $R^3$, $R^4$, $R^5$, $R^7$, $R^8$, $R^9$, $R^{9'}$, J, m, and n, or combinations thereof, as described herein. For a compound of Formula (V) or (VI), each of the $R^6$ groups described herein may be combined with any $R^1$, $R^2$, $R^3$, $R^4$, $R^5$, $R^7$, $R^8$, $R^9$, $R^{9'}$, $R^1$, J, Z, m, q, and r, or combinations thereof, as described herein. For a compound of Formula (VII), each of the $R^6$ groups described herein may be combined with any $R^1$, $R^2$, $R^3$, $R^4$, $R^5$, $R^7$, $R^8$, $R^9$, $R^{9'}$, J, Z, n, and m, or combinations thereof, as described herein. For a compound of Formula (VIII), each of the $R^6$ groups described herein may be combined with any $R^1$, $R^2$, $R^3$, $R^4$, $R^5$, $R^7$, $R^8$, $R^9$, $R^{9'}$, $R^{12}$, J, p, and n, or combinations thereof, as described herein.

In some embodiments, a compound of Formula (II) is selected from the group consisting of:

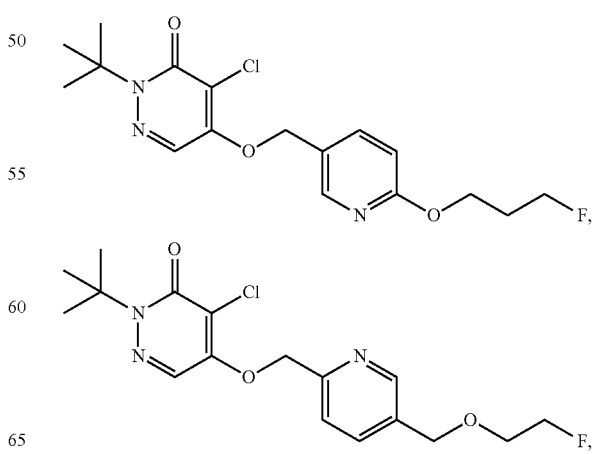

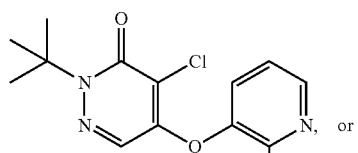

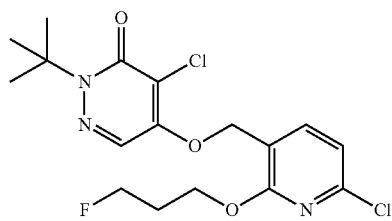

or a pharmaceutically acceptable salt thereof, wherein F is optionally $^{18}$F. In some embodiments, a compound of Formula (IV) is of the formula:

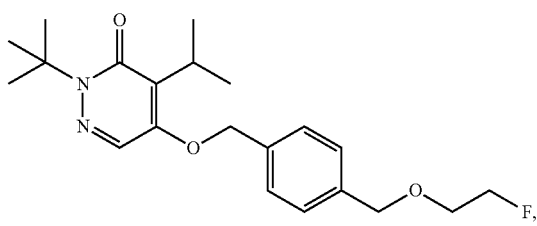 [SMILES: CC(C)c1c(OCc2ccc(COCCF)cc2)cnn(C(C)(C)C)c1=O]

or a pharmaceutically acceptable salt thereof, wherein F is optionally $^{18}$F. In some embodiments, a compound of Formula (VIII) is of the formula:

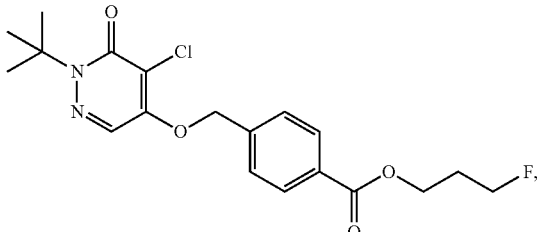

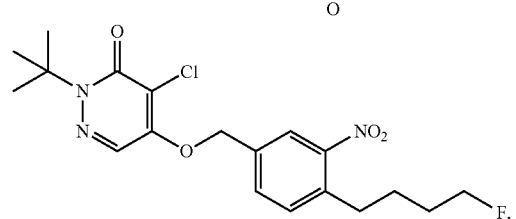

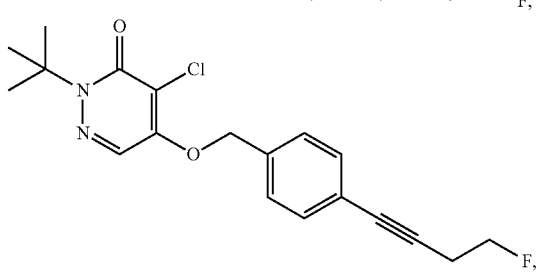

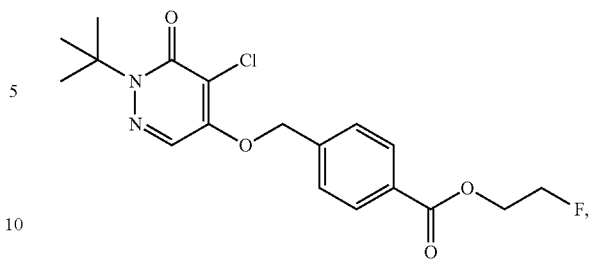

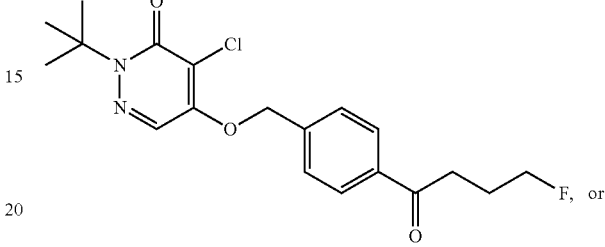

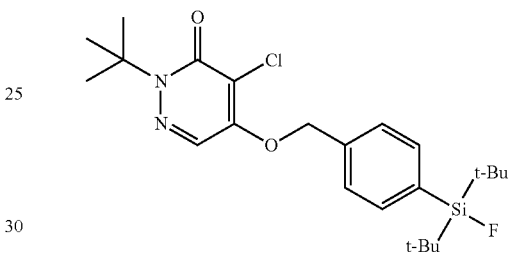

or a pharmaceutically acceptable salt thereof, wherein F is optionally $^{18}$F. In some embodiments, a compound of Formula (V) or (VI) is selected from the group consisting of:

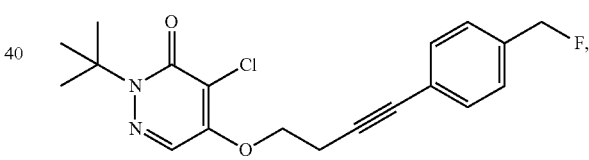

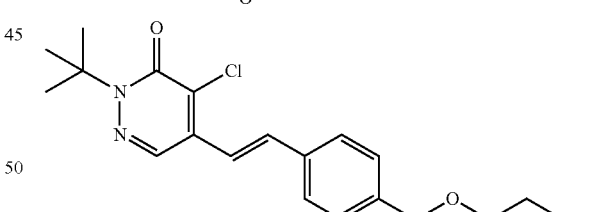

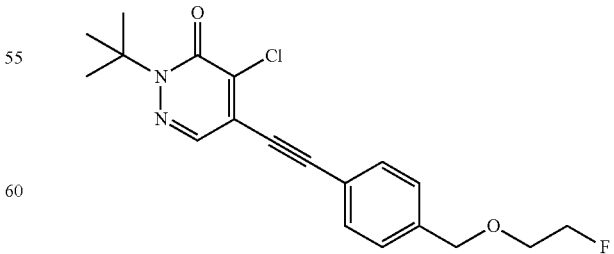

or a pharmaceutically acceptable salt thereof, wherein F is optionally $^{18}$F. In some embodiments, a compound of Formula (VII) is of the formula:

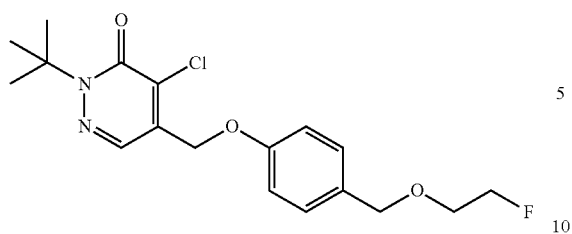
or a pharmaceutically acceptable salt thereof, wherein F is optionally $^{18}$F.
In some embodiments, the compound is selected from the group consisting of:
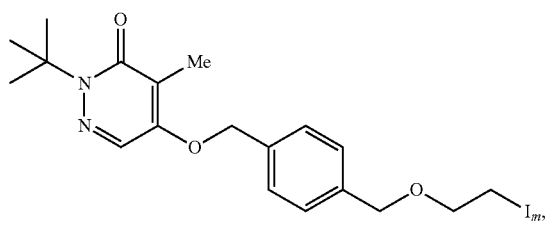
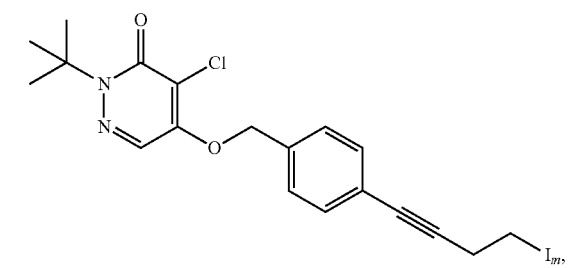
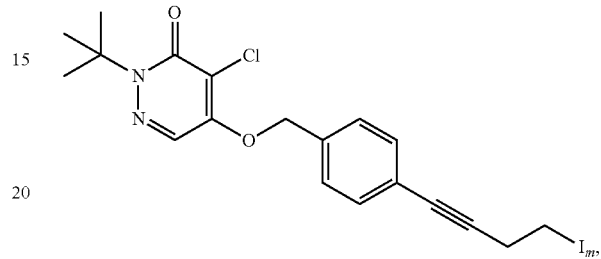
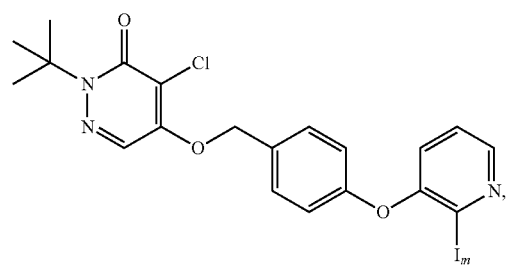
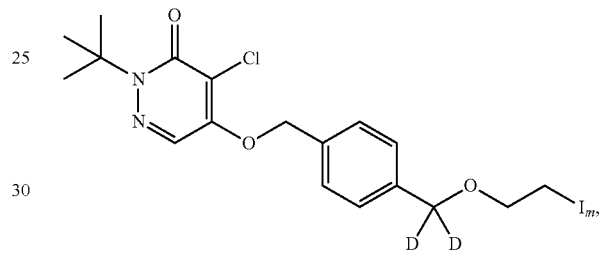
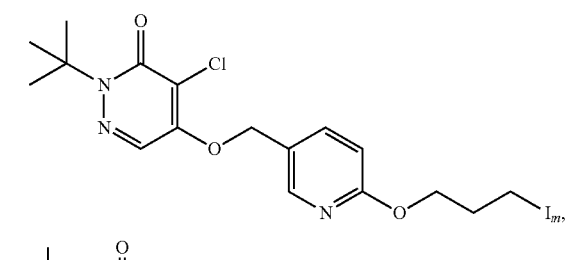
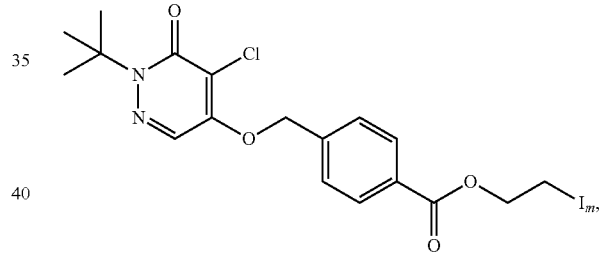
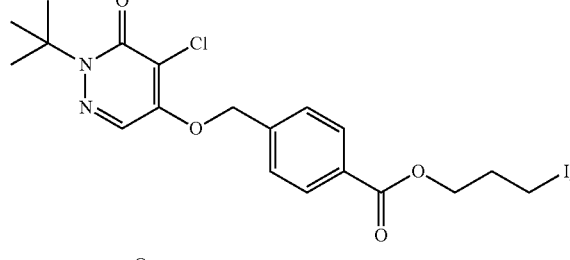
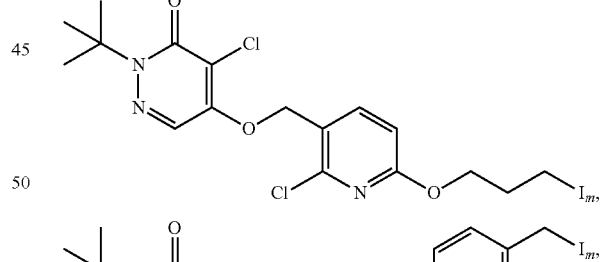
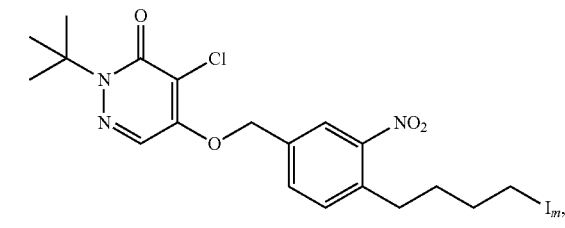
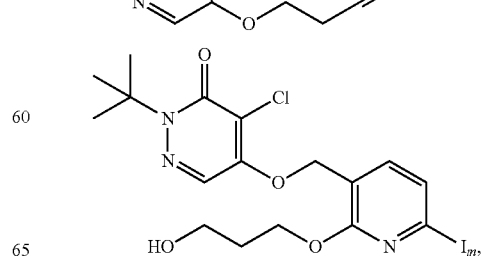

-continued
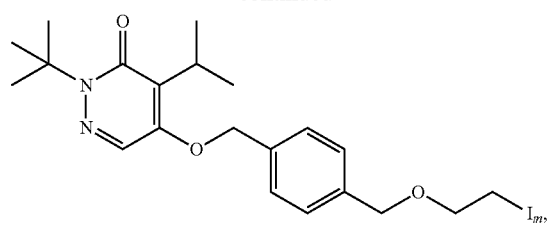
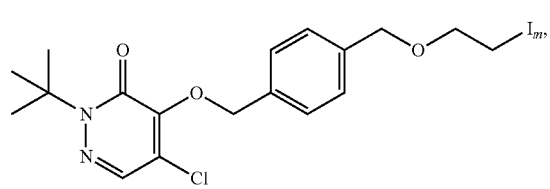
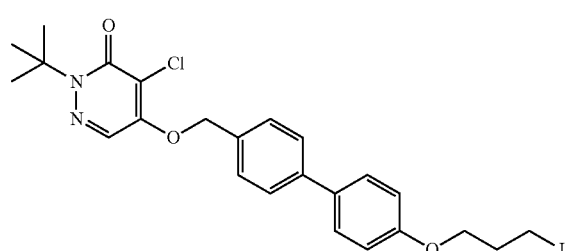
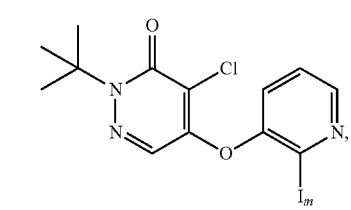
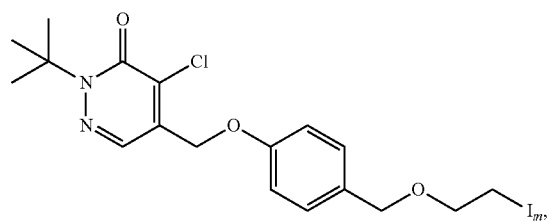
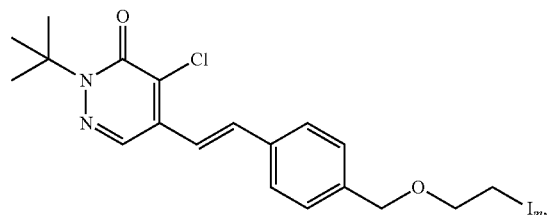
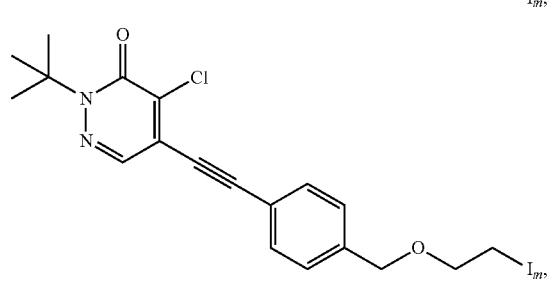
-continued
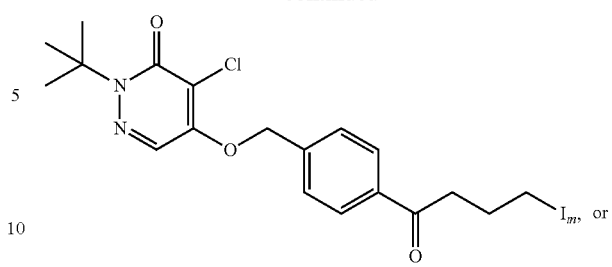
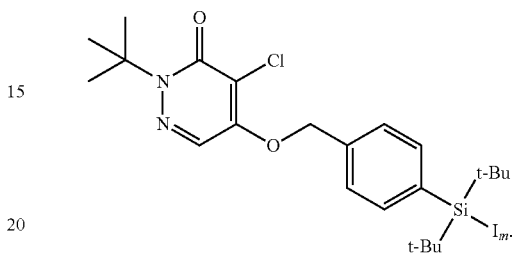
or a pharmaceutically acceptable salt thereof, wherein $I_m$ is an imaging moiety. In some embodiments, the $I_m$ is $^{18}F$. In some embodiments, the compound is selected from the group consisting of:
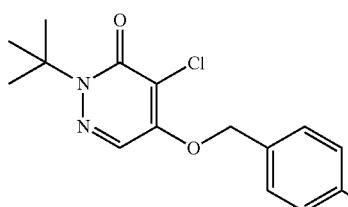
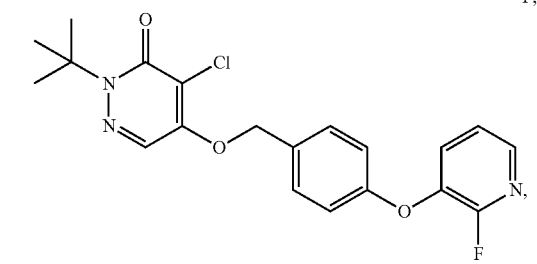
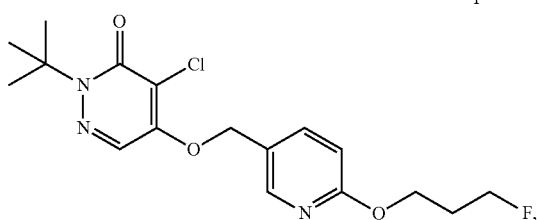
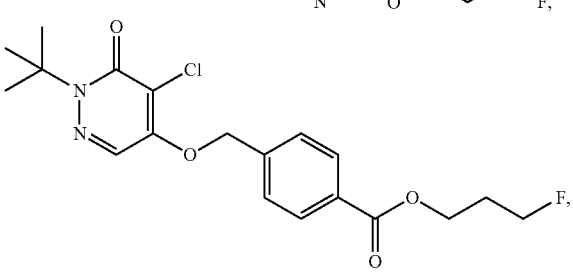

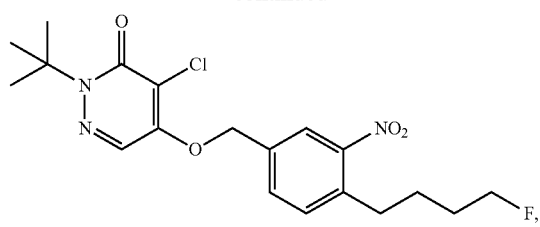
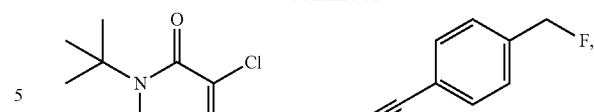
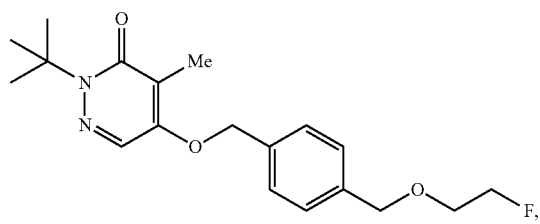
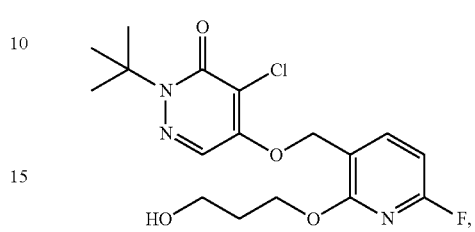
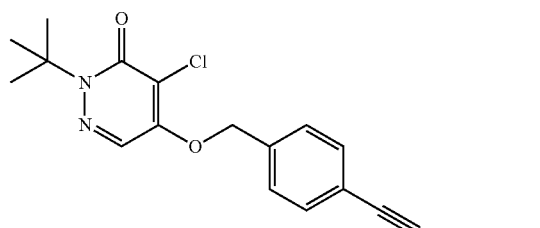
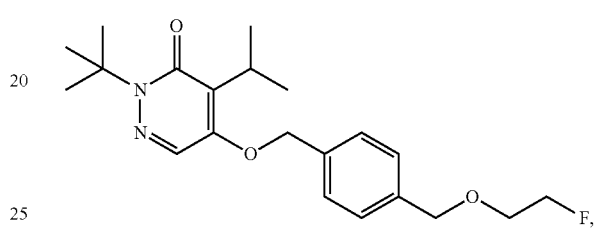
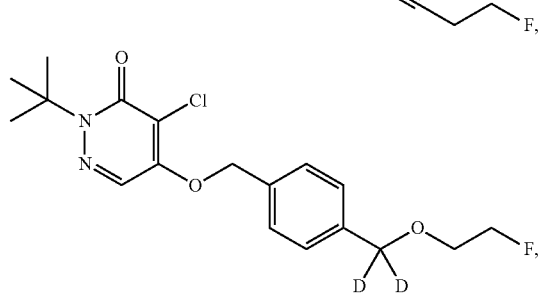
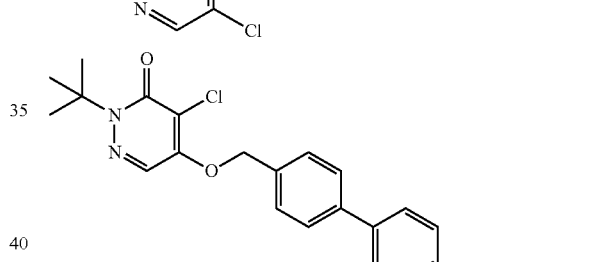
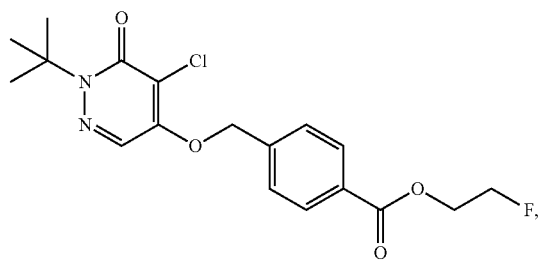
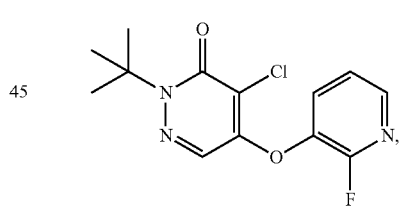
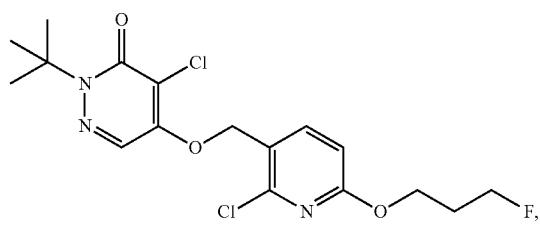
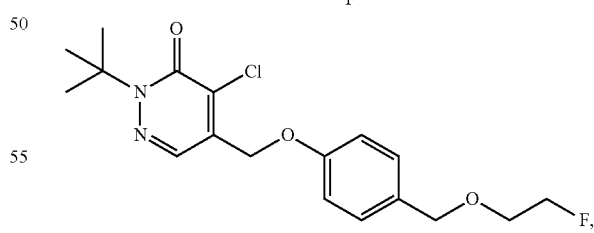
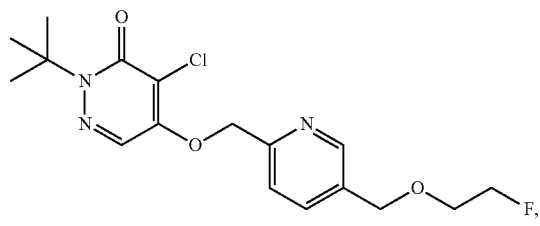
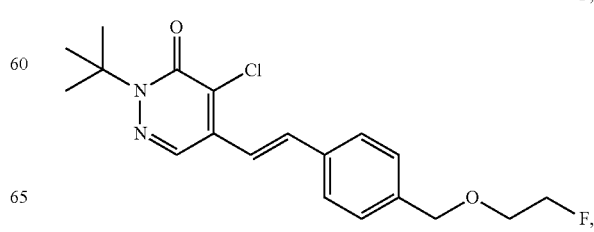

-continued
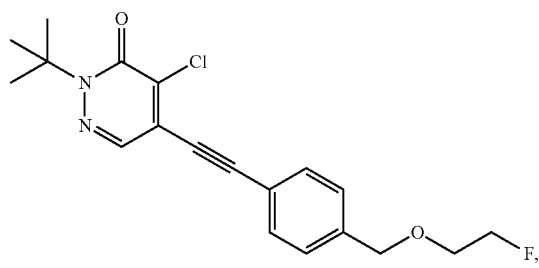
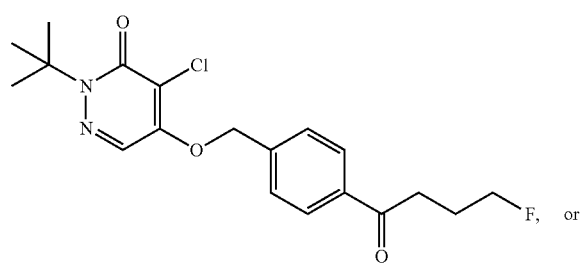
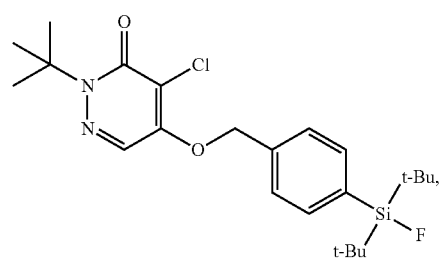
or a pharmaceutically acceptable salt thereof. In some embodiments, each F is $^{18}$F.
In some embodiments, the compound is:
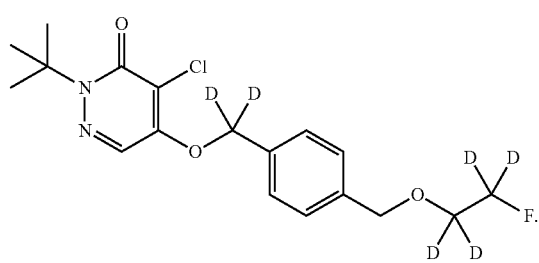 [SMILES: [2H]C([2H])(Oc1cnn(C(C)(C)C)c(=O)c1Cl)c1ccc(COC([2H])([2H])C([2H])([2H])F)cc1]
In some embodiments, the compound is selected from the group consisting of:
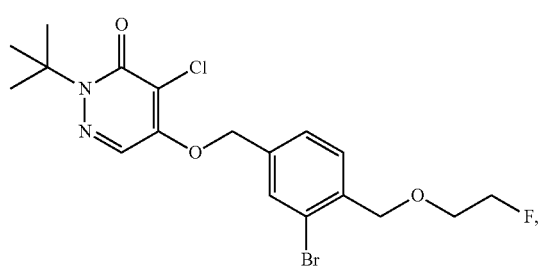
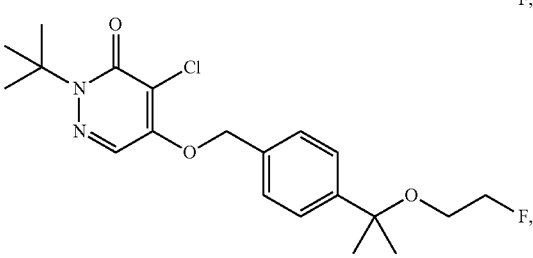
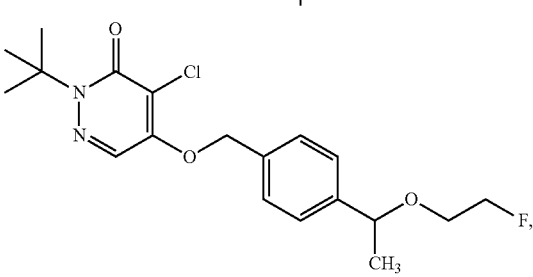

-continued
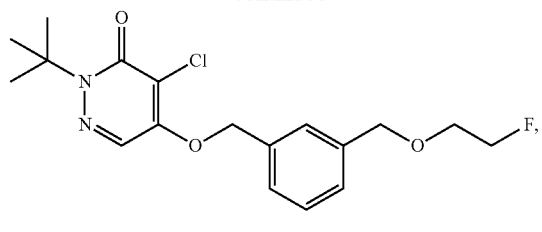
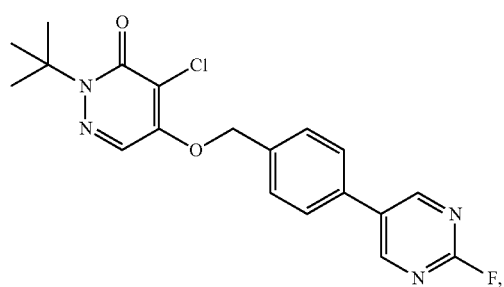
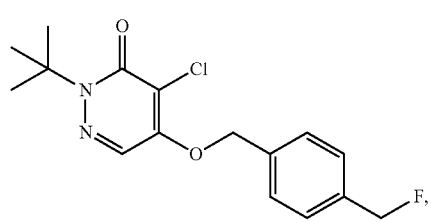
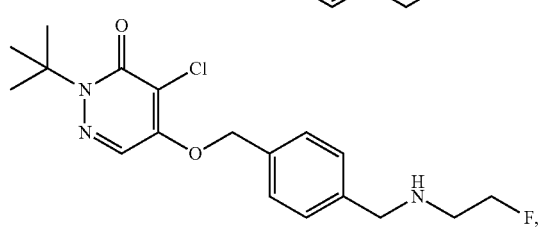
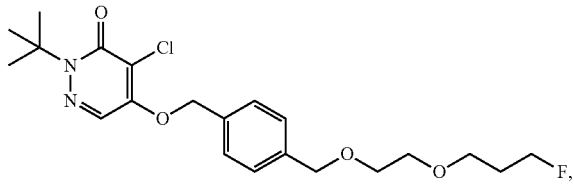
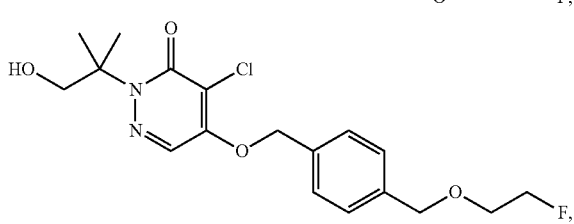
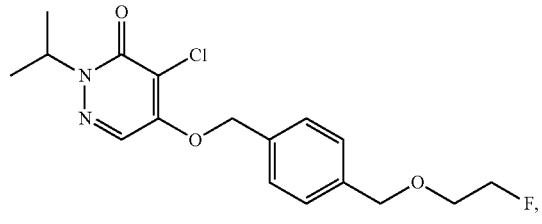
-continued
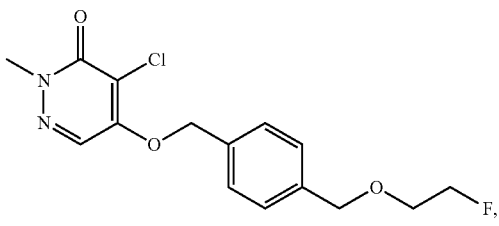
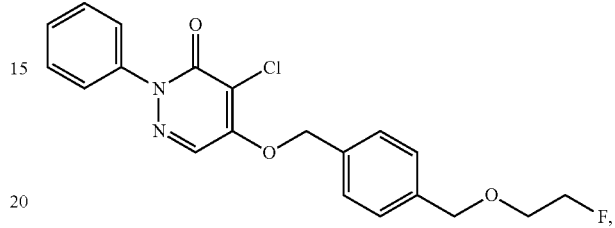
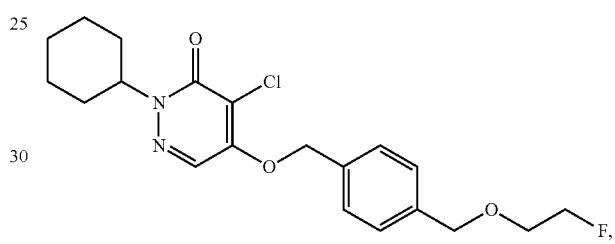
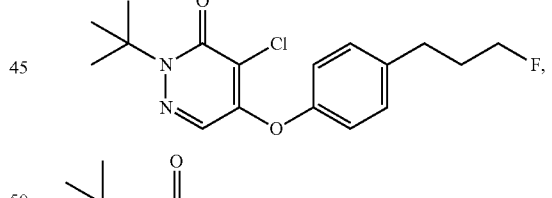
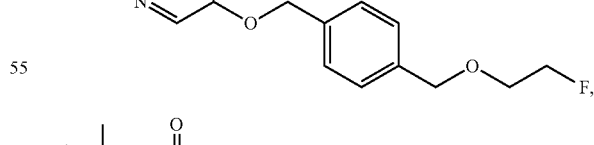
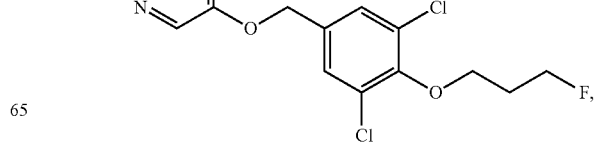

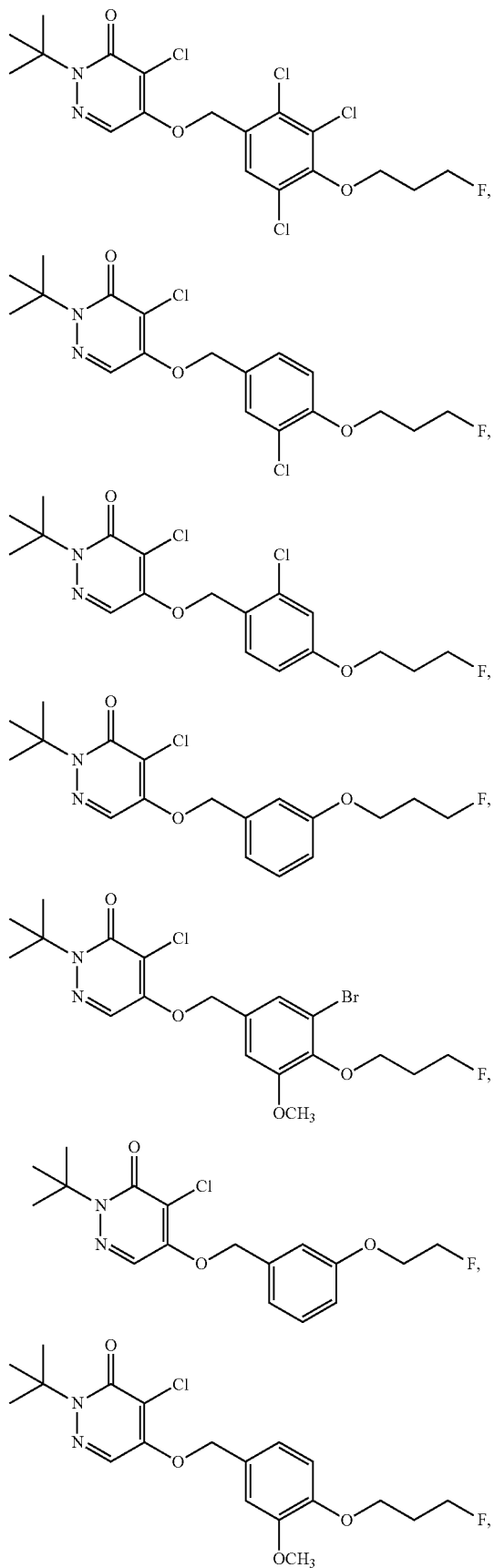

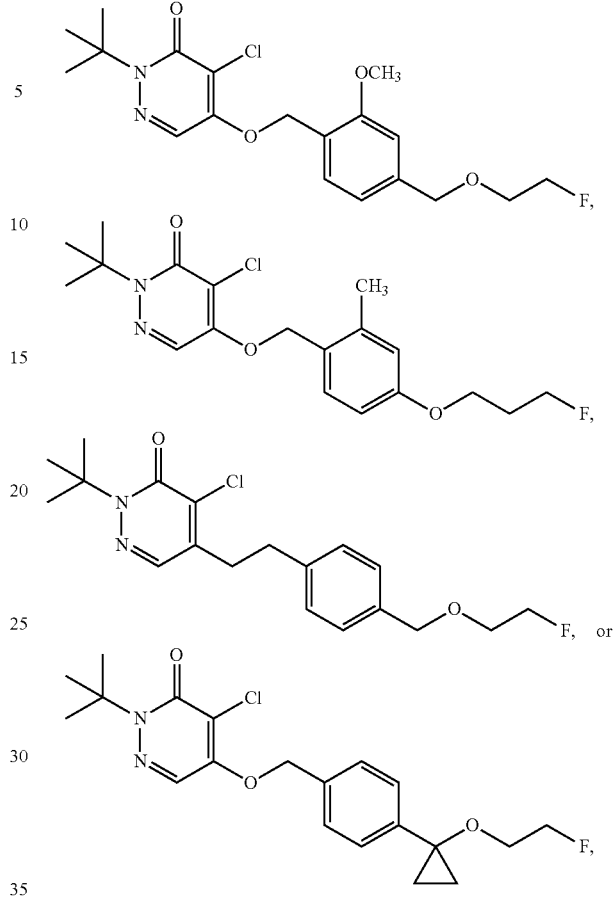

or a pharmaceutically acceptable salt thereof. In some embodiments, each F is $^{18}$F.

In some embodiments, a compound is provided comprising the structure:

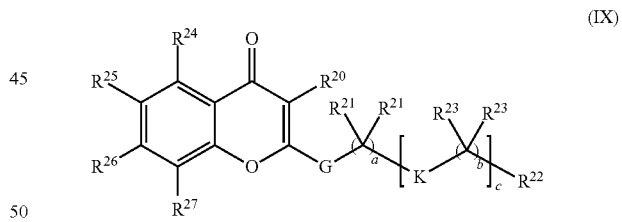

(IX)

or a pharmaceutically acceptable salt thereof, wherein:

$R^{20}$ is selected from the group consisting of hydrogen, heteroalkyl optionally substituted, alkoxy optionally substituted, alkoxyalkyl optionally substituted, aryl optionally substituted, heteroaryl optionally substituted, halo, haloalkyl, —CN, and —NO$_2$;

each $R^{21}$ and $R^{23}$ is independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two $R^{21}$ or any two $R^{23}$ may be joined together to form a ring;

$R^{22}$ is selected from the group consisting of hydrogen, alkyl optionally substituted, heteroalkyl optionally substituted, alkoxyalkyl optionally substituted, halo, haloalkyl, —OR$^{28}$, —Si(R$^9$)$_3$, —B(R$^{9'}$)$_3$, and an imaging moiety;

$R^{24}$, $R^{25}$, $R^{26}$, and $R^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halo, and an imaging moiety;

each $R^{9'}$ is independently selected from the group consisting of halo, alkyl optionally substituted, aryl optionally substituted, and an imaging moiety;

$R^{28}$ is selected from the group consisting of hydrogen, alkyl optionally substituted, and heteroalkyl optionally substituted;

G is O, S, or NR$^{28}$;

a is 0, 1, 2, 3, or 4;

each K is independently arylene, heteroarylene, alkenylene, or alkynylene, each optionally substituted;

each b is independently 0, 1, 2, 3, or 4; and c is 1 or 2, provided at least one imaging moiety is present in the compound.

In some embodiments, a compound is provided comprising the structure:

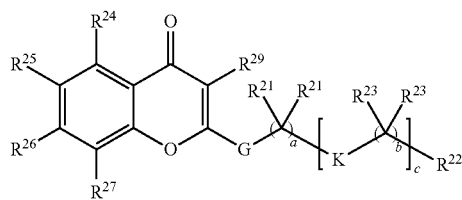

(X)

or a pharmaceutically acceptable salt thereof, wherein:

each $R^{21}$ and $R^{23}$ is independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two $R^{21}$ or any two $R^{23}$ may be joined together to form a ring;

$R^{22}$ is selected from the group consisting of hydrogen, alkyl optionally substituted, heteroalkyl optionally substituted, alkoxyalkyl optionally substituted, halo, haloalkyl, —OR$^{28}$, —Si(R$^9$)$_3$, —B(R$^{9'}$)$_3$, and an imaging moiety;

$R^{24}$, $R^{25}$, $R^{26}$, and $R^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halogen, and an imaging moiety;

each $R^{9'}$ is independently selected from the group consisting of halo, alkyl optionally substituted, aryl optionally substituted, and an imaging moiety;

$R^{28}$ is selected from the group consisting of hydrogen, alkyl optionally substituted, and heteroalkyl optionally substituted;

$R^{29}$ is selected from the group consisting of hydrogen, alkyl optionally substituted, heteroalkyl optionally substituted, aryl optionally substituted, heteroaryl optionally substituted, halo, haloalkyl, alkoxy optionally substituted, alkoxyalkyl optionally substituted, —CN, —NO$_2$, and an imaging moiety;

G is O, S, or NR$^{28}$;

a is 0, 1, 2, 3, or 4;

each K is independently arylene, heteroarylene, alkenylene, or alkynylene, each optionally substituted, provided at least one K is alkenylene or alkynylene;

each b is independently 0, 1, 2, 3, or 4; and c is 1 or 2, provided at least one imaging moiety is present in the compound.

In some embodiments, a compound of Formula (IX) comprises the structure:

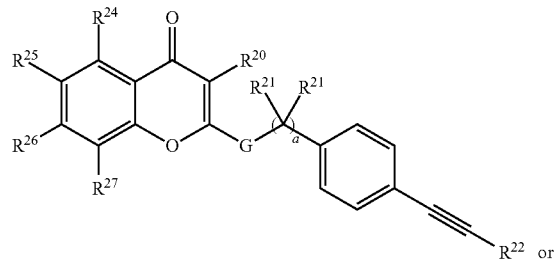

or

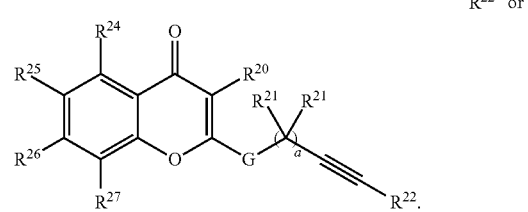

In some embodiments, a compound of Formula (X) comprises the structure:

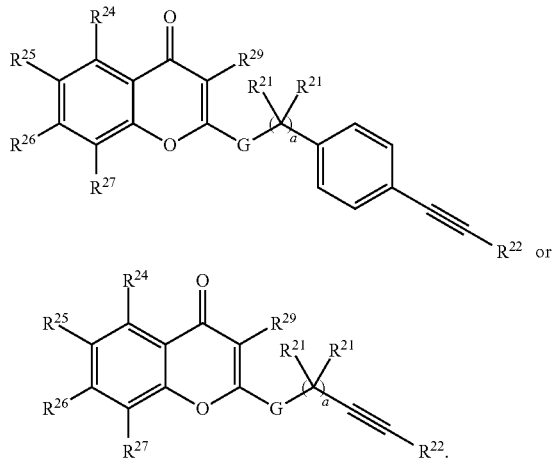

The following description of $R^{20}$ groups may be used in connection with a compound of Formula (IX). In some embodiments, $R^{20}$ is selected from the group consisting of hydrogen, heteroalkyl optionally substituted, alkoxy optionally substituted, alkoxyalkyl optionally substituted, aryl optionally substituted, heteroaryl optionally substituted, halo, haloalkyl, —CN, and —$NO_2$. In some embodiments, $R^{20}$ is hydrogen. In some embodiments, $R^{20}$ is heteroalkyl optionally substituted. In some embodiments, $R^{20}$ is alkoxy optionally substituted. In some embodiments, $R^{20}$ is alkoxyalkyl optionally substituted. In some embodiments, $R^{20}$ is halo. In some embodiments, $R^{20}$ is F. In some embodiments, $R^{20}$ is Cl. In some embodiments, $R^{20}$ is Br. In some embodiments, $R^{20}$ is I. In some embodiments, $R^{20}$ is haloalkyl. In some embodiments, $R^{20}$ is aryl optionally substituted. In some embodiments, $R^{20}$ is unsubstituted aryl. In some embodiments, $R^{20}$ is phenyl optionally substituted. In some embodiments, $R^{20}$ is unsubstituted phenyl. In some embodiments, $R^{20}$ is cycloalkyl optionally substituted. For a compound of Formula (IX), each of the $R^{20}$ groups described herein may be combined with any $R^7$, $R^8$, $R^{21}$, $R^{22}$, $R^{23}$, $R^{24}$, $R^{25}$, $R^{26}$, $R^{27}$, $R^{28}$, G, a, K, b, and c, or combinations thereof, as described herein.

The following description of $R^{29}$ groups may be used in connection with a compound of Formula (X). In some embodiments, $R^{29}$ is selected from the group consisting of $R^{29}$ is selected from the group consisting of hydrogen, alkyl optionally substituted, heteroalkyl optionally substituted, aryl optionally substituted, heteroaryl optionally substituted, halo, haloalkyl, —CN, —$NO_2$, and an imaging moiety. In some embodiments, $R^{29}$ is hydrogen. In some embodiments, $R^{29}$ is alkyl optionally substituted. In some embodiments, $R^{29}$ is unsubstituted alkyl. In some embodiments, $R^{29}$ is methyl, ethyl, n-propyl, i-propyl, n-butyl, i-butyl, or t-butyl. In some embodiments, $R^{29}$ is methyl. In some embodiments, $R^{29}$ is heteroalkyl optionally substituted. In some embodiments, $R^{29}$ is alkoxy optionally substituted. In some embodiments, $R^{29}$ is alkoxyalkyl optionally substituted. In some embodiments, $R^{29}$ is halo. In some embodiments, $R^{29}$ is F. In some embodiments, $R^{29}$ is Cl. In some embodiments, $R^{29}$ is Br. In some embodiments, $R^{29}$ is I. In some embodiments, $R^{29}$ is haloalkyl. In some embodiments, $R^{29}$ is aryl optionally substituted. In some embodiments, $R^{29}$ is unsubstituted aryl. In some embodiments, $R^{29}$ is phenyl optionally substituted. In some embodiments, $R^{29}$ is unsubstituted phenyl. In some embodiments, $R^{29}$ is cycloalkyl optionally substituted. In some embodiments, $R^{29}$ is —CN. In some embodiments, $R^{29}$ is —$NO_2$. In some embodiments, $R^{29}$ is an imaging moiety For a compound of Formula (X), each of the $R^{29}$ groups described herein may be combined with any $R^7$, $R^8$, $R^{21}$, $R^{22}$, $R^{23}$, $R^{24}$, $R^{25}$, $R^{26}$, $R^{27}$, $R^{28}$, G, a, K, b, and c, or combinations thereof, as described herein.

The following description of $R^{21}$ and $R^{23}$ groups may be used in connection with a compound of Formula (IX) or (X). In some embodiments, $R^{21}$ and $R^{23}$ are each independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two $R^{21}$ or any two $R^{23}$ may be joined together to form a ring. In some embodiments, any two of $R^{21}$ and $R^{23}$ may be joined together to form a ring. In some cases, the ring formed may comprise a total of 4, 5, 6, 7, 8, or more, atoms. In some cases, the ring comprises 5 or 6 atoms. In some embodiments, each of $R^{21}$ and $R^{23}$ is H. In some embodiments, at least one $R^{21}$ and $R^{23}$ is $^2$H. In some embodiments, each of $R^{21}$ and $R^{23}$ is $^2$H. In some embodiments, each of $R^{21}$ and $R^{23}$ is H or alkyl optionally substituted. In some embodiments, each of $R^{21}$ and $R^{23}$ is H or unsubstituted alkyl. In some embodiments, at least one $R^{21}$ and $R^{23}$ is not H. In some embodiments, at least one $R^{21}$ or $R^{23}$ is an imaging moiety. For a compound of Formula (IX), each of the $R^{21}$ and/or $R^{23}$ groups described herein may be combined with any $R^7$, $R^8$, $R^{20}$, $R^{22}$, $R^{24}$, $R^{25}$, $R^{26}$, $R^{27}$, $R^{28}$, G, a, K, b, and c, or combinations thereof, as described herein. For a compound of Formula (X), each of the $R^{21}$ and/or $R^{23}$ groups described herein may be combined with any $R^7$, $R^8$, $R^{22}$, $R^{24}$, $R^{25}$, $R^{26}$, $R^{27}$, $R^{28}$, $R^{29}$, G, a, K, b, and c, or combinations thereof, as described herein.

The following description of $R^{24}$, $R^{25}$, $R^{26}$, and $R^{27}$ groups may be used in connection with a compound of Formula (IX) or (X). In some embodiments, $R^{24}$, $R^{25}$, $R^{26}$, and $R^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —$NO_2$, —OH, —C(=O)$R^8$, —C(=O)O$R^8$, —OC(=O)$R^8$, —C(=O)N($R^7$)$_2$, —N($R^7$)C(=O)$R^8$, —CN, and an imaging moiety. In some embodiments, each of $R^{24}$, $R^{25}$, $R^{26}$, and $R^{27}$ are H. In some embodiments, at least one $R^{24}$, $R^{25}$, $R^{26}$, and $R^{27}$ is not H. In some embodiments, each of $R^{24}$, $R^{25}$, $R^{26}$, and $R^{27}$ is H or alkyl optionally substituted. In some embodiments, each of $R^{24}$, $R^{25}$, $R^{26}$, and $R^{27}$ is H or unsubstituted alkyl. For a compound of Formula (IX), each of the $R^{24}$, $R^{25}$, $R^{26}$, and $R^{27}$ groups described herein may be combined with any $R^7$, $R^8$, $R^{20}$, $R^{21}$, $R^{22}$, $R^{23}$, $R^{28}$, G, a, K, b, and c, or combinations thereof, as described herein. For a compound of Formula (X), each of the $R^{24}$, $R^{25}$, $R^{26}$, and $R^{27}$ groups described herein may be combined with any $R^7$, $R^8$, $R^{21}$, $R^{22}$, $R^{23}$, $R^{28}$, $R^{29}$, G, a, K, b, and c, or combinations thereof, as described herein.

The following description of G groups may be used in connection with a compound of Formula (IX) or (X). In some embodiments, G is O, S, or $NR^{28}$. In some embodiments, G is O. In some embodiments, G is S. In some embodiments, G is $NR^{28}$, wherein $R^{28}$ is selected from the group consisting of hydrogen, alkyl optionally substituted, and heteroalkyl optionally substituted. In some embodiments, G is NH. In some embodiments, G is $NR^{28}$ wherein $R^{28}$ is H or alkyl optionally substituted. In some embodiments, G is $NR^{28}$, wherein $R^{28}$ is alkyl optionally substituted. In some embodiments, G is $NR^{28}$, wherein $R^{28}$ is unsubstituted alkyl. For a compound of Formula (IX), each of the G groups described herein may be combined with any $R^7$, $R^8$, $R^{20}$, $R^{21}$, $R^{22}$, $R^{23}$, $R^{24}$, $R^{25}$, $R^{26}$, $R^{27}$, $R^{28}$, a, K, b, and c, or combinations thereof, as described herein. For a compound of Formula (X), each of the G groups described herein may be combined with any $R^7$, $R^8$, $R^{21}$, $R^{22}$, $R^{23}$, $R^{24}$, $R^{25}$, $R^{26}$, $R^{27}$, $R^{28}$, $R^{29}$, a, K, b, and c, or combinations thereof, as described herein.

The following description of a, b, and c variables may be used in connection with a compound of Formula (IX) or (X). In some embodiments, a is 0. In some embodiments, wherein a is 1. In some embodiments, a is 2. In some embodiments, a is 3. In some embodiments, a is 4. In some embodiments, b is 0. In some embodiments, wherein b is 1. In some embodiments, b is 2. In some embodiments, b is 3. In some embodiments, b is 4. In some embodiments, c is 1. In some embodiments, c is 2. In some embodiments, a is 1, b is 1, and c is 1. In some embodiments, a is 2, b is 2, and c is 1. In some embodiments, a is 2, b is 2, and c is 2. For a compound of Formula (IX), each of the a, b, and c variables described herein may be combined with any $R^7$, $R^8$, $R^{20}$, $R^{21}$, $R^{22}$, $R^{23}$, $R^{24}$, $R^{25}$, $R^{26}$, $R^{27}$, $R^{28}$, G, and K, or combinations thereof, as described herein. For a compound of Formula (X), each of the a, b, and c variables described herein may be combined with any $R^7$, $R^8$, $R^{21}$, $R^{22}$, $R^{23}$, $R^{24}$, $R^{25}$, $R^{26}$, $R^{27}$, $R^2$, $R^{29}$, G, and K, or combinations thereof, as described herein.

The following description of groups may be used in connection with a compound of Formula (IX) or (X). In some embodiments, at least one K is alkynylene. In some embodiments, at least one K is alkenylene. In some embodiments,

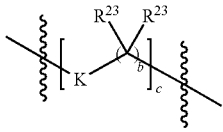

has the structure:

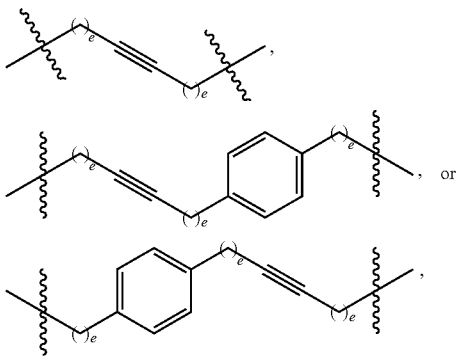

wherein each e is independently 1, 2, 3, or 4. In some embodiments, each e is 1. For a compound of Formula (IX), each of the above groups may be combined with any $R^7$, $R^8$, $R^{20}$, $R^{21}$, $R^{22}$, $R^{24}$, $R^{25}$, $R^{26}$, $R^{27}$, $R^{28}$, G, and a, or combinations thereof, as described herein. For a compound of Formula (X), each of the above groups may be combined with any $R^7$, $R^8$, $R^{21}$, $R^{22}$, $R^{24}$, $R^{25}$, $R^{26}$, $R^{27}$, $R^{28}$, $R^{29}$, G, and a, or combinations thereof, as described herein.

The following description of $R^{22}$ groups may be used in connection with a compound of Formula (IX) or (X). In some embodiments, $R^{22}$ is selected from the group consisting of hydrogen, alkyl optionally substituted, heteroalkyl optionally substituted, alkoxyalkyl optionally substituted, halo, haloalkyl, $-OR^{28}$, and an imaging moiety. In some embodiments, $R^{22}$ is $-Si(R^9)_3$ or $-B(R^9)_3$. In some embodiments, $R^{22}$ is hydrogen. In some embodiments, $R^{22}$ is alkyl optionally substituted. In some embodiments, $R^{22}$ is unsubstituted alkyl. In some embodiments, $R^{22}$ is heteroalkyl optionally substituted. In some embodiments, $R^{22}$ is unsubstituted heteroalkyl. In some embodiments, $R^{22}$ is alkoxyalkyl optionally substituted. In some embodiments, $R^{22}$ is unsubstituted alkoxyalkyl. In some embodiments, $R^{22}$ is halo. In some embodiments, $R^{22}$ is F. In some embodiments, $R^{22}$ is Cl. In some embodiments, $R^{22}$ is Br. In some embodiments, $R^{22}$ is I. In some embodiments, $R^{22}$ is haloalkyl. In some embodiments, $R^{22}$ is $-OR^{28}$, wherein $R^{28}$ is selected from the group consisting of hydrogen, alkyl optionally substituted, and heteroalkyl optionally substituted. In some embodiments, $R^{22}$ is OH. In some embodiments, $R^{22}$ is $OR^{28}$, wherein $R^{28}$ is H or alkyl optionally substituted. In some embodiments, $R^{22}$ is $OR^{28}$, wherein $R^{28}$ is alkyl optionally substituted. In some embodiments, $R^{22}$ is $OR^{28}$, wherein $R^{28}$ is unsubstituted alkyl. In some embodiments, $R^{22}$ is an imaging moiety. In some embodiments, $R^{22}$ is substituted with an imaging moiety. In some embodiments, $R^{22}$ is alkyl optionally substituted, alkoxy optionally substituted, or alkoxyalkyl optionally substituted, each substituted with an imaging moiety. In some embodiments, $R^{22}$ is $-(CH_2)_jI_m$; wherein $I_m$ is an imaging moiety and j is 1, 2, 3, 4, 5, or 6. In some cases, $R^{22}$ is $-(CH_2)I_m$, $-(CH_2)_2I_m$, $-(CH_2)_3I_m$, $-(CH_2)_4I_m$, $-(CH_2)_5I_m$, $-(CH_2)_6I_m$, $-(CH_2)_7I_m$, $-(CH_2)_8I_m$, $-(CH_2)_9I_m$, or $-(CH_2)_{10}I_m$. In some cases, $R^{22}$ is $-(CH_2)^{18}F$, $-(CH_2)_2{}^{18}F$, $-(CH_2)_3{}^{18}F$, $-(CH_2)_4{}^{18}F$, $-(CH_2)_5{}^{18}F$, $-(CH_2)_6{}^{18}F$, $-(CH_2)_7{}^{18}F$, $-(CH_2)_8{}^{18}F$, $-(CH_2)_9{}^{18}F$, or $-(CH_2)_{10}{}^{18}F$. In some embodiments, $R^{22}$ is $-O(CH_2)_jI_m$; wherein $I_m$ is an imaging moiety and j is 1, 2, 3, 4, 5, or 6. In some cases, $R^{22}$ is $-O(CH_2)I_m$, $-O(CH_2)_2I_m$, $-O(CH_2)_3I_m$, $-O(CH_2)_4I_m$, $-O(CH_2)_5I_m$, $-O(CH_2)_6I_m$, $-O(CH_2)_7I_m$, $-O(CH_2)_8I_m$, $-O(CH_2)_9I_m$, or $-O(CH_2)_{10}I_m$. In some cases, $R^{22}$ is $-O(CH_2)^{18}F$, $-O(CH_2)_2{}^{18}F$, $-O(CH_2)_3{}^{18}F$, $-O(CH_2)_4{}^{18}F$, $-O(CH_2)_5{}^{18}F$, $-O(CH_2)_6{}^{18}F$, $-O(CH_2)_7{}^{18}F$, $-O(CH_2)_8{}^{18}F$, $-O(CH_2)_9{}^{18}F$, or $-O(CH_2)_{10}{}^{18}F$. In some embodiments, $R^{22}$ is $-(CH_2)_jO(CH_2)_jI_m$; wherein $I_m$ is an imaging moiety and each j is independently 1, 2, 3, 4, 5, or 6. In some embodiments, $R^{22}$ is $-(CH_2)O(CH_2)_jI_m$; wherein $I_m$ is an imaging moiety and each j is independently 1, 2, 3, 4, 5, or 6. In some cases, $R^{22}$ is $-CH_2O(CH_2)I_m$, $-CH_2O(CH_2)_2I_m$, $-CH_2O(CH_2)_3I_m$, $-CH_2O(CH_2)_4I_m$, $-CH_2O(CH_2)_5I_m$, $-CH_2O(CH_2)_6I_m$, $-CH_2O(CH_2)_7I_m$, $-CH_2O(CH_2)_8I_m$, $-CH_2O(CH_2)_9I_m$, or $-CH_2O(CH_2)_{10}I_m$. In some cases, $R^{22}$ is $-CH_2O(CH_2)^{18}F$, $-CH_2O(CH_2)_2{}^{18}F$, $-CH_2O(CH_2)_3{}^{18}F$, $-CH_2O(CH_2)_4{}^{18}F$, $-CH_2O(CH_2)_5{}^{18}F$, $-CH_2O(CH_2)_6{}^{18}F$, $-CH_2O(CH_2)_7{}^{18}F$, $-CH_2O(CH_2)_8{}^{18}F$, $-CH_2O(CH_2)_9{}^{18}F$, or $-CH_2O(CH_2)_{10}{}^{18}F$. In some embodiments, $R^{22}$ is $-C\equiv C-(CH_2)_jI_m$; wherein $I_m$ is an imaging moiety and j is 1, 2, 3, 4, 5, or 6. In some embodiments, $R^{22}$ is $-[(CH_2)_jO]_j(CH_2)_jI_m$; wherein $I_m$ is an imaging moiety and each j is independently 1, 2, 3, 4, 5, or 6. In some embodiments, $R^{22}$ is $-O[(CH_2)_3O]_j(CH_2)_jI_m$; wherein $I_m$ is an imaging moiety and each j is independently 1, 2, 3, 4, 5, or 6. In some embodiments, $R^{22}$ is optionally substituted alkyl substituted with an imaging moiety. In some embodiments, $R^{22}$ is —C(=O)O(CH$_2$)$_j$I$_m$; wherein I$_m$ is an imaging moiety and j is 1, 2, 3, 4, 5, or 6. In some embodiments, $R^{22}$ is —C(=O) (CH$_2$)$_j$I$_m$; wherein I$_m$ is an imaging moiety and j is 1, 2, 3, 4, 5, or 6. In some embodiments, $R^{22}$ is —(CH$_2$)$_j$NH (CH$_2$)$_j$I$_m$; wherein I$_m$ is an imaging moiety and each j is independently 1, 2, 3, 4, 5, or 6. In some embodiments, $R^{22}$ is Si(R$^9$)$_2$I$_m$, wherein each $R^9$ is alkyl optionally substituted and wherein I$_m$ is an imaging moiety. In some embodiments, $R^{22}$ is B(R$^{9'}$)$_2$I$_m$, wherein each $R^{9'}$ is alkyl optionally substituted and wherein I$_m$ is an imaging moiety. In some embodiments, $R^{22}$ is selected from the group consisting of —C≡C—CH$_2$CH$_2$CH$_2$I$_m$, —C≡C—CH$_2$CH$_2$I$_m$, —C≡C—CH$_2$I, —CH$_2$I$_m$, —(CH$_2$)$_2$I$_m$, —(CH$_2$)$_3$I$_m$, —(CH$_2$)$_4$I$_m$, —(CH$_2$)$_5$I$_m$, —(CH$_2$)$_6$I$_m$, —OCH$_2$I$_m$, —O(CH$_2$)$_2$I$_m$, —O(CH$_2$)$_3$I$_m$, —O(CH$_2$)$_4$I$_m$, —O(CH$_2$)$_5$I$_m$, —O(CH$_2$)$_6$I$_m$, —CH$_2$O(CH$_2$)$_2$I$_m$, —CH(CH$_3$)O(CH$_2$)$_2$I$_m$, —CH$_2$O (CH$_2$)$_3$I$_m$, —CD$_2$O(CH$_2$)$_2$I$_m$, —(CH$_2$)$_2$O(CH$_2$)$_2$I$_m$, —CHBrC(CH$_3$)$_2$I$_m$, —CHClC(CH$_3$)$_2$I$_m$, —CHFC(CH$_3$)$_2$I$_m$, —C(=O)OCH$_2$I$_m$, —C(=O)O(CH$_2$)$_2$I$_m$, —C(=O)O (CH$_2$)$_3$I$_m$, —CH$_2$NH(CH$_2$)$_2$I$_m$, —CH$_2$NHCH$_2$I$_m$, —CH$_2$O (CH$_2$)$_2$O(CH$_2$)$_2$I$_m$, —CH$_2$O(CH$_2$)$_2$O(CH$_2$)$_3$I$_m$, —O (CH$_2$)$_2$O(CH$_2$)$_2$I$_m$, —C(=O)(CH$_2$)$_2$I$_m$, and —C(=O) (CH$_2$)$_3$I$_m$. In some embodiments, wherein I$_m$ is $^{18}$F. In some embodiments, $R^{22}$ is selected from the group consisting of:

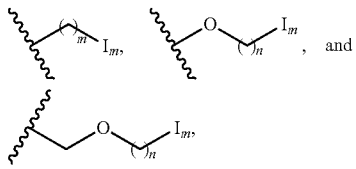

wherein m and n is an integer between 1 and 6, inclusive, and I$_m$ is an imaging moiety. In some embodiments, $R^{22}$ is selected from the group consisting of:

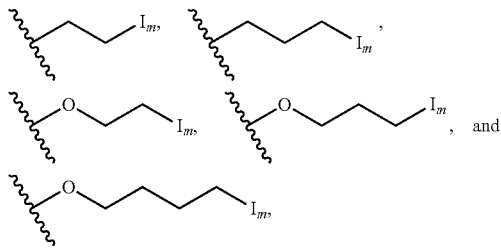

wherein I$_m$ is an imaging moiety. In some embodiments, $R^{22}$ is selected from the group consisting of:

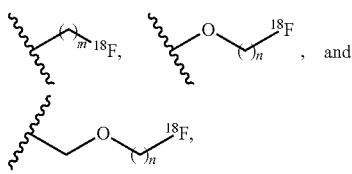

wherein m and n is an integer between 1 and 6, inclusive. In some embodiments, $R^{22}$ is selected from the group consisting of:

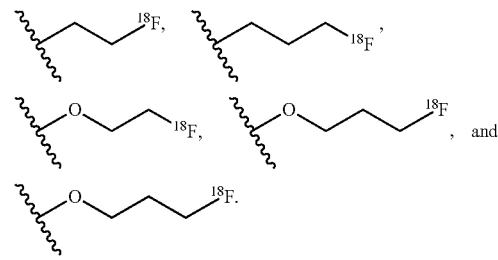

For a compound of Formula (IX), each of the $R^{22}$ groups described herein may be combined with any $R^7$, $R^8$, $R^{20}$, $R^{21}$, $R^{23}$, $R^{24}$, $R^{25}$, $R^{26}$, $R^{27}$, $R^{28}$, G, a, K, b, and c, or combinations thereof, as described herein. For a compound of Formula (X), each of the $R^{22}$ groups described herein may be combined with any $R^7$, $R^8$, $R^{21}$, $R^{23}$, $R^{24}$, $R^{25}$, $R^{26}$, $R^{27}$, $R^{28}$, $R^{29}$, G, a, K, b, and c, or combinations thereof, as described herein.

In some embodiments, for a compound of Formula (IX), the at least one imaging moiety is present in $R^7$, $R^8$, $R^{20}$, $R^{21}$, $R^{22}$, $R^{23}$, $R^{24}$, $R^{25}$, $R^{26}$, $R^{27}$, or $R^{28}$. In some embodiments, a compound of Formula (X) or (IX) comprises a single imaging moiety. In some embodiments, for a compound of Formula (X), the at least one imaging moiety is present in $R^7$, $R^8$, $R^{21}$, $R^{22}$, $R^{23}$, $R^{24}$, $R^{25}$, $R^{26}$, $R^{27}$, $R^{28}$, or $R^{29}$. In some embodiments, for a compound of Formula (X) or (IX), the at least one imaging moiety is present in $R^{22}$. As noted above, as will be understood by those of ordinary skill in the art, when referring to an imaging moiety, the imaging moiety "is present" in a group in embodiments wherein 1) the imaging moiety is the group (e.g., $R^{22}$ is an imaging moiety) or b) the group comprises the imaging moiety (e.g., $R^{22}$ is substituted with an imaging moiety). In some embodiments, for a compound of Formula (IX), $R^7$, $R^8$, $R^{20}$, $R^{21}$, $R^{22}$, $R^{23}$, $R^{24}$, $R^{25}$, $R^{26}$, $R^{27}$, or $R^{28}$ comprises the at least one imaging moiety. In some embodiments, for a compound of Formula (X), $R^7$, $R^8$, $R^{21}$, $R^{22}$, $R^{23}$, $R^{24}$, $R^{25}$, $R^{26}$, $R^{27}$, $R^{28}$, or $R^{29}$ comprises the at least one imaging moiety. In some embodiments, for a compound of Formula (IX), $R^7$, $R^8$, $R^{21}$, $R^{22}$, $R^{23}$, $R^{24}$, $R^{25}$, $R^{26}$, $R^{27}$, is the at least one imaging moiety. In some embodiments, for a compound of Formula (X) $R^7$, $R^8$, $R^{21}$, $R^{22}$, $R^{23}$, $R^{24}$, $R^{25}$, $R^{26}$, $R^{27}$, or $R^{29}$ is the at least one imaging moiety. For a compound of Formula (IX), each of the above placements of the imaging moieties may be combined with any $R^7$, $R^8$, $R^{20}$, $R^{21}$, $R^{22}$, $R^{23}$, $R^{24}$, $R^{25}$, $R^{26}$, $R^{27}$, $R^{28}$, G, a, K, b, and c, or combinations thereof, as described herein. For a compound of Formula (X), each of the above placements of the imaging moieties may be combined with any $R^7$, $R^8$, $R^{21}$, $R^{22}$, $R^{23}$, $R^{24}$, $R^{25}$, $R^{26}$, $R^{27}$, $R^{28}$, $R^{29}$, G, a, K, b, and c, or combinations thereof, as described herein.

The following description of the imaging moiety may be used in connection with a compound of Formula (IX) and (X). In some embodiments, the at least one imaging moiety is selected from the group consisting of $^{11}$C, $^{13}$N, $^{18}$F, $^{76}$Br, $^{89}$Zr, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, and $^{68}$Ga. In some embodiments, the at least one imaging moiety is $^{18}$F. Imaging moieties are described in more detail herein.

In some embodiments, a compound of Formula (IX) is selected from the group consisting of:

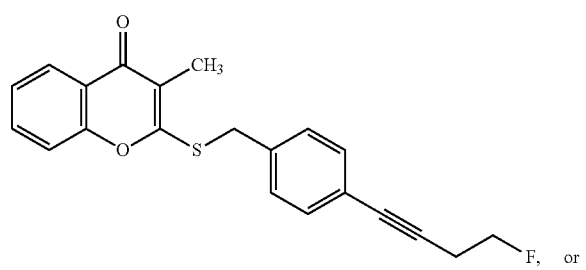

F, or

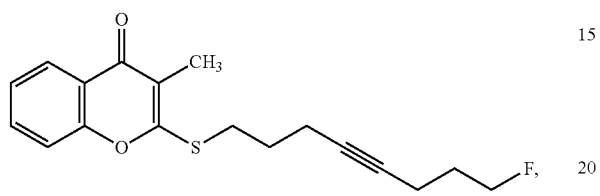

F, or a pharmaceutically acceptable salt thereof, wherein F is optionally $^{18}$F.

In some embodiments, a compound is selected from the group consisting of:

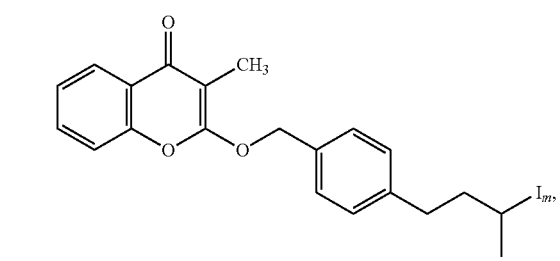

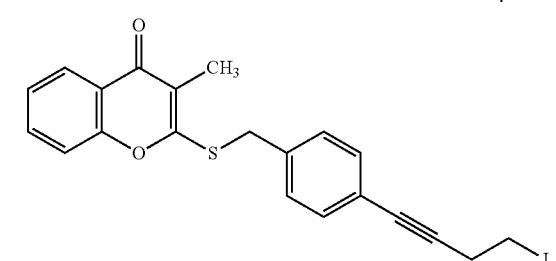

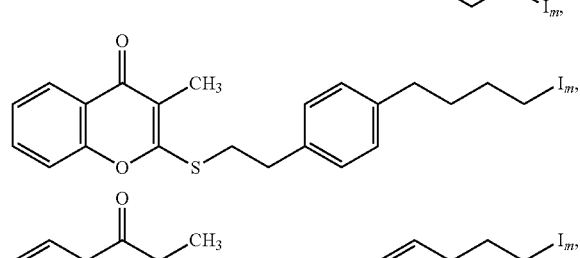

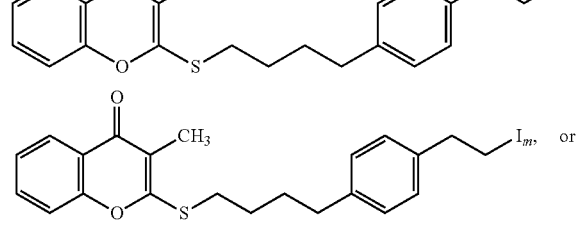

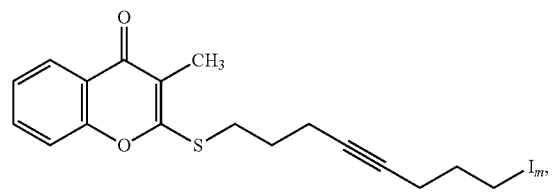

or a pharmaceutically acceptable salt thereof, wherein $I_m$ is an imaging moiety. In some embodiments, $I_m$ is $^{18}$F. In some embodiments, a compound is selected from the group consisting of:

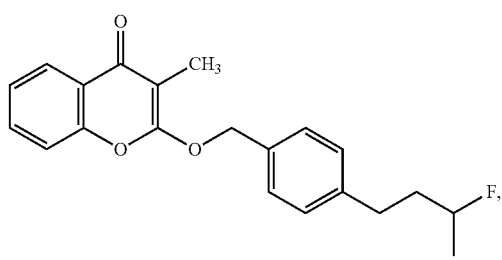

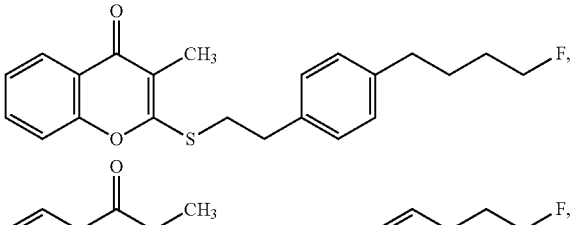

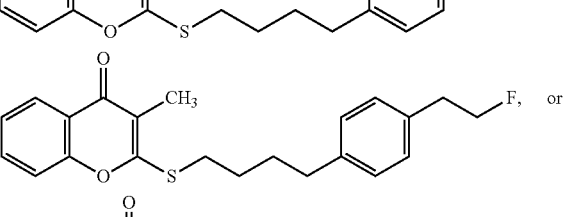

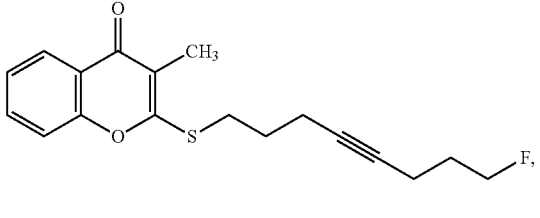

or a pharmaceutically acceptable salt thereof. In some embodiments, each F is $^{18}$F. In some embodiments, a compound is:

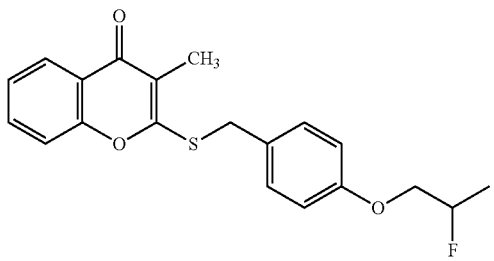 [SMILES: Cc1c(SCc2ccc(OCC(C)F)cc2)oc2ccccc2c1=O]

or a pharmaceutically acceptable salt thereof. In some embodiments, each F is $^{18}$F.

In some embodiments, a compound is selected from the group consisting of:

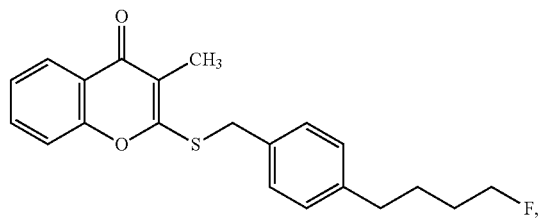

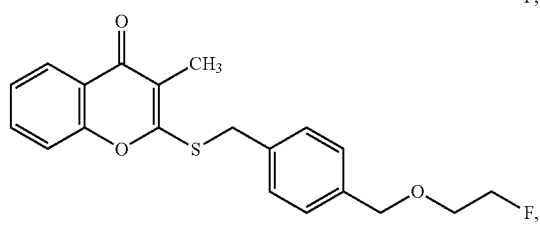

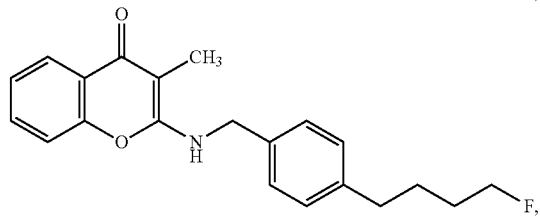

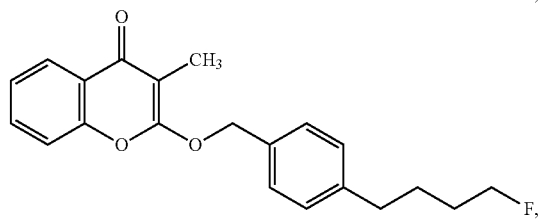

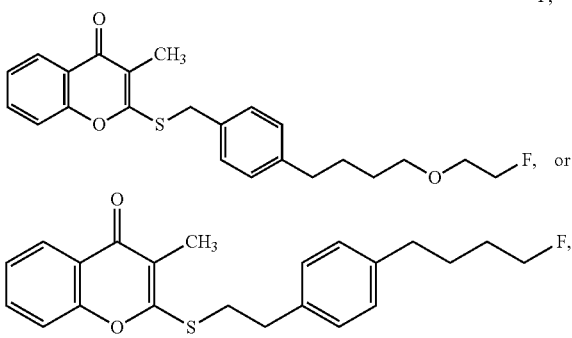

or a pharmaceutically acceptable salt thereof. In some embodiments, each F is $^{18}$F.

It should be understood, that any hydrogen molecule of a structure described herein may, in some embodiments, may be optionally substituted and/or enriched in $^2$H. In some cases, at least one $^2$H has been substituted for a $^1$H.

As used herein, the term "imaging agent" refers to any chemical compound that includes an imaging moiety. Typically, the imaging agent may be administered to a subject in order to provide information relating to at least a portion of the subject (e.g., human). In some cases, an imaging agent may be used to highlight a specific area of a subject, rendering organs, blood vessels, tissues, and/or other portions more detectable and/or more clearly imaged. By increasing the detectability and/or image quality of the object being studied, the presence and extent of disease and/or injury can be determined. An "imaging moiety" refers to an atom or group of atoms that is capable of producing a detectable signal itself (e.g., radioisotopes), or upon exposure to an external source of energy (e.g., electromagnetic radiation, ultrasound, and the like). In certain cases, the imaging moiety may alter its local chemical and/or magnetic and/or electronic environment. Non-limiting examples of imaging moieties include C, $^{13}$N, $^{18}$F, $^{76}$Br, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, $^{68}$Ga, and $^{89}$Zr. In some embodiments, the imaging moiety is associated with a group comprising the structure —B(R$^{9'}$)$_2$I$_m$ or —Si(R$^9$)$_2$I$_m$, wherein I$_m$ is an imaging moiety, optionally $^{18}$F. In some embodiments, the imaging moiety is directly associated (i.e., through a covalent bond) with a compound as described herein (e.g., in the case of $^{18}$F, $^{76}$Br, $^{124}$I, or $^{131}$I). In some embodiments, the imaging moiety is associated with the compound through non-covalent interactions (e.g., electrostatic interactions). In some embodiments, the imaging moiety is associated with the compound through a chelator (e.g., in the case of $^{64}$Cu, $^{89}$Zr, $^{99m}$Tc, and $^{111}$In). Chelators are described in more detail herein. In some embodiments, the imaging moiety is selected from the group consisting of $^{18}$F, $^{76}$Br, $^{124}$I, $^{131}$I, $^{64}$Cu, $^{89}$Zr, $^{99m}$Tc, and $^{111}$In. In certain embodiments, the imaging moiety is $^{18}$F. In certain embodiments, the imaging moiety is $^{76}$Br. In certain embodiments, the imaging moiety is $^{124}$I. In certain embodiments, the imaging moiety is $^{131}$I. In some cases, the imaging moiety is $^{18}$F, $^{76}$Br, or $^{124}$I. In some cases, the imaging moiety is $^{18}$F or $^{76}$Br. In some cases, an imaging agent comprises a single imaging moiety. In some cases, an imaging agent comprises more than one imaging moiety (e.g., two imaging moieties). As used herein, the term "imaging agent" encompasses contrast agents. In some embodiments, an imaging agent is a contrast agent. The term "contrast agent" refers to a type of imaging agent comprising an imaging moiety that produces a detectable signal in response to an external source of energy. In certain cases, the contrast agent may comprise an imaging moiety that absorbs and/or reflects and/or transmits the external source of energy.

In some embodiments, a composition comprising a compound of the invention or a plurality of compounds is enriched with compounds including an isotope such as a radioisotope. In such a case, the plurality or composition may be referred to as being "isotopically enriched." An "isotopically enriched" composition refers to a composition comprising a percentage of one or more isotopes of an element that is greater than the percentage of that isotope that occurs naturally. For example, a composition that is isotopically enriched with a fluoride species may be "isotopically enriched" with fluorine-18 ($^{18}$F). Thus, with regard to a plurality of compounds, when a particular atomic position is designated as $^{18}$F, it is to be understood that the abundance (or frequency) of $^{18}$F at that position (in the plurality) is greater than the natural abundance (or frequency) of $^{18}$F, which is essentially zero.

In some embodiments, an atom designated as being enriched may have a minimum isotopic enrichment factor of about 0.001% (i.e., about 1 out of $10^5$ atoms is the desired isotope of the atom), about 0.002%, about 0.003%, about 0.004%, about 0.005%, about 0.006%, about 0.007%, about 0.008%, about 0.009%, about 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The minimum isotopic enrichment factor, in some instances, may range from about 0.001% to about 1%. For example, in embodiments wherein the imaging moiety is fluorine, a fluorine designated as $^{18}$F may have a minimum isotopic enrichment factor of about 0.001% (i.e., about 1 out of $10^5$ fluorine species is $^{18}$F), about 0.002%, about 0.003%, about 0.004%, about 0.005%, about 0.006%, about 0.007%, about 0.008%, about 0.009%, about 0.01%, about 0.05%, about 0.1%, about 0.2%, about 0.3%, about 0.4%, about 0.5%, about 0.75%, about 1%, about 2%, about 3%, about 4%, about 5%, about 10%, about 15%, about 20%, about 30%, about 40%, about 50%, about 60%, about 70%, about 80%, about 90%, about 95%, or greater. The isotopic enrichment of a composition or plurality of compounds provided herein can be determined using conventional analytical methods known to one of ordinary skill in the art, including, for example, mass spectrometry and HPLC.

In some embodiments, compositions, methods, uses, and/or systems described herein include or use compounds described herein. In some embodiments, the compounds are imaging agents. In some embodiments, the compounds are contrast agents. In some embodiments, the compounds are precursor to imaging agents or contrast agents.

Chelators

In some cases, an imaging moiety may be associated with a compound as described herein via association with a chelator (e.g., in embodiments where the imaging moiety is $^{64}$Cu, $^{68}$Ga, $^{89}$Zr, $^{99m}$Tc, $^{111}$In). The chelator is typically covalently attached to the compound. However, in certain embodiments, the chelator may be associated with the compound through non-covalent interactions. The term chelator is given its ordinary meaning in the art and generally refers to a chemical moiety capable of complexing an imaging moiety (e.g., a metal ion and/or radionuclide), wherein the complex is stable under physiological conditions. For example, generally, the imaging moiety remains complexed with the chelator in vivo. In some embodiments, the chelator is the moiety or group on a compound that binds to an imaging moiety through one or more donor atoms and/or groups. The chelator may be any chelator known in the art for complexing a medically useful metal ion or radionuclide. In some embodiments, the chelator comprises one, two, three, four, five, six, seven, eight, nine, or ten donor atoms and/or groups. In embodiments where the chelator comprises more than one donor atom and/or group, the donor atoms/groups may be the same or different. The chelator may be monodentate, bidentate, tridentate, tetradentate, pentadentate, or more. Non-limiting examples of donor atoms/groups include —OH, —O$^-$, —COOR', —COO$^-$, —N(R')$_2$, =N$^-$, —SR', —S$^-$, —OPO$_3^-$, or —OPO$_3$R', wherein each R' can be the same or different and is hydrogen, alkyl, alkenyl, alkynyl, cycloalkyl, alkylaryl, alkylcarbonyl, aryl, arylalkyl, alkylarylalkyl, alkoxy, alkoxyalkyl, alkoxycarbonyl, heteroalkyl, heterocyclyl, heterocyclylalkyl, each optionally substituted. In some cases, the chelator may be a macrocycle. Non-limiting examples of chelators are described in International PCT Publication No. WO2011/005322 and U.S. Pat. No. 6,511,648, each of which is incorporated herein by reference for all purposes. In some embodiments, the chelator comprises diaminodithiol, mercaptoacetyltriglycine, monoaminomonoamide, picolylamine monoacetic acid, 1,4,7,10-tetraazacyclododecane-1,4,7,10-tetraacetic acid, bis(thiosemicarbazone), propyleneamine oxime, ethylenediaminetetraacetic acid, or diethylenetriaminepentaacetic acid. In some embodiments, the chelator comprises a metal atom (e.g., Al), wherein an imaging moiety (e.g., $^{18}$F) associates with the metal atom.

In some cases, an imaging moiety associated with a chelator may be further associated with one or more ancillary or co-ligands. "Ancillary" or "co-ligands" may be ligands which serve to complete the coordination sphere of the imaging moiety together with the chelator. In some embodiments, the imaging moiety coordination sphere may comprise one or more bonding atoms and/or groups from the chelators and optionally, one or more ancillary and/or co-ligands. Ancillary or co-ligands useful in the preparation of radiopharmaceuticals and in diagnostic kits useful for the preparation of said radiopharmaceuticals may be comprised of one or more oxygen, nitrogen, carbon, sulfur, phosphorus, arsenic, selenium, and tellurium donor atoms. Conditions for effecting association of an imaging moiety with a chelator will depend on the type of chelator being used and are well known in the art.

Imaging Agent Precursors

In another aspect of the invention, imaging agent precursors useful in the preparation of imaging agents as described herein are provided. In certain embodiments, an imaging agent precursor comprises a leaving group (e.g., a sulfonate, halide) that can be replaced with a nucleophile in a substitution reaction to form an imaging agent. The imaging agent precursor may also include functional groups that are optionally protected. In some embodiments, an imaging agent precursor has a substantially similar structure as an imaging agent described above (e.g., a compound comprising at least one imaging moiety), except that the imaging moiety or the substituent which includes the imaging moiety instead includes a leaving group. In certain embodiments, an imaging agent precursor has a substantially similar structure as an imaging agent described above, except that the chelator group is not yet associated with an imaging moiety.

As used herein, the term "leaving group" is given its ordinary meaning in the art of synthetic organic chemistry and refers to an atom or a group capable of being displaced by a nucleophile. Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, haloformates, —NO$_2$, trialkylammonium, and aryliodonium salts. In some embodiments, the leaving group is a sulfonic acid ester. In some embodiments, the sulfonic acid ester comprises the formula —OSO$_2$R' wherein R' is selected from the group consisting alkyl optionally, alkenyl optionally substituted, heteroalkyl optionally substituted, aryl optionally substituted, heteroaryl optionally substituted, arylalkyl optionally substituted, and heterarylalkyl optionally substituted. In some embodiments, R' is substituted or unsubstituted $C_1$-$C_6$ alkyl. In some embodiments, R' is methyl. In some embodiments, R' is —CF$_3$. In some embodiments, R' is substituted or unsubstituted aryl. In some embodiments, R' is substituted or unsubstituted phenyl. In some embodiments R' is:

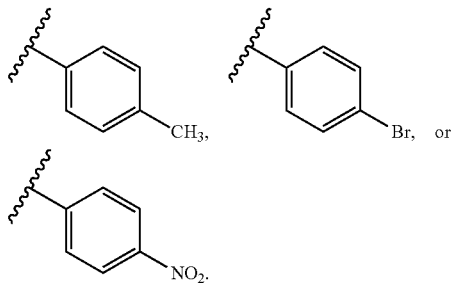

In some cases, the leaving group is toluenesulfonate (tosylate, Ts), methanesulfonate (mesylate, Ms), p-bromobenzenesulfonyl (brosylate, Bs), or trifluoromethanesulfonate (triflate, Tf). In some cases, the leaving group is a brosylate (p-bromobenzenesulfonyl). In some cases, the leaving group is a nosylate (2-nitrobenzenesulfonyl). In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate.

In some embodiments, a compound is provided comprising the structure:

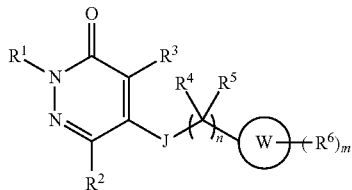

(XI)

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-NO_2$, and a leaving group;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-CN$, $-NO_2$, and a leaving group;

J is selected from the group consisting of $N(R^7)$, S, O, $C(=O)$, $C(=O)O$, $OC(=O)$, $C(=O)N(R^7)$, $N(R^7)C(=O)$, $CH_2O$, and a bond;

$R^4$ and $R^5$ are each independently selected from the group consisting of hydrogen, alkyl optionally substituted, and a leaving group, or optionally any two of $R^4$ and $R^5$ are joined together to form a ring;

n is 0, 1, 2, or 3;

W is heteroaryl, naphthyl, heterocyclyl, or aryl;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, $-N(R^7)_2$, $-NO_2$, $-OH$, $-C(=O)R^8$, $-C(=O)OR^8$, $-OC(=O)R^8$, $-C(=O)N(R^7)_2$, $-N(R^7)C(=O)R^8$, $-CN$, $-Si(R^9)_3$, $-B(R^9)_3$, $-OR^8$, and a leaving group;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halo, and a leaving group; and each $R^{9'}$ is independently selected from the group consisting of halo, alkyl optionally substituted, aryl optionally substituted, and leaving group, provided that at least one leaving group is present in the compound; and provided that when W is aryl, a) $R^3$ is not halo, alkyl or haloalkyl, or b) at least one $R^6$ is selected from the group consisting of alkynyl optionally substituted, alkenyl optionally substituted, alkyl substituted with $-CN$, alkyl substituted with $-C(=O)OR^8$, alkyl substituted with $-C(=O)R^8$, alkyl substituted with $-N(R^7)_2$, $-CN$, $-NO_2$, $-N(R^7)_2$, $-C(=O)OR^8$, $-OC(=O)R^8$, $-C(=O)R^8$, $-C(=O)N(R^7)_2$, and $-N(R^7)C(=O)R^8$.

In some embodiments, a compound is provided comprising the structure:

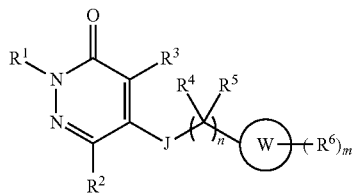

(XII)

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-NO_2$, and a leaving group;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO₂, and a leaving group;

J is selected from the group consisting of N(R⁷), S, O, C(=O), C(=O)O, OC(=O), C(=O)N(R⁷), N(R⁷)C(=O), CH₂O, and a bond;

R⁴ and R⁵ are each independently selected from the group consisting of hydrogen, alkyl optionally substituted, and a leaving group, or optionally any two of R⁴ and R⁵ are joined together to form a ring;

n is 0, 1, 2, or 3;

W is heteroaryl, naphthyl, or heterocyclyl;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹')₃, —OR⁸, and a leaving group;

m is 0, 1, 2, 3, 4, 5, 6, or 7;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halo, and a leaving group; and each R⁹' is independently selected from the group consisting of halo, alkyl optionally substituted, aryl optionally substituted, and a leaving group, provided that at least one leaving group is present in the compound.

In some embodiments, a compound is provided comprising the structure:

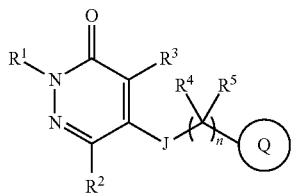

(XIII)

or a salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and a leaving group;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO₂, and a leaving group;

J is selected from the group consisting of N(R⁷), S, O, C(=O), C(=O)O, OC(=O), C(=O)N(R⁷), N(R⁷)C(=O), CH₂O, and a bond;

R⁴ and R⁵ are each independently selected from the group consisting of hydrogen, alkyl optionally substituted, and a leaving group, or optionally any two of R⁴ and R⁵ are joined together to form a ring;

n is 0, 1, 2, or 3;

Q has the structure:

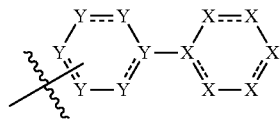

each Y and each X is independently selected from the group consisting of C, C(R⁶), C(R⁶)₂, N, NR⁷, O, and S, provided at least one Y is not C or C(R⁶);

each ====== is independently a single or double bond.

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹')₃, —OR⁸, and a leaving group;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halo, and a leaving group; and each R⁹' is independently selected from the group consisting of halo, alkyl optionally substituted, aryl optionally substituted, and a leaving group, provided that at least one leaving group is present in the compound.

In some embodiments, a compound is provided comprising the structure:

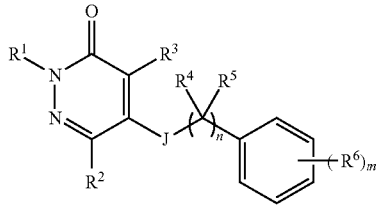

(XIV)

or a salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and a leaving group;

R³ is selected from the group consisting of hydrogen, unsubstituted alkyl or alkyl optionally substituted with a moiety other than a halogen, heteroalkyl optionally substituted, alkoxy optionally substituted, alkoxyalkyl optionally substituted, aryl optionally substituted, heteroaryl optionally substituted, —CN, and —NO₂;

J is selected from the group consisting of N(R⁷), S, O, C(=O), C(=O)O, OC(=O), C(=O)N(R⁷), N(R⁷)C(=O), CH₂O, and a bond;

R⁴ and R⁵ are each independently selected from the group consisting of hydrogen, alkyl optionally substituted, and a leaving group, or optionally any two of R⁴ and R⁵ are joined together to form a ring;

n is 0, 1, 2, or 3;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹')₃, —OR⁸, and a leaving group;

m is 0, 1, 2, 3, 4, or 5;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halo, and a leaving group; and each R⁹' is independently selected from the group consisting of halo, alkyl optionally substituted, aryl optionally substituted, and a leaving group, provided that at least one leaving group is present in the compound.

In some embodiments, a compound is provided comprising the structure:

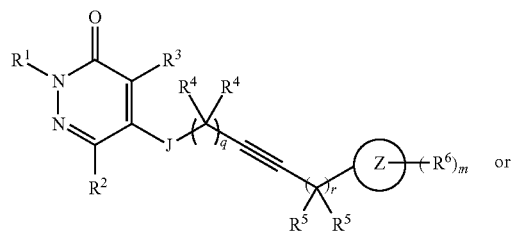

(XV)

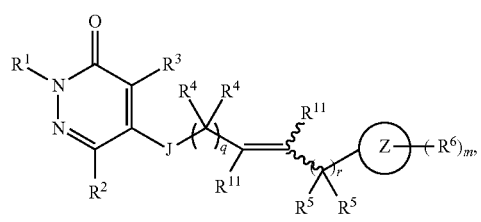

(XVI)

or a salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and a leaving group;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO₂, and a leaving group;

J is selected from the group consisting of N(R⁷), S, O, C(=O), C(=O)O, OC(=O), C(=O)N(R⁷), N(R⁷)C(=O), CH₂O, and a bond;

each R⁴, R⁵, and R¹¹ is independently selected from the group consisting of hydrogen, alkyl optionally substituted, and a leaving group, or optionally any two of R⁴ or any two of R⁵ are joined together to form a ring;

q, and r are each independently 0, 1, 2, or 3;

Z is selected from the group consisting of aryl, heteroaryl, heterocyclyl, and a bond;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^9$)$_3$, —O$R^8$, and a leaving group;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halo, and a leaving group; and each $R^{9'}$ is independently selected from the group consisting of halo, alkyl optionally substituted, aryl optionally substituted, and a leaving group, provided that at least one leaving group is present in the compound.

In some embodiments, a compound is provided comprising the structure:

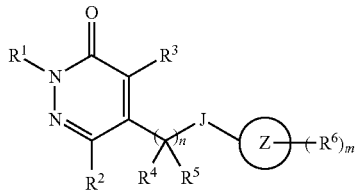

(XVII)

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, —NO$_2$, haloalkyl, and a leaving group;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and a leaving group;

J is selected from the group consisting of N($R^7$), S, O, C(=O), C(=O)O, OC(=O), C(=O)N($R^7$), N($R^7$)C(=O), and —CH$_2$O;

each $R^4$ and $R^5$ is independently selected from the group consisting of hydrogen, alkyl optionally substituted, and a leaving group, or optionally any two of $R^4$ and $R^5$ are joined together to form a ring;

n is 1, 2, or 3;

Z is selected from the group consisting of aryl, heteroaryl, heterocyclyl, and a bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^9$)$_3$, —O$R^8$, and a leaving group;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halo, and a leaving group; and each $R^{9'}$ is independently selected from the group consisting of halo, alkyl optionally substituted, aryl optionally substituted, and a leaving group, provided that at least one leaving group is present in the compound.

In some embodiments, a compound is provided comprising the structure:

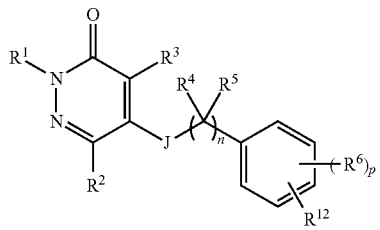

(XVIII)

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and a leaving group;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and a leaving group;

J is selected from the group consisting of consisting of N($R^7$), S, O, C(=O), C(=O)O, OC(=O), C(=O)N($R^7$), N($R^7$)C(=O), CH$_2$O, and a bond;

R⁴ and R⁵ are each independently selected from the group consisting of hydrogen, alkyl optionally substituted, and a leaving group, or optionally any two of R⁴ and R⁵ are joined together to form a ring;

n is 0, 1, 2, or 3;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹')₃, —OR⁸, and a leaving group;

p is 0, 1, 2, 3, or 4;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring; and each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halo, and a leaving group;

each R⁹' is independently selected from the group consisting of halo, alkyl optionally substituted, aryl optionally substituted, and a leaving group; and R¹² is selected from the group consisting of alkynyl optionally substituted, alkenyl optionally substituted, alkyl substituted with —CN, alkyl substituted with —C(=O)OR⁸, alkyl substituted with —C(=O)R⁸, alkyl substituted with —N(R⁷)₂, —CN, —NO₂, —N(R⁷)₂, —C(=O)OR⁸, —OC(=O)R⁸, —C(=O)R⁸, —C(=O)N(R⁷)₂, and —N(R⁷)C(=O)R⁸, provided that at least one leaving group is present in the compound.

In some embodiments, a compound is provided comprising the structure:

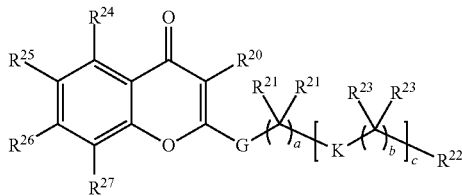

(XIX)

or a salt thereof, wherein:

R²⁰ is selected from the group consisting of hydrogen, heteroalkyl optionally substituted, alkoxy optionally substituted, alkoxyalkyl optionally substituted, aryl optionally substituted, heteroaryl optionally substituted, halo, haloalkyl, —CN, and —NO₂;

each R²¹ and R²³ is independently selected from the group consisting of hydrogen, alkyl optionally substituted, heteroalkyl optionally substituted, alkoxy optionally substituted, alkoxyalkyl optionally substituted, halo, haloalkyl, and a leaving group, or optionally any two R²¹ or any two R²³ may be joined together to form a ring;

R²² is selected from the group consisting of hydrogen, alkyl optionally substituted, heteroalkyl optionally substituted, alkoxyalkyl optionally substituted, halo, haloalkyl, —OR²⁸, —Si(R⁹)₃, —B(R⁹')₃, and a leaving group;

R²⁴, R²⁵, R²⁶, and R²⁷ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO₂, —OH, —C(=O)R⁸, —C(=O)OR⁸, —OC(=O)R⁸, —C(=O)N(R⁷)₂, —N(R⁷)C(=O)R⁸, —CN, and a leaving group;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring; and each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halo, and a leaving group;

each R⁹' is independently selected from the group consisting of halo, alkyl optionally substituted, aryl optionally substituted, and a leaving group;

R²⁸ is selected from the group consisting of hydrogen, alkyl optionally substituted, and heteroalkyl optionally substituted;

G is O, S, or NR⁸;

a is 0, 1, 2, 3, or 4;

each K is independently arylene, heteroarylene, alkenylene, or alkynylene, each optionally substituted;

each b is independently 0, 1, 2, 3, or 4; and c is 1 or 2, provided at least one leaving group is present in the compound.

In some embodiments, a compound is provided comprising the structure:

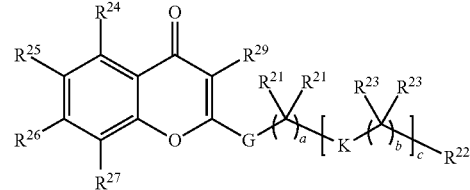

(XX)

or a salt thereof, wherein:

each R²¹ and R²³ is independently selected from the group consisting of hydrogen, alkyl optionally substituted, heteroalkyl optionally substituted, alkoxy optionally substituted, alkoxyalkyl optionally substituted, halo, haloalkyl, and a leaving group, or optionally any two $R^{21}$ or any two $R^{23}$ may be joined together to form a ring;

$R^{22}$ is selected from the group consisting of hydrogen, alkyl optionally substituted, heteroalkyl optionally substituted, alkoxyalkyl optionally substituted, halo, haloalkyl, —$OR^{28}$, —$Si(R^9)_3$, —$B(R^{9'})_3$, and a leaving group;

$R^{24}$, $R^{25}$, $R^{26}$, and $R^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —$NO_2$, —OH, —$C(=O)R^8$, —$C(=O)OR^8$, —$OC(=O)R^8$, —$C(=O)N(R^7)_2$, —$N(R^7)C(=O)R^8$, —CN, and a leaving group;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring; and each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halo, and a leaving group;

each $R^{9'}$ is independently selected from the group consisting of halo, alkyl optionally substituted, aryl optionally substituted, and a leaving group;

$R^{28}$ is selected from the group consisting of hydrogen, alkyl optionally substituted, and heteroalkyl optionally substituted;

$R^{29}$ is selected from the group consisting of hydrogen, alkyl optionally substituted, heteroalkyl optionally substituted, aryl optionally substituted, heteroaryl optionally substituted, halo, haloalkyl, —CN, —$NO_2$, and a leaving group;

G is O, S, or $NR^{28}$;

a is 0, 1, 2, 3, or 4;

each K is independently arylene, heteroarylene, alkenylene, or alkynylene, each optionally substituted, provided at least one K is alkenylene, or alkynylene;

each b is independently 0, 1, 2, 3, or 4; and c is 1 or 2, provided at least one leaving group is present in the compound.

In each of the above compounds comprising Formula (XI), (XII), (XIII), (XIV), (XV), (XVI), (XVII), (XVIII), (XIX), or (XX), each group and/or variable may optionally be selected from the groups and/or variables provided above for the corresponding imaging agents having Formula (I), (II), (III), (IV), (V), (VI), (VII), (VIII), (IX), or (X), respectively, wherein each imaging moiety in the groups provided for a compound comprising Formula (I), (II), (III), (IV), (V), (VI), (VII), (VIII), (IX), or (X) is replaced with a leaving group.

The following description of $R^6$ groups may be used in connection with a compound of Formula (I), (II), (III), (IV), (V), (VI), (VII), or (VIII). In some embodiments, for a compound of Formula (I), (II), (III), (IV), (V), (VI), (VII), or (VIII), all but one $R^6$ is H. That is, all $R^6$ are H and one $R^6$ is not H. In some cases, the one $R^6$ which is not H is substituted with the at least one leaving group. In some cases, the one $R^6$ which is not H is the at least one leaving group. In some embodiments, for a compound of Formula (I), (II), (III), (IV), (V), (VI), (VII), or (VIII), at least one $R^6$ is alkyl optionally substituted, alkoxy optionally substituted, or alkoxyalkyl optionally substituted, each substituted with a leaving group. In some embodiments, for a compound of Formula (I), (II), (III), (IV), (V), (VI), (VII), or (VIII), at least one $R^6$ is —$(CH_2)_jL_G$; wherein $L_G$ is a leaving group and j is 1, 2, 3, 4, 5, or 6. In some cases, at least one $R^6$ is —$(CH_2)L_G$, —$(CH_2)_2L_G$, —$(CH_2)_3L_G$, —$(CH_2)_4L_G$, —$(CH_2)_5L_G$, —$(CH_2)_6L_G$, —$(CH_2)_7L_G$, —$(CH_2)_8L_G$, —$(CH_2)_9L_G$, or —$(CH_2)_{10}L_G$. In some embodiments, at least one $R^6$ is —$O(CH_2)_jL_G$; wherein $L_G$ is a leaving group and j is 1, 2, 3, 4, 5, or 6. In some cases, at least one $R^6$ is —$O(CH_2)_5L_G$, —$O(CH_2)_6L_G$, —$O(CH_2)_7L_G$, —$O(CH_2)_8L_G$, —$O(CH_2)_9L_G$, or —$O(CH_2)_{10}L_G$. In some embodiments, at least one $R^6$ is —$(CH_2)_jO(CH_2)_jL_G$; wherein $L_G$ is a leaving group and each j is independently 1, 2, 3, 4, 5, or 6. In some embodiments, at least one $R^6$ is —$(CH_2)O(CH_2)_jL_G$; wherein $L_G$ is a leaving group and each j is independently 1, 2, 3, 4, 5, or 6. In some cases, at least one $R^6$ is —$CH_2O(CH_2)L_G$, —$CH_2O(CH_2)_2L_G$, —$CH_2O(CH_2)_3L_G$, —$CH_2O(CH_2)_4L_G$, —$CH_2O(CH_2)_5L_G$, —$CH_2O(CH_2)_6L_G$, —$CH_2O(CH_2)_7L_G$, —$CH_2O(CH_2)_8L_G$, —$CH_2O(CH_2)_9L_G$, or —$CH_2O(CH_2)_{10}L_G$. In some embodiments, at least one $R^6$ is —C≡C—$(CH_2)_jL_G$; wherein $L_G$ is a leaving group and j is 1, 2, 3, 4, 5, or 6. In some embodiments, at least one $R^6$ is —$[(CH_2)_jO]_j(CH_2)_jL_G$; wherein $L_G$ is a leaving group and each j is independently 1, 2, 3, 4, 5, or 6. In some embodiments, at least one $R^6$ is —$O[(CH_2)_jO]_j(CH_2)_jL_G$; wherein $L_G$ is a leaving group and each j is independently 1, 2, 3, 4, 5, or 6. In some embodiments, at least one $R^6$ is optionally substituted alkyl substituted with a leaving group. In some embodiments, at least one $R^6$ is —$C(=O)O(CH_2)_jL_G$; wherein $L_G$ is a leaving group and j is 1, 2, 3, 4, 5, or 6. In some embodiments, at least one $R^6$ is —$C(=O)(CH_2)_jL_G$; wherein $L_G$ is a leaving group and j is 1, 2, 3, 4, 5, or 6. In some embodiments, at least one $R^6$ is —$(CH_2)_jNH(CH_2)_jL_G$; wherein $L_G$ is a leaving group and each j is independently 1, 2, 3, 4, 5, or 6. In some embodiments, at least one $R^6$ is $Si(R^9)_2L_G$, wherein each $R^9$ is alkyl optionally substituted and wherein $L_G$ is a leaving group. In some embodiments, at least one $R^6$ is $B(R^{9'})_2L_G$, wherein each $R^{9'}$ is alkyl optionally substituted and wherein $L_G$ is a leaving group, or optionally, two $R^{9'}$ join together to form a ring which is a portion of leaving, or optionally, one $R^{9'}$ is absent, for example:

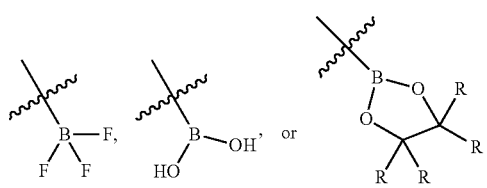

(e.g., wherein each R is alkyl or aryl), In some embodiments, at least one $R^6$ is selected from the group consisting of —C≡C—$CH_2CH_2CH_2L_G$, —C≡C—$CH_2CH_2L_G$, —C≡C—$CH_2L_G$, —$CH_2L_G$, —$(CH_2)_2L_G$, —$(CH_2)_3L_G$, —$(CH_2)_4L_G$, —$(CH_2)_5L_G$, —$(CH_2)_6L_G$, —$OCH_2L_G$, —$O(CH_2)_2L_G$, —$O(CH_2)_3L_G$, —$O(CH_2)_4L_G$, —$O(CH_2)_5L_G$, —$O(CH_2)_6L_G$, —$CH_2O(CH_2)_2L_G$, —$CH(CH_3)O(CH_2)_2L_G$, —$CH_2O(CH_2)_3L_G$, —$CD_2O(CH_2)_2L_G$, —$(CH_2)_2O(CH_2)_2L_G$, —$CHBrC(CH_3)_2L_G$, —$CHClC(CH_3)_2L_G$, —CHFC(CH$_3$)$_2$L$_G$, —C(=O)OCH$_2$L$_G$, —C(=O)O(CH$_2$)$_2$L$_G$, —C(=O)O(CH$_2$)$_3$L$_G$, —CH$_2$NH(CH$_2$)$_2$L$_G$, —CH$_2$NHCH$_2$L$_G$, —CH$_2$O(CH$_2$)$_2$O(CH$_2$)$_2$L$_G$, —CH$_2$O(CH$_2$)$_2$O(CH$_2$)$_3$L$_G$, —O(CH$_2$)$_2$O(CH$_2$)$_2$L$_G$, —C(=O)(CH$_2$)$_2$L$_G$, and —C(=O)(CH$_2$)$_3$L$_G$. For a compound of Formula (XI) or (XII), each of the R$^6$ groups described herein may be combined with any R$^1$, R$^2$, R$^3$, R$^4$, R$^5$, R$^7$, R$^8$, R$^9$, R$^{9'}$, J, W, m, and n, or combinations thereof, as described herein. For a compound of Formula (XIII), each of the R$^6$ groups described herein may be combined with any R$^1$, R$^2$, R$^3$, R$^4$, R$^5$, R$^7$, R$^8$, R$^9$, R$^{9'}$, Q, J, and n, or combinations thereof, as described herein. For a compound of Formula (XIV), each of the R$^6$ groups described herein may be combined with any R$^1$, R$^2$, R$^3$, R$^4$, R$^5$, R$^7$, R$^8$, R$^9$, R$^{9'}$, J, m, and n, or combinations thereof, as described herein. For a compound of Formula (XV) or (XVI), each of the R$^6$ groups described herein may be combined with any R$^1$, R$^2$, R$^3$, R$^4$, R$^5$, R$^7$, R$^8$, R$^9$, R$^{9'}$, R11, J, Z, m, q, and r, or combinations thereof, as described herein. For a compound of Formula (XVII), each of the R$^6$ groups described herein may be combined with any R$^1$, R$^2$, R$^3$, R$^4$, R$^5$, R$^7$, R$^8$, R$^9$, R$^{9'}$, J, Z, n, and m, or combinations thereof, as described herein. For a compound of Formula (XVIII), each of the R$^6$ groups described herein may be combined with any R$^1$, R$^2$, R$^3$, R$^4$, R$^5$, R$^7$, R$^8$, R$^9$, R$^{9'}$, R$^{12}$, J, p, and n, or combinations thereof, as described herein.

The following description of R$^{22}$ groups may be used in connection with a compound of Formula (XIX) or (XX). In some embodiments, R$^{22}$ is a leaving group. In some embodiments, R$^{22}$ is substituted with a leaving group. In some embodiments, R$^{22}$ is alkyl optionally substituted, alkoxy optionally substituted, or alkoxyalkyl optionally substituted, each substituted with a leaving group. In some embodiments, R$^{22}$ is —Si(R$^9$)$_3$ or —B(R$^{9'}$)$_3$. In some embodiments, R$^{22}$ is —(CH$_2$)$_j$L$_G$; wherein L$_G$ is a leaving group and j is 1, 2, 3, 4, 5, or 6. In some cases, R$^{22}$ is —(CH$_2$)L$_G$, —(CH$_2$)$_2$L$_G$, —(CH$_2$)$_3$L$_G$, —(CH$_2$)$_4$L$_G$, —(CH$_2$)$_5$L$_G$, —(CH$_2$)$_6$L$_G$, —(CH$_2$)$_7$L$_G$, —(CH$_2$)$_8$L$_G$, —(CH$_2$)$_9$L$_G$, or —(CH$_2$)$_{10}$L$_G$. In some embodiments, R$^{22}$ is —O(CH$_2$)$_j$L$_G$; wherein L$_G$ is a leaving group and j is 1, 2, 3, 4, 5, or 6. In some cases, R$^{22}$ is —O(CH$_2$)L$_G$, —O(CH$_2$)$_2$L$_G$, —O(CH$_2$)$_3$L$_G$, —O(CH$_2$)$_4$L$_G$, —O(CH$_2$)$_5$L$_G$, —O(CH$_2$)$_6$L$_G$, —O(CH$_2$)$_7$L$_G$, —O(CH$_2$)$_8$L$_G$, —O(CH$_2$)$_9$L$_G$, or —O(CH$_2$)$_{10}$L$_G$. In some embodiments, R$^{22}$ is —(CH$_2$)O(CH$_2$)$_j$L$_G$; wherein L$_G$ is a leaving group and each j is independently 1, 2, 3, 4, 5, or 6. In some embodiments, R$^{22}$ is —(CH$_2$)O(CH$_2$)$_j$L$_G$; wherein L$_G$ is a leaving group and each j is independently 1, 2, 3, 4, 5, or 6. In some cases, R$^{22}$ is —CH$_2$O(CH$_2$)L$_G$, —CH$_2$O(CH$_2$)$_2$L$_G$, —CH$_2$O(CH$_2$)$_3$L$_G$, —CH$_2$O(CH$_2$)$_4$L$_G$, —CH$_2$O(CH$_2$)$_5$L$_G$, —CH$_2$O(CH$_2$)$_6$L$_G$, —CH$_2$O(CH$_2$)$_7$L$_G$, —CH$_2$O(CH$_2$)$_8$L$_G$, —CH$_2$O(CH$_2$)$_9$L$_G$, or —CH$_2$O(CH$_2$)$_{10}$L$_G$. In some embodiments, R$^{22}$ is —C≡C—(CH$_2$)$_j$L$_G$; wherein L$_G$ is a leaving group and j is 1, 2, 3, 4, 5, or 6. In some embodiments, R$^{22}$ is —[(CH$_2$)$_j$O]$_j$(CH$_2$)$_j$L$_G$; wherein L$_G$ is a leaving group and each j is independently 1, 2, 3, 4, 5, or 6. In some embodiments, R$^{22}$ is —O[(CH$_2$)$_j$O]$_j$(CH$_2$)$_j$L$_G$; wherein L$_G$ is a leaving group and each j is independently 1, 2, 3, 4, 5, or 6. In some embodiments, R$^{22}$ is optionally substituted alkyl substituted with a leaving group. In some embodiments, R$^{22}$ is —C(=O)O(CH$_2$)$_j$L$_G$; wherein L$_G$ is a leaving group and j is 1, 2, 3, 4, 5, or 6. In some embodiments, R$^{22}$ is —C(=O)(CH$_2$)L$_G$; wherein L$_G$ is a leaving group and j is 1, 2, 3, 4, 5, or 6. In some embodiments, R$^{22}$ is —(CH$_2$)$_j$NH(CH$_2$)$_j$L$_G$; wherein L$_G$ is a leaving group and each j is independently 1, 2, 3, 4, 5, or 6. In some embodiments, R$^{22}$ is Si(R$^9$)$_2$L$_G$, wherein each R$^9$ is alkyl optionally substituted and wherein L$_G$ is a leaving group. In some embodiments, R$^{22}$ is B(R$^{9'}$)$_2$L$_G$, wherein each R$^{9'}$ is alkyl optionally substituted and wherein L$_G$ is a leaving group. In some embodiments, R$^{22}$ is selected from the group consisting of —C≡C—CH$_2$CH$_2$CH$_2$L$_G$, —C≡C—CH$_2$CH$_2$L$_G$, —C≡C—CH$_2$L$_G$, —CH$_2$L$_G$, —(CH$_2$)$_2$L$_G$, —(CH$_2$)$_3$L$_G$, —(CH$_2$)$_4$L$_G$, —(CH$_2$)$_5$L$_G$, —(CH$_2$)$_6$L$_G$, —OCH$_2$L$_G$, —O(CH$_2$)$_2$L$_G$, —O(CH$_2$)$_3$L$_G$, —O(CH$_2$)$_4$L$_G$, —O(CH$_2$)$_5$L$_G$, —O(CH$_2$)$_6$L$_G$, —CH$_2$O(CH$_2$)$_2$L$_G$, —CH(CH$_3$)O(CH$_2$)$_2$L$_G$, —CH$_2$O(CH$_2$)$_3$L$_G$, —CD$_2$O(CH$_2$)$_2$L$_G$, —(CH$_2$)$_2$O(CH$_2$)$_2$L$_G$, —CHBrC(CH$_3$)$_2$L$_G$, —CHClC(CH$_3$)$_2$L$_G$, —CHFC(CH$_3$)$_2$L$_G$, —C(=O)OCH$_2$L$_G$, —C(=O)O(CH$_2$)$_2$L$_G$, —C(=O)O(CH$_2$)$_3$L$_G$, —CH$_2$NH(CH$_2$)$_2$L$_G$, —CH$_2$NHCH$_2$L$_G$, —CH$_2$O(CH$_2$)$_2$O(CH$_2$)$_2$L$_G$, —CH$_2$O(CH$_2$)$_2$O(CH$_2$)$_3$L$_G$, —O(CH$_2$)$_2$O(CH$_2$)$_2$L$_G$, —C(=O)(CH$_2$)$_2$L$_G$, and —C(=O)(CH$_2$)$_3$L$_G$. For a compound of Formula (XIX), each of the R$^{22}$ groups described herein may be combined with any R$^7$, R$^8$, R$^{20}$, R$^{21}$, R$^{23}$, R$^{24}$, R$^{25}$, R$^{26}$, R$^{27}$, R$^{28}$, G, a, K, b, and c, or combinations thereof, as described herein. For a compound of Formula (XX), each of the R$^{22}$ groups described herein may be combined with any R$^7$, R$^8$, R$^{21}$, R$^{23}$, R$^{24}$, R$^{25}$, R$^{26}$, R$^{27}$, R$^{28}$, R$^{29}$, G, a, K, b, and c, or combinations thereof, as described herein.

As described in more detail herein, in some embodiments, a diagnostic kit is provided comprising one or more vials containing a compound as described in this section or a salt thereof (e.g., a compound comprising Formula (XI), (XII), (XIII), (XIV), (XV), (XVI), (XVII), (XVIII), (XIX), or (XX)), and optionally other components. In some embodiments, the diagnostic kit is for the preparation of diagnostic agents for imaging, detecting, and/or monitoring myocardial perfusion in a subject. In some embodiments, said other components are selected from the group consisting of ancillary ligands, reducing agents, transfer ligands, buffers, lyophilization aids, stabilization aids, solubilization aids, and bacteriostats.

As described in more detail herein, in some embodiments, methods for forming an imaging agent are provided, the method comprising reacting a compound as described in this section or a salt thereof (e.g., a compound comprising Formula (XI), (XII), (XIII), (XIV), (XV), (XVI), (XVII), (XVIII), (XIX), or (XX)) with an $^{18}$F-containing species to produce an imaging agent comprising $^{18}$F (e.g., a compound comprising Formula (I), (II), (III), (IV), (V), (VI), (VII), (VIII), (IX), or (X), respectively).

Salts

In some embodiments, the imaging agents and precursors described herein may be salts. In some cases, the salt is a pharmaceutically acceptable salt. However, in the case of imaging agent precursors, the salt may not necessarily be a pharmaceutically acceptable salt. Those of ordinary skill in the art will be aware of suitable counter anions for forming a salt of the imaging agents and imaging agent precursors described herein. In addition, those of ordinary skill in the art will be aware that the counter anion $X^\ominus$ may have a charge of less than −1 (e.g., −2, −3), and in such embodiments, each counter anion $X^\ominus$ may be associated with more than one molecule of the compound. In some embodiments, the counter ion is a halide, phosphate, hydrogen phosphate, dihydrogen phosphate, hydrogen sulfate, sulfate, trifluoroacetate, toluenesulfonate, acetate, formate, citrate, ascorbate, mesylate (methanesulfonate), triflate (trifluoromethanesulfonate), tartrate, lactate, or benzoate. Additional non-limiting examples of suitable counter anions include the conjugate base of inorganic acids (e.g., chloride, bromide, iodide, fluoride, nitrate, sulfate, phosphate) or from the conjugate base of organic acids (e.g., carboxylate, acetate, benzoate, tartrate, adipate, lactate, formate, maleate, glutamate, ascorbate, citrate, gluconate, oxalate, succinate, pamoate, salicylate, isethionate, succinamate, mono-diglycollate, di-isobutyrate, glucoheptonate). Still yet other non-limiting examples of salts include adipate, alginate, aminosalicylate, anhydromethylenecitrate, arecoline, aspartate, bisulfate, camphorate, digluconate, dihydrobromide, disuccinate, glycerophosphate, hemisulfate, fluoride, iodide, methylenebis(salicylate), napadisylate, oxalate, pectinate, persulfate, phenylethylbarbiturate, picrate, propionate, thiocyanate, tosylate, undecanoate, acetate, benzenesulfonate, benzoate, bicarbonate, bitartrate, bromide, calcium edentate, camyslate, carbonate, chloride, citrate, dihydrochloride, edentate, edisylate, estolate, esylate, fumarate, gluceptate, gluconate, glutamate, glycollylarsanilate, hexylresorcinate, hydrabamine, bromide, chloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, teoclate, and triethiodide (see Berge et al., *Journal of Pharmaceutical Sciences,* 66(1), 1977, 1-19).

Methods of Synthesizing Imaging Agents

In other aspects, methods are provided for synthesizing imaging agents. The methods described herein may be used for the synthesis of a variety of imaging agents as described herein from imaging agent precursors as described herein. Generally, an imaging agent may be synthesized by reacting an imaging agent precursor with a reactant comprising the imaging moiety. In some cases, the reaction involves the formation of a covalent bond between the imaging agent precursor and the imaging moiety of the reactant. In other cases, however, the reaction involves non-covalent association of an imaging moiety with an imaging agent precursor (e.g., via chelation). The following sections provide a number of non-limiting embodiments for forming an imaging agent from an imaging agent precursor. Those of ordinary skill in the art will be aware of other suitable methods and techniques for forming an imaging agent from an imaging agent precursor. In addition, other steps which may be conducted in connection with the synthesis of an imaging agent (e.g., formulation, purification) are also described.

In some cases, the imaging agent is formed by reacting an imaging agent precursor with an imaging moiety. In certain embodiments, a method involves reacting an imaging agent precursor comprising a leaving group with a source of an imaging moiety (e.g., a fluoride species). For example, the imaging moiety replaces the leaving group via a substitution reaction, such as an $S_N2$ or $S_N1$ reaction. That is, during the reaction an imaging moiety replaces the leaving group, thereby producing the imaging agent.

The methods described herein may be used for the synthesis of a wide variety of imaging agents from an imaging agent precursor. Generally, the imaging agent precursor may include at least one leaving group that may be displaced by an imaging moiety, such as an $^{18}F$ species. Imaging agent precursors may be synthesized using methods known to those of ordinary skill in the art.

A. General Reaction Conditions

The synthetic methods described herein may be carried out in any suitable solvent, including, but not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane.), and alcohol solvents (e.g., ethanol, methanol, propanol, isopropanol, tert-butanol). In certain embodiments, a protic solvent is used. In other embodiments, an aprotic solvent is used. Non-limiting examples of solvents useful in the synthetic methods include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine.

The methods may be carried out at any suitable temperature. In some cases, the method is carried out at about room temperature (e.g., about 20° C., between about 20° C. and about 25° C., about 25° C., or the like). In some cases, however, the method is carried out at a temperature below or above room temperature, for example, at about −78° C. at about −70° C., about −50° C., about −30° C., about −10° C., about −0° C., about 10° C., about 30° C., about 40° C., about 50° C., about 60° C., about 70° C., about 80° C., about 90° C., about 100° C., about 120° C., about 140° C., or the like. In some embodiments, the method is carried out at temperatures above room temperature, for example, between about 25° C. and about 120° C., or between about 25° C. and about 100° C., or between about 40° C. and about 120° C., or between about 80° C. and about 120° C. The temperature may be maintained by reflux of the solution. In some cases, the method is carried out at temperatures between about −78° C. and about 25° C., or between about 0° C. and about 25° C.

The methods described herein may be carried out at any suitable pH, for example, equal to or less than about 13, equal to or less than about 12, equal to or less than about 11, equal to or less than about 10, equal to or less than about 9, equal to or less than about 8, equal to or less than about 7, or equal to or less than about 6. In some cases, the pH may be greater than or equal to 1, greater than or equal to 2, greater than or equal to 3, greater than or equal to 4, greater than or equal to 5, greater than or equal to 6, greater than or equal to 7, or greater than or equal to 8. In some cases, the pH may be between about 2 and about 12, or between about 3 and about 11, or between about 4 and about 10, or between about 5 and about 9, or between about 6 and about 8, or about 7.

The percent yield of a product may be greater than about 60%, greater than about 70%, greater than about 75%, greater than about 80%, greater than about 85%, greater than about 90%, greater than about 92%, greater than about 95%, greater than about 96%, greater than about 97%, greater than about 98%, greater than about 99%, or greater.

B1. Halogenation

In some embodiments, an imaging agent is formed by reacting an imaging agent precursor with an imaging moiety. In certain embodiments, an imaging agent precursor comprises at least one leaving group that is susceptible to being displaced by an imaging moiety, such as, for example, a halogen (e.g., $^{18}F$, $^{76}Br$, $^{124}I$, $^{131}I$). Thus, in certain embodiments, the methods described herein involve reacting an imaging agent precursor comprising a leaving group with a source of an imaging moiety.

In some embodiments, a halide displaces a leaving group on a provided imaging agent precursor via a substitution reaction, such as an $S_N2$ or $S_N1$ reaction, thereby producing an imaging agent. For example, a halide such as fluoride may displace a sulfonate leaving group of the imaging agent precursor to yield a fluorinated imaging agent. In certain embodiments, a substitution reaction is a one-step procedure which does not require a subsequent deprotection step. That is, the substitution step is performed on a fully deprotected imaging agent precursor. In certain embodiments, a substitution reaction provided by the present invention produces a fluorinated imaging agent (e.g., an imaging agent comprising $^{18}$F).

In some embodiments, a provided imaging agent is synthesized via an aryl or heteroaryl halogenation reaction (e.g., aryl fluorination, aryl bromination, aryl iodination). Many techniques for synthesizing aryl or heteroaryl halides are known in the art. For example, in certain embodiments, an imaging agent comprising an $^{124}$I, $^{131}$I, or $^{76}$Br imaging moiety is synthesized via a Sandmeyer reaction from an aryl diazonium imaging agent precursor, with or without the use of copper(I) catalysis (see, for example, Beletskaya et al., *Synthesis,* 2007, 2534-2538; Hubbard et al., *J. Org. Chem.,* 2008, 73, 316-319; Filimonov et al., *Org. Lett.,* 2008, 10, 3961-3964; Krasnokutskaya et al., *Synthesis,* 2007, 81-84). In other embodiments, an imaging agent comprising an $^{18}$F imaging moiety is synthesized via a related Balz-Schiemann reaction from a diazonium imaging agent precursor. In certain embodiments, an imaging agent comprising a $^{124}$I or $^{131}$I imaging moiety is synthesized via an "aromatic Finkelstein" reaction from an aryl bromide imaging agent precursor (see, for example, A. Klapars, S. L. Buchwald, *J. Am. Chem. Soc.,* 2002, 124, 14844-14845). In other embodiments, an imaging agent comprising an $^{124}$I, $^{131}$I, or $^{76}$Br imaging moiety is synthesized by allowing a boronic acid or ester imaging agent precursor to react with the appropriate N-halosuccinimide reagent (Thiebes et al., *Synlett,* 1998, 141-142) or copper bromide reagent (see, for example, Murphy et al., *J. Am. Chem. Soc.,* 2007, 129, 15434-15435; Thompson et al., *Synthesis,* 2005, 547-550). In some embodiments, an imaging agent comprising a $^{76}$Br imaging moiety is synthesized via an organotrifluoroborate imaging agent precursor (see, for example, G. W. Kabalka, A. R. Mereddy, *Organometallics,* 2004, 23, 4519-4521). One of ordinary skill in the art will appreciate that there are many other conditions under which activated or deactivated arenes may be halogenated (see, for example, Kraszkiewicz et al., *Synthesis,* 2006, 1195-1199; Ganguly et al., *Synthesis,* 2010, 1467-1472; Iskra et al., *Synthesis,* 2004, 1869-1873; Castanet et al., *Tetrahedron Lett.,* 2002, 43, 5047-5048; Prakash et al., *J. Am. Chem. Soc.,* 2004, 126, 15570-15776; Lulinski et al., *Synthesis,* 2004, 441-445; Ganguly et al., *Synthesis,* 2005, 1103-1108; Rajesh et al., *Org. Chem.,* 2007, 72, 5867-5869; Kumar et al., *Synthesis,* 2010, 1629-1632; Zhou et al., *Synthesis,* 2011, 207-209; Menzel et al., *J. Org. Chem.,* 2006, 71, 2188-2191), and such a reaction may be employed in certain embodiments to synthesize imaging agents described herein. One of ordinary skill in the art will also appreciate that many of the aryl halogenation reactions described herein will also be effective for generating a haloalkene- or haloalkyne-containing imaging agent, as well as haloheteroaryl-containing imaging agents.

In some embodiments, an imaging agent comprising an $^{18}$F imaging moiety is synthesized via an aryl fluorination. See, for example, Furuya et al., *Synthesis,* 2010(11): 1804-1821 (2010), for an informative review of aryl fluorination reactions. For example, in certain embodiments, an imaging agent comprising an $^{18}$F imaging moiety is synthesized via a nucleophilic fluorination reaction. Examples of nucleophilic fluorination reactions include, but are not limited to, the Halex process (Adams et al., *Chem Soc Rev* 1999; 28:225; Horwitz et al., *J. Org. Chem* 1961; 26:3392; Barlin et al., *J. Chem. Soc., Perkin Trans* 1 1972:1269; Pike et al., *J. Chem. Soc., Chem Commun* 1995:2215; Shah et al., *J. Chem. Soc., Perkin Trans* 1 1998:2043; Ermert et al., *J Labelled Compd Radiopharm* 2004; 47:429), fluorodenitration (Adams et al., *Chem Soc Rev* 1999; 28:225; Adams et al., *J. Fluorine Chem* 1998; 92:127), displacement of ammonium with fluoride (Angelini et al., *J. Fluorine Chem* 1985; 27:177), and fluorination of diaryliodonium salts (Zhdankin et al., *Chem Rev* 2008; 108:5299; Beringer et al., *J. Am. Chem Soc* 1953; 75:2708; Ross et al., *J. Am. Chem Soc* 2007; 129:8018). Trialkylammonium fluoride reagents may also be employed in nucleophilic fluorination reactions (Sun et al., *Angew. Chem., Int. Ed* 2006; 45:2720; Grushin et al., *Organometallics* 2008; 27:4825). In certain embodiments, a nucleophilic fluorination reaction is Palladium catalyzed (see, for example, Grushin et al., *Organometallics* 2008; 27:4825; Watson et al., *Science* 2009; 325:1661). In other embodiments, an imaging agent comprising an $^{18}$F imaging moiety is synthesized via an electrophilic fluorination reaction. Examples of electrophilic fluorination reactions include, but are not limited to, fluorination of aryl Grignard reagents (Anbarasan P, Neumann H, Beller M. *Angew Chem, Int Ed.* 2010; 49:2219), fluorination of arylmagnesium reagents (Yamada S, Gavryushin A, Knochel P. *Angew Chem, Int Ed.* 2010; 49:2215), fluorination of organometallic reagents such as arylzinc halides, arylsilanes, arylstannanes, arylgermaniums, arylboronic ester, or arylboronic acids (Bryce et al., *J. Chem. Soc, Chem Commun* 1986:1623; Tius et al., *Synth Commun* 1992; 22:1461; Cazorla et al., *Tetrahedron Lett* 2009; 50:3936), fluorination of arylsilanes (Lothian et al., *Synlett* 1993:753), and fluorodestannylation reactions (Lothian et al., *Synlett* 1993:753; Namavari et al., *Appl Radiat Isot* 1992; 43:989.). In some embodiments, an electrophilic fluorination reaction employs stoichiometric or catalytic palladium (see, for example, Furuya et al., *Angew Chem, Int Ed* 2008; 47:5993) or silver (see, for example, Furuya et al., *J. Am. Chem Soc* 2009; 131:1662; Furuya et al., *Org Lett* 2009; 11:2860).

B2. Fluorination

It should be understood, that while the following section focuses on fluorination reactions, this is by no means limiting, and the teachings of this section may be applied to other halogenation reactions.

In some embodiments, a method for synthesizing an imaging agent comprises contacting an imaging agent precursor of the invention with a fluoride species resulting in the fluoride species replacing the leaving group of the precursor to produce an imaging agent. In some embodiments, an inventive method employs a reaction described herein, such as in the description of halogenation reactions above.

In certain embodiments, a method for synthesizing an imaging agent involves a nucleophilic fluorination reaction. It will be understood that the discussion of nucleophilic fluorination is exemplary of the methods described herein and is not limiting. In certain embodiments, an imaging agent precursor comprising a leaving group is reacted in the presence of a fluoride species, whereby $S_N2$ or $S_N1$ displacement of the leaving group by the fluoride species produces an imaging agent. In some embodiments, for a composition, a fluoride species is isotopically enriched with $^{18}$F.

Those of ordinary skill in the art will be aware of suitable conditions for fluorinating a compound. For example, see International Patent Application PCT/US2011/024109, filed Feb. 8, 2011, to Cesati et al., and International Patent Application No. PCT/US2005/004687, filed Feb. 11, 2005, to Casebier et al., each incorporated by reference herein for all purposes. In some cases, the source of fluorine is a fluoride salt (e.g., KF, NaF, tetralkylammonium fluoride).

In some embodiments, a fluorinating agent for use in a provided method is a source of fluoride. In certain embodiments, a fluorinating agent for use in a provided method is NaF or KF. In certain embodiments, a fluorinating agent for use in a provided method is isotopically enriched with $^{18}$F. In certain embodiments, suitable conditions for a fluorination reaction according to the present invention comprise the presence of an ammonium salt or a bicarbonate salt.

The fluorine source may comprise or be associated with or may be used in connection with another reagent. In some embodiments, an additional reagent may be capable of enhancing the reactivity of the fluorine species or otherwise facilitating conversion of the precursor to the imaging agent. For example, in certain embodiments, an additional reagent is used in combination with a multidentate ligand, such as a crown ether or a cryptand that is capable of chelating a metal ion. In certain embodiments, a multidentate ligand is, for example, 4,7,13,16,21,24-hexaoxa-1,10-diazabicyclo [8.8.8]-hexacosane (i.e., Kryptofix® 222). In certain embodiments, when KF is a fluorine source, cryptands having a high affinity for potassium are useful as they chelate potassium and thereby increase the reactivity of the fluoride ion. In some embodiments, cryptands having an affinity for potassium near that of Kryptofix® 222 (e.g., 75%, 80%, 85%, 90%, 95%, or more of the Kryptofix® 222's affinity for potassium) are used. The reaction conditions may comprise one or more solvents.

In some embodiments, the fluorination occurs in the presence of $K_2CO_3$ and Kryptofix® 222 (or any another cryptand having affinity for the cation of interest, including for example potassium, near that of Kryptofix® 222) in MeCN (acetonitrile) alone or in combination with another solvent. In some embodiments, the molar ratio of $K_2CO_3$ to imaging agent precursor ranges from about 0.25:1 to about 5:1, for example 0.5:1 to 1:1.

In some embodiments, fluorination occurs in the presence of tetraalkylammonium carbonate or tetraalkylammonium bicarbonate in MeCN as the solvent. In some embodiments, the molar ratio of tetraalkylammonium carbonate or bicarbonate to imaging agent precursor is less than about 2:1. Other molar ratios are provided herein.

In certain embodiments, the synthetic methods described herein involve a single-step preparation of imaging agents of the invention. In certain embodiments, a single-step method involves fluorination of a precursor in the presence of, for example, $K_2CO_3$/Kryptofix® 222 (or other suitable alternatives to Kryptofix® 222) or tetraalkylammonium carbonate or bicarbonate (e.g., in MeCN alone or in an MeCN mixture).

In certain embodiments, single-step preparation methods are particularly suitable when particular salt forms of the imaging agent precursors of the invention are used, such as halide, acetate, formate, citric, ascorbate, trifluoroacetate, tolunesulfonate, benzoate, acetate, phosphate, sulfate, tosylate, and mesylate.

In some embodiments, one or more reagents are used in a reaction mixture comprising an imaging agent precursor and a fluoride species. A "reagent," also referred to as an "additive," is used herein to mean any chemical compound added to a reaction mixture. A reagent may be consumed or not consumed during the reaction. A reagent may be a stoichiometric or catalytic reagent. Exemplary reagents include catalysts, salts, oxidants, reductants, chelating agents, bases, acids, metals, phase transfer reagents, and others as would be appreciated by one of skill in the art.

A reagent may, in some embodiments, facilitate reaction between an imaging agent precursor and a fluoride species and/or may aid in stabilizing a resultant imaging agent. For example, in certain embodiments, a fluoride species may have relatively low reactivity (e.g., nucleophilicity), and addition of certain reagents may enhance the reactivity of the fluoride species. As an illustrative embodiment, a fluorine species may be a negatively charged fluoride ion (e.g., an isotopically enriched $^{18}$F ion), and a reagent may be used to bind to any positively charged counter ions present within the reaction mixture, thereby enhancing the reactivity of the fluoride ion. An example of such a reagent is a cryptand such as, but not limited to, Kryptofix® (e.g., Kryptofix® 222). In some embodiments, a reagent decreases the rate of undesired side reactions.

In some embodiments, a reagent may be combined with a fluoride species prior to its contact with an imaging agent precursor. For example, in certain embodiments, a solution comprising a fluoride species and a reagent is prepared, and the solution is added to an imaging agent precursor. In other embodiments, a solid comprising a fluoride species and a reagent is prepared, and the solid is contacted with an imaging agent precursor in solution. In certain embodiments, a fluoride species is adsorbed onto a solid support (e.g., an anion exchange column), and a solution comprising the reagent is used to elute the fluoride species from the solid support. The eluted solution is then contacted with the imaging agent precursor, or is concentrated to produce a solid, which is then contacted with the imaging agent precursor in solution.

In some embodiments, a provided reagent is a bicarbonate salt. As used herein, the term "bicarbonate salt" refers to a salt comprising a bicarbonate or hydrogen carbonate ion ($HCO_3^-$ ion). In some embodiments, a bicarbonate salt is a metal bicarbonate, such as sodium bicarbonate, calcium bicarbonate, potassium bicarbonate, and magnesium bicarbonate. In certain embodiments, a bicarbonate salt is potassium bicarbonate ($KHCO_3$). In some embodiments, a bicarbonate salt comprises a non-metal counter ion, such as ammonium bicarbonate. For example, a bicarbonate salt may be a tetraalkylammonium bicarbonate salt having the formula, $R^4NHCO_3$, wherein R is alkyl. In some embodiments, R may be lower alkyl, such as methyl, ethyl, propyl, butyl, pentyl, hexyl, or the like. In certain embodiments, the ammonium salt is $Et_4NHCO_3$. In other embodiments, the salt is $Me_4NHCO_3$, $i\text{-}Pr_4NHCO_3$, $n\text{-}Pr_4NHCO_3$, $n\text{-}Bu_4NHCO_3$, $i\text{-}Bu_4NHCO_3$, or $t\text{-}Bu_4NHCO_3$.

In some embodiments, a provided reagent is a carbonate salt. As used herein, the term "carbonate salt" refers to a salt comprising a carbonate ion ($CO_3^{-2}$ ion). In some embodiments, a carbonate salt is a metal carbonate, such as sodium carbonate, calcium carbonate, potassium carbonate, and magnesium carbonate. In certain embodiments, a carbonate salt is potassium carbonate ($K_2CO_3$). In some embodiments, a carbonate salt comprises a non-metal counter ion, such as ammonium carbonate. For example, a carbonate salt may be a tetraalkylammonium carbonate salt having the formula, $(R_4N)_2CO_3$, wherein R is alkyl. In some embodiments, R may be a lower alkyl, such as methyl, ethyl, propyl, butyl, pentyl, hexyl, or the like. In certain embodiments, the ammonium salt is $(Et_4N)_2CO_3$. In other embodiments, the salt is $(Me_4N)_2CO_3$, $(i\text{-}Pr_4N)_2CO_3$, $(n\text{-}Pr_4N)_2CO_3$, $(n\text{-}Bu_4N)_2CO_3$, $(i\text{-}Bu_4N)_2CO_3$, or $(t\text{-}Bu_4N)_2CO_3$.

Without wishing to be bound by any particular theory, use of bicarbonate, carbonate, and/or ammonium salt(s) may aid in decreasing the rate of competing reactions such as hydrolysis during nucleophilic fluorination of an imaging agent precursor.

In some embodiments, a reagent is a salt comprising a cation that forms a weakly coordinating salt with a fluoride species. As used herein, a "cation that forms a weakly coordinating salt with a fluoride species" refers to a cation that renders a fluoride species reactive in the context of a fluorination reaction. For example, a cation may not strongly bind to the fluoride species, allowing the fluoride species to act as a nucleophile during a nucleophilic fluorination reaction. Those of ordinary skill the art would be able to select an appropriate cation that would be suitable as a weakly coordinating counter ion for a fluoride species. For example, a cation may be have a relatively large atomic radius and/or may be a weak Lewis base. In some cases, a cation may be selected to be lipophilic. In some cases, a cation may comprise one or more alkyl groups. Examples of weakly coordinating cations include cesium ions, ammonium ions, weakly coordinating salts of hexamethylpiperidindium, $S(NMe_2)_3$, $P(NMe_2)_4$, tetraaalkylphosphonium salts, tetraarylphosphonium salts, (e.g., tetraphenylphosphonium), hexakis(dimethylamino)diphosphazenium, and tris(dimethylamino)sulfonium.

In some embodiments, a provided reagent is an ammonium salt, i.e., a salt comprising a substituted or unsubstituted ammonium ion. In some embodiments, an ammonium ion is a weakly coordinating cation. In some embodiments, an ammonium salt has the formula, $R_4NX$, where each R can be the same or different and is alkyl, heteroalkyl, aryl, heteroaryl, or heterocyclic, each optionally substituted, and X is a negatively charged counter ion. In some cases, R is alkyl, heteroalkyl, aryl, heteroaryl, or heterocyclic, each optionally substituted. In some embodiments, ammonium salt may include a range of negatively charged counter ions, including halides, carbonates, and bicarbonates. Examples of ammonium salts include, but are not limited to, ammonium bicarbonate salts, ammonium hydroxide salts, ammonium acetate salts, ammonium lactate salts, ammonium trifluoroacetate salts, ammonium methanesulfonate salts, ammonium p-toluenesulfonate salts, ammonium nitrate salts, ammonium halide salts (e.g., ammonium iodide salts), and ammonium bisulfate salts.

In one set of embodiments, an ammonium salt is a tetraalkylammonium salt, such as a tetraalkylammonium bicarbonate salt. For example, an ammonium salt may have the formula, $R_4NHCO_3$, wherein each R is independently alkyl. In some cases, R is optionally substituted. In some embodiments, the alkyl group is a lower $C_1-C_6$ alkyl group. In some embodiments, an tetraalkylammonium salt is a basic tetraalkylammonium salt.

In some embodiments, a salt (e.g., bicarbonate salt and/or ammonium salt) may be utilized in the reaction such that the molar ratio of the salt to the imaging agent precursor is less than or equal to about 2:1. In some cases, the molar ratio is less than or equal to about 2:1, less than or equal to about 1.9:1, less than or equal to about 1.8:1, less than or equal to about 1.7:1, less than or equal to about 1.6:1, less than or equal to about 1.5:1, less than or equal to about 1.4:1, or less than or equal to about 1.3:1, or less than or equal to about 1.25:1, or less than or equal to about 1.2:1, or less than or equal to about 1.1:1, or less than or equal to about 1:1, or less than or equal to about 0.75:1, or less than or equal to about 0.5:1, or less than or equal to about 0.25:1, or less than or equal to about 0.1:1, or less than or equal to about 0.05:1. In some cases, the ratio is greater than about 0.05:1, greater than about 0.01:1, or greater than about 0.25:1. In some embodiments, the molar ratio of salt additive to imaging agent precursor is between about 0.5:1 to about 1:1, or about 0.25:1 to about 1:1, or about 0.25:1 to about 0.75:1, about 1.49:1 to about 0.05:1, or between about 1.4:1 to about 0.25:1, or between about 0.25:1 and about 1.4:1, or between about 0.25:1 and about 1.25:1.

In some embodiments, a reagent is used in combination with a species capable of enhancing the reactivity of the fluoride species or otherwise facilitating conversion of the imaging agent precursor to the imaging agent. For example, a species may be a compound capable of chelating one or more ions (e.g., metal ions) that may be present within the reaction mixture. Without wishing to be bound by theory, a species may be used to chelate a counter ion to a fluoride species, such as a potassium ion, thereby increasing the reactivity (e.g., nucleophilicity) of the fluoride species. In certain embodiments, a reagent is used in combination with a multidentate ligand, such as a crown ether or a cryptand that is capable of chelating a metal ion. The multidentate ligand (e.g., cryptand) may be selected based on the metal ion to be chelated. A multidentate ligand may be, for example, 4,7,13,16,21,24-hexaoxa-1,10-diazabicyclo [8.8.8]-hexacosane (e.g., Kryptofix® 222). Other cryptands will be known to those of ordinary skill in the art. Some embodiments involve use of a carbonate salt in combination with 4,7,13,16,21,24-hexaoxa-1,10-diazabicyclo[8.8.8]-hexacosane. In a specific embodiment, $K_2CO_3$ and/or $KHCO_3$ is used in combination with 4,7,13,16,21,24-hexaoxa-1,10-diazabicyclo[8.8.8]-hexacosane.

In another set of embodiments, it may be advantageous to utilize the methods described herein in the absence of a cryptand. The term "cryptand" is given its ordinary meaning in the art and refers to a bi- or a polycyclic multidentate ligand for a cation. For example, inventive methods may be carried out using an ammonium salt, in the absence of a cryptand (e.g., 4,7,13,16,21,24-hexaoxa-1,10-diazabicyclo [8.8.8]-hexacosane). In some embodiments, cryptands may increase the pH of the reaction solution, which in the presence of another reagent (e.g., carbonate salt) may adversely affect the yield and/or purity of the fluorination reaction. Accordingly, in certain embodiments, carrying out the fluorination reaction, in the absence of a cryptand, and optionally in the presence of another reagent (e.g., ammonium and/or bicarbonate salt) may increase the yield and/or purity of the reaction.

In another set of embodiments, a method according to the present invention is performed in the absence of a carbonate salt.

Those of ordinary skill in the art will be able to select and/or determine an appropriate set of reaction conditions (e.g., concentration, temperature, pressure, reaction time, solvents) suitable for use in a particular application. In some embodiments, an imaging agent may be further processed using one or more purification techniques, and may optionally be combined with additional components, such as a stabilizing agent.

In some embodiments, an imaging agent is formed as a salt (e.g., a pharmaceutically acceptable salt). Pharmaceutically acceptable excipients and other aspects of pharmaceutically acceptable compositions are described herein.

Those of ordinary skill in the art would be able to select a source of a fluoride species suitable for use in the methods described herein. The term "fluoride species" as used herein refers to a fluoride atom or group of atoms comprising at least one fluoride atom, wherein the fluoride atom is capable of reacting with another compound (e.g., an imaging agent precursor). In some embodiments, an isotopically-enriched $^{18}F$ species may be produced by the nuclear reaction $^{18}O$ $(p,n)^{18}F$ from proton bombardment of $[^{18}O]H_2O$ in a cyclotron. In certain embodiments, a method may involve treating a solution of the $^{18}F$ species to remove any impurities, such as unreacted $[^{18}O]H_2O$. For example, a solution of the $^{18}F$ species may be filtered through an anion exchange column, where the $^{18}$F species is retained on the cationic resin matrix while the [$^{18}$O]H$_2$O is eluted. The $^{18}$F species is then removed by washing the anion exchange column with various mixtures of solvents and optional reagents (e.g., salt), forming an $^{18}$F-containing solution. In some embodiments, an anion exchange column is washed with an aqueous solution of a salt, such as K$_2$CO$_3$ or Et$_4$NHCO$_3$. In other embodiments, a column is washed (e.g., with aqueous K$_2$CO$_3$), and the resulting solution diluted (e.g., with MeCN) and/or concentrated (e.g., to dryness using elevated temperature and/or reduced pressure). Anhydrous [$^{18}$F]KF and/or [$^{18}$F]Et$_4$NF may be obtained and reacted with a compound or a salt thereof.

In some embodiments, a $^{18}$F-containing solution is combined with additional components prior to reaction with an imaging agent precursor. For example, one or more solvents may be added to dilute a $^{18}$F-containing solution to a desired concentration. In certain embodiments, a $^{18}$F-containing solution is diluted with acetonitrile (MeCN). In certain embodiments, a $^{18}$F-containing solution is diluted with acetonitrile (MeCN) and t-BuOH.

In some embodiments, a $^{18}$F-containing solution may be concentrated to dryness by exposure to elevated temperature and/or reduced pressure to form an anhydrous $^{18}$F-containing solid. In some embodiments, a $^{18}$F-containing solid may further comprise one or more reagents (e.g., salts). The chemical composition of a $^{18}$F-containing solid may depend on the number and kind of reagents used in preparation of the $^{18}$F-containing solution. For example, a solution of potassium carbonate may be used to elute a $^{18}$F species from the anion exchange column, thereby resulting in an $^{18}$F-containing solid comprising [$^{18}$F]KF. In another example, a solution of tetraethylammonium bicarbonate is used to elute a $^{18}$F species from the anion exchange column, thereby resulting in an $^{18}$F-containing solid comprising [$^{18}$F]Et$_4$NF.

In some embodiments, a solution comprising a $^{18}$F species is heated to a temperature ranging from room temperature to about 200° C. For example, a solution comprising a [$^{18}$F]-fluoride may be heated to elevated temperatures to encourage evaporation of the solvent (e.g., to about 110° C.). In some embodiments, a solution is heated to a temperature ranging from about 90-120° C. or from about 100-150° C. In some embodiments, a solution is heated to about 75° C., about 85° C., about 95° C., about 105° C., about 115° C., about 125° C., or greater. In some embodiments, a solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some embodiments, a solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular process. In some embodiments, a solution is concentrated to dryness at about 150 mm Hg and about 115° C. In some embodiments, a solution is concentrated to dryness at about 375 mm Hg and about 115° C. In some embodiments, a solution is concentrated to dryness at about 400 mbar and about 110-150° C. In some embodiments, a solution is concentrated to dryness at about 280 mbar and about 95-115° C.

In certain embodiments, a fluoride species and/or a reagent, if present, is then contacted with an imaging agent precursor under conditions that result in conversion of the imaging agent precursor to the imaging agent product via nucleophilic fluorination. Those of ordinary skill in the art would be able to select conditions suitable for use in a particular reaction. For example, in certain embodiments, the ratio of fluoride species to imaging agent precursor may be selected to be about 1:10,000 or more, about 1:5000 or more, about 1:3000 or more, about 1:2000 or more, about 1:1000 or more, about 1:500 or more, about 1:100 or more, about 1:50 or more, about 1:10 or more, about 1:5 or more, or, in some cases, about 1:1 or more. In some embodiments, a fluoride species may be present at about 10 mol %, or about 5 mol %, or about 3 mol %, or about 2 mol %, or about 1 mol % or about 0.5 mol %, or about 0.1 mol %, or about 0.05 mol %, or about 0.01 mol % relative to the amount of imaging agent precursor. In some embodiments, a fluoride species is isotopically enriched with $^{18}$F. For example, in some embodiments, the ratio of $^{18}$F species to imaging agent precursor may be selected to be about 1:1,000,000 or more, or about 1:500,000 or more, or about 1:250,000 or more, or about 1:100,000 or more, or about 1:50,000 or more, or about 1:25,000 or more, or about 1:10,000 or more, about 1:5000 or more, about 1:3000 or more, about 1:2000 or more, about 1:1000 or more, about 1:500 or more, about 1:100 or more, about 1:50 or more, about 1:10 or more, about 1:5 or more, or, in some cases, about 1:1 or more.

In some embodiments, a nucleophilic fluorination reaction is carried out in the presence of one or more solvents, for example, an organic solvent, a non-organic solvent (e.g., an aqueous solvent), or a combination thereof. In some embodiments, the solvent is a polar solvent or a non-polar solvent. In some embodiments, the solvent is an aqueous solution, such as water. In some embodiments, the solvent comprises at least about 0.001% water, at least about 0.01% water, at least about 0.1% water, at least about 1% water, at least about 5%, at least about 10%, at least about 20% water, at least about 30% water, at least about 40% water, at least about 50% water, or greater. In some embodiments, the solvent may comprise between about 0.1% and about 100% water, about 1% to about 90%, about 1% to about 70%, about 1% to about 50%, or about 10% to about 50%. In some embodiments, the solvent comprises no more than about 10% water, about 5% water, about 4% water, about 3% water, about 2% water, about 1% water, or about 0.5% water. In some embodiments, the solvent comprises between about 0.01% water and about 5% water, or between about 0.01% water and about 2% water, or between about 0.1% water and about 0.2% water.

Other examples of solvents useful in the methods include, but are not limited to, non-halogenated hydrocarbon solvents (e.g., pentane, hexane, heptane, cyclohexane), halogenated hydrocarbon solvents (e.g., dichloromethane, chloroform, fluorobenzene, trifluoromethylbenzene), aromatic hydrocarbon solvents (e.g., toluene, benzene, xylene), ester solvents (e.g., ethyl acetate), ether solvents (e.g., tetrahydrofuran, dioxane, diethyl ether, dimethoxyethane), and alcohol solvents (e.g., ethanol, methanol, propanol, isopropanol, tert-butanol). Other non-limiting examples of solvents include acetone, acetic acid, formic acid, dimethyl sulfoxide, dimethyl formamide, acetonitrile, p-cresol, glycol, petroleum ether, carbon tetrachloride, hexamethyl-phosphoric triamide, triethylamine, picoline, and pyridine. In some embodiments, a provided reaction is carried out in a polar solvent, such as acetonitrile. In some embodiments, a solvent may be selected so as to reduce and/or minimize the formation of side products. In certain embodiments, a fluorination reaction is carried out in MeCN as solvent. In certain embodiments, a fluorination reaction is carried out in t-BuOH as solvent. In certain embodiments, a fluorination reaction is carried out in a mixture of MeCN and t-BuOH as solvent. In certain embodiments, a fluorination reaction is carried out in DMF as solvent. In certain embodiments, a fluorination reaction is carried out in DMSO as solvent. In certain embodiments, a fluorination reaction is carried out in THF as solvent.

In certain embodiments, an anhydrous $^{18}$F-containing solid, optionally comprising a reagent, may be contacted with a solution of an imaging agent precursor (e.g., a tosylate precursor), and the resulting solution is heated to an elevated temperature for a select period of time. A solution may be, for example, an acetonitrile solution. In other embodiments, a solution of an $^{18}$F species and reagent, if present, is contacted with a solid imaging agent precursor or a solution of an imaging agent precursor.

Some embodiments involve contacting an imaging agent precursor with a fluoride species in a solution having a pH below about 13, below about 12, or below about 11. In some cases, a solution has a pH between about 8 and about 9, or between about 8 and about 10, or between about 7 and about 8. In certain embodiments, a pH range for the fluorination reaction is greater than about 6, or greater than about 7, or between about 7-13, between and including 6-12, between and including 7-12, between and including 8-12, between and including 9-12, and between and including 10-12.

In some cases, a solution comprising a $^{18}$F species, imaging agent precursor, and, optionally, a reagent, is heated to an elevated temperature for a period of time. For example, a solution may be heated to about 50° C., about 60° C., about 70° C., about 80° C., about 90° C., about 100° C., about 110° C., about 120° C., about 150° C., about 170° C., about 200° C., about 225° C., about 250° C., or greater, for a period of about 5 minutes or less, about 10 minutes or less, about 20 minutes or less, about 30 minutes or less. It should be understood that other temperatures and reaction times may be used. In some embodiments, upon completion of the reaction, the reaction mixture is cooled (e.g., to room temperature) and optionally diluted with a solvent, such as water, or mixtures of solvents, such as water/acetonitrile. In some embodiments, a reaction mixture is heated to elevated temperatures to encourage evaporation of the solvent (e.g., to about 95° C.). In some embodiments, a solution is heated to a temperature ranging from about 55-125° C. In some cases, a solution is heated to about 65° C., about 75° C., about 85° C., about 95° C., about 105° C., about 115° C., or greater. In some cases, a solution is placed under a reduced pressure of about 100 mm Hg, about 125 mm Hg, about 150 mm Hg, about 175 mm Hg, about 200 mm Hg, about 225 mm Hg, about 250 mm Hg, about 275 mm Hg, about 300 mm Hg, about 325 mm Hg, about 350 mm Hg, about 375 mm Hg, about 400 mm Hg, or greater. In some cases, a solution is placed under a reduced pressure of about 100 mbar, about 125 mbar, about 150 mbar, about 175 mbar, about 200 mbar, about 225 mbar, about 250 mbar, about 275 mbar, about 280 mbar, about 300 mbar, about 325 mbar, about 350 mbar, about 375 mbar, about 400 mbar, about 450 mbar, about 500 mbar, or greater. Those of ordinary skill in the art would be able to select and/or determine conditions suitable for a particular process. In some embodiments, a solution is concentrated to dryness under a flow of inert gas at about 95° C.

In some embodiments, upon completion of a fluorination reaction, the resulting imaging agent is optionally subjected to one or more purification steps. In some embodiments, an imaging agent may be reconstituted in a solvent prior to purification (e.g., by chromatography such as HPLC). In some cases, an imaging agent is dissolved in water, acetonitrile, or combinations thereof. In some embodiments, following formation of a solution comprising an imaging agent and a solvent and prior to purification (e.g., by HPLC), the solution is heated. In a particular embodiment, an imaging agent is reconstituted in a water/acetonitrile mixture and heated (e.g., to a temperature of about 90-100° C.) for about 1 minute, about 3 minutes, about 5 minutes, about 10 minutes, about 20 minutes, about 30 minutes, or more. Following heating of the mixture, the solution may be optionally cooled prior to purification.

C. Purification and Formulation

In some cases, the synthesis, purification, and/or formulation of an imaging agent is performed using an automated reaction system optionally comprising a cassette, wherein the cassette comprises a synthesis module, a purification module, and/or a formulation module. Automated reaction systems and cassettes are described herein.

Purification and isolation may be performed using methods known to those skilled in the art, including separation techniques like chromatography, or combinations of various separation techniques known in the art, for example, extractions, distillation, and crystallization. In one embodiment, high performance liquid chromatography (HPLC) is used with a solvent, or mixture of solvents, as the eluent, to recover the product. In some cases, the eluent includes a mixture of water and acetonitrile, such as a 20:80 water:acetonitrile mixture. The content of water in the eluent may vary from, for example, about 1% to about 30%. In some cases, HPLC purification may be performed using a C-18 column. The product may be analyzed (e.g., by HPLC) to determine yield (e.g., radiochemical yield) and/or radiochemical purity. The radiochemical purity may be greater than about 50%, about 60%, about 70%, about 80%, about 90%, about 95%, about 97%, about 98%, about 99%, or more. The percent yield of a product may be greater than 10%, greater than 20%, greater than 30%, greater than 40%, greater than 50%, greater than about 60%, greater than about 70%, greater than about 75%, greater than about 80%, greater than about 85%, greater than about 90%, greater than about 92%, greater than about 95%, greater than about 96%, greater than about 97%, greater than about 98%, greater than about 99%, or greater. In some embodiments, the radiochemical yield ranges from 15-50%.

The product may be further processed using additional purification techniques, such as filtration. In some cases, the imaging agent is purified using HPLC, to produce a solution of HPLC mobile phase and the imaging agent. The HPLC mobile phase may be subsequently exchanged for a solution of ascorbic acid or a salt thereof, and ethanol solution, by filtration through a C-18 resin (e.g., C18 Sep-Pak® cartridge). In some embodiments, the solution of the HPLC mobile phase and the imaging agent is filtered through a C-18 resin, where the imaging agent remains on the resin and the other components, such as acetonitrile and/or other solvents or components, are removed via elution. The C-18 resin may be further washed with a solution of ascorbic acid or a salt thereof, and the filtrate discarded. To recover the purified imaging agent, the C-18 resin is washed with a solvent, such as ethanol, and the resulting solution is optionally further diluted with an ascorbic acid solution or a salt thereof, as described herein.

Optionally, the recovered product is combined with one or more stabilizing agents, such as ascorbic acid or a salt thereof. For example, a solution comprising the purified imaging agent may be further diluted with a solution of ascorbic acid or a salt thereof. As described herein, a formulation may be prepared via an automated reaction system comprising a cassette.

In some cases, a solution comprising the imaging agent product may be sterile filtered (e.g., using a 13 mm diameter, Millipore, Millex PVDF 0.22 m sterilizing filter) into a sterile product vial. The sterile product vial may be a commercially available, pre-sterilized unit that is not opened during the production process, as any imaging agents (or other components) may be aseptically inserted through the septum prior to use. Those of ordinary skill in the art would be able to select suitable vials and production components, including commercially available, pre-sterilized units comprising a 0.22 m pore size membrane venting filter and quality control sampling syringes.

Following aseptic filtration, individual doses may be filled in syringes, labeled, and shipped to a clinical site. Dosing administration techniques, kits, cassettes, methods and systems (e.g., automated reaction systems) for synthesis of the imaging agent, and testing procedures are described herein. In some embodiments, the product is dispensed into a 3 or 5 mL syringe and labeled for distribution. Labels may be prepared at a radiopharmacy and applied to a syringe shield and shipping container. Additional labels may be provided in the shipping container for inclusion in clinical site records.

Uses of Imaging Agents

In another aspect, methods of imaging using the imaging agents described herein are provided. Such methods of imaging a subject include administering a composition or formulation that includes an imaging agent as described herein to the subject by injection, infusion, or any other known method of administration, and imaging a region of interest of the subject. Regions of interest may include, but are not limited to, the heart, a portion of the heart, the cardiovascular system, cardiac vessels, blood vessels (e.g., arteries and/or veins), brain, pancreas, adrenal glands, other organs, and tumors.

In some embodiments, the methods of imaging comprise (a) administering to a subject a composition that includes a compound as described herein comprising at least one imaging moiety (e.g., an imaging agent), and (b) acquiring at least one image of at least a portion of the subject. In some cases, the step of acquiring employs positron emission tomography (PET) for visualizing the distribution of the imaging agent within at least a portion of the subject. As will be understood by those of ordinary skill in the art, imaging using methods of this disclosure may include full body imaging of a subject, or imaging of a specific body region, organ, or tissue of the subject that is of interest. For example, if a subject is known to have, or is suspected of having myocardial ischemia, methods of this disclosure may be used to image the heart of the subject. In some embodiments, imaging may be limited to the heart or may include the heart and its associated vasculature.

In some embodiments of the invention, methods of diagnosing or assisting in diagnosing a disease or condition, assessing efficacy of treatment of a disease or condition, or imaging in a subject with a known or suspected cardiovascular disease or condition are provided. A cardiovascular disease can be any disease of the heart or other organ or tissue nourished by the vascular system. The vascular system includes coronary arteries, and all peripheral arteries supplying nourishment to the peripheral vascular system and the brain, as well as veins, arterioles, venules, and capillaries. Examples of cardiovascular diseases include diseases of the heart, such as coronary artery disease, myocardial infarction, myocardial ischemia, angina pectoris, congestive heart failure, cardiomyopathy (congenital or acquired), arrhythmia, or valvular heart disease. In some embodiments, the methods disclosed herein are useful for monitoring and measuring coronary artery disease and/or myocardial perfusion. For example, a method described herein can determine the presence or absence of coronary artery disease and/or the presence or absence of myocardial infarct. Conditions of the heart may include damage, not brought on by disease but resulting from injury—e.g., traumatic injury, surgical injury. In some cases, methods of the invention may include determining a parameter of, or the presence or absence of, myocardial ischemia, rest (R) and/or stress (S) myocardial blood flows (MBFs), coronary flow reserve (CFR), coronary artery disease (CAD), left ventricular ejection fraction (LVEF), end-systolic volume (ESV), end-diastolic volume (EDV), and the like.

Without wishing to be bound by any particular theory, an imaging agent as described herein is thought to bind to the mitochondrial complex I of the electron transport chain with high affinity. In some embodiments, the imaging agent shows selective uptake to the heart due to the high density of mitochondria in the myocardium. Regions of interest may include, but are not limited to, the heart, cardiovascular system, cardiac vessels, blood vessels (e.g., arteries, veins) brain, and other organs. A parameter of interest, such as blood flow, cardiac wall motion, etc., can be imaged and detected using methods and/or systems of the invention. In some aspects of the invention, methods for evaluating perfusion, including myocardial perfusion, are provided.

In some embodiments, a method of imaging a portion of a subject comprises administering to the subject a compound (e.g., an imaging agent) as described herein and acquiring at least one image of a portion of the subject. In some embodiments, a method of imaging a portion of a subject comprises administering to a subject a compound as described herein (e.g., an imaging agent); detecting radiation emitted by the compound; and forming an image therefrom. In some embodiments, an effective amount of the compound is administered to the subject.

In some cases, a subject to whom a method of the invention is applied, may have signs or symptoms suggestive of myocardial ischemia or myocardial infarction. In some cases methods of the invention can be used to identify early or pre-disease conditions that indicate that a subject is at increased risk of a disease. In some instances, methods of the invention can be used to determine a subject's risk of future cardiac events such as myocardial infarction or cardiac death. Imaging methods of the invention can be used to detect myocardial ischemia in subjects already diagnosed as having a myocardial ischemia disorder or condition, or in subjects that have no history or diagnosis of such a condition. In other instances, methods of the invention can be used to obtain measurements that provide a diagnosis or aid in providing a diagnosis of a myocardial ischemia disorder or condition. In some instances, a subject may already be undergoing drug therapy for a disorder or condition associated with myocardial ischemia, while in other instances a subject may not be undergoing therapy for myocardial ischemia. In some embodiments, methods of the invention can be used to assess efficacy of a treatment for a disease or condition. For example, the heart can be visualized using imaging agents of the invention before, during, and/or after treatment of a condition affecting the heart of a subject. Such visualization may be used to assess a disease or condition and aid in the selection of a treatment regimen, e.g., therapy, surgery, or medications, for the subject.

A PET imaging agent may have a high first-pass extraction fraction and can track regional myocardial blood flow over a wide range. These features may permit detection of milder decreases in coronary flow reserve and accurate estimation of absolute myocardial blood flow (MBF). PET imaging agents of the invention provide these and other features and are also available as a unit dose from regional PET radiopharmacies, obviating the need for on-site cyclotrons or costly Rb-82 generators.

In some embodiments of the invention, a compound as described herein (e.g., comprising at least one imaging moiety) is used as an imaging agent in combination with positron emission tomography (PET) or with other imaging methods including, but not limited to SPECT imaging. In some embodiments of the invention, a compound as described herein comprising at least one imaging moiety is administered to a subject and imaged in the subject using PET. As will be known to those of ordinary skill in the art, PET is a noninvasive technique that allows serial images and measurements to be obtained in a single subject over a time period. PET imaging used in methods of the invention may be carried out using known systems, methods, and/or devices. In some embodiments of the invention, PET imaging is conducted using a cardiac imaging system. A cardiac imaging system may include PET imaging functionality and a control unit configured to drive the imaging functionality to perform a PET imaging procedure on a portion of the subject before, during, and/or after administration of the imaging agent to the subject. In some cases, the control unit is configured to drive the imaging functionality to perform a PET imaging procedure. The control unit may comprise a computer system and/or software. In such a case, the computer system may be programmed or configured to execute the required methods for acquiring and/or analyzing the images. Further, the system may include a data storage device that is readable by a machine, embodying a set of instructions executable by the machine to perform the required methods of acquiring and/or analyzing the images.

The useful dosage of the imaging agent to be administered and the particular mode of administration will vary depending upon such factors as age, weight, and particular region to be imaged, as well as the particular imaging agent used, the diagnostic use contemplated, and the form of the formulation, for example, suspension, emulsion, microsphere, liposome, or the like, as described herein, and as will be readily apparent to those skilled in the art.

In some embodiments, an imaging agent is administered at a low dosage and the dosage increased until the desirable diagnostic effect is achieved. In one embodiment, the above-described imaging agents may be administered by intravenous injection, usually in a saline solution, at a dose of about 0.1 to about 100 mCi (and all combinations and subcombinations of dosage ranges and specific dosages therein), or between about 0.5 and about 50 mCi, or between about 0.1 mCi and about 30 mCi, or between 0.5 mCi and about 20 mCi. In some embodiments, the dosage range is per 70 kg body weight. For use as nuclear medicine imaging agents, the imaging agent dosages, administered by intravenous injection, may range from about 0.1 pmol/kg to about 1000 pmol/kg (and all combinations and subcombinations of dosage ranges and specific dosages therein), and in some embodiments, less than 150 pmol/kg.

Imaging systems and components thereof will be known to those of ordinary skill in the art. Many imaging systems and components (e.g., cameras, software for analyzing the images, etc.) are known and commercially available, for example, a Siemens Biograph-64 scanner. Any technique, software, or equipment that reduces or eliminates motion in static perfusion images may be used in methods of the invention, because spatial blurring and artifacts can be caused by patient motion during image acquisition. In some embodiments of the invention, images may be acquired in list mode, and may be static, dynamic, or gated images. An appropriate period of time for acquiring images can be determined by one of ordinary skill in the art, and may vary depending on the cardiac imaging system, the imaging agent (e.g., amount administered, composition of the imaging agent, subject parameters, area of interest). As used herein a "period of acquiring images" or an "image acquisition period" may be a period of obtaining a single continuous image, or may be a period during which one or more individual discrete images are obtained. Thus, a period of image acquisition can be a period during which one or more images of one or more regions of a subject are acquired.

In some embodiments of the invention, a period of image acquisition after administration of an imaging agent of the invention to a subject may be between about 30 seconds and about 60 minutes, between about 1 minute and about 30 minutes, between about 5 minutes and about 20 minutes, or at least about 1 minute, about 3 minutes, about 5 minutes, about 6 minutes, about 7 minutes, about 8 minutes, about 9 minutes, about 10 minutes, about 15 minutes, about 20 minutes, about 30 minutes, 4 about 5 minutes, about 60 minutes, or greater. For example, in a rest/stress imaging protocol there would be at least two periods of image acquisition with at least one corresponding to the rest segment and at least one corresponding to the stress segment. In some embodiments, imaging may be continuous over the imaging period of time, or images may be acquired at intervals such as in periodic or gated imaging.

In some aspects of the invention, gated acquisition is used to acquire images from a subject to whom an imaging agent has been administered. Gated imaging can be used in various aspects of the invention, and for example, may provide images of a beating heart of a subject and may be used to attain a functional evaluation of how well a heart is beating. Gated imaging can be performed by acquiring separate images from the subject at specific intervals during a period of image acquisition. A non-limiting example of gated imaging is a case when a period of image acquisition is about 10 minutes long, and images are acquired at repeated intervals during the 10 minute period. The frequency of acquisition of images during the period can be set by the operator, for example, the frequency can be at least every about 1 msec, about 5 msec, about 10 msec, about 20 msec, about 50 msec, about 100 msec, about 125 msec, about 250 msec, or more. The length of the interval is set by the operator to be triggered by an event, such as a cardiac R wave, with the length of the interval is defined by the number of time bins desired per R wave to R wave interval. Those of skill in the art will be familiar with the concept and methods of gated image acquisition and can use known methods to obtain gated images using an imaging agent.

Image acquisition in gated imaging can be triggered at specific intervals, for example, image acquisition can be triggered using an EKG of the heart. In a non-limiting example, an R wave-gated scanner may trigger acquisition of an image and the mean length of time between one R wave of a heart and the next can be stored. The number of images to collect can then be determined. For example, a first image can be acquired at 125 msec, a second image can be acquired at 250 msec, a third image can be acquired at 375 msec, etc.—thus images in that R interval may be acquired at 125 msec intervals. When the next R interval begins, the collection of images resets and image data is then acquired into the "first" image at 125 msec from that R interval start time, and then into the "second" image collected 250 msec from that R interval start time, etc. Thus, within each R interval image acquisition is added into the initial image of the series and incremented into successive images in the series so that a sequence of images can be collected at a desired frequency with the zero time being reset at the start of each R interval. Acquired gated images can be used to provide an image of heart motion and can provide information on heart wall thickness, whether or not one or more sections of the heart are not moving or beating (e.g., a wall motion defect). Use of gated imaging may provide data with which to judge perfusion of the heart, such as ejection fraction, and to visualize and identify reduced, absent, paradoxical or asynchronous wall motion. Use of gated imaging may also provide data with which to improve assessment of myocardial perfusion, judge cardiac function and to visualize and identify asynchronous wall motion.

In some cases, PET imaging may be used to assess myocardial viability via the ability of this technique to demonstrate metabolic consequences of myocardial ischemia. Using PET imaging, myocardial segments that are likely to improve after revascularization can be identified. In some cases, PET imaging may be used in the detection of coronary artery disease and can also serve as an alternative test for subjects who cannot undergo treadmill exercise stress testing. In some embodiments, a stress test method (e.g., pharmacological stress, exercise stress) may be employed with PET using methods of the invention to qualitatively or quantitatively assess one or more parameters of cardiac function during infusion of the imaging agent. Agents for, and methods of, inducing stress, for example, using exercise or pharmacological stress are well known in the art. Suitable induction of stress can be carried out using established, known agents and methods. Functions usefully measured using methods of the invention include, but are not limited to, in various embodiments, imaging of myocardial perfusion, imaging, or measurement of ventricular function, and measuring coronary blood flow velocity.

In some cases, methods for imaging the heart of a subject may include administering a first dose of an imaging agent to the subject while the subject is at rest, acquiring at least one first image of the heart, followed by subjecting the subject to stress (e.g., exercise stress or pharmacological stress) and administering a second dose of the imaging agent to the subject during the period of stress, and acquiring at least one other image of the heart.

In some embodiments, the dose of the imaging agent to be used during exercise-induced stress in a rest/stress protocol is greater than that necessary for pharmacologically-induced stress with the ratio of exercise-induced stress dose to pharmacologically-induced stress dose being greater than or equal to about 1.2, about 1.3, about 1.4, about 1.5, about 1.6, about 1.7, about 1.8, about 1.9, or greater. With respect to pharmacological stress, in some embodiments of the invention that involve rest/stress imaging methods, the dose of the imaging agent administered for imaging during the pharmacological stress is a minimum of two times the dose of the imaging agent administered for imaging at rest. With respect to exercise stress, in some embodiments of the invention that involve rest/stress imaging methods, the dose of the imaging agent administered for imaging during the exercise-induced stress is a minimum of three times the dose of the imaging agent administered for imaging at rest. In some embodiments of the invention, for imaging first at rest followed by imaging with stress, the dose of the imaging agent administered at rest will be lower than the dose of the imaging agent administered at stress. In some cases, imaging methods of the invention may be completed in a single day (e.g., less than about 24 hours, less than about 12 hours, less than about 6 hours, less than about 4 hours, less than about 2 hours, less than about 1 hour), as described herein. In other cases, methods may be completed in longer periods of time, e.g., over more than about 24 hours, about 36 hours, or about 48 hours.

For stress testing in methods, a subject may be subjected to stress using procedures known to those of ordinary skill in the art. In some cases, the subject may be subjected to stress using procedures including exercise stress and/or pharmacological stress. Pharmacological stress may be induced by administering to the subject a pharmacological agent such as a vasodilator. Examples of useful pharmacological stress agents, include, but are not limited to adenosine, dobutamine, dipyridamole, regadenoson, binodeneson, apadeneson, and other adenosine A2a receptor agonists. Dosing and administration of pharmacological stress inducing agents, such as vasodilators, are well known in the art and can be determined for use in conjunction with methods and systems of the invention. Exercise stress may be induced using a treadmill, exercise bicycle, hand crank, or other equipment suitable to increase a subject's heart rate through increased exertion.

An imaging agent may be provided in any suitable form, for example, in a pharmaceutically acceptable form. In some cases, an imaging agent is included in a pharmaceutically acceptable composition. In some embodiments, an imaging agent is provided as a composition comprising ethanol, sodium ascorbate, and water. In some cases, the composition comprises less than 20 weight % ethanol, less than 15 weight % ethanol, less than 10 weight % ethanol, less than 8 weight % ethanol, less than 6 weight % ethanol, less than 5 weight % ethanol, less than 4 weight % ethanol, less than 3 weight % ethanol, or less ethanol. In some cases, the composition comprises less than 100 mg/mL, less than 75 mg/mL, less than 60 mg/mL, less than 50 mg/mL, less than 40 mg/mL, less than 30 mg/mL, or less sodium ascorbate in water. In some embodiments, the composition comprises about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, or about 200 mg/mL. In a particular non-limiting embodiment, an imaging agent is provided as a solution in water comprising less than 4% ethanol and less than about 50 mg/mL sodium ascorbate in water.

In some embodiments, the pH of the composition is between about 1.5 and about 8, or between about 1.5 and about 7, or between about 1.5 and 6, or between about 1.5 and 5, or between 1.5 and 4, or between 2 and 7, or between 3 and 7, or between 4 and 7, or between 5 and 7, or between 5 and 6, or between 5.5 and 6. In some embodiments, the pH is about 5.8. In some embodiments, the pH of the composition is about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, or about 3.5. In some embodiments, the pH of the composition is between about 1.5 and about 1.6. In some embodiments, the pH of the composition is between about 1.5 and about 1.9. In some embodiments, the pH of the composition is between about 2.1 and about 3.5. In some embodiments, the pH of the composition is between about 2.4 and about 3.5. In some embodiments, the pH of the composition is between about 2.5 and about 3.5. In some embodiments, the pH of the composition is between 2.1 and about 2.3.

An imaging agent may be provided as composition for injection, which may be prepared in an injection syringe. For example, the imaging agent may be prepared by a radiopharmacy (e.g., using the methods described herein) and/or a PET manufacturing center and provided to a health-care professional for administration. In some aspects of the invention, the imaging agent is provided, for example, in a syringe or other container, with ≤50 mg/mL sodium ascorbate in water, ≤4 weight % ethanol, and about 1 to 14 mCi of the imaging agent.

In some embodiments, a dose of an imaging agent may be diluted with saline (e.g., as described herein), if needed to obtain a practical dose volume. For example, if the activity concentration of an imaging agent is so high that only 0.1 mL is need for an appropriate dose for a subject, the solution can be diluted, e.g., with sterile saline, so the syringe contains 0.5 ml to 4 or more mL of an imaging agent solution for administration. In some embodiments of the invention, an injection volume for an imaging agent is between 0.5 and 5 mL, 1 and 4 mL, 2 and 3 mL, at least 0.5 mL, 1 mL, 2 mL, 3 mL, 4 mL, 5 mL, 6 mL, 7 mL, 8 mL, 9 mL, 10 mL, or more. Those of skill in the art will recognize how to dilute an imaging agent to produce a sufficient dose volume for administration. In some embodiments, an imaging agent is provided in a container such as a vial, bottle, or syringe, and may be transferred, as necessary, into a suitable container, such as a syringe for administration.

Syringes that include an adsorbent plunger tip may result in 10 to 25% of an imaging agent activity remaining in the syringe after injection. Syringes lacking an adsorbent plunger tip may be used, such as a 3 or 5 mL NORM-JECT (Henke Sass Wolf, Dudley, Mass.) or other equivalent syringe lacking an adsorbent plunger tip. Reduction of adsorption in the syringe can increase the amount of an imaging agent that is transferred from the syringe and administered to the subject in methods of the invention. A syringe used in methods of the invention may comprise an imaging agent, and be a non-adsorbing, or reduced adsorbent syringe. In some embodiments a non-adsorbent or reduced-adsorbent syringe is a syringe that has been coated or treated to reduce adsorption of the imaging agent. In some embodiments, a non-adsorbent or reduced-adsorbent syringe is a syringe that lacks an adsorbent plunger tip. In some embodiments, a syringe used in conjunction with the invention adsorbs less than 20%, 19%, 18%, 17%, 16%, 15%, 14%, 13%, 12%, 11%, 10%, 9%, 8%, 7%, 6%, 5%, 4%, 3%, 2%, 1%, or 0.5% of the imaging agent it contains. In certain aspects of the invention, a syringe that contains an imaging agent does not include a rubber or latex tip on the plunger. In some cases a syringe used in methods of the invention, includes a plunger that adsorbs less than 20%, 19%, 18%, 17%, 16%, 15%, 14%, 13%, 12%, 11%, 10%, 9%, 8%, 7%, 6%, 5%, 4%, 3%, 2%, 1%, or 0.5% of an imaging agent that the syringe contains. A syringe of the invention may also comprise sodium ascorbate, ethanol, and water, and certain embodiments of the invention include a syringe containing an imaging agent in a solution comprising less than 4 weight % ethanol and less than about 50 mg/mL sodium ascorbate in water. A syringe of the invention may be a syringe that is latex free, rubber free, and/or lubricant free. A syringe of the invention may contain an imaging agent in an amount between about 1.5 and about 14 mCi. A syringe of the invention may contain about 20 mCi or less of an imaging agent.

Components of a composition comprising an imaging agent may be selected depending on the mode of administration to the subject. Various modes of administration that effectively deliver imaging agents of the invention to a desired tissue, cell, organ, or bodily fluid will be known to one of ordinary skill in the art. In some embodiments, the imaging agent is administered intravenously (e.g., intravenous bolus injection) using methods known to those of ordinary skill in the art. As used herein, a dose that is "administered to a subject" means an amount of the imaging agent that enters the body of the subject. In some embodiments, due to factors such as partial retention of an imaging agent in a syringe, tubing, needles, catheter, or other equipment used to administer the imaging agent to a subject, the amount of an imaging agent that is measured or determined to be in the a syringe or other equipment prepared for administration may be more than the amount in the dose that is administered to the subject. In some embodiments, an injection of an imaging agent is followed by a flushing injection of normal saline, into the subject, using the same tubing, needle, port, etc., used for administration of an imaging agent. Flushing may be performed immediately following administration of an imaging agent, or up to 1 min, 2 min, 3 min, 5 min, or more, after the administration. The volume of saline or other agent for flushing may be up to 5 mL, 6 mL, 7 mL, 8 mL, 9 mL, 10 mL, 15 mL, 20 mL, or more. As will be understood by those of ordinary skill in the art, in embodiments where an imaging agent is administered using a syringe or other container, the true amount of the imaging agent administered to the subject may be corrected for any imaging agent that remains in the container. For example, the amount of radioactivity remaining in the container, and tubing and needle or delivery instrument that carried the imaging agent from the container and into the subject can be determined after the imaging agent has been administered to the subject and the difference between the starting amount of radioactivity and the amount remaining after administration indicates the amount that was delivered into the subject. In some cases, the container or injection device (e.g., catheter, syringe) may be rinsed with a solution (e.g., saline solution) following administration of the imaging agent.

In some embodiments of the invention, the total amount of an imaging agent administered to a subject over a given period of time, e.g., in one session, is less than or equal to about 50 mCi, less than or equal to 40 mCi, less than or equal to 30 mCi, less than or equal to 20 mCi, less than or equal to 18 mCi, less than or equal to 16 mCi, less than or equal to 15 mCi, less than or equal to 14 mCi, less than or equal to 13 mCi, less than or equal to 12 mCi, less than or equal to 10 mCi, less than or equal to 8 mCi, less than or equal to 6 mCi, less than or equal to 4 mCi, less than or equal to 2 mCi, less than or equal to 1 mCi, less than or equal to 0.5 mCi. The total amount administered may be determined based on a single dose or multiple doses administered to a subject within a given time period of up to 1 minute, 10 minutes, 30 minutes, 1 hour, 2 hours, 6 hours, 12 hours, 24 hours, 48 hours, or more.

Based on radiation dose studies, the desirable maximum dose administered to a subject may be based on determining the amount of an imaging agent which limits the radiation dose to about 5 rem to the critical organ and/or about 1 rem effective dose (ED) or lower, as will be understood by those of ordinary skill in the art. In some embodiments, the desirable maximum dose or total amount of an imaging agent administered is less than or equal to about 25 mCi, or less than or equal to about 14 mCi over a period of time of up to 30 min, 1 hour, 2 hours, 6 hours, 12 hours, 24 hours, 48 hours, or more. In some embodiments, the maximum dose of an imaging agent administered to a subject may be less than 3.5 μg per 50 kg of body weight per day. That is, in some embodiments of the invention, the maximum dose of an imaging agent administered to a subject may be less than about 0.07 μg of an imaging agent per kg of body weight per day.

Exemplary Cassettes and Reaction Systems

In some embodiments, systems, methods, kits, and cassettes are provided for the synthesis of an imaging agent as described herein. In some embodiments, an imaging agent may be prepared using an automated reaction system comprising a disposable or single use cassette. The cassette may comprise all the non-radioactive reagents, solvents, tubing, valves, reaction vessels, and other apparatus and/or components necessary to carry out the preparation of a given batch of imaging agent. The cassette allows the reaction system to have the flexibility to make a variety of different imaging agents with minimal risk of cross-contamination, by simply changing the cassette. By the term "cassette" is meant a piece of apparatus designed to fit removably and interchangeably onto automated reaction systems, in such a way that mechanical movement of moving parts of the automated reaction system controls the operation of the cassette from outside the cassette, i.e., externally. In certain embodiments, a cassette comprises a linear arrangement of valves, each linked to a port where various reagents, cartridges, syringes, and/or vials can be attached, by either needle puncture of a septum-sealed vial, or by gas-tight, marrying joints. Each valve may have a male-female joint which interfaces with a corresponding moving arm of the automated synthesizer. External rotation of the arm can control the opening or closing of the valve when the cassette is attached to the automated reaction system. Additional moving parts of the automated reaction system are designed to clip onto syringe plunger tips, and thus raise or depress syringe barrels. An automated reaction system may further include a controller and one or more controllable valves in electrical communication with the controller. An automated reaction system may also include additional vessels, valves, sensors, heaters, pressurizing elements, etc., in electrical communication with the controller. An automated reaction system may be operated by a controller using suitable software for control of valve openings and closings, heating, cooling, pressure levels, fluid movement, flow rate, etc. The automated reaction system may optionally include a computer operating system, software, controls, etc., or other component. In addition, the automated reaction system may comprise a mount for the cassette. In some embodiments, a cassette of the present invention comprises one or more syringes for introducing one or more reagents. In addition, in some embodiments, improved methods employed in combination with cassettes and automated reactions systems are provided. Use of the cassettes and/or improved methods can result in improved liquid handling efficiency, resulting in increased imaging agent recovery (e.g., via reduced retention of the imaging agent in the cassette), as described herein.

Examples of automated reaction systems (e.g., a nucleophilic reaction system), include, but are not limited to, the Explora GN or RN synthesis system (Siemens Medical Solutions USA, Inc.), Tracerlab-MX synthesis system (GE Healthcare), Eckert & Zeigler Modular-Lab Synthesis system, NEPTIS® synthesis system, etc., which are commonly available at PET manufacturing facilities.

Figure 16:
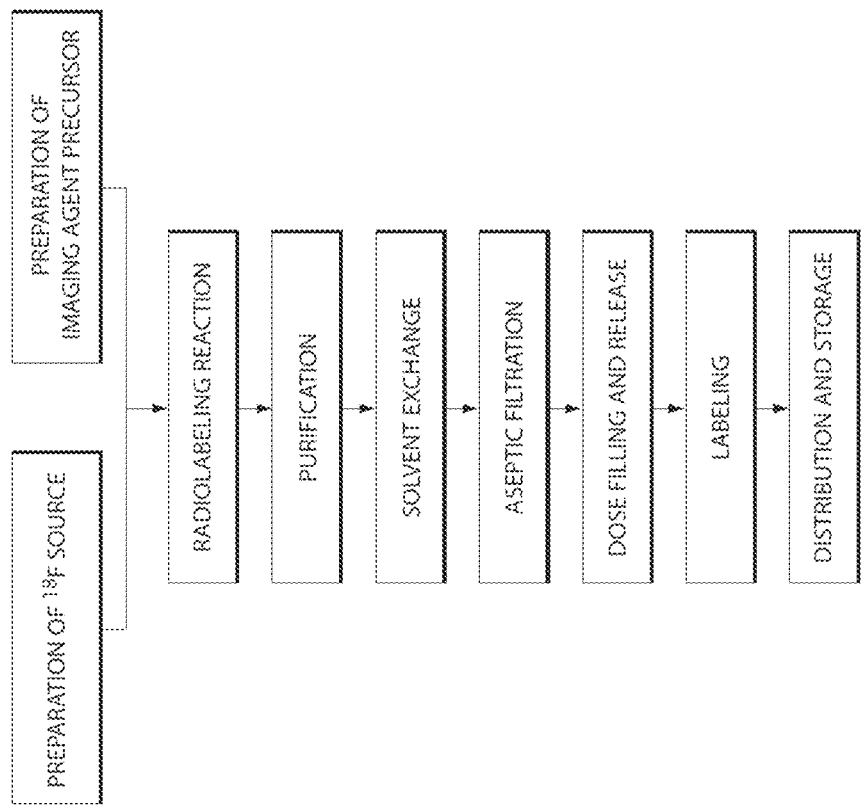
FIG. 16 shows a flow chart describing a method for synthesizing an imaging agent, according to some embodiments.

The automated reaction systems may carry out numerous steps, as outlined in FIG. 16, including, but not limited to, preparation of the $^{18}$F fluoride species, providing an imaging agent precursor, optionally in a solution (e.g., an imaging agent precursor in acetonitrile), a radiolabeling reaction (e.g., reaction of the $^{18}$F species and the imaging agent precursor to form the imaging agent) optionally in a synthesis module, purification (e.g., by preparative HPLC), solvent exchange (e.g., by Sep-Pak), aseptic filtration, and release into a container. For example, see Example 68.

Figure 17:
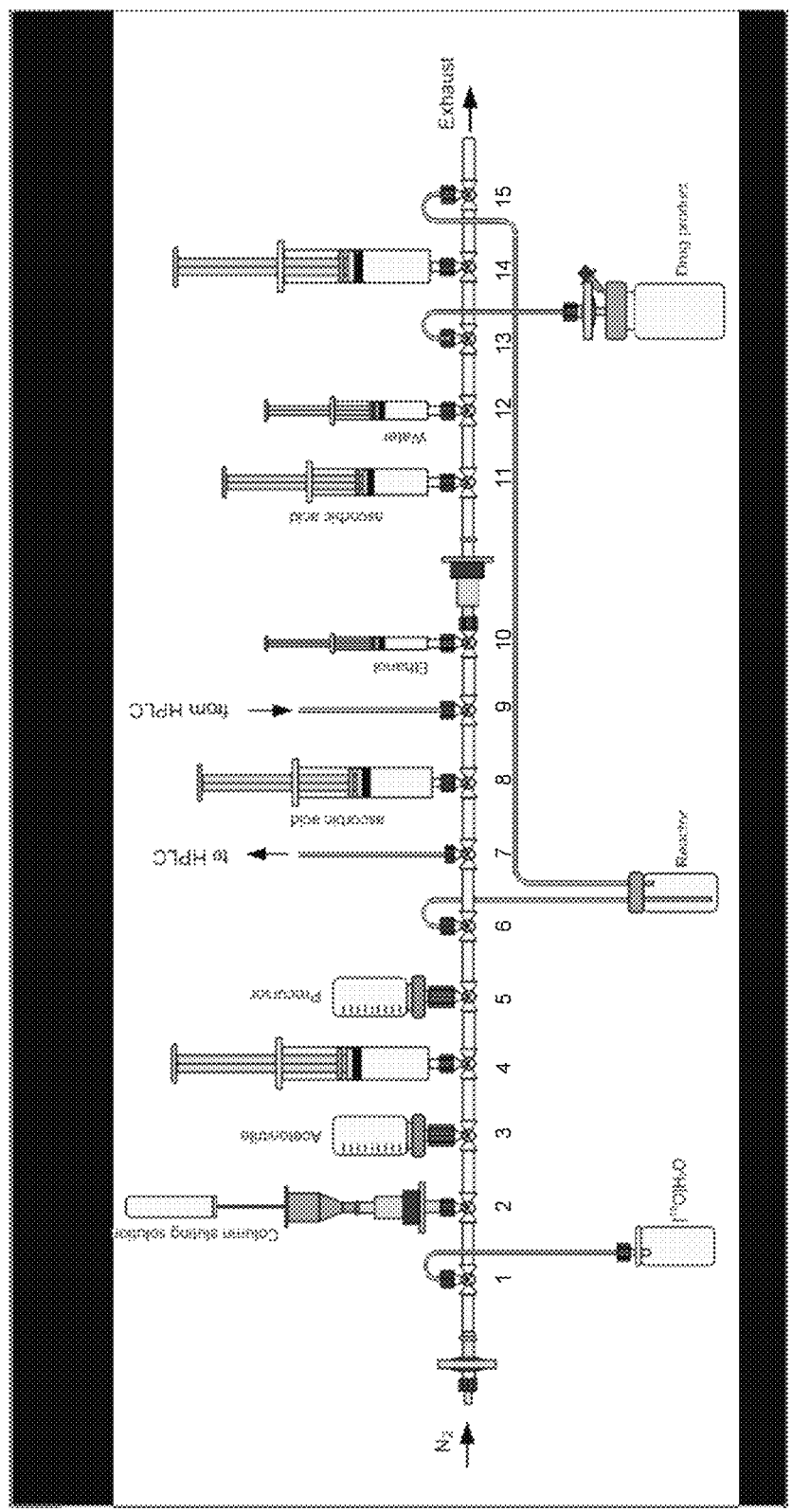
FIG. 17 shows a schematic representation of a cassette, with associated columns and reagents for synthesizing an imaging agent using an automated synthesis module, according to some embodiments.

In some embodiments, the automated reaction system may make use of a cassette comprising a reaction module in fluid connection with a purification module and/or a formulation module. FIG. 17 shows a schematic representation of a cassette in connection with exemplary reaction systems for synthesizing an imaging agent comprising a reaction module, a purification module, and/or a formulation module, according to some embodiments.

In some embodiments, the reaction module may include a reaction chamber in which conversion of the imaging agent precursor to the imaging agent is performed. The reaction module may include a source of a fluoride species (e.g., $^{18}$F), a source of the imaging agent precursor, a source of an additive (e.g., salt additive), and other sources of additional components such as solvents, each of which may optionally be fluidly connected to the reaction chamber. In some embodiments, one or more reagents are provided via a syringe as opposed to vials or reservoirs as previously reported. The reaction module may also comprise an anion exchange column for purification of the fluoride species, prior to introduction into the reaction chamber.

Upon reaction, the resulting imaging agent product is transferred from the reaction module to the purification module for further processing, treatment, and/or purification. The purification module may include, for example, a column (e.g., an HPLC column) fluidly connected to one or more sources of solvents to be used as eluents. The purification module may further comprise a source of a stabilizing agent (e.g., ascorbic acid or a salt thereof), which may be added to the imaging agent upon purification (e.g., by HPLC). The purified imaging agent is then transferred to the formulation module, where further purification and formulation may be performed. The formulation module may include a filter for aseptic filtration and/or a C-18 column for solvent exchange.

In some embodiments, a cassette comprises a reaction module and a formulation module. A reaction module of the invention may include a source of $^{18}$F, a filter to remove unreacted [$^{18}$O]H$_2$O, a source of an ammonium salt, a source for a diluent for the $^{18}$F, a source for an imaging agent precursor, a source for an H$_2$O diluent for the imaging agent precursor, a reaction vessel for reacting the $^{18}$F and the imaging agent precursor, a solid phase extraction column (e.g., a C-18 column, or other suitable column) in fluid communication with the reaction vessel. The solid phase extraction column includes a solid sorbent to adsorb the radiolabeled imaging agent product on the sorbent. At least a portion of the residual reaction impurities pass through solid phase extraction column without adsorbing on the sorbent. The reaction module also includes a source of wash solutions in fluid communication with the solid phase extraction column for providing wash solutions to elute the remaining impurities on the sorbent, and includes a source of an eluent (e.g., as H$_2$O/MeCN, or other suitable eluent) in fluid communication with the solid phase extraction column for eluting the radiolabeled imaging agent product off the sorbent. The reaction module may also include a source of a diluent for the eluted radiolabeled imaging agent.

A formulation module of an apparatus of the invention may be in fluid communication with a reaction module and may include a solid phase extraction cartridge that includes a solid sorbent (e.g., C-18, or other suitable sorbent) to adsorb the diluted radiolabeled imaging agent, a source of wash solutions (e.g., comprising ascorbic acid, a salt thereof, or other suitable wash solution) in fluid communication with the solid phase extraction cartridge for providing wash solutions to wash off any remaining impurities on the sorbent, and a source of eluting fluid (e.g., ethanol, or other suitable eluting fluid) in fluid communication with the solid phase extraction cartridge for eluting the radiolabeled imaging agent product off the sorbent. In some embodiments, the wash solution(s) is provided in a syringe which may provide certain advantages, as described herein. The formulation module may also include a source of a diluent (e.g., comprising ascorbic acid, a salt thereof, or other suitable diluent), for diluting the eluted radiolabeled imaging agent. The formulation module may also be in fluid communication with a sterilizing filter (e.g., a Sartorius Minisart RC15 sterilizing filter, or other suitable sterilizing filter).

In a particular embodiment, a cassette is provided for use with an automated synthesis module, for example, a GE TracerLab MX synthesis module. In one embodiment, a cassette comprises a disposable sterilized assembly of molded stopcock manifolds specifically designed for use with the automated synthesis module (e.g., GE TracerLab MX synthesis module). Individual manifolds are connected in a linear or non-linear fashion to form a directional array that dictates the flow path of reagents used in the preparation of an imaging agent. In some embodiments, the main body of the cassette contains at least one manifold comprising a plurality of manifold positions (e.g., stockcocks). For example, the main body may comprise at least one, two, three, four or more, manifolds. The cassette may comprise between 1 to 20 manifold positions, between 1 to 15 manifold positions, between 5 and 20 manifold positions, between 5 and 15 manifold positions. Each of the manifolds may or may not be symmetrical. In one embodiment, the main body of the cassette contains three plastic manifolds each fitted with five standard molded stopcocks, thereby having a total of 15 total manifold positions. Individual stopcocks are adapted with luer fittings to accommodate solvents, reagents, syringes, tubing required for gas and liquid handling, etc. The stopcocks are adapted for solvents and reagents and may be fitted with plastic spikes upon which inverted punch vials are located, while those featuring tubing and syringes are fitted with male luer connections according to function. In some embodiments, the cassette comprises a linear arrangement of a plurality of stopcock manifolds connected to one or more of the components selected from the group consisting of a gas inlet, anion exchange cartridge, C-18 cartridge, syringe, solvent reservoir, reaction vessel, HPLC system, collection vessel, reservoirs for solutions of ascorbic acid or salt thereof, and exhaust outlet. In some embodiments, the reservoirs for solutions of ascorbic acid or salt thereof comprise a syringe. In some cases, the cassette further comprises tubing. In some cases, the cassette further comprises an imaging agent synthesis module, wherein the apparatus is fluidically connected to the cassette. In some cases, the apparatus is capable carrying out the method of synthesizing an imaging agent as described herein.

In some embodiments, the cassette configuration provided for the preparation of an imaging agent is depicted in FIG. 17. In some embodiments, the cassette configuration comprises a linear arrangement of a plurality of stopcock manifolds arranged in the order:

1) luer connections (2) to gas inlet and [$^{18}$O]H$_2$O recovery;
2) anion exchange cartridge—column eluting solution (optionally 1 mL punch vial);
3) spike connection for acetonitrile (optionally 10 mL punch vial);
4) empty syringe (optionally 30 mL);
5) reservoir with solution of imaging agent precursor (optionally 10 mL punch vial);
6) reaction vessel;
7) outlet to HPLC;
8) syringe (optionally 20 mL) with solution of ascorbic acid or salt thereof (e.g., at pH 2);
9) inlet from HPLC;
10) ethanol reservoir (optionally 3 mL syringe);
11) syringe (optionally 10 mL) with solution of ascorbic acid or salt thereof (e.g., at pH 5.8);
12) syringe (optionally 5 mL) with water;
13) final product vial;
14) empty syringe (optionally 30 mL); and
15) reaction vessel and exhaust.

In some embodiments, the linear arrangement disclosed above can be changed to switch the reagent at position 3 with the reagent at position 5 and/or to switch the reagent at position 11 with the reagent at position 13.

The cassettes and corresponding methods described herein provide unexpected results as compared to previously described cassettes and methods. In some cases, the use of syringes as reservoirs for reagents (e.g., ascorbic acid or salt thereof) results in overall reduced production cost and improved liquid handling efficiency during the manufacture of an imaging agent. In addition, a variation in the configuration of the placement of the components of the cassette also results in improved liquid handling efficiency as well as increased drug product recovery during the manufacture of an imaging agent. This may be due to reduced exposure to the plastic manifold which can result in less adsorption of the imaging agent during the delivery process. In some cases, the variation of the cassette comprises repositioning one of the reagents (e.g., to position 11) and the final product vial (e.g., to position 13). In some embodiments, improved methods of use of the cassettes are provided. In some embodiments, computer control of the cassettes is employed to execute a unique sequence of mechanical events dictated by the individual tracers. In some cases, a discrete sequence file is employed to describe the essential synthetic parameters (e.g. reaction time and temperature) and to adapt the preferred reagent and cassette configuration for the selected imaging agent. In some embodiments, sequence modifications as compared to previously described methods may be incorporated based upon the novel reagent containers (e.g., syringes) and cassette configurations as described herein. For example, in some embodiments, unique programming sequences are employed to add nitrogen gas into the syringe containers thereby providing for complete reagent transfer. Additionally, for example, in some embodiments, overall sequence timing is modified as compared to previously described methods to provide shorter sequence durations (e.g., such that preparatory occurs in a parallel fashion rather than as a linear series).

Exemplary Kits

In some embodiments, systems, methods, kits, and cassettes kits for the preparation of an imaging agent are provided for detecting, imaging, and/or monitoring myocardial perfusion. In some embodiments, kits for the administration of an imaging agent are provided. Kits of the invention may include, for example, a container comprising an imaging agent or an imaging agent precursor, and instructions for use. Kits may include a sterile, non-pyrogenic, formulation comprising a predetermined amount of an imaging agent or precursor thereof and optionally other components. In some aspects of the invention, a kit may include one or more syringes that contain an imaging agent or precursor thereof to be prepared for administration to a subject. A container that may be used in conjunction with an imaging agent (e.g., to deliver and/or administer an imaging agent to a subject) may be a syringe, bottle, vial, tubes, etc. Exemplary syringes that may be included in a kit of the invention are syringes lacking an adsorbent plunger tip, such as a 3 or 5 mL NORM-JECT (Henke Sass Wolf, Dudley, Mass.), or other equivalent syringe lacking an adsorbent plunger tip. An imaging agent or precursor thereof may be provided in a kit and additional preparations before use may optionally include diluting the imaging agent to a usable concentration. Instructions in a kit of the invention may relate to methods for preparing the imaging agent, methods of diluting the imaging agent, methods of administering the imaging agent to a subject for diagnostic imaging, or other instructions for use.

In some cases, a kit can also include one or more vials containing a diluent for preparing an imaging agent composition for administration to a subject (e.g., human). A diluent vial may contain a diluent such as physiological saline, water, buffered solution, etc. for diluting an imaging agent. For example, the imaging agent may be packaged in a kit in a ready-to-inject formulation, or may require some reconstitution or dilution whereby a final composition/formulation for injection or infusion is prepared.

Instructions in a kit of the invention may also include instructions for administering the imaging agent to a subject and may include information on dosing, timing, stress induction, etc. For example, a kit may include an imaging agent or precursor thereof described herein, along with instructions describing the intended application and the proper administration of the agent. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for human administration. In some cases, the instructions can include instructions for mixing a particular amount of the diluent with a particular amount of a concentrated solution of the imaging agent or precursor thereof or a solid preparation of the imaging agent, or precursor thereof whereby a final formulation for injection or infusion is prepared for example, such that the resulting solution is at a suitable concentration for administration to a subject (e.g., at a concentration as described herein). A kit may include a whole treatment regimen of the inventive compound (e.g., a rest dose and a stress dose).

The kit may contain any one or more of the components described herein in one or more containers. As an example, in one embodiment, the kit may include instructions for mixing one or more components of the kit and/or isolating and mixing a sample and applying to a subject. The kit may include a container housing an agent described herein. The agent may be in the form of a liquid, gel or solid (powder). The agent may be prepared sterilely, packaged in syringe and shipped refrigerated. Alternatively it may be housed in a vial or other container for storage. A second container may have other agents prepared sterilely. Alternatively the kit may include an active agent premixed and shipped in a syringe, vial, tube, or other container. The kit may have one or more or all of the components required to administer the agents to a patient, such as a syringe, topical application devices, or iv needle tubing and bag.

It also will be understood that containers containing the components of a kit of the invention, whether the container is a bottle, a vial (e.g., with a septum), an ampoule, an infusion bag, or the like, can include additional indicia such as conventional markings that change color when the preparation has been autoclaved or otherwise sterilized. A kit of the invention may further include other components, such as syringes, labels, vials, tubing, catheters, needles, ports, and the like. In some aspect of the invention, a kit may include one or more syringes containing the imaging agent sufficient for administration.

Buffers useful in the preparation of imaging agents or precursor thereof and kits include, for example, phosphate, citrate, sulfosalicylate, and acetate buffers. A more complete list can be found in the United States Pharmacopoeia. Lyophilization aids useful in the preparation of imaging agents and kits include, for example, mannitol, lactose, sorbitol, dextran, FICOLL® polymer, and polyvinylpyrrolidine (PVP). Stabilization aids useful in the preparation of imaging agents and kits include, for example, ascorbic acid, cysteine, monothioglycerol, sodium bisulfite, sodium metabisulfite, gentisic acid, and inositol.

Solubilization aids useful in the preparation of imaging agents and kits include, for example, ethanol, glycerin, polyethylene glycol, propylene glycol, polyoxyethylene sorbitan monooleate, sorbitan monoloeate, polysorbates, poly(oxyethylene)-poly(oxypropylene)-poly(oxyethylene) block copolymers ("Pluronics") and lecithin. In certain embodiments, the solubilizing aids are polyethylene glycol, cyclodextrins, and Pluronics. Bacteriostats useful in the preparation of imaging agents and kits include, for example, benzyl alcohol, benzalkonium chloride, chlorbutanol, and methyl, propyl, or butyl paraben.

Pharmaceutical Compositions

Once a compound as described herein (e.g., an imaging agent) has been prepared or obtained, it may be combined with one or more pharmaceutically acceptable excipients to form a pharmaceutical composition that is suitable for administration to a subject, including a human. As would be appreciated by one of skill in this art, the excipients may be chosen, for example, based on the route of administration as described below, the imaging agent being delivered, time course of delivery of the agent, and/or the health/condition of the subject. The pharmaceutical composition may be a solid or liquid.

Pharmaceutical compositions of the present invention and for use in accordance with the present invention may include a pharmaceutically acceptable excipient or carrier. As used herein, the term "pharmaceutically acceptable excipient" or "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium iodide, sodium metabisulfite, sodium nitrite, sodium sulfite, and sodium thiosulfate.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorohexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical Mantoux method of intradermal administration.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The pharmaceutical compositions of this invention can be administered to humans and/or to other animals parenterally (e.g., by intravenous, intramuscular, subcutaneous, or intraperitoneal injection). The mode of administration will vary depending on the intended use, as is well known in the art.

Further Embodiments

Certain embodiments are further contemplated herein.

Embodiment 1. In embodiment 1, provided is a compound comprising the structure:

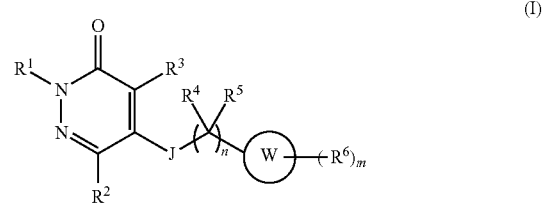

(I)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —$NO_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —$NO_2$, and an imaging moiety;

J is selected from the group consisting of $N(R^7)$, S, O, C(=O), C(=O)O, OC(=O), C(=O)N($R^7$), N($R^7$)C(=O), $CH_2O$, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

W is heteroaryl, naphthyl, heterocyclyl, or aryl;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^9$)$_3$, —OR$^8$, and an imaging moiety;

m is 0, 1, 2, 3, 4, 5, 6, or 7;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety; and each R$^{9'}$ is independently selected from the group consisting of halo, alkyl optionally substituted, aryl optionally substituted, and an imaging moiety, provided that at least one imaging moiety is present in the compound; and provided that when W is aryl, a) R$^3$ is not halo, alkyl or haloalkyl, or b) at least one R$^6$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$.

Embodiment 2. The compound of embodiment 1, wherein the compound comprises the structure:

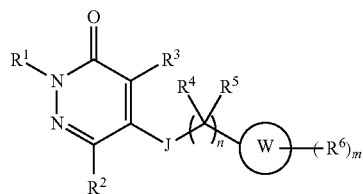

(II)

or a pharmaceutically acceptable salt thereof, wherein:

R$^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R$^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

R$^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(=O), C(=O)O, OC(=O), C(=O)N(R$^7$), N(R$^7$)C(=O), CH$_2$O, and a bond;

R$^4$ and R$^5$ are each independently selected from the group consisting of hydrogen, alkyl optionally substituted, and an imaging moiety, or optionally any two of R$^4$ and R$^5$ are joined together to form a ring;

n is 0, 1, 2, or 3;

W is heteroaryl, naphthyl, or heterocyclyl;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^9$)$_3$, —OR$^8$, and an imaging moiety;

m is 0, 1, 2, 3, 4, 5, 6, or 7;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety; and each R$^{9'}$ is independently selected from the group consisting of halo, alkyl optionally substituted, aryl optionally substituted, and an imaging moiety, provided that at least one imaging moiety is present in the compound.

Embodiment 3. The compound of embodiment 1 or 2, wherein W is heteroaryl.

Embodiment 4. The compound of embodiment 1 or 2, wherein W is naphthyl.

Embodiment 5. The compound of embodiment 1 or 2, wherein W is heterocyclyl.

Embodiment 6. The compound of embodiment 1 or 2, wherein W is:

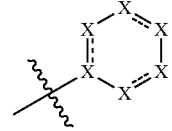

wherein each X is independently selected from the group consisting of C, C(R$^6$), C(R$^6$)$_2$, N, NR$^7$, O, and S; and wherein each ══ is independently a single or double bond, provided at least one X is not C or C(R$^6$).

Embodiment 7. The compound of embodiment 1 or 2, wherein W is:

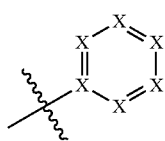

wherein each X is independently C, C(R⁶) or N, provided at least one X is not C or C(R⁶).

Embodiment 8. The compound of embodiment 1 or 2, wherein W is:

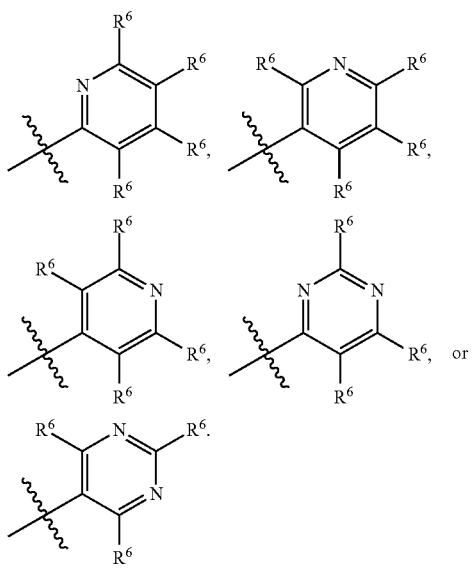

Embodiment 9. The compound of embodiment 1 or 2, wherein W is:

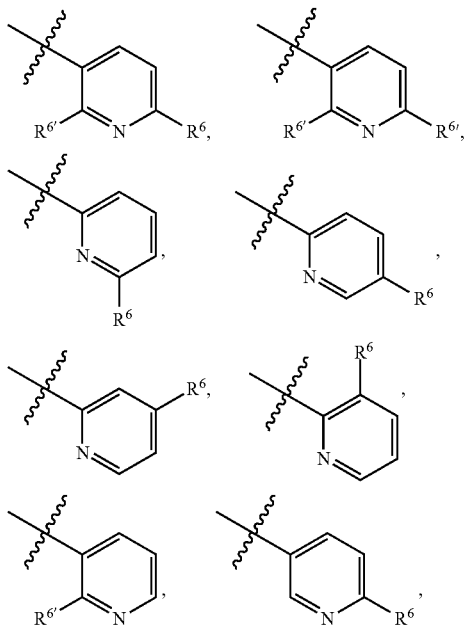

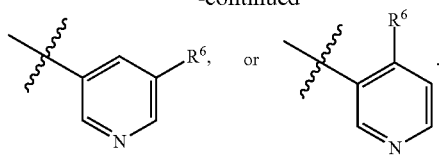

wherein $R^{6'}$ is halo or hydrogen; and optionally, wherein $R^{6'}$ is fluoro, chloro, bromo, or hydrogen.

Embodiment 10. The compound of embodiment 9, wherein $R^6$ is $-O(CH_2)_j I_m$; wherein j is 1, 2, 3, 4, 5, or 6; and optionally, wherein $I_m$ is $^{18}F$.

Embodiment 11. The compound of embodiment 9, wherein $R^6$ is $-(CH_2)_jO(CH_2)_j I_m$; wherein $I_m$ is an imaging moiety and each j is independently 1, 2, 3, 4, 5, or 6; and optionally, wherein $I_m$ is $^{18}F$.

Embodiment 12. The compound of embodiment 1 or 2, wherein W is:

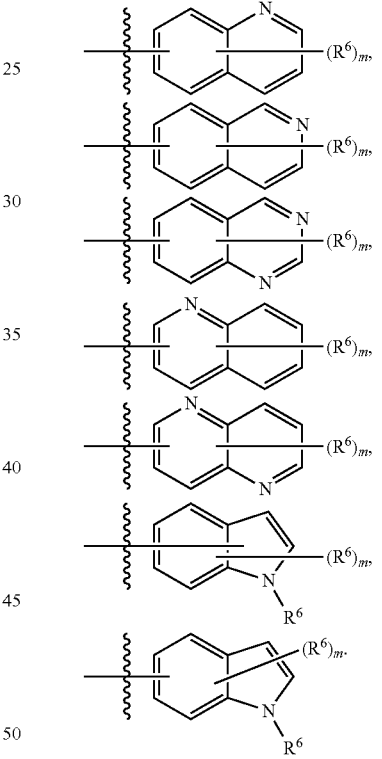

Embodiment 13. The compound of embodiment 1 or 2, wherein W is:

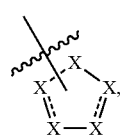

each X is independently selected from the group consisting of C, C(R⁶), C(R⁶)₂, N, NR⁷, O, and S; and each ═══ is independently a single or double bond, provided at least one X is not C or C(R⁶).

Embodiment 14. The compound of embodiment 1 or 2, wherein the compound is selected from the group consisting of:

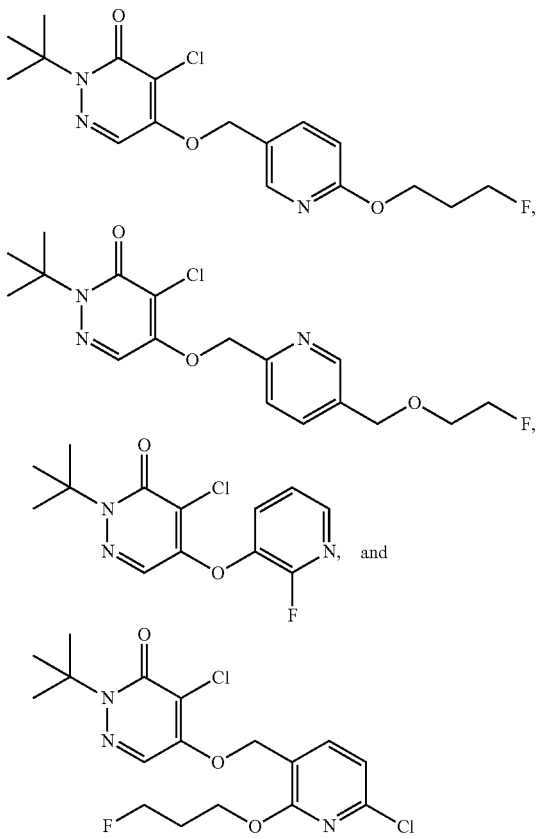

or a pharmaceutically acceptable salt thereof, wherein F is optionally $^{18}$F.

Embodiment 15. The compound of embodiment 1 or 2, wherein the compound comprises the structure:

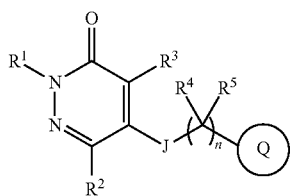

(III)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N($R^7$), S, O, C(=O), C(=O)O, OC(=O), C(=O)N($R^7$), N($R^7$)C(=O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

Q has the structure:

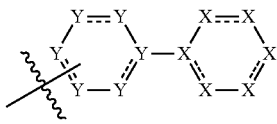

each Y and each X is independently selected from the group consisting of C, C($R^6$), C($R^6$)$_2$, N, N$R^7$, O, and S, provided at least one Y is not C or C($R^6$), optionally, wherein one X and/or one Y is absent;

each ═══ is independently a single or double bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —NO$_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each $R^9$ is independently selected from the group consisting of hydrogen, alkyl optionally substituted, aryl optionally substituted, haloalkyl, halogen, and an imaging moiety; and each $R^{9'}$ is independently selected from the group consisting of halo, alkyl optionally substituted, aryl optionally substituted, and an imaging moiety, provided that at least one imaging moiety is present in the compound.

Embodiment 16. The compound of embodiment 15, wherein each Y and each X is independently selected from the group consisting of C, C($R^6$), C($R^6$)$_2$, N, N$R^7$, O, and S, provided at least one Y is not C or C($R^6$).

Embodiment 17. The compound of embodiment 15, wherein one Y is absent or one X is absent.

Embodiment 18. The compound of embodiment 15, wherein Q is:

127
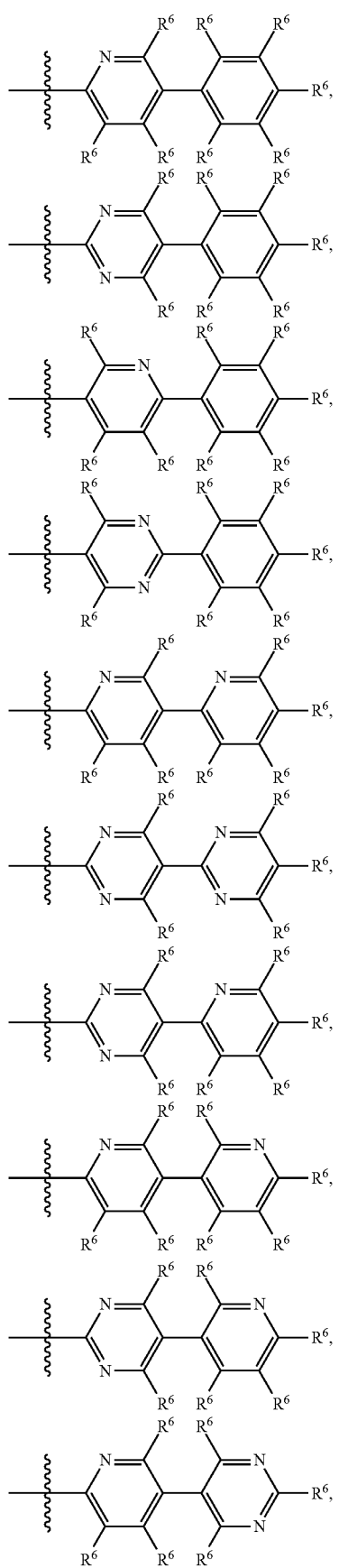
128
-continued
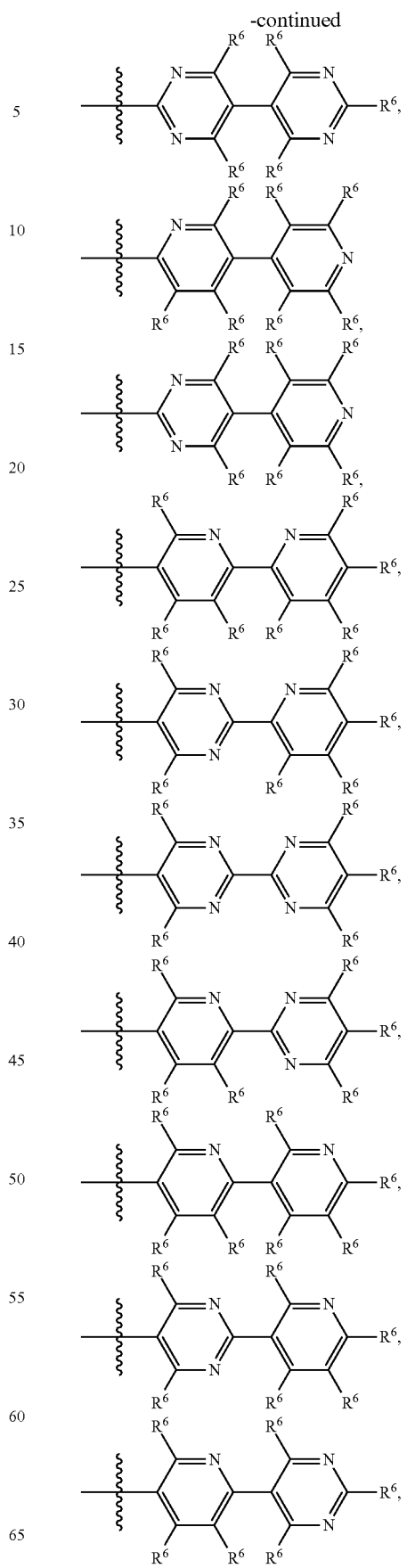

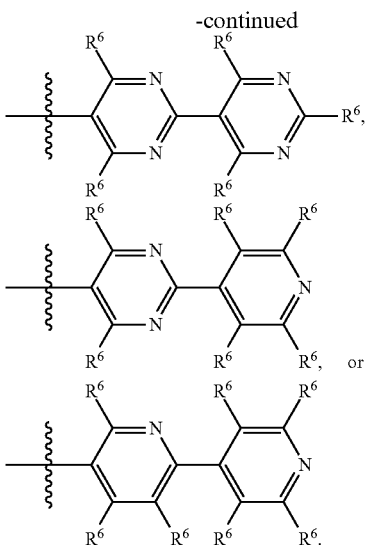

Embodiment 19. The compound of any one of embodiments 1-13 and 15-18, wherein the at least one imaging moiety is present in $R^1$, $R^2$, $R^3$, $R^4$, $R^5$, or $R^6$.

Embodiment 20. The compound of any one of embodiments 1-13 and 15-19, wherein $R^1$ is alkyl optionally substituted.

Embodiment 21. The compound of any one of embodiments 1-13 and 15-19, wherein $R^1$ is methyl, ethyl, n-propyl, i-propyl, n-butyl, i-butyl, or t-butyl.

Embodiment 22. The compound of any one of embodiments 1-13 and 15-19, wherein $R^1$ is —C(CH$_3$)$_2$CH$_2$OH.

Embodiment 23. The compound of any one of embodiments 1-13 and 15-19, wherein $R^1$ is t-butyl.

Embodiment 24. The compound of any one of embodiments 1-13 and 15-19, wherein $R^1$ is aryl optionally substituted.

Embodiment 25. The compound of any one of embodiments 1-13 and 15-19, wherein $R^1$ is phenyl optionally substituted.

Embodiment 26. The compound of any one of embodiments 1-13 and 15-19, wherein $R^1$ is unsubstituted phenyl.

Embodiment 27. The compound of any one of embodiments 1-13 and 15-19, wherein $R^1$ is cycloalkyl optionally substituted.

Embodiment 28. The compound of any one of embodiments 1-13 and 15-19, wherein $R^1$ is cyclohexyl optionally substituted.

Embodiment 29. The compound of any one of embodiments 1-13 and 15-28, wherein $R^2$ is H.

Embodiment 30. The compound of any one of embodiments 1-13 and 15-29, wherein J is a bond.

Embodiment 31. The compound of any one of embodiments 1-13 and 15-29, wherein J is O.

Embodiment 32. The compound of any one of embodiments 1-13 and 15-29, wherein J is S.

Embodiment 33. The compound of any one of embodiments 1-13 and 15-32, wherein n is 0.

Embodiment 34. The compound of any one of embodiments 1-13 and 15-32, wherein n is 1.

Embodiment 35. The compound of any one of embodiments 1-13 and 15-32, wherein n is 2.

Embodiment 36. The compound of any one of embodiments 1-13 and 15-32, wherein n is 3.

Embodiment 37. The compound of any one of embodiments 1-13 and 15-36, wherein each of $R^4$ and $R^5$ is H.

Embodiment 38. The compound of any one of embodiments 1-13 and 15-36, wherein at least one $R^4$ and $R^5$ is $^2$H, and optionally, wherein each of $R^4$ and $R^5$ is $^2$H.

Embodiment 39. The compound of any one of embodiments 1-13 and 15-38, wherein $R^3$ is halo.

Embodiment 40. The compound of any one of embodiments 1-13 and 15-38, wherein $R^3$ is Cl.

Embodiment 41. The compound of any one of embodiments 1-13 and 15-38, wherein $R^3$ is Br.

Embodiment 42. The compound of any one of embodiments 1-13 and 15-38, wherein $R^3$ is H.

Embodiment 43. The compound of any one of embodiments 1-13 and 15-38, wherein $R^3$ is alkyl optionally substituted.

Embodiment 44. The compound of any one of embodiments 1-13 and 15-38, wherein $R^3$ is unsubstituted alkyl.

Embodiment 45. The compound of any one of embodiments 1-13 and 15-38, wherein $R^3$ is methyl, ethyl, n-propyl, i-propyl, n-butyl, i-butyl, or t-butyl.

Embodiment 46. The compound of any one of embodiments 1-13 and 15-38, wherein $R^3$ is methyl.

Embodiment 47. The compound of embodiment 1, wherein the compound comprises the structure:

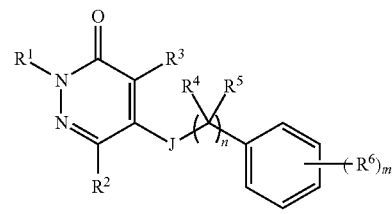

(IV)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

$R^3$ is selected from the group consisting of hydrogen, unsubstituted alkyl or alkyl optionally substituted with a moiety other than a halogen, heteroalkyl optionally substituted, alkoxy optionally substituted, alkoxyalkyl optionally substituted, aryl optionally substituted, heteroaryl optionally substituted, —CN, and —NO$_2$;

J is selected from the group consisting of N(R$^7$), S, O, C(=O), C(=O)O, OC(=O), C(=O)N(R$^7$), N(R$^7$)C(=O), CH$_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^{9'}$)$_3$, —OR$^8$, and an imaging moiety;

m is 0, 1, 2, 3, 4, or 5;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety; and each R$^{9'}$ is independently selected from the group consisting of halo, alkyl optionally substituted, aryl optionally substituted, and an imaging moiety, provided that at least one imaging moiety is present in the compound.

Embodiment 48. The compound of embodiment 47, wherein R$^3$ is alkyl optionally substituted.

Embodiment 49. The compound of embodiment 47, wherein R$^3$ is unsubstituted alkyl.

Embodiment 50. The compound of embodiment 47, wherein R$^3$ is methyl, ethyl, n-propyl, i-propyl, n-butyl, i-butyl, or t-butyl.

Embodiment 51. The compound of embodiment 47, wherein R$^3$ is methyl.

Embodiment 52. The compound of any one of embodiments 47-51, wherein the at least one imaging moiety is present in R$^1$, R$^2$, R$^3$, R$^4$, R$^5$, or R$^6$.

Embodiment 53. The compound of any one of embodiments 47-52, wherein R$^1$ is alkyl optionally substituted.

Embodiment 54. The compound of any one of embodiments 47-52, wherein R$^1$ is methyl, ethyl, n-propyl, i-propyl, n-butyl, i-butyl, or t-butyl.

Embodiment 55. The compound of any one of embodiments 47-52, wherein R$^1$ is —C(CH$_3$)$_2$CH$_2$OH.

Embodiment 56. The compound of any one of embodiments 47-52, wherein R$^1$ is t-butyl.

Embodiment 57. The compound of any one of embodiments 47-52, wherein R$^1$ is aryl optionally substituted.

Embodiment 58. The compound of any one of embodiments 47-52, wherein R$^1$ is phenyl optionally substituted.

Embodiment 59. The compound of any one of embodiments 47-52, wherein R$^1$ is unsubstituted phenyl.

Embodiment 60. The compound of any one of embodiments 47-52, wherein R$^1$ is cycloalkyl optionally substituted.

Embodiment 61. The compound of any one of embodiments 47-52, wherein R$^1$ is cyclohexyl optionally substituted.

Embodiment 62. The compound of any one of embodiments 47-61, wherein R$^2$ is H.

Embodiment 63. The compound of any one of embodiments 47-62, wherein J is a bond.

Embodiment 64. The compound of any one of embodiments 47-62, wherein J is O.

Embodiment 65. The compound of any one of embodiments 47-62, wherein J is S.

Embodiment 66. The compound of any one of embodiments 47-65, wherein n is 0.

Embodiment 67. The compound of any one of embodiments 47-65, wherein n is 1.

Embodiment 68. The compound of any one of embodiments 47-65, wherein n is 2.

Embodiment 69. The compound of any one of embodiments 47-68, wherein each of R$^4$ and R$^5$ is H.

Embodiment 70. The compound of any one of embodiments 47-68, wherein at least one R$^4$ and R$^5$ is $^2$H, and optionally, wherein each of R$^4$ and R$^5$ is $^2$H.

Embodiment 71. The compound of embodiment 47, wherein the compound is of the formula:

or a pharmaceutically acceptable salt thereof, wherein F is optionally $^{18}$F.

Embodiment 72. In embodiment 72, provided is a compound comprising the structure:

(V)

(VI)

or a pharmaceutically acceptable salt thereof, wherein:

R$^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R$^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and an imaging moiety;

R$^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(=O), C(=O)O, OC(=O), C(=O)N(R$^7$), N(R$^7$)C(=O), CH$_2$O, and a bond;

each R$^4$, R$^5$, and R$^{11}$ is independently selected from the group consisting of hydrogen, alkyl optionally substituted, and an imaging moiety, or optionally any two of R$^4$ or any two of R$^5$ are joined together to form a ring;

q, and r are each independently 0, 1, 2, or 3;

Z is selected from the group consisting of aryl, heteroaryl, heterocyclyl, and a bond;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^{9'}$)$_3$, —OR$^8$, and an imaging moiety;

m is 0, 1, 2, 3, 4, 5, 6, or 7;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety; and each R$^{9'}$ is independently selected from the group consisting of halo, alkyl optionally substituted, aryl optionally substituted, and an imaging moiety, provided that at least one imaging moiety is present in the compound.

Embodiment 73. In embodiment 73, provided is a compound comprising the structure:

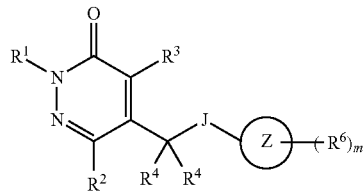

(VII)

or a pharmaceutically acceptable salt thereof, wherein:

R$^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R$^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, —NO$_2$, haloalkyl, and an imaging moiety;

R$^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and an imaging moiety;

J is selected from the group consisting of N(R$^7$), S, O, C(=O), C(=O)O, OC(=O), C(=O)N(R$^7$)$_2$, N(R$^7$)C(=O), and —CH$_2$O;

each R$^4$ and R$^5$ is independently selected from the group consisting of hydrogen, alkyl optionally substituted, and an imaging moiety, or optionally any two of R$^4$ or any two of R$^5$ are joined together to form a ring;

n is 1, 2, or 3;

Z is selected from the group consisting of aryl, heteroaryl, heterocyclyl, and a bond;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^{9'}$)$_3$, —OR$^8$, and an imaging moiety;

m is 0, 1, 2, 3, 4, 5, 6, or 7;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety; and each R$^{9'}$ is independently selected from the group consisting of halo, alkyl optionally substituted, aryl optionally substituted, and an imaging moiety, provided that at least one imaging moiety is present in the compound.

Embodiment 74. The compound of embodiment 72 or 73, wherein Z is aryl.

Embodiment 75. The compound of embodiment 72 or 73, wherein Z is phenyl.

Embodiment 76. The compound of embodiment 72 or 73, wherein Z is naphthyl.

Embodiment 77. The compound of embodiment 72 or 73, wherein Z is heteroaryl.

Embodiment 78. The compound of embodiment 72 or 73, wherein Z is heterocyclyl.

Embodiment 79. The compound of embodiment 72 or 73, wherein Z is:

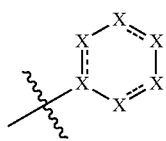

wherein each X is independently selected from the group consisting of C, C(R$^6$), C(R$^6$)$_2$, N, NR$^7$, O, and S; and wherein each ====== is independently a single or double bond.

Embodiment 80. The compound of embodiment 72 or 73, wherein Z is:

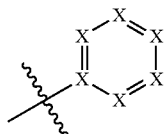

wherein each X is independently C, C(R$^6$) or N.

Embodiment 81. The compound of embodiment 79 or 80, wherein at least one X is not C or C(R$^6$).

Embodiment 82. The compound of embodiment 72, 73, or 80, wherein Z is:

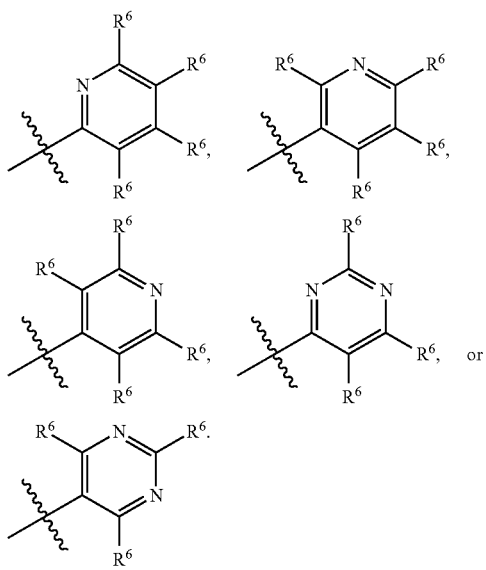

Embodiment 83. The compound of embodiment 72, 73, or 80, wherein Z is:

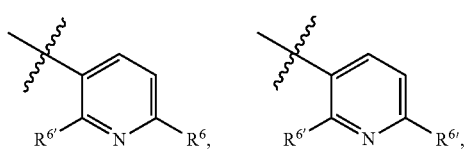

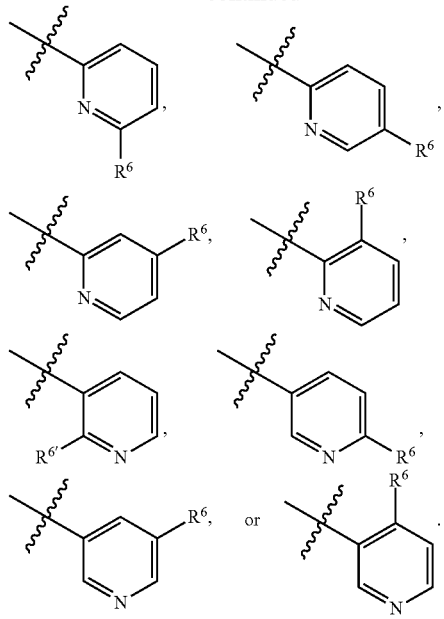

wherein R$^{6'}$ is halo or hydrogen.

Embodiment 84. The compound of embodiment 83, wherein R$^{6'}$ is fluoro, chloro, bromo, or hydrogen.

Embodiment 85. The compound of embodiment 83, wherein R$^6$ is —O(CH$_2$)$_j$I$_m$; wherein I$_m$ is an imaging moiety and j is 1, 2, 3, 4, 5, or 6.

Embodiment 86. The compound of embodiment 83, wherein R$^6$ is —(CH$_2$)$_j$O(CH$_2$)$_j$I$_m$; wherein I$_m$ is an imaging moiety and each j is independently 1, 2, 3, 4, 5, or 6.

Embodiment 87. The compound of embodiment 72 or 73, wherein Z is:

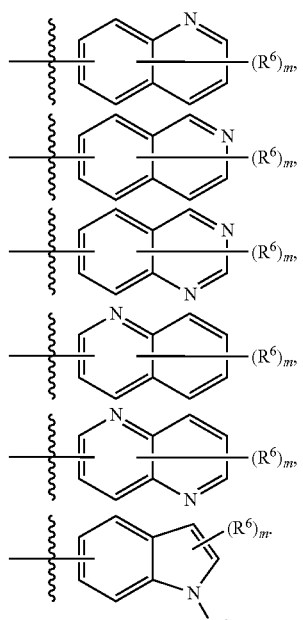

Embodiment 88. The compound of embodiment 72 or 73, wherein Z is:

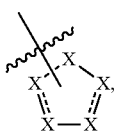

each X is independently selected from the group consisting of C, C(R⁶), C(R⁶)₂, N, NR⁷, O, and S; and
each ====== is independently a single or double bond.

Embodiment 89. The compound of embodiment 88, wherein at least one X is not C or C(R⁶).

Embodiment 90. The compound of embodiment 72 or 73, wherein Z has the structure:

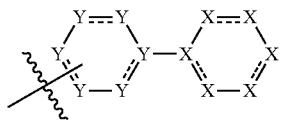

each Y and each X is independently selected from the group consisting of C, C(R⁶), C(R⁶)₂, N, NR⁷, O, and S;
each ====== is independently a single or double bond.

Embodiment 91. The compound of embodiment 90, wherein at least one Y is not C or C(R⁶).

Embodiment 92. The compound of embodiment 90 or 91, wherein at least one X is not C or C(R⁶).

Embodiment 93. The compound of embodiment 72, 73, or 90, wherein Z is:

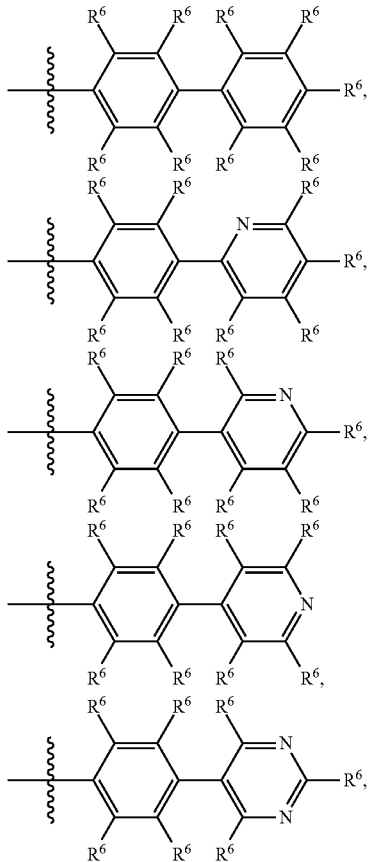

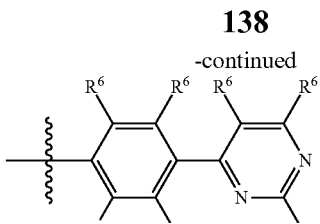

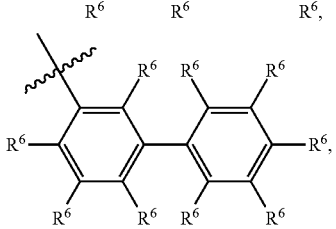

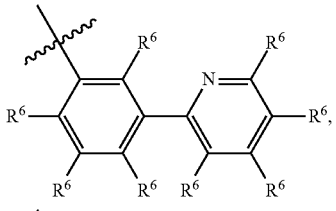

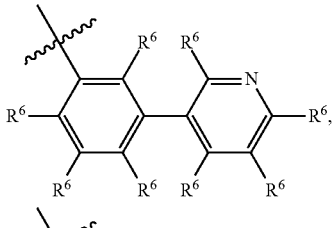

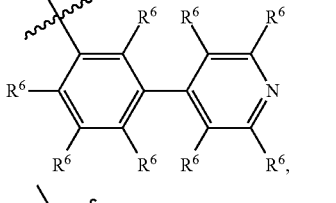

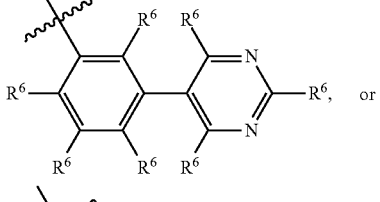

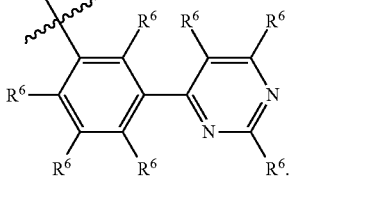

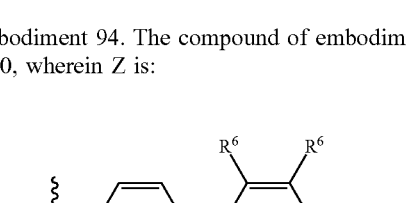 or

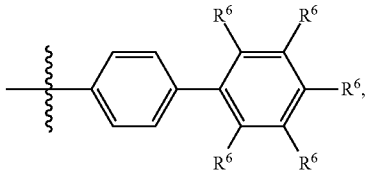

Embodiment 94. The compound of embodiment 72, 73, or 90, wherein Z is:

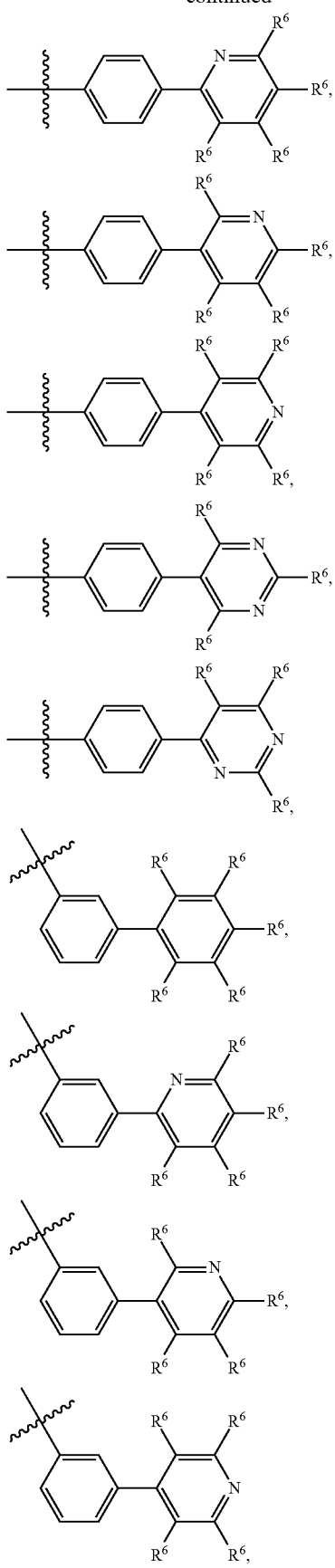

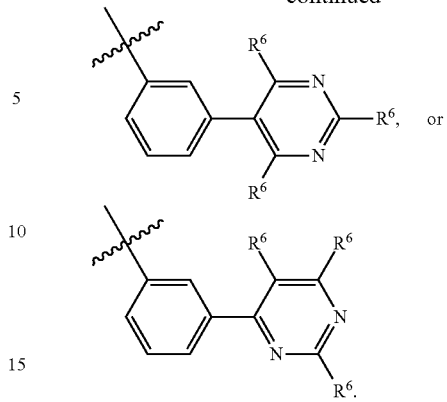

Embodiment 95. The compound of any one of embodiments 73 or 72-94, wherein J is a bond.
Embodiment 96. The compound of any one of embodiments 73 or 72-94, wherein J is O.
Embodiment 97. The compound of any one of embodiments 73 or 72-94, wherein J is S.
Embodiment 98. The compound of any one of embodiments 72-97, wherein q is 0.
Embodiment 99. The compound of any one of embodiments 72-97, wherein q is 1.
Embodiment 100. The compound of any one of embodiments 72-97, wherein q is 2.
Embodiment 101. The compound of any one of embodiments 72-100, wherein r is 0.
Embodiment 102. The compound of any one of embodiments 72-100, wherein r is 1.
Embodiment 103. The compound of any one of embodiments 72-100, wherein r is 2.
Embodiment 104. The compound of any one of embodiments 72-97, wherein q and r are each 0.
Embodiment 105. The compound of any one of embodiments 72-97, wherein q and r are each 1.
Embodiment 106. The compound of any one of embodiments 73 or 74-83, wherein n is 0.
Embodiment 107. The compound of any one of embodiments 73 or 74-83, wherein n is 1.
Embodiment 108. The compound of any one of embodiments 73 or 74-83, wherein n is 2.
Embodiment 109. The compound of any one of embodiments 72-91, or 107-108, wherein each of $R^4$ and $R^5$ is H.
Embodiment 110. The compound of any one of embodiments 72-109, wherein each $R^{11}$ is H.
Embodiment 111. The compound of any one of embodiments 73 or 72-110, wherein the at least one imaging moiety is present in $R^1$, $R^2$, $R^3$, $R^4$, $R^5$, $R^6$, or $R^{11}$.
Embodiment 112. The compound of any one of embodiments 73 or 72-111, wherein $R^1$ is alkyl optionally substituted.
Embodiment 113. The compound of any one of embodiments 73 or 72-111, wherein $R^1$ is methyl, ethyl, n-propyl, i-propyl, n-butyl, i-butyl, or t-butyl.
Embodiment 114. The compound of any one of embodiments 73 or 72-111, wherein $R^1$ is —$C(CH_3)_2CH_2OH$.
Embodiment 115. The compound of any one of embodiments 73 or 72-111, wherein $R^1$ is t-butyl.
Embodiment 116. The compound of any one of embodiments 73 or 72-111, wherein $R^1$ is aryl optionally substituted.

Embodiment 117. The compound of any one of embodiments 73 or 72-111, wherein $R^1$ is phenyl optionally substituted.

Embodiment 118. The compound of any one of embodiments 73 or 72-111, wherein $R^1$ is unsubstituted phenyl.

Embodiment 119. The compound of any one of embodiments 73 or 72-111, wherein $R^1$ is cycloalkyl optionally substituted.

Embodiment 120. The compound of any one of embodiments 73 or 72-111, wherein $R^1$ is cyclohexyl optionally substituted.

Embodiment 121. The compound of any one of embodiments 73 or 72-120, wherein $R^2$ is H.

Embodiment 122. The compound of any one of embodiments 73 or 72-121, wherein $R^3$ is halo.

Embodiment 123. The compound of any one of embodiments 73 or 72-121, wherein $R^3$ is Cl.

Embodiment 124. The compound of any one of embodiments 73 or 72-121, wherein $R^3$ is Br.

Embodiment 125. The compound of any one of embodiments 73 or 72-121, wherein $R^3$ is H.

Embodiment 126. The compound of any one of embodiments 73 or 72-121, wherein $R^3$ is alkyl optionally substituted.

Embodiment 127. The compound of any one of embodiments 73 or 72-121, wherein $R^3$ is unsubstituted alkyl.

Embodiment 128. The compound of any one of embodiments 73 or 72-121, wherein $R^3$ is methyl, ethyl, n-propyl, i-propyl, n-butyl, i-butyl, or t-butyl.

Embodiment 129. The compound of any one of embodiments 73 or 72-121, wherein $R^3$ is methyl.

Embodiment 130. The compound of embodiment 72, wherein the compound is selected from the group consisting of:

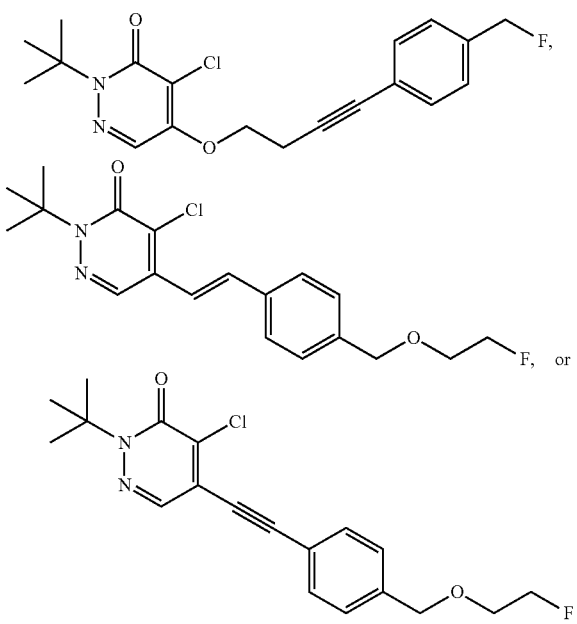

or a pharmaceutically acceptable salt thereof, wherein F is optionally $^{18}$F.

Embodiment 131. The compound of embodiment 73, wherein the compound is of the formula:

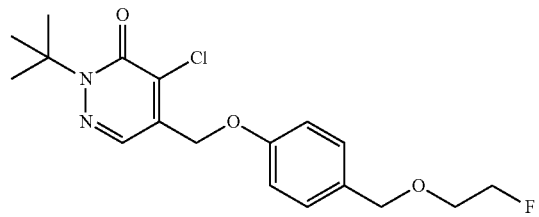 [SMILES: CC(C)(C)n1ncc(COc2ccc(COCCF)cc2)c(Cl)c1=O]

or a pharmaceutically acceptable salt thereof, wherein F is optionally $^{18}$F. structure:

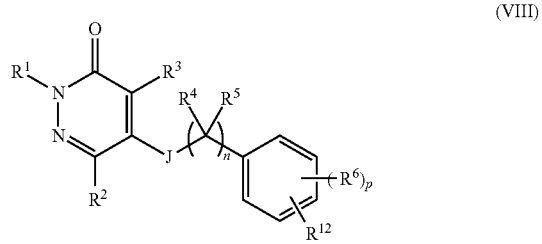

(VIII)

or a pharmaceutically acceptable salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —$NO_2$, and an imaging moiety;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —$NO_2$, and an imaging moiety;

J is selected from the group consisting of consisting of $N(R^7)$, S, O, C(=O), C(=O)O, OC(=O), C(=O)N($R^7$), N($R^7$)C(=O), $CH_2$O, and a bond;

$R^4$ and $R^5$ are each independently selected from the group consisting of hydrogen, alkyl optionally substituted, and an imaging moiety, or optionally any two of $R^4$ and $R^5$ are joined together to form a ring;

n is 0, 1, 2, or 3;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N($R^7$)$_2$, —$NO_2$, —OH, —C(=O)$R^8$, —C(=O)O$R^8$, —OC(=O)$R^8$, —C(=O)N($R^7$)$_2$, —N($R^7$)C(=O)$R^8$, —CN, —Si($R^9$)$_3$, —B($R^{9'}$)$_3$, —O$R^8$, and an imaging moiety;

p is 0, 1, 2, 3, or 4;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two $R^7$ may be joined together to form a ring; and each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

$R^{12}$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$;

each $R^9$ is independently selected from the group consisting of hydrogen, alkyl optionally substituted, aryl optionally substituted, haloalkyl, halogen, and an imaging moiety; and each $R^{9'}$ is independently selected from the group consisting of halo, alkyl optionally substituted, aryl optionally substituted, and an imaging moiety, provided that at least one imaging moiety is present in the compound.

Embodiment 133. The compound of embodiment 132, wherein $R^{12}$ is —NO$_2$, —C(=O)(CH$_2$)$_u$I$_m$, —C(=O)O(CH$_2$)$_u$I$_m$, —C≡C(CH$_2$)$_u$I$_m$, or —Si(alkyl)$_2$I$_m$; wherein I$_m$ is an imaging moiety and u is 1, 2, 3, 4, 5, or 6.

Embodiment 134. The compound of any one of embodiments 132-133, wherein the at least one imaging moiety is present in $R^1$, $R^2$, $R^3$, $R^4$, $R^5$, $R^6$, or $R^{12}$.

Embodiment 135. The compound of any one of embodiments 132-133, wherein the at least one imaging moiety is present in $R^1$, $R^3$, $R^4$, $R^5$, $R^6$, or $R^{12}$.

Embodiment 136. The compound of any one of embodiments 132-134, wherein $R^1$ is alkyl optionally substituted.

Embodiment 137. The compound of any one of embodiments 132-134, wherein $R^1$ is methyl, ethyl, n-propyl, i-propyl, n-butyl, i-butyl, or t-butyl.

Embodiment 138. The compound of any one of embodiments 132-134, wherein $R^1$ is —C(CH$_3$)$_2$CH$_2$OH.

Embodiment 139. The compound of any one of embodiments 132-134, wherein $R^1$ is t-butyl.

Embodiment 140. The compound of any one of embodiments 132-134, wherein $R^1$ is aryl optionally substituted.

Embodiment 141. The compound of any one of embodiments 132-134, wherein $R^1$ is phenyl optionally substituted.

Embodiment 142. The compound of any one of embodiments 132-134, wherein $R^1$ is unsubstituted phenyl.

Embodiment 143. The compound of any one of embodiments 132-134, wherein $R^1$ is cycloalkyl optionally substituted.

Embodiment 144. The compound of any one of embodiments 132-134, wherein $R^1$ is cyclohexyl optionally substituted.

Embodiment 145. The compound of any one of embodiments 132-144, wherein $R^2$ is H.

Embodiment 146. The compound of any one of embodiments 132-145, wherein J is a bond.

Embodiment 147. The compound of any one of embodiments 132-145, wherein J is O.

Embodiment 148. The compound of any one of embodiments 132-145, wherein J is S.

Embodiment 149. The compound of any one of embodiments 132-148, wherein n is 0.

Embodiment 150. The compound of any one of embodiments 132-148, wherein n is 1.

Embodiment 151. The compound of any one of embodiments 132-148, wherein n is 2.

Embodiment 152. The compound of any one of embodiments 132-151, wherein each of $R^4$ and $R^5$ is H.

Embodiment 153. The compound of any one of embodiments 132-151, wherein at least one $R^4$ and $R^5$ is $^2$H, and optionally, wherein each of $R^4$ and $R^5$ is $^2$H.

Embodiment 154. The compound of any one of embodiments 132-153, wherein $R^3$ is halo.

Embodiment 155. The compound of any one of embodiments 132-153, wherein $R^3$ is Cl.

Embodiment 156. The compound of any one of embodiments 132-153, wherein $R^3$ is Br.

Embodiment 157. The compound of any one of embodiments 132-153, wherein $R^3$ is H.

Embodiment 158. The compound of any one of embodiments 132-153, wherein $R^3$ is alkyl optionally substituted.

Embodiment 159. The compound of any one of embodiments 132-153, wherein $R^3$ is unsubstituted alkyl.

Embodiment 160. The compound of any one of embodiments 132-153, wherein $R^3$ is methyl, ethyl, n-propyl, i-propyl, n-butyl, i-butyl, or t-butyl.

Embodiment 161. The compound of any one of embodiments 132-153, wherein $R^3$ is methyl.

Embodiment 162. The compound of embodiment 132, wherein the compound is selected from the group consisting of:

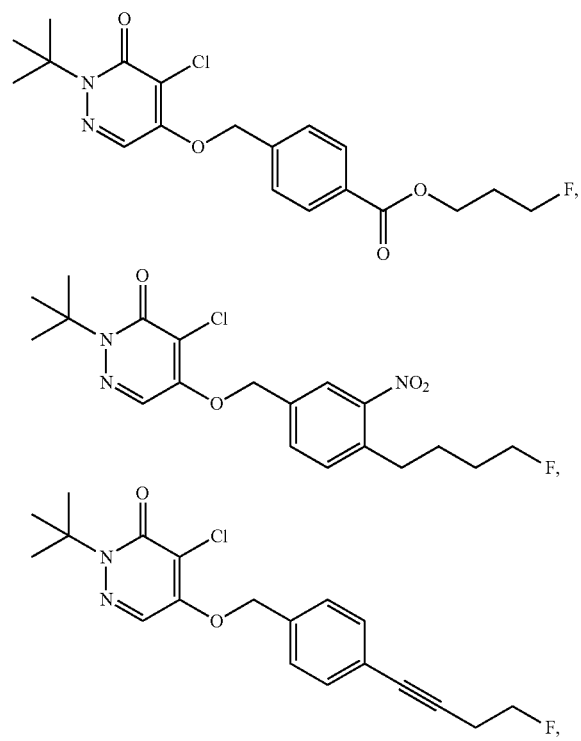

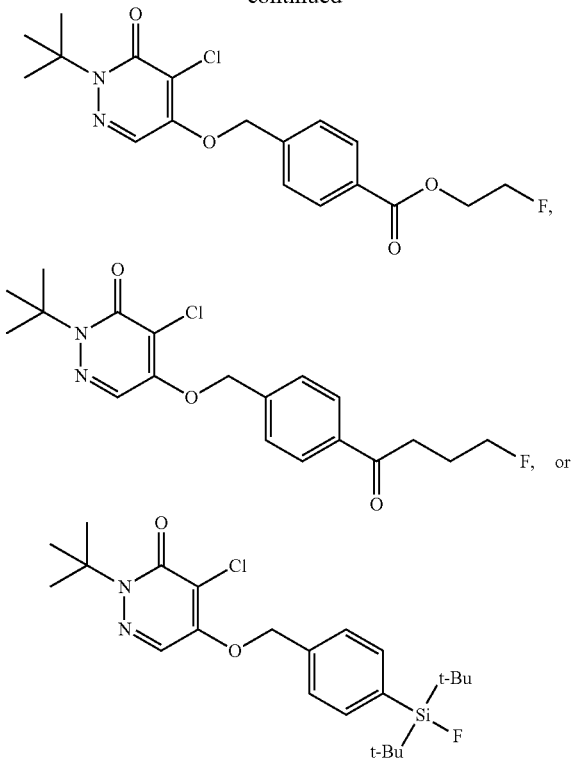

or a pharmaceutically acceptable salt thereof, wherein F is optionally $^{18}$F.

Embodiment 163. The compound of any one of embodiments 1-13, 15-70, 72-124, and 132-161, wherein the at least one imaging moiety is present in $R^6$.

Embodiment 164. The compound of any one of embodiments 1-13, 15-70, 72-124, 132-161, and 163, wherein at least one $R^6$ is substituted with the at least one imaging moiety.

Embodiment 165. The compound of any one of embodiments 1-13, 15-70, 72-124, 132-161, and 163-164, wherein the at least one imaging moiety is selected from the group consisting of $^{11}$C, $^{13}$N, $^{18}$F, $^{76}$Br, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, and $^{68}$Ga.

Embodiment 166. The compound of any one of embodiments 1-13, 15-70, 72-124, 132-161, and 163-165, wherein the at least one imaging moiety is $^{18}$F.

Embodiment 167. The compound of any one of embodiments 1-13, 15-70, 72-124, 132-161, and 163-165, wherein the at least one imaging moiety is associated with a group comprising the structure —B($R^{9'}$)$_2$($I_m$), wherein $I_m$ is an imaging moiety, optionally $^{18}$F.

Embodiment 168. The compound of any one of embodiments 1-13, 15-70, 72-124, 132-161, and 163-165, wherein the at least one imaging moiety is associated with a group comprising the structure —Si($R^{9'}$)$_2$($I_m$), wherein $I_m$ is an imaging moiety, optionally $^{18}$F.

Embodiment 169. The compound of any one of embodiments 1-13, 15-70, 72-124, 132-161, and 163-168, wherein all but one $R^6$ is H.

Embodiment 170. The compound of embodiment 169, wherein one $R^6$ is substituted with the at least one imaging moiety.

Embodiment 171. The compound of any one of embodiments 1-13, 15-70, 72-124, 132-161, and 163-166, wherein at least one $R^6$ is alkyl optionally substituted, alkoxy optionally substituted, alkoxyalkyl optionally substituted, each substituted with an imaging moiety.

Embodiment 172. The compound of any one of embodiments 1-13, 15-70, 72-124, 132-161, and 163-166, wherein at least one $R^6$ is —O(CH$_2$)$_j$I$_m$; wherein $I_m$ is an imaging moiety and j is 1, 2, 3, 4, 5, or 6.

Embodiment 173. The compound of any one of embodiments 1-13, 15-70, 72-124, 132-161, and 163-166, wherein at least one $R^6$ is —(CH$_2$)$_j$O(CH$_2$)$_j$I$_m$; wherein $I_m$ is an imaging moiety and each j is independently 1, 2, 3, 4, 5, or 6.

Embodiment 174. The compound of any one of embodiments 1-13, 15-70, 72-124, 132-161, and 163-166, wherein at least one $R^6$ is —C≡C—(CH$_2$)$_j$I$_m$; wherein $I_m$ is an imaging moiety and j is 1, 2, 3, 4, 5, or 6.

Embodiment 175. The compound of any one of embodiments 1-13, 15-70, 72-124, 132-161, and 163-166, wherein at least one $R^6$ is —[(CH$_2$)$_j$O]$_j$(CH$_2$)$_j$I$_m$; wherein $I_m$ is an imaging moiety and each j is independently 1, 2, 3, 4, 5, or 6.

Embodiment 176. The compound of any one of embodiments 1-13, 15-70, 72-124, 132-161, and 163-166, wherein at least one $R^6$ is —O[(CH$_2$)$_j$O]$_j$(CH$_2$)$_j$I$_m$; wherein $I_m$ is an imaging moiety and each j is independently 1, 2, 3, 4, 5, or 6.

Embodiment 177. The compound of any one of embodiments 1-13, 15-70, 72-124, 132-161, and 163-166, wherein at least one $R^6$ is optionally substituted alkyl substituted with an imaging moiety.

Embodiment 178. The compound of any one of embodiments 1-13, 15-70, 72-124, 132-161, and 163-166, wherein at least one $R^6$ is —C(=O)O(CH$_2$)$_j$I$_m$; wherein $I_m$ is an imaging moiety and j is 1, 2, 3, 4, 5, or 6.

Embodiment 179. The compound of any one of embodiments 1-13, 15-70, 72-124, 132-161, and 163-166, wherein at least one $R^6$ is —C(=O)(CH$_2$)$_j$I$_m$; wherein $I_m$ is an imaging moiety and j is 1, 2, 3, 4, 5, or 6.

Embodiment 180. The compound of any one of embodiments 1-13, 15-70, 72-124, 132-161, and 163-166, wherein at least one $R^6$ is —(CH$_2$)$_j$NH(CH$_2$)$_j$I$_m$; wherein $I_m$ is an imaging moiety and each j is independently 1, 2, 3, 4, 5, or 6.

Embodiment 181. The compound of any one of embodiments 1-13, 15-70, 72-124, 132-161, and 163-166, wherein at least one $R^6$ is Si($R^9$)$_2$ $I_m$, wherein each $R^9$ is alkyl optionally substituted and wherein $I_m$ is an imaging moiety.

Embodiment 182. The compound of any one of embodiments 1-13, 15-70, 72-124, 132-161, and 163-166, wherein the at least one imaging moiety is associated with a group comprising the structure —B($R^{9'}$)$_2$($I_m$), wherein $I_m$ is an imaging moiety, optionally $^{18}$F.

Embodiment 183. The compound of any one of embodiments 1-13, 15-70, 72-124, 132-161, and 163-166, wherein at least one $R^6$ is selected from the group consisting of —C≡C—CH$_2$CH$_2$CH$_2$I$_m$, —C≡C—CH$_2$CH$_2$I$_m$, —C≡C—CH$_2$I$_m$, —CH$_2$I$_m$, —(CH$_2$)$_2$I$_m$, —(CH$_2$)$_3$I$_m$, —(CH$_2$)$_4$I$_m$, —(CH$_2$)$_5$I$_m$, —(CH$_2$)$_6$I$_m$, —OCH$_2$I$_m$, —O(CH$_2$)$_2$I$_m$, —O(CH$_2$)$_3$I$_m$, —O(CH$_2$)$_4$I$_m$, —O(CH$_2$)$_5$I$_m$, —O(CH$_2$)$_6$I$_m$, —CH$_2$O(CH$_2$)$_2$I$_m$, —CH(CH$_3$)O(CH$_2$)$_2$I$_m$, —CH$_2$O(CH$_2$)$_3$I$_m$, —CD$_2$O(CH$_2$)$_2$I$_m$, —(CH$_2$)$_2$O(CH$_2$)$_2$I$_m$, —CHBrC(CH$_3$)$_2$I$_m$, —CHClC(CH$_3$)$_2$I$_m$, —CHFC(CH$_3$)$_2$I$_m$, —C(=O)OCH$_2$I$_m$, —C(=O)O(CH$_2$)$_2$I$_m$, —C(=O)O(CH$_2$)$_3$I$_m$, —CH$_2$NH(CH$_2$)$_2$I$_m$, —CH$_2$NHCH$_2$I$_m$, —CH$_2$O(CH$_2$)$_2$O(CH$_2$)$_2$I$_m$, —CH$_2$O(CH$_2$)$_2$O(CH$_2$)$_3$I$_m$, —O(CH$_2$)$_2$O(CH$_2$)$_2$I$_m$, —C(=O)(CH$_2$)$_2$I$_m$, and —C(=O)(CH$_2$)$_3$I$_m$; optionally, wherein I$_m$ is $^{18}$F.

Embodiment 184. The compound of any one of embodiments 1-13, 15-70, 72-124, 132-161, and 163-166, wherein at least one R$^6$ is an imaging moiety, optionally, wherein the imaging moiety is $^{18}$F.

Embodiment 185. The compound of any one of embodiments 1-13, 15-70, 72-124, 132-161, and 163-166, wherein at least one R$^6$ is optionally substituted with at least one $^2$H.

Embodiment 186. The compound of any one of embodiments 1-13, 15-70, 72-124, 132-161, and 163-166, wherein at least one R$^6$ is —Si(R$^9$)$_3$.

Embodiment 187. The compound of any one of embodiments 1-13, 15-70, 72-124, 132-161, and 163-166, wherein at least one R$^6$ is —B(R$^{9'}$)$_3$.

Embodiment 188. The compound of any one of embodiments 1-13, 15-70, 72-124, 132-161, and 163-187, wherein at least one R$^6$ is —NO$_2$.

Embodiment 189. The compound of any one of embodiments 1-13, 15-70, 72-124, 132-161, and 163-187, wherein at least one R$^6$ is halo.

Embodiment 190. The compound of any one of embodiments 1-13, 15-70, 72-124, 132-161, and 163-187, wherein at least one R$^6$ is Cl.

Embodiment 191. The compound of any one of embodiments 1-13, 15-70, 72-124, 132-161, and 163-187, wherein at least one R$^6$ is Br.

Embodiment 192. The compound of any one of embodiments 1-13, 15-70, 72-124, 132-161, and 163-187, wherein at least one R$^6$ is F.

Embodiment 193. In embodiment 193, provided is a compound comprising the formula:

(IX)

or a pharmaceutically acceptable salt thereof, wherein:

R$^{20}$ is selected from the group consisting of hydrogen, heteroalkyl optionally substituted, alkoxy optionally substituted, alkoxyalkyl optionally substituted, aryl optionally substituted, heteroaryl optionally substituted, halo, haloalkyl, —CN, and —NO$_2$;

each R$^{21}$ and R$^{23}$ is independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two R$^{21}$ or any two R$^{23}$ may be joined together to form a ring;

R$^{22}$ is selected from the group consisting of hydrogen, alkyl optionally substituted, heteroalkyl optionally substituted, alkoxyalkyl optionally substituted, halo, haloalkyl, —OR$^{28}$, —Si(R$^9$)$_3$, —B(R$^{9'}$)$_3$, and an imaging moiety;

R$^{24}$, R$^{25}$, R$^{26}$, and R$^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, and an imaging moiety;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring; and each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety;

each R$^{9'}$ is independently selected from the group consisting of halo, alkyl optionally substituted, aryl optionally substituted, and an imaging moiety;

R$^{28}$ is selected from the group consisting of hydrogen, alkyl optionally substituted, and heteroalkyl optionally substituted;

G is O, S, or NR$^{28}$;

a is 0, 1, 2, 3, or 4;

each K is independently arylene, heteroarylene, alkenylene, or alkynylene, each optionally substituted;

each b is independently 0, 1, 2, 3, or 4; and c is 1 or 2, provided at least one imaging moiety is present in the compound.

Embodiment 194. In embodiment 194, provided is a compound comprising the formula:

(X)

or a pharmaceutically acceptable salt thereof, wherein:

each R$^{21}$ and R$^{23}$ is independently selected from the group consisting of hydrogen, alkyl optionally substituted, heteroalkyl optionally substituted, alkoxy optionally substituted, alkoxyalkyl optionally substituted, halo, haloalkyl, and an imaging moiety, or optionally any two R$^{21}$ or any two R$^{23}$ may be joined together to form a ring;

R$^{22}$ is selected from the group consisting of hydrogen, alkyl optionally substituted, heteroalkyl optionally substituted, alkoxyalkyl optionally substituted, halo, haloalkyl, —OR$^{28}$, —Si(R$^9$)$_3$, —B(R$^{9'}$)$_3$, and an imaging moiety;

R$^{24}$, R$^{25}$, R$^{26}$, and R$^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, and an imaging moiety;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R$^9$ is independently selected from the group consisting of hydrogen, alkyl optionally substituted, aryl optionally substituted, haloalkyl, halogen, and an imaging moiety;

each R$^{9'}$ is independently selected from the group consisting of halo, alkyl optionally substituted, aryl optionally substituted, and an imaging moiety;

R$^{28}$ is selected from the group consisting of hydrogen, alkyl optionally substituted, and heteroalkyl optionally substituted;

R$^{29}$ is selected from the group consisting of hydrogen, alkyl optionally substituted, heteroalkyl optionally substituted, aryl optionally substituted, heteroaryl optionally substituted, optionally substituted alkoxy, optionally substituted alkoxyalkyl, halo, haloalkyl, —CN, —NO$_2$, and an imaging moiety;

G is O, S, or NR$^{28}$;

a is 0, 1, 2, 3, or 4;

each K is independently arylene, heteroarylene, alkenylene, or alkynylene, each optionally substituted, provided at least one K is alkenylene, or alkynylene;

each b is independently 0, 1, 2, 3, or 4; and c is 1 or 2, provided at least one imaging moiety is present in the compound.

Embodiment 195. The compound of embodiment 193, wherein R$^{29}$ is alkyl optionally substituted.

Embodiment 196. The compound of embodiment 193, wherein R$^{29}$ is methyl, ethyl, n-propyl, i-propyl, n-butyl, i-butyl, or t-butyl.

Embodiment 197. The compound of embodiment 193, wherein R$^{29}$ is methyl.

Embodiment 198. The compound of embodiment 194, wherein the compound comprises the structure:

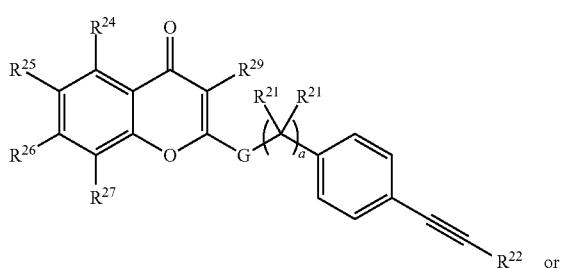

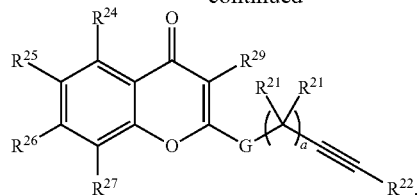

Embodiment 199. The compound of embodiment 193, wherein the compound comprises the structure:

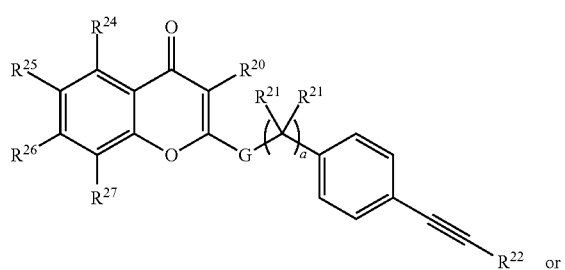

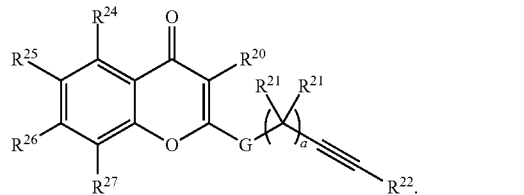

Embodiment 200. The compound of any one of embodiments 193-199, wherein each of R$^{24}$, R$^{25}$, R$^{26}$, and R$^{27}$ are H.

Embodiment 201. The compound of any one of embodiments 193-200, wherein G is O.

Embodiment 202. The compound of any one of embodiments 193-200, wherein G is S.

Embodiment 203. The compound of any one of embodiments 193-200, wherein G is NR$^{28}$.

Embodiment 204. The compound of any one of embodiments 193-200, wherein G is NH.

Embodiment 205. The compound of any one of embodiments 193-204, wherein a is 0.

Embodiment 206. The compound of any one of embodiments 193-204, wherein a is 1.

Embodiment 207. The compound of any one of embodiments 193-204, wherein a is 2.

Embodiment 208. The compound of any one of embodiments 193-204, wherein a is 3.

Embodiment 209. The compound of any one of embodiments 193-204, wherein a is 4.

Embodiment 210. The compound of any one of embodiments 193-197 or 200-209, wherein at least one K is alkynylene.

Embodiment 211. The compound of any one of embodiments 193-197 or 200-209, wherein

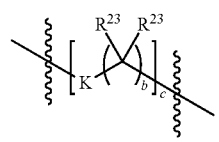

has the structure:

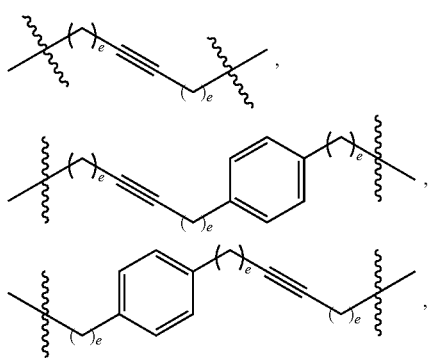

wherein each e is independently 1, 2, 3, or 4.

Embodiment 212. The compound of any one of embodiments 193-211, wherein each $R^{21}$ is H.

Embodiment 213. The compound of any one of embodiments 193-212, wherein $R^{22}$ is —O(CH$_2$)$_j$I$_m$; wherein I$_m$ is an imaging moiety and j is 1, 2, 3, 4, 5, or 6.

Embodiment 214. The compound of any one of embodiments 193-212, wherein $R^{22}$ is —(CH$_2$)$_j$O(CH$_2$)$_j$I$_m$; wherein I$_m$ is an imaging moiety and each j is independently 1, 2, 3, 4, 5, or 6.

Embodiment 215. The compound of any one of embodiments 193-212, wherein $R^{22}$ is —[(CH$_2$)$_j$O]$_j$(CH$_2$)$_j$I$_m$; wherein I$_m$ is an imaging moiety and each j is independently 1, 2, 3, 4, 5, or 6.

Embodiment 216. The compound of any one of embodiments 193-212, wherein $R^{22}$ is —O[(CH$_2$)$_j$O]$_j$(CH$_2$)$_j$I$_m$; wherein I$_m$ is an imaging moiety and each j is independently 1, 2, 3, 4, 5, or 6.

Embodiment 217. The compound of any one of embodiments 193-212, wherein $R^{22}$ is optionally substituted alkyl substituted with an imaging moiety.

Embodiment 218. The compound of any one of embodiments 193-212, wherein the at least one imaging moiety is present in $R^{21}$, $R^{22}$, $R^{23}$, $R^{24}$, $R^{25}$, $R^{26}$, or $R^{27}$.

Embodiment 219. The compound of any one of embodiments 193-212, wherein the at least one imaging moiety is present in $R^{21}$, $R^{22}$, $R^{23}$, $R^{24}$, $R^{25}$, $R^{26}$, $R^{27}$ or $R^{29}$.

Embodiment 220. The compound of any one of embodiments 193-212, wherein the at least one imaging moiety is present in $R^{21}$, $R^{22}$, or $R^{23}$.

Embodiment 221. The compound of any one of embodiments 193-212, wherein the at least one imaging moiety is present in $R^{22}$.

Embodiment 222. The compound of any one of embodiments 193-212, wherein $R^{22}$ comprises the at least one imaging moiety.

Embodiment 223. The compound of any one of embodiments 193-212, wherein $R^{22}$ is an imaging moiety.

Embodiment 224. The compound of any one of embodiments 193-223, wherein the at least one imaging moiety is selected from the group consisting of $^{11}$C, $^{13}$N, $^{18}$F, $^{76}$Br, $^{89}$Zr, $^{123}$I, $^{124}$I, $^{125}$I, $^{131}$I, $^{99m}$Tc, $^{95}$Tc, $^{111}$In, $^{62}$Cu, $^{64}$Cu, $^{67}$Ga, and $^{68}$Ga.

Embodiment 225. The compound of any one of embodiments 193-224, wherein the at least one imaging moiety is $^{18}$F.

Embodiment 226. The compound of embodiment 194, wherein the compound is selected from the group consisting of:

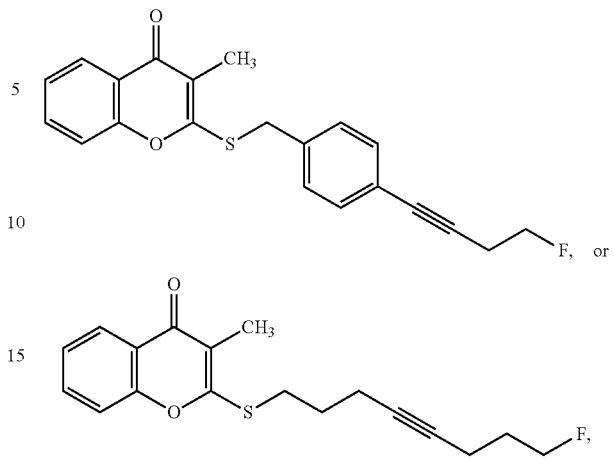

or a pharmaceutically acceptable salt thereof, wherein F is optionally $^{18}$F.

Embodiment 227. In embodiment 227, provided is a compound is selected from the group consisting of:

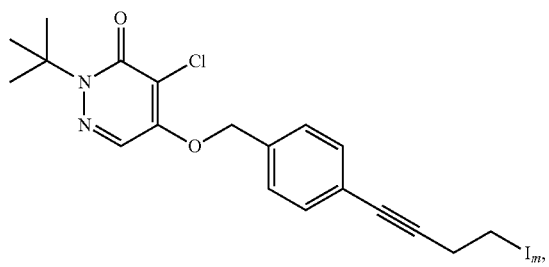

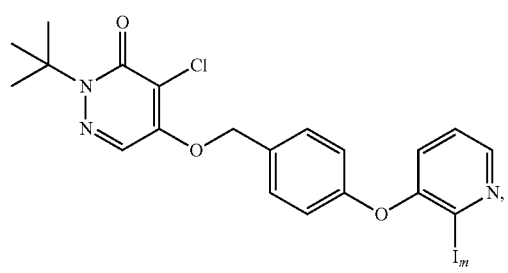

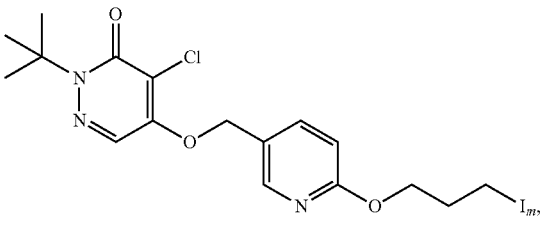

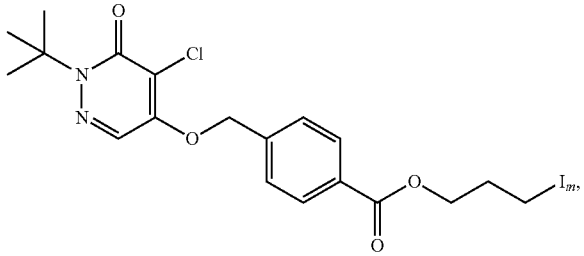

153
-continued
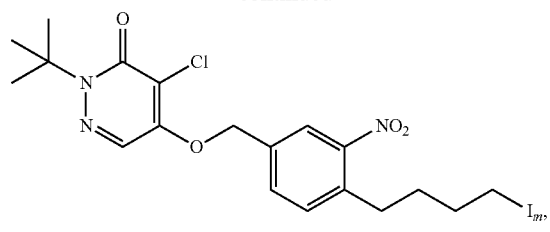
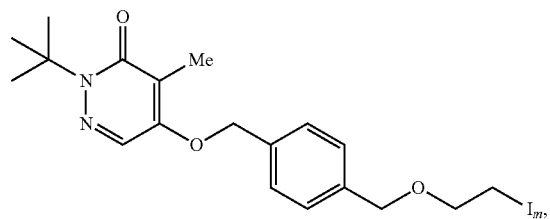
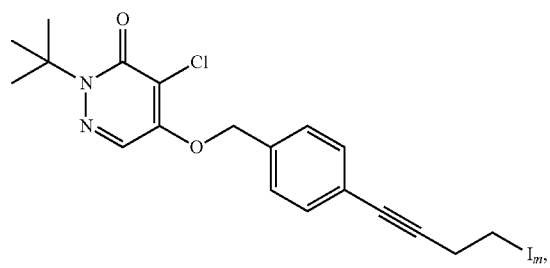
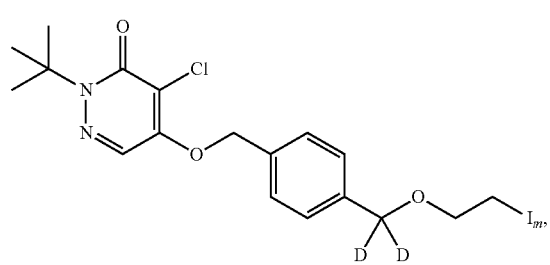
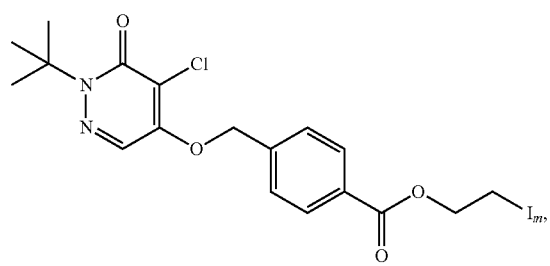
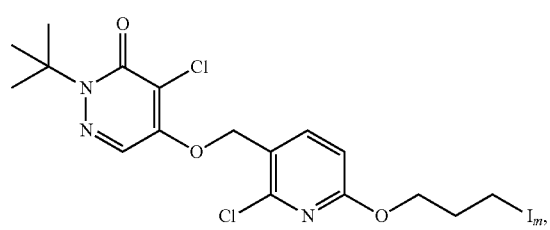
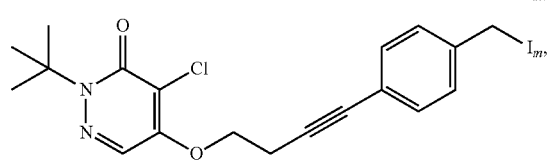
154
-continued
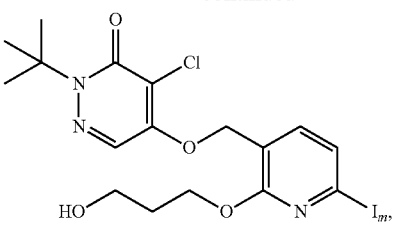
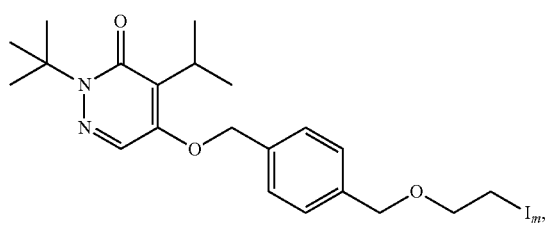
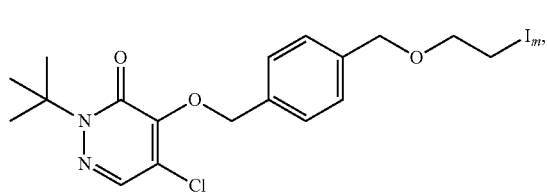
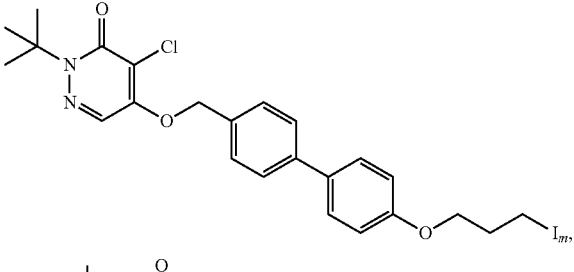
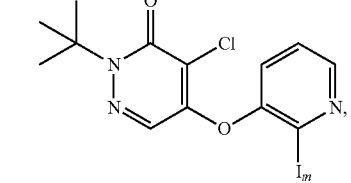
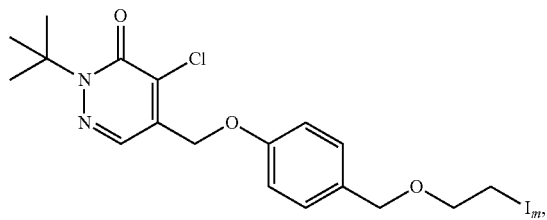
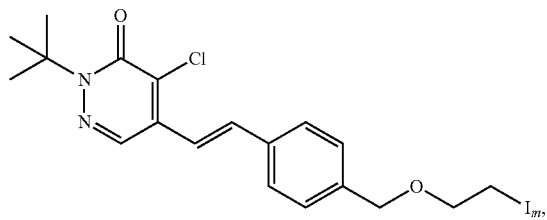

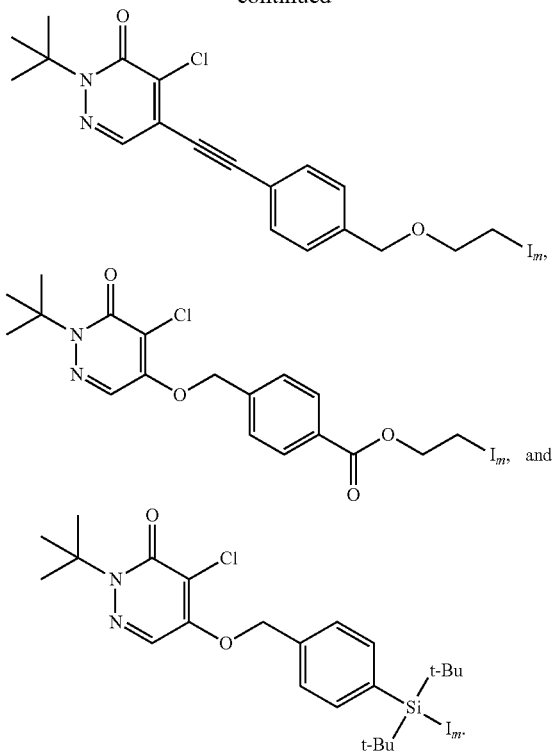
or a pharmaceutically acceptable salt thereof, wherein $I_m$ is an imaging moiety.
Embodiment 228. The compound of embodiment 227, wherein the compound is selected from the group consisting of:
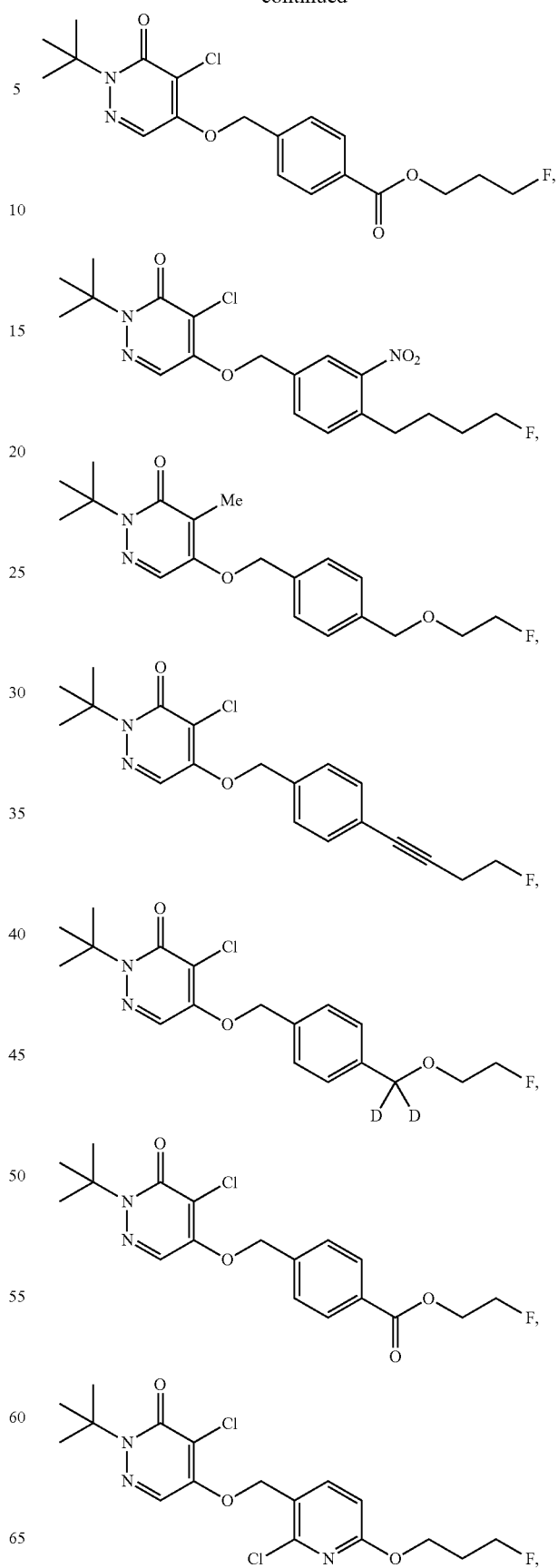

157
-continued
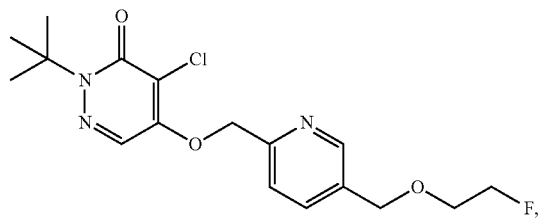
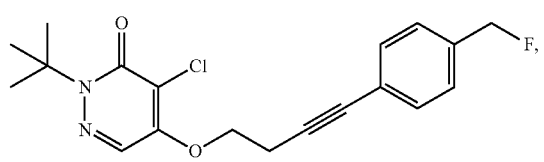
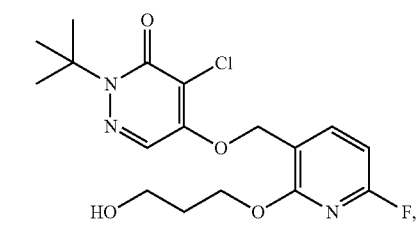
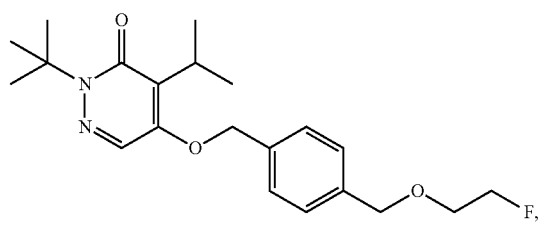
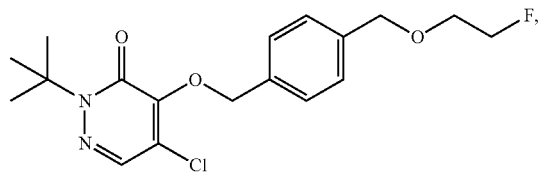
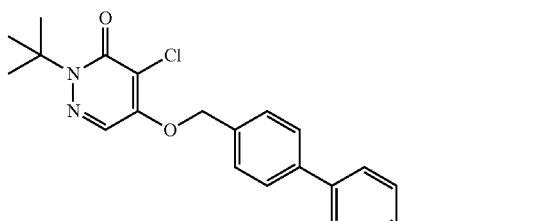
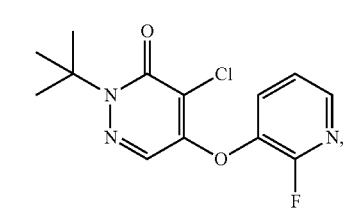
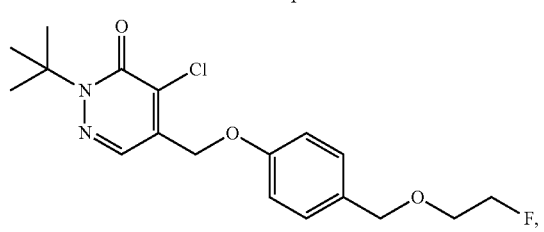
158
-continued
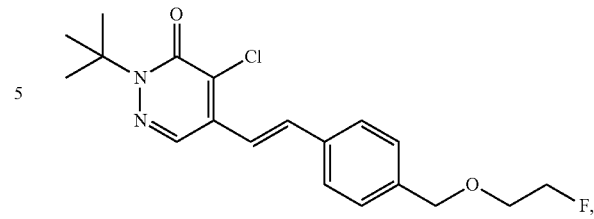
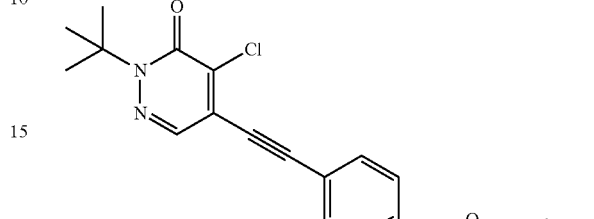
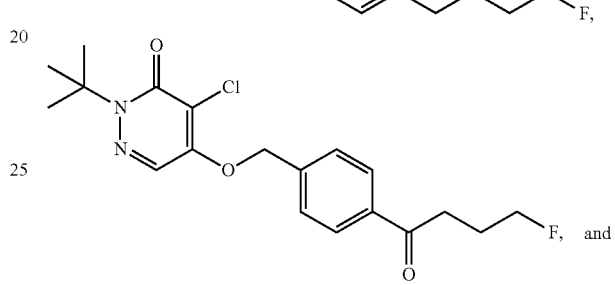
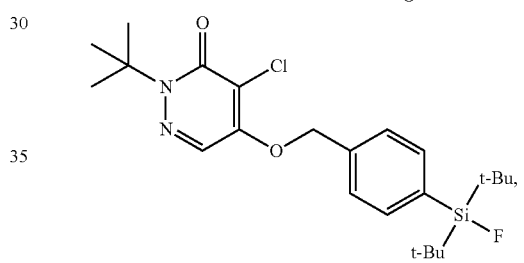
or a pharmaceutically acceptable salt thereof, wherein each F is optionally $^{18}$F.
Embodiment 229. In embodiment 229, provided is a compound selected from the group consisting of:
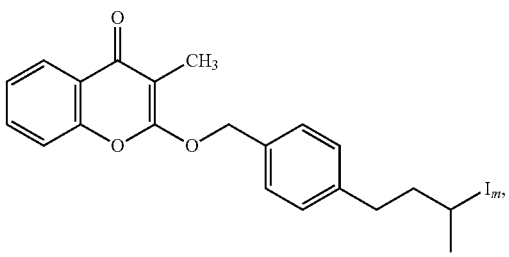
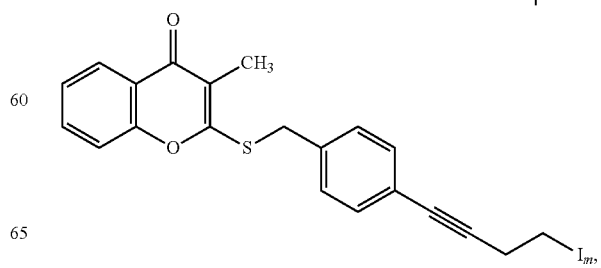

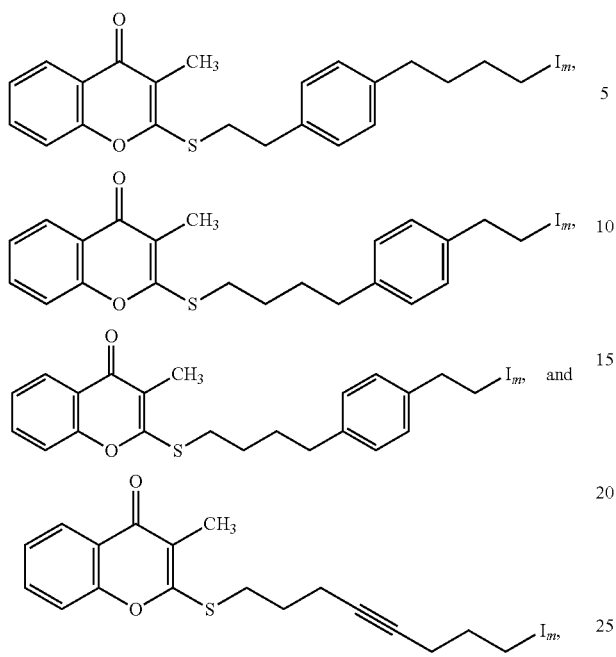

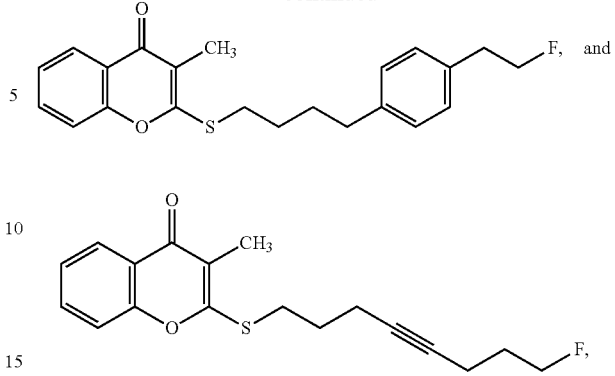

or a pharmaceutically acceptable salt thereof, wherein $I_m$ is an imaging moiety.

Embodiment 230. The compound of embodiment 229, wherein the compound is selected from the group consisting of:

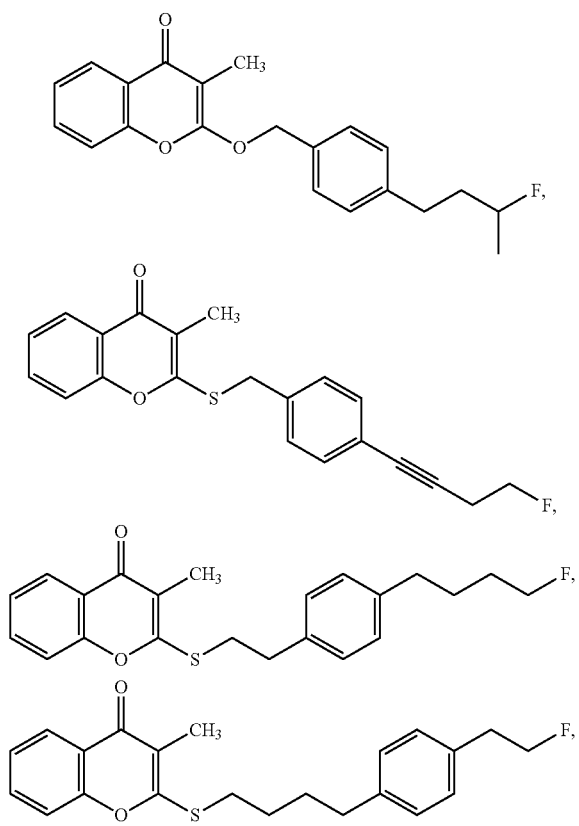

or a pharmaceutically acceptable salt thereof, wherein each F is optionally $^{18}F$.

Embodiment 231. In embodiment 231, provided is a pharmaceutical composition comprising a compound or a salt thereof of any preceding embodiment, and optionally a pharmaceutically acceptable excipient.

Embodiment 232. In embodiment 232, provided is a sterile aqueous solution comprising a compound or a salt thereof of any preceding embodiment.

Embodiment 233. Use of a compound or a salt thereof of any preceding embodiment as an imaging agent.

Embodiment 234. Use of a compound or a salt thereof of any preceding embodiment in myocardial perfusion imaging.

Embodiment 235. Use of a compound or salt thereof of any preceding embodiment in the manufacture of a medicament for detecting, imaging or monitoring myocardial perfusion.

Embodiment 236. In embodiment 236, provided is a method of imaging a portion of a subject, comprising:
administering to the subject a compound or a salt thereof of any preceding embodiment, or a composition of embodiment 231, or a sterile aqueous solution of embodiment 232; and
acquiring at least one image of a portion of the subject.

Embodiment 237. In embodiment 237, provided is a method of imaging a portion of a subject, comprising:
administering to a subject a compound or a salt thereof of any preceding embodiment or a salt thereof, or a pharmaceutical composition of embodiment 231, or a sterile aqueous solution of embodiment 232;
detecting radiation emitted by the compound; and
forming an image therefrom.

Embodiment 238. The method of embodiment 237, wherein the portion of the subject imaged is a portion of the heart.

Embodiment 239. In embodiment 239, provided is a diagnostic kit comprising one or more vials containing a precursor to a compound or a salt thereof of any preceding embodiment; and optionally other components.

Embodiment 240. The diagnostic kit of embodiment 239, wherein the diagnostic kit is for the preparation of diagnostic agents for imaging, detecting, and/or monitoring myocardial perfusion in a subject.

Embodiment 241. The diagnostic kit of embodiment 239 or 240, wherein said other components are selected from the group consisting of ancillary ligands, reducing agents, transfer ligands, buffers, lyophilization aids, stabilization aids, solubilization aids, and bacteriostats.

Embodiment 242. In embodiment 242, provided is a method of imaging myocardial perfusion, comprising:

administering to a patient a compound or a salt thereof of any preceding embodiment, or a pharmaceutical composition of embodiment 231, or a sterile aqueous solution of embodiment 232; and
scanning the patient using diagnostic imaging.
Embodiment 243. In embodiment 243, provided is a method of detecting myocardial perfusion, comprising:
administering to a patient a compound or a salt thereof of any preceding embodiment, or a pharmaceutical composition of embodiment 231, or a sterile aqueous solution of embodiment 232; and
scanning the patient using diagnostic imaging.
Embodiment 244. In embodiment 244, provided is a method of monitoring myocardial perfusion, comprising:
administering to a patient a compound or a salt thereof of any preceding embodiment, or a pharmaceutical composition of embodiment 231, or a sterile aqueous solution of embodiment 232; and
scanning the patient using diagnostic imaging.
Embodiment 245. In embodiment 245, provided is a compound comprising the structure:

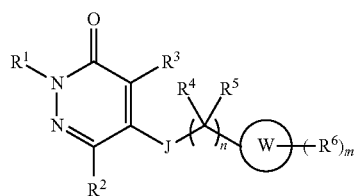

(XI)

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-NO_2$, and a leaving group;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-CN$, $-NO_2$, and a leaving group;

J is selected from the group consisting of $N(R^7)$, S, O, $C(=O)$, $C(=O)O$, $OC(=O)$, $C(=O)N(R^7)$, $N(R^7)C(=O)$, $CH_2O$, and a bond;

$R^4$ and $R^5$ are each independently selected from the group consisting of hydrogen, alkyl optionally substituted, and a leaving group, or optionally any two of $R^4$ and $R^5$ are joined together to form a ring;

n is 0, 1, 2, or 3;

W is heteroaryl, naphthyl, heterocyclyl or aryl;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, $-N(R^7)_2$, $-NO_2$, $-OH$, $-C(=O)R^8$, $-C(=O)OR^8$, $-OC(=O)R^8$, $-C(=O)N(R^7)_2$, $-N(R^7)C(=O)R^8$, $-CN$, $-Si(R^9)_3$, $-B(R^{9'})_3$, $-OR^8$, and a leaving group;

m is 0, 1, 2, 3, 4, 5, 6, or 7;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halogen, and a leaving group; and each $R^{9'}$ is independently selected from the group consisting of halo, alkyl optionally substituted, aryl optionally substituted, and a leaving group, provided that at least one leaving group is present in the compound; and provided that when W is aryl, a) $R^3$ is not halo, alkyl or haloalkyl, or b) at least one $R^6$ is selected from the group consisting of alkynyl optionally substituted, alkenyl optionally substituted, alkyl substituted with $-CN$, alkyl substituted with $-C(=O)OR^8$, alkyl substituted with $-C(=O)R^8$, alkyl substituted with $-N(R^7)_2$, $-CN$, $-NO_2$, $-N(R^7)_2$, $-C(=O)OR^8$, $-OC(=O)R^8$, $-C(=O)R^8$, $-C(=O)N(R^7)_2$, and $-N(R^7)C(=O)R^8$.

Embodiment 246. The compound of embodiment 245, wherein the compound comprises the structure:

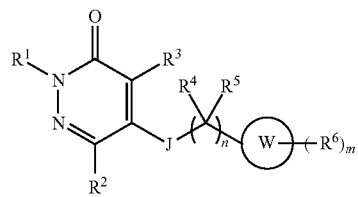

(XII)

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-NO_2$, and a leaving group;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, $-CN$, $-NO_2$, and a leaving group;

J is selected from the group consisting of N(R$^7$), S, O, C(=O), C(=O)O, OC(=O), C(=O)N(R$^7$), N(R$^7$)C(=O), CH$_2$O, and a bond;

R$^4$ and R$^5$ are each independently selected from the group consisting of hydrogen, alkyl optionally substituted, and a leaving group, or optionally any two of R$^4$ and R$^5$ are joined together to form a ring;

n is 0, 1, 2, or 3;

W is heteroaryl, naphthyl, or heterocyclyl;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^9$)$_3$, —OR$^8$, and a leaving group;

m is 0, 1, 2, 3, 4, 5, 6, or 7;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R$^7$ may be joined together to form a ring; and each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R$^9$ is independently selected from the group consisting of hydrogen, alkyl optionally substituted, aryl optionally substituted, haloalkyl, halogen, and a leaving group; and each R$^{9'}$ is independently selected from the group consisting of halo, alkyl optionally substituted, aryl optionally substituted, and a leaving group, provided that at least one leaving group is present in the compound.

Embodiment 247. The compound of embodiment 245, wherein the compound comprises the structure:

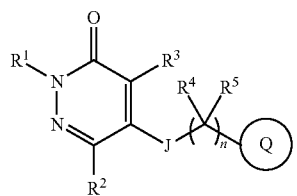

(XIII)

or a salt thereof, wherein:

R$^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

R$^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and a leaving group;

R$^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and a leaving group;

J is selected from the group consisting of N(R$^7$), S, O, C(=O), C(=O)O, OC(=O), C(=O)N(R$^7$), N(R$^7$)C(=O), CH$_2$O, and a bond;

R$^4$ and R$^5$ are each independently selected from the group consisting of hydrogen, alkyl optionally substituted, and a leaving group, or optionally any two of R$^4$ and R$^5$ are joined together to form a ring;

n is 0, 1, 2, or 3;

Q has the structure:

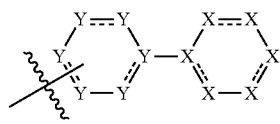

each Y and each X is independently selected from the group consisting of C, C(R$^6$), C(R$^6$)$_2$, N, NR$^7$, O, and S, provided at least one Y is not C or C(R$^6$);

each ══════ is independently a single or double bond;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^9$)$_3$, —OR$^8$, and a leaving group;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R$^7$ may be joined together to form a ring; each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R$^9$ is independently selected from the group consisting of hydrogen, alkyl optionally substituted, aryl optionally substituted, haloalkyl, halogen, and a leaving group; and each R$^{9'}$ is independently selected from the group consisting of halo, alkyl optionally substituted, aryl optionally substituted, and a leaving group, provided that at least one leaving group is present in the compound.

Embodiment 248. The compound of embodiment 245, wherein the compound comprises the structure:

(XIV)

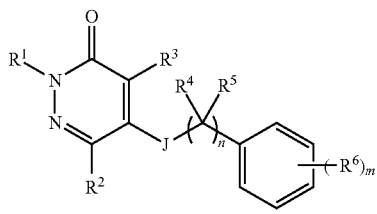

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and a leaving group;

$R^3$ is selected from the group consisting of hydrogen, unsubstituted alkyl or alkyl optionally substituted with a moiety other than a halogen, heteroalkyl optionally substituted, alkoxy optionally substituted, alkoxyalkyl optionally substituted, aryl optionally substituted, heteroaryl optionally substituted, —CN, and —NO$_2$;

J is selected from the group consisting of N(R$^7$), S, O, C(═O), C(═O)O, OC(═O), C(═O)N(R$^7$), N(R$^7$)C(═O), CH$_2$O, and a bond;

$R^4$ and $R^5$ are each independently selected from the group consisting of hydrogen, alkyl optionally substituted, and a leaving group, or optionally any two of $R^4$ and $R^5$ are joined together to form a ring;

n is 0, 1, 2, or 3;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(═O)R$^8$, —C(═O)OR$^8$, —OC(═O)R$^8$, —C(═O)N(R$^7$)$_2$, —N(R$^7$)C(═O)R$^8$, —CN, —Si(R$^9$)$_3$, —B(R$^{9'}$)$_3$, —OR$^8$, and a leaving group;

m is 0, 1, 2, 3, 4, or 5;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring; and each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halogen, and a leaving group; and each $R^{9'}$ is independently selected from the group consisting of halo, alkyl optionally substituted, aryl optionally substituted, and a leaving group, provided that at least one leaving group is present in the compound.

Embodiment 249. In embodiment 249, provided is a compound comprising the structure:

(XV)

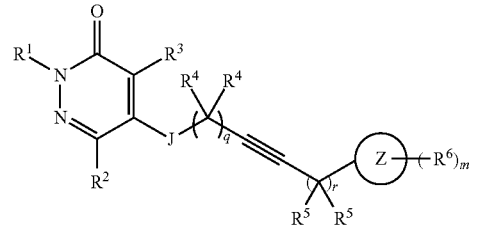

or (XVI)

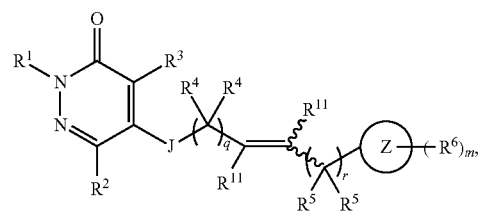

or a salt thereof, wherein:

$R^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

$R^2$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO$_2$, and a leaving group;

$R^3$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO$_2$, and a leaving group;

J is selected from the group consisting of N(R$^7$), S, O, C(═O), C(═O)O, OC(═O), C(═O)N(R$^7$), N(R$^7$)C(═O), CH$_2$O, and a bond;

each $R^4$, $R^5$, and $R^{11}$ is independently selected from the group consisting of hydrogen, alkyl optionally substituted, and a leaving group, or optionally any two of $R^4$ or any two of $R^5$ are joined together to form a ring;

q, and r are each independently 0, 1, 2, or 3;

Z is selected from the group consisting of aryl, heteroaryl, heterocyclyl, and a bond;

each $R^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(═O)R$^8$, —C(=O)OR⁸, —OC(=O)R⁸, —C(=O)N(R⁷)₂, —N(R⁷)C(=O)R⁸, —CN, —Si(R⁹)₃, —B(R⁹)₃, —OR⁸, and a leaving group;

m is 0, 1, 2, 3, 4, 5, 6, or 7;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halogen, and a leaving group; and each R⁹' is independently selected from the group consisting of halo, alkyl optionally substituted, aryl optionally substituted, and a leaving group, provided that at least one leaving group is present in the compound.

Embodiment 250. In embodiment 250, provided is a compound comprising the structure:

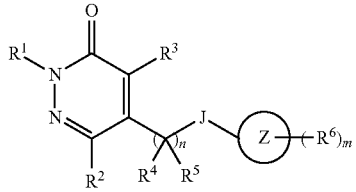

(XVII)

or a salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, —NO₂, haloalkyl, and a leaving group;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO₂, and a leaving group;

J is selected from the group consisting of N(R⁷), S, O, C(=O), C(=O)O, OC(=O), C(=O)N(R⁷)₂, N(R⁷)C(=O), and —CH₂O;

each R⁴ and R⁵ is independently selected from the group consisting of hydrogen, alkyl optionally substituted, and a leaving group, or optionally any two of R⁴ or any two of R⁵ are joined together to form a ring;

n is 1, 2, or 3;

Z is selected from the group consisting of aryl, heteroaryl, heterocyclyl, and a bond;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹)₃, —OR⁸, and a leaving group;

m is 0, 1, 2, 3, 4, 5, 6, or 7;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R⁷ may be joined together to form a ring; and each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R⁹ is independently selected from the group consisting of hydrogen, alkyl optionally substituted, aryl optionally substituted, haloalkyl, halogen, and a leaving group; and each R⁹' is independently selected from the group consisting of halo, alkyl optionally substituted, aryl optionally substituted, and a leaving group, provided that at least one leaving group is present in the compound.

Embodiment 251. The compound of embodiment 245, wherein the compound comprises the structure:

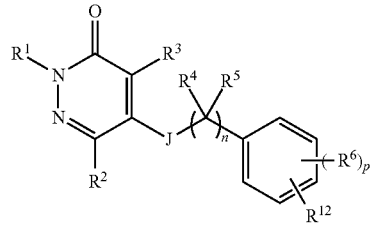

(XVIII)

or a salt thereof, wherein:

R¹ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and a leaving group;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and a leaving group;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —CN, —NO₂, and a leaving group;

J is selected from the group consisting of consisting of N(R$^7$), S, O, C(=O), C(=O)O, OC(=O), C(=O)N(R$^7$), N(R$^7$)C(=O), CH$_2$O, and a bond;

R$^4$ and R$^5$ are each independently selected from the group consisting of hydrogen, alkyl optionally substituted, and a leaving group, or optionally any two of R$^4$ and R$^5$ are joined together to form a ring;

n is 0, 1, 2, or 3;

each R$^6$ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R$^7$)$_2$, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, —Si(R$^9$)$_3$, —B(R$^9$)$_3$, —OR$^8$, and a leaving group;

p is 0, 1, 2, 3, or 4;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R$^7$ may be joined together to form a ring;

each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

R$^{12}$ is selected from the group consisting of alkynyl optionally substituted, alkenyl optionally substituted, alkyl substituted with —CN, alkyl substituted with —C(=O)OR$^8$, alkyl substituted with —C(=O)R$^8$, alkyl substituted with —N(R$^7$)$_2$, —CN, —NO$_2$, —N(R$^7$)$_2$, —C(=O)OR$^8$, —OC(=O)R$^8$, —C(=O)R$^8$, —C(=O)N(R$^7$)$_2$, and —N(R$^7$)C(=O)R$^8$;

each R$^9$ is independently selected from the group consisting of hydrogen, alkyl optionally substituted, aryl optionally substituted, haloalkyl, halogen, and a leaving group; and each R$^{9'}$ is independently selected from the group consisting of halo, alkyl optionally substituted, aryl optionally substituted, and a leaving group, provided that at least one leaving group is present in the compound.

Embodiment 252. In embodiment 252, provided is a compound comprising the formula:

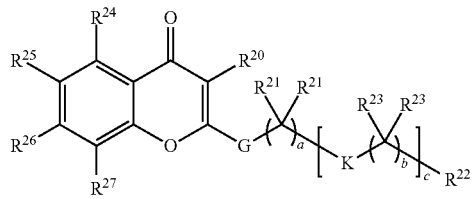

(XIX)

or a salt thereof, wherein:

R$^{20}$ is selected from the group consisting of hydrogen, heteroalkyl optionally substituted, alkoxy optionally substituted, alkoxyalkyl optionally substituted, aryl optionally substituted, heteroaryl optionally substituted, halo, haloalkyl, —CN, and —NO$_2$;

each R$^{21}$ and R$^{23}$ is independently selected from the group consisting of hydrogen, alkyl optionally substituted, heteroalkyl optionally substituted, alkoxy optionally substituted, alkoxyalkyl optionally substituted, halo, haloalkyl, and a leaving group, or optionally any two R$^{21}$ or any two R$^{23}$ may be joined together to form a ring;

R$^{22}$ is selected from the group consisting of hydrogen, alkyl optionally substituted, heteroalkyl optionally substituted, alkoxyalkyl optionally substituted, halo, haloalkyl, —OR$^{28}$, —Si(R$^9$)$_3$, —B(R$^9$)$_3$, and a leaving group;

R$^{24}$, R$^{25}$, R$^{26}$, and R$^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —NO$_2$, —OH, —C(=O)R$^8$, —C(=O)OR$^8$, —OC(=O)R$^8$, —C(=O)N(R$^7$)$_2$, —N(R$^7$)C(=O)R$^8$, —CN, and a leaving group;

each R$^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two R$^7$ may be joined together to form a ring; each R$^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each R$^9$ is independently selected from the group consisting of hydrogen, alkyl optionally substituted, aryl optionally substituted, haloalkyl, halogen, and a leaving group;

each R$^{9'}$ is independently selected from the group consisting of halo, alkyl optionally substituted, aryl optionally substituted, and a leaving group;

R$^2$ is selected from the group consisting of hydrogen, alkyl optionally substituted, and heteroalkyl optionally substituted;

G is O, S, or NR$^{28}$;

a is 0, 1, 2, 3, or 4;

each K is independently arylene, heteroarylene, alkenylene, or alkynylene, each optionally substituted;

each b is independently 0, 1, 2, 3, or 4; and c is 1 or 2, provided at least one leaving group is present in the compound.

Embodiment 253. In embodiment 253, provided is a compound comprising the formula:

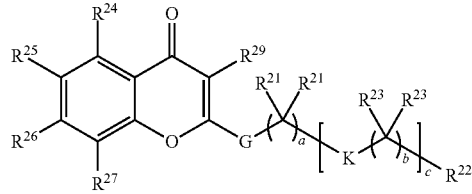

(XX)

or a salt thereof, wherein:

each R$^{21}$ and R$^{23}$ is independently selected from the group consisting of hydrogen, alkyl optionally substituted, heteroalkyl optionally substituted, alkoxy optionally substituted, alkoxyalkyl optionally substituted, halo, haloalkyl, and a leaving group, or optionally any two $R^{21}$ or any two $R^{23}$ may be joined together to form a ring; $R^{22}$ is selected from the group consisting of hydrogen, alkyl optionally substituted, heteroalkyl optionally substituted, alkoxyalkyl optionally substituted, halo, haloalkyl, —$OR^{28}$, —$Si(R^9)_3$, —$B(R^9)_3$, and a leaving group;

$R^{24}$, $R^{25}$, $R^{26}$, and $R^{27}$ are each independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —$NO_2$, —OH, —$C(=O)R^8$, —$C(=O)OR^8$, —$OC(=O)R^8$, —$C(=O)N(R^7)_2$, —$N(R^7)C(=O)R^8$, —CN, and a leaving group;

each $R^7$ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and a leaving group, or optionally, any two $R^7$ may be joined together to form a ring;

each $R^8$ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and a leaving group;

each $R^9$ is independently selected from the group consisting of hydrogen, alkyl optionally substituted, aryl optionally substituted, haloalkyl, halogen, and a leaving group;

each $R^{9'}$ is independently selected from the group consisting of halo, alkyl optionally substituted, aryl optionally substituted, and a leaving group;

$R^{28}$ is selected from the group consisting of hydrogen, alkyl optionally substituted, and heteroalkyl optionally substituted;

$R^{29}$ is selected from the group consisting of hydrogen, alkyl optionally substituted, heteroalkyl optionally substituted, aryl optionally substituted, heteroaryl optionally substituted, halo, haloalkyl, —C, —$NO_2$, and a leaving group;

G is O, S, or $NR^{28}$;

a is 0, 1, 2, 3, or 4;

each K is independently arylene, heteroarylene, alkenylene, or alkynylene, each optionally substituted, provided at least one K is alkenylene, or alkynylene;

each b is independently 0, 1, 2, 3, or 4; and c is 1 or 2, provided at least one leaving group is present in the compound.

Embodiment 254. In embodiment 254, provided is a diagnostic kit comprising one or more vials containing a compound of any one of embodiments 245-253 or a salt thereof; and optionally other components.

Embodiment 255. The diagnostic kit of embodiment 254, wherein the diagnostic kit is for the preparation of diagnostic agents for imaging, detecting, and/or monitoring myocardial perfusion in a subject.

Embodiment 256. The diagnostic kit of embodiment 254 or 255, wherein said other components are selected from the group consisting of ancillary ligands, reducing agents, transfer ligands, buffers, lyophilization aids, stabilization aids, solubilization aids, and bacteriostats.

Embodiment 257. In embodiment 257, provided is a method for forming an imaging agent, comprising reacting a compound of any one of embodiments 245-253 or a salt thereof with an $^{18}F$-containing species to produce a imaging agent comprising $^{18}F$.

Embodiment 258. In embodiment 258, provided is a cassette for the preparation of an imaging agent comprising the components arranged as shown in FIG. 17.

Embodiment 259. The cassette as in embodiment 258, wherein the imaging agent has the formula:

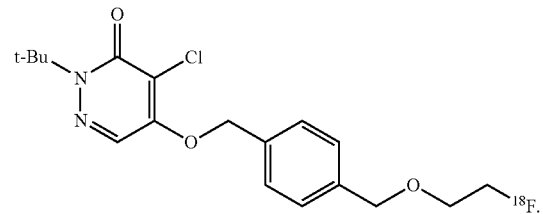

Embodiment 260. In embodiment 260, provided is an apparatus for synthesizing an imaging agent comprising a linear arrangement of a plurality of stopcock manifolds arranged in the order:

1) luer connections (2) to gas inlet and [18O]H2O recovery;
2) anion exchange cartridge—column eluting solution;
3) spike connection for acetonitrile;
4) empty syringe;
5) reservoir with solution of imaging agent precursor;
6) reaction vessel;
7) outlet to HPLC;
8) syringe with solution of a stabilizing agent;
9) inlet from HPLC;
10) ethanol reservoir;
11) syringe with solution of a stabilizing agent;
12) syringe with water;
13) final product vial;
14) empty syringe; and
15) reaction vessel and exhaust.

Embodiment 261. In embodiment 261, provided is an apparatus for synthesizing an imaging agent comprising a linear arrangement of a plurality of stopcock manifolds arranged in the order:

1) luer connections (2) to gas inlet and [18O]H2O recovery;
2) anion exchange cartridge—column eluting solution;
3) reservoir with solution of imaging agent precursor;
4) empty syringe;
5) spike connection for acetonitrile;
6) reaction vessel;
7) outlet to HPLC;
8) syringe with solution of a stabilizing agent;
9) inlet from HPLC;
10) ethanol reservoir;
11) syringe with solution of a stabilizing agent;
12) syringe with water;
13) final product vial;
14) empty syringe; and
15) reaction vessel and exhaust.

Embodiment 262. In embodiment 262, provided is an apparatus for synthesizing an imaging agent comprising a linear arrangement of a plurality of stopcock manifolds arranged in the order:

1) luer connections (2) to gas inlet and [18O]H2O recovery;
2) anion exchange cartridge—column eluting solution;
3) reservoir with solution of imaging agent precursor;
4) empty syringe;
5) spike connection for acetonitrile;
6) reaction vessel;
7) outlet to HPLC;
8) syringe with solution of a stabilizing agent;
9) inlet from HPLC;
10) ethanol reservoir;
11) final product vial;
12) syringe with water;
13) syringe with solution of a stabilizing agent
14) empty syringe; and
15) reaction vessel and exhaust.

Embodiment 263. In embodiment 263, provided is an apparatus for synthesizing an imaging agent comprising a linear arrangement of a plurality of stopcock manifolds arranged in the order:
1) luer connections (2) to gas inlet and [18O]H2O recovery;
2) anion exchange cartridge—column eluting solution;
3) spike connection for acetonitrile;
4) empty syringe;
5) reservoir with solution of imaging agent precursor;
6) reaction vessel;
7) outlet to HPLC;
8) syringe with solution of a stabilizing agent;
9) inlet from HPLC;
10) ethanol reservoir;
11) final product vial;
12) syringe with water;
13) syringe with solution of a stabilizing agent;
14) empty syringe; and
15) reaction vessel and exhaust.

Embodiment 264. The apparatus of any one of embodiments 260-263, further comprising tubing.

Embodiment 265. The apparatus of any one of embodiments 260-264, further comprising an imaging agent synthesis module, wherein the apparatus is fluidically connected to the apparatus.

Embodiment 266. The apparatus of any one of embodiments 260-265, wherein the apparatus is capable of preparing an imaging agent comprising the formula:

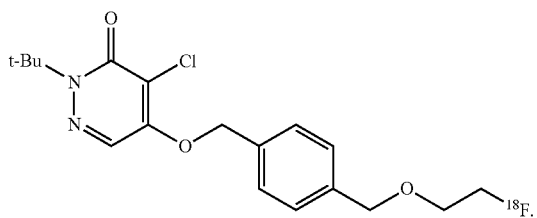

Embodiment 267. The apparatus of any one of embodiments 260-266, wherein the solution of a stabilizing agent comprises a solution comprising ascorbic acid or a salt thereof.

Embodiment 268. The apparatus of any one of embodiments 267, wherein the syringe with solution of ascorbic acid or salt thereof at position 8 comprises a solution of ascorbic acid at pH 2.

Embodiment 269. The apparatus of any one of embodiments 260-268, wherein the syringe with solution of ascorbic acid or salt thereof at position 11 comprises a solution of ascorbic acid at pH 5.8.

Definitions

For convenience, certain terms employed in the specification, examples, and appended claims are listed here.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "alkylene" as used herein refers to a bivalent alkyl group. An "alkylene" group is a polymethylene group, i.e., —(CH$_2$)$_z$—, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, alkoxyalkyl, amino, thioester, poly(ethylene glycol), and alkyl-substituted amino.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamnethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "halo" and "halogen" as used herein refer to an atom selected from the group consisting of fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino," as used herein, refers to a primary ($—NH_2$), secondary ($—NHR_x$), tertiary ($—NR_xR_y$), or quaternary ($—N^+R_xR_yR_z$) amine, where $R_x$, $R_y$, and $R_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, methylethylamino, iso-propylamino, piperidino, trimethylamino, and propylamino.

The term "alkyne" is given its ordinary meaning in the art and refers to branched or unbranched unsaturated hydrocarbon groups containing at least one triple bond. Non-limiting examples of alkynes include acetylene, propyne, 1-butyne, 2-butyne, and the like. The alkyne group may be substituted and/or have one or more hydrogen atoms replaced with a functional group, such as a hydroxyl, halogen, alkoxy, and/or aryl group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "aryloxy" refers to the group, —O-aryl.

The term "acyloxy" refers to the group, —O-acyl.

The term "alkoxyalkyl" refers to an alkyl group substituted with at least one alkoxy group (e.g., one, two, three, or more, alkoxy groups). For example, an alkoxyalkyl group may be —($C_{1-6}$-alkyl)-O—($C_{1-6}$-alkyl), optionally substituted. In some cases, the alkoxyalkyl group may be optionally substituted with another alkyoxyalkyl group (e.g., —($C_{1-6}$-alkyl)-O—($C_{1-6}$-alkyl)-O—($C_{1-6}$-alkyl), optionally substituted.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like. In some embodiments, a substituent may also be an imaging moiety (e.g., $^{18}F$) or a group for associating an imaging moiety (e.g., a chelator). Nitrogen-protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference. For example, nitrogen protecting groups include, but are not limited to, carbamates (including methyl, ethyl and substituted ethyl carbamates (e.g., Troc), to name a few), amides, cyclic imide derivatives, N-alkyl and N-aryl amines, imine derivatives, and enamine derivatives, to name a few. In some embodiments, the nitrogen-protecting group is carbobenzyloxy (Cbz), p-methoxybenzyl carbonyl (MeOZ), t-butyloxycarbonyl (Boc), 9-fluorenylmethyloxycarbonyl (Fmoc), acetyl (Ac), benzoyl (Bz), benzyl (Bn), p-methoxybenzyl (PMB), 3,4-dimethoxybenzyl (DMPM), p-methoxyphenyl (PMP), or p-toluenesulfonyloxy (Ts).

Nitrogen-protecting groups such as amide groups include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen-protecting groups such as carbamate groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-Boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen-protecting groups such as sulfonamide groups include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen-protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

As used herein, the term "determining" generally refers to the analysis of a species or signal, for example, quantitatively or qualitatively, and/or the detection of the presence or absence of the species or signals.

The term "diagnostic imaging," as used herein, refers to a procedure used to detect an imaging agent.

The term "diagnosis" as used herein encompasses identification, confirmation, and/or characterization of a condition, a disease, and/or a disorder.

A "diagnostic kit" or "kit" comprises a collection of components, termed the formulation, in one or more vials which are used by the practicing end user in a clinical or pharmacy setting to synthesize diagnostic radiopharmaceuticals. For example, the kit may be used by the practicing end user in a clinical or pharmacy setting to synthesize and/or use diagnostic radiopharmaceuticals. In some embodiments, the kit may provide all the requisite components to synthesize and use the diagnostic pharmaceutical except those that are commonly available to the practicing end user, such as water or saline for injection and/or the radioisotope (e.g., $^{18}$F), equipment for processing the kit during the synthesis and manipulation of the radiopharmaceutical, if required, equipment necessary for administering the radiopharmaceutical to the subject such as syringes, shielding, imaging equipment, and the like. In some embodiments, imaging agents may be provided to the end user in their final form in a formulation contained typically in one vial or syringe, as either a lyophilized solid or an aqueous solution.

As used herein, a "portion of a subject" refers to a particular region of a subject, location of the subject. For example, a portion of a subject may be the brain, heart, vasculature, cardiac vessels, tumor, etc., of a subject.

As used herein a "session" of testing may be a single testing protocol that a subject undergoes.

As used herein, the term "subject" refers to a human or non-human mammal or animal. Non-human mammals include livestock animals, companion animals, laboratory animals, and non-human primates. Non-human subjects also specifically include, without limitation, horses, cows, pigs, goats, dogs, cats, mice, rats, guinea pigs, gerbils, hamsters, mink, and rabbits. In some embodiments of the invention, a subject is referred to as a "patient." In some embodiments, a patient or subject may be under the care of a physician or other health care worker, including, but not limited to, someone who has consulted with, received advice from or received a prescription or other recommendation from a physician or other health care worker.

Any of the compounds described herein may be in a variety of forms, such as, but not limited to, salts, solvates, hydrates, tautomers, and isomers.

In certain embodiments, the imaging agent is a pharmaceutically acceptable salt of the imaging agent. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counter ions such as halide, hydroxide, carboxylate, sulfate, phosphate, nitrate, loweralkyl sulfonate and aryl sulfonate.

In certain embodiments, the compound is in the form of a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the compound described herein may exist in various tautomeric forms. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

In certain embodiments, the compounds described herein may exist in various isomeric forms. The term "isomer" as used herein includes any and all geometric isomers and stereoisomers (e.g., enantiomers, diasteromers, etc.). For example, "isomer" includes cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

These and other aspects of the present invention will be further appreciated upon consideration of the following Examples, which are intended to illustrate certain particular embodiments of the invention but are not intended to limit its scope, as defined by the claims.

EXAMPLES

General Experimental Protocols

Method A:

A cooled (0° C.) aqueous solution of mucochloric acid was treated with sodium carbonate in one portion then stirred until complete dissolution was observed. The resulting mixture was then treated with the substituted hydrazine, and stirred 2.5-5 h while slowly warming to ambient temperature. The newly formed precipitate was then collected, exhaustively washed with water, partially dried on the funnel then dissolved in acetic acid and heated to reflux. After 30 min, the solution was cooled to ambient temperature and all volatiles removed in vacuo. The crude pyridazinone was then dissolved in an appropriate organic solvent, washed with aqueous base, dried, filtered and concentrated in vacuo. The crude material thus obtained was typically used without additional purification, but alternatively may be further purified by chromatography on silica.

Method B:

A solution of the substituted pyridazinone and either a benzylic alcohol or benzylic bromide in dimethylformamide was treated with cesium carbonate then optionally heated to 55-80° C. After cooling to ambient temperature, the crude product was isolated as a solution in ethyl acetate, washed with water and aqueous sodium chloride then dried, filtered and concentrated. Subsequent purification by chromatography on silica afforded the title compound.

Method C:

A dichloromethane solution of the benzylic alcohol was treated with phosphorous tribromide at ambient temperature. After 1-3 h, the resulting mixture was diluted with water and the layers separated. The aqueous layer was washed with additional dichloromethane, and the combined extracts dried, filtered and concentrated. The crude material thus obtained was typically used without additional purification, but alternatively may be further purified by chromatography on silica.

Method D:

A dichloromethane solution of the alcohol, p-toluenesulfonyl chloride, 4-dimethylaminopyridine, and a base was prepared at ambient temperature. After 1-3 h, the resulting mixture was diluted with water and the layers separated. The aqueous layer was washed with additional dichloromethane, and the combined extracts further washed with aqueous sodium chloride then dried, filtered, and concentrated. Subsequent purification by chromatography on silica afforded the title compound.

Method E:

A suspension of potassium tert-butoxide in 2-fluoroethanol was heated to 60° C., maintained 20 min then treated with a solution of the benzylic halide in tetrahydrofuran. The resulting mixture was heated to reflux, maintained 2-24 h then cooled to ambient temperature and treated with water. The aqueous layer was separated then extracted with ethyl acetate. The combined organic layers were dried over sodium sulfate, filtered and concentrated in vacuo. Subsequent purification by chromatography on silica afforded the title compound.

Method F:

A suspension of the phenol, 3-fluoropropyl p-toluenesulfonate, and cesium carbonate in dimethylformamide was heated to 60-65° C. and maintained overnight. After cooling to ambient temperature, the resulting mixture was treated with water, and the aqueous layer extracted with ethyl acetate. The combined organic layers were washed with water, saturated aqueous sodium chloride, dried over sodium sulfate, filtered and concentrated in vacuo.

Example 1

Preparation of 4-chloro-5-((4-((2-fluoroethoxy)methyl)benzyl)oxy)-2-isopropylpyridazin-3(2H)-one Part A—Preparation of 4,5-dichloro-2-isopropylpyridrazin-3(2H)-one

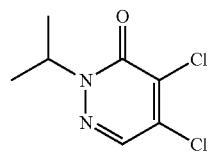

Prepared according to General Method A, using mucochloric acid (1.07 g, 6.33 mmol), sodium carbonate (0.336 g, 3.17 mmol), and isopropylhydrazine hydrochloride (0.700 g, 6.33 mmol). Isolated yield—0.629 g; 47.9%. $^1$H NMR (CDCl$_3$, 300 MHz): δ 7.82 (s, 1H), 5.27 (m, 1H), 1.37 (d, J=6.6 Hz, 6H); $^{13}$C NMR (CDCl$_3$, 75 MHz): δ 156.3, 135.9, 135.3, 133.8, 51.4, 20.9; HRMS-TOF (m/z): [M+H]$^+$ HRMS: Calcd. for C$_7$H$_8$$^{35}$Cl$_2$N$_2$O: 207.0086, found 207.0085.

Part B—Preparation of 4-chloro-5-((4-((2-fluoroethoxy)methyl)benzyl)oxy)-2-isopropylpyridazin-3(2H)-one

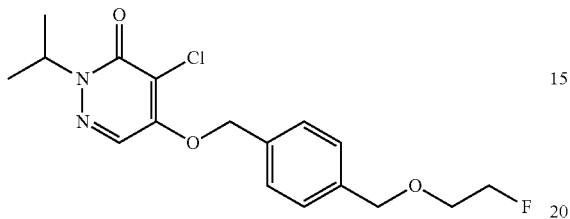

Prepared according to General Method B, using the product of Example 1A (45.5 mg, 0.220 mmol), (4-((2-fluoroethoxy)methyl)phenyl)methanol (41 mg, 0.22 mmol; e.g., see Radeke, H.; Hanson, K.; Yalamanchili, P.; Hayes, M.; Zhang, Z.-Q.; Azure, M.; Yu, M.; Guaraldi, M.; Kagan, M.; Robinson, S.; Casebier, D. Synthesis and Biological evaluation of the mitochondrial complex I inhibitor 2-[4-(4-fluorobutyl)benzylsulfanyl]-3-methylchromene-4-one as a potential cardiac positron emission tomography tracer. J. Med. Chem. 2007, 50, 4304-4315.), and cesium carbonate (0.215 g, 0.661 mmol) in dimethylformamide (2.20 mL) at 55° C. Isolated yield—49 mg; 63%. $^1$H NMR (CDCl$_3$, 300 MHz): δ7.66 (s, 1H), 7.41 (d, J=7.5 Hz, 2H), 7.37 (d, J=8.6 Hz, 2H), 5.17 (s, 2H), 4.68 (m, 1H), 4.62 (s, 2H), 4.53 (m, 1H), 3.80 (m, 1H), 3.71 (m, 1H), 3.54-3.45 (m, 1H), 1.27 (d, J=7.1 Hz, 6H); $^{13}$C NMR (CDCl$_3$, 75 MHz): δ 162.3, 154.2, 138.3, 135.4, 129.3, 128.1, 127.4, 125.8, 83.1 (d, J$_{CF}$=165 Hz), 73.0, 70.8, 69.4 (d, J$_{CF}$=22.5 Hz), 65.0, 19.5; HRMS-TOF (m/z): [M+H]$^+$ HRMS: Calcd. for C$_{17}$H$_{20}$$^{35}$ClFN$_2$O$_3$: 355.1219, found 355.1217.

Example 2

Preparation of 2-((4-(((5-chloro-1-isopropyl-6-oxo-1,6-dihydropyridazin-4-yl)oxy)methyl) benzyl)oxy) ethyl-4-methylbenzenesulfonate Part A—Preparation of methyl 4-(((5-chloro-1-isopropyl-6-oxo-1,6-dihydropyridazin-4-yl)oxy) methyl)benzoate

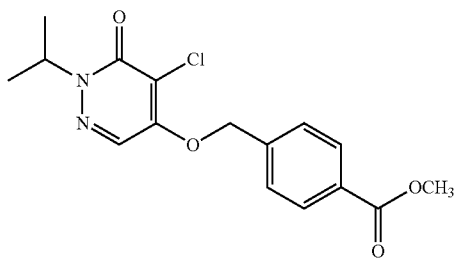 [SMILES: COC(=O)c1ccc(COc2cnn(C(C)C)c(=O)c2Cl)cc1]

Prepared according to General Method B, using the product of Example 1A (0.629 g, 3.01 mmol), 4-hydroxymethyl benzoate (0.550 g, 3.31 mmol), and cesium carbonate (1.57 g, 4.82 mmol) in dimethylformamide (30.0 mL) at 60° C. Isolated yield—0.604 g; 59.6%. $^1$H NMR (CDCl$_3$, 300 MHz): δ 8.08 (d, J=8.5 Hz, 2H), 7.82 (s, 1H), 7.50 (d, J=8.5 Hz, 2H), 5.39 (s, 2H), 5.30 (m, 1H), 3.90 (s, 3H), 1.33 (d, J=6.7 Hz, 6H); $^{13}$C NMR (CDCl$_3$, 75 MHz): δ 166.5, 158.3, 153.6, 139.7, 130.5, 130.2, 129.7, 126.7, 117.5, 71.2, 52.0, 50.7, 20.9; HRMS-TOF (m/z): [M+H]$^+$ HRMS: Calcd. for C$_{16}$H$_{17}$$^{35}$ClN$_2$O$_4$: 337.0950, found 337.0948.

Part B—Preparation of 4-chloro-5-((4-(hydroxymethyl)benzyl)oxy)-2-isopropylpyridazin-3(2H)-one

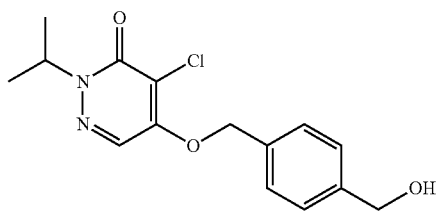 [SMILES: CC(C)n1ncc(OCc2ccc(CO)cc2)c(Cl)c1=O]

To a solution of the product of Example 2A (0.604 g, 1.79 mmol), in tetrahydrofuran at 0° C. was added lithium aluminum hydride (0.9 mL, 0.9 mmol, 1 M solution in tetrahydrofuran) dropwise. The resulting mixture was stirred 3 h then treated with water (20 mL). The aqueous layer was separated and extracted with ethyl acetate (3×50 mL). The combined organic layers were washed with saturated aqueous sodium chloride (50 mL), dried over sodium sulfate, filtered and concentrated to yield an orange solid (0.186 g). $^1$H NMR (CDCl$_3$, 300 MHz): δ 7.82 (s, 1H), 7.41 (br s, 4H), 5.32 (s, 2H), 5.28 (m, 1H), 4.72 (s, 2H), 1.28 (d, J=6.7 Hz, 6H); $^{13}$C NMR (CDCl$_3$, 75 MHz): δ 158.5, 153.8, 141.8, 134.0, 127.5, 127.4, 127.0, 117.4, 71.8, 64.8, 50.7, 20.9; HRMS-TOF (m/z): [M+H]$^+$ HRMS: Calcd. for C$_{15}$H$_{17}$$^{35}$ClN$_2$O$_3$: 309.1000, found 309.1001.

Part C—Preparation of 5-((4-(bromomethyl)benzyl)oxy)-4-chloro-2-isopropylpyridazin-3(2H)-one

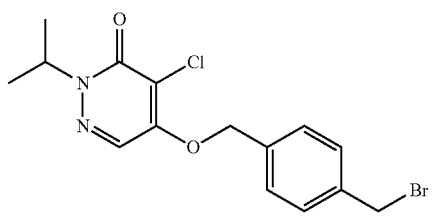 [SMILES: CC(C)n1ncc(OCc2ccc(CBr)cc2)c(Cl)c1=O]

Prepared according to General Method C, using the product of Example 2B (0.186 g, 0.602 mmol) and phosphorous tribromide (0.3 mL, 0.3 mmol, 1 M in dichloromethane). Isolated yield—0.128 g; 57.2%. $^1$H NMR (CDCl$_3$, 300 MHz): δ 8.07 (s, 1H), 7.34 (m, 4H), 5.23 (s, 2H), 5.21 (m, 1H), 4.41 (s, 2H), 1.24 (d, J=6.6 Hz, 6H); $^{13}$C NMR (CDCl$_3$, 75 MHz): δ 158.4, 153.7, 138.5, 135.0, 129.6, 127.5, 126.9, 117.2, 71.5, 50.7, 32.8, 21.0; HRMS-TOF (m/z): [M+H]$^+$ HRMS: Calcd. for C$_{15}$H$_{16}$$^{79}$Br$^{35}$ClN$_2$O$_2$: 371.0156, found 371.0155.

Part D—Preparation of 4-chloro-5-((4-((2-hydroxyethoxy)methyl)benzyl)oxy)-2-isopropylpyridazin-3 (2H)-one

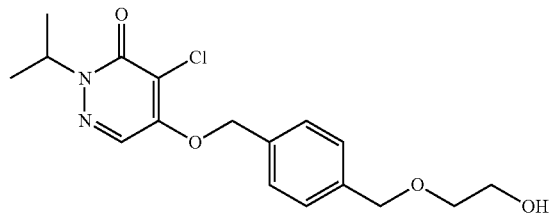 [SMILES: CC(C)n1ncc(OCc2ccc(COCCO)cc2)c(Cl)c1=O]

A suspension of potassium tert-butoxide (48 mg, 0.43 mmol) in ethylene glycol (0.685 mL) was heated to 60° C. for 30 min. The product of Example 2C (0.691 g, 1.86 mmol), dissolved in tetrahydrofuran (21.0 mL) was added dropwise. After completion of the addition, the reaction mixture was heated at reflux. After 6 h the reaction mixture was cooled and quenched with water (10 mL). The aqueous layer was separated then extracted with ethyl acetate (3×20 mL). The combined organic layers were dried over sodium sulfate, filtered and concentrated in vacuo. The crude material was then purified by silica gel chromatography (80-100% diethyl ether in hexanes) to afford the desired product as a white solid (2.8 mg, <1% yield). $^1$H NMR (CDCl$_3$, 300 MHz): δ 7.76 (br s, 1H), 7.31 (s, 4H), 5.23 (s, 2H), 5.19 (m, 1H), 4.48 (s, 2H), 3.67 (m, 2H), 3.52 (m, 2H), 1.23 (d, J=6.7 Hz, 6H); $^{13}$C NMR (CDCl$_3$, 75 MHz): δ 158.4, 153.8, 138.9, 134.2, 128.2, 127.3, 127.0, 117.2, 72.7, 71.8, 71.7, 61.8, 50.7, 20.9; HRMS-TOF (m/z): [M+H]$^+$ HRMS: Calcd. for C$_{17}$H$_{21}$$^{35}$ClN$_2$O$_4$: 353.1263, found 353.1267.
m Part E—Preparation of 2-((4-(((5-chloro-1-isopropyl-6-oxo-1,6-dihydropyridazin-4-yl)oxy)methyl)benzyl)oxy)ethyl-4-methylbenzenesulfonate

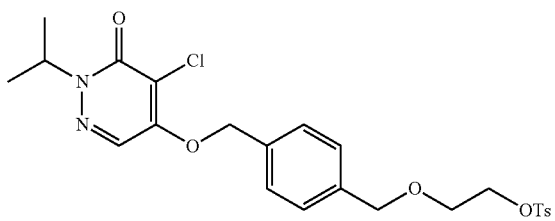 [SMILES: Cc1ccc(S(=O)(=O)OCCOCc2ccc(COc3cnn(C(C)C)c(=O)c3Cl)cc2)cc1]

Prepared according to General Method D, using the product of Example 2D (85.6 mg, 0.243 mmol), p-toluenesulfonyl chloride (55.6 mg, 0.292 mmol), 4-dimethylaminopyridine (35.6 mg, 0.291 mmol), and diisopropylethylamine (0.051 mL, 0.292 mmol). Isolated yield—53 mg; 43%. $^1$H (CDCl$_3$, 300 MHz): δ 7.82 (s, 1H), 7.80 (d, J=8.3 Hz, 2H), 7.38 (d, J=8.3 Hz, 2H), 7.33-7.27 (m, 4H), 5.31 (s, 2H), 5.28 (m, 1H), 4.51 (s, 2H), 4.20 (m, 2H), 3.69 (m, 2H), 2.44 (s, 3H), 1.33 (d, J=6.7 Hz, 6H); $^{13}$C (CDCl$_3$, 75 MHz): δ 158.4, 153.7, 144.8, 138.5, 134.3, 133.0, 129.8, 128.1, 128.0, 127.3, 127.0, 117.4, 72.7, 71.8, 69.2, 67.8, 50.7, 21.7, 20.9; HRMS-TOF (m/z): [M+H]$^+$ HRMS: Calcd. for C$_{24}$H$_{27}$$^{35}$ClN$_2$O$_6$S: 507.1351, found 507.1349.

Example 3

Preparation of 4-chloro-5-((4-((2-fluoroethoxy)methyl) benzyl)oxy)-2-methylpyridazin-3(2H)-one Part A—Preparation of 4,5-dichloro-2-methylpyridazin-3(2H)-one

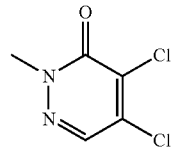

Prepared according to General Method A, using mucochloric acid (2.03 g, 12.1 mmol), sodium carbonate (0.640 g, 6.03 mmol), and methyl hydrazine (0.555 g, 12.1 mmol). Isolated yield—0.840 g; 38.8%. $^1$H NMR (CDCl$_3$, 300 MHz): δ 7.70 (s, 1H), 3.75 (s, 3H); $^{13}$C NMR (CDCl$_3$, 75 MHz): δ 156.8, 136.5, 135.3, 134.0, 41.0; HRMS-TOF (m/z): [M+H]$^+$ HRMS: Calcd. for C$_5$H$_4$$^{35}$Cl$_2$N$_2$O: 178.9773, found 178.9773.

Part B—Preparation of 4-chloro-5-((4-((2-fluoroethoxy)methyl)benzyl)oxy)-2-methylpyridazin-3(2H)-one

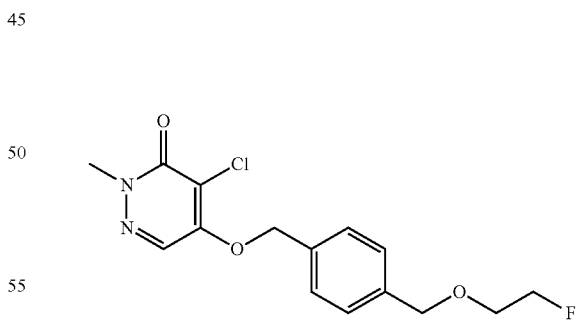

Prepared according to General Method B, using the product of Example 3A (47 mg, 0.26 mmol), (4-((2-fluoroethoxy)methyl)phenyl)methanol (0.141 g, 0.770 mmol), and cesium carbonate (0.251 g, 0.770 mmol) in dimethylformamide (2.50 mL) at 80° C. Isolated yield—38 mg; 45%. $^1$H NMR (CDCl$_3$, 300 MHz): δ 7.67 (s, 1H), 7.33 (s, 4H), 5.25 (br s, 2H), 4.61 (m, 1H), 4.54 (s, 2H), 4.45 (m, 1H), 3.72 (m, 1H), 3.71 (s, 3H), 3.63 (m, 1H); $^{13}$C NMR (CDCl$_3$, 75 MHz): δ 158.9, 154.4, 138.8, 134.1, 128.2, 127.3, 127.2, 117.7, 83.1 (d, $J_{CF}$=165 Hz), 72.9, 72.0, 69.4 (d, $J_{CF}$=22.5 Hz), 40.7; HRMS-TOF (m/z): [M+H]$^+$ HRMS: Calcd. for $C_{15}H_{16}{}^{35}ClFN_2O_3$: 395.1532, found 395.1522.

Example 4

Preparation of 4-chloro-5-((4-((2-fluoroethoxy)methyl)benzyl)oxy)-2-phenylpyridazin-3(2H)-one Part A—Preparation of 4,5-dichloro-2-phenylpyridazin-3(2H)-one

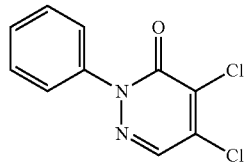 [SMILES: O=c1c(Cl)c(Cl)cnn1-c1ccccc1]

Prepared according to General Method A, using muco-chloric acid (0.985 g, 5.83 mmol), sodium carbonate (0.309 g, 2.91 mmol), and phenyl hydrazine hydrochloride (0.843 g, 5.83 mmol). Isolated yield—1.31 g; 93.2%. $^1$H NMR (CDCl$_3$, 300 MHz): δ 7.91 (s, 1H), 7.59-7.54 (m, 2H), 7.48-7.39 (m, 3H); $^{13}$C NMR (CDCl$_3$, 75 MHz): δ 156.1, 140.9, 136.4, 136.1, 135.3, 128.9, 128.8, 125.2; HRMS-TOF (m/z): [M+H]$^+$ HRMS: Calcd. for $C_{10}H_6{}^{35}Cl_2N_2O$: 240.9930, found 240.9932.

Part B—Preparation of 4-chloro-5-((4-((2-fluoroethoxy)methyl)benzyl)oxy)-2-phenylpyridazin-3(2H)-one

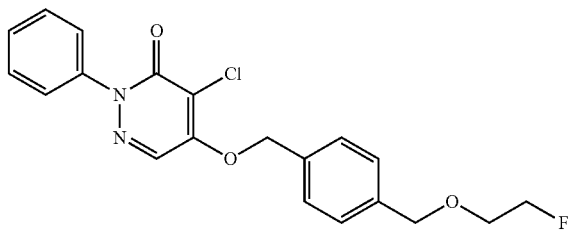 [SMILES: O=c1c(Cl)c(OCc2ccc(COCCF)cc2)cnn1-c1ccccc1]

Prepared according to General Method B, using the product of Example 4A (0.070 g, 0.290 mmol), (4-((2-fluoroethoxy)methyl)phenyl)methanol (0.160 g, 0.870 mmol), and cesium carbonate (0.283 g, 0.870 mmol) in dimethylformamide (2.90 mL) at 80° C. Isolated yield—45 mg; 40%. $^1$H NMR (CDCl$_3$, 300 MHz): δ 7.84 (s, 1H), 7.49-7.30 (m, 9H), 5.31 (s, 2H), 4.59 (m, 1H), 4.54 (s, 2H), 4.44 (m, 1H), 3.71 (m, 1H), 3.61 (m, 1H); $^{13}$C NMR (CDCl$_3$, 75 MHz): δ 158.3, 154.0, 141.2, 138.9, 134.0, 128.8, 128.3, 128.2, 128.0, 127.4, 127.1, 125.3, 81.6 (d, $J_{CF}$=60 Hz), 73.1, 72.1, 69.5 (d, $J_{CF}$=15 Hz); HRMS-TOF (m/z): [M +H]$^+$ HRMS: Calcd. for $C_{20}H_{18}{}^{35}ClFN_2O_3$: 327.0906, found 327.0901.

Example 5

Preparation of 4-chloro-2-cyclohexyl-5-((4-((2-fluoroethoxy)methyl)benzyl)oxy)pyridazin-3(2H)-one Part A—Preparation of 4,5-dichloro-2-cyclohexylpyridrazin-3(2H)-one

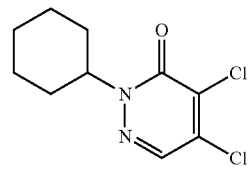 [SMILES: O=c1c(Cl)c(Cl)cnn1C1CCCCC1]

Prepared according to General Method A, using muco-chloric acid (0.443 g, 2.62 mmol), sodium carbonate (0.138 g, 1.31 mmol), and cyclohexyl hydrazine hydrochloride (0.403 g, 2.62 mmol). Isolated yield—0.440 g; 67.9%. $^1$H NMR (CDCl$_3$, 600 MHz): δ 7.74 (s, 1H), 4.77 (tt, J=11.6, 3.6 Hz, 1H), 1.79 (m, 4H), 1.68-1.56 (m, 3H), 1.44-1.30 (m, 2H), 1.21-1.06 (m, 1H); $^{13}$C NMR (CDCl$_3$, 150 MHz): δ 156.3, 135.7, 135.1, 133.6, 58.5, 31.1, 25.4, 25.2; HRMS-TOF (m/z): [M+H]$^+$ HRMS: Calcd. for $C_{10}H_{12}{}^{35}Cl_2N_2O$: 247.0399, found 247.0399.

Part B—Preparation of 4-chloro-2-cyclohexyl-5-((4-((2-fluoroethoxy)methyl)benzyl)oxy) pyridazin-3 (2H)-one

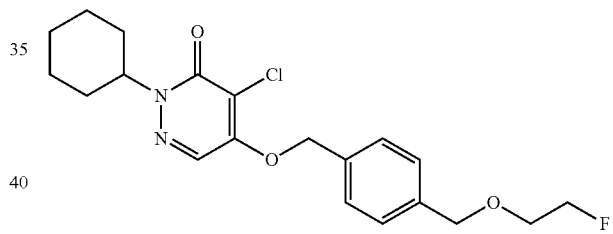

Prepared according to General Method B, using the product of Example 5A (31 mg, 0.13 mmol), (4-((2-fluoroethoxy)methyl)phenyl)methanol (29 mg, 0.16 mmol), and cesium carbonate (0.123 g, 0.380 mmol) in dimethylformamide (1.26 mL) at 55° C. Isolated yield—25 mg; 49%. HRMS-TOF (m/z): [M+H]$^+$ HRMS: Calcd. for $C_{20}H_{24}{}^{35}ClN_2O_3$: 389.1063, found 389.1054.

Example 6

Preparation of 2-(tert-butyl)-5-((4-((2-fluoroethoxy)methyl)benzyl)oxy)pyridazin-3(2H)-one

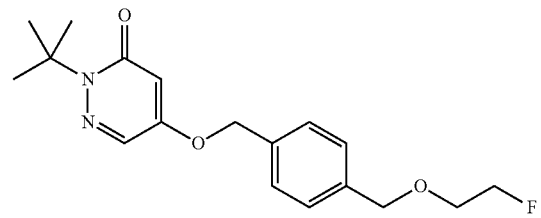 [SMILES: CC(C)(C)n1ncc(OCc2ccc(COCCF)cc2)cc1=O]

2-(tert-Butyl)-4-chloro-5-((4-((2-fluoroethoxy)methyl)benzyl)oxy)pyridazin-3(2H)-one (0.184 g, 0.50 mmol; e.g., see Purohit, A.; Radeke, H. S.; Azure, M.; Hanson, K.; Benetti, R.; Su, F.; Yalamanchili, P.; Yu, M.; Hayes, M.; Guaraldi, M.; Kagan, M.; Robinson, S.; Casebier, D. Synthesis and Biological Evaluation of Pyridazinone Analogs as Potential Cardiac Positron Emission Tomography Tracers J. Med. Chem. 2008, 51, 2954) was suspended in dry toluene (5.00 mL), successively treated with tributyltin hydride (0.161 g, 0.60 mmol) and 2,2'-azobis(2-methylpropionitrile) (0.004 mg, 0.025 mmol), then heated to reflux and maintained 20 h. After cooling to ambient temperature, all volatiles were removed in vacuo, and the residue directly purified by chromatography on silica (30×190 mm) using a step gradient from 3:1 hexanes/ethyl acetate (400 mL) to 2:1 hexanes/ethyl acetate (500 mL). The main product peak eluting 550-750 mL was collected, pooled and concentrated in vacuo to a colorless oil (0.101 g, 0.302 mmol; 60.3%). $^1$H NMR: (600 MHz, DMSO-$d_6$) δ 7.72 (1H, d, J=2.9 Hz), 7.43 (2H, AB, $J_{AB}$=8.1 Hz), 7.37 (2H, AB, $J_{AB}$=8.1 Hz), 6.26 (1H, d, J=2.9 Hz), 5.11 (s, 2H), 4.63-4.58 (1H, m), 4.54 (2H, s), 4.53-4.49 (1H, m), 3.73-3.68 (1H, m), 3.68-3.63 (1H, m), 1.55 (9H, s). $^{13}$C NMR: (151 MHz, DMSO-$d_6$) δ 161.5, 158.4, 138.4, 134.4, 130.2, 128.1, 127.6, 105.5, 82.9 (d, $J_{CF}$=166 Hz), 71.6, 69.8, 69.0 (d, $J_{CF}$=19.0 Hz), 63.6, 27.6. HRMS Calcd. for $C_{18}H_{23}FN_2O_3$(M+H): 335.1766; found: 335.1766. TLC: $R_f$ 0.38 (silica gel, 1:1 hexanes/ethyl acetate, CAM).

Example 7

Preparation of 4-bromo-2-(tert-butyl)-5-((4-((2-fluoroethoxy)methyl)benzyl)oxy)pyridazin-3(2H)-one

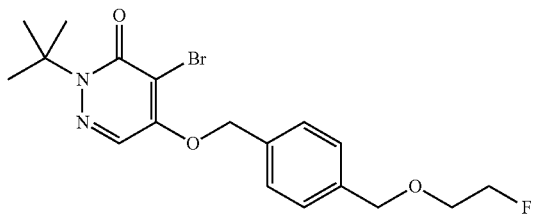

Prepared according to General Method B, using 4,5-dibromo-2-(tert-butyl)pyridazin-3(2H)-one (0.310 g, 1.00 mmol; e.g., see Taniguchi M.; Ochiai Y.; Hirose M.; Hirata K.; Baba M. (Nissan Chemical Industries) Benzylthio pyridazinone derivatives, preparation thereof, and insecticidal acaricidal, fungicidal compositions. U.S. Pat. No. 4,877,787, Oct. 31, 1989), (4-((2-fluoroethoxy)methyl)phenyl)methanol (92.1 mg, 0.500 mmol), and cesium carbonate (0.326 g, 1.00 mmol) in dimethylformamide (2.50 mL) at 65° C. Isolated yield—0.121 g; 58.5%. $^1$H NMR: (300 MHz, $CDCl_3$) δ 7.62 (1H, s), 7.41 (4H, s), 5.32 (2H, s), 4.73-4.64 (1H, m), 4.61 (2H, s), 4.57-4.48 (1H, m), 3.85-3.75 (1H, m), 3.75-3.65 (1H, m), 1.63 (9H, s). $^{13}$C NMR: (75 MHz, $CDCl_3$) δ 159.3, 155.8, 138.8, 134.6, 128.4, 127.4, 124.8, 110.5, 83.3 (d, $J_{CF}$=169 Hz), 73.2, 71.8, 69.7 (d, $J_{CF}$=19.6 Hz), 66.7, 28.1. HRMS Calcd. for $C_{18}H_{22}^{79}BrFN_2O_3$ (M+H): 413.0871; found: 413.0876. TLC: R 0.31 (silica gel, 7:3 hexanes/ethyl acetate, CAM).

Example 8

Preparation of 4-chloro-2-cyclohexyl-5-((4-((2-fluoroethoxy)methyl)benzyl)oxy)pyridazin-3(2H)-one

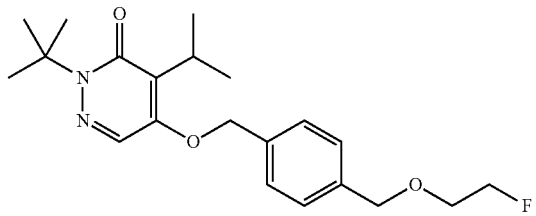 [SMILES: CC(C)c1c(OCc2ccc(COCCF)cc2)cnn(C(C)(C)C)c1=O]

To a cooled (0° C.) solution of isopropyl magnesium bromide (0.087 mL, 2 M solution in tetrahydrofuran) was added 2-(tert-butyl)-4-chloro-5-((4-((2-fluoroethoxy)methyl)benzyl)oxy)-4-pyridazin-3(2H)-one (32 mg, 0.087 mmol) dissolved in tetrahydrofuran (0.783 mL). The reaction was stirred at 0° C. for 2 h then treated with additional equivalents of isopropyl magnesium bromide (0.261 mL, 2M solution in tetrahydrofuran). After 24 h, the reaction was quenched with water (0.5 mL) and diluted with ethyl acetate (20 mL). The organic layer was separated, washed with saturated aqueous sodium chloride (3×50 mL), dried over magnesium sulfate, filtered and concentrated in vacuo. The crude material was then purified using silica gel chromatography 3:1 hexanes/ethyl acetate to afford the desired product as a clear oil (12.0 mg, 36.6% yield). 1H NMR ($CDCl_3$, 300 MHz): δ 7.67 (s, 1H), 7.41 (d, J=7.5 Hz, 2H), 7.37 (d, J=8.7 Hz, 2H), 5.17 (s, 2H), 4.68 (m, 1H), 4.62 (s, 2H), 4.53 (m, 1H), 3.80 (m, 1H), 3.71 (m, 1H), 3.50 (m, 1H), 1.62 (s, 9H), 1.27 (d, J=7.1 Hz, 6H); $^{13}$C NMR ($CDCl_3$, 75 MHz): δ 162.3, 154.2, 138.3, 135.4, 129.3, 128.1, 127.4, 125.8, 83.1 (d, $J_{CF}$=165 Hz), 73.0, 70.8, 69.4 (d, $J_{CF}$=22.5 Hz), 65.0, 28.1, 24.6, 19.5; HRMS-TOF (m/z): $[M+H]^+$ HRMS: Calcd. for $C_{21}H_{29}FN_2O_3$: 377.2235, found 377.2231.

Example 9

Preparation of 2-(tert-butyl)-4-chloro-5-((4-((2-fluoroethoxy)-$d_2$-methyl)benzyl)oxy)pyridazin-3(2H)-one Part A—Preparation of 2-(tert-butyl)-4-chloro-5-((4-($d_2$-hydroxymethyl)benzyl)oxy)pyridazin-3(2H)-one

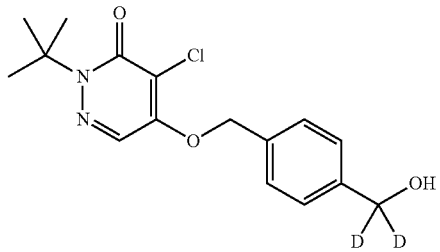 [SMILES: [2H]C([2H])(O)c1ccc(COc2cnn(C(C)(C)C)c(=O)c2Cl)cc1]

To a solution of methyl 4-(((1-tert-butyl)-5-chloro-6-oxo-1,6-dihydropyridazin-4-yl)oxy)methyl)benzoate (1.50 g, 4.28 mmol; e.g., see Cesati, R; Cheesman, E. H.; Lazewatsky, J.; Radeke, S.; Castner, J. F.; Mongeau, E.; Zdankiewicz, D. D.; Siegler, R. W.; Devine, M. Methods and apparatus for synthesizing imaging agents, and intermediates thereof PCT Int. Appl. (2011), WO 2011/097649, Aug. 8, 2011) in tetrahydrofuran (42.8 mL) at 0° C. was added lithium aluminum deuteride (2.14 mL, 2.14 mmol, 1 M solution in tetrahydrofuran) dropwise. The resulting mixture was stirred for 2 h then treated with water (20 mL). The aqueous layer was separated and extracted with ethyl acetate (3×50 mL). The combined organic layers were washed with saturated aqueous sodium chloride, dried over sodium sulfate, filtered and concentrated to yield a white solid (1.36 g, 97.8% yield). 1H NMR (CDCl$_3$, 300 MHz): δ 7.64 (s, 1H), 7.35 (br s, 4H), 5.24 (s, 2H), 1.56 (s, 9H); $^{13}$C NMR (CDCl$_3$, 75 MHz, partial): δ 159.0, 153.7, 141.5, 134.3, 127.5, 127.3, 125.1, 118.4, 71.7, 64.4, 27.9; HRMS-TOF (m/z): [M+H]$^+$ HRMS: Calcd. for C$_{16}$H$_{17}$D$_2$$^{35}$ClN$_2$O$_3$: 325.1283, found 325.1284.

Part B—Preparation 5-((4-(bromo-d$_2$-methyl)benzyl)oxy)-2-(tert-butyl)-4-chloropyridazin-3(2H)-one

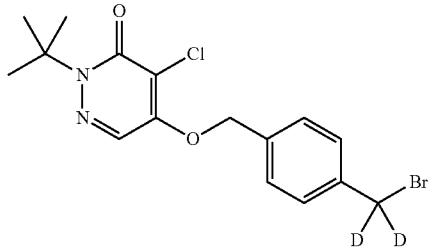 [SMILES: [2H]C([2H])(Br)c1ccc(COc2cnn(C(C)(C)C)c(=O)c2Cl)cc1]

Prepared according to General Method C, using the product of Example 9A (0.882 g, 2.72 mmol) and phosphorous tribromide (1.36 mL, 1.36 mmol, 1 M in dichloromethane). Isolated yield—0.981 g; 93.0%. $^1$H NMR (CDCl$_3$, 300 MHz): δ 7.64 (s, 1H), 7.37 (d, J=8.5 Hz, 2H), 7.32 (d, J=8.5 Hz, 2H), 5.23 (s, 2H), 1.59 (s, 9H); $^{13}$C NMR (CDCl$_3$, 75 MHz, partial): δ 159.0, 153.6, 138.3, 135.1, 129.6, 127.5, 125.0, 118.4, 71.4, 66.5, 27.9; HRMS-TOF (m/z): [M+H]$^+$ HRMS: Calcd. for C$_{16}$H$_{16}$D$_2$$^{79}$Br$^{35}$ClN$_2$O$_2$: 387.0438, found 387.0439.

Part C—Preparation of 2-(tert-butyl)-4-chloro-5-((4-((2-fluoroethoxy)-d$_2$-methyl)benzyl)oxy)pyridazin-3(2H)-one

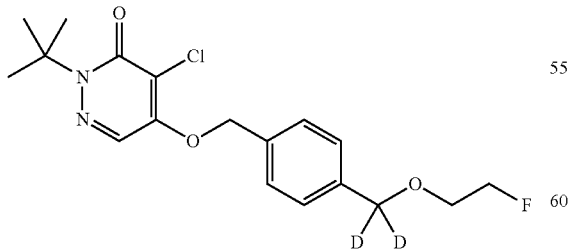

Prepared according to General Method E, using potassium tert-butoxide (25.3 mg, 0.225 mmol), 2-fluoroethanol (14.5 mg, 0.226 mmol) and the product of Example 9B (0.105 g, 0.271 mmol). Isolated yield—7.5 mg; 9.8%. $^1$H NMR (CDCl$_3$, 300 MHz): δ 7.74 (s, 1H), 7.33 (s, 4H), 5.24 (s, 2H), 4.60 (m, 1H), 4.45 (s, 1H), 3.72 (m, 1H), 3.63 (m, 1H), 1.56 (s, 9H); $^{13}$C NMR (CDCl$_3$, 75 MHz, partial): δ 159.0, 153.7, 138.6, 134.4, 128.3, 127.3, 125.1, 118.4, 83.1 (d, J$_{CF}$=165 Hz), 71.7, 69.4 (d, J$_{CF}$=15 Hz), 66.4, 27.9; HRMS-TOF (m/z): [M +H]$^+$ HRMS: Calcd. for C$_{18}$H$_{20}$D$_2$$^{35}$ClFN$_2$O$_3$: 371.1501, found 371.1507.

Example 10

Preparation of 2-((4-(((1-(tert-butyl)-5-chloro-6-oxo-1,6-dihydropyridazin-4-yl)oxy)-d$_2$-methyl) benzyl)oxy)ethyl-4-methylbenzenesulfonate Part A—Preparation of 2-(tert-butyl)-4-chloro-5-((4-((2-hydroxyethoxy)-d$_2$-methyl)benzyl) oxy) pyridazin-3(2H)-one

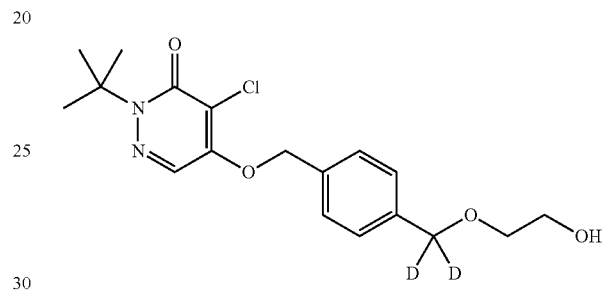

A suspension of potassium tert-butoxide (0.174 g, 1.55 mmol) in ethylene glycol (0.685 mL) was heated to 60° C. for 20 min then treated with a solution of the product of Example 9B (0.720 g, 1.86 mmol) in tetrahydrofuran (21 mL). The resulting mixture was heated to reflux, maintained 16 h then cooled to ambient temperature and treated with water (15 mL). The aqueous layer was separated then extracted with ethyl acetate (3×50 mL). The combined organic layers were dried over sodium sulfate, filtered and concentrated in vacuo. The crude material was then purified using silica gel chromatography (20-50% ethyl acetate in hexanes) to afford the desired product as a yellow oil (0.144 g, 25.2% yield). $^1$H NMR (CDCl$_3$, 300 MHz): δ 7.65 (s, 1H), 7.33 (s, 4H), 5.24 (s, 2H), 3.71 (m, 2H), 3.54 (m, 2H), 1.56 (s, 9H); $^{13}$C NMR (CDCl$_3$, 75 MHz, partial): δ 159.0, 153.6, 138.6, 134.4, 128.3, 127.2, 125.0, 118.3, 71.6, 71.5, 66.4, 61.9, 27.8; HRMS-TOF (m/z): [M+H]$^+$ HRMS: Calcd. for C$_{18}$H$_{21}$D$_2$$^{35}$ClN$_2$O$_4$: 369.1545, found 369.1548.

Part B—Preparation of 2-((4-(((1-(tert-butyl)-5-chloro-6-oxo-1,6-dihydropyridazin-4-yl)oxy)-d$_2$-methyl)benzyl)oxy)ethyl-4-methylbenzenesulfonate

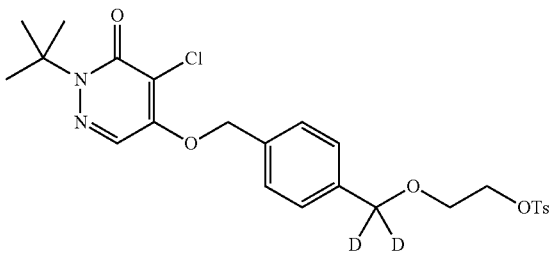 [SMILES: [2H]C([2H])(OCCOS(=O)(=O)c1ccc(C)cc1)c1ccc(COc2cnn(C(C)(C)C)c(=O)c2Cl)cc1]

Prepared according to General Method D, using the product of Example 10A (78.2 mg, 0.213 mmol), p-toluenesulfonyl chloride (48.6 mg, 0.255 mmol), 4-dimethylaminopyridine (31.2 mg, 0.255 mmol), and diisopropylethylamine (0.044 mL, 0.255 mmol). Isolated yield—32.8 mg; 29.4%. $^1$H (CDCl$_3$, 600 MHz): δ 7.72 (d, J=8.4 Hz, 2H), 7.65 (s, 1H), 7.31 (d, J=8.3 Hz, 2H), 7.26-7.19 (m, 4H), 5.23 (s, 2H), 4.13 (m, 2H), 3.62 (m, 2H), 2.37 (s, 3H), 1.51 (s, 9H); $^{13}$C (CDCl$_3$, 150 MHz, partial): δ 159.0, 153.6, 144.8, 138.3, 134.4, 133.0, 129.8, 128.2, 128.0, 127.2, 125.0, 118.3, 71.6, 69.2, 67.7, 66.4, 27.8, 21.6; HRMS-TOF (m/z): [M+H]$^+$ HRMS: Calcd. for C$_{25}$H$_{27}$D$_2$$^{35}$ClN$_2$O$_6$S: 523.1633, found 523.1629.

Example 11

Preparation of 2-(2-(4-(((1-(tert-butyl)-5-chloro-6-oxo-1,6-dihydropyridazin-4-yl)oxy)methyl)phenoxy)ethoxy)ethyl-4-methylbenzenesulfonate Part A—Preparation of 2-(2-(4-(hydroxymethyl)phenoxy)ethoxy)ethanol

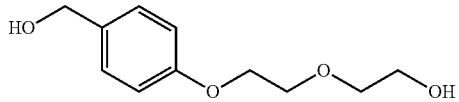 [SMILES: OCCOCCOc1ccc(CO)cc1]

A suspension of potassium iodide (1.10 g, 6.58 mmol), methyl-4-hydroxybenzoate (2.00 g, 13.1 mmol), cesium carbonate (8.53 g, 26.2 mmol), and 2-(2-chloroethoxy)ethanol (3.60 mL, 34.0 mmol) in cyclohexanone (40.0 mL) was heated to reflux and maintained 24 h. After cooling to ambient temperature, the solids were removed by filtration and the resulting filtrate concentrated to an orange oil that was directly used in the subsequent reduction without further purification.

A tetrahydrofuran solution (35.0 mL) of the crude ester was cooled to 0° C. then treated with lithium aluminum hydride (9.12 mL, 9.12 mmol, 1 M tetrahydrofuran solution). Upon complete addition, the resulting mixture was warmed to ambient temperature and stirred overnight then treated with water (20 mL). The layers were then separated and the aqueous layer extracted with ethyl acetate (2×50 mL). The combined organic layers were then dried over sodium sulfate, filtered and concentrated to a yellow oil (0.789 g, 28.4% yield). $^1$H NMR (CDCl$_3$, 300 MHz): δ 7.21 (m, 2H), 6.83 (m, 2H), 4.55 (s, 2H), 4.07 (m, 2H), 3.80 (m, 2H), 3.70 (m, 2H), 2.60 (m, 2H).

Part B—Preparation of 2-(tert-butyl)-4-chloro-5-((4-(2-(2-hydroxyethoxy)ethoxy)benzyl)oxy)pyridazin-3(2H)-one

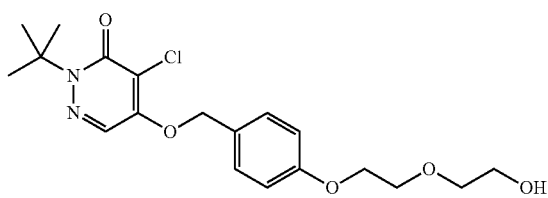 [SMILES: CC(C)(C)n1ncc(OCc2ccc(OCCOCCO)cc2)c(Cl)c1=O]

A solution of 2-(tert-butyl)-4-chloro-5-hydroxypyridrazin-3(2H)-one$^4$ (0.375 g, 1.85 mmol) in tetrahydrofuran (15.4 mL) was successively treated with the product of Example 11A, (0.327 g, 1.54 mmol), triphenylphosphine (0.609 g, 2.32 mmol), and diethylazodicarboxylate (0.404 g, 2.32 mmol) at ambient temperature. After 1 h, all volatiles were removed in vacuo and the residue directly purified by silica gel chromatography using 4:1 diethyl ether/ethyl acetate to afford the desired product (20 mg, 3% yield). $^1$H NMR (CDCl$_3$, 300 MHz): δ 7.72 (s, 1H), 7.31 (m, 2H), 6.96 (m, 2H), 5.25 (s, 2H), 4.16 (m, 2H), 3.88 (m, 2H), 3.76 (m, 2H), 3.68 (m, 2H), 1.63 (s, 9H).

Part C—Preparation of 2-(2-(4-(((1-(tert-butyl)-5-chloro-6-oxo-1,6-dihydropyridazin-4-yl)oxy)methyl)phenoxy)ethoxy)ethyl-4-methylbenzenesulfonate

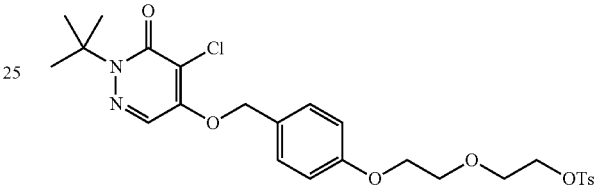

Prepared according to General Method D, using the product of Example 11B, (19.7 mg, 0.0495 mmol), p-toluenesulfonyl chloride (11.3 mg, 0.0594 mmol), 4-dimethylaminopyridine (7.26 mg, 0.0594 mmol), and diisopropylethylamine (0.010 mL, 0.0594 mmol). Isolated yield—5.2 mg; 19%. $^1$H (CDCl$_3$, 300 MHz): δ 7.72 (d, J=8.3 Hz, 2H), 7.66 (s, 1H), 7.28-7.19 (m, 4H), 6.85 (m, 2H), 5.18 (s, 2H), 4.14 (m, 2H), 3.99 (m, 2H), 3.74-3.68 (m, 4H), 2.34 (s, 3H), 1.56 (s, 9H).

Example 12

Preparation of 2-(tert-butyl)-4-chloro-5-((4-(2-(2-fluoroethoxy)ethoxy)benzyl)oxy)pyridazin-3(2H)-one

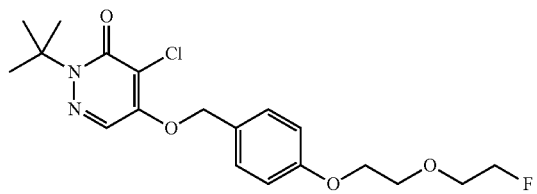 [SMILES: CC(C)(C)n1ncc(OCc2ccc(OCCOCCF)cc2)c(Cl)c1=O]

A solution of the product of Example 11C (1.90 mg, 0.0034 mmol), tetraethylammonium fluoride (0.85 mg, 0.0046 mmol), and tetraethylammonium bicarbonate (0.88 mg, 0.0046 mmol) in acetonitrile (0.70 mL) was heated to 90° C. and maintained 10 min. After cooling to ambient temperature, all volatiles were removed in vacuo and the residue directly purified by preparative thin layer chromatography using 4:1 hexanes/ethyl acetate to afford the desired product (0.2 mg, 15% yield). API-ES [M+Na] 421.1.

Example 13

Preparation of 2-(tert-butyl-4-chloro-5-((4-(2-fluoroethoxy)benzyl)oxy)pyridazin-3(2H)-one

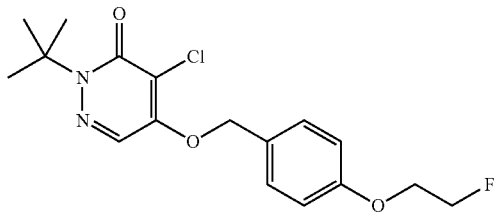 [SMILES: CC(C)(C)n1ncc(OCc2ccc(OCCF)cc2)c(Cl)c1=O]

Prepared according to General Method B, using of 2-(tert-butyl)-4,5-dichloropyridrazin-3(2H)-one[3] (68 mg, 0.31 mmol), (4-(2-fluoroethoxy)phenyl)methanol (53 mg, 0.31 mmol, e.g., see Zhou, D.; Chu, W.; Rothfuss, J.; Zeng, C.; Xu, J.; Jones, L.; Welch, M. J.; Mach, R. H. Synthesis, radiolebeling and in vivo evaluation of an $^{18}$F-labeled isatin analog for imaging caspase-3 activation in apoptosis Bioorg. Med. Chem. Lett. 2006, 16, 5041-5045), and cesium carbonate (0.303 g, 0.930 mmol) in dimethylformamide (3.10 mL) at 50° C. Isolated yield—25 mg; 23%. $^1$H NMR (CDCl$_3$, 300 MHz): δ 7.72 (s, 1H), 7.33 (m, 2H), 6.95 (m, 2H), 5.25 (s, 2H), 4.84 (m, 1H), 4.68 (m, 1H), 4.29 (m, 1H), 4.16 (m, 1H), 1.57 (s, 9H).
m Example 14

Preparation of 2-(4-(((1-(tert-butyl)-5-chloro-6-oxo-1,6-dihydropyridazin-4-yl)oxy)methyl)phenoxy)ethyl-4-methylbenzenesulfonate Part A—Preparation of methyl 4-(2-hydroxyethoxy)benzoate

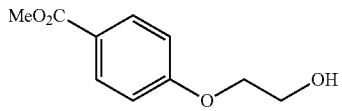 [SMILES: COC(=O)c1ccc(OCCO)cc1]

A suspension of methyl 4-hydroxybenzoate (1.52 g, 1.00 mmol), 1-bromoethanol (1.05 mL, 1.5 mmol), and cesium carbonate (8.13 g, 2.5 mmol) in dimethylformamide (100 mL) was heated to 65° C. and maintained overnight. After cooling to ambient temperature, the resulting mixture was diluted with water (250 mL) then extracted with ethyl acetate (3×250 mL). The combined organic layers were washed with water and saturated aqueous sodium chloride then dried over sodium sulfate, filtered and concentrated to a yellow oil (1.83 g, 93.3% yield). $^1$H NMR (CDCl$_3$, 300 MHz): δ 7.92 (m, 2H), 6.86 (m, 2H), 4.45 (s, 3H), 4.08 (m, 2H), 3.92 (m, 2H); $^{13}$C NMR (CDCl$_3$, 75 MHz): δ 166.8, 162.4, 131.6, 123.1, 114.2, 69.4, 61.3, 51.9; HRMS-TOF (m/z): [M+H]$^+$ HRMS: Calcd. for C$_{10}$H$_{12}$O$_4$: 197.0808, found 197.0811.

Part B—Preparation of (4-(2-((tert-butyldimethylsilyl)oxy)ethoxy)phenyl)methanol

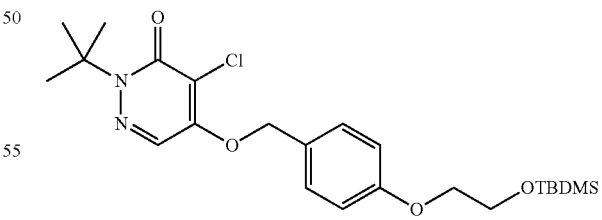

A solution of the product of Example 14A (1.00 g, 5.07 mmol), in dimethylformamide (50.0 mL) was successively treated with tert-butyldimethylsilyl chloride (1.14 g, 7.61 mmol) and imidazole (0.518 g, 7.61 mmol) at ambient temperature. After 1 h, the solution was diluted with 0.1 N hydrochloric acid (30 mL) then extracted with ethyl acetate (3×150 mL). The combined organic layers were washed with saturated aqueous sodium chloride, dried over sodium sulfate, filtered, and concentrated in vacuo to obtain a crude oil, which was used without further purification in the subsequent step.

The crude silyl ether (0.965 g, 3.11 mmol) was dissolved in tetrahydrofuran (31.1 mL), cooled to 0° C. then treated with lithium aluminum hydride (1.55 mL, 1.55 mmol, 1 M solution of lithium aluminum hydride in tetrahydrofuran) and warmed to ambient temperature. After 4 h, the resulting mixture was treated with water (10 mL) and the layers separated. The aqueous layer was extracted with ethyl acetate (3×50 mL) and the combined organic layers dried over sodium sulfate, filtered then concentrated in vacuo to afford an oil (0.779 g, 54.4% yield). $^1$H NMR (DMSO-d$_6$, 300 MHz): δ 7.14 (m, 2H), 6.80 (m, 2H), 4.96 (t, J=5.7 Hz, 1H), 4.35 (d, J=5.6 Hz, 2H), 3.95-3.83 (m, 4H), 0.80 (s, 9H), 0.01 (s, 6H).

Part C—Preparation of 2-(tert-butyl)-5-((4-(2-((tert-butyldimethylsilyl)oxy)ethoxy)benzyl)oxy)-4-chloropyridazin-3(2H)-one A solution of 2-(tert-butyl)-4-chloro-5-hydroxypyridazin-3(2H)-one (0.465 g, 2.29 mmol) in tetrahydrofuran (27.6 mL) was successively treated was added the product of Example 14B (0.779 g, 2.76 mmol), triphenylphosphine (0.905 g, 3.45 mmol), and diisopropylazodicarboxylate (0.686 mL, 3.45 mmol) at ambient temperature. After 20 min, the resulting mixture was treated with water (5 mL), the aqueous layer separated then extracted with ethyl acetate (3×50 mL). The combined organic layers were dried over sodium sulfate, filtered, and concentrated in vacuo. The crude material was then purified using silica gel chromatography (20-50% ethyl acetate in hexanes) to afford the desired product as a clear oil (0.359 g, 33.6% yield). $^1$H NMR (CDCl$_3$, 300 MHz): δ 7.63 (s, 1H), 7.23 (m, 2H), 6.86 (m, 2H), 5.15 (s, 2H), 4.01 (m, 2H), 3.87 (m, 2H), 1.53 (s, 9H), 0.82 (s, 9H), 0.01 (s, 6H); $^{13}$C NMR (CDCl$_3$, 75 MHz, partial): δ 159.1, 153.7, 129.0, 127.4, 125.3, 118.4, 115.0, 71.8, 69.9, 66.4, 61.4, 27.9, 26.6, −3.6; HRMS-TOF (m/z): [M+H]$^+$ HRMS: Calcd. for C$_{23}$H$_{35}$$^{35}$ClN$_2$O$_4$Si: 467.2127, found 467.2128.

Part D—Preparation of 2-(tert-butyl)-4-chloro-5-((4-(2-hydroxyethoxy)benzyl)oxy)pyridazin-3(2H)-one

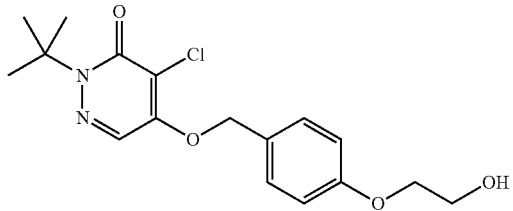 [SMILES: CC(C)(C)n1ncc(OCc2ccc(OCCO)cc2)c(Cl)c1=O]

A solution of the product of Example 14C (0.240 g, 0.513 mmol) in tetrahydrofuran (5.13 mL) was treated with tetrabutylammonium fluoride (1.03 mL, 1.03 mmol, 1 M solution in tetrahydrofuran) dropwise at ambient temperature. After 40 min, the resulting mixture was diluted with water (5 mL) the aqueous layer was separated then extracted with ethyl acetate (3×15 mL). The combined organic layers were dried over sodium sulfate, filtered, and concentrated to afford an off white solid (0.157 g, 86.7% yield). $^1$H NMR (CDCl$_3$, 300 MHz): δ7.62 (s, 1H), 7.27 (m, 2H), 7.89 (m, 2H), 5.18 (s, 2H), 4.03 (m, 2H), 3.90 (m, 2H), 1.57 (s, 9H); $^{13}$C NMR (CDCl$_3$, 75 MHz, partial): δ 159.1, 153.8, 129.0, 127.4, 125.3, 118.4, 115.0, 71.7, 69.3, 66.4, 61.4, 27.9; HRMS-TOF (m/z): [M+H]$^+$ HRMS: Calcd. for C$_{17}$H$_{21}$$^{35}$ClN$_2$O$_4$: 375.1082, found 375.1079.

Part E—Preparation of 2-(4-(((1-(tert-butyl)-5-chloro-6-oxo-1,6-dihydropyridazin-4-yl)oxy)methyl)phenoxy)ethyl-4-methylbenzenesulfonate

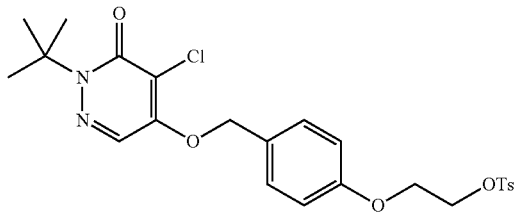 [SMILES: Cc1ccc(S(=O)(=O)OCCOc2ccc(COc3cnn(C(C)(C)C)c(=O)c3Cl)cc2)cc1]

Prepared according to General Method D, using the product of Example 14D (0.157 g, 0.446 mmol), p-toluenesulfonyl chloride (0.102 g, 0.536 mmol), 4-dimethylaminopyridine (81.9 mg, 0.67 mmol), and triethylamine (0.075 mL, 0.536 mmol). Isolated yield—0.120 g; 53.1%. $^1$H (CDCl$_3$, 600 MHz): δ 7.74 (d, J=8.3 Hz, 2H), 7.64 (s, 1H), 7.28-7.19 (m, 4H), 6.75 (m, 2H), 5.16 (s, 2H), 4.30 (m, 2H), 4.09 (m, 2H), 2.38 (s, 3H), 1.56 (s, 9H); $^{13}$C NMR (CDCl$_3$, 150 MHz): δ 159.0, 158.5, 153.7, 145.0, 132.9, 129.9, 128.9, 128.0, 127.7, 125.2, 118.4, 115.0, 71.7, 67.9, 66.4, 65.6, 27.9, 21.6; HRMS-TOF (m/z): [M+H]$^+$ HRMS: Calcd. for C$_{24}$H$_{27}$$^{35}$ClN$_2$O$_6$S: 507.1351, found 507.1365.

Example 15

Preparation of 2-(1-(4-(((1-(tert-butyl)-5-chloro-6-oxo-1,6-dihydropyridazin-4-yl)oxy)methyl) phenyl)ethoxy)ethyl 4-methylbenzenesulfonate Part A—Preparation of 2-(tert-butyl)-4-chloro-5-((4-(2-methyl-1,3-dioxolan-2-yl)benzyl)oxy) pyridazin-3(2H)-one

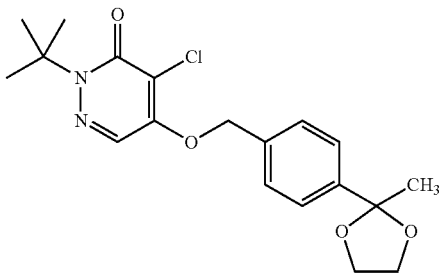 [SMILES: CC1(c2ccc(COc3cnn(C(C)(C)C)c(=O)c3Cl)cc2)OCCO1]

A solution of 2-(tert-butyl)-4,5-dichloro-2-hydropyridazin-3-one (1.66 g, 7.50 mmol) and (4-(2-methyl-1,3-dioxolan-2-yl)phenyl)methanol (0.971 g, 5.00 mmol; e.g., see Takebayashi, S.; Dabral, N.; Miskolzie, M.; Bergens, S. H. J. Am. Chem. Soc., 2011, 133, 25, 9666-9669) in dry dimethylformamide (50.0 mL) was treated with cesium carbonate (3.26 g, 10.0 mmol) in one portion at ambient temperature. The resulting suspension was then immersed in a pre-heated oil bath, and maintained at 65° C., with vigorous stirring, 4 h.

After cooling to ambient temperature, the suspension was maintained an additional 12 h, then partitioned between ethyl acetate and water (50 mL each), with transfer to a separatory funnel. The layers were then separated, and the aqueous layer washed with ethyl acetate (2×50 mL). The combined ethyl acetate washes were further washed with saturated aqueous sodium chloride (5×50 mL), then dried over magnesium sulfate, filtered and concentrated in vacuo to a yellow solid. The crude material was then purified by chromatography on silica (40×220 mm) using 7:3 pentane/ethyl acetate. The main product peak eluting 400-700 mL was collected, pooled and concentrated in vacuo to a white solid. The purified material was then recrystallized from hot ethyl acetate/pentane to afford colorless needles (1.33 g, 3.51 mmol; 70.1%). $^1$H NMR: (300 MHz, DMSO-d$_6$) δ 8.27 (1H, s), 7.52-7.36 (4H, m), 5.44 (2H, s), 4.07-3.93 (2H, m), 3.76-3.60 (2H, m), 1.57 (9H, s), 1.55 (3H, s). $^{13}$C NMR: (75 MHz, DMSO-d$_6$) δ 157.8, 153.9, 143.6, 134.9, 127.7, 126.2, 125.4, 115.5, 107.9, 71.2, 65.4, 64.1, 27.5, 27.2. HRMS Calcd. for C$_{19}$H$_{23}$$^{35}$ClN$_2$O$_4$ (M+H): 379.1419; found: 379.1416. TLC: R$_f$ 0.39 (silica gel, 7:3 pentane/ethyl acetate, uv).

Part B—Preparation of 2-(tert-butyl)-4-chloro-5-((4-(1-(2-hydroxyethoxy)ethyl)benzyl)oxy)pyridazin-3(2H)-one

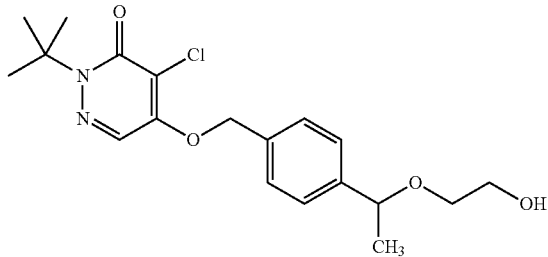 [SMILES: CC(OCCO)c1ccc(COc2cnn(C(C)(C)C)c(=O)c2Cl)cc1]

A 25 mL flame-dried round bottom flask was charged with zirconium chloride (0.233 g, 1.00 mmol) and dry tetrahydrofuran (3.00 mL) at ambient temperature. The resulting solution was then treated with sodium borohydride (75.7 mg, 2.00 mmol), in one portion, followed by the product of Example 15A (1.00 mmol; 2.00 mL of a 0.5 M solution in tetrahydrofuran), dropwise over 3 min at ambient temperature. After 1.5 h, excess sodium borohydride was then consumed by the dropwise addition of water and the resulting solution partitioned between ethyl acetate and water (25 mL each) with transfer to a separatory funnel. The layers were then separated, and the aqueous layer washed with ethyl acetate (2×25 mL). The combined ethyl acetate washes were then dried over magnesium sulfate, filtered and concentrated in vacuo. The crude material thus obtained was then purified by chromatography on silica (30×170 mm) using 1:1 pentane/ethyl acetate. The main product peak eluting 250-460 mL was collected, pooled and concentrated in vacuo to a colorless oil (0.289 g, 0.758 mmol; 75.8%). $^1$H NMR: (300 MHz, CDCl$_3$) δ 7.74 (1H, s), 7.45-7.29 (4H, m), 5.29 (2H, s), 4.47 (1H, q, J=6.5 Hz), 3.79-3.63 (2H, m), 3.52-3.35 (2H, m), 1.63 (9H, s), 1.46 (3H, d, J=6.5 Hz). $^{13}$C NMR: (75 MHz, CDCl$_3$) δ 159.0, 153.7, 144.3, 134.1, 127.4, 126.7, 125.1, 118.3, 71.7, 69.8, 66.4, 62.0, 27.9, 23.9. HRMS Calcd. for C$_{19}$H$_{25}$$^{35}$ClN$_2$O$_4$ (M+H): 381.1576; found: 381.1574.

Part C—Preparation of 2-(1-(4-(((1-(tert-butyl)-5-chloro-6-oxo-1,6-dihydropyridazin-4-yl)oxy)methyl)phenyl)ethoxy)ethyl 4-methylbenzenesulfonate

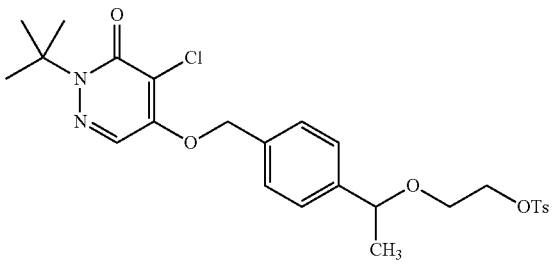 [SMILES: Cc1ccc(S(=O)(=O)OCCOC(C)c2ccc(COc3cnn(C(C)(C)C)c(=O)c3Cl)cc2)cc1]

A solution of the product of Example 15B (95.2 mg, 0.250 mmol) in dry pyridine (0.50 mL) was cooled to 0° C. then treated with p-toluenesulfonyl chloride (95.3 mg, 0.50 mmol) in one portion. After 0.25 h, the resulting solution was then warmed to ambient temperature and maintained 3.25 h, when additional p-toluenesulfonyl chloride (95.3 mg, 0.50 mmol) was added. After 0.75 h, the resulting solution was diluted with ethyl acetate (150 mL) and water (50 mL), with transfer to a separatory funnel. The layers were then separated and the ethyl acetate layer successively washed with 0.1 M hydrochloric acid and saturated aqueous sodium bicarbonate (3×50 mL each), then dried over magnesium sulfate, filtered and concentrated in vacuo. The crude material thus obtained was then purified by chromatography on silica (30×175 mm) using 3:2 pentane/ethyl acetate. The main product peak eluting 150-250 mL was collected, pooled and concentrated in vacuo to a colorless oil (62.1 mg, 0.116 mmol; 46.4%). $^1$H NMR: (300 MHz, DMSO-d$_6$) δ 8.28 (1H, s), 7.82-7.71 (2H, AA'BB', J$_{AB}$=8.3 Hz, J$_{AA'}$=2.0 Hz), 7.45 (2H, AB, d, J$_{AB}$=8.6 Hz), 7.42 (2H, AB, J$_{AB}$=8.1 Hz), 7.28 (2H, AB, J$_{AB}$=8.1 Hz), 5.44 (2H, s), 4.42 (1H, q, J=6.4 Hz), 4.11 (2H, ABdd, J$_{AB}$=11.2 Hz, J$_{dd}$=5.7, 3.0 Hz), 3.40 (2H, ABdd, J$_{AB}$=11.9 Hz, J$_{dd}$=5.6, 3.0 Hz), 2.41 (3H, s), 1.57 (9H, s), 1.27 (3H, d, J=6.4 Hz). $^{13}$C NMR: (75 MHz, DMSO-d$_6$) δ 157.8, 153.9, 144.8, 143.6, 134.5, 132.5, 130.1, 127.9, 127.6, 126.2, 126.2, 115.5, 76.7, 71.3, 70.1, 65.5, 65.4, 27.5, 23.4, 21.0. HRMS Calcd. for C$_{26}$H$_{31}$$^{35}$ClN$_2$O$_6$S (M+H): 535.1644; found: 535.1657. TLC: R$_f$ 0.58 (silica gel, 1:1 pentane/ethyl acetate, uv).

Example 16

Preparation of 2-(tert-butyl)-4-chloro-5-((4-(1-(2-fluoroethoxy)ethyl)benzyl)oxy)pyridazin-3(2H)-one

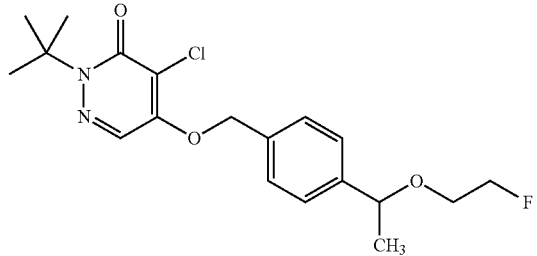 [SMILES: CC(OCCF)c1ccc(COc2cnn(C(C)(C)C)c(=O)c2Cl)cc1]

A solution of the product of Example 15C (79.7 mg, 0.150 mmol) and 4,7,13,16,21,24-hexaoxa-1,10-diazabicyclo[8.8.8]hexacosane (113 mg, 0.200 mmol) in dry acetonitrile (1.50 mL) was treated with potassium fluoride (17.4 mg, 0.300 mmol) in one portion at ambient temperature. The resulting suspension was then immersed in a pre-heated oil bath, and maintained at 90° C. for 0.25 h. After cooling to ambient temperature, all volatiles were removed in vacuo, and the residue directly purified by chromatography on silica (30×160 mm) using 1:1 pentane/diethyl ether. The main product peak eluting 140-220 mL was collected, pooled and concentrated in vacuo to a colorless oil (42.6 mg, 0.111 mmol; 74.2%). $^1$H NMR: (300 MHz, CDCl$_3$) δ 7.74 (1H, s), 7.45-7.30 (4H, m), 5.29 (2H, s), 4.53 (2H, ddd, J=47.7, 4.7, 3.7 Hz), 4.51 (1H, q, J=6.5 Hz), 3.69-3.53 (1H, m), 3.59-3.44 (1H, m), 1.63 (9H, s), 1.47 (3H, d, J=6.5 Hz). $^{13}$C NMR: (75 MHz, CDCl$_3$) δ 159.0, 153.7, 144.2, 134.1, 127.4, 126.7, 125.1, 118.3, 83.1 (d, J$_{CF}$=169 Hz), 78.1, 71.7, 67.7 (d, J$_{CF}$=19.8 Hz), 66.4, 27.8, 24.0. $^{19}$F NMR (282 MHz, CDCl$_3$) δ −223.2 (tt, J=47.8, 29.6 Hz). HRMS Calcd. for C$_{19}$H$_{24}$$^{35}$ClFN$_2$O$_3$(M+H): 383.1532; found: 383.1531. TLC: R$_f$ 0.40 (silica gel, 1:1 pentane/diethyl ether, uv).

Example 17

Preparation of 2-(tert-butyl)-4-chloro-5-((4-((2-fluoropropoxy)ethoxy)methyl)benzyl) oxy)pyridazin-3(2H)-one

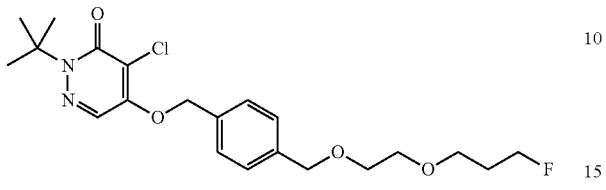

A suspension of potassium tert-butoxide (0.174 g, 1.55 mmol), 3-fluoropropyl p-toluenesulfonate (0.152 g, 0.654 mmol), and 2-(tert-butyl)-4-chloro-5-((4-((2-fluoroethoxy)methyl)benzyl)oxy)-4-pyridazin-3(2H)-one (0.200 g, 0.59 mmol) in tetrahydrofuran (5.90 mL) was heated to reflux and maintained overnight. After cooling to ambient temperature, the resulting mixture was treated with water (15 mL), the aqueous layer separated then extracted with ethyl acetate (3×50 mL). The combined organic layers were dried over sodium sulfate, filtered and concentrated in vacuo. The crude material was then purified by preparative thin layer chromatography on silica using 4:1 hexanes/ethyl acetate to afford the desired product as a yellow oil (0.8 mg, 1% yield). API-ES (m/z): [M+H] 427.2.

Example 18

Preparation of 2-(tert-butyl)-4-chloro-5-((4-(((2-fluoroethyl)amino)methyl)benzyl)oxy)pyridazin-3(2H)-one

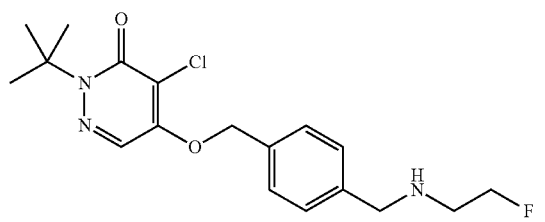 [SMILES: CC(C)(C)n1ncc(OCc2ccc(CNCCF)cc2)c(Cl)c1=O]

A solution of 5-((4-(bromomethyl)benzyl)oxy)-2-(tert-butyl)-4-chloropyridazin-3(2H)-one[3] (0.200 g, 0.521 mmol) in dimethylformamide (5.20 mL) was successively treated with 2-fluoroethylamine hydrochloride (62.2 mg, 0.625 mmol) and diisopropylethylamine (0.136 mL, 0.782 mmol) at ambient temperature. After 2 d, the resulting mixture was diluted with water (50 mL), the aqueous layer separated then extracted with ethyl acetate (3×50 mL). The combined organic layers were dried over sodium sulfate, filtered and concentrated in vacuo. The crude material was then purified using silica gel chromatography (50-80% ethyl acetate in hexanes) to afford the desired product as a clear oil (17.2 mg, 9.0% yield). $^1$H NMR (CDCl$_3$, 600 MHz): δ 7.64 (s, 1H), 7.40 (d, J=8.2 Hz, 2H), 7.34 (d, J=8.3 Hz, 2H), 5.22 (s, 2H), 4.65 (m, 1H), 4.50 (m, 1H), 3.90 (s, 2H), 2.97 (m, 1H), 2.88 (m, 1H), 1.56 (s, 9H); $^{13}$C NMR (CDCl$_3$, 150 MHz): δ 158.0, 152.7, 138.1, 133.1, 128.0, 126.9, 126.4, 117.3, 81.8 (d, $J_{CF}$=165 Hz), 70.7, 65.4, 51.8, 47.4 (d, $J_{CF}$=22.5 Hz), 26.9; HRMS-TOF (m/z): [M+H]$^+$ HRMS: Calcd. for C$_{18}$H$_{23}$$^{35}$ClFN$_3$O$_2$: 368.1536, found 368.1533.

Example 19

Preparation of 2-(tert-butyl)-4-chloro-5-((4-(fluoromethyl)benzyl)oxy)pyridazin-3(2H)-one

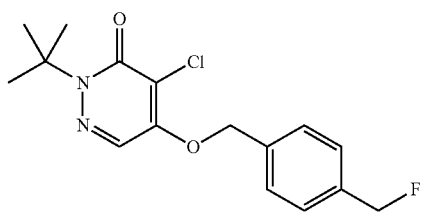 [SMILES: CC(C)(C)n1ncc(OCc2ccc(CF)cc2)c(Cl)c1=O]

A solution of 5-((4-(bromomethyl)benzyl)oxy)-2-(tert-butyl)-4-chloropyridazin-3(2H)-one[3] (0.110 g, 0.285 mmol) in dry acetonitrile (2.85 mL) was treated with silver fluoride (72.4 mg, 0.570 mmol) in one portion at ambient temperature. After 0.25 h, the resulting suspension was then immersed in a pre-heated oil bath, and maintained at 65° C. for 0.75 h, when additional silver fluoride (72.4 mg, 0.570 mmol) was added. After 1 h, the resulting suspension was cooled to ambient temperature, all volatiles removed in vacuo, and the residue directly purified by chromatography on silica (25×185 mm) using 4:1 hexanes/ethyl acetate. The main product peak eluting 280-420 mL was collected, pooled and concentrated in vacuo to a white solid (64.6 mg, 0.199 mmol; 69.8%). $^1$H NMR: (300 MHz, DMSO-d$_6$) δ 8.25 (1H, s), 7.56-7.42 (4H, m), 5.48 (2H, d, J=1.4 Hz), 5.43 (2H, d, J=47.7 Hz), 1.57 (9H, s). $^{13}$C NMR: (75 MHz, DMSO-d$_6$) δ 157.8, 153.8, 136.4 (d, $J_{CF}$=16.7 Hz), 135.9 (d, $J_{CF}$=3.1 Hz), 128.1 (d, $J_{CF}$=5.7 Hz), 127.9 (d, $J_{CF}$=1.4 Hz), 126.1, 115.6, 83.8 (d, $J_{CF}$=162 Hz), 71.1, 65.4, 27.4. $^{19}$F NMR: (282 MHz, DMSO-d$_6$) δ −205.4 (t, J=47.7 Hz). HRMS Calcd. for C$_{16}$H$_{18}$$^{35}$ClFN$_2$O$_2$ (M+H): 325.1114; found: 325.1117. TLC: R$_f$ 0.24 (silica gel, 4:1 hexanes/ethyl acetate, uv).

Example 20

Preparation of 2-(tert-butyl)-4-chloro-5-((4'-fluoro-[1,1'-biphenyl]-4-yl)methoxy)pyridazin-3(2H)-one Part A—Preparation of (4'-fluoro-[1,1'-biphenyl]-4-yl)methanol

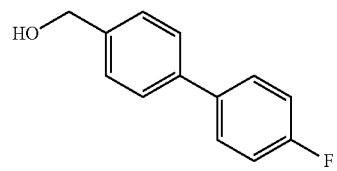 [SMILES: OCc1ccc(-c2ccc(F)cc2)cc1]

A solution of 4-(4-fluorophenyl)benzoic acid (0.500 g, 2.31 mmol) in tetrahydrofuran (23.1 mL) was cooled to 0° C., treated with lithium aluminum hydride (1.15 mL, 1.15 mmol, 1 M solution in tetrahydrofuran) then warmed to ambient temperature and stirred overnight. The resulting mixture was then treated with water (20 mL), the aqueous layer separated then extracted with ethyl acetate (3×100 mL). The combined organic layers were washed with saturated aqueous sodium chloride, dried over sodium sulfate, filtered and concentrated to a white solid (0.290 g, 62.1% yield). $^1$H NMR (CDCl$_3$, 300 MHz): δ 7.48-7.44 (m, 2H), 7.46 (d, J=8.5 Hz, 2H), 7.36 (d, J=8.5 Hz, 2H), 7.04 (m, 2H), 4.67 (s, 2H); $^{13}$C NMR (CDCl$_3$, 75 MHz): δ 161.5 (d, J$_{CF}$=240 Hz), 138.9, 138.7, 136.0 (d, J$_{CF}$=7.5 Hz), 127.7 (d, J$_{CF}$=7.5 Hz), 126.5, 126.2, 114.6 (d, J$_{CF}$=22.5 Hz), 64.0; HRMS-TOF (m/z): [M+H]$^+$ HRMS: Calcd. for C$_{13}$H$_{11}$FO: 203.0867, found 203.0868.

Part B—Preparation of 2-(tert-butyl)-4-chloro-5-((4'-fluoro-[1,1'-biphenyl]-4-yl)methoxy)pyridazin-3(2H)-one

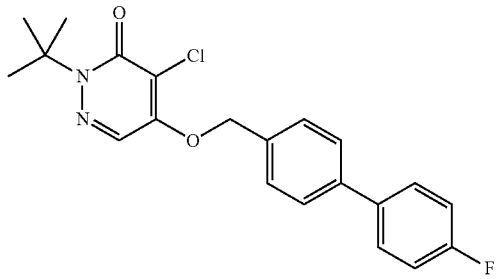 [SMILES: CC(C)(C)n1ncc(OCc2ccc(-c3ccc(F)cc3)cc2)c(Cl)c1=O]

Prepared according to General Method B, using 2-(tert-butyl)-4,5-dichloropyridazin-3(2H)-one (0.288 g, 1.30 mmol), the product of Example 20A, (0.290 g, 1.43 mmol), and cesium carbonate (0.680 g, 2.09 mmol) in dimethylformamide (13.0 mL) at 60° C. Isolated yield—0.144 g; 28.6%. $^1$H NMR (CDCl$_3$, 300 MHz): δ 7.68 (s, 1H), 7.53 (d, J=8.5 Hz, 2H), 7.53-7.45 (m, 2H), 7.40 (d, J=8.5 Hz, 2H), 7.06 (m, 2H), 5.28 (s, 2H), 1.54 (s, 9H); $^{13}$C NMR (CDCl$_3$, 75 MHz): δ 162.7 (d, J$_{CF}$=247.5 Hz), 159.0, 153.7, 140.8, 136.5 (d, J$_{CF}$=7.5 Hz), 133.9, 128.7 (d, J$_{CF}$=7.5 Hz), 127.7, 127.6, 125.1, 118.4, 115.8 (d, J$_{CF}$=22.5 Hz), 71.6, 66.4, 27.9; HRMS-TOF (m/z): [M+H]$^+$ HRMS: Calcd. for C$_{21}$H$_{20}$$^{35}$ClFN$_2$O$_2$: 387.1270, found 387.1268.

Example 21

Preparation of 2-(tert-butyl)-4-chloro-5-((5-((2-fluoroethoxy)methyl)pyridin-2-yl)methoxy)pyridazin-3(2H)-one Part A—Preparation of methyl 6-(((1-(tert-butyl)-5-chloro-6-oxo-1,6-dihydropyridazin-4-ol)oxy)methyl)nicotinate

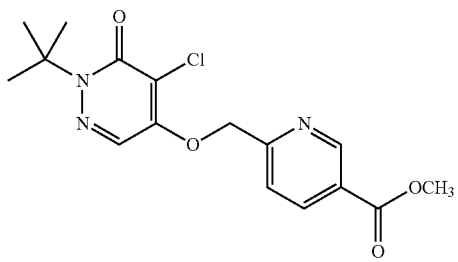 [SMILES: COC(=O)c1ccc(COc2cnn(C(C)(C)C)c(=O)c2Cl)nc1]

Prepared according to General Method B, using 2-(tert-butyl)-4-chloro-5-hydroxypyridazin-3(2H)-one (0.917 g, 4.54 mmol), methyl 6-(bromomethyl)nicotinate (0.994 g, 4.32 mmol), and cesium carbonate (2.25 g, 6.91 mmol) in dimethylformamide (21.0 mL) at 60° C. Isolated yield—0.666 g; 41.7%. $^1$H NMR (CDCl$_3$, 300 MHz): δ 9.22 (d, J=1.3 Hz, 1H), 8.41 (dd, J=8.1, 2.1 Hz, 1H), 7.79 (s, 1H), 7.69 (d, J=8.2 Hz, 1H), 5.48 (s, 2H), 3.99 (s, 3H), 1.66 (s, 9H); $^{13}$C NMR (CDCl$_3$, 75 MHz): δ 165.2, 159.1, 158.9, 153.3, 150.4, 138.6, 125.9, 124.7, 120.8, 118.5, 70.7, 66.7, 52.6, 27.8; HRMS-TOF (m/z): [M+H]$^+$ HRMS: Calcd. for C$_{16}$H$_{18}$$^{35}$ClN$_3$O$_4$: 352.1059, found 352.1059.

Part B—Preparation of 2-(tert-butyl)-4-chloro-5-((5-(hydroxymethyl)pyridin-2-yl)methoxy)pyridazin-3(2H)-one

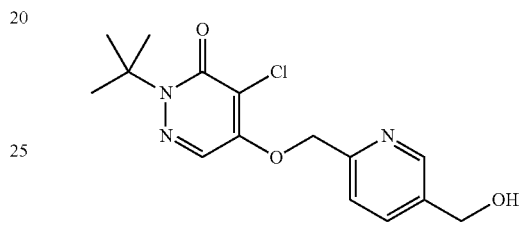

A solution of the product of Example 21A (0.333 g, 0.945 mmol) in tetrahydrofuran (9.45 mL) was cooled to 0° C., treated with lithium aluminum hydride (0.472 mL, 0.5 mmol, 1M solution in tetrahydrofuran) then warmed to ambient temperature. After 4 h, the resulting mixture was treated with water (10 mL), the aqueous layer separated then extracted with ethyl acetate (3×50 mL). The combined organic layers were washed with saturated aqueous sodium chloride, dried over sodium sulfate, filtered and concentrated to a yellow oil (0.290 g, 94.8% yield). $^1$H NMR (DMSO-d$_6$, 600 MHz): δ 8.59 (d, 1H, J=1.4 Hz), 8.32 (s, 1H), 7.87 (dd, J=7.9, 2.2 Hz, 1H), 7.57 (m, 1H), 5.58 (s, 2H), 5.39 (t, J=5.74 Hz, 1H), 4.61 (d, J=5.6 Hz, 2H), 1.64 (s, 9H); $^{13}$C NMR (DMSO-d$_6$, 150 MHz): δ 157.8, 153.9, 153.4, 147.8, 137.4, 135.5, 126.3, 121.6, 115.5, 71.8, 64.8, 50.7, 20.9; HRMS-TOF (m/z): [M+H]$^+$ HRMS: Calcd. for C$_{15}$H$_{18}$$^{35}$ClN$_3$O$_3$: 324.1109, found 324.111.

Part C—Preparation of 5-((5-(bromomethyl)pyridin-2-yl)methoxy)-2-(tert-butyl)-4-chloropyridazin-3(2H)-one

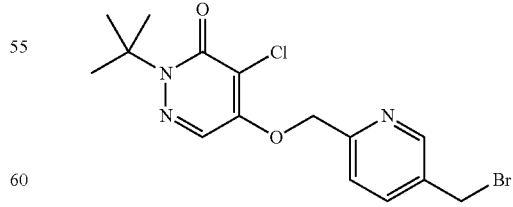

Prepared according to General Method C, using product of Example 21B (0.289 g, 0.891 mmol) and phosphorous tribromide (0.446 mL, 0.446 mmol, 1 M in dichloromethane). Isolated yield—0.212 g; 61.5%. $^1$H NMR (DMSO-d$_6$, 300 MHz): δ 8.73 (d, J=1.4 Hz, 1H), 8.31 (s, 1H), 8.03 (dd, J=8.1, 2.3 Hz, 1H), 7.61 (d, J=8.0 Hz, 1H), 5.60 (s, 2H), 4.83 (s, 2H), 1.64 (s, 9H); $^{13}$C NMR (DMSO-d$_6$, 75 MHz): δ 157.8, 154.8, 153.8, 149.6, 138.0, 133.8, 126.3, 121.8, 115.6, 71.8, 66.4, 30.4, 27.5. HRMS-TOF (m/z): [M+H]$^+$ HRMS: Calcd. for C$_{15}$H$_{17}$$^{79}$Br$^{35}$ClN$_3$O$_2$: 386.0265, found 386.0267.

Part D—Preparation of 2-(tert-butyl)-4-chloro-5-((5-((2-fluoroethoxy)methyl)pyridin-2-yl)methoxy)pyridazin-3(2H)-one

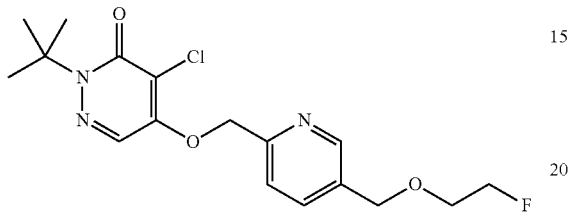

Prepared according to General Method A, using potassium tert-butoxide (25.9 mg, 0.231 mmol), 2-fluoroethanol (14.8 mg, 0.231 mmol) and the product of Example 21C (0.100 g, 0.260 mmol). Isolated yield—23.8 mg; 27.9%. $^1$H NMR (CDCl$_3$, 300 MHz): δ 8.51 (d, J=1.5 Hz, 1H), 7.73 (s, 1H), 7.72 (dd, J=7.3, 2.17 Hz, 1H), 7.47 (d, J=8.1 Hz, 1H), 5.34 (s, 2H), 4.47 (m, 1H), 4.45 (s, 2H), 4.46 (m, 1H), 3.77 (m, 1H), 3.67 (m, 1H), 1.48 (s, 9H); HRMS-TOF (m/z): [M+H]$^+$ HRMS: Calcd. for C$_{17}$H$_{21}$$^{35}$ClFN$_3$O$_3$: 370.1328, found 370.1328.

Example 22

Preparation of 5-((3-bromo-4-((2-fluoroethoxy)methyl)benzyl)oxy)-2-(tert-butyl)-4-chloropyridazin-3(2H)-one Part A—Preparation of methyl 2-bromo-4-(((1-(tert-butyl)-5-chloro-6-oxo-1,6-dihydropyridazin-4-yl)oxy)methyl)benzoate

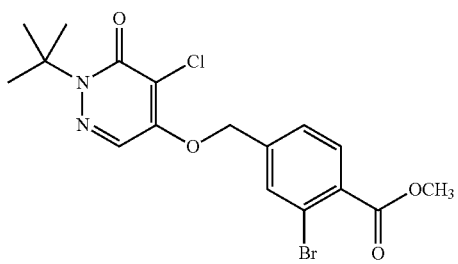 [SMILES: COC(=O)c1ccc(COc2cnn(C(C)(C)C)c(=O)c2Cl)cc1Br]

Prepared according to General Method B, using 2-(tert-butyl)-4-chloro-5-hydroxypyridazin-3(2H)-one (0.750 g, 3.70 mmol), methyl 2-bromo-4-bromomethyl benzoate (1.09 g, 3.52 mmol), and cesium carbonate (1.37 g, 4.22 mmol) in dimethylformamide (35.0 mL) at 70° C. Isolated yield—0.695 g; 46.0%. $^1$H NMR (CDCl$_3$, 300 MHz): δ 7.84 (m, 1H), 7.73 (m, 1H), 7.69 (s, 1H), 7.44 (m, 1H), 5.32 (s, 2H), 3.93 (s, 3H), 1.64 (s, 9H); $^{13}$C NMR (CDCl$_3$, 75 MHz): δ 165.2, 158.9, 153.3, 139.9, 132.4, 132.3, 131.9, 125.4, 124.7, 122.3, 118.7, 70.2, 66.6, 52.6, 27.8; HRMS-TOF (m/z): [M+H]$^+$ HRMS: Calcd. for C$_{17}$H$_{18}$$^{79}$Br$^{35}$ClN$_2$O$_4$: 429.0211, found 429.0209.

Part B—Preparation of 5-((3-bromo-4-(hydroxymethyl)benzyl)oxy)-2-(tert-butyl)-4-chloropyridazin-3(2H)-one

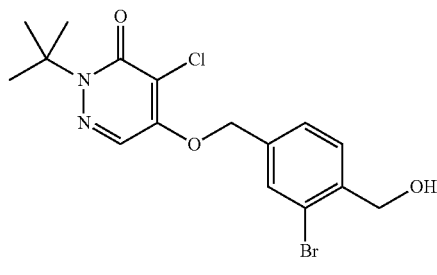 [SMILES: CC(C)(C)n1ncc(OCc2ccc(CO)c(Br)c2)c(Cl)c1=O]

A solution of the product of Example 22A (0.300 g, 0.697 mmol), in tetrahydrofuran (2.50 mL) was cooled −20° C., treated with diisobutylaluminum hydride (1.57 mL, 1.57 mmol, 1 M solution in dichloromethane) the warmed to ambient temperature and stirred overnight. The resulting mixture was treated with water (10 mL), the aqueous layer separated then extracted with ethyl acetate (3×50 mL). The combined organic layers were dried over sodium sulfate, filtered and concentrated in vacuo. The crude material was then purified by silica gel chromatography (0-50% ethyl acetate in hexanes) to afford the desired product as a yellow oil (0.109 g, 38.9% yield). $^1$H NMR (DMSO-d$_6$, 300 MHz): δ 8.59 (d, J=1.4 Hz, 1H), 8.32 (s, 1H), 7.87 (dd, J=7.9, 2.2 Hz, 1H), 7.57 (m, 1H), 5.58 (s, 2H), 5.39 (t, J=5.7 Hz, 1H), 4.61 (d, J=5.6 Hz, 2H), 1.64 (s, 9H); $^{13}$C NMR (DMSO-d$_6$, 75 MHz): δ 159.0, 153.4, 140.4, 136.0, 131.0, 129.2, 126.1, 124.9, 122.8, 118.5, 70.7, 66.6, 64.7, 27.9; HRMS-TOF (m/z): [M+H]$^+$ HRMS: Calcd. for C$_{16}$H$_{18}$$^{79}$Br$^{35}$ClN$_2$O$_3$: 401.0262, found 401.0266.

Part C—Preparation of 5-((3-bromo-4-(bromomethyl)benzyl)oxy)-2-(tert-butyl)-4-chloropyridazin-3(2H)-one

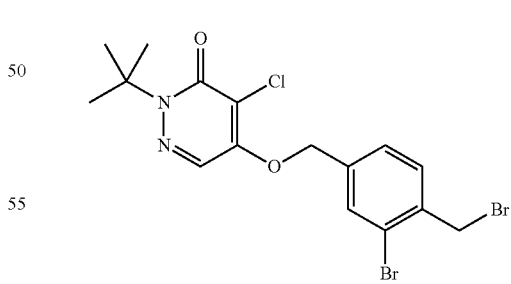

Prepared according to General Method C, using the product of Example 22B (0.109 g, 0.270 mmol) and phosphorous tribromide (0.135 mL, 0.135 mmol, 1 M in dichloromethane). Isolated yield—87.1 mg; 69.4%. $^1$H NMR (CDCl$_3$, 300 MHz): δ 7.69 (s, 1H), 7.64 (d, J=1.4 Hz, 1H), 7.51 (d, J=7.9 Hz, 1H), 7.36 (dd, J=7.9, 1.7 Hz, 1H), 5.27 (s, 2H), 4.60 (s, 2H), 1.64 (s, 9H); $^{13}$C NMR (CDCl$_3$, 75 MHz): δ 158.9, 153.3, 137.6, 137.2, 131.7, 131.6, 126.4, 124.9, 124.8 118.6, 70.4, 66.6, 32.6, 27.9; HRMS-TOF (m/z): [M+H]+ HRMS: Calcd. for $C_{16}H_{17}{}^{79}Br_2{}^{35}ClN_2O_2$: 464.9397, found 464.9400.

Part D—Preparation of 2-(tert-butyl)-4-chloro-5-((5-((2-fluoroethoxy)methyl)pyridin-2-yl)methoxy)pyridazin-3(2H)-one

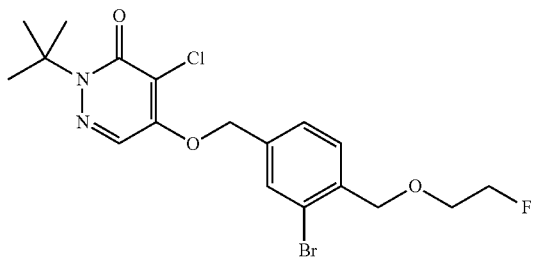 [SMILES: CC(C)(C)n1ncc(OCc2ccc(COCCF)c(Br)c2)c(Cl)c1=O]

Prepared according to General Method E, using potassium tert-butoxide (9.5 mg, 0.084 mmol), 2-fluoroethanol (5.4 mg, 0.084 mmol) and the product of Example 22C (43.5 mg, 0.0940 mmol). Isolated yield—3.0 mg; 8.0%. $^1$H NMR (CDCl$_3$, 300 MHz): δ 7.69 (s, 1H), 7.61 (d, 1H, J=1.4 Hz), 7.57 (d, J=8.0 Hz, 1H), 7.38 (dd, J=6.3, 1.6 Hz, 1H), 5.27 (s, 2H), 4.72 (m, 1H), 4.66 (s, 2H), 4.56 (m, 1H), 3.89 (m, 1H), 3.79 (m, 1H), 1.64 (s, 9H); $^{13}$C NMR (CDCl$_3$, 75 MHz): δ 159.0, 153.4, 138.0, 136.0, 131.0, 129.4, 126.1, 124.9, 122.9, 118.6, 83.0 (d, $J_{CF}$=165 Hz), 72.3, 70.7, 70.1 (d, $J_{CF}$=15 Hz), 66.5, 27.9; HRMS-TOF (m/z): [M+H]+ HRMS: Calcd. for $C_{18}H_{21}{}^{79}Br^{35}ClFN_2O_3$: 447.0481, found 447.0471.

Example 23

Preparation of 2-(tert-butyl)-4-chloro-5-((4-((2-fluoroethoxy)methyl)-2,5-dimethylbenzyl)oxy)pyridazin-3(2H)-one Part A—Preparation of 2-(tert-butyl)-4-chloro-5-((4-(chloromethyl)-2,5-dimethylbenzyl)oxy)pyridazin-3(2H)-one

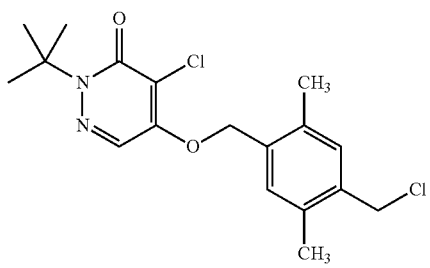 [SMILES: Cc1cc(COc2cnn(C(C)(C)C)c(=O)c2Cl)c(C)cc1CCl]

Prepared according to General Method B, using 2-(tert-butyl)-4-chloro-5-hydroxypyridrazin-3(2H)-one (0.500 g, 2.47 mmol), 2, 5-bis(chloromethyl)-p-xylene (1.00 g, 5.00 mmol), and cesium carbonate (2.60 g, 8.00 mmol) in dimethylformamide (25.0 mL). Isolated yield—0.410 g; 44.9%. $^1$H NMR (CDCl$_3$, 300 MHz): δ 7.68 (s, 1H), 7.13 (m, 2H), 5.17 (s, 2H), 4.51 (s, 2H), 2.34 (s, 3H), 2.28 (s, 3H), 1.58 (s, 9H); $^{13}$C NMR (CDCl$_3$, 75 MHz): δ 159.0, 153.7, 136.2, 135.1, 134.5, 133.3, 132.2, 130.7, 125.0, 118.3, 70.3, 66.4, 44.2, 27.9, 18.4, 18.3; HRMS-TOF (m/z): [M+H]+ HRMS: Calcd. for $C_{18}H_{22}{}^{35}Cl_2N_2O_2$: 369.1131, found 369.1134.

Part B—Preparation of 2-(tert-butyl)-4-chloro-5-((4-((2-fluoroethoxy)methyl)-2,5-dimethylbenzyl)oxy)pyridazin-3(2H)-one

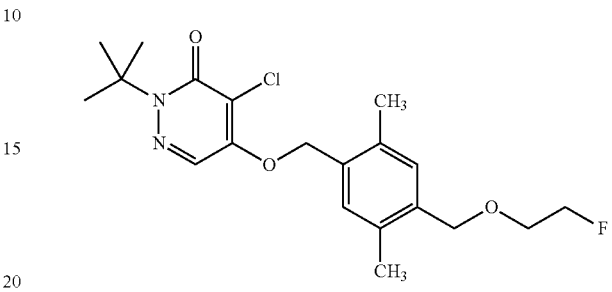

Prepared according to General Method E, using potassium tert-butoxide (38.0 mg, 0.339 mmol), 2-fluoroethanol (14.5 mg, 0.226 mmol) and the product of Example 23A (0.100 g, 0.271 mmol). Isolated yield—18.3 mg; 20.4%. $^1$H NMR (CDCl$_3$, 300 MHz): δ 7.69 (s, 1H), 7.61 (d, J=14.9 Hz, 1H), 7.57 (d, J=12.6 Hz, 1H), 5.18 (s, 2H), 4.49 (m, 1H), 4.46 (s, 2H), 4.44 (m, 1H), 3.73 (m, 1H), 3.64 (m, 1H), 2.28 (s, 3H), 2.25 (3H, s), 1.53 (s, 9H); $^{13}$C NMR (CDCl$_3$, 75 MHz): δ 158.1, 152.8, 135.6, 133.5, 133.1, 131.2, 130.1, 129.5, 124.1, 117.2, 82.1 (d, $J_{CF}$=165 Hz), 70.4, 69.5, 68.6 (d, $J_{CF}$=22.5 Hz), 65.4, 26.9, 17.4, 17.3; HRMS-TOF (m/z): [M+H]+ HRMS: Calcd. for $C_{20}H_{26}{}^{35}ClFN_2O_3$: 397.1689, found 397.1687.

Example 24

Preparation of 2-(tert-butyl)-4-chloro-5-((4-(3-fluoropropoxy)-3-methoxybenzyl)oxy)pyridazin-3(2H)-one Part A—Preparation of (4-(3-fluoropropoxy)-3-methoxyphenyl)methanol

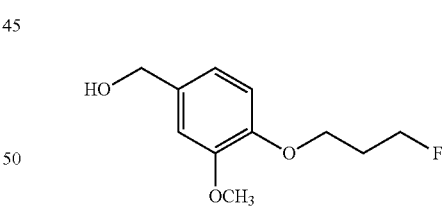

Prepared according to General Method F, using 4-hydroxy-3-methoxybenzaldehyde (0.688 g, 4.52 mmol), 3-fluoropropyl p-toluenesulfonate (1.00 g, 4.30 mmol), and cesium carbonate (2.24 mg, 6.89 mmol) in dimethylformamide (43.0 mL) at 60° C. Isolated yield—0.517 g; 56.1%. $^1$H NMR (CDCl$_3$, 300 MHz): δ 9.78 (s, 1H), 7.37 (dd, J=8.1, 1.9 Hz, 1H), 7.35 (m, 1H), 7.63 (d, J=8.1 Hz, 1H), 4.68 (t, J=5.7 Hz, 1H), 4.53 (t, J=5.7 Hz, 1H), 4.18 (t, J=6.3 Hz, 2H), 3.12 (s, 3H), 2.24 (m, 1H), 2.15 (m, 1H); $^{13}$C NMR (CDCl$_3$, 75 MHz): δ 190.8, 153.8, 150.0, 130.3, 126.7, 111.7, 109.5, 80.5 (d, $J_{CF}$=165 Hz), 64.8 (d, $J_{CF}$=7.5 Hz), 56.0, 30.2 (d, $J_{CF}$=22.5 Hz).

A solution of the crude 4-(3-fluoropropoxy)-3-methoxybenzaldehyde (0.839 g, 3.90 mmol) in ethanol (39.0 mL)

was treated sodium borohydride (0.112 g, 2.90 mmol) in one portion at ambient temperature. The resulting mixture was stirred overnight, then treated with water (50 mL) and concentrated in vacuo to remove the ethanol. The resulting aqueous solution was extracted with ethyl acetate (3×150 mL), and the combined organic layers dried over sodium sulfate, filtered and concentrated to afford the desired product (0.807 g, 96.6% yield). $^1$H NMR (CDCl$_3$, 600 MHz): δ 6.87 (br s, 1H), 6.81 (br s, 2H), 4.68 (m, 1H), 4.56 (s, 2H), 4.52 (m, 1H), 4.08 (t, J=6.3 Hz, 2H), 3.81 (s, 3H), 2.19 (m, 1H), 2.11 (m, 1H); $^{13}$C NMR (CDCl$_3$, 150 MHz): δ 149.7, 147.8, 121.5, 119.5, 113.4, 111.8, 81.9 (d, $J_{CF}$=157.5 Hz), 65.3. 65.0 (d, $J_{CF}$=7.5 Hz), 56.0, 30.5 (d, $J_{CF}$=22.5 Hz); HRMS-TOF (m/z): [M+Na]$^+$ HRMS: Calcd. for C$_{11}$H$_{15}$FO$_3$: 237.0897, found 237.0898.

Part B—Preparation of 2-(tert-butyl)-4-chloro-5-((4-(3-fluoropropoxy)-3-methoxybenzyl)oxy)pyridazin-3(2H)-one

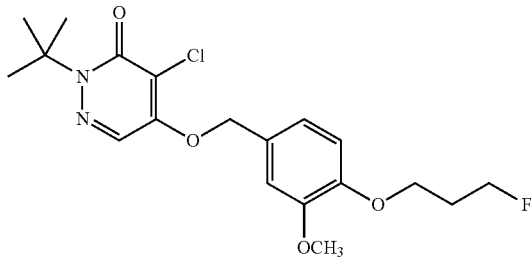 [SMILES: COc1cc(COc2cnn(C(C)(C)C)c(=O)c2Cl)ccc1OCCCF]

A solution of 2-(tert-butyl)-4-chloro-5-hydroxy-pyridrazin-3(2H)-one (0.200 g, 0.990 mmol) in tetrahydrofuran (8.24 mL) was successively treated with the product of Example 24A (0.254 g, 1.19 mmol), triphenylphosphine (0.388 g, 1.48 mmol), and diisopropylazodicarboxylate (0.291 mL, 1.48 mmol) at ambient temperature. The resulting mixture was stirred overnight then concentrated in vacuo to a yellow oil. The crude material was then purified by preparative thin layer chromatography on silica using 98:2 hexanes/diethyl ether to afford the desired product (12.6 mg, 3.2% yield). $^1$H NMR (CDCl$_3$, 300 MHz): δ 7.65 (s, 1H), 6.86 (m, 3H), 5.18 (s, 2H), 4.68 (t, J=5.7 Hz, 1H), 4.52 (t, J=5.7 Hz, 1H), 4.09 (t, J=6.3 Hz, 2H), 3.08 (s, 3H), 2.24-2.07 (m, 2H), 1.56 (s, 9H); $^{13}$C NMR (CDCl$_3$, 75 MHz, partial): δ 159.0, 153.8, 150.0, 148.7, 127.8, 125.3, 120.0, 113.2, 110.9, 80.7 (d, $J_{CF}$=165 Hz), 72.0, 66.4, 64.9 (d, $J_{CF}$=7.5 Hz), 56.0, 30.4 (d, $J_{CF}$=22.5 Hz), 27.9; HRMS-TOF (m/z): [M+H]$^+$ Calcd. for C$_{19}$H$_{24}$$^{35}$ClFN$_2$O$_4$: 399.1481, found 399.1484.

Example 25

Preparation of 2-(tert-butyl)-4-chloro-5-((3-chloro-4-(3-fluoropropoxy)benzyl)oxy)pyridazin-3(2H)-one Part A—Preparation of (3-chloro-4-(3-fluoropropoxy)phenyl)methanol

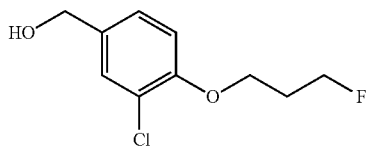 [SMILES: OCc1ccc(OCCCF)c(Cl)c1]

Prepared according to General Method F, using 3-chloro-4-hydroxybenzaldehyde (0.300 g, 1.92 mmol), 3-fluoropropyl p-toluenesulfonate (424 g, 1.83 mmol), and cesium carbonate (0.951 g, 2.93 mmol) in dimethylformamide (19.0 mL) at 65° C. Isolated yield—0.262 g; 66.1%. $^1$H NMR (CDCl$_3$, 300 MHz): δ 9.89 (s, 1H), 7.93 (d, J=2.1 Hz, 1H), 7.78 (dd, J=8.5, 2.1 Hz, 1H), 7.06 (d, J=8.5 Hz, 1H), 4.80 (t, J=5.7 Hz, 1H), 4.64 (t, J=5.7 Hz, 1H), 4.28 (t, J=6.0 Hz, 2H), 2.33 (m, 1H), 2.22 (m, 1H); $^{13}$C NMR (CDCl$_3$, 75 MHz): δ 189.6, 159.1, 131.3, 130.4, 130.4, 124.0, 112.6, 80.2 (d, $J_{CF}$=165 Hz), 64.9 (d, $J_{CF}$=7.5 Hz), 30.2 (d, $J_{CF}$=22.5 Hz).

A solution of the crude 3-chloro-4-(3-fluoropropoxy)benzaldehyde (0.262 g, 1.21 mmol) in ethanol (8.95 mL) was treated with sodium borohydride (25.4 mg, 0.671 mmol) in one portion at ambient temperature. The resulting mixture was stirred overnight, then treated with water (10 mL) and concentrated in vacuo to remove the ethanol. The resulting aqueous solution was extracted with ethyl acetate (3×50 mL), and the combined organic layers dried over sodium sulfate, filtered and concentrated to afford the desired product as a white solid (0.242 g, 91.5% yield). $^1$H NMR (CDCl$_3$, 300 MHz): δ 7.32 (d, J=2.1 Hz, 1H), 7.13 (dd, J=8.4, 2.2 Hz, 1H), 6.86 (d, J=8.4 Hz, 1H), 4.71 (t, J=5.6 Hz, 1H), 4.57 (t, J=5.6 Hz, 1H), 4.54 (s, 2H), 4.09 (t, J=6.0 Hz, 2H), 2.19 (m, 1H), 2.11 (m, 1H); $^{13}$C NMR (CDCl$_3$, 75 MHz): δ 153.7, 134.4, 129.2, 126.5, 123.1, 113.5, 80.6 (d, $J_{CF}$=165 Hz), 64.8 (d, $J_{CF}$=7.5 Hz), 64.4, 30.4 (d, $J_{CF}$=22.5 Hz); HRMS-TOF (m/z): [M+H]$^+$ HRMS: Calcd. for C$_{10}$H$_{12}$$^{35}$ClFO$_2$: 217.0437, found 217.0442.

Part B—Preparation of 2-(tert-butyl)-4-chloro-5-((3-chloro-4-(3-fluoropropoxy)benzyl)oxy)pyridazin-3(2H)-one

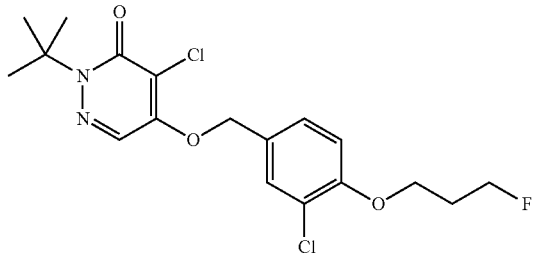 [SMILES: CC(C)(C)n1ncc(OCc2ccc(OCCCF)c(Cl)c2)c(Cl)c1=O]

A solution of 2-(tert-butyl)-4-chloro-5-hydroxy-pyridrazin-3(2H)-one (0.186 g, 0.920 mmol) in THF (7.60 mL) was successively treated with the product of Example 25A (0.242 g, 1.10 mmol), triphenylphosphine (0.362 g, 1.38 mmol), and diisopropylazodicarboxylate (0.362 g, 1.38 mmol) at ambient temperature. The resulting mixture was stirred overnight then concentrated in vacuo to a yellow oil. The crude material was then purified by silica gel chromatography using 4:1 dichloromethane/methanol to afford the desired product as a white solid (53.8 mg, 14.5% yield). $^1$H NMR (CDCl$_3$, 300 MHz): δ 7.65 (s, 1H), 7.36 (d, J=2.2 Hz, 1H), 7.20 (dd, J=2.3, 4.8 Hz, 1H), 6.89 (d, J=8.5 Hz, 1H), 5.14 (s, 2H), 4.70 (t, J=5.8 Hz, 1H), 4.54 (t, J=5.8 Hz, 1H), 4.10 (t, J=6.0 Hz, 2H), 2.16 (m, 1H), 2.11 (m, 1H), 1.56 (s, 9H); $^{13}$C NMR (CDCl$_3$, 75 MHz): δ 159.0, 154.6, 153.5, 129.4, 128.1, 127.0, 125.1, 123.45, 118.4, 113.5, 80.4 (d, $J_{CF}$=165 Hz), 71.0, 66.4, 64.7 (d, $J_{CF}$=7.5 Hz), 30.3 (d, $J_{CF}$=22.5 Hz), 27.8; HRMS-TOF (m/z): [M+H]$^+$ HRMS: Calcd. for C$_{18}$H$_{21}$ClFN$_2$O$_3$: 403.0986, found 403.0985.

Example 26

Preparation of 3-(4-(((1-(tert-butyl)-5-chloro-6-oxo-1,6-dihydropyridazin-4-yl)oxy)methyl)-2-chlorophenoxy)propyl 4-methylbenzenesulfonate

Part A—Preparation of 3-chloro-4-(3-hydroxypropoxy)benzaldehyde

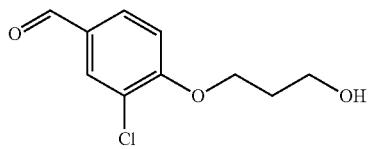 [SMILES: O=Cc1ccc(OCCCO)c(Cl)c1]

A suspension of 3-chloro-4-hydroxybenzaldehyde (0.500 g, 3.20 mmol), 1-bromopropanol (0.271 mL, 3.0 mmol), and cesium carbonate (2.44 g, 7.50 mmol) in dimethylformamide (32.0 mL) was heated to 60° C. and maintained overnight. After cooling to ambient temperature, the resulting mixture was diluted with water (150 mL) and the aqueous layer was extracted with ethyl acetate (3×150 mL). The combined organic layers were washed with water, saturated aqueous sodium chloride, dried over sodium sulfate, filtered and concentrated to a yellow oil (0.322 g, 46.9% yield). $^1$H NMR (CDCl$_3$, 300 MHz): δ 9.77 (s, 1H), 7.83 (d, J=2.1 Hz, 1H), 7.68 (dd, J=8.5, 2.0 Hz, 1H), 6.98 (d, J=8.5 Hz, 1H), 4.22 (t, J=5.9 Hz, 2H), 4.15 (t, J=5.7 Hz, 2H), 2.11-2.03 (m, 2H); $^{13}$C NMR (CDCl$_3$, 75 MHz): δ 189.8, 159.1, 131.2, 130.6, 130.3, 123.8, 112.4, 67.2, 60.0, 31.6.

Part B—Preparation of 4-(3-((tert-butyldimethylsilyl)oxy)propoxy)-3-chlorophenyl)methanol

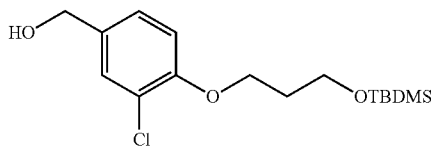 [SMILES: CC(C)(C)[Si](C)(C)OCCCOc1ccc(CO)cc1Cl]

A solution of the product of Example 26A (0.312 g, 1.45 mmol), in dimethylformamide (14.5 mL) was successively treated with tert-butyldimethylsilyl chloride (0.329 g, 2.18 mmol) and imidazole (0.149 g, 2.18 mmol) at ambient temperature then stirred overnight. The resulting mixture was diluted with 0.1 N hydrochloric acid (30 mL) then extracted with ethyl acetate (2×50 mL). The combined organic layers were washed with saturated aqueous sodium chloride, dried over sodium sulfate, filtered, and concentrated in vacuo. The crude material was then purified by silica gel chromatography (0-50% ethyl acetate in hexanes) to afford the desired product as a clear oil (0.167 g, 35.0% yield). $^1$H NMR (CDCl$_3$, 300 MHz): δ 9.81 (s, 1H), 7.87 (d, J=2.1 Hz, 1H), 7.72 (dd, J=8.5, 2.1 Hz, 1H), 7.03 (d, J=8.6 Hz, 1H), 4.20 (t, J=6.1 Hz, 2H), 3.81 (t, J=5.8 Hz, 2H), 2.07-1.99 (m, 2H), 0.84 (s, 9H), 0.01 (s, 6H); $^{13}$C NMR (CDCl$_3$, 75 MHz): δ 189.7, 159.4, 131.2, 130.5, 130.1, 124.0, 112.5, 65.9, 65.8, 59.0, 32.0, 25.9, 18.3, -5.5; HRMS-TOF (m/z): [M+H]$^+$ for C$_{16}$H$_{25}$ClO$_3$Si: 329.1334, found 329.1329.

A solution of the silyl ether (0.176 g, 0.536 mmol) in ethanol (6.00 mL) was treated with sodium borohydride (15.2 mg, 0.402 mmol) in one portion at ambient temperature then stirred overnight. The resulting mixture was then diluted with water (10 mL) and concentrated in vacuo to remove the ethanol. The resulting aqueous solution was extracted with ethyl acetate (3×50 mL) and the combined organic layers dried over sodium sulfate, filtered and concentrated to afford the desired product as an oil (0.164 g, 92.5% yield). $^1$H NMR (CDCl$_3$, 300 MHz): δ 7.34 (d, J=2.2 Hz, 1H), 7.16 (dd, J=8.3, 2.2 Hz, 1H), 6.86 (d, J=8.4 Hz, 1H), 4.57 (s, 2H), 4.09 (t, J=6.1 Hz, 2H), 3.80 (t, J=5.9 Hz, 2H), 2.03-1.95 (m, 2H), 0.84 (s, 9H), 0.01 (s, 6H); $^{13}$C NMR (CDCl$_3$, 75 MHz): δ 154.1, 133.7, 129.2, 126.5, 123.0, 113.2, 65.6, 64.5, 59.3, 32.2, 25.9, 18.5, -5.4; HRMS-TOF (m/z): [M+H]$^+$ HRMS: Calcd. for C$_{16}$H$_{27}$$^{35}$ClO$_3$Si: 331.1491, found 331.1493.

Part C—Preparation of 2-(tert-butyl)-5-((4-(3-((tert-butyldimethylsilyl)oxy)propoxy)-3-chlorobenzyl)oxy)-4-chloropyridazin-3(2H)-one

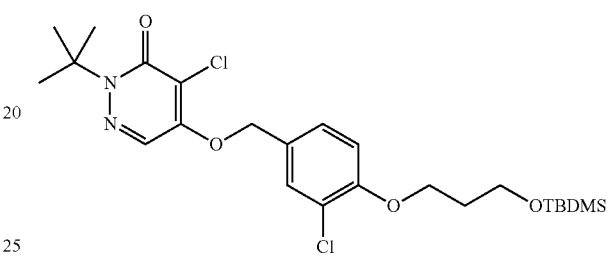

A solution of 2-(tert-butyl)-4-chloro-5-hydroxypyridazin-3(2H)-one (82.8 mg, 0.410 mmol) in tetrahydrofuran (4.90 mL) was successively treated with the product of Example 27B (0.162 g, 0.490 mmol), triphenylphosphine (0.161 g, 0.615 mmol), and diethylazodicarboxylate (0.107 g, 0.615 mmol) at ambient temperature. After 20 min, the resulting mixture was diluted with water (5 mL), the aqueous layer separated then extracted with ethyl acetate (2×50 mL). The combined organic layers were dried over sodium sulfate, filtered, and concentrated in vacuo. The crude material was then purified by silica gel chromatography (0-10% gradient ethyl acetate in hexanes) to afford the desired product as a clear oil (0.127 g, 60.1% yield). $^1$H NMR (CDCl$_3$, 300 MHz): δ 7.67 (s, 1H), 7.37 (d, J=2.2 Hz, 1H), 7.21 (dd, J=2.3, 8.5 Hz, 1H), 6.89 (d, J=8.5 Hz, 1H), 5.17 (s, 2H), 4.11 (t, J=6.1 Hz, 2H), 3.80 (t, J=5.9 Hz, 2H), 2.04-1.96 (m, 2H), 1.60 (s, 9H), 0.84 (s, 9H), 0.01 (s, 6H); $^{13}$C NMR (CDCl$_3$, 75 MHz): δ 159.0, 155.0, 153.6, 129.3, 127.6, 127.0, 125.1, 123.3, 118.5, 113.3, 71.1, 66.4, 65.6, 59.2, 32.2, 27.9, 25.9, 18.3, -5.4.

Part D—Preparation of 2-(tert-butyl)-4-chloro-5-((3-chloro-4-(3-hydroxypropoxy)benzyl)oxy)pyridazin-3(2H)-one

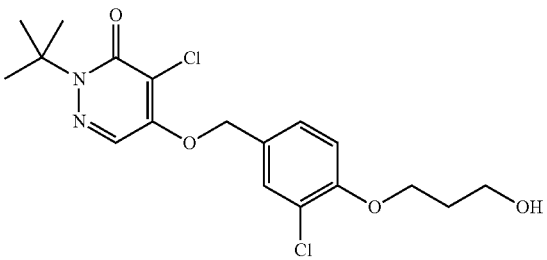 [SMILES: CC(C)(C)n1ncc(OCc2ccc(OCCCO)c(Cl)c2)c(Cl)c1=O]

A solution of the product of Example 27C (0.127 g, 0.246 mmol), in tetrahydrofuran (2.5 mL) was treated with tetrabutylammonium fluoride (0.49 mL, 0.49 mmol, of a 1 M solution in tetrahydrofuran) at ambient temperature. After 40 min, the resulting mixture was diluted with water (5 mL), the aqueous layer separated then extracted with ethyl acetate (2×20 mL). The combined organic layers were dried over sodium sulfate, filtered, and concentrated in vacuo. The crude material was then purified by silica gel chromatography (0-80% ethyl acetate in hexanes) to afford the desired product (71.6 mg, 72.5% yield). $^1$H NMR (CDCl$_3$, 300 MHz): δ 7.63 (s, 1H), 7.36 (d, J=2.2 Hz, 1H), 7.21 (dd, J=8.5, 3.0 Hz, 1H), 6.90 (d, J=8.5 Hz, 1H), 5.14 (s, 2H), 4.15 (t, J=5.8 Hz, 2H), 3.84 (t, J=5.7 Hz, 2H), 2.08-1.99 (m, 2H), 1.57 (s, 9H); $^{13}$C NMR (CDCl$_3$, 75 MHz): δ 159.0, 154.6, 153.5, 129.3, 128.1, 127.0, 125.1, 123.3, 118.6, 113.3, 71.0, 67.4, 66.5, 60.5, 31.7, 27.9; HRMS-TOF (m/z): [M+H]$^+$ for C$_{18}$H$_{22}$$^{35}$Cl$_2$N$_2$O$_4$: 401.1029, found 401.1023.

Part E—Preparation of 3-(4-(((1-(tert-butyl)-5-chloro-6-oxo-1,6-dihydropyridazin-4-yl)oxy)methyl)-2-chlorophenoxy)propyl 4-methylbenzenesulfonate

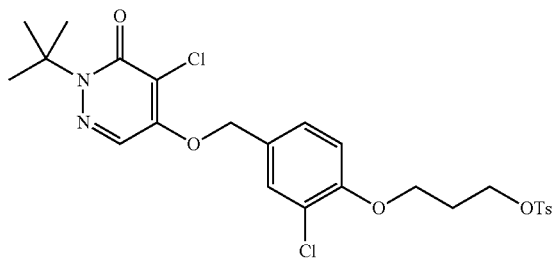 [SMILES: Cc1ccc(S(=O)(=O)OCCCOc2ccc(COc3cnn(C(C)(C)C)c(=O)c3Cl)cc2Cl)cc1]

Prepared according to General Method D, using the product of Example 27D (35.8 mg, 0.089 mmol), p-toluenesulfonyl chloride (20.5 mg, 0.107 mmol), 4-dimethylaminopyridine (16.3 mg, 0.13 mmol), and diisopropylethylamine (0.015 mL, 0.107 mmol). Isolated yield—29.8 mg; 60.3%. $^1$H (CDCl$_3$, 300 MHz): δ 7.68 (d, J=8.3 Hz, 2H), 7.65 (s, 1H), 7.31 (d, J=2.2 Hz, 2H), 7.17 (m, 1H), 7.15 (d, J=8.3 Hz, 2H), 5.13 (s, 2H), 4.22 (t, J=5.9 Hz, 2H), 3.95 (t, J=5.7 Hz, 2H), 2.27 (s, 3H), 2.14-2.07 (m, 2H), 1.57 (s, 9H); $^{13}$C (CDCl$_3$, 75 MHz): δ 159.0, 154.4, 153.5, 144.8, 132.7, 129.8, 129.4, 128.1, 127.8, 127.0, 125.0, 123.5, 118.3, 113.28, 71.0, 66.7, 66.5, 64.2, 28.8, 27.9, 21.6; HRMS-TOF (m/z): [M+H]$^+$ HRMS: Calcd. for C$_{25}$H$_{28}$$^{35}$Cl$_2$N$_2$O$_6$S: 555.1118, found 555.1138.

Example 27

Preparation of 2-(tert-butyl)-4-chloro-5-((3, 5-dichloro-4-(3-fluoropropoxy)benzyl)oxy)pyridazin-3(2H)-one Part A—Preparation of (3,5-dichloro-4-(3-fluoropropoxy)phenyl)methanol

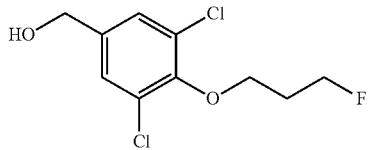 [SMILES: OCc1cc(Cl)c(OCCCF)c(Cl)c1]

Prepared according to General Method F, using 3,5-dichloro-4-hydroxybenzaldehyde (0.860 g, 4.50 mmol), 3-fluoropropyl p-toluenesulfonate (1.00 g, 4.29 mmol), and cesium carbonate (2.49 g, 7.64 mmol) in dimethylformamide (45.0 mL) at 65° C. $^1$HRMS-TOF (m/z): [M+H]$^+$ HRMS: Calcd. for C$_{10}$H$_9$Cl$_2$FO$_2$: 251.0036, found 251.0038.

A solution of the crude aldehyde (1.32 g, 5.26 mmol) in ethanol (5.26 mL) was treated with sodium borohydride (0.149 g, 3.94 mmol) in one portion at ambient temperature. After 3 d, the resulting mixture was diluted with water (20 mL) and concentrated in vacuo to remove the ethanol. The resulting aqueous solution was extracted with ethyl acetate (3×50 mL) and the combined organic layers dried over sodium sulfate, filtered and concentrated to afford the desired product as a clear oil (1.21 g, 90.9% yield). $^1$H NMR (CDCl$_3$, 300 MHz): δ 7.24 (s, 2H), 4.76 (t, J=5.8 Hz, 1H), 4.61 (t, J=5.8 Hz, 1H), 4.56 (s, 2H), 4.07 (t, J=6.0 Hz, 2H), 2.20 (m, 1H), 2.13 (m, 1H); $^{13}$C NMR (CDCl$_3$, 75 MHz): δ 150.4, 138.3, 129.5, 127.2, 81.4 (d, J$_{CF}$=165 Hz), 69.2 (d, J$_{CF}$=7.5 Hz), 63.7, 31.2 (d, J$_{CF}$=22.5 Hz).

Part B—Preparation of 2-(tert-butyl)-4-chloro-5-((3, 5-dichloro-4-(3-fluoropropoxy)benzyl)oxy)pyridazin-3(2H)-one

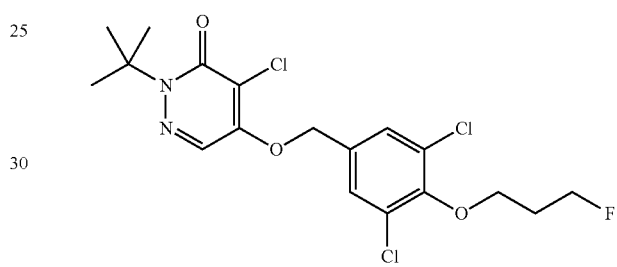

Prepared according to General Method B, using 2-(tert-butyl)-4,5-dichloropyridazin-3(2H)-one (0.195 g, 0.872 mmol), the product of Example 27A (0.138 g, 0.545 mmol), and cesium carbonate (0.213 g, 0.654 mmol) in dimethylformamide (8.50 mL) at 65° C. Isolated yield—0.192 g; 80.5% $^1$H NMR (CDCl$_3$, 300 MHz): δ 7.61 (s, 1H), 7.29 (s, 2H), 5.12 (s, 2H), 4.76 (t, J=5.8 Hz, 1H), 4.58 (t, J=5.8 Hz, 1H), 4.10 (t, J=6.0 Hz, 2H), 2.20 (m, 1H), 2.14 (m, 1H), 1.57 (s, 9H); HRMS: Calcd. for C$_{18}$H$_{20}$$^{35}$Cl$_3$FN$_2$O$_3$: 437.0596, found 437.0609.

Example 28

Preparation of 5-((3-bromo-4-(3-fluoropropoxy)-5-methoxybenzyl)oxy)-2-(tert-butyl)-4-chloropyridazin-3(2H)-one Part A—Preparation of 3-bromo-4-(3-fluoropropoxy)-5-methoxybenzaldehyde

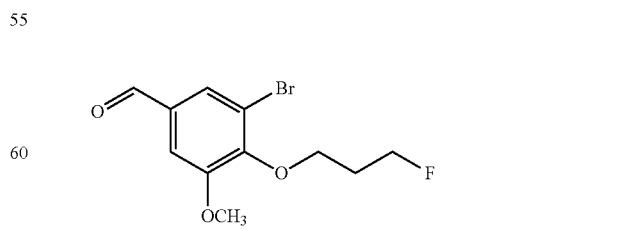

3-Bromo-4-hydroxy-5-methoxybenzaldehyde (0.578 g, 2.50 mmol), triphenylphosphine (0.820 g, 3.13 mmol) and 3-fluoropropan-1-ol (0.244 mL, 3.25 mmol) were combined in dry tetrahydrofuran (12.5 mL), then cooled to 0° C. and treated with diethyl azodicarboxylate (0.472 mL, 3.00 mmol) dropwise over 0.25 h. After 0.25 h, the resulting solution was warmed to ambient temperature and maintained an additional 0.25 h. All volatiles were then removed in vacuo and the residue directly purified by chromatography on silica (50×155 mm) using 3:1 pentane/diethyl ether. The main product peak eluting 700-1200 mL was collected, pooled and concentrated in vacuo to a colorless oil (0.555 g, 1.91 mmol; 76.3%). $^1$H NMR: (300 MHz, CDCl$_3$) δ 9.84 (1H, s), 7.65 (1H, d, J=1.8 Hz), 7.38 (1H, d, J=1.8 Hz), 4.75 (2H, dt, J=47.0, 5.8 Hz), 4.24 (2H, t, J=6.0 Hz), 3.92 (3H, s), 2.19 (2H, dtt, J=25.7, 5.9, 5.9 Hz). $^{13}$C NMR: (75 MHz, CDCl$_3$) δ 189.8, 154.1, 150.8, 133.0, 128.8, 118.0, 110.0, 80.8 (d, $J_{CF}$=164 Hz), 69.2 (d $J_{CF}$=5.4 Hz), 56.2, 31.3 (d, $J_{CF}$=20.2 Hz). 19F NMR (282 MHz, CDCl$_3$) δ -222.0 (tt, J=46.9, 25.7 Hz). HRMS Calcd. for $C_{11}H_{12}^{79}BrFO_3$ (M+H): 291.1027; found: 291.0030. TLC: R$_f$ 0.26 (silica gel, 3:1 pentane/diethyl ether, KMnO$_4$).

Part B—Preparation of 5-((3-bromo-4-(3-fluoropropoxy)-5-methoxybenzyl)oxy)-2-(tert-butyl)-4-chloropyridazin-3(2H)-one

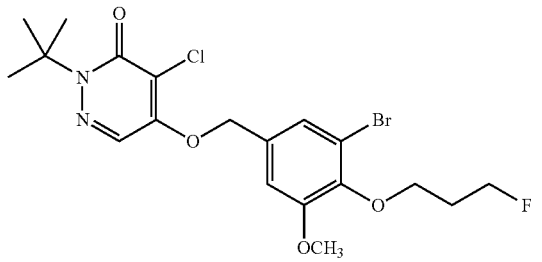 [SMILES: COc1cc(COc2cnn(C(C)(C)C)c(=O)c2Cl)cc(Br)c1OCCCF]

A solution of the product of part A (0.146 g, 0.500 mmol) in wet methanol (5.00 mL) was cooled to 0° C. then treated with sodium borohydride (37.8 mg, 1.00 mmol) in one portion. After 0.25 h, excess sodium borohydride was consumed by the dropwise addition of saturated aqueous ammonium chloride (2 mL), and the resulting solution warmed to ambient temperature. After 0.5 h, the resulting mixture was partitioned between ethyl acetate and saturated aqueous sodium bicarbonate (25 mL each), with transfer to a separatory funnel, and the layers separated. The aqueous layer was then washed with ethyl acetate (2×25 mL), and the combined ethyl acetate washes dried over magnesium sulfate, filtered and concentrated in vacuo to a colorless oil.

The crude oil thus obtained was dissolved in dry dimethylformamide (5.00 mL) then successively treated with 2-(tert-butyl)-4,5-dichloro-2-hydropyridazin-3-one$^3$ (0.166 g, 0.750 mmol) and cesium carbonate (0.326, 1.00 mmol) in one portion at ambient temperature. The resulting suspension was then immersed in a pre-heated oil bath, and maintained at 65° C., with vigorous stirring, 21 h. After cooling to ambient temperature, the suspension was partitioned between ethyl acetate and water (20 mL each), with transfer to a separatory funnel, and the layers separated. The aqueous layer was then washed with ethyl acetate (2×20 mL) and the combined ethyl acetate washes dried over magnesium sulfate, filtered and concentrated in vacuo to an amber oil. The crude material was then purified by chromatography on silica (30×180 mm) using 7:3 pentane/ethyl acetate. The main product peak eluting 200-350 mL was collected, pooled and concentrated in vacuo to a white solid (0.191 g, 0.400 mmol; 79.9%). $^1$H NMR: (300 MHz, CDCl$_3$) δ 7.71 (1H, s), 7.15 (1H, d, J=1.9 Hz), 6.92 (1H, d, J=2.0 Hz), 5.21 (2H, s), 4.74 (2H, dt, J=47.1, 5.9 Hz), 4.13 (2H, t, J=6.0 Hz), 3.86 (3H, s), 2.17 (2H, dtt, J=25.5, 6.0, 6.0 Hz), 1.64 (9H, s). $^{13}$C NMR: (75 MHz, CDCl$_3$) δ 158.9, 154.1, 153.4, 145.8, 131.9, 125.0, 123.2, 118.6, 118.0, 110.2, 81.0 (d, $J_{CF}$=164 Hz), 71.0, 68.9 (d, $J_{CF}$=5.5 Hz), 66.5, 56.1, 31.3 (d, $J_{CF}$=20.2 Hz), 27.8. HRMS Calcd. for $C_{19}H_{23}^{79}Br^{35}ClN_2O_4$ (M+H): 477.0587; found: 477.0589. TLC: R$_f$ 0.15 (silica gel, 4:1 pentane/ethyl acetate, CAM).

Example 29

Preparation of 2-(tert-butyl)-4-chloro-5-((2-chloro-4-(3-fluoropropoxy)benzyl)oxy)pyridazin-3(2H)-one Part A—Preparation of (2-chloro-4-(3-fluoropropoxy)phenyl)methanol

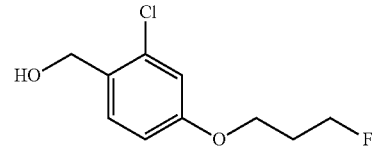 [SMILES: OCc1ccc(OCCCF)cc1Cl]

Prepared according to General Method F, using methyl 2-chloro-4-hydroxybenzoate (0.354 g, 2.26 mmol), 3-fluoropropyl p-toluenesulfonate (0.500 g, 2.15 mmol), and cesium carbonate (1.12 g, 3.44 mmol) in dimethylformamide (22.6 mL) at 60° C. Isolated yield—0.510 g). $^1$H NMR (CDCl$_3$, 300 MHz): δ 7.81 (d, J=8.9 Hz, 1H), 6.90 (d, J=2.5 Hz, 1H), 6.75 (dd, J=8.8, 2.5 Hz, 1H), 4.64 (t, J=5.7 Hz, 1H), 4.49 (t, J=5.8 Hz, 1H), 4.07 (t, J=6.1 Hz, 2H), 3.82 (s, 3H), 2.16 (m, 1H), 2.09 (m, 1H); $^{13}$C NMR (CDCl$_3$, 75 MHz): δ 165.5, 161.7, 135.9, 133.4, 121.8, 117.0, 112.9, 80.3 (d, $J_{CF}$=165 Hz), 64.1 (d, $J_{CF}$=7.5 Hz), 52.1, 30.2 (d, $J_{CF}$=22.5 Hz).

A solution of the alcohol (0.510 g, 2.35 mmol) in ethanol (23.5 mL) was treated with sodium borohydride (66.7 mg, 1.76 mmol) in one portion at ambient temperature then stirred overnight. The resulting mixture was diluted with water (20 mL) and concentrated in vacuo to remove the ethanol. The resulting aqueous solution was extracted with ethyl acetate (3×50 mL) and the combined organic layers dried over sodium sulfate, filtered and concentrated to afford the desired product as a clear oil (0.388 g, 78.5% yield). $^1$H NMR (CDCl$_3$, 300 MHz): δ 7.80 (d, J=8.8 Hz, 1H), 6.90 (d, J=2.6 Hz, 1H), 6.75 (dd, J=8.8, 2.5 Hz, 1H), 4.64 (t, J=6.4 Hz, 1H), 4.65 (s, 2H), 4.49 (t, J=5.8 Hz, 1H), 4.07 (t, J=6.2 Hz, 2H), 2.16 (m, 1H), 2.09 (m, 1H); $^{13}$C NMR (CDCl$_3$, 75 MHz): δ 158.9, 135.8, 133.3, 130.1, 117.0, 112.8, 80.3 (d, $J_{CF}$=165 Hz), 64.1 (d, $J_{CF}$=7.5 Hz), 61.1, 30.2 (d, $J_{CF}$=22.5 Hz); $^1$HRMS-TOF (m/z): [M–H]$^+$ HRMS: Calcd. for $C_{10}H_{12}^{35}ClFO_2$: 217.0437, found 217.0453.

Part B—Preparation of 2-(tert-butyl)-4-chloro-5-((2-chloro-4-(3-fluoropropoxy) benzyl) oxy) pyridazin-3(2H)-one

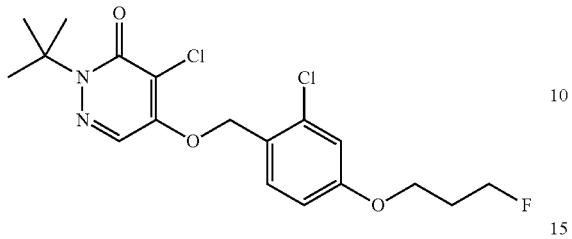

Prepared according to General Method B, using 2-(tert-butyl)-4,5-dichloropyridrazin-3(2H)-one (0.358 g, 1.62 mmol), the product of Example 29A, (0.388 g, 1.78 mmol), and cesium carbonate (0.845 g, 2.59 mmol) in dimethylformamide (16.2 mL) at 60° C. Isolated yield—0.251 g; 38.4% yield. $^1$H NMR (CDCl$_3$, 300 MHz): δ 7.67 (s, 1H), 7.35 (d, J=8.6 Hz, 1H), 6.91 (d, J=2.5 Hz, 1H), 6.79 (dd, J=8.7, 2.5 Hz, 1H), 5.26 (s, 2H), 4.65 (t, J=5.7 Hz, 1H), 4.49 (t, J=5.7 Hz, 1H), 4.04 (t, J=6.3 Hz, 2H), 2.15 (m, 1H), 2.06 (m, 1H), 1.57 (s, 9H); $^{13}$C NMR (CDCl$_3$, 75 MHz): δ 159.7, 153.6, 133.7, 130.1, 125.2, 124.7, 118.5, 115.8, 113.7, 80.3 (d, J$_{CF}$=165 Hz), 68.9, 66.4, 64.0 (d, J$_{CF}$=7.5 Hz), 30.4, 30.1, 27.9; HRMS-TOF (m/z): [M+H]$^+$ HRMS: Calcd. for C$_{18}$H$_{21}$$^{35}$Cl$_2$FN$_2$O$_3$: 403.0986, found 403.0994.

Example 30

Preparation of 2-(tert-butyl)-4-chloro-5-((4-(3-fluoropropoxy)-2-methylbenzyl)oxy)pyridazin-3(2H)-one Part A—Preparation of (4-(3-fluoropropoxy)-2-methylphenyl)methanol

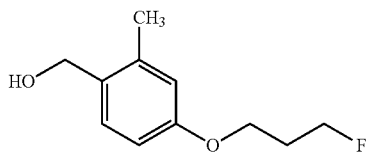

Prepared according to General Method F, using 4-hydroxy-2-methylbenzaldehyde (0.614 g, 4.50 mmol), 3-fluoropropyl p-toluenesulfonate (1.00 g, 4.29 mmol), and cesium carbonate (2.49 g, 7.64 mmol) in dimethylformamide (45.0 mL) at 60° C. $^1$H NMR (CDCl$_3$, 300 MHz): δ 10.13 (s, 1H), 7.77 (d, J=8.6 Hz, 1H), 6.86 (dd, J=8.6, 4.6 Hz, 1H), 6.77 (d, J =2.3 Hz, 1H), 4.75 (t, J=5.7 Hz, 1H), 4.59 (t, J=5.7 Hz, 1H), 4.18 (t, J=6.1 Hz, 2H), 2.66 (s, 3H), 2.27 (m, 1H), 2.15 (m, 1H); HRMS-TOF (m/z): [M+H]$^+$ HRMS: Calcd. for C$_{11}$H$_{13}$FO$_2$: 197.0976, found 197.0972.

A cooled (0° C.) solution of 4-(3-fluoropropoxy)-2-methylbenzaldehyde (0.840 g, 4.28 mmol) in tetrahydrofuran (42.8 mL) was treated with lithium aluminum hydride (2.14 mL, 2.14 mmol, of 1 M tetrahydrofuran solution) then warmed to ambient temperature. The resulting mixture was stirred overnight then diluted with water (20 mL). The aqueous layer was then separated and extracted with ethyl acetate (3×50 mL). The combined organic layers were dried over sodium sulfate, filtered and concentrated to a dark orange oil (0.800 g, 94.3% yield). $^1$H NMR (CDCl$_3$, 300 MHz): δ 7.24 (m, 1H), 6.73 (m, 2H), 4.72 (t, J=5.8 Hz, 1H), 4.63 (s, 2H), 4.56 (t, J=5.8 Hz, 1H), 4.09 (t, J=6.0 Hz, 2H), 2.36 (s, 3H), 2.20 (m, 1H), 2.10 (m, 1H).

Part B—Preparation of 2-(tert-butyl)-4-chloro-5-((4-(3-fluoropropoxy)-2-methylbenzyl) oxy) pyridazin-3(2H)-one

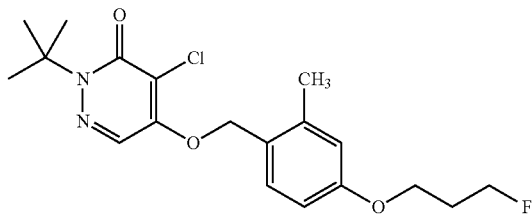 [SMILES: Cc1cc(OCCCF)ccc1COc1cnn(C(C)(C)C)c(=O)c1Cl]

Prepared according to General Method B, using 2-(tert-butyl)-4,5-dichloropyridrazin-3(2H)-one (0.480 g, 2.37 mmol), the product of Example 30A, (0.940 g, 4.74 mmol), and cesium carbonate (1.70 g, 5.28 mmol) in dimethylformamide (24.0 mL) at 65° C. overnight. Isolated yield—38.6 mg; 4.3% yield. $^1$H NMR (CDCl$_3$, 300 MHz): δ 7.50 (s, 1H), 7.19 (m, 1H), 6.66 (m, 2H), 5.09 (s, 2H), 4.64 (m, 1H), 4.48 (m, 1H), 4.02 (t, J=6.2 Hz, 2H), 2.27 (s, 3H), 2.14 (m, 1H), 2.03 (m, 1H), 1.57 (s, 9H); HRMS-TOF (m/z): [M+H]$^+$ HRMS: Calcd. for C$_{19}$H$_{24}$$^{35}$ClFN$_2$O$_3$: 386.1532, found 383.1537.

Example 31

Preparation of 2-(tert-butyl)-4-chloro-5-((4-((2-fluoroethoxy)methyl)-2-methoxybenzyl)oxy)pyridazin-3(2H)-one Part A—Preparation of methyl 4-(((1-(tert-butyl)-5-chloro-6-oxo-1,6-dihydropyridazin-4-yl)oxy)methyl)-3-methoxybenzoate

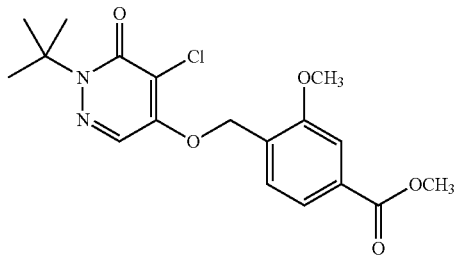 [SMILES: COC(=O)c1ccc(COc2cnn(C(C)(C)C)c(=O)c2Cl)c(OC)c1]

Prepared according to General Method B, using 2-(tert-butyl)-4-chloro-5-hydroxypyridrazin-3(2H)-one (0.617 g, 3.05 mmol), methyl 4-(bromomethyl)-3-methoxybenzoate (0.750 g, 2.91 mmol), and cesium carbonate (1.51 g, 4.64 mmol) in dimethylformamide (15.0 mL) at ambient temperature. Isolated yield—1.11 g; >98%. 1H NMR (CDCl$_3$, 300 MHz): δ 7.65 (s, 1H), 7.63 (dd, J=7.9, 1.4 Hz, 1H), 7.51 (d, J=1.4 Hz, 1H), 7.44 (d, J=7.9 Hz, 1H), 5.30 (s, 2H), 3.90 (s, 3H), 3.86 (s, 3H), 1.57 (s, 9H); $^{13}$C NMR (CDCl$_3$, 75 MHz): δ 166.6, 159.0, 156.3, 153.7, 131.6, 128.4, 127.7, 125.0, 122.4, 118.2, 111.1, 66.7, 66.4, 55.7, 52.3, 27.9; HRMS-TOF (m/z): [M+H]$^+$ HRMS: Calcd. for $C_{18}H_{21}{}^{35}ClN_2O_5$: 381.1212, found 381.1206.

Part B—Preparation of 2-(tert-butyl)-4-chloro-5-((4-(hydroxymethyl)-2-methoxybenzyl)oxy)pyridazin-3(2H)-one

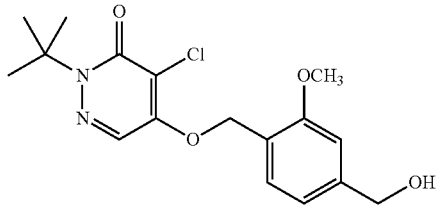 [SMILES: COc1cc(CO)ccc1COc1cnn(C(C)(C)C)c(=O)c1Cl]

A solution of the product of Example 31A (1.11 g, 2.92 mmol), in tetrahydrofuran (29.0 mL) at 0° C. was treated with lithium aluminum hydride (1.46 mL, 1.46 mmol, 1 M solution in tetrahydrofuran) then warmed to ambient temperature. The resulting mixture was stirred overnight then diluted with water (50 mL). The aqueous layer was separated then extracted with ethyl acetate (3×50 mL). The combined organic layers were dried over sodium sulfate, filtered and concentrated to an amorphous orange solid (0.890 g, 86.4% yield). $^1$H NMR (CDCl$_3$, 300 MHz): δ 7.68 (s, 1H), 7.31 (d, J=7.5 Hz, 1H), 7.89 (m, 2H), 5.27 (s, 2H), 4.64 (s, 2H), 3.85 (s, 3H), 1.56 (s, 9H); $^{13}$C NMR (CDCl$_3$, 75 MHz): δ 159.1, 156.9, 153.9, 143.2, 128.7, 125.4, 122.5, 119.1, 118.0, 109.1, 67.0, 66.3, 65.1, 55.5, 27.9; HRMS-TOF (m/z): [M+H]$^+$ HRMS: Calcd. for $C_{17}H_{21}{}^{35}ClN_2O_4$: 353.1263, found 353.1257.

Part C—Preparation of 5-((4-(bromomethyl)-2-methoxybenzyl)oxy)-2-(tert-butyl)-4-chloro-pyridazin-3(2H)-one

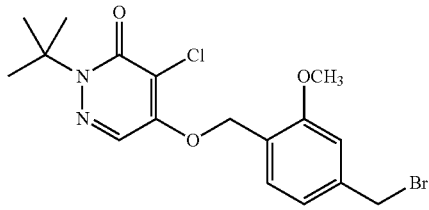 [SMILES: COc1cc(CBr)ccc1COc1cnn(C(C)(C)C)c(=O)c1Cl]

Prepared according to General Method C, using the product of Example 31B (0.448 g, 1.26 mmol) and phosphorous tribromide (0.631 mL, 0.63 mmol, 1 M in dichloromethane). Isolated yield—0.429 g; 81.9%. $^1$H NMR (CDCl$_3$, 300 MHz): δ 7.67 (s, 1H), 7.32 (d, J=7.7 Hz, 1H), 6.98 (dd, J=7.7, 1.6 Hz, 1H), 6.88 (d, J=1.5 Hz, 1H), 5.25 (s, 2H), 4.42 (s, 2H), 3.82 (s, 3H), 1.57 (s, 9H); $^{13}$C NMR (CDCl$_3$, 75 MHz): δ 159.1, 156.7, 153.8, 139.6, 128.7, 125.2, 123.7, 121.5, 118.1, 111.1, 66.8, 66.3, 55.6, 33.1, 27.9; HRMS-TOF (m/z): [M+H]$^+$ HRMS: Calcd. for $C_{17}H_{20}{}^{79}Br^{35}ClN_2O_3$: 415.0419, found 415.0416.

Part D—Preparation of 2-(tert-butyl)-4-chloro-5-((4-((2-fluoroethoxy)methyl)-2-methoxybenzyl)oxy)pyridazin-3(2H)-one

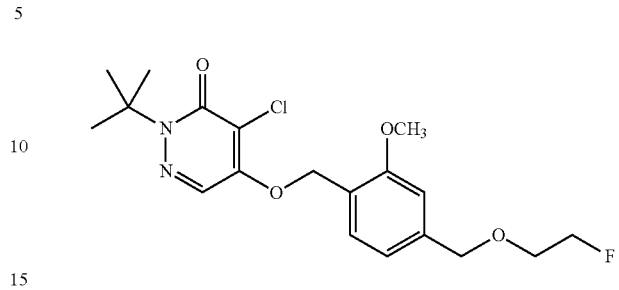

Prepared according to General Method E, using potassium tert-butoxide (38 mg, 0.340 mmol), 2-fluoroethanol (14.5 mg, 0.226 mmol) and the product of Example 31C (0.112 g, 0.271 mmol). Isolated yield—2.3 mg; 2.6%. $^1$H NMR (CDCl$_3$, 300 MHz): δ 7.68 (s, 1H), 7.30 (d, J=7.5 Hz, 1H), 6.9 (s, 1H), 6.88 (d, J=8.0 Hz, 1H), 5.27 (s, 2H), 4.62 (m, 1H), 4.53 (s, 2H), 4.46 (m, 1H), 3.82 (s, 3H), 3.73 (m, 1H), 3.63 (m, 1H), 1.56 (s, 9H); $^{13}$C NMR (CDCl$_3$, 75 MHz): δ 158.1, 155.8, 152.9, 139.1, 127.5, 124.3, 121.7, 119.0, 117.0, 108.6, 82.1 (d, $J_{CF}$=165 Hz), 72.0, 68.5 (d, $J_{CF}$=22.5 Hz), 65.9, 65.3, 54.5, 26.9; HRMS-TOF (m/z): [M+H]$^+$ HRMS: Calcd. for $C_{19}H_{24}{}^{35}ClFN_2O_3$: 399.1481, found 399.1479.

Example 32

Preparation of 2-(tert-butyl)-4-chloro-5-((3-(3-fluoropropoxy)benzyl)oxy)pyridazin-3(2H)-one Part A—Preparation of (3-(3-fluoropropoxy)phenyl)methanol

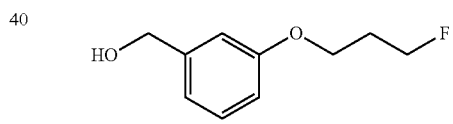

Prepared according to General Method F, using 3-hydroxybenzaldehyde (0.552 g, 4.52 mmol), 3-fluoropropyl p-toluenesulfonate (0.998 g, 4.30 mmol), and cesium carbonate (2.24 g, 6.90 mmol) in dimethylformamide (45.2 mL) at 60° C. Isolated yield—0.700 g; 89.4%. $^1$H NMR (CDCl$_3$, 300 MHz): δ 9.91 (s, 1H), 7.40-7.37 (m, 2H), 7.34 (m, 1H), 7.11 (m, 1H), 4.66 (t, J=5.8 Hz, 1H), 4.52 (t, J=5.7 Hz, 1H), 4.10 (t, J=6.1 Hz, 2H), 2.17 (m, 1H), 2.09 (m, 1H); $^{13}$C NMR (CDCl$_3$, 75 MHz): δ 192.0, 159.4, 137.9, 130.1, 123.6, 121.8, 113.0, 80.5 (d, $J_{CF}$=165 Hz), 63.9 (d, $J_{CF}$=7.5 Hz), 30.3 (d, $J_{CF}$=22.5 Hz). HRMS-TOF (m/z): [M+H]$^+$ HRMS: Calcd. for $C_{10}H_{11}FO_2$: 183.0816, found 183.0827.

A cooled (0° C.) solution of 3-(3-fluoropropoxy) benzaldehyde (0.700 g, 3.82 mmol) dissolved in ethanol (38 mL) was treated with sodium borohydride (72.3 mg, 1.91 mmol) then warmed to ambient temperature. After 2 h, the resulting mixture was diluted with water (20 mL) and concentrated in vacuo to remove the ethanol. The resulting aqueous solution was extracted with ethyl acetate (3×50 mL) and the combined organic layers dried over sodium sulfate, filtered and concentrated to afford the desired product as a yellow oil (0.625 g, 88.8% yield). $^1$H NMR (CDCl$_3$, 300 MHz): δ 7.20

(m, 1H), 6.87 (m, 2H), 6.76 (dd, J=8.3, 2.1 Hz, 1H), 4.65 (t, J=5.8 Hz, 1H), 4.60 (s, 2H), 4.50 (t, J=5.8 Hz, 1H), 4.04 (t, J=6.1 Hz, 2H), 2.14 (m, 1H), 2.04 (m, 1H); $^{13}$C NMR (CDCl$_3$, 75 MHz): δ 159.1, 142.6, 129.6, 119.3, 113.8, 113.0, 80.7 (d, J$_{CF}$=165 Hz), 65.2, 63.5 (d, J$_{CF}$=7.5 Hz), 30.6 (d, J$_{CF}$=22.5 Hz). $^1$HRMS-TOF (m/z): [M+H]$^+$ HRMS: Calcd. for C$_{10}$H$_{13}$FO$_2$: 185.0972, found 186.0967.

Part B—Preparation of 2-(tert-butyl)-4-chloro-5-((3-(3-fluoropropoxy)benzyl)oxy)pyridazin-3(2H)-one

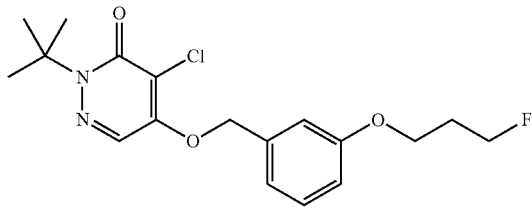 [SMILES: CC(C)(C)n1ncc(OCc2cccc(OCCCF)c2)c(Cl)c1=O]

Prepared according to General Method B, using of 2-(tert-butyl)-4,5-dichloropyridrazin-3(2H)-one (0.339 g, 1.53 mmol), the product of Example 32A (0.313 g, 1.69 mmol), and cesium carbonate (0.798 g, 2.45 mmol) in dimethylformamide (17.0 mL) at 60° C. Isolated yield—0.122 g, 21.6% yield. $^1$H NMR (CDCl$_3$, 300 MHz): δ 7.63 (s, 1H), 7.25 (m, 1H), 6.92-6.81 (m, 3H), 5.21 (s, 2H), 4.66 (t, J=5.8 Hz, 1H), 4.50 (t, J=5.8 Hz, 1H), 4.04 (t, J=6.1 Hz, 2H), 2.15 (m, 1H), 2.07 (m, 1H), 1.57 (s, 9H); (CDCl$_3$, 75 MHz): δ 159.3, 159.0, 153.7, 136.5, 130.1, 125.1, 119.3, 118.4, 114.7, 113.9, 80.6 (d, J$_{CF}$=165 Hz), 71.7, 66.4, 63.6 (d, J$_{CF}$=7.5 Hz), 30.4 (d, J$_{CF}$=22.5 Hz), 27.9; HRMS-TOF (m/z): [M+H]$^+$ HRMS: Calcd. for C$_{18}$H$_{22}$$^{35}$ClFN$_2$O$_3$: 369.1376, found 369.1379.

Example 33

Preparation of 2-(tert-butyl)-4-chloro-5-((3-(2-fluoroethoxy)benzyl)oxy)pyridazin-3(2H)-one Part A—Preparation of (3-(2-fluoroethoxy)phenyl)methanol

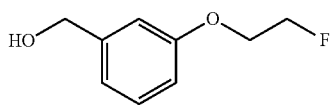 [SMILES: OCc1cccc(OCCF)c1]

A suspension of 3-hydroxybenzaldehyde (1.02 g, 8.33 mmol), 1-bromo-2-fluoroethane (1.00 g, 7.93 mmol), and cesium carbonate (4.13 g, 12.7 mmol) in dimethylformamide (83.0 mL) was heated to 60° C. and maintained overnight. After cooling to ambient temperature, the resulting mixture was diluted with water (100 mL), and the aqueous layer extracted with ethyl acetate (3×150 mL). The combined organic layers were washed with water (150 mL) and saturated aqueous sodium chloride (150 mL) then dried over sodium sulfate, filtered and concentrated to an orange oil (1.34 g). $^1$H NMR (CDCl$_3$, 300 MHz): δ 9.91 (s, 1H), 7.44-7.33 (m, 3H), 7.19-7.13 (m, 1H), 4.79 (m, 1H), 4.63 (m, 1H), 4.26 (m, 1H), 4.17 (m, 1H); $^{13}$C NMR (CDCl$_3$, 75 MHz): δ 192.0, 159.0, 137.9, 130.2, 124.1, 122.2, 112.7, 81.9 (d, J$_{CF}$=165 Hz), 67.4 (d, J$_{CF}$=22.5 Hz); $^1$HRMS-TOF (m/z): [M+H]$^+$ HRMS: Calcd. for C$_9$H$_9$FO$_2$: 169.0659, found 169.0660.

A cooled (0° C.) solution of the aldehyde (1.34 g) in ethanol (39.5 mL) was treated with sodium borohydride (0.150 g, 3.97 mmol) in one portion then warmed to ambient temperature. After 2 h, the resulting mixture was diluted with water (20 mL) and concentrated in vacuo to remove the ethanol. The resulting aqueous solution was extracted with ethyl acetate (3×50 mL) and the combined organic layers dried over sodium sulfate, filtered and concentrated to afford the desired product as a yellow oil (1.28 g, 94.8% yield). $^1$H NMR (CDCl$_3$, 300 MHz): δ 7.20 (m, 1H), 6.89 (m, 2H), 6.78 (m, 1H), 4.75 (m, 1H), 4.60 (s, 2H), 4.59 (m, 1H), 4.20 (m, 1H), 4.10 (m, 1H); $^{13}$C NMR (CDCl$_3$, 75 MHz): δ 158.7, 142.7, 129.7, 119.7, 114.0, 113.0, 81.9 (d, J$_{CF}$=165 Hz), 67.2 (d, J$_{CF}$=22.5 Hz), 65.2; $^1$HRMS-TOF (m/z): [M+H]$^+$ HRMS: Calcd. for C$_9$H$_{11}$FO$_2$: 171.0816, found 171.0815.

Part B—Preparation of 2-(tert-butyl)-4-chloro-5-((3-(2-fluoroethoxy)benzyl)oxy)pyridazin-3(2H)-one

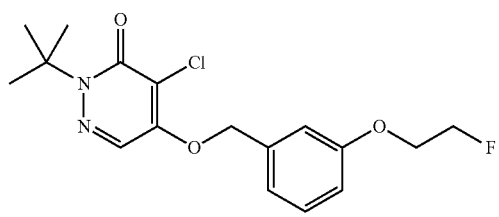 [SMILES: CC(C)(C)n1ncc(OCc2cccc(OCCF)c2)c(Cl)c1=O]

Prepared according to General Method B, using 2-(tert-butyl)-4,5-dichloropyridrazin-3(2H)-one (0.587 g, 2.66 mmol), the product of Example 33A, (0.500 g, 2.92 mmol), and cesium carbonate (1.38 g, 4.25 mmol) in dimethylformamide (26.6 mL) at 60° C. Isolated yield—20 mg, 2.1% yield. $^1$H NMR (CDCl$_3$, 300 MHz): δ 7.63 (s, 1H), 7.26 (m, 1H), 6.95-6.84 (m, 3H), 5.22 (s, 2H), 4.78 (m, 1H), 4.62 (m, 1H), 4.21 (m, 1H), 4.11 (m, 1H), 1.56 (s, 9H). $^{13}$C NMR (CDCl$_3$, 75 MHz): δ 159.0, 158.9, 153.6, 136.6, 130.2, 125.1, 119.3, 114.9, 114.8, 113.2, 81.9 (d, J$_{CF}$=7.5 Hz), 71.6, 67.2 (d, J$_{CF}$=22.5 Hz), 66.4, 27.9. HRMS-TOF (m/z): [M+H]$^+$ HRMS: Calcd. for C$_{17}$H$_{20}$$^{35}$ClFN$_2$O$_3$: 355.1219, found 355.1218.

Example 34

Preparation of 2-(3-(((1-(tert-butyl)-5-chloro-6-oxo-1,6-dihydropyridazin-4-yl)oxy)methyl)phenoxy)ethyl 4-methylbenzenesulfonate Part A—Preparation of 3-(2-hydroxyethoxy)benzaldehyde

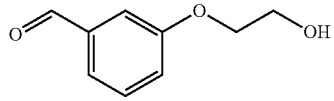 [SMILES: O=Cc1cccc(OCCO)c1]

A suspension of 3-hydroxybenzaldehyde (1.02 g, 8.33 mmol), 1-bromoethanol (0.991 g, 7.93 mmol), and cesium carbonate (4.13 g, 12.7 mmol) in dimethylformamide (20.0 mL) was heated to 60° C. and maintained overnight. After cooling to ambient temperature, the resulting mixture was diluted with water (50 mL), and the aqueous layer extracted with ethyl acetate (3×50 mL). The combined organic layers were washed with water (150 mL) and saturated aqueous sodium chloride then dried over sodium sulfate, filtered and concentrated to yield a yellow oil. The crude material was then purified by silica gel chromatography 4:1 hexanes/ethyl acetate to afford the desired product as a white solid (1.38 g, >98% yield). $^1$H NMR (CDCl$_3$, 300 MHz): δ 9.98 (s, 1H), 7.48-7.41 (m, 3H), 7.23-7.19 (m, 1H), 4.16 (m, 2H), 4.00 (m, 2H); HRMS-TOF (m/z): [M+H]$^+$ HRMS: Calcd. for C$_9$H$_{10}$O$_3$: 167.0703, found 167.0696.

Part B—Preparation of (3-(2-((tert-butyldimethylsilyl)oxy)ethoxy)phenyl)methanol

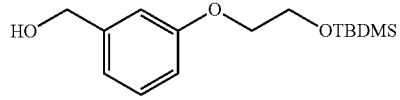 [SMILES: CC(C)(C)[Si](C)(C)OCCOc1cccc(CO)c1]

A solution of the product of Example 34A (1.38 g), in dimethylformamide (8.3 mL) was successively treated with tert-butyldimethylsilyl chloride (1.88 g, 12.5 mmol) and imidazole (0.850 g, 12.5 mmol) then stirred at ambient temperature overnight. The resulting mixture was then diluted with water (50 mL) and extracted with ethyl acetate (3×100 mL). The combined organic layers were washed with saturated aqueous sodium chloride, dried over sodium sulfate, filtered, and concentrated in vacuo to a yellow oil (0.597 g, 26.8% yield). $^1$H NMR (CDCl$_3$, 300 MHz): δ 9.87 (s, 1H), 7.35-7.29 (m, 3H), 7.11-7.08 (m, 1H), 4.00 (m, 2H), 3.89 (m, 2H), 0.84 (s, 9H), 0.01 (s, 6H); $^{13}$C NMR (CDCl$_3$, 75 MHz): δ 189.7, 159.4, 137.8, 130.0, 123.5, 122.0, 113.0, 69.6, 61.9, 25.6, 18.4, −5.2; HRMS-TOF (m/z): [M +H]$^+$ for C$_{15}$H$_{24}$O$_3$Si: 281.1567, found 281.1563.

A solution of the silyl ether (0.597 g, 2.13 mmol) in ethanol (21.0 mL) was treated with sodium borohydride (60.4 mg, 1.60 mmol) in one portion at ambient temperature. After 3 h, the resulting mixture was diluted with water (10 mL) and concentrated in vacuo to remove the ethanol. The resulting aqueous solution was extracted with ethyl acetate (3×50 mL) and the combined organic layers dried over sodium sulfate, filtered and concentrated to afford the desired product as a milky white oil (0.600 g, >98% yield). $^1$H NMR (CDCl$_3$, 300 MHz): δ7.16 (m, 1H), 6.84 (m, 2H), 6.74 (dd, J=9.0, 2.5 Hz, 1H), 4.57 (s, 2H), 3.94 (m, 2H), 3.87 (m, 2H), 0.81 (s, 9H), 0.01 (s, 6H); $^{13}$C NMR (CDCl$_3$, 75 MHz): δ 159.3, 142.5, 129.6, 119.1, 114.0, 113.0, 69.3, 65.3, 62.0, 25.6, 18.4, −5.2; HRMS-TOF (m/z): [M+H]$^+$ HRMS: Calcd. for C$_{15}$H$_{26}$O$_3$Si: 283.1724, found 283.1717.

Part C—Preparation of 2-(tert-butyl)-5-((3-(2-((tert-butyldimethylsilyl)oxy)ethoxy)benzyl)oxy)-4-chloropyridazin-3(2H)-one

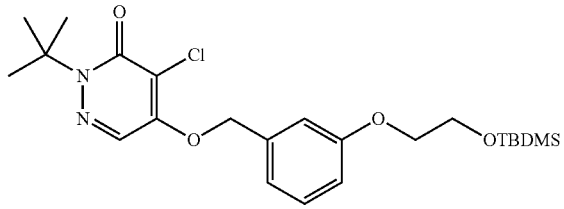 [SMILES: CC(C)(C)n1ncc(OCc2cccc(OCCO[Si](C)(C)C(C)(C)C)c2)c(Cl)c1=O]

Prepared according to General Method B, using 2-(tert-butyl)-4,5-dichloropyridazin-3(2H)-one (0.711 g, 3.19 mmol), the product of Example 34B (0.600 g, 2.13 mmol), and cesium carbonate (0.834 g, 2.56 mmol) in dimethylformamide (32.0 mL) at 60° C. Isolated yield—0.159 g, 16.0% yield. $^1$H NMR (CDCl$_3$, 300 MHz): δ 7.62 (s, 1H), 7.21 (m, 1H), 6.82-6.79 (m, 3H), 5.19 (s, 2H), 3.95 (m, 2H), 3.88 (m, 2H), 1.53 (s, 9H), 0.80 (s, 9H), −0.01 (s, 6H); $^{13}$C NMR (CDCl$_3$, 75 MHz): δ 159.5, 159.0, 153.7, 136.5, 130.0, 125.1, 119.1, 118.2, 114.8, 113.2, 71.7, 69.4, 66.4, 62.0, 27.9, 25.9, 18.4, −5.2; HRMS-TOF (m/z): [M+H]$^+$ HRMS: Calcd. for C$_{23}$H$_{35}$$^{35}$ClN$_2$O$_4$Si: 467.2127, found 467.2129.

Part D—Preparation of 2-(tert-butyl)-4-chloro-5-((3-(2-hydroxyethoxy)benzyl)oxy)pyridazin-3(2H)-one

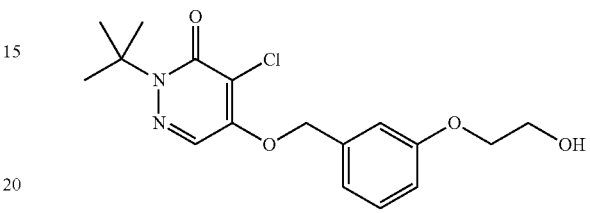

A solution of the product of Example 34C (0.140 g, 0.300 mmol), in tetrahydrofuran (3.0 mL) was treated with tetrabutylammonium fluoride (0.60 mL, 0.60 mmol, of 1 M solution in tetrahydrofuran) at ambient temperature. After 1 h, the resulting mixture was diluted with water (10 mL), the aqueous layer separated then extracted with ethyl acetate (2×20 mL). The combined organic layers were dried over sodium sulfate, filtered, and concentrated in vacuo. The crude material was then purified by silica gel chromatography (20-50% ethyl acetate in hexanes) to afford the desired product (0.105 g, >98% yield). 1H NMR (CDCl$_3$, 300 MHz): δ 7.57 (s, 1H), 7.16 (m, 1H), 6.83 (m, 2H), 6.76 (dd, J=7.5, 2.0 Hz, 1H), 5.13 (s, 2H), 3.95 (m, 2H), 3.82 (m, 2H), 1.47 (s, 9H); $^{13}$C NMR (CDCl$_3$, 75 MHz): δ 159.1, 159.0, 153.6, 153.6, 130.0, 125.0, 119.3, 118.2, 114.6, 113.1, 71.5, 69.2, 66.4, 61.2, 27.8; HRMS-TOF (m/z): [M+H]$^+$ HRMS: Calcd. for C$_{17}$H$_{21}$$^{35}$ClN$_2$O$_4$: 353.1263, found 353.1259.

Part E—Preparation of 2-(3-(((1-(tert-butyl)-5-chloro-6-oxo-1,6-dihydropyridazin-4-yl)oxy)methyl)phenoxy)ethyl 4-methylbenzenesulfonate

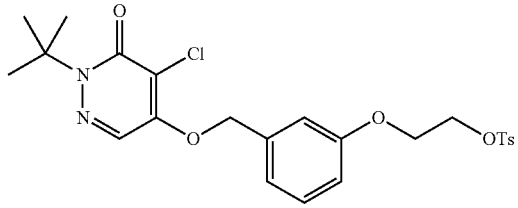 [SMILES: Cc1ccc(S(=O)(=O)OCCOc2cccc(COc3cnn(C(C)(C)C)c(=O)c3Cl)c2)cc1]

Prepared according to General Method D, using the product of Example 34D (52.4 mg, 0.149 mmol), p-toluenesulfonyl chloride (34.1 mg, 0.179 mmol), 4-dimethylaminopyridine (22.0 mg, 0.179 mmol), and diisopropylethylamine (0.032 mL, 0.179 mmol). Isolated yield—48.5 mg, 64.2% yield. $^1$H (CDCl$_3$, 300 MHz): δ 7.75 (d, J=8.4 Hz, 2H), 7.63 (s, 1H), 7.29-7.20 (m, 3H), 6.92 (d, J=7.1 Hz, 1H), 6.79 (m, 1H), 6.72 (dd, J=8.2, 2.0 Hz, 1H), 5.19 (s, 2H), 4.30 (m, 2H), 4.09 (m, 2H), 2.38 (s, 3H), 1.56 (s, 9H); $^{13}$C NMR (CDCl$_3$, 75 MHz): δ 158.0, 157.5, 152.6, 144.0, 135.6, 131.8, 129.1, 128.9, 127.0, 124.0, 118.8, 117.3, 113.8, 112.1, 70.5, 66.9, 64.5, 26.8, 20.6. HRMS-TOF (m/z): [M +H]$^+$ HRMS: Calcd. for C$_{24}$H$_{27}$$^{35}$ClN$_2$O$_6$S: 507.1351, found 507.1354.

Example 35

Preparation of 2-(tert-butyl)-4-chloro-5-((3-((2-fluoroethoxy)methyl)benzyl)oxy)pyridazin-3(2H)-one Part A—Preparation of methyl 3-(((1-(tert-butyl)-5-chloro-6-oxo-1,6-dihydropyridazin-4-yl)oxy)methyl)benzoate

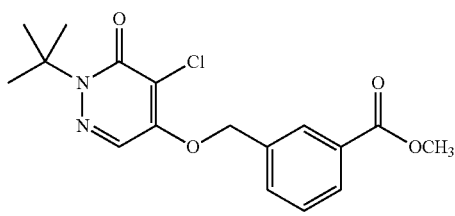 [SMILES: COC(=O)c1cccc(COc2cnn(C(C)(C)C)c(=O)c2Cl)c1]

Prepared according to General Method B, using 2-(tert-butyl)-4-chloro-5-hydroxypyridrazin-3(2H)-one (0.750 g, 3.70 mmol), methyl 4-(bromomethyl)benzoate (0.806 g, 3.52 mmol), and cesium carbonate (1.45 g, 4.45 mmol) in dimethylformamide (7.5 mL) at ambient temperature. Isolated yield—0.643 g, 52.1% yield. $^1$H NMR (CDCl$_3$, 300 MHz): δ 8.01-7.96 (m, 2H), 7.65 (s, 1H), 7.59-7.41 (m, 2H), 5.27 (s, 2H), 3.86 (s, 3H), 1.56 (s, 9H); $^{13}$C NMR (CDCl$_3$, 75 MHz): δ 166.5, 159.0, 153.5, 135.4, 131.5, 130.9, 129.2, 128.2, 127.8, 125.0, 118.6, 71.4, 66.5, 52.3, 27.9.

Part B—Preparation of 2-(tert-butyl)-4-chloro-5-((3-(hydroxymethyl)benzyl)oxy)pyridazin-3(2H)-one

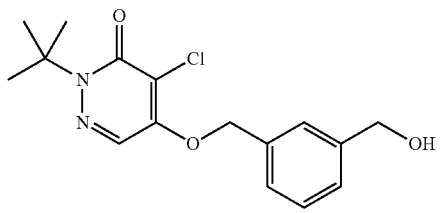 [SMILES: CC(C)(C)n1ncc(OCc2cccc(CO)c2)c(Cl)c1=O]

A cooled (0° C.) solution of the product of Example 35A (0.643 g, 1.83 mmol), in tetrahydrofuran (6.5 mL) was treated with lithium diisobutylaluminum hydride (2.25 mL, 2.25 mmol, 1 M solution in hexanes) then warmed to ambient temperature and stirred overnight. The resulting solution was diluted with water (50 mL), the aqueous layer was separated then extracted with ethyl acetate (3×150 mL). The combined organic layers were dried over sodium sulfate, filtered and concentrated in vacuo. The crude material was then purified by silica gel chromatography (5-50% ethyl acetate in hexanes) to afford the desired product as a white solid (0.403 g, 68.2% yield). $^1$H NMR (CDCl$_3$, 300 MHz): δ 7.74 (s, 1H), 7.45-7.28 (m, 4H), 5.34 (s, 2H), 4.76 (s, 2H), 1.65 (s, 9H); $^{13}$C NMR (CDCl$_3$, 75 MHz): δ 159.0, 153.7, 141.8, 135.3, 129.2, 127.3, 126.3, 125.5, 125.1, 118.4, 71.8, 66.4, 64.9, 27.9; HRMS-TOF (m/z): [M+H]$^+$ HRMS: Calcd. for C$_{16}$H$_{19}$$^{35}$ClN$_2$O$_3$: 323.1157, found 323.1154.

Part C—Preparation of 5-((3-(bromomethyl) benzyl) oxy)-2-(tert-butyl)-4-chloropyridazin-3(2H)-one

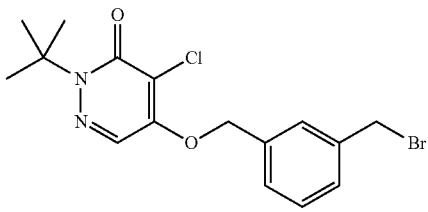 [SMILES: CC(C)(C)n1ncc(OCc2cccc(CBr)c2)c(Cl)c1=O]

Prepared according to General Method C, using the product of Example 35B (0.190 g, 0.590 mmol) and phosphorous tribromide (0.280 mL, 0.29 mmol, 1 M in dichloromethane) dropwise. Isolated yield—0.203 g, 89.2% yield. $^1$H NMR (CDCl$_3$, 300 MHz): δ 7.64 (s, 1H), 7.37-7.28 (m, 4H), 5.23 (s, 2H), 4.43 (s, 2H), 1.56 (s, 9H); $^{13}$C NMR (CDCl$_3$, 75 MHz): δ159.0, 153.6, 138.7, 135.6, 129.3, 129.2, 127.6, 127.1, 125.1, 118.5, 71.5, 66.5, 32.8, 27.9; HRMS-TOF (m/z): [M+H]$^+$ for C$_{16}$H$_{18}$$^{79}$Br$^{35}$ClN$_2$O$_2$: 385.0313, found 385.0316.

Part D—Preparation of 2-(tert-butyl)-4-chloro-5-((3-((2-fluoroethoxy)methyl)benzyl)oxy)pyridazin-3(2H)-one

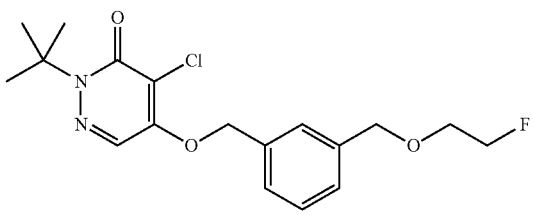

Prepared according to General Method E, using potassium tert-butoxide (25.9 mg, 0.231 mmol), 2-fluoroethanol (14.8 mg, 0.231 mmol) and the product of Example 35C (0.100 g, 0.260 mmol). Isolated yield—2.3 mg; 2.7%. $^1$H NMR (CDCl$_3$, 300 MHz): δ 7.65 (s, 1H), 7.37-7.30 (m, 4H), 5.25 (s, 2H), 4.62 (m, 1H), 4.55 (s, 2H), 4.46 (m, 1H), 3.73 (m, 1H), 3.64 (m, 1H), 1.56 (s, 9H); $^{13}$C NMR (CDCl$_3$, 75 MHz): δ 159.1, 153.7, 138.8, 135.2, 129.1, 128.0, 126.5, 126.2, 125.1, 118.4, 83.0 (d, J$_{CF}$=165 Hz), 73.0, 71.8, 69.7 (d, J$_{CF}$=22.5 Hz), 66.4, 28.9; HRMS-TOF (m/z): [M+H]$^+$ for C$_{18}$H$_{22}$$^{35}$ClFN$_2$O$_3$: 369.1376, found 369.1373.

Example 36

Preparation of 2-((3-(((1-(tert-butyl)-5-chloro-6-oxo-1,6-dihydropyridazin-4-yl)oxy)methyl)benzyl) oxy)ethyl 4-methylbenzenesulfonate Part A—Preparation of 2-(tert-butyl)-4-chloro-5-((3-((2-hydroxyethoxy)methyl)benzyl)oxy)pyridazin-3(2H)-one

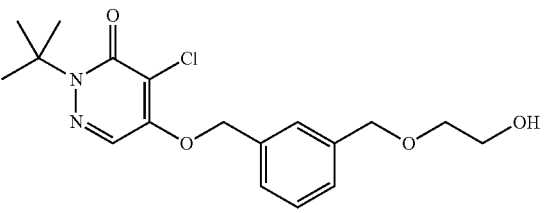 [SMILES: CC(C)(C)n1ncc(OCc2cccc(COCCO)c2)c(Cl)c1=O]

A suspension of potassium tert-butoxide (25.3 mg, 0.226 mmol) and ethylene glycol (111 mg, 1.79 mmol) were heated to 60° C. and maintained 20 min. The product of Example 35C (0.104 g, 0.271 mmol), dissolved in tetrahydrofuran (3 mL) was added dropwise. After completion of the addition, the reaction mixture was heated at reflux, maintained overnight, then cooled and quenched with water (15 mL). The aqueous layer was separated then extracted with ethyl acetate (3×25 mL). The combined organic layers were dried over sodium sulfate, filtered and concentrated in vacuo. The crude material was then purified by silica gel chromatography using 4:1 hexanes/ethyl acetate to afford the desired product as a clear oil (60.2 mg, 60.6% yield). $^1$H NMR (CDCl$_3$, 300 MHz): δ 7.73 (s, 1H), 7.44-7.29 (m, 4H), 5.32 (s, 2H), 4.59 (s, 2H), 3.78 (m, 2H), 3.62 (m, 2H), 1.63 (s, 9H); $^{13}$C NMR (CDCl$_3$, 75 MHz): δ 159.1, 153.7, 139.0, 135.2, 129.2, 128.1, 126.5, 126.2, 125.1, 118.4, 72.9, 71.8, 71.6, 66.4, 61.9, 27.9.

Part B—Preparation of 2-((3-(((1-(tert-butyl)-5-chloro-6-oxo-1,6-dihydropyridazin-4-yl)oxy)ethyl)benzyl)oxy)ethyl 4-methylbenzenesulfonate

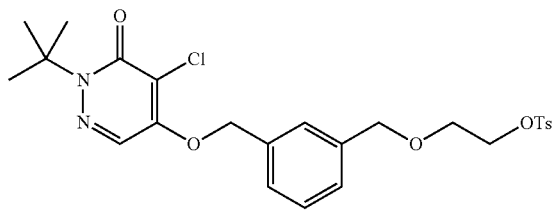 [SMILES: Cc1ccc(S(=O)(=O)OCCOCc2cccc(COc3cnn(C(C)(C)C)c(=O)c3Cl)c2)cc1]

Prepared according to General Method D, using the product of Example 36A (50.2 mg, 0.137 mmol), p-toluenesulfonyl chloride (31.3 mg, 0.165 mmol), 4-dimethylaminopyridine (21.0 mg, 0.165 mmol), and diisopropylethylamine (0.016 mL, 0.165 mmol). Isolated yield—21.2 mg; 29.7%. $^1$H (CDCl$_3$, 300 MHz): δ 7.73 (d, J=8.4 Hz, 2H), 7.66 (s, 1H), 7.34-7.19 (m, 6H), 5.23 (s, 2H), 4.45 (s, 2H), 4.06 (m, 2H), 3.62 (m, 2H), 2.38 (s, 3H), 1.56 (s, 9H); $^{13}$C (CDCl$_3$, 75 MHz): δ 159.0, 153.7, 144.9, 138.6, 135.2, 133.0, 129.8, 129.1, 127.9, 127.8, 126.5, 126.1, 125.1, 118.3, 72.8, 71.8, 69.2, 67.8, 66.4, 27.9, 21.6; HRMS-TOF (m/z): [M+H]$^+$ for C$_{25}$H$_{29}$$^{35}$ClN$_2$O$_6$S: 521.1508, found 521.1500.

Example 37

Preparation of 2-((4-(((1-(tert-butyl)-5-chloro-6-oxo-1,6-dihydropyridazin-4-yl)oxy)methyl)benzyl)oxy)ethyl methyl carbonate

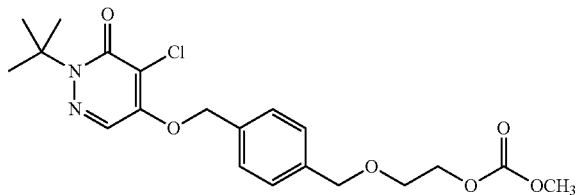 [SMILES: COC(=O)OCCOCc1ccc(COc2cnn(C(C)(C)C)c(=O)c2Cl)cc1]

A solution of 2-(tert-butyl)-4-chloro-5-((4-((2-hydroxyethoxy) methyl) benzyl) oxy) pyridazin-3(2H)-one (0.147 g, 0.400 mmol; e.g., see Casebier, David S.; Robinson, Simon P.; Purohit, Ajay; Radeke, Heike S.; Azure, Michael T.; Dischino, Douglas D. (Bristol-Myers Squibb) Preparation of contrast agents for myocardial perfusion imaging comprising an imaging moiety and deguelin, pyridaben, pyrimidifen, tebufenpyrad, fenazaquin, and analogs thereof. PCT Int. Appl. WO 2005/079391. Sep. 1, 2005) in pyridine (2.00 mL) was cooled to 0° C. then treated with methyl chloroformate (34 μL, 0.44 mmol) in one portion. After 1.25 h, additional methyl chloroformate (34 μL, 0.44 mmol) was added. After an additional 1.5 h, a final addition of methyl chloroformate (34 μL, 0.44 mmol) was performed. After 0.25 h, the solution was diluted with ethyl acetate, with transfer to a separatory funnel, then washed with a 5% aqueous solution of CuSO$_4$, dried over magnesium sulfate, filtered and concentrated in vacuo. The crude material thus obtained was then purified by chromatography on silica (30×175 mm) using 3:2 pentane/ethyl acetate. The main product peak eluting 175-280 mL was collected, pooled and concentrated in vacuo to a colorless oil (0.144 g, 0.339 mmol; 84.7%). $^1$H NMR: (300 MHz, DMSO-d$_6$) δ 8.26 (1H, s), 7.45 (2H, AB, J$_{AB}$=8.2 Hz), 7.37 (2H, AB, J$_{AB}$=8.4 Hz), 5.45 (2H, s), 4.52 (2H, s), 4.29-4.19 (2H, m), 3.69 (3H, s), 3.68-3.60 (2H, m), 1.57 (9H, s). $^{13}$C NMR: (75 MHz, DMSO-d$_6$) δ 157.8, 155.2, 153.8, 138.6, 134.6, 127.8, 127.7, 126.2, 115.6, 71.5, 71.3, 67.5, 66.7, 65.4, 54.6, 27.4. HRMS Calcd. for C$_{20}$H$_{25}$$^{35}$ClN$_2$O$_6$(M+H): 425.1474; found: 425.1470. TLC: R$_f$ 0.50 (silica gel, 1:1 pentane/ethyl acetate, CAM).

Example 38

Preparation of 2-((4-(((1-(tert-butyl)-5-chloro-6-oxo-1,6-dihydropyridazin-4-yl)oxy)methyl)benzyl)oxy)ethyl 2-cyanoacetate

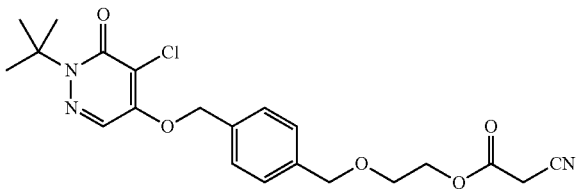 [SMILES: CC(C)(C)n1ncc(OCc2ccc(COCCOC(=O)CC#N)cc2)c(Cl)c1=O]

A solution of 2-(tert-butyl)-4-chloro-5-((4-((2-hydroxyethoxy) methyl) benzyl) oxy) pyridazin-3(2H)-one$^6$ (0.183 g, 0.500 mmol) and cyanoacetic acid (85.1 mg, 1.00 mmol) in dry dichloromethane (2.50 mL) was treated with N-(3-dimethylaminopropyl)-N'-ethylcarbodiimide hydrochloride (0.191 g, 1.00 mmol) in one portion at ambient temperature. After 0.25 h, all volatiles were removed in vacuo, and the residue directly purified by chromatography on silica (30× 180 mm) using 1:1 pentane/ethyl acetate. The main product peak eluting 175-325 mL was collected, pooled and concentrated in vacuo to a colorless oil (0.206 g, 0.476 mmol; 95.1%). $^1$H NMR: (300 MHz, CDCl$_3$) δ 7.72 (1H, s), 7.43-7.37 (4H, m), 5.31 (2H, s), 4.57 (2H, s), 4.41-4.38 (2H, m), 3.75-3.72 (2H, m), 3.49 (2H, s), 1.63 (9H, s). $^{13}$C NMR: (75 MHz, CDCl$_3$) δ 162.9, 159.0, 153.6, 138.3, 134.5, 128.2, 127.3, 125.0, 118.3, 112.8, 72.8, 71.6, 67.5, 66.4, 65.8, 27.8, 24.7. HRMS Calcd. for C$_{21}$H$_{24}$$^{35}$ClN$_3$O$_5$ (M+H): 434.1477; found: 434.1474. TLC: R$_f$ 0.41 (silica gel, 1:1 pentane/ethyl acetate, uv).

Example 39

Preparation of 2-(tert-butyl)-4-chloro-5-((6-(3-fluoropropoxy)pyridine-3-yl)methoxy)pyridazin-3(2H)-one Part A—Preparation of (6-(3-fluoropropoxy)pyridine-3-yl)methanol

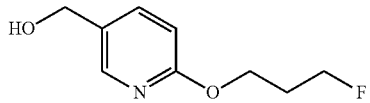 [SMILES: OCc1ccc(OCCCF)nc1]

A suspension of sodium hydride (26.4 mg, 1.10 mmol) and 3-fluoropropanol (78.0 mg, 1.00 mmol) in dimethylformamide (1.0 mL) was maintained at ambient temperature for 25 min then treated with a solution of methyl 6-bromonicotinate (0.216 g, 1.00 mmol) in dimethylformamide (0.5 mL). After 1 h, the resulting mixture was diluted with water (2 mL), the aqueous layer separated then extracted with ethyl acetate (2×10 mL). The combined organic layers were dried over sodium sulfate and concentrated in vacuo to a yellow oil.

A solution of methyl 6-(3-fluoropropoxy) nicotinate in tetrahydrofuran was added dropwise to a cooled (0° C.) solution of lithium aluminum hydride (0.14 mL, 0.14 mmol, 1 M in tetrahydrofuran) and the resulting mixture warmed to ambient temperature. After 2 h, the solution was diluted with water, the aqueous layer separated then extracted with ethyl acetate (3×10 mL). The combined organic layers were dried over sodium sulfate and concentrated in vacuo. The crude material was then purified by silica gel chromatography (0-60% ethyl acetate in hexanes) to afford the desired product as a yellow oil (22.3 mg, 12.0% yield). $^1$H NMR (CDCl$_3$, 300 MHz): δ 8.06-7.99 (m, 1H), 7.55 (dd, J=2.4, 8.4 Hz, 1H), 6.66 (d, J=8.5 Hz, 1H), 4.63 (t, J=5.9 Hz, 1H), 4.54 (s, 2H), 4.47 (t, J=5.9 Hz, 1H), 4.30 (t, J=6.2 Hz, 2H), 2.18-2.01 (m, 2H). $^{13}$C NMR (75 MHz, CDCl$_3$) δ 162.4, 144.7, 137.4, 128.1, 109.9, 79.9 (d, J$_{CF}$=165 Hz), 61.4, 60.8, (d, J$_{CF}$=7.5 Hz), 29.2 (d, J$_{CF}$=22.5 Hz).

Part B—Preparation of 2-(tert-butyl)-4-chloro-5-((6-(3-fluoropropoxy)pyridine-3-yl)methoxy)pyridazin-3(2H)-one

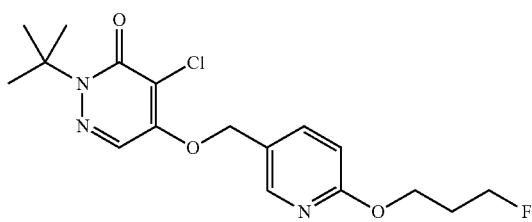 [SMILES: CC(C)(C)n1ncc(OCc2ccc(OCCCF)nc2)c(Cl)c1=O]

Prepared according to General Method B, using 2-(tert-butyl)-4-chloro-5-hydroxypyridrazin-3(2H)-one (22.3 mg, 0.100 mmol), the product of Example 39A (18.7 mg, 0.100 mmol), and cesium carbonate (52.5, 0.161 mmol) in dimethylformamide (1.0 mL) at ambient temperature. Isolated yield—15.3 mg; 41.4%. $^1$H NMR (CDCl$_3$, 300 MHz): δ 8.12 (d, J=1.9 Hz, 1H), 7.69 (s, 1H), 7.60 (dd, J=2.5, 8.5 Hz, 1H), 6.73 (d, J=8.7 Hz, 1H), 5.15 (s, 2H), 4.64 (t, J=5.8 Hz, 1H), 4.48 (t, J=5.8 Hz, 1H), 4.39 (t, J=6.2 Hz, 2H), 2.19-2.02 (m, 2H), 1.56 (s, 9H); $^{13}$C NMR (CDCl$_3$, 150 MHz): δ 163.1, 157.9, 152.4, 145.3, 137.5, 124.1, 122.3, 117.7, 110.5, 79.8 (d, J$_{CF}$=165 Hz), 68.5, 65.4, 61.0 (d, J$_{CF}$=7.5 Hz), 29.1 (d, J$_{CF}$=22.5 Hz), 26.8; HRMS Calcd. for C$_{17}$H$_{21}$$^{35}$ClFN$_3$O$_5$(M+H): 370.1328; found: 370.1331.

Example 40

Preparation of 2-(tert-butyl)-5-((4-((2-fluoroethoxy)benzyl)oxy)-4-methylpyridazin-3(2H)-one

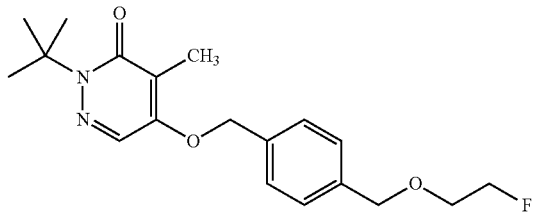 [SMILES: Cc1c(OCc2ccc(COCCF)cc2)cnn(C(C)(C)C)c1=O]

Prepared according to General Method B, using 2-(tert-butyl)-5-chloro-4-methylpyridazin-3(2H)-one$^6$ (0.100 g, 0.500 mmol), (4-((2-fluoroethoxy)methyl)phenyl)methanol (0.110 g, 0.600 mmol), and cesium carbonate (0.261 g, 0.800 mmol) in dimethylformamide (5.0 mL) at 65° C. Isolated yield—49 mg; 28.1%. $^1$H NMR (CDCl$_3$, 300 MHz): δ 7.61 (s, 1H), 7.30 (br s, 4H), 5.10 (s, 2H), 4.59 (m, 1H), 4.53 (s, 2H), 4.43 (m, 1H), 3.71 (m, 1H), 3.61 (m, 1H), 1.98 (s, 3H), 1.55 (s, 9H); $^{13}$C NMR (75 MHz, CDCl$_3$) δ 162.1, 153.3, 137.2, 134.3, 127.0, 126.2, 124.5, 120.1, 82.0 (d, J$_{CF}$=165 Hz), 71.9, 69.8, 68.4 (d, J$_{CF}$=22.5 Hz), 63.9, 27.0, 7.7; HRMS-TOF (m/z): [M+H]$^+$ HRMS: Calcd. for C$_{19}$H$_{25}$FN$_2$O$_3$: 349.1922, found 349.1916.

Example 41

Preparation of 2-((4-(((1-(tert-butyl)-5-methyl-6-oxo-1,6-dihydropyridazin-4yl)-oxy)methyl)benzyl)oxy)ethyl 4-methylbenzenesulfonate Part A—Preparation of 5-((4-(1,3-dioxolan-2-yl)benzyl)oxy)-2-(tert-butyl)-4-methylpyridazin-3(2H)-one

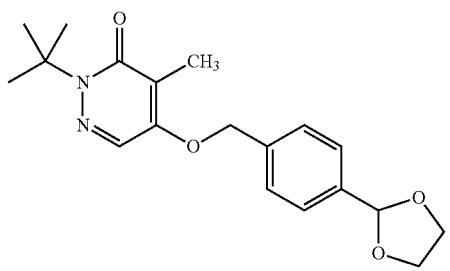 [SMILES: Cc1c(OCc2ccc(C3OCCO3)cc2)cnn(C(C)(C)C)c1=O]

Prepared according to General Method B, using 2-(tert-butyl)-5-chloro-4-methylpyridazin-3(2H)-one (0.200 g, 1.00 mmol), (4-(1,3-dioxolan-2-yl)phenyl)methanol (0.150 g, 0.830 mmol), and cesium carbonate (0.540 g, 1.66 mmol) in dimethylformamide (10.0 mL) at 60° C. Isolated yield—

56.5 mg; 19.8%. $^1$H NMR (CDCl$_3$, 300 MHz): δ 7.67 (s, 1H), 7.51 (d, J=8.3 Hz, 2H), 7.39 (d, J=8.2 Hz, 2H), 5.81 (s, 1H), 5.20 (s, 2H), 4.26-3.84 (m, 4H), 2.05 (s, 3H), 1.57 (s, 9H); $^{13}$C NMR (CDCl$_3$, 75 MHz): δ 163.1, 154.3, 138.2, 136.8, 127.0, 126.9, 125.5, 121.1, 103.3, 70.6, 65.3, 64.9, 28.0, 8.7; HRMS-TOF (m/z): [M+H]$^+$ HRMS: Calcd. for C$_{19}$H$_{24}$N$_2$O$_4$: 345.1809, found 345.1806.

Part B—Preparation of 2-(tert-butyl)-5-((4-((2-hydroxyethoxy)methyl)benzyl)oxy)-4-methylpyridazin-3(2H)-one

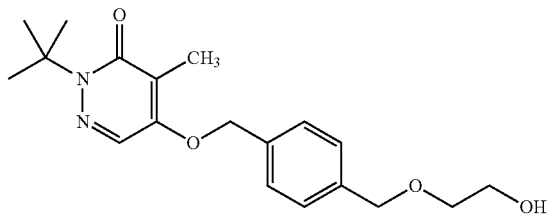 [SMILES: Cc1c(OCc2ccc(COCCO)cc2)cnn(C(C)(C)C)c1=O]

A solution of the product of Example 41A (55.7 mg, 0.162 mmol) in tetrahydrofuran (0.8 mL) was added dropwise to a suspension of zirconium chloride (37.8 mg, 0.162 mmol) and sodium borohydride (12.3 mg, 0.324 mmol) in tetrahydrofuran (0.80 mL) at ambient temperature. After 2 h, the resulting mixture was diluted with water (5 mL), the aqueous layer separated then extracted with ethyl acetate (3×10 mL). The combined organic layers were dried over sodium sulfate, filtered and concentrated to a clear oil (50.6 mg, 90.2% yield). 1H NMR (CDCl$_3$, 300 MHz): δ 7.62 (s, 1H), 7.30 (br s, 4H), 5.10 (s, 2H), 4.50 (s, 2H), 3.70 (m, 2H), 3.54 (dd, J=3.9, 5.3 Hz, 2H), 1.98 (s, 3H), 1.55 (s, 9H); $^{13}$C NMR (CDCl$_3$, 75 MHz): δ 162.1, 153.4, 137.4, 134.3, 127.1, 126.8, 126.2, 119.3, 71.8, 70.5, 69.8, 63.9, 60.8, 27.0, 7.7; HRMS-TOF (m/z): [M+H]$^+$ HRMS: Calcd. for C$_{19}$H$_{26}$N$_2$O$_4$: 347.1965, found 347.1960.

Part C—Preparation of 2-((4-(((1-(tert-butyl)-5-methyl-6-oxo-1,6-dihydropyridazin-4yl)-oxy)methyl)benzyl)oxy)ethyl 4-methylbenzenesulfonate

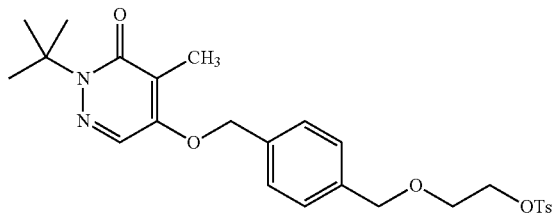

Prepared according to General Procedure D, using the product of Example 41B (46.8 mg, 0.135 mmol), p-toluenesulfonyl chloride (30.9 mg, 0.162 mmol), 4-dimethylaminopyridine (5.4 mg, 0.54 mmol), and diisopropylethylamine (0.026 mL, 0.189 mmol). Isolated yield—42.6 mg; 63.0%. $^1$H (CDCl$_3$, 300 MHz): δ 7.80 (d, 2H, J=8.33 Hz), 7.69 (s, 1H), 7.33 (m, 6H), 5.18 (s, 2H), 4.50 (s, 2H), 4.21 (m, 2H), 3.69 (m, 2H), 2.43 (s, 3H), 2.05 (s, 3H), 1.63 (s, 9H); $^{13}$C NMR (75 MHz, CDCl$_3$) δ 163.1, 154.3, 144.7, 138.0, 135.3, 133.0, 129.7, 128.0, 127.9, 127.2, 125.5, 121.2, 72.8, 70.8, 69.1, 67.7, 64.9, 28.0, 21.6, 8.7.

Example 43

Preparation of 2-(tert-butyl)-4-chloro-5-((4-(4-fluorobut-1-yn-1-yl)benzyl)oxy)pyridazin-3(2H)-one Part A—Preparation of (4-(4-((tert-butyldimethylsilyl)oxy)but-1-yn-1-yl)phenyl)methanol

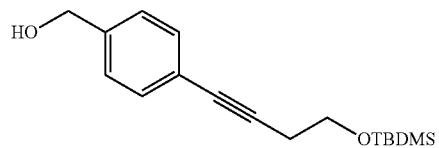 [SMILES: CC(C)(C)[Si](C)(C)OCCC#Cc1ccc(CO)cc1]

A solution of methyl 4-(4-hydroxybut-1-yn-1-yl)benzoate (0.771 g, 3.77 mmol),$^1$ in dimethylformamide (37.0 mL) was successively treated with tert-butylchlorodimethylsilane (0.848 g, 5.63 mmol), and imidazole (0.386 g, 5.67 mmol) at ambient temperature. After 2 h, the resulting mixture was diluted with water (150 mL), the aqueous layer separated then extracted with ethyl acetate (3×200 mL). The combined organic layers were dried over sodium sulfate, filtered and concentrated to yield to a yellow oil (1.50 g).

The crude silyl ether was dissolved in tetrahydrofuran (47.0 mL) then cooled to 0° C. and treated with lithium aluminum hydride (4.71 mL, 4.71 mmol, 1 M in tetrahydrofuran). The resulting solution then warmed slowly to ambient temperature and, after 2 h, was diluted with water (20 mL). The aqueous layer was separated then extracted with ethyl acetate (3×50 mL) and the combined organic layers washed with saturated aqueous sodium chloride, dried over sodium sulfate, filtered, and concentrated in vacuo (1.22 g, >98% crude yield). $^1$H (CDCl$_3$, 300 MHz): δ 7.29 (d, J=8.28 Hz, 2H), 7.18 (d, J=8.47 Hz, 2H), 4.58 (s, 2H), 3.72 (t, J=7.05 Hz, 2H), 2.53 (t, J=7.03 Hz, 2H), 0.82 (s, 6H); 0.01 (s, 9H); HRMS-TOF (m/z): [M+H]$^+$ HRMS: Calcd. for C$_{17}$H$_{26}$O$_2$Si: 291.1775, found 291.1763.

Part B—Preparation of 2-(tert-butyl)-5-((4-(4-((tert-butyldimethylsilyl)oxy)but-1-yn-1-yl)benzyl)oxy)-4-chloropyridazinone-3(2H)-one

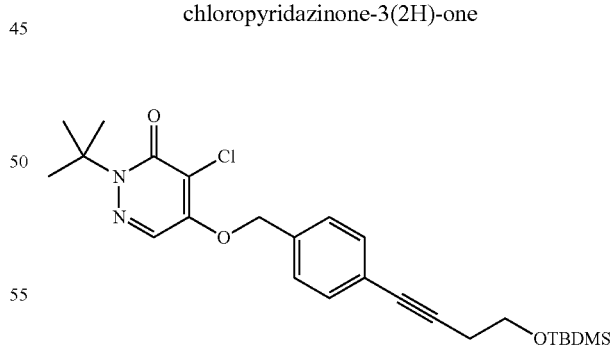

Prepared according to General Method B, using 2-(tert-butyl)-4,5-dichloropyridrazin-3(2H)-one (0.318 g, 1.45 mmol), the product of Example 43A (0.500 g, 1.73 mmol), and cesium carbonate (0.750 g, 2.31 mmol) in dimethylformamide (14.5 mL) at 60° C. Isolated yield—0.242 g; 35.1%. $^1$H NMR (CDCl$_3$, 300 MHz): δ δ 7.58 (s, 1H), 7.33 (d, J=8.3 Hz, 2H), 7.22 (d, J=8.4 Hz, 2H), 5.19 (s, 2H), 3.72 (t, J=7.0 Hz, 2H), 2.53 (t, J=6.9 Hz, 2H), 1.44 (s, 9H), 0.82 (s, 9H), 0.20 (s, 6H); $^{13}$C NMR (CDCl$_3$, 75 MHz, partial): δ 159.0, 153.5, 134.2, 132.1, 127.1, 126.8, 125.1, 124.4, 118.4, 88.3, 80.9, 71.5, 66.4, 61.8, 27.8, 25.8, 23.8, −5.2; HRMS-TOF (m/z): [M+H]⁺ HRMS: Calcd. for $C_{25}H_{35}{}^{35}ClN_2O_3Si$: 475.2178, found 475.2162.

Part C—Preparation of 2-(tert-butyl)-4-chloro-5-((4-(4-hydroxybut-1-yn-1-yl)benzyl)oxy)pyridazinone-3 (2H)-one

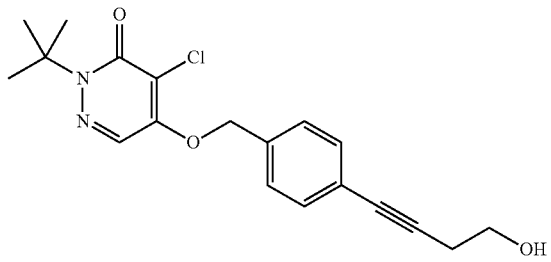 [SMILES: CC(C)(C)n1ncc(OCc2ccc(C#CCCO)cc2)c(Cl)c1=O]

A solution of the product of Example 43B (0.242 g, 0.510 mmol) dissolved in tetrahydrofuran (10.0 mL) was treated with a solution of tetrabutylammonium fluoride (1.02 mL, 1.02 mmol, 1 M in tetrahydrofuran) at ambient temperature. After 2 h, the resulting mixture was concentrated in vacuo and the residue directly purified by silica gel chromatography (0-60% ethyl acetate in hexanes) to afford the desired product as an oil (0.120 g, 65.2% yield). ¹H NMR (CDCl₃, 300 MHz): δ 7.68 (s, 1H), 7.45 (d, J=8.3 Hz, 2H), 7.34 (d, J=8.4 Hz, 2H), 5.29 (s, 2H), 3.82 (m, 4H), 1.63 (s, 9H); ¹³C NMR (CDCl₃, 75 MHz): δ 158.9, 153.5, 134.5, 132.2, 126.9, 125.0, 123.9, 118.4, 87.4, 81.8, 71.4, 66.4, 61.1, 27.8, 23.8; HRMS-TOF (m/z): [M+H]⁺ HRMS: Calcd. for $C_{19}H_{21}{}^{35}ClN_2O_3$: 361.1313, found 361.1309.

Part D—Preparation of 2-(tert-butyl)-4-chloro-5-((4-(4-fluorobut-1-yn-1-yl)benzyl)oxy)pyridazin-3 (2H)-one

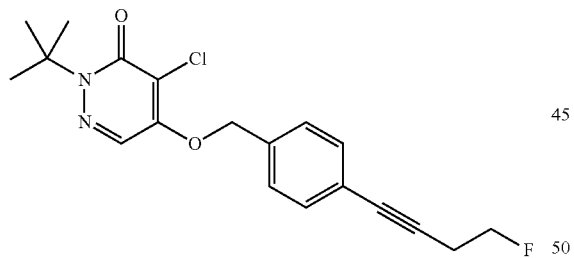

A cooled (0° C.) solution of the product of Example 43C (0.050 g, 0.138 mmol) in dichloromethane (0.10 mL) was treated with Deoxofluor (0.152 mmol, 33.7 mg, 50% in toluene) then maintained 1.5 h. The resulting mixture was diluted with water (1 mL), the aqueous layer separated then extracted with dichloromethane (3×2 mL). The combined organic layers were dried over sodium sulfate, filtered and concentrated in vacuo. The crude material was then purified by preparative thin layer chromatography on silica using 3:2 hexanes/ethyl acetate to afford the desired product (11.5 mg, 23.0% yield). ¹H NMR (CDCl₃, 300 MHz): δ 7.61 (s, 1H), 7.38 (d, J=8.3 Hz, 2H), 7.27 (d, J=8.4 Hz, 2H), 5.22 (s, 2H), 4.59 (t, J=6.6 Hz, 1H), 4.44 (t, J=6.6 Hz, 1H), 2.78 (dt, J=19.6, 6.6 Hz, 2H), 1.56 (s, 9H); ¹³C NMR (CDCl₃, 75 MHz): δ 157.9, 152.5, 133.6, 131.2, 125.8, 124.0, 122.8, 117.4, 84.4 (d, $J_{CF}$=15 Hz), 80.3 (d, $J_{CF}$=165 Hz), 80.6, 70.4, 65.4, 26.8, 20.6 (d, $J_{CF}$=22.5 Hz); HRMS-TOF (m/z): [M+H]⁺ HRMS: Calcd. for $C_{19}H_{20}{}^{35}ClFN_2O_2$: 363.1270, found 363.1270.

Example 44

Preparation of 4-(4-(((1-(tert-butyl)-5-chloro-6-oxo-1,6-dihydropyridazin-4-yl)-oxy)methyl)benzyl)but-3-yn-1-yl 4-methylbenzenesulfonate

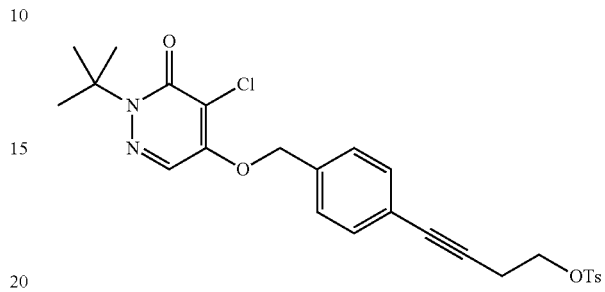

Prepared according to General Method D, using the product of Example 43C (77.4 mg, 0.215 mmol), p-toluenesulfonyl chloride (49.2 mg, 0.258 mmol), 4-dimethylaminopyridine (1.1 mg, 0.0086 mmol), and triethylamine (0.042 mL, 0.30 mmol). Isolated yield—42.2 mg; 38.1%. ¹H (CDCl₃, 300 MHz): δ 7.75 (d, J=8.3 Hz, 2H), 7.61 (s, 1H), 7.36-7.21 (m, 6H), 5.22 (s, 2H), 4.12 (t, J=6.9 Hz, 2H), 2.72 (t, J=6.9 Hz, 2H), 2.35 (s, 3H), 1.56 (s, 9H); ¹³C (CDCl₃, 75 MHz): δ 158.9, 153.5, 144.9, 134.7, 132.9, 132.1, 129.8, 127.9, 126.8, 125.0, 123.5, 118.4, 84.8, 82.0, 71.4, 67.6, 66.4, 27.8, 21.6, 20.4; HRMS-TOF (m/z): [M+H]⁺ HRMS: Calcd. for $C_{26}H_{27}{}^{35}ClN_2O_6S$: 515.1402, found 515.1409.

Example 45

Preparation of 2-fluoroethyl 4-(((1-(tert-butyl)-5-chloro-6-oxo-1,6-dihydropyridazin-4-yl)oxy)methyl) benzoate

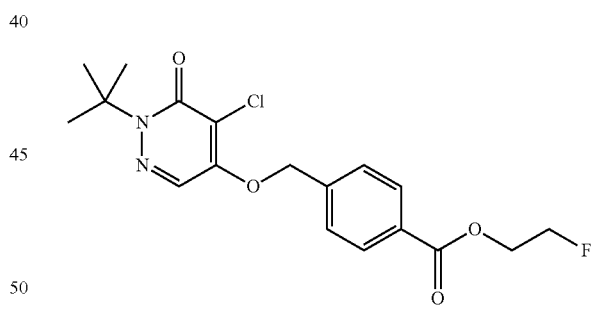

A suspension of 2-fluoroethanol (2 mL) and potassium tert-butoxide (0.0300 g, 0.267 mmol) was heated to 60° C., maintained 20 min then treated with a solution of methyl 4-(((1-(tert-butyl)-5-chloro-6-oxo-1,6-dihydropyridazin-4-yl)oxy)methyl)benzoate (93.5 mg, 0.267 mmol)⁴ in tetrahydrofuran (0.70 mL). The resulting mixture was stirred overnight then cooled to ambient temperature and diluted with water (5 mL). The aqueous layer was separated, extracted with ethyl acetate (3×20 mL), and the combined organic layers washed with saturated aqueous sodium chloride, dried over sodium sulfate, filtered, and concentrated in vacuo. The crude material was then purified by silica gel chromatography (0-80% diethyl ether in hexanes) to afford the desired product as a white solid (11.7 mg, 11.4% yield). ¹H (CDCl₃, 300 MHz): δ 8.17-8.08 (m, 2H), 7.70 (s, 1H), 7.51 (d, J=8.0 Hz, 2H), 5.38 (s, 2H), 4.81 (m, 1H), 4.61-4.67 (m, 2H), 4.53

(m, 1H), 1.63 (s, 9H); $^{13}$C NMR (CDCl$_3$, 75 MHz): δ 164.7, 157.9, 152.3, 139.1, 129.4, 129.0, 125.7, 123.8, 117.5, 80.2 (d, J$_{CF}$=165 Hz), 70.1, 65.4 (d, J$_{CF}$=22.5 Hz), 62.8, 20.0.

Example 46

Preparation of 2-(tosyloxy)ethyl 4-(((1-(tert-butyl)-5-chloro-6-oxo-1,6-dihydropyridazin-4-yl)oxy)methyl)benzoate Part A—Preparation of 2-hydroxyethyl 4-(((1-(tert-butyl)-5-chloro-6-oxo-1,6-dihydropyridazin-4-yl)oxy)methyl)benzoate

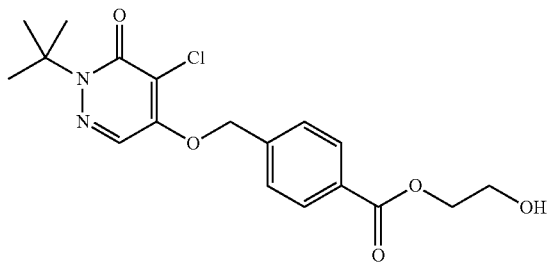 [SMILES: CC(C)(C)n1ncc(OCc2ccc(C(=O)OCCO)cc2)c(Cl)c1=O]

A suspension of ethylene glycol (15 mL) and potassium tert-butoxide (0.224 g, 2.00 mmol) was heated to 60° C., maintained 20 min then treated with a solution of methyl 4-(((1-(tert-butyl)-5-chloro-6-oxo-1,6-dihydropyridazin-4-yl)oxy)methyl)benzoate (0.773 g, 2.20 mmol) in tetrahydrofuran (5.0 mL). After 1.5 h, the resulting mixture was cooled to ambient temperature and diluted with water (50 mL). The aqueous layer was separated then extracted with toluene (3×100 mL), and the combined organic layers were washed with saturated aqueous sodium chloride, dried over sodium sulfate, filtered, and concentrated. The crude material was then purified by silica gel chromatography (40-60% ethyl acetate in hexanes) to afford the desired product as a white solid (47.7 mg, 5.3% yield). $^1$H (CDCl$_3$, 300 MHz): δ 8.11 (d, J=8.4 Hz, 2H), 7.71 (s, 1H), 7.49 (d, J=8.5 Hz, 2H), 5.37 (s, 2H), 4.59-4.34 (m, 2H), 4.04-3.86 (m, 2H), 1.63 (s, 9H); HRMS-TOF (m/z): [M+H]$^+$ HRMS: Calcd. for C$_{18}$H$_{21}$$^{35}$ClN$_2$O$_5$: 381.1212, found 384.1206.

Part B—Preparation of 2-(tosyloxy) ethyl 4-(((1-(tert-butyl)-5-chloro-6-oxo-1,6-dihydropyridazin-4-yl)oxy)methyl)benzoate

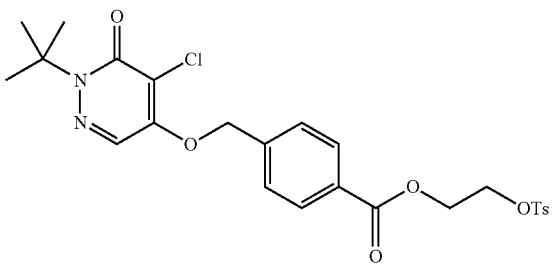 [SMILES: Cc1ccc(S(=O)(=O)OCCOC(=O)c2ccc(COc3cnn(C(C)(C)C)c(=O)c3Cl)cc2)cc1]

Prepared according the General Method D, using the product of Example 46A (47.1 mg, 0.124 mmol), p-toluenesulfonyl chloride (28.3 mg, 0.148 mmol), 4-dimethylaminopyridine (0.60 mg, 0.0049 mmol), and triethylamine (0.024 mL, 1.4 mmol). Isolated yield—33.6 mg; 50.6%. $^1$H (CDCl$_3$, 300 MHz): δ 8.07-7.96 (m, 2H), 7.78 (s, 1H), 7.71 (m, 2H), 7.49 (d, J=8.3 Hz, 2H), 7.29 (d, J=8.0 Hz, 2H), 5.37 (s, 2H), 4.54-4.46 (m, 2H), 4.41-4.32 (m, 2H), 2.40 (s, 3H), 1.64 (s, 9H); $^{13}$C NMR (CDCl$_3$, 75 MHz): δ 165.4, 158.9, 153.4, 145.0, 140.2, 132.8, 130.4, 129.9, 129.7, 127.9, 127.5, 126.7, 118.5, 71.0, 67.5, 66.6, 62.2, 27.8, 21.6; HRMS-TOF (m/z): [M+H]$^+$ HRMS: Calcd. for C$_{25}$H$_{27}$$^{35}$ClN$_2$O$_7$S: 535.1300, found 535.1290.

Example 47

Preparation of 2-(tert-butyl)-4-chloro-5-((4'-(3-fluoropropoxy)-[1,1'-biphenyl]-4-yl)methoxy)pyridazin-3(2H)-one Part A—Preparation of 4'-(3-fluoropropoxy)-[1,1'-biphenyl]-4-carbaldehyde

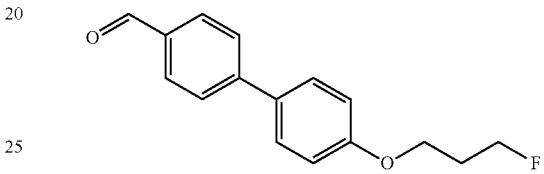

Prepared according to General Method F, using 4'-hydroxy-[1,1'biphenyl]-4-carbaldehyde (0.500 g, 2.52 mmol), 3-fluoropropyl p-toluenesulfonate (0.557 g, 2.40 mmol), and cesium carbonate (1.25 g, 3.84 mmol) in dimethylformamide (25.2 mL) was at ambient temperature. The crude material was further purified by silica gel chromatography (0-60% ethyl acetate in hexanes) to afford the desired product as a white solid (0.380 g, 61.3% yield). $^1$H NMR (CDCl$_3$, 300 MHz): δ 10.03 (s, 1H), 7.97-7.87 (m, 2H), 7.75-7.68 (m, 2H), 7.63-7.53 (m, 2H), 7.06-6.96 (m, 2H), 4.75 (t, J=5.7 Hz, 1H), 4.59 (t, J=5.7 Hz, 1H), 4.16 (t, J=6.1 Hz, 2H), 2.21 (m, 2H); $^{13}$C NMR (CDCl$_3$, 75 MHz, CDCl$_3$) δ 191.8, 159.3, 146.7, 134.7, 132.2, 130.2, 128.5, 127.0, 115.0, 80.6 (d, J$_{CF}$=165 Hz), 63.7 (d, J$_{CF}$=7.5 Hz), 30.4 (d, J$_{CF}$=22.5 Hz); HRMS-TOF (m/z): [M+H]$^+$ HRMS: Calcd. for C$_{16}$H$_{15}$FO$_2$: 259.1129, found 259.1131.

Part B—Preparation of 4'-(3-fluoropropoxy)-[1,1'-biphenyl]-4-yl)methanol

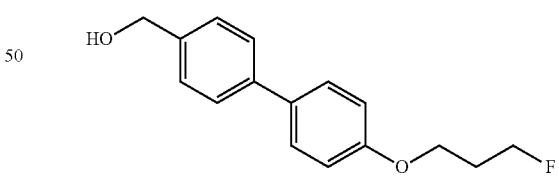

A cooled (0° C.) solution of the product of Example 47A (0.190 g, 0.730 mmol) dissolved in tetrahydrofuran (7.3 mL) was treated with a solution of lithium aluminum hydride (0.40 mL, 0.40 mmol, 1 M in tetrahydrofuran) then warmed to ambient temperature. After 2 h, the resulting mixture was diluted with water (10 mL), the aqueous layer separated then extracted with ethyl acetate (3×50 mL). The combined organic layers were dried over sodium sulfate and concentrated to a white solid (0.170 g, 89.5% yield). $^1$H NMR (CDCl$_3$, 300 MHz): δ 7.60-7.47 (m, 4H), 7.42 (d, J=8.4 Hz, 2H), 7.03-6.88 (m, 2H), 4.83-4.63 (m, 3H), 4.59 (t, J=5.7 Hz, 1H), 4.15 (t, J=6.1 Hz, 2H), 2.20 (m, 2H); $^{13}$C NMR (75

MHz, CDCl$_3$) δ 158.3, 140.2, 139.2, 133.5, 128.1, 127.4, 126.8, 114.8, 80.7 (d, J$_{CF}$=165 Hz), 65.1, 63.7 (d, J$_{CF}$=7.5 Hz), 30.4 (d, J$_{CF}$=22.5 Hz); HRMS-TOF (m/z): [M+Na]$^+$ HRMS: Calcd. for C$_{16}$H$_{17}$FO$_2$: 261.1285, found 261.1282.

Part C—Preparation of 2-(tert-butyl)-4-chloro-5-((4'-(3-fluoropropoxy)-[1,1'-biphenyl]-4-yl)methoxy)pyridazin-3(2H)-one

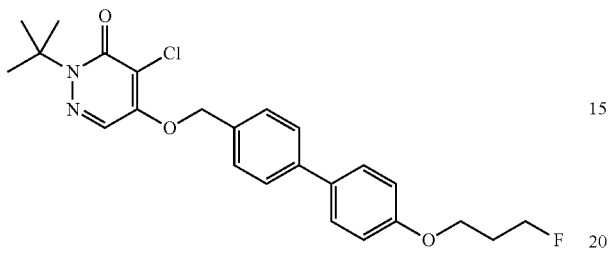

Prepared according to General Procedure B, using 2-(tert-butyl)-4,5-dichloropyridrazin-3(2H)-one (0.120 g, 0.540 mmol), the product of Example 47B (0.170 g, 0.650 mmol), and cesium carbonate (0.265 g, 0.816 mmol) in dimethylformamide (6.5 mL) at 65° C. Isolated yield—12.7 mg; 5.3%. $^1$H NMR (CDCl$_3$, 300 MHz): δ 7.53 (s, 1H), 7.49-7.38 (m, 6H), 6.94-6.85 (m, 2H), 5.53 (s, 2H), 4.67 (t, J=5.7 Hz, 1H), 4.51 (t, J=5.7 Hz, 1H), 4.07 (t, J=6.1 Hz, 2H), 2.12 (m, 2H), 1.57 (s, 9H); $^{13}$C NMR (CDCl$_3$, 75 MHz): δ 160.7, 158.4, 150.5, 140.8, 134.9, 133.3, 129.0, 128.1, 126.6, 124.5, 114.8, 80.7 (d, J$_{CF}$=165 Hz), 73.4, 65.7, 63.6 (d, J$_{CF}$=22.5 Hz), 30.5 (d, J$_{CF}$=7.5 Hz), 27.8; HRMS-TOF (m/z): [M +Na]$^+$ HRMS: Calcd. for C$_{24}$H$_{26}$$^{35}$ClFN$_2$O$_3$: 445.1689, found 445.1684.

Example 48

Preparation of 2-(tert-butyl)-4-chloro-5-((4-(2-fluoropyrimidin-5-yl)-benzyl)oxy)pyridazin-3(2H) one Part A—Preparation of 2-(tert-butyl)-4-chloro-5-((4-(4, 4, 5, 5-tetramethyl-1,3,2-dioxaborolan-2-yl)benzyl)oxy)pyridazin-3(2H)-one

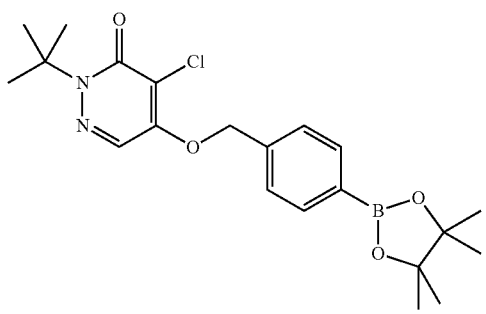 [SMILES: CC(C)(C)n1ncc(OCc2ccc(B3OC(C)(C)C(C)(C)O3)cc2)c(Cl)c1=O]

A solution of 2-(tert-butyl)-4-chloro-5-hydroxypyridrazin-3(2H)-one (0.537 g, 2.65 mmol) in tetrahydrofuran (22.1 mL) was successively treated with (4-(4,4,5,5-tetramethyl-1,3,2-dioxaborolan-2-yl)phenyl)methanol (0.745 g, 3.18 mmol), triphenylphosphine (1.04 g, 3.97 mmol), and diisopropylazodicarboxylate (0.782 mL, 3.97 mmol) at ambient temperature. After 45 min, the resulting mixture was diluted with water (20 mL), the aqueous layer separated then extracted with ethyl acetate (3×50 mL). The combined organic layers were dried over sodium sulfate, filtered and concentrated in vacuo. The crude material was suspended in diethyl ether, stirred 3 h then collected by filtration and purified by silica gel chromatography using 4:1 hexane/ethyl acetate to afford the desired product as a white solid (0.347 g, 31.3% yield). $^1$H NMR (300 MHz, DMSO-d6): δ 8.22 (s, 1H), 7.73 (d, J=8.0 Hz, 2H), 7.47 (d, J=8.0 Hz, 2H), 5.49 (s, 2H), 1.57 (s, 9H), 1.30 (s, 12H); $^{13}$C NMR (75 MHz, DMSO-d6, partial): δ 157.7, 153.5, 138.6, 134.7, 126.9, 125.1, 115.6, 83.7, 71.1, 65.3, 27.4, 24.6; HRMS-TOF (m/z): [M+Na]$^+$ HRMS: Calcd. for C$_{21}$H$_{28}$B$^{35}$ClN$_2$O$_4$: 419.1907, found 419.1903.

Part B—Preparation of 2-(tert-butyl)-4-chloro-5-((4-(2-chloropyrimidin-5-yl)benzyl)oxy)pyridazin-3(2H)-one

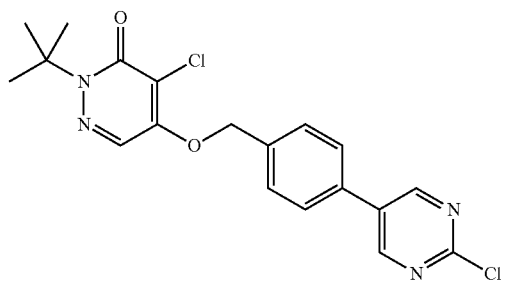 [SMILES: CC(C)(C)n1ncc(OCc2ccc(-c3cnc(Cl)nc3)cc2)c(Cl)c1=O]

2-Chloro-5-bromopyrimidine (41.3 mg, 0.215 mmol) and tetrakis(triphenylphosphine) palladium (0) (7.0 mg, 2.5 mol %) were dissolved in 1,2-dimethoxyethane (1.0 mL) at ambient temperature, maintained 15 min then successively treated with the product of Example 48A (0.090 g, 0.215 mmol) as a solution in 1,2-dimethoxyethane (1.2 mL) and aqueous potassium carbonate (0.43 mL, 0.43 mmol). The resulting mixture was warmed to 80° C., maintained 1.5 h then cooled to ambient temperature and diluted with water (2 mL). The aqueous layer was separated then extracted with ethyl acetate (3×10 mL), and the combined organic layers dried over sodium sulfate, filtered and concentrated to a light yellow solid (59.0 mg, 67.7% yield). $^1$H NMR (DMSO-d$_6$, 300 MHz): δ 9.26 (s, 2H), 8.40 (s, 1H), 8.01 (d, J=8.3 Hz, 2H), 7.75 (d, J=8.3 Hz, 2H), 5.65 (s, 2H), 1.69 (s, 9H); $^{13}$C NMR (75 MHz, DMSO-d$_6$): δ 159.0, 158.0, 157.7, 153.7, 136.5, 132.6, 131.7, 128.5, 127.3, 126.1, 115.7, 70.9, 65.4, 27.5

Part C—Preparation of 2-(tert-butyl)-4-chloro-5-((4-(2-fluoropyrimidin-5-yl)benzyl)oxy)pyridazin-3(2H)-one

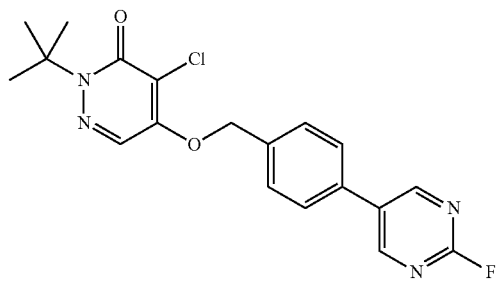 [SMILES: CC(C)(C)n1ncc(OCc2ccc(-c3cnc(F)nc3)cc2)c(Cl)c1=O]

A solution of the product of Example 48B (97.0 mg, 0.024 mmol), in dimethyl sulfoxide (0.25 mL) was treated with potassium fluoride (1.43 mg, 0.024 mmol) and Kryptofix™ (18 mg, 0.48 mmol) then heated to 80° C. and maintained 10 min. The resulting mixture was cooled to ambient temperature then diluted with 1 mL of dichloromethane and directly purified by preparative thin layer chromatography on silica using 4:1 hexanes/ethyl acetate to afford the desired product as a white solid (1.3 mg, 13.9% yield). $^1$H NMR (DMSO-d$_6$, 600 MHz): δ 9.22 (d, J=1.6 Hz, 2H), 8.35 (s, 1H), 7.96-7.90 (m, 2H), 7.69 (d, J=8.3 Hz, 2H), 5.81 (s, 2H), 1.64 (s, 9H); $^{13}$C NMR (DMSO-d$_6$, 150 MHz, partial): δ 159.3 (d, $J_{CF}$=15 Hz), 136.2, 129.5, 128.5, 127.2, 126.1, 71.0, 65.4, 27.4; $^{19}$F NMR (DMSO-d$_6$, 262 MHz): δ -49.19 (br s, 1H).

Example 49

Preparation of 2-(tert-butyl)-4-chloro-5-((4-(4-(fluoromethyl)phenyl)but-3-yn-1-yl)oxy)pyridazin-3(2H)-one Part A—Preparation of 2-(tert-butyl)-4-chloro-5-((4-(4-hydroxymethyl)phenyl)but-3-yn-1-yl)oxy)pyridazin-3(2H)-one

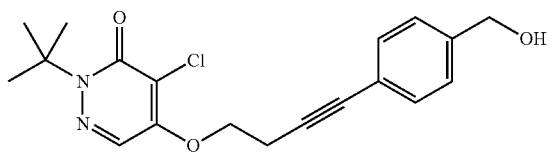 [SMILES: CC(C)(C)n1ncc(OCCC#Cc2ccc(CO)cc2)c(Cl)c1=O]

2-(tert-Butyl)-4-chloro-5-hydroxypyridrazin-3(2H)-one (62.0 mg, 0.368 mmol), triphenylphosphine (0.145 g, 0.552 mmol) and methyl 4-(4-hydroxybut-1-yn-1-yl) benzoate (74.4 mg, 0.442 mmol)$^1$ were combined in dry tetrahydrofuran (3.7 mL), then cooled to 0° C. and treated with diethyl azodicarboxylate (0.109 mL, 0.552 mmol). The resulting mixture warmed slowly to ambient temperature, and after 1.5 h was diluted with water (10 mL). The aqueous layer was separated then extracted with ethyl acetate (3×20 mL), and the combined organic layers dried over sodium sulfate, filtered and concentrated in vacuo. The crude material was purified by silica gel chromatography (0-80% ethyl acetate in hexanes) to afford the desired product (40 mg).

A cooled (0° C.) solution of the ester (40.0 mg, 0.103 mmol) in tetrahydrofuran (1.0 mL) was treated with a solution of lithium aluminum hydride (0.05 mL, 0.05 mmol, 1 M in tetrahydrofuran) then warmed to ambient temperature. After 2 h, the resulting mixture was diluted with water (2 mL), the aqueous layer separated then extracted with ethyl acetate (3×5 mL). The combined organic layers were dried over sodium sulfate, filtered and concentrated in vacuo. The crude material was purified by silica gel chromatography (0-20% ethyl acetate in hexanes) to afford the desired product (31.5 mg, 23.7% yield). $^1$H NMR (CDCl$_3$, 300 MHz): δ 7.72 (s, 1H), 7.33-7.28 (m, 2H), 7.24-7.18 (m, 2H), 4.61 (s, 2H), 4.35 (t, J=6.8 Hz, 2H), 2.89 (t, J=6.88 Hz, 2H); 1.57 (s, 9H); $^{13}$C NMR (CDCl$_3$, 75 MHz): δ 159.0, 153.6, 141.0, 131.7, 126.7, 125.1, 122.0, 118.3, 84.2, 82.8, 68.4, 66.4, 64.8, 27.8, 20.8; HRMS-TOF (m/z): [M+H]$^+$ HRMS: Calcd. for C$_{19}$H$_{21}$$^{35}$ClN$_2$O$_3$: 361.1313, found 361.1315.

Part B—Preparation of 2-(tert-butyl)-4-chloro-5-((4-(4-(fluoromethyl)phenyl)but-3-yn-1-yl)oxy)pyridazin-3(2H)-one

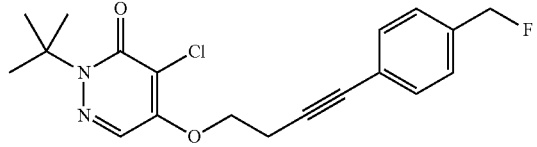 [SMILES: CC(C)(C)n1ncc(OCCC#Cc2ccc(CF)cc2)c(Cl)c1=O]

A cooled (0° C.) solution of the product of Example 49A (31.8 mg, 0.088 mmol) in dichloromethane (1.0 mL) was treated with Deoxofluor (21.3 mg, 0.096 mmol; 50% in toluene) and maintained 1.5 h. The resulting mixture was diluted with water (1 mL), the aqueous layer separated then extracted with dichloromethane (3×2 mL). The combined organic layers were dried over sodium sulfate, filtered and concentrated in vacuo. The crude material was then purified by preparative thin layer chromatography on silica using 4:1 hexanes/ethyl acetate to afford the desired product (11.5 mg, 36.0% yield). $^1$H NMR (CDCl$_3$, 300 MHz): δ 7.71 (s, 1H), 7.37-7.29 (m, 2H), 7.26-7.19 (m, 2H), 5.37 (s, 1H), 5.21 (s, 1H), 4.35 (t, J=6.8 Hz, 2H), 2.90 (t, J=6.8 Hz, 2H), 1.57 (s, 9H); $^{13}$C NMR (CDCl$_3$, 75 MHz): δ 159.0, 153.6, 136.2 (d, $J_{CF}$=22.5 Hz), 131.8, 127.2 (d, $J_{CF}$=7.5 Hz), 125.1, 123.3, 118.3, 84.0 (d, $J_{CF}$=165 Hz), 84.8, 82.5, 68.3, 66.4, 27.8, 20.8; HRMS-TOF (m/z): [M+H]$^+$ HRMS: Calcd. for C$_{19}$H$_{20}$$^{35}$ClFN$_2$O$_3$: 363.1270, found 363.1268.

Example 50

Preparation of 2-(tert-butyl)-4-chloro-5-((2,3,5-dichloro-4-(3-fluoropropoxy)benzyl)oxy)pyridazin-3(2H)-one Part A—Preparation of (2,3,5-dichloro-4-(3-fluoropropoxy)phenyl)methanol

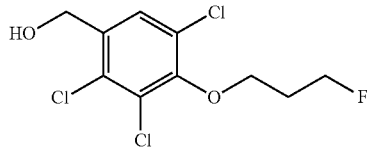 [SMILES: OCc1cc(Cl)c(OCCCF)c(Cl)c1Cl]

Prepared according to General Method F, using 2,3,5-dichloro-4-hydroxymethylbenzoate (1.00 g, 4.52 mmol), 3-fluoropropyl p-toluenesulfonate (1.26 g, 5.42 mmol), and cesium carbonate (2.35 g, 7.23 mmol) in dimethylformamide (45.0 mL) at 65° C. Isolated yield—0.650 g; 50.4%.

A solution of the crude ester (63.0 mg, 0.200 mmol) dissolved in ethanol (2.0 mL) was treated with sodium borohydride (5.7 mg, 0.15 mmol) in one portion at ambient temperature. The resulting mixture was stirred 2 d then diluted with water (20 mL) and concentrated in vacuo to remove the ethanol. The resulting aqueous solution was extracted with ethyl acetate (3×100 mL) and the combined organic layers dried over sodium sulfate, filtered and concentrated in vacuo. The crude material was purified by silica gel chromatography using 4:1 hexanes/ethyl acetate to afford the desired product (52.7 mg, 91.6% yield). $^1$H NMR (CDCl$_3$, 300 MHz): δ 7.42 (s, 1H), 4.75 (t, J=5.8 Hz, 1H), 4.66 (s, 2H), 4.59 (t, J=5.8 Hz, 1H), 4.07 (t, J=6.0 Hz, 2H), 2.16 (m, 2H); $^{13}$C NMR (CDCl$_3$, 150 MHz): δ 151.3, 136.3, 129.8, 129.0, 127.7, 127.0, 80.6 (d, J$_{CF}$=165 Hz), 69.3 (d, J$_{CF}$=7.5 Hz), 62.3, 31.1 (d, J$_{CF}$=22.5 Hz).

Part B—Preparation of 2-(tert-butyl)-4-chloro-5-((2,3,5-dichloro-4-(3-fluoropropoxy)benzyl)oxy)pyridazin-3(2H)-one

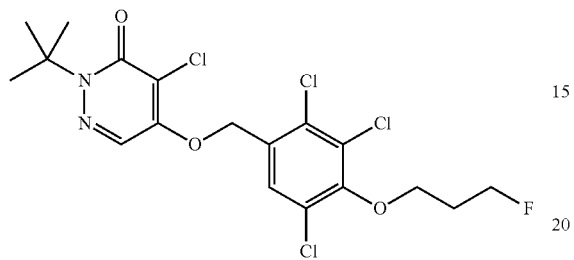

Prepared according to General Method B, using 2-(tert-butyl)-4,5-dichloropyridrazin-3(2H)-one (39.2 mg, 0.178 mmol), the product of Example 50A (61.2 mg, 0.213 mmol), and cesium carbonate (92.5 mg, 0.284 mmol) in dimethylformamide (1.7 mL) at 65° C. Isolated yield—23.0 mg; 27.4%. $^1$H NMR (CDCl$_3$, 300 MHz): δ 7.89-7.68 (br s, 1H), 7.67-7.41 (br s, 1H), 5.32 (s, 2H), 4.93-4.74 (m, 1H), 4.75-4.54 (m, 1H), 4.19 (m, 2H), 2.41-2.11 (m, 2H), 1.56 (s, 9H); $^{13}$C NMR (CDCl$_3$, 75 MHz) δ 158.8, 153.1, 152.5, 130.7, 130.0, 129.6, 128.2, 127.4, 124.7, 118.7, 80.4 (d, J$_{CF}$=165 Hz), 69.4 (d, J$_{CF}$=7.5 Hz), 68.6, 66.6, 31.1 (d, J$_{CF}$=22.5 Hz), 27.8; HRMS: Calcd. for C$_{18}$H$_{19}$$^{35}$Cl$_4$FN$_2$O$_3$: 471.0207, found 471.0206.

Example 51

Preparation of 2-(tert-butyl)-4-chloro-5-(4-((2-fluoroethoxy)methyl)phenyl)pyridazin-3(2H)-one Part A—Preparation of 5-((4-(1,3-dioxolan-2-yl)phenyl)-2-(tert-butyl)-4-chloropyridazin-3(2H)-one

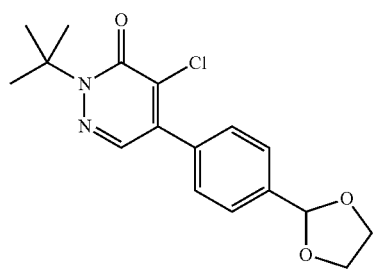 [SMILES: CC(C)(C)n1ncc(-c2ccc(C3OCCO3)cc2)c(Cl)c1=O]

A cooled (0° C.) solution of 2-(tert-butyl)-4,5-dichloropyridrazin-3(2H)-one (3.00 g, 13.6 mmol) in diethyl ether (6.5 mL) was treated with (4-(1,3-dioxolan)-2-yl)phenyl magnesium bromide solution (27.3 mL, 13.6 mmol, 0.5 M in tetrahydrofuran) and maintained 30 min. The resulting mixture was diluted with water (20 mL), the aqueous layer separated then extracted with ethyl acetate (3×50 mL). The combined organic layers were dried over sodium sulfate, filtered and concentrated in vacuo. The crude material was then purified by silica gel purification (0-30% ethyl acetate in hexanes) to afford the desired product as a white solid (2.87 g, 63.0% yield). $^1$H NMR (CDCl$_3$, 300 MHz) δ 7.81 (s, 1H), 7.59 (d, J=8.1 Hz, 2H), 7.48 (d, J=8.4 Hz, 2H), 5.91 (s, 1H), 4.25-3.94 (m, 4H), 1.68 (s, 9H).

Part B—Preparation of 2-(tert-butyl)-4-chloro-5-((4-(2-hydroxyethoxy)methyl)phenyl)pyridazin-3(2H)-one

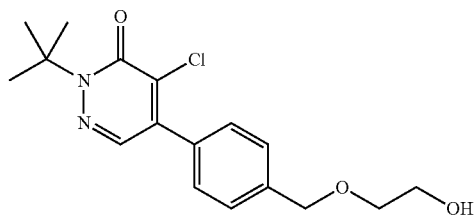 [SMILES: CC(C)(C)n1ncc(-c2ccc(COCCO)cc2)c(Cl)c1=O]

A solution of the product of Example 51A (0.342 g, 1.02 mmol) in tetrahydrofuran (2.0 mL) was added dropwise to a suspension of zirconium chloride (0.238 g, 1.02 mmol) and sodium borohydride (77.3 mg, 2.04 mmol) in tetrahydrofuran (3.1 mL) at ambient temperature. After 3 h, the resulting mixture was diluted with water (10 mL), the aqueous layer separated then extracted with ethyl acetate (3×20 mL). The combined organic layers were dried over sodium sulfate, filtered and concentrated to a clear oil (0.322 g, 93.7% yield). $^1$H NMR (CDCl$_3$, 300 MHz): δ 7.72 (s, 1H), 7.36 (br s, 4H), 4.54 (s, 2H), 3.70 (m, 2H), 3.56 (m, 2H), 1.59 (s, 9H); $^{13}$C NMR (CDCl$_3$, 75 MHz): 159.6, 153.2, 139.0, 135.1, 134.9, 131.0, 129.8, 127.2, 72.9, 71.4, 66.0, 61.9, 27.8; HRMS-TOF (m/z): [M+H]$^+$ HRMS: Calcd. for C$_{17}$H$_{21}$$^{35}$ClFN$_2$O$_3$: 337.1313, found 337.1311.

Part C—Preparation of 2-(tert-butyl)-4-chloro-5-(4-((2-fluoroethoxy)methyl)phenyl)pyridazin-3(2H)-one

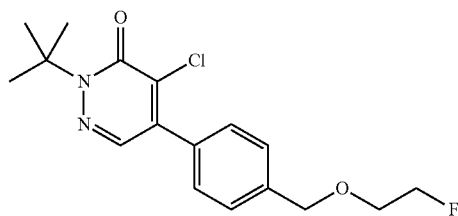 [SMILES: CC(C)(C)n1ncc(-c2ccc(COCCF)cc2)c(Cl)c1=O]

A cooled (0° C.) solution of the product of Example 51B (0.100 g, 0.297 mmol) in dichloromethane (3.0 mL) was treated with Deoxofluor (72.3 mg, 0.326 mmol; 50% in toluene) and maintained 2 h. The resulting mixture was diluted with water (10 mL), the aqueous layer separated then extracted with dichloromethane (3×10 mL). The combined organic layers were dried over sodium sulfate, filtered and concentrated in vacuo. The crude material was then purified by preparative thin layer chromatography on silica using 4:1 hexanes/ethyl acetate to afford the desired product as a white solid (19.7 mg, 19.6% yield). $^1$H NMR (CDCl$_3$, 300 MHz): δ 7.72 (s, 1H), 7.36 (s, 4H), 4.60 (m, 1H), 4.57 (s, 2H), 4.46-4.39 (m, 1H), 3.75-3.68 (m, 1H), 3.65-3.58 (m, 1H), 1.58 (s, 9H); $^{13}$C NMR (CDCl$_3$, 75 MHz): δ 159.6, 153.1, 138.8, 135.1, 134.9, 131.0, 129.8, 127.2, 83.0 (d, $J_{CF}$=165 Hz), 72.9, 69.2 (d, $J_{CF}$=22.5 Hz), 66.0, 27.8; HRMS-TOF (m/z): [M+H]$^+$ HRMS: Calcd. for C$_{17}$H$_{20}$$^{35}$ClFN$_2$O$_2$: 339.1270, found 339.1268.

Example 52

Preparation of 2-(tert-butyl)-4-chloro-5-(4-(3-fluoropropyl)phenoxy)pyridazin-3(2H)-one Part A—Preparation of methyl 3-(4-((1-(tert-butyl)-5-chloro-6-oxo-1,6-dihydropyridazin-4-yl)oxy)phenyl)propanoate

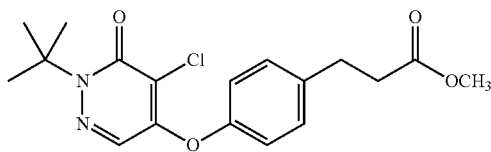 [SMILES: COC(=O)CCc1ccc(Oc2cnn(C(C)(C)C)c(=O)c2Cl)cc1]

Prepared according to General Method B, using 2-(tert-butyl)-4,5-dichloropyridrazin-3(2H)-one (0.750 g, 3.39 mmol), methyl 3-(4-hydroxyphenyl)propionate (0.734 g, 4.07 mmol), and cesium carbonate (1.76 g, 5.43 mmol) in dimethylformamide (34.0 mL) at room temperature overnight. Isolated yield—0.960 g; 77.6%. $^1$H NMR (CDCl$_3$, 300 MHz): δ 7.40 (s, 1H), 7.25 (d, J=7.8 Hz, 2H), 7.05-6.99 (m, 2H), 3.68 (s, 3H), 2.97 (m, 2H), 2.64 (m, 2H), 1.64 (s, 9H); $^{13}$C NMR (CDCl$_3$, 75 MHz) δ 172.9, 158.9, 152.9, 152.2, 138.2, 130.1, 127.0, 120.2, 119.8, 66.4, 51.6, 35.5, 30.1, 27.8; HRMS: Calcd. for C$_{18}$H$_{21}$$^{35}$ClN$_2$O$_4$: 365.1263, found 365.1259.

Part B—Preparation of 2-(tert-butyl)-4-chloro-5-(4-(3-hydroxypropyl)phenoxy)pyridazin-3(2H)-one

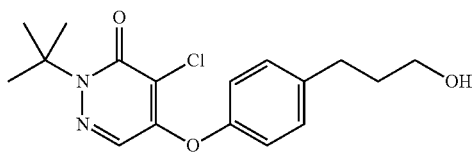 [SMILES: CC(C)(C)n1ncc(Oc2ccc(CCCO)cc2)c(Cl)c1=O]

A cooled (0° C.) solution of the product of Example 52A (0.473 g, 1.30 mmol) in tetrahydrofuran (13 mL) was treated with lithium aluminum hydride (0.65 mL, 0.65 mmol, 1 M in tetrahydrofuran) then warmed to ambient temperature. After 1 h, the resulting mixture was diluted with water (10 mL), the aqueous layer separated then extracted with ethyl acetate (3×50 mL). The combined organic layers were washed with saturated aqueous sodium chloride, dried over sodium sulfate, filtered, and concentrated to a light yellow solid (0.384 g, 87.7%). $^1$H (CDCl$_3$, 600 MHz): δ 7.40 (s, 1H), 7.25 (d, J=7.7 Hz, 2H), 7.05-6.98 (m, 2H), 3.75-3.65 (m, 2H), 2.79-2.68 (m, 2H), 1.97-1.82 (m, 2H), 1.65 (s, 9H); $^{13}$C NMR (CDCl$_3$, 150 MHz) δ 158.9, 153.0, 151.9, 139.6, 130.1, 127.0, 120.0, 119.7, 66.4, 61.9, 34.1, 31.3, 27.8; HRMS-TOF (m/z): [M+H]$^+$ HRMS: Calcd. for C$_{17}$H$_{21}$$^{35}$ClN$_2$O$_3$: 337.1313, found 337.1319.

Part C—Preparation of 2-(tert-butyl)-4-chloro-5-(4-(3-fluoropropyl)phenoxy)pyridazin-3(2H)-one

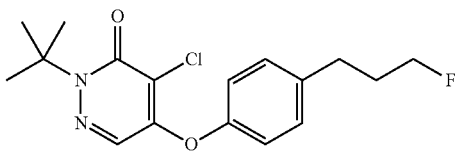 [SMILES: CC(C)(C)n1ncc(Oc2ccc(CCCF)cc2)c(Cl)c1=O]

A cooled (0° C.) solution of the product of Example 52B (50.0 mg, 0.149 mmol) in dichloromethane (0.1 mL) was treated with Deoxofluor (36.0 mg, 0.164 mmol; 50% in toluene) and maintained 1.5 h. The resulting mixture was diluted with water (1 mL), the aqueous layer separated then extracted with dichloromethane (2×10 mL). The combined organic portions were dried over sodium sulfate, filtered and concentrated in vacuo. The crude material was then purified by silica gel chromatography (0-50% ethyl acetate in hexanes) to afford the desired product as a yellow oil (5.6 mg, 11.1% yield). $^1$H NMR (CDCl$_3$, 600 MHz, contains small amount of alcohol starting material): δ 7.34 (s, 1H), 7.18 (d, J=8.0 Hz, 2H), 6.96 (m, 2H), 4.48 (t, J=5.8 Hz, 1H), 4.32 (t, J=5.8 Hz, 1H), 3.47 (t, J=6.3 Hz, 2H), 2.02 (m, 2H), 1.58 (s, 9H); $^{13}$C NMR (CDCl$_3$, 150 MHz, contains small amount of alcohol starting material): δ 157.9, 151.9, 151.1, 137.8, 129.3 (129.2), 126.0, 118.8, 81.8 (d, $J_{CF}$=165 Hz), 65.4, 42.9, 31.1 (d, $J_{CF}$=22.5 Hz), 29.7 (d, $J_{CF}$=7.5 Hz), 26.84; HRMS-TOF (m/z): [M+H]$^+$ HRMS: Calcd. for C$_{17}$H$_{20}$$^{35}$ClFN$_2$O$_2$: 339.1270, found 339.1268.

Example 53

Preparation of 2-(tert-butyl)-4-chloro-5-((2-fluoropyridin-3-yl)oxy)pyridazin-3(2H)-one Part A—Preparation of 2-(tert-butyl)-4-chloro-5-((2-nitropyridin-3-yl)oxy)pyridazin-3(2H)-one

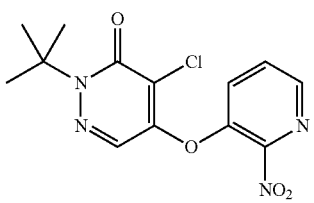 [SMILES: CC(C)(C)n1ncc(Oc2cccnc2[N+](=O)[O-])c(Cl)c1=O]

Prepared according to General Method B, using 2-(tert-butyl)-4,5-dichloropyridrazin-3(2H)-one (0.221 g, 1.00 mmol), 2-nitropyridin-3-ol (0.140 g, 1.00 mmol), and cesium carbonate (0.170 g, 0.52 mmol) in dimethylformamide (2.0 mL) at 80° C. Isolated yield—0.120 g; 37.0%. $^{1}$H NMR (300 MHz, DMSO-d$_{6}$): δ 8.52 (dd, J=4.5, 1.3 Hz, 1H), 8.22 (dd, J=8.4, 1.3 Hz, 1H), 8.00 (s, 1H), 7.92 (dd, J=8.4, 4.5 Hz, 1H), 1.60 (s, 9H); $^{13}$C NMR (75 MHz, DMSO-d$_{6}$): δ 157.62, 151.15, 144.95, 142.38, 138.09, 132.05, 130.95, 128.14, 121.01, 65.99, 27.33. HRMS Calcd. for C$_{13}$H$_{13}$$^{35}$ClN$_{4}$O$_{4}$ (M+H): 325.0698; found: 325.0697.

Part B—Preparation of 2-(tert-butyl)-4-chloro-5-((2-fluoropyridin-3-yl)oxy)pyridazin-3(2H)-one

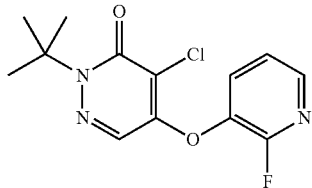 [SMILES: CC(C)(C)n1ncc(Oc2cccnc2F)c(Cl)c1=O]

A solution of the product of Example 53A (35.7 mg, 0.110 mmol), potassium fluoride (9.0 mg, 0.15 mmol), and Kryptofix™ (60.2 mg, 0.16 mmol) in dimethylsulfoxide (2.5 mL) was heated to 125° C. and maintained 30 min. The resulting mixture was then cooled to ambient temperature and diluted with ethyl acetate (40 mL). The organic layer was separated then washed with water (2×50 mL) and saturated aqueous sodium chloride, dried over magnesium sulfate, filtered and concentrated in vacuo. The crude material was then purified by silica gel chromatography (10-40% ethyl acetate in hexanes) to afford the desired product as colorless oil (25.0 mg, 76.3% yield). $^{1}$H NMR (300 MHz, DMSO-d$_{6}$): δ 8.14 (dt, J=4.8, 1.6 Hz, 1H), 8.00 (ddd, J=10.2, 7.9, 1.6 Hz, 1H), 7.93 (s, 1H), 7.45 (ddd, J=7.9, 4.8, 0.9 Hz, 1H), 1.60 (s, 9H); $^{13}$C NMR (75 MHz, DMSO-d$_{6}$): δ 157.63, 151.52, 143.31 (d, J$_{CF}$=13.5 Hz), 136.40, 136.04, 131.60 (d, J$_{CF}$=3.0 Hz), 127.70, 123.54 (d, J$_{CF}$=4.5 Hz), 120.18, 65.94, 27.34; $^{19}$F NMR (282 MHz, DMSO-d6): δ −83.96 (d, J=10.2 Hz). HRMS Calcd. for C$_{13}$H$_{13}$$^{35}$ClFN$_{3}$O$_{2}$ (M+H): 298.0753; found: 298.0753.

Example 54

Preparation of 2-(tert-butyl)-4-chloro-5-((4-(6-nitro-pyridin-3-yl)benzyl)oxy)pyridazin-3(2H)-one

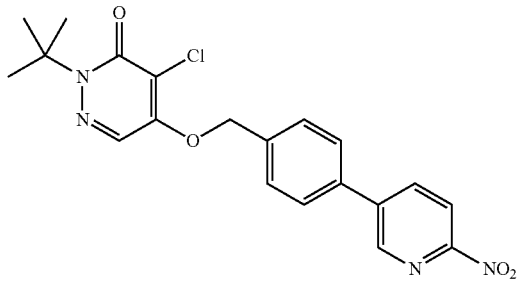 [SMILES: CC(C)(C)n1ncc(OCc2ccc(-c3ccc([N+](=O)[O-])nc3)cc2)c(Cl)c1=O]

A solution of 5-bromo-2-nitropyridine (50.7 mg, 0.250 mmol) and tetrakis (triphenylphosphine) palladium (0) (6.7 mg; 2.3 mol %) in dimethoxyethane (1.5 mL), was successively treated with the product of Example 48A (0.105 g, 0.250 mmol) as a solution in 1.5 mL dimethoxyethane, and aqueous potassium carbonate (0.50 mmol; 0.50 mL) at ambient temperature. The resulting mixture was heated to 80° C., maintained 2 h then cooled back to ambient temperature and diluted with ethyl acetate (50 mL). The organic layer was separated, washed with water (2×50 mL) and saturated aqueous sodium chloride then dried over magnesium sulfate, filtered and concentrated in vacuo. The crude material was then purified by silica gel chromatography (20-50% ethyl acetate in hexanes) to afford the desired product as a faint yellow solid (75.0 mg, 72.3% yield). $^{1}$H NMR (300 MHz, DMSO-d$_{6}$): δ 9.46 (dd, J=2.7, 0.7 Hz, 1H), 8.68 (dd, J=8.8, 2.7 Hz, 1H), 8.36-8.23 (m, 4H), 7.71-7.61 (m, 2H), 5.57 (s, 2H), 1.58 (s, 9H); $^{13}$C NMR (75 MHz, DMSO-d$_{6}$): δ 160.45, 157.79, 153.78, 144.87, 143.15, 138.17, 136.64, 132.71, 128.22, 127.89, 126.17, 120.68, 115.73, 70.90, 65.43, 27.46. HRMS Calcd. for C$_{20}$H$_{19}$$^{35}$ClN$_{4}$O$_{4}$ (M+H): 415.1168; found: 415.1168.

Example 55

Preparation of 2-(tert-butyl)-4-chloro-5-((4-(6-fluoropyridin-3-yl)benzyl)oxy)pyridazin-3(2H)-one

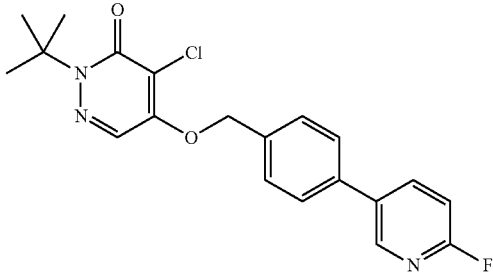 [SMILES: CC(C)(C)n1ncc(OCc2ccc(-c3ccc(F)nc3)cc2)c(Cl)c1=O]

A solution of 5-bromo-2-fluoropyridine (37.0 mg, 0.210 mmol) and tetrakis (triphenyl-phosphine) palladium (0) (9.0 mg; 3.9 mol %) in dimethoxyethane (1.0 mL) was successively treated with the product of Example 48A (85.0 mg, 0.200 mmol) as a solution in 1.0 mL dimethoxyethane, and aqueous potassium carbonate (0.50 mmol; 0.50 mL) at ambient temperature. The resulting mixture was heated to 80° C., maintained 2 h then cooled back to ambient temperature and diluted with ethyl acetate (50 mL). The organic layer was separated, washed with water (2×50 mL) and saturated aqueous sodium chloride then dried over magnesium sulfate, filtered and concentrated in vacuo. The crude material was then purified by silica gel chromatography (20-50% ethyl acetate in hexanes) to afford the desired product as white solid (50.0 mg, 64.5% yield). $^{1}$H NMR (300 MHz, DMSO-d$_{6}$): δ 8.58 (dt, J=2.6, 0.8 Hz, 1H), 8.38-8.24 (m, 2H), 7.87-7.74 (m, 2H), 7.65-7.54 (m, 2H), 7.30 (ddd, J=8.6, 2.9, 0.7 Hz, 1H), 5.52 (s, 2H), 1.58 (s, 9H); $^{13}$C NMR (75 MHz, DMSO-d$_{6}$) δ 157.79, 153.82, 145.45 (d, J$_{CF}$=15.0 Hz), 140.34 (d, J$_{CF}$=8.3 Hz), 136.01, 135.39, 133.62 (d, J$_{CF}$=4.5 Hz), 128.52, 127.17, 126.18, 115.67, 109.89, 109.39, 71.03, 65.40, 27.47; $^{19}$F NMR (282 MHz, DMSO-$d_6$): δ −70.87 (dd, J=8.0, 2.8 Hz). HRMS Calcd. for $C_{20}H_{19}{}^{35}ClFN_3O_2$(M+H): 388.1223; found: 388.1217.

Example 56

Preparation of 2-(tert-butyl)-4-chloro-5-((4-((2-fluoropyridin-3-yl)oxy)benzyl)oxy)pyridazin-3(2H)-one Part A—Preparation of 2-nitro-3-(p-tolyoxy)pyridine

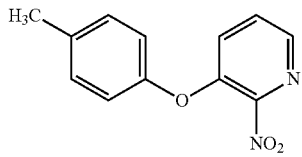 [SMILES: Cc1ccc(Oc2cccnc2[N+](=O)[O-])cc1]

A suspension of p-cresol (0.325 g, 3.00 mmol), 3-bromo-2-nitropyridine (0.404 g, 2.00 mmol), and potassium carbonate (0.345 g, 2.50 mmol) in acetonitrile (2.0 mL) was heated at 70° C. and maintained 16 h. The resulting mixture was cooled to room temperature and diluted with ethyl acetate (100 mL) then washed with water (2×100 mL) and saturated aqueous sodium chloride, dried over magnesium sulfate, filtered and concentrated in vacuo. The crude material was then purified by silica gel chromatography (0-20% ethyl acetate in hexanes) to obtain the desired product (46.0 mg, 10.0% yield). $^1$H NMR (300 MHz, CDCl$_3$): δ 8.22 (dd, J=4.4, 1.5 Hz, 1H), 7.48 (dd, J=8.4, 4.4 Hz, 1H), 7.41 (dd, J=8.4, 1.5 Hz, 1H), 7.31-7.19 (m, 2H), 7.05-6.95 (m, 2H), 2.39 (s, 3H); $^{13}$C NMR (75 MHz, CDCl$_3$, partial): δ 152.16, 146.82, 141.31, 135.46, 130.85, 128.53, 128.07, 119.74, 20.78.

Part B—Preparation of 3-(4-(bromomethyl)phenoxy)-2-nitropyridine

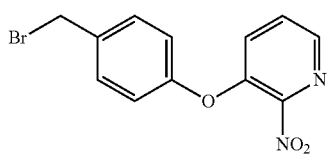 [SMILES: O=[N+]([O-])c1ncccc1Oc1ccc(CBr)cc1]

A solution of the product of Example 56A (0.039 g, 0.170 mmol), N-bromosuccinimide (35.0 mg, 0.200 mmol), and benzoyl peroxide (1 mg) in 1,2-dichloroethane (4.0 mL) was heated to reflux and maintained 2 h. The resulting mixture was cooled to room temperature and diluted with dichloromethane (20 mL), the organic layer separated then washed with water (2×20 mL) and saturated aqueous sodium chloride, dried over magnesium sulfate, filtered and concentrated. The crude yellow oil was then purified by silica gel chromatography (10-40% ethyl acetate in hexanes) to obtain the desired product as a faint yellow oil (45.0 mg, 85.6% yield). $^1$H NMR (300 MHz, CDCl$_3$) δ 8.30 (dd, J=4.3, 1.6 Hz, 1H), 7.59-7.43 (m, 4H), 7.12-7.02 (m, 2H), 4.52 (s, 2H); $^{13}$C NMR (75 MHz, CDCl$_3$, partial) δ 154.79, 145.77, 142.31, 135.07, 131.13, 129.28, 128.74, 119.64, 32.33.

Part C—Preparation of 2-(tert-butyl)-4-chloro-5-((4-((2-nitropyridin-3-yl)oxy)benzyl)oxy)pyridazin-3(2H)-one

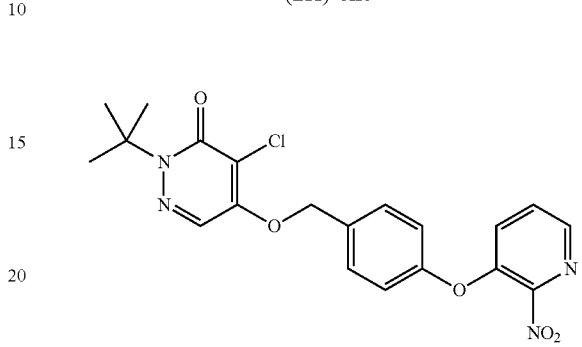

Prepared according to General Method B, using 2-(tert-butyl)-4-chloro-5-pyridazin-3(2H)-one (21.0 mg, 0.100 mmol), the product of Example 56B (31.0 mg, 0.100 mmol), and cesium carbonate (33.0 mg, 0.100 mmol) in dimethylformamide (1.0 mL) at 80° C. Isolated yield—20.0 mg; 46.4%. $^1$H NMR (300 MHz, CDCl$_3$): δ 8.22 (dd, J=4.3, 1.7 Hz, 1H), 7.68 (s, 1H), 7.54-7.34 (m, 4H), 7.04 (d, J=8.7 Hz, 2H), 5.23 (s, 2H), 1.57 (s, 9H); $^{13}$C NMR (75 MHz, CDCl$_3$, partial): δ 158.95, 155.27, 153.50, 145.64, 142.47, 131.98, 129.45, 129.39, 128.79, 124.98, 119.72, 118.54, 71.17, 66.53, 27.86. HRMS Calcd. for $C_{20}H_{19}{}^{35}ClN_4O_5$ (M+H): 431.1117; found: 431.1110.

Part D—Preparation of 2-(tert-butyl)-4-chloro-5-((4-((2-fluoropyridin-3-yl)oxy)benzyl)oxy)pyridazin-3(2H)-one

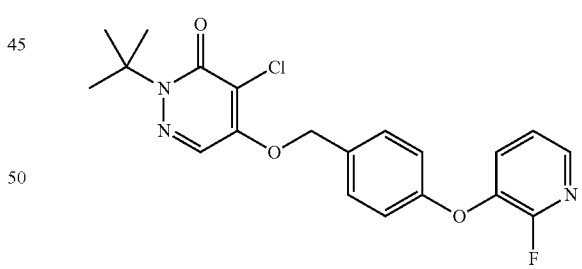

A solution of the product of Example 56C (12.0 mg, 0.030 mmol), potassium fluoride (3.5 mg, 0.06 mmol), and Kryptofix™ (26.0 mg, 0.070 mmol) in dimethylsulfoxide (2.0 mL) was heated to 125° C. and maintained 30 min. The resulting mixture was cooled to room temperature and diluted with ethyl acetate (40 mL) then washed with water (2×40 mL) and saturated aqueous sodium chloride, dried over magnesium sulfate, filtered and concentrated. The crude material was then purified by preparative thin layer chromatography on silica (1% methanol in dichloromethane) to obtain the desired product (9.0 mg, 74.3% yield). $^1$H NMR (300 MHz, CDCl$_3$): δ 7.94 (d, J=4.7 Hz, 1H), 7.67 (s, 1H), 7.47-7.30 (m, 3H), 7.12 (ddd, J=7.9, 4.8, 0.9 Hz, 1H), 7.02-6.90 (m, 2H), 5.21 (s, 2H), 1.57 (s, 9H); $^{13}$C NMR (75 MHz, CDCl$_3$): δ 159.00, 156.99, 156.75, 153.80, 153.60, 141.76 (d, $J_{CF}$=13.5 Hz), 130.60 (d, $J_{CF}$=3.8 Hz), 130.46, 129.12, 125.09, 122.19, 118.50, 118.03, 71.37, 66.47, 27.87; $^{19}$F NMR (282 MHz, CDCl$_3$): δ −81.30 (d, J=9.8 Hz). HRMS Calcd. for $C_{20}H_{19}{}^{35}ClFN_3O_3$ (M+H): 404.1172; found: 404.1176.

Example 57

Preparation of 3-fluoropropyl 4-(((1-(tert-butyl)-5-chloro-6-oxo-1,6-dihydropyridazin-4-yl)oxy)methyl) benzoate Part A—Preparation of 3-(tosyloxy) propyl 4-(((1-(tert-butyl)-5-chloro-6-oxo-1,6-dihydropyridazin-4-yl)oxy)methyl) benzoate

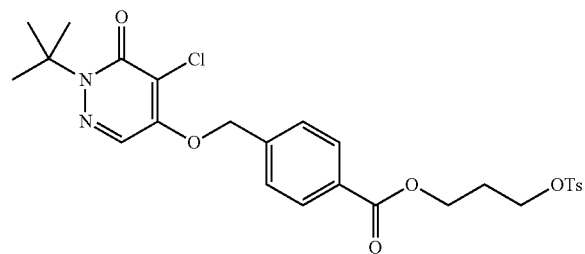 [SMILES: Cc1ccc(S(=O)(=O)OCCCOC(=O)c2ccc(COc3cnn(C(C)(C)C)c(=O)c3Cl)cc2)cc1]

A solution of methyl 4-(((1-(tert-butyl)-5-chloro-6-oxo-1,6-dihydropyridazin-4-yl)oxy)methyl)benzoate$^3$ (0.702 g, 2.00 mmol) in tetrahydrofuran/water (10.0 mL; 4:1 v/v) was cooled to 0° C. and treated with lithium hydroxide hydrate (0.252 g, 6.00 mmol) in one portion. After 0.25 h, the now opaque solution was warmed to ambient temperature and maintained 16 h. The resulting solution was then diluted with water (50 mL), with transfer to a separatory funnel, washed with diethyl ether (3×50 mL), and acidified with 1 M hydrochloric acid. The now acidic solution was further washed with warm ethyl acetate (3×50 mL) and the combined ethyl acetate washes dried over magnesium sulfate, filtered and concentrated in vacuo to a white powder. Subsequent recrystallization from hot ethyl acetate/pentane afforded the purified 4-(((1-(tert-butyl)-5-chloro-6-oxo-1,6-dihydropyridazin-4-yl)oxy)methyl)benzoic acid as colorless needles.

The intermediate acid thus obtained was dissolved in dry dimethylformamide (20.0 mL) then successively treated with propane-1,3-diyl bis(4-methylbenzenesulfonate) (1.15 g, 3.00 mmol) and potassium carbonate (0.415 g, 3.00 mmol) in one portion at ambient temperature. After 5 h, the resulting suspension was partitioned between ethyl acetate and water (50 mL each), with transfer to a separatory funnel, and the layers separated. The aqueous layer was then washed with ethyl acetate (2×50 mL) and the combined ethyl acetate washes dried over magnesium sulfate, filtered and concentrated in vacuo. The crude material was then purified by chromatography on silica using a step gradient from 7:3 pentane/ethyl acetate (500 mL) to 3:2 pentane/ethyl acetate (1000 mL). The main product peak eluting 1075-1275 mL was collected, pooled and concentrated in vacuo to a colorless oil (0.566 g, 1.03 mmol; 51.6%). $^1$H NMR: (300 MHz, DMSO-d$_6$) δ 8.25 (1H, s), 7.89 (2H, AA'BB', $J_{AB}$=8.3 Hz, $J_{AA'}$=2.0 Hz), 7.75 (2H, AA'BB', $J_{AB}$=8.3 Hz, $J_{AA'}$=2.0 Hz), 7.57 (2H, d, J=8.6 Hz), 7.35 (2H, d, J=7.9 Hz), 5.57 (2H, s), 4.23 (2H, d, J=5.9 Hz), 4.18 (2H, t, J=5.7 Hz), 2.27 (3H, s), 2.04 (2H, tt, J=5.9, 5.9 Hz), 1.57 (9H, s). $^{13}$C NMR: (75 MHz, DMSO-d$_6$) δ 165.0, 157.7, 153.7, 144.8, 140.8, 132.0, 130.0, 129.5, 129.4, 127.5, 126.1, 115.8, 70.7, 67.5, 65.4, 60.5, 27.5, 27.4, 20.9. HRMS Calcd. for $C_{26}H_{29}{}^{35}ClN_2O_7S$ (M+H): 549.1457; found: 549.1467. TLC: $R_f$ 0.33 (silica gel, 1:1 pentane/ethyl acetate, uv).

Part B—Preparation of 3-fluoropropyl 4-(((1-(tert-butyl)-5-chloro-6-oxo-1,6-dihydropyridazin-4-yl) oxy)methyl)benzoate

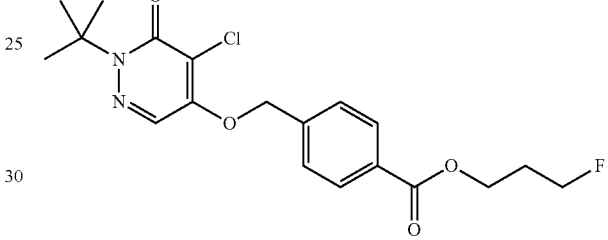

A solution of methyl 4-(((1-(tert-butyl)-5-chloro-6-oxo-1, 6-dihydropyridazin-4-yl)oxy)methyl)benzoate$^3$ (0.702 g, 2.00 mmol) in tetrahydrofuran/water (10.0 mL; 4:1 v/v) was cooled to 0° C. and treated with lithium hydroxide hydrate (0.252 g, 6.00 mmol) in one portion. After 0.25 h, the now opaque solution was warmed to ambient temperature and maintained 16 h. The resulting solution was then diluted with water (50 mL), with transfer to a separatory funnel, washed with diethyl ether (3×50 mL), and acidified with 1 M hydrochloric acid. The now acidic solution was further washed with warm ethyl acetate (3×50 mL) and the combined ethyl acetate washes dried over magnesium sulfate, filtered and concentrated in vacuo to a white powder.

The intermediate acid thus obtained was dissolved in dry dimethylformamide (5.00 mL) then successively treated with 3-fluoropropyl 4-methylbenzenesulfonate (0.697 g, 3.00 mmol) and potassium carbonate (0.415 g, 3.00 mmol) in one portion at ambient temperature. After 0.25 h, the resulting solution was warmed to 55° C., maintained 1.5 h, then cooled to ambient temperature and diluted with ethyl acetate (150 mL each) with transfer to a separatory funnel. The ethyl acetate solution thus obtained was then washed with saturated aqueous sodium chloride (5×50 mL), dried over magnesium sulfate, filtered and concentrated in vacuo to an amber oil. The crude material was then purified by chromatography on silica (30×200 mm) using 3:1 pentane/ ethyl acetate. The main product peak eluting 300-560 mL was collected, pooled and concentrated in vacuo to a white solid (0.680 g, 1.71 mmol; 85.7%). $^1$H NMR: (300 MHz, DMSO-d$_6$) δ 8.23 (1H, s), 8.03 (2H, AA'BB', $J_{AB}$=8.5 Hz, $J_{AA'}$=1.9 Hz), 7.60 (2H, AA'BB', $J_{AB}$=8.7 Hz, $J_{BB'}$=1.9 Hz), 5.56 (2H, s), 4.61 (2H, dt, J=47.2, 5.9 Hz), 4.38 (2H, t, J=6.3

Hz), 2.11 (2H, dtt, J=25.9, 6.1, 6.1 Hz) 1.57 (9H, s). $^{19}$F NMR: (282 MHz, DMSO-d$_6$) δ −220.4 (1F, tt, J=47.1, 25.8 Hz). $^{13}$C NMR: (75 MHz, DMSO-d$_6$) δ 165.3, 157.7, 153.7, 140.8, 129.6, 129.5, 127.5, 126.1, 115.8, 80.9 (d, J=161.9 Hz), 70.7, 65.4, 61.0 (d, J=5.6 Hz), 29.2 (d, J=19.6 Hz), 27.4. HRMS Calcd. for C$_{19}$H$_{22}$$^{35}$ClFN$_2$O$_4$ (M+H): 397.1325; found: 397.1330. TLC: R$_f$ 0.24 (silica gel, 3:1 pentane/ethyl acetate, uv).

Example 58

Preparation of 2-(tert-butyl)-4-chloro-5-((4-(2-(2-fluoroethoxy)propan-2-yl)benzyl)oxy) pyridazin-3(2H)-one Part A—Preparation of 2-(tert-butyl)-4-chloro-5-((4-(2-hydroxypropan-2-yl)benzyl)oxy)pyridazin-3(2H)-one

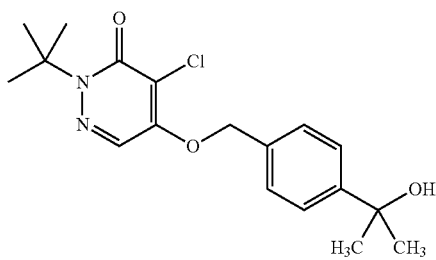 [SMILES: CC(C)(O)c1ccc(COc2cnn(C(C)(C)C)c(=O)c2Cl)cc1]

A solution of 2-(tert-butyl)-4,5-dichloropyridazin-3(2H)-one (0.995 g, 4.50 mmol) and 2-(4-(hydroxymethyl)phenyl)propan-2-ol (0.499 g, 3.00 mmol; e.g., see Machacek, Michelle R.; Haidle, Andrew; Zabierek, Anna A.; Konrad, Kaleen M.; Altman, Michael D. (Merck & Co., Inc.) Preparation of thiazolecarboxamides as inhibitors of Janus kinases. PCT Int. Appl. WO 2010/011375. Jan. 28, 2010) in dry dimethylformamide (15.0 mL) was treated with cesium carbonate (1.96 g, 6.00 mmol) in one portion at ambient temperature. The resulting suspension was then immersed in a pre-heated oil bath and maintained 2.5 h at 80° C. Left unattended, the suspension was cooled to ambient temperature and maintained 20 h. The resulting suspension was then partitioned between ethyl acetate (150 mL) and water (25 mL), with transfer to a separatory funnel, and the layers separated. The ethyl acetate layer was then washed with saturated aqueous sodium chloride (5×25 mL), dried over magnesium sulfate, filtered and concentrated in vacuo to an amber oil. The crude material was then purified by chromatography on silica (40×170 mm) using 3:2 hexanes/ethyl acetate. The main product peak eluting 400-700 mL was collected, pooled and concentrated in vacuo to a white solid. Subsequent recrystallization from hot ethyl acetate/pentane afford the desired product as colorless needles (0.682 g, 1.95 mmol; 64.9%). $^1$H NMR: (300 MHz, DMSO-d$_6$) δ 8.26 (s, 1H), 7.51 (2H, AB, J$_{AB}$=8.3 Hz), 7.39 (2H, AB, J$_{AB}$=8.3 Hz), 5.42 (s, 2H), 5.01 (s, 1H), 1.57 (s, 9H), 1.42 (s, 6H). $^{13}$C NMR: (75 MHz, DMSO-d$_6$) δ 157.8, 153.9, 151.0, 132.8, 127.4, 126.2, 124.8, 115.5, 71.4, 70.5, 65.3, 31.8, 27.4. HRMS Calcd. for C$_{18}$H$_{23}$$^{35}$ClN$_2$O$_3$ (M+H): 351.1470; found: 351.1474. TLC: R$_f$ 0.16 (silica gel, 7:3 hexanes/ethyl acetate, CAM).

Part B—Preparation of 2-(tert-butyl)-4-chloro-5-((4-(2-(2-fluoroethoxy)propan-2-yl)benzyl)oxy) pyridazin-3(2H)-one

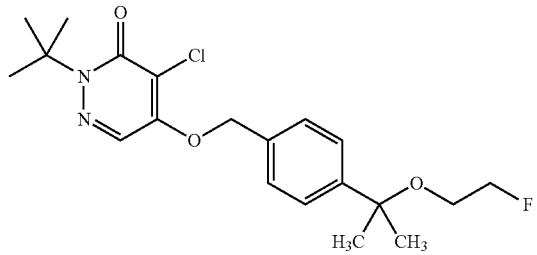 [SMILES: CC(C)(OCCF)c1ccc(COc2cnn(C(C)(C)C)c(=O)c2Cl)cc1]

A solution of the product of part A (0.105 g, 0.300 mmol) in 2-fluoroethanol (1.75 mL) was treated with 11.4 mg p-toluenesulfonic acid hydrate (0.06 mmol; 20 mol %) in one portion at ambient temperature. After 24 h, all volatiles were removed in vacuo, and the residue directly purified by chromatography on silica (30×185 mm) using 4:1 hexanes/ethyl acetate. The main product peak eluting 360-450 mL was collected, pooled and concentrated in vacuo to a colorless oil (81.2 mg, 0.205 mmol; 68.3%). $^1$H NMR: (300 MHz, DMSO-d$_6$) δ 8.28 (1H, s), 7.55-7.39 (4H, m), 5.44 (2H, s), 4.62-4.52 (1H, m), 4.47-4.36 (1H, m), 3.46-3.34 (1H, m), 3.36-3.25 (1H, m), 1.58 (9H, s), 1.49 (6H, s). $^{19}$F NMR: (282 MHz, DMSO-d$_6$) δ −222.01 (1F, tt, J=47.8, 30.6 Hz). $^{13}$C NMR: (75 MHz, DMSO-d$_6$) δ 157.8, 153.9, 146.3, 133.9, 127.7, 126.1, 125.8, 115.5, 83.17 (d, J=166.3 Hz), 76.3, 71.2, 65.3, 61.89 (d, J =19.2 Hz), 28.0, 27.4. HRMS Calcd. for C$_{20}$H$_{26}$$^{35}$ClFN$_2$O$_3$(M+H): 397.1689; found: 397.1695. TLC: R$_f$ 0.51 (silica gel, 3:2 hexanes/ethyl acetate, uv).

Example 59

Preparation of 2-(tert-butyl)-4-chloro-5-((4-((2-fluoroethoxy)methyl)phenyl)ethynyl)pyridazin-3(2H)-one Part A—Preparation of (4-(1,3-dioxolan-2-yl)phenyl)methanol

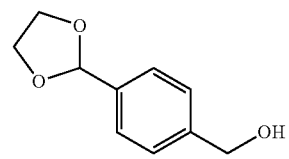 [SMILES: OCc1ccc(C2OCCO2)cc1]

Methyl 4-formylbenzoate (4.92 g, 30.0 mmol) was dissolved in dry toluene (50.0 mL), successively treated with ethylene glycol (1.84 mL, 33.0 mmol) and p-toluenesulfonic acid (57.1 mg, 0.300 mmol), then heated to reflux under Dean-Stark conditions; acetal formation was complete within 1 h. The solution was then cooled to 22° C. and directly treated with sodium bis(2-methoxyethoxy)aluminum hydride (45.0 mmol; 12.7 mL of a 70.3 wt. % solution in toluene) at a rate of 0.5 mL/min using a syringe pump. Upon completion of the addition, the resulting solution was cooled to 0° C., carefully treated with a saturated aqueous solution of potassium sodium tartrate (100 mL) then vigorously stirred 1 h; steady formation of a clear solution was observed. The resulting biphase was then diluted with ethyl acetate (50 mL), with transfer to a conical funnel, and the layers separated. The aqueous layer was then washed with ethyl acetate (3×50 mL) and the combined ethyl acetate and toluene solutions dried over magnesium sulfate, filtered and concentrated in vacuo to a colorless oil. The crude product was then purified by chromatography on silica (50×135 mm) using 1:1 pentane/ethyl acetate. The main product peak eluting 425-725 mL was collected, pooled and concentrated in vacuo to a colorless oil, which solidified in the freezer (4.50 g, 83.2% over two steps). $^1$H NMR: (600 MHz, CDCl$_3$) δ 7.48 (2H, AB, J$_{AB}$=8.1 Hz), 7.39 (2H, AB, J$_{AB}$=8.3 Hz), 5.82 (1H, s), 4.71 (2H, d, J=6.0 Hz), 4.08 (4H, AA'BB', J$_{AA'}$=J$_{BB'}$=7.2 Hz, J$_{AB}$=−7.5 Hz, J$_{AB'}$=6.4 Hz), 1.63 (1H, t, J=6.0 Hz). $^{13}$C NMR: (75 MHz, CDCl$_3$) δ 142.0, 137.2, 126.8, 126.6, 103.5, 65.3, 64.9.

Part B—Preparation of
4-((2-fluoroethoxy)methyl)benzaldehyde

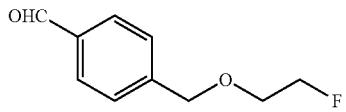 [SMILES: O=Cc1ccc(COCCF)cc1]

A solution of the product of Example 59A (1.80 g, 10.0 mmol) in dry acetonitrile (50.0 mL) was successively treated with 1-bromo-2-fluoroethane (3.73 mL, 50.0 mmol) and powdered potassium hydroxide (5.61 g, 0.100 mol) in one portion at ambient temperature. After 0.5 h, the resulting suspension was warmed to 80° C. then maintained 2.5 h. After cooling to ambient temperature, the suspension was diluted with water (100 mL), with transfer to a separatory funnel then washed with ethyl acetate (3×100 mL). The combined ethyl acetate washes were dried over magnesium sulfate, filtered and concentrated in vacuo to a colorless that was directly purified by chromatography on silica (50×195 mm) using 1:1 pentane/diethyl ether to afford 2-(4-((2-fluoroethoxy)methyl)phenyl)-1,3-dioxolane as a colorless oil (2.04 g, 9.02 mmol; 90.2%). The purified acetal (0.423 g, 2.00 mmol) was then dissolved in wet acetone (8.00 mL) and directly treated with dilute hydrochloric acid (2.00 mmol; 2.00 mL of a 1.0 N solution in water) at ambient temperature. After stirring 18 h, the resulting mixture was partitioned between diethyl ether and saturated aqueous sodium bicarbonate (50 mL each), with transfer to a conical funnel, and the layers separated. The aqueous layer was then washed with diethyl ether (2×50 mL) and the combined ethereal solutions dried over magnesium sulfate, filtered and concentrated in vacuo. Purification by bulb-to-bulb distillation under reduced pressure afforded the title compound as a colorless oil (0.340 g, 1.87 mmol; 93.4%).

Part C—Preparation of
1-ethynyl-4-((2-fluoroethoxy)methyl)benzene

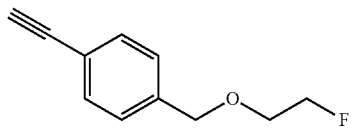

Carbontetrabromide (1.06 g, 3.20 mmol), zinc dust (0.210 g, 3.20 mmol) and triphenylphosphine (0.840 g, 3.20 mmol) were added to a solution of the product of Example 59B (0.290 g, 1.60 mmol) in dichloromethane (10.0 mL) at ambient temperature. The crude dibromo intermediate was isolated using standard workup procedures, dissolved in dry tetrahydrofuran (8.00 mL) then cooled to −78° C. and treated with a solution of n-butyllithium in tetrahydrofuran (2.00 mL). The resulting mixture was then warmed to ambient temperature, treated with water and extracted with ethyl acetate. The ethyl acetate solution was washed with water and saturated aqueous sodium chloride then dried over magnesium sulfate, filtered and concentrated in vacuo. The crude material thus obtained was then purified by chromatography on silica (12 g) using 9:1 hexanes/ethyl acetate, to afford the title compound (0.190 g, 66.6%). $^1$H NMR (300 MHz, DMSO-d$_6$) δ 7.50-7.44 (m, 2H), 7.38-7.32 (m, 2H), 4.67-4.63 (m, 1H), 4.55 (s, 2H), 4.51-4.47 (m, 1H), 4.16 (s, 1H), 3.76-3.72 (m, 1H), 3.66-3.62 (m, 1H). $^{13}$C NMR (75 MHz, DMSO-d$_6$) δ 139.19, 131.60, 127.51, 120.72, 83.68 (d, J=51.8 Hz), 81.82, 80.62, 71.41, 69.10 (d, J=18.8 Hz).

Part D—Preparation of 2-(tert-butyl)-4-chloro-5-
((4-((2-fluoroethoxy)methyl)phenyl)ethynyl)
pyridazin-3(2H)-one

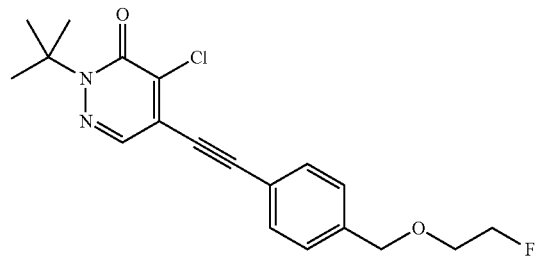 [SMILES: CC(C)(C)n1ncc(C#Cc2ccc(COCCF)cc2)c(Cl)c1=O]

A solution of 1-(tert-butyl)-5-chloro-6-oxo-1,6-dihydro-pyridazin-4-yl trifluoromethane sulfonate (0.175 g, 0.523 mmol), the product of Example 59C (95.0 mg, 0.533 mmol), trans-dichloro(triphenylphosphine)palladium (II) (11.0 mg, 0.0157 mmol; 3.0 mol %), copper(I) iodide (30.0 mg, 0.158 mmol), n-tetrabutylammonium iodide (0.576 g, 1.55 mmol) and triethylamine (220 μL, 1.58 mmol) in anhydrous tetrahydrofuran (5.00 mL) was stirred 2 h at ambient temperature then diluted with ethyl acetate, and filtered through Celite with transfer to a separatory funnel. The ethyl acetate solution was then washed with water and saturated aqueous sodium chloride, dried over magnesium sulfate, filtered and concentrated in vacuo. The crude material thus obtained was then purified by chromatography on silica (4 g) using 3:1 hexanes/ethyl acetate, to afford the title compound (90.0 mg, 46.5%). $^1$H NMR (300 MHz, DMSO-d$_6$) δ 8.06 (s, 1H), 7.66-7.63 (m, 2H), 7.48-7.45 (m, 2H), 4.68-4.66 (m, 1H), 4.61 (s, 2H), 4.52-4.50 (m, 1H), 3.79-3.76 (m, 1H), 3.69-3.66 (m, 1H), 1.60 (s, 9H). $^{13}$C NMR (75 MHz, DMSO-d$_6$) δ 155.85, 141.13, 136.51, 134.28, 131.97, 127.71, 124.57, 119.20, 102.11, 84.02, 81.58 (d, J=36.0 Hz), 71.33, 69.25 (d, J=19.5 Hz), 65.89, 27.30. $^{19}$F NMR (282 MHz, DMSO-d$_6$) δ −221.61 (tt, J=48.0, 31.1 Hz). HRMS Calcd. for C$_{19}$H$_{20}$$^{35}$ClFN$_2$O$_2$ (M+H): 363.1270; found: 363.1266.

Example 60

Preparation of (E)-2-(tert-butyl)-4-chloro-5-(4-((2-fluoroethoxy)methyl)styryl)pyridazin-3(2H)-one Part A—Preparation of 1-((2-fluoroethoxy)methyl)-4-vinylbenzene

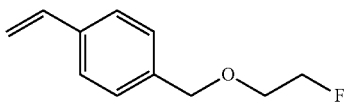

A suspension of methyltriphenylphosphonium bromide (0.260 g, 0.728 mmol) and sodium hydride (80.0 mg, 3.33 mmol) in dry tetrahydrofuran (2.50 mL) was cooled to 0° C. then treated with the product of Example 59A (0.110 g, 0.604 mmol). The resulting mixture then warmed slowly to ambient temperature as the ice melted. After 2 h total, the suspension was diluted with diethyl ether with transfer to a separatory funnel then washed with water and saturated aqueous sodium chloride, dried over magnesium sulfate, filtered and concentrated in vacuo. The crude material thus obtained was then purified by chromatography on silica (4 g) using 9:1 hexanes/ethyl acetate, to afford the title compound (40.0 mg, 36.7%). $^1$H NMR (300 MHz, CDCl$_3$) δ 7.40-7.29 (m, 2H), 7.24 (d, J=8.2 Hz, 2H), 6.64 (dd, J=17.6, 10.9 Hz, 1H), 5.67 (dd, J=17.6, 1.0 Hz, 1H), 5.17 (dd, J=10.9, 0.9 Hz, 1H), 4.64-4.56 (m, 1H), 4.52 (s, 2H), 4.47-4.38 (m, 1H), 3.75-3.65 (m, 1H), 3.64-3.55 (m, 1H). 19F NMR (282 MHz, CDCl$_3$) δ −223.12 (tt, J=48.0, 31.1 Hz).

Part B—Preparation of (E)-2-(tert-butyl)-4-chloro-5-(4-((2-fluoroethoxy)methyl) styryl)pyridazin-3(2H)-one

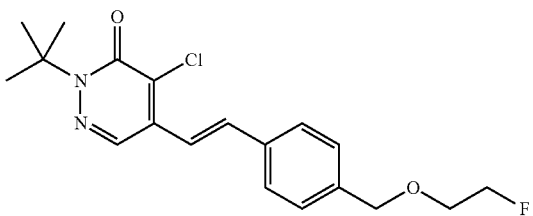 [SMILES: CC(C)(C)n1ncc(/C=C/c2ccc(COCCF)cc2)c(Cl)c1=O]

A solution of 1-(tert-butyl)-5-chloro-6-oxo-1,6-dihydropyridazin-4-yl trifluoromethane sulfonate (0.180 g, 0.538 mmol), the product of Example 60A (0.140 g, 0.777 mmol), trans-dichlorobis(tri-o-tolylphosphine)palladium (II) (40.0 mg, 0.057 mmol; 7.3 mol %) and triethylamine (120 μL, 0.860 mmol) in dry dimethylformamide (5.00 mL) was warmed to 110° C. and maintained 2 h. After cooling to ambient temperature, the resulting mixture was diluted with ethyl acetate, and filtered through Celite with transfer to a separatory funnel. The ethyl acetate solution was then washed with water and saturated aqueous sodium chloride, dried over magnesium sulfate, filtered and concentrated in vacuo. The crude material thus obtained was then purified by chromatography on silica (4 g) using 4:1 hexanes/ethyl acetate, to afford the title compound (50.0 mg, 25.5%). $^1$H NMR (300 MHz, CDCl$_3$) δ 8.04 (s, 1H), 7.60-7.57 (m, 2H), 7.44-7.41 (m, 2H), 7.29 (d, J=6.0 Hz, 1H), 4.72-4.69 (m, 1H), 4.65 (s, 2H), 4.56-4.53 (m, 1H), 3.84-3.81 (m, 1H), 3.74-3.71 (m, 1H), 1.69 (s, 9H). $^{13}$C NMR (75 MHz, DMSO-d$_6$) δ 157.59, 139.74, 136.58, 135.09, 134.98, 132.73, 130.83, 128.16, 127.58, 120.07, 83.08 (d, J=168.0 Hz), 72.87, 69.42 (d, J=19.5 Hz), 66.08, 27.85. $^{19}$F NMR (282 MHz, DMSO) δ −223.04 (tt, J=47.9, 28.2 Hz). HRMS Calcd. for C$_{19}$H$_{22}$$^{35}$ClFN$_2$O$_2$(M+H): 365.1427; found: 365.1421.

Example 61

Preparation of 2-(tert-butyl)-4-chloro-5-((4-((2-fluoroethoxy)methyl)phenyl)ethynyl)pyridazin-3(2H)-one Part A—Preparation of (E)-methyl 4-(2-(1-(tert-butyl)-5-chloro-6-oxo-1,6-dihydropyridazin-4-yl)vinyl)benzoate

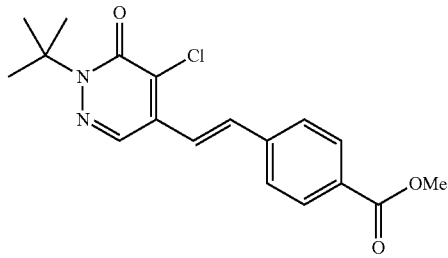 [SMILES: COC(=O)c1ccc(/C=C/c2cnn(C(C)(C)C)c(=O)c2Cl)cc1]

A solution of 1-(tert-butyl)-5-chloro-6-oxo-1,6-dihydropyridazin-4-yl trifluoromethane sulfonate (0.400 g, 1.20 mmol), methyl 4-vinylbenzoate (0.210 g, 1.29 mmol), trans-dichlorobis(tri-o-tolylphosphine)palladium (II)(40.0 mg, 0.057 mmol; 4.8 mol %) and triethylamine (80.0 μL, 0.574 mmol) in dry dimethylformamide (2.00 mL) was warmed to 110° C. and maintained 2 h. After cooling to ambient temperature, the resulting mixture was diluted with ethyl acetate, and filtered through Celite with transfer to a separatory funnel. The ethyl acetate solution was then washed with water with and saturated aqueous sodium chloride, dried over magnesium sulfate, filtered and concentrated in vacuo. The crude material thus obtained was then purified by chromatography on silica (12 g) using 4:1 hexanes/ethyl acetate, to afford the title compound (80.0 mg, 19.2%). $^1$H NMR (300 MHz, CDCl$_3$) δ 8.12-8.08 (m, 2H), 8.03 (s, 1H), 7.68-7.62 (m, 2H), 7.48-7.32 (m, 2H), 3.96 (s, 3H), 1.70 (s, 9H).

Part B—Preparation of methyl 4-(2-(1-(tert-butyl)-5-chloro-6-oxo-1,6-dihydropyridazin-4-yl)ethyl)benzoate

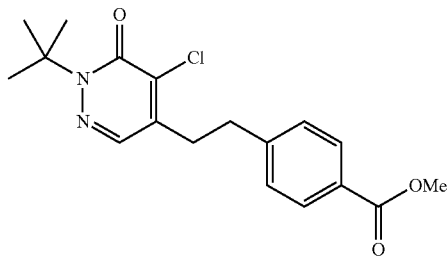 [SMILES: COC(=O)c1ccc(CCc2cnn(C(C)(C)C)c(=O)c2Cl)cc1]

A solution of the product of Example 61A (50.0 mg, 0.144 mmol) in 2:1 methanol/dichloromethane (15.0 mL) was treated with platinum(II) oxide (20.0 mg, 0.088 mmol) in one portion at ambient temperature. The resulting suspension was stirred under a hydrogen atmosphere then filtered through a mixture of Celite and silica gel and the resulting filtrate concentrated in vacuo. The crude material thus obtained was then purified by chromatography on silica (4 g) using 4:1 hexanes/ethyl acetate, to afford the title compound (30.0 mg, 59.7%). $^1$H NMR (300 MHz, CDCl$_3$) δ 8.00 (d, 2H, J=8.3 Hz), 7.47 (s, 1H), 7.28 (d, 2H, J=8.2 Hz), 3.93 (s, 3H), 3.00-2.94 (m, 4H), 1.66 (s, 9H).

Part C—Preparation of 2-(tert-butyl)-4-chloro-5-(4-(hydroxymethyl)phenethyl)pyridazin-3(2H)-one

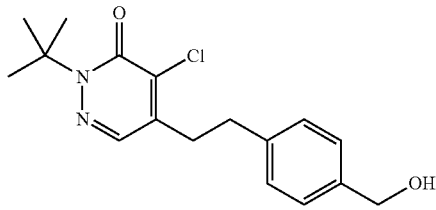 [SMILES: CC(C)(C)n1ncc(CCc2ccc(CO)cc2)c(Cl)c1=O]

A solution of the product of Example 61B (30.0 mg, 0.086 mmol) in tetrahydrofuran (2.00 mL) was cooled to 0° C. then treated with lithium aluminum hydride (0.4 mL, 0.4 mmol of a 1 M solution in tetrahydrofuran) and warmed to ambient temperature. After 1 h, the resulting mixture was diluted with water (20 mL), the aqueous layer separated then washed with dichloromethane (3×20 mL). The combined organic washes were further washed with saturated aqueous sodium chloride then dried over magnesium sulfate, filtered and concentrated to in vacuo to yield the title compound (20.0 mg) that was used without additional purification in the subsequent reaction.

Part D—Preparation of 5-(4-(bromomethyl)phenethyl)-2-(tert-butyl)-4-chloropyridazin-3(2H)-one

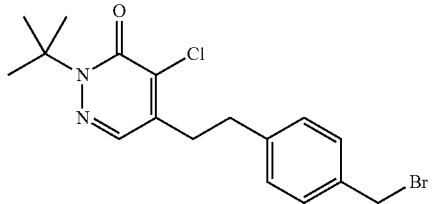 [SMILES: CC(C)(C)n1ncc(CCc2ccc(CBr)cc2)c(Cl)c1=O]

A solution of the product of Example 61C (20.0 mg, 0.062 mmol) in dichloromethane (1.00 mL) was directly treated with phosphorous tribromide (0.030 mmol; 30 L of a 1 M solution in dichloromethane) then stirred 1 h at ambient temperature. The resulting mixture was then diluted with dichloromethane (20 mL), with transfer to a separatory funnel, and washed with water and saturated aqueous sodium chloride, dried over magnesium sulfate, filtered, and concentrated in vacuo to yield the title compound (20.0 mg) that was used without additional purification in the subsequent reaction. $^1$H NMR (300 MHz, CDCl$_3$) δ 7.49 (s, 1H), 7.33-7.28 (m, 2H), 7.23-7.17 (m, 2H), 4.56 (s, 2H), 3.80-3.74 (m, 2H), 3.63-3.57 (m, 2H), 2.93 (s, 4H), 1.67 (s, 9H).

Part E—Preparation of 2-(tert-butyl)-4-chloro-5-(4-((2-hydroxyethoxy)methyl)phenethyl) pyridazin-3(2H)-one

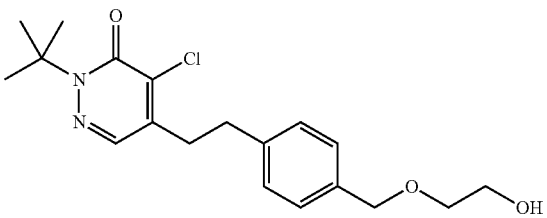 [SMILES: CC(C)(C)n1ncc(CCc2ccc(COCCO)cc2)c(Cl)c1=O]

A suspension of sodium hydride (0.20 mmol; 8.0 mg of a 60% dispersion in mineral oil) and ethylene glycol (10.0 μL, 0.18 mmol), was treated with a solution of the product of Example 61D (20.0 mg, 0.052 mmol) in dry tetrahydrofuran (2.00 mL) and the resulting mixture heated to reflux. After 4 h, the reaction mixture was cooled to ambient temperature, diluted with diethylether (20 mL) then transferred to a separatory funnel, washed with water and saturated aqueous sodium chloride, dried over magnesium sulfate, filtered and concentrated in vacuo. The crude material thus obtained was then purified by chromatography on silica (4 g) using 7:3 hexanes/ethyl acetate, to afford the title compound (5.5 mg, 29.0%). $^1$H NMR (300 MHz, CDCl$_3$) δ 7.50 (s, 1H), 7.32-7.28 (m, 2H), 7.22-7.18 (m, 2H), 4.57 (s, 2H), 3.80-3.76 (m, 2H), 3.63-3.59 (m, 2H), 2.93 (s, 4H), 1.67 (s, 9H).

Part F—Preparation of 2-((4-(2-(1-(tert-butyl)-5-chloro-6-oxo-1,6-dihydropyridazin-4-yl)ethyl)benzyl) oxy)ethyl 4-methylbenzenesulfonate

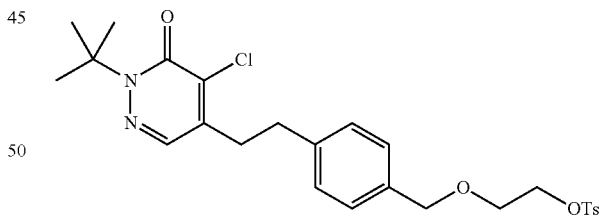

Prepared according the General Method D, using the product of Example 61E (5.5 mg, 0.015 mmol), p-toluenesulfonyl chloride (8.0 mg, 0.042 mmol), 4-dimethylaminopyridine (one crystal), and triethylamine (0.010 mL, 0.072 mmol). Isolated yield—5.0 mg; 64.2%. $^1$H NMR (300 MHz, CDCl$_3$) δ 7.87-7.79 (m, 2H), 7.50 (s, 1H), 7.39-7.30 (m, 2H), 7.25-7.17 (m, 4H), 4.49 (s, 2H), 4.27-4.17 (m, 2H), 3.73-3.63 (m, 2H), 2.93 (s, 4H), 2.46 (s, 3H), 1.67 (s, 9H). $^{13}$C NMR (75 MHz, CDCl$_3$) δ 157.53, 144.74, 140.72, 139.49, 135.95, 135.18, 134.90, 133.11, 129.78, 128.35, 128.05, 127.96, 72.96, 69.21, 67.52, 66.26, 33.56, 32.69, 27.77, 21.63.

Part G—Preparation of 2-(tert-butyl)-4-chloro-5-((4-((2-fluoroethoxy)methyl)phenyl)ethynyl)pyridazin-3(2H)-one

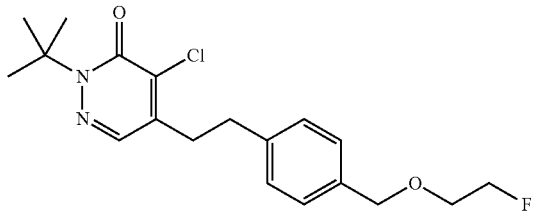 [SMILES: CC(C)(C)n1ncc(CCc2ccc(COCCF)cc2)c(Cl)c1=O]

A solution of the product of Example 59C (40.0 mg, 0.110 mmol) in 1:1 ethyl acetate/hexanes (10.0 mL) was treated with 5% palladium on calcium carbonate, poisoned with lead (20.0 mg, 0.094 mmol) in one portion at ambient temperature. The resulting suspension was stirred under a hydrogen atmosphere then filtered through a mixture of Celite and silica gel and the resulting filtrate concentrated in vacuo. The crude material thus obtained was then purified by chromatography on silica (4 g) using 4:1 hexanes/ethyl acetate, to afford the title compound (20.0 mg, 49.6%). $^1$H NMR (300 MHz, DMSO-$d_6$) δ 7.89 (s, 1H), 7.29-7.22 (m, 4H), 4.65-4.62 (m, 1H), 4.50 (s, 2H), 4.49-4.46 (m, 1H), 3.72-3.69 (m, 1H), 3.62-3.59 (m, 1H), 2.91-2.89 (m, 4H), 1.58 (s, 9H). $^{13}$C NMR (75 MHz, DMSO-$d_6$) δ 156.34, 141.37, 139.41, 136.10, 135.56, 133.71, 128.15, 127.71, 82.95 (d, J=164 Hz), 71.78, 68.82 (d, J=18.8 Hz), 65.27, 32.62, 31.78, 27.34. $^{19}$F NMR (282 MHz, DMSO) δ −221.51 (tt, J=48.0, 31.1 Hz). HRMS Calcd. for $C_{19}H_{24}{}^{35}ClFN_2O_2$ (M+H): 367.1583; found: 367.1580.

Example 62

Preparation of Silyl Derivatives

Part A—Preparation of 2-(tert-butyl)-4-chloro-5-((4-(di-tert-butylsilyl)benzyl)oxy)pyridazin-3(2H)-one

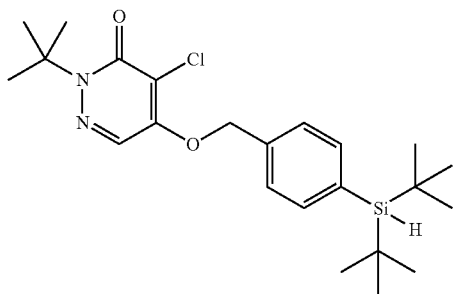 [SMILES: CC(C)(C)n1ncc(OCc2ccc([Si](F)(C(C)(C)C)C(C)(C)C)cc2)c(Cl)c1=O]

A solution of 2-(tert-butyl)-4-chloro-5-hydroxypyridrazin-3(2H)-one (0.476 g, 2.36 mmol) in tetrahydrofuran (23.6 mL) was successively treated with (4-(di-tert-butylsilyl) phenyl) methanol (0.706 g, 2.82 mmol; e.g., see James, D.; Escudier, J.-M.; Amigues, E.; Schulz, J.; Virty, C.; Bordenave, T.; Szlosek-pinaud, M.; Fouquet, E. A "click chemistry" approach to the efficient synthesis of modified nucleosides and oligonucleotides for PET imaging. Tetrahedron Lett., 2010, 51, 1230-1232), triphenylphosphine (0.929 g, 3.54 mmol), and diethylazodicarboxylate (0.617 g, 3.54 mmol) at ambient temperature. After 90 min, the resulting mixture was diluted with water (50 mL), with transfer to a separatory funnel and the aqueous layer separated then washed with ethyl acetate (3×100 mL). The combined organic washes were dried over sodium sulfate, filtered, and concentrated in vacuo to an orange oil. The crude material was then triturated with diethyl ether for 2 h and the resulting suspension filtered to remove the suspended triphenylphosphine oxide. The filtrate was purified by chromatography on silica using a 0-50% ethyl acetate in hexanes gradient to afford the title compound as a white solid (0.227 g, 22.1%). $^1$H NMR: (300 MHz, CDCl$_3$) δ 7.76 (s, 1H), 7.64 (d, 2H, J=8.12 Hz), 7.40 (d, 2H, J=8.12 Hz), 5.34 (s, 2H), 3.90 (s, 1H), 1.55 (s, 9H), 1.07 (s, 18H); $^{13}$C NMR: (75 MHz, CDCl$_3$) δ 159.04, 153.78, 136.49, 136.29, 135.43, 126.03, 125.18, 98.55, 71.91, 66.38, 28.87, 27.87, 18.99. HRMS Calcd. for $C_{23}H_{35}{}^{35}ClN_2O_2Si$ (M+Na): 429.1736; found: 429.1729.

Part B—Preparation of 2-(tert-butyl)-4-chloro-5-((4-(di-tert-butylfluorosilyl)benzyl)oxy)pyridazin-3(2H)-one

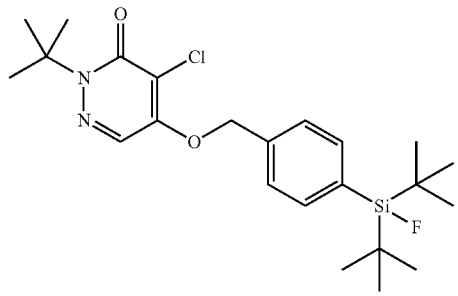

A solution of the product of Example 62A (5.0 mg, 0.011 mmol) in dimethylsulfoxide (0.3 mL) was added to a mixture of 4,7,13,16,21,24-hexaoxa-1,10-diazabicyclo[8.8.8]hexacosane (8.7 mg, 0.023 mmol) and potassium fluoride (0.6 mg, 0.011 mmol) then warmed to 35° C. After 10 min, the resulting mixture was cooled to ambient temperature then diluted with water (0.5 mL) with transfer to a separatory funnel. The aqueous layer was then washed with ethyl acetate (3×2 mL) and the combined washes dried over sodium sulfate, filtered and concentrated in vacuo to an oil. The crude material thus obtained was then purified by preparative thin-layer chromatography on silica using 4:1 hexanes/ethyl acetate to afford the title compound as a white solid (3.2 mg, 70.6%; e.g., see Mu L.; Hoehne, A.; Schubiger, P. A.; Ametamey, S. M.; Graham, K.; Cyr, J. E.; Dinkelborg, L.; Stellfeld, T.; Srinivasan, A.; Voigtmann, U.; Klar, U. Silicon-based Building blocks for one step 18F-radiolabeling of peptides for PET imaging. Angew. Chem. Int. Ed. 2008, 47, 4922-4925). $^1$H NMR: (300 MHz, CDCl$_3$) δ 7.72-7.59 (m, 3H), 7.33 (d, 2H, J=8.14 Hz), 5.24 (s, 2H), 1.57 (s, 9H), 0.97 (s, 18H). $^{13}$C NMR (75 MHz, CDCl$_3$, partial) δ 158.03, 152.73, 135.12, 133.66 (d, J=4.5 Hz), 125.09, 124.12, 98.97, 70.79, 65.43, 26.87, 26.29, 19.23 (d, J=12.0 Hz). $^{19}$F NMR: (282 MHz, CDCl$_3$) δ −188.74 (1F, s). HRMS Calcd. for $C_{23}H_{34}{}^{35}ClFN_2O_2Si$ (M+H): 453.2135; found: 453.2139.

Part C—Preparation of 2-(tert-butyl)-4-chloro-5-((4-(diisopropylsilyl)benzyl)oxy)pyridazin-3(2H)-one

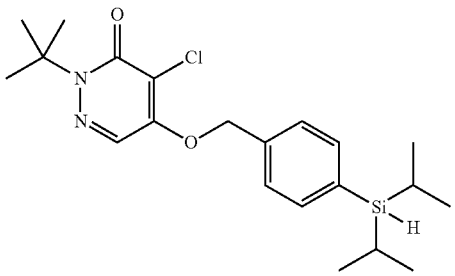

A solution of 2-(tert-butyl)-4-chloro-5-hydroxy-pyridrazin-3(2H)-one (0.476 g, 2.36 mmol) in tetrahydrofuran (23.6 mL) was successively treated with (4-(diisopropylsilyl) phenyl) methanol (0.627 g, 2.82 mmol; e.g., see James, D.; Escudier, J.-M.; Amigues, E.; Schulz, J.; Virty, C.; Bordenave, T.; Szlosek-pinaud, M.; Fouquet, E. A "click chemistry" approach to the efficient synthesis of modified nucleosides and oligonucleotides for PET imaging. Tetrahedron Lett., 2010, 51, 1230-1232), triphenylphosphine (0.929 g, 3.54 mmol), and diethylazodicarboxylate (0.617 g, 3.54 mmol) at ambient temperature. After 2 h, the resulting mixture was diluted with water (50 mL), with transfer to a separatory funnel and the aqueous layer separated then washed with ethyl acetate (3×100 mL). The combined organic washes were dried over sodium sulfate, filtered, and concentrated in vacuo to an oil. The crude material was then triturated with diethyl ether for 2 h and the resulting suspension filtered to remove the suspended triphenylphosphine oxide. The filtrate was purified by chromatography on silica using a 0-50% ethyl acetate in hexanes gradient to afford the title compound as a white solid (0.259 g, 27.0% yield). $^1$H NMR: (300 MHz, CDCl$_3$) δ 7.55 (s, 1H), 7.38 (d, 2H, J=8.03 Hz), 7.19 (d, 2H, J=8.12 Hz), 5.12 (s, 2H), 3.77 (m, 1H), 1.46 (s, 9H), 1.05 (m, 2H), 0.87 (dd, J=6.0 Hz, 6H), 0.82 (dd, J=6.0 Hz, 6H). $^{13}$C NMR (75 MHz, CDCl$_3$) δ 159.03, 153.76, 136.01, 135.63, 135.21, 126.18, 125.14, 71.90, 66.39, 27.87, 18.61, 18.45, 10.65. HRMS Calcd. for C$_{21}$H$_{31}$$^{35}$ClN$_2$O$_2$Si (M+H): 407.1916; found: 407.1922.

Part D—Preparation of 2-(tert-butyl)-4-chloro-5-((4-(diisopropylfluorosilyl)benzyl)oxy)pyridazin-3(2H)-one

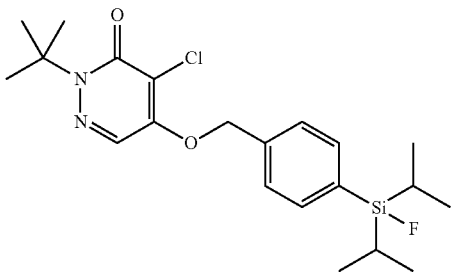 [SMILES: CC(C)[Si](F)(c1ccc(COc2cnn(C(C)(C)C)c(=O)c2Cl)cc1)C(C)C]

A solution of the product of Example 62C (5.0 mg, 0.011 mmol) in tetrahydrofuran (0.3 mL) was added to a solution of tetrabutylammonium fluoride (0.011 mmol; 0.011 mL of a 1 M solution in tetrahydrofuran at −78° C. After 6 h, the resulting mixture was warmed to −20° C. and maintained an additional 20 h. After warming to ambient temperature, the crude mixture was directly purified by preparative thin-layer chromatography on silica using 9:1 hexanes/ethyl acetate to afford the title compound as a colorless oil (4.2 mg, 82.4%). 1H NMR: (300 MHz, CDCl$_3$) δ 7.66 (s, 1H), 7.58-7.49 (m, 2H), 7.37 (d, 2H, J=7.84 Hz), 5.24 (s, 2H), 1.57 (s, 9H), 1.16-1.25 (m, 2H), 0.96-0.94 (m, 12H). $^{13}$C NMR (75 MHz, CDCl$_3$, partial) δ 159.01, 153.70, 136.53, 134.43 (d, J=3.7 Hz), 126.29, 125.08, 71.76, 66.43, 27.87, 16.65, 16.62, 12.30 (d, J=12.7 Hz). $^{19}$F NMR: (282 MHz, CDCl$_3$) δ −187.01 (t, J=5.6 Hz).

Example 63

Preparation of 2-(tert-butyl)-4-chloro-5-((4-(4-fluorobutanoyl)benzyl)oxy)pyridazin-3(2H)-one

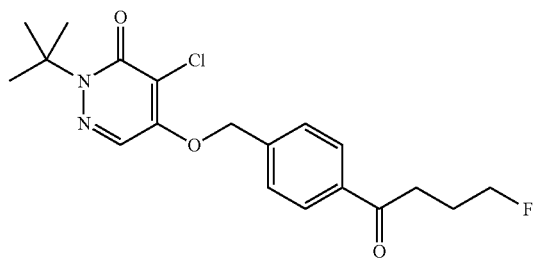 [SMILES: CC(C)(C)n1ncc(OCc2ccc(C(=O)CCCF)cc2)c(Cl)c1=O]

A solution of the product of Example 43D in 1,4-dioxane is treated with [(IPr)AuCl](e.g., see Marion, N.; Ramon, R.; Nolan, S. P. [(NHC)AuI]-Catalyzed Acid Free Hydration of Alkynes at Part-Per-Million Catalyst Loadings. J. Am. Chem. Soc. 2009, 131, 448-449) and silver hexafluoroantiminate at ambient temperature. After 1 min, water is added and the resulting mixture warmed to 120° C. and maintained overnight. After cooling to ambient temperature, all volatile materials are removed in vacuo and the residue purified by chromatography on silica to afford the title compound.

Example 64

Part A—Preparation of Submitochondrial Particles from Bovine Heart

Bovine heart mitochondria were prepared as described by Lester et al. (e.g., see Lester R. L.; Smith A. L. Studies on the electron transport system. 28. The mode of reduction of tetrazolium salts by beef heart mitochondria; role of coenzyme Q and other lipids. Biochim Biophys. Acta. 1961, 47, 475-96). In brief, bovine heart was minced and 200 g of ground heart tissue was suspended in 400 mL of 0.25 M sucrose, 0.01 M Tris-Cl, 1 mM Tris-succinate, and 0.2 mM ethylenediamine tetra-acetic acid (EDTA) and homogenized in a Waring blender. The homogenate was centrifuged for 20 min at 1,200×g and the supernatant was centrifuged for 15 min at 26,000×g resulting in a mitochondrial pellet. The protein concentration of the mitochondrial samples as measured by BioRad Protein Assay Kit (BioRad Life Science Research, Hercules, Calif.) was adjusted to 20 mg/mL using 0.25 M sucrose, 10 mM Tris-acetate pH 7.5, 1.5 mM adenosine triphosphate (ATP), and 10 mM magnesium chloride. The samples were stored at −80° C.

Bovine submitochondrial particles (SMPs) were prepared from mitochondria as described by Matsuno-Yagi et al. (e.g., see Matsuno-Yagi, A.; Hatefi, Y. Studies on the mechanism of oxidative phosphorylation. Catalytic site cooperativity in ATP synthesis. J. Biol. Chem. 1985, 260, 11424-7). In brief, isolated bovine heart mitochondria were sonicated in batches of 15 mL for 1 minute with a digital Branson sonifier (Branson, Danbury, Conn.) at 70% maximum output in an ice bath. The sonicated suspension was centrifuged at 16,000×g for 10 min, and the supernatant was centrifuged at 150,000×g for 45 min at 4° C. The submitochondrial pellet was resuspended in buffer containing 0.25 M Sucrose, 10 mM Tris-acetate, pH 7.5. The protein concentration was determined using the BioRad Protein Assay Kit (BioRad Life Science Research, Hercules Calif.), and the samples were stored at −80° C., at a concentration of 20 mg/mL.

Part B—Submitochondrial Particle (SMP) Catalytic Activity and Compound Inhibition Assay The procedure for determining catalytic activity of submitochondrial particles was adapted from Satoh et al. (e.g., see Satoh T, Miyoshi H, Sakamoto K, Iwamura H. Comparison of the inhibitory action of synthetic capsaicin analogues with various NADH-ubiquinone oxidoreductases. Biochim Biophys Acta. 1996, 1273, 21-30). NADH-DB reductase activity was measured using a stirred cuvette in a spectrophotometer (Hewlett-Packard, Houston Tex.) at 37° C., as the rate of NADH oxidation at 340 nm ($\epsilon$=5.4 mM$^{-1}$ ×cm$^{-1}$) for 120 seconds. The final volume of the reaction was 2.5 mL, containing 50 mM K$_2$HPO$_4$ (pH 7.4), 0.4 µM Antimycin A, and 2 mM potassium cyanide. The final SMP concentration was 45 µg/mL. The enzyme reaction was initiated by the addition of 100 µM decyl ubiquinone and 50 µM NADH. Inhibitors at varying concentrations were pre-incubated with the reaction mixture containing SMPs for 4 min prior to initiation of the reaction. The IC$_{50}$ value was determined as the concentration of the inhibitor required for 50% inhibition of the NADH oxidation. The IC$_{50}$ value was calculated using GraphPad Prism Version 4 (GraphPad, San Diego, Calif.).

TABLE 1

MC1 inhibition data

| Example | IC$_{50}$ (nM) |
|---|---|
| flurpiridaz | <100 |
| 1 | >1000 |
| 3 | >1000 |
| 4 | >1000 |
| 5 | >1000 |
| 6 | >1000 |
| 7 | <100 |
| 8 | >1000 |
| 9 | <100 |
| 12 | ≤1000 |
| 16 | ≤1000 |
| 17 | ≤1000 |
| 18 | ≤1000 |
| 19 | ≤1000 |
| 20 | <100 |
| 21 | ≤1000 |
| 22 | <100 |
| 23 | ≤1000 |
| 25 | <100 |
| 27 | <100 |
| 28 | ≤1000 |
| 29 | <100 |
| 31 | >1000 |
| 32 | <100 |
| 33 | ≤1000 |
| 35 | ≤1000 |

TABLE 1-continued

MC1 inhibition data

| Example | IC$_{50}$ (nM) |
|---|---|
| 36 | ≤1000 |
| 37 | <100 |
| 38 | ≤1000 |
| 39 | <100 |
| 40 | <100 |
| 43 | <100 |
| 45 | <100 |
| 47 | >1000 |
| 49 | >1000 |
| 50 | <100 |
| 51 | >1000 |
| 52 | >1000 |
| 54 | <100 |
| 55 | <100 |
| 60 | >4000 |
| 61 | ≤1000 |
| 48B | <100 |
| 48C | ≤1000 |
| 53A | >1000 |
| 53B | >1000 |
| 56C | <100 |
| 56D | <100 |
| 57B | <100 |
| 58A | ≤1000 |
| 58B | ≤1000 |
| 59D | >4000 |
| 62A | >1000 |
| 62B | ≤1000 |
| 62C | ≤1000 |
| 62D | >1000 |

Example 65

Preparation of Imaging Agents Using a Custom Robotic Device

Part A—Preparation of [$^{18}$F]Fluoride

[$^{18}$F]Fluoride was produced by proton bombardment of [$^{18}$O]H$_2$O in a cyclotron; the nuclear chemical transformation is shown below and may be summarized as $^{18}$O(p,n)$^{18}$F. For purposes of the bombardment, the chemical form of the $^{18}$O is H$_2$$^{18}$O. The chemical form of the resulting $^{18}$F is fluoride ion.

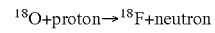

$^{18}$O+proton→$^{18}$F+neutron

According to established industry procedures, [$^{18}$O]H$_2$O (2-3 mL) housed within a tantalum target body using Havar® foil, was bombarded with 11 MeV protons (nominal energy); where the proton threshold energy for the reaction is 2.57 MeV and the energy of maximum cross section is 5 MeV. Target volume, bombardment time and proton energy each may be adjusted to manage the quantity of [$^{18}$F]fluoride produced.

Part B—Preparation of Imaging Agents Using a Custom Robotic Device

[$^{18}$F]Fluoride prepared according to Example 65A was applied to a previously activated MP1 anion exchange resin (BioRad) contained within a small volume plastic housing. The loaded cartridge was then placed into an elution loop located within a custom designed robotic radiosynthesis system and introduced when needed using one of the following methods.

Method A: [$^{18}$F]Fluoride (1 Ci) was transferred from the resin to a glass vessel using an aqueous solution of tetraethylammonium bicarbonate (1.1-1.3 molar equivalents). The resulting mixture was then concentrated to dryness at elevated temperature (120° C.) and reduced pressure. Anhydrous acetonitrile was then added to the concentrated solution and all volatiles removed once again using elevated temperature (70° C.) and reduced pressure.

Method B: [$^{18}$F]Fluoride (1 Ci) was transferred from the resin to a glass vessel using an aqueous solution of potassium bicarbonate (3 molar equivalents). The resulting mixture was then concentrated to dryness at elevated temperature (120° C.) and reduced pressure. A solution of Kryptofix™ (4 molar equivalents) in anhydrous acetonitrile was then added to the concentrated solution and all volatiles removed once again using elevated temperature (70° C.) and reduced pressure.

A solution of the desired precursor (5-10 μmol) in anhydrous acetonitrile was then added to the glass reaction vessel in order to solvate both [$^{18}$F]fluoride and the remaining reaction components. The resulting solution was then transferred to a new glass vessel, heated to 90° C. and maintained 10 min. After cooling to ambient temperature, the solution was diluted with water and directly purified by HPLC using a Waters Xterra C18 column (250×10 mm; 10μ) in combination with various mixtures of water/acetonitrile for proper purification; both uv (220 nm) and radiation (NaI) detectors were utilized to determine the optimal peak collection window. The purified product thus obtained was concentrated in vacuo then formulated in saline containing ≤10% ethanol. During routine preparation, ~50 mCi of the fluorinated product was prepared within 75 min.

TABLE 2

Synthetic parameters using a custom robotic device

| Precursor | Example | Base | $K_{222}$ | RCY | RCP |
|---|---|---|---|---|---|
| 36 | 65A | Et$_4$NHCO$_3$ | No | 5% | 99% |
| 36 | 65A | KHCO$_3$ | Yes | 6% | 99% |
| 11 | 65B | Et$_4$NHCO$_3$ | No | 1% | Low |
| 26 | 65C | KHCO$_3$ | Yes | 7% | 99% |
| 14 | 65D | KHCO$_3$ | Yes | 13% | Low |

Example 66

Part A—Preparation of Imaging Agents Using the Explora RN Chemistry Module

[$^{18}$F]fluoride (1 Ci) produced according to Example 65A was transferred from cyclotron to the synthesis module then filtered through an anion exchange column (QMA, Waters, Inc.) to remove unreacted [$^{18}$O]H$_2$O; [$^{18}$F]fluoride was retained within the cationic resin matrix. The column was then washed with aqueous tetraethylammonium bicarbonate (1 molar equivalent) with transfer to the reaction vessel. The resulting solution was diluted with acetonitrile then concentrated to dryness; 150 mm Hg at 115° C. for 4 min. The mixture of anhydrous [$^{18}$F]tetraethylammonium fluoride and tetraethylammonium bicarbonate thus obtained was treated with an acetonitrile solution of the required precursor (1 molar equivalent) then warmed to 90° C. and maintained 20 min.

Alternatively, [$^{18}$F]fluoride (1 Ci) produced according to Example 65A was transferred from cyclotron to the synthesis module then filtered through an anion exchange column (QMA, Waters, Inc.) to remove unreacted [$^{18}$O]H$_2$O; [$^{18}$F]fluoride was retained within the cationic resin matrix. The column was then washed with aqueous potassium carbonate (1 molar equivalent) with transfer to the reaction vessel. The resulting solution was treated with an acetonitrile solution of Kryptofix™ (2 molar equivalents) then concentrated to dryness; 150 mm Hg at 115° C. for 4 min. The mixture of anhydrous [$^{18}$F]potassium fluoride, potassium carbonate and Kryptofix™ thus obtained was treated with the required precursor (1 molar equivalent; 10-50% dimethyl sulfoxide in acetonitrile) then warmed to 90-125° C. and maintained 10 min.

Alternatively, [$^{18}$F]fluoride (1 Ci) produced according to Example 65A was transferred from cyclotron to the synthesis module then filtered through a previously activated MP1 anion exchange resin (BioRad) to remove unreacted [$^{18}$O] H$_2$O; [$^{18}$F]fluoride was retained within the cationic resin matrix. The loaded cartridge was then placed into an elution loop located within a custom designed robotic radiosynthesis system then washed with aqueous tetraethylammonium bicarbonate (1 molar equivalent) with transfer to the reaction vessel. The solution was concentrated to dryness at 280 mbar, 95-115° C., 4 min then treated with an acetonitrile solution of the required precursor (1 molar equivalent), warmed to 90° C. and maintained 10 min.

After cooling the crude reaction mixtures to 35° C., the resulting solution was diluted with water then directly purified by HPLC on a Waters Xterra MS C18 column (10 i; 10×250 mm) using a water/acetonitrile eluent. The main product peak was collected, diluted with ascorbic acid then formulated in 5% ethanol in ascorbic acid. During routine preparation, ~250 mCi of the fluorinated product was prepared.

TABLE 3

Synthetic parameters using the Explora RN chemistry module

| Precursor | Example | RCY | RCP |
|---|---|---|---|
| 10 | 66A | 15% | 99% |
| 36 | 66B | 4%$^a$ | 99% |
| 34 | 66C | 13% | 99% |
| 15 | 66D | 29% | 99% |
| 2 | 66E | 33% | 99% |
| 41 | 66F | 35% | 99% |
| 46 | 66G | 6% | 99% |
| 57A | 66H | 19% | 99% |
| 44 | 66I | 5% | 99% |
| 48B | 66J | 9% | 99% |
| 61F | 66K | 20% | 99% |
| 62A | 66L | 14%$^a$ | 99% |
| 56C | 66M | 39% | 99% |

$^a$Combination of Kryptofix™ and potassium carbonate was utilized.

Part B—Preparation of Imaging Agents Using the GE TracerLab MX Chemistry Module

FIG. 17 depicts a schematic representation of the preferred cassette configuration used during the preparation of imaging agents on the GE TracerLab MX chemistry module.

The product of Example 65A was transferred from cyclotron to the synthesis module then filtered through an anion exchange column to remove unreacted [$^{18}$O]H$_2$O; [$^{18}$F] fluoride was retained within the cationic resin matrix. The column was then washed with tetraethylammonium bicarbonate (28.8 μmol; 0.500 mL of a 57.5 mM solution in water) with transfer to the reaction vessel. The resulting solution was diluted with acetonitrile then concentrated to dryness. Additional acetonitrile was then added and the drying process repeated several times. The mixture of anhydrous tetraethylammonium fluoride and tetraethylammonium bicarbonate thus obtained was treated with the precursor compound (23.0 μmol; 2.00 mL of a 11.5 mM solution in acetonitrile) then warmed to 90° C. and maintained 10 min. The resulting solution was then diluted with water and directly purified by HPLC on a Waters Xterra MS C18 column using a water/acetonitrile eluent. The main product peak was collected, diluted with ascorbic acid then filtered through a C18 Sep-Pak® cartridge to remove acetonitrile; the fluorinated compound was retained within the C18 resin matrix and the filtrate discarded. The loaded cartridge was successively washed with ascorbic acid, the filtrate discarded, then absolute ethanol, and the filtrate collected. The ethanol concentrate of the imaging agent thus obtained was further diluted with ascorbic acid then automatically delivered to the final product vial through a 0.22 μm sterilizing filter.

2-(tert-Butyl)-4-chloro-5-((4-((2-fluoroethoxy)methyl)benzyl)oxy)pyridazin-3(2H)-one may be prepared from 2-((4-(((1-(tert-butyl)-5-chloro-6-oxo-1,6-dihydropyridazin-4-yl)oxy)methyl)benzyl)oxy)ethyl 4-methylbenzenesulfonate in 52% radiochemical yield using the method described herein. An average decrease in drug product retention of 1.5% was observed using the revised cassette configuration described herein.

Part C—Preparation of Imaging Agents Using the ORA NEPTIS Chemistry Module

FIG. 17 depicts a schematic representation of the preferred cassette configuration used during the preparation of imaging agents on the ORA NEPTIS chemistry module.

The product of Example 65A was transferred from cyclotron to the synthesis module then filtered through an anion exchange column to remove unreacted [$^{18}$O]H$_2$O; [$^{18}$F]fluoride was retained within the cationic resin matrix. The column was then washed with tetraethylammonium bicarbonate (28.8 μmol; 0.500 mL of a 57.5 mM solution in water) with transfer to the reaction vessel. The resulting solution was diluted with acetonitrile then concentrated to dryness. Additional acetonitrile was then added and the drying process repeated several times. The mixture of anhydrous tetraethylammonium fluoride and tetraethylammonium bicarbonate thus obtained was treated with the precursor compound (23.0 μmol; 2.00 mL of a 11.5 mM solution in acetonitrile) then warmed to 90° C. and maintained 10 min. The resulting solution was then diluted with water and directly purified by HPLC on a Waters Xterra MS C18 column using a water/acetonitrile eluent. The main product peak was collected, diluted with ascorbic acid then filtered through a C18 Sep-Pak® cartridge to remove acetonitrile; the fluorinated compound was retained within the C18 resin matrix and the filtrate discarded. The loaded cartridge was successively washed with ascorbic acid, the filtrate discarded, then absolute ethanol, and the filtrate collected. The ethanol concentrate of the imaging agent thus obtained was further diluted with ascorbic acid then automatically delivered to the final product vial through a 0.22 μm sterilizing filter.

2-(tert-Butyl)-4-chloro-5-((4-((2-fluoroethoxy)methyl)benzyl)oxy)pyridazin-3(2H)-one may be prepared from 2-((4-(((1-(tert-butyl)-5-chloro-6-oxo-1,6-dihydropyridazin-4-yl)oxy)methyl)benzyl)oxy)ethyl 4-methylbenzenesulfonate in 48% radiochemical yield using the method described herein.

Example 67

Tissue Distribution and Imaging in Rats

Part A—Tissue Distribution

Anesthetized (sodium pentobarbital at 50 mg/kg, ip or isoflurane gas inhalation) Male Sprague Dawley rats (250-350 g) received an iv injection of the imaging agent (~15 μCi) via the tail vein. At 15 or 60 min post injection, the animals were euthanized and the required tissue samples harvested. All samples were then weighed and counted for radioactivity (Wallac Wizard 1480 or Packard Cobra II Autogamma); regional tissue uptake of the imaging agent was thus expressed as a percentage of the total injected dose per gram of tissue (% ID/g).

The generic structure depicted below highlights specific structural features evaluated during distribution experiments. Tables 4-6 summarize results from select studies.

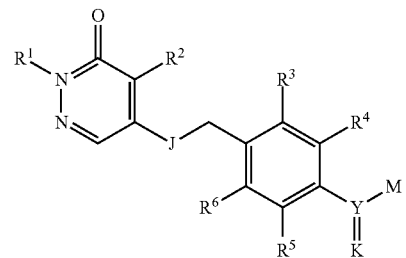

TABLE 4

| Structure correlation table | | | | | | | | | | |
|---|---|---|---|---|---|---|---|---|---|---|
| Example | R$^1$ | R$^2$ | R$^3$ | R$^4$ | R$^5$ | R$^6$ | J | K | M | Y |
| 67A | t-Bu | Cl | H | CH$_2$O(CH$_2$)$_2$F | H | H | O | N/A | N/A | H |
| 67B | t-Bu | Cl | H | H | H | H | O | N/A | (CH$_2$)$_2$O(CH$_2$)$_2$F | O |
| 67C | t-Bu | Cl | H | Cl | H | H | O | N/A | (CH$_2$)$_3$F | O |
| 67D | t-Bu | Cl | H | H | H | H | O | N/A | (CH$_2$)$_2$F | O |
| 67E | t-Bu | Cl | H | H | H | H | O | D,D | O(CH$_2$)$_2$F | C |
| 67F | t-Bu | Cl | H | O(CH$_2$)$_2$F | H | H | O | N/A | N/A | H |

TABLE 4-continued

Structure correlation table

| Example | R¹ | R² | R³ | R⁴ | R⁵ | R⁶ | J | K | M | Y |
|---|---|---|---|---|---|---|---|---|---|---|
| 67G | t-Bu | Cl | H | H | H | H | O | CH₃,H | O(CH₂)₂F | C |
| 67H | i-Pr | Cl | H | H | H | H | O | H,H | O(CH₂)₂F | C |
| 67I | t-Bu | CH₃ | H | H | H | H | O | H,H | O(CH₂)₂F | C |
| 67J | t-Bu | Cl | H | H | H | H | O | O | O(CH₂)₂F | C |
| 67K | t-Bu | Cl | H | H | H | H | O | N/A | C≡C(CH₂)₂F | bond |
| 67L | t-Bu | Cl | H | H | H | H | O | N/A | 2-fluoropyrimidin-5-yl | bond |
| 67M | t-Bu | Cl | H | H | H | H | CH₂ | H,H | O(CH₂)₂F | C |
| 67N | t-Bu | Cl | H | H | H | H | O | t-Bu,t-Bu | F | Si |
| 67O | t-Bu | Cl | H | H | H | H | O | N/A | 2-fluoropyridin-3-yl | O |

TABLE 5

Summary of imaging agent distribution at 15 min (% ID/g ± SEM)

| Example | Blood | Liver | Heart | Lung | Spleen |
|---|---|---|---|---|---|
| 67A | 0.03 ± 0.01 | 0.08 ± 0.03 | 0.65 ± 0.36 | 0.07 ± 0.01 | 0.05 ± 0.01 |
| 67B | 0.49 ± 0.02 | 2.33 ± 0.09 | 1.66 ± 0.06 | 0.49 ± 0.06 | 0.41 ± 0.01 |
| 67C | 0.26 ± 0.05 | 2.67 ± 0.17 | 4.21 ± 0.29 | 0.50 ± 0.08 | 0.37 ± 0.05 |
| 67D | 1.11 | 3.61 | 3.63 | 1.00 | 0.37 |
| 67E | 0.17 ± 0.02 | 0.66 ± 0.09 | 4.80 ± 0.27 | 0.39 ± 0.05 | 0.36 ± 0.08 |
| 67F | 0.32 ± 0.05 | 0.40 ± 0.04 | 1.92 ± 0.15 | 0.41 ± 0.03 | 0.28 ± 0.01 |
| 67G | 0.50 ± 0.18 | 0.33 ± 0.10 | 2.19 ± 0.36 | 0.46 ± 0.12 | 0.32 ± 0.11 |
| 67H | 0.45 ± 0.02 | 0.46 ± 0.01 | 1.14 ± 0.09 | 0.41 ± 0.01 | 0.34 ± 0.03 |
| 67I | 0.11 ± 0.02 | 0.33 ± 0.02 | 2.34 ± 0.57 | 0.19 ± 0.03 | 0.18 ± 0.01 |
| 67J | 0.50 ± 0.02 | 0.32 ± 0.01 | 1.19 ± 0.25 | 0.39 ± 0.02 | 0.34 ± 0.01 |
| 67K | 0.07 ± 0.03 | 0.99 ± 0.06 | 2.68 ± 0.35 | 0.37 ± 0.15 | 0.31 ± 0.09 |
| 67L | 0.14 ± 0.01 | 1.71 ± 0.36 | 1.19 ± 0.18 | 0.29 ± 0.03 | 0.18 ± 0.01 |
| 67M | 0.53 ± 0.13 | 0.96 ± 0.10 | 2.54 ± 0.20 | 0.97 ± 0.13 | 0.35 ± 0.05 |
| 67N | 0.22 ± 0.04 | 4.91 ± 0.49 | 0.65 ± 0.09 | 1.31 ± 0.24 | 3.47 ± 0.80 |
| 67O | 0.07 ± 0.03 | 0.99 ± 0.06 | 2.68 ± 0.35 | 0.37 ± 0.15 | 0.31 ± 0.09 |

| Example | Pancreas | Kidney | Brain | Femur | Muscle |
|---|---|---|---|---|---|
| 67A | 0.15 ± 0.05 | 0.38 ± 0.08 | 0.14 ± 0.05 | 0.06 ± 0.02 | 0.09 ± 0.04 |
| 67B | N/A | 2.25 ± 0.05 | 0.37 ± 0.02 | 0.80 ± 0.12 | 0.19 ± 0.00 |
| 67C | N/A | 3.04 ± 0.21 | 0.42 ± 0.01 | 0.33 ± 0.01 | 0.24 ± 0.04 |
| 67D | N/A | 3.81 | 0.74 | 0.21 | 0.14 |
| 67E | 0.82 ± 0.07 | 2.61 ± 0.18 | 0.97 ± 0.11 | 0.50 ± 0.04 | 0.77 ± 0.09 |
| 67F | 0.52 ± 0.04 | 1.04 ± 0.10 | 0.50 ± 0.04 | 0.44 ± 0.04 | 0.60 ± 0.06 |
| 67G | 0.41 ± 0.03 | 0.88 ± 0.05 | 0.59 ± 0.03 | 0.40 ± 0.05 | 0.35 ± 0.04 |
| 67H | 0.44 ± 0.03 | 0.78 ± 0.01 | 0.43 ± 0.05 | 0.36 ± 0.04 | 0.38 ± 0.02 |
| 67I | 0.43 ± 0.10 | 1.13 ± 0.11 | 0.49 ± 0.10 | 0.28 ± 0.04 | 0.28 ± 0.13 |
| 67J | 0.23 ± 0.02 | 0.39 ± 0.01 | 0.36 ± 0.01 | 0.28 ± 0.02 | 0.38 ± 0.04 |
| 67K | 0.55 ± 0.10 | 1.35 ± 0.14 | 0.36 ± 0.04 | 0.27 ± 0.02 | 0.28 ± 0.02 |
| 67L | 0.36 ± 0.06 | 0.65 ± 0.07 | 0.30 ± 0.05 | 0.31 ± 0.01 | 0.27 ± 0.02 |
| 67M | N/A | 0.79 ± 0.07 | 0.55 ± 0.31 | 0.52 ± 0.19 | 0.24 ± 0.04 |
| 67N | N/A | 0.51 ± 0.09 | 0.03 ± 0.00 | 0.14 ± 0.02 | 0.06 ± 0.00 |
| 67O | 0.55 ± 0.10 | 1.35 ± 0.14 | 0.36 ± 0.04 | 0.27 ± 0.02 | 0.28 ± 0.02 |

TABLE 6

Summary of imaging agent distribution at 60 min (% ID/g ± SEM)

| Example | Blood | Liver | Heart | Lung | Spleen |
|---|---|---|---|---|---|
| 67A | 0.11 ± 0.02 | 0.11 ± 0.02 | 0.84 ± 0.22 | 0.11 ± 0.02 | 0.09 ± 0.02 |
| 67B | 0.26 ± 0.04 | 1.34 ± 0.22 | 1.58 ± 0.13 | 0.27 ± 0.03 | 0.20 ± 0.04 |
| 67C | 0.20 ± 0.07 | 0.65 ± 0.12 | 4.54 ± 0.29 | 0.61 ± 0.32 | 0.18 ± 0.05 |
| 67D | 1.00 | 1.49 | 4.66 | 0.96 | 0.23 |
| 67E | 0.26 ± 0.03 | 0.53 ± 0.06 | 3.61 ± 0.45 | 0.34 ± 0.03 | 0.25 ± 0.01 |
| 67F | 0.48 ± 0.01 | 0.39 ± 0.04 | 0.87 ± 0.02 | 0.44 ± 0.03 | 0.31 ± 0.01 |
| 67G | 0.47 ± 0.04 | 0.32 ± 0.03 | 0.98 ± 0.16 | 0.38 ± 0.03 | 0.28 ± 0.03 |

TABLE 6-continued

Summary of imaging agent distribution at 60 min (% ID/g ± SEM)

| | | | | | |
|---|---|---|---|---|---|
| 67H | 0.55 ± 0.02 | 0.40 ± 0.02 | 0.55 ± 0.03 | 0.42 ± 0.01 | 0.35 ± 0.02 |
| 67I | 0.16 ± 0.01 | 0.30 ± 0.01 | 1.78 ± 0.15 | 0.19 ± 0.01 | 0.13 ± 0.00 |
| 67J | 0.58 ± 0.04 | 0.35 ± 0.02 | 0.50 ± 0.03 | 0.42 ± 0.02 | 0.37 ± 0.02 |
| 67K | 0.03 ± 0.00 | 0.83 ± 0.17 | 2.46 ± 0.27 | 0.15 ± 0.03 | 0.11 ± 0.02 |
| 67L | 0.10 ± 0.02 | 2.06 ± 0.27 | 0.62 ± 0.12 | 0.21 ± 0.02 | 0.11 ± 0.02 |
| 67M | 0.73 ± 0.16 | 0.43 ± 0.04 | 0.55 ± 0.06 | 1.03 ± 0.22 | 0.26 ± 0.03 |
| 67O | 0.03 ± 0.00 | 0.83 ± 0.17 | 2.46 ± 0.27 | 0.15 ± 0.03 | 0.11 ± 0.02 |

| Example | Pancreas | Kidney | Brain | Femur | Muscle |
|---|---|---|---|---|---|
| 67A | 0.13 ± 0.03 | 0.23 ± 0.03 | 0.14 ± 0.03 | 0.17 ± 0.04 | 0.18 ± 0.04 |
| 67B | N/A | 1.17 ± 0.20 | 0.30 ± 0.02 | 0.78 ± 0.22 | 0.15 ± 0.04 |
| 67C | N/A | 1.77 ± 0.25 | 0.44 ± 0.03 | 0.84 ± 0.07 | 0.26 ± 0.02 |
| 67D | N/A | 1.71 | 0.69 | 0.26 | 0.18 |
| 67E | 0.43 ± 0.05 | 0.98 ± 0.04 | 0.62 ± 0.04 | 0.69 ± 0.05 | 0.69 ± 0.17 |
| 67F | 0.48 ± 0.01 | 0.60 ± 0.03 | 0.38 ± 0.01 | 0.57 ± 0.04 | 0.43 ± 0.07 |
| 67G | 0.26 ± 0.01 | 0.44 ± 0.02 | 0.39 ± 0.05 | 0.58 ± 0.06 | 0.33 ± 0.01 |
| 67H | 0.32 ± 0.02 | 0.49 ± 0.03 | 0.43 ± 0.02 | 0.71 ± 0.06 | 0.31 ± 0.02 |
| 67I | 0.23 ± 0.02 | 0.48 ± 0.04 | 0.36 ± 0.01 | 0.31 ± 0.02 | 0.35 ± 0.09 |
| 67J | 0.23 ± 0.03 | 0.42 ± 0.02 | 0.43 ± 0.02 | 0.40 ± 0.03 | 0.31 ± 0.02 |
| 67K | 0.38 ± 0.02 | 0.83 ± 0.08 | 0.36 ± 0.03 | 0.37 ± 0.05 | 0.39 ± 0.04 |
| 67L | 0.33 ± 0.08 | 0.40 ± 0.08 | 0.22 ± 0.03 | 0.78 ± 0.15 | 0.20 ± 0.06 |
| 67M | N/A | 0.43 ± 0.04 | 2.33 ± 0.12 | 0.43 ± 0.03 | 0.31 ± 0.04 |
| 67O | 0.38 ± 0.02 | 0.83 ± 0.08 | 0.36 ± 0.03 | 0.37 ± 0.05 | 0.39 ± 0.04 |

Part B—PET Imaging and Data Reconstruction

PET imaging was performed in Male Sprague Dawley rats anesthetized as outlined above. The animal was then positioned in a microPET camera (Focus220, CTI Molecular Imaging or Philips MOSAIC HP) and injected with the imaging agent (~1 mCi) via a tail vein catheter. Image acquisition was initiated immediately following injection and was terminated at 60 min. Following acquisition, the images were reconstructed in a matrix of 256×256 or 128×128 pixels (microPET Manager and ASIPro or PETview, respectively) and decay corrected. Serial tomographic images were thus generated using 5 or 10 min intervals.

Figure 2:
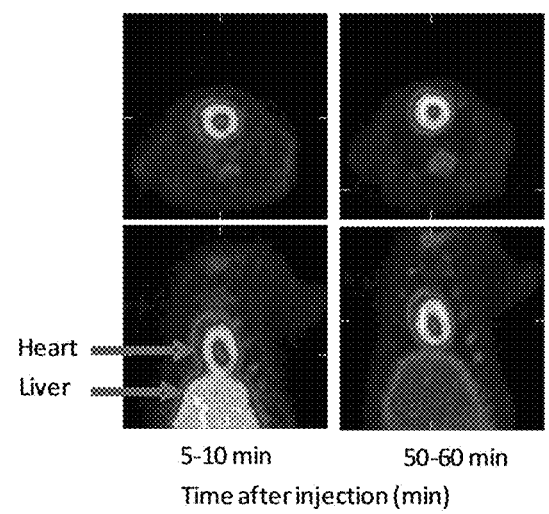
Figure 3:
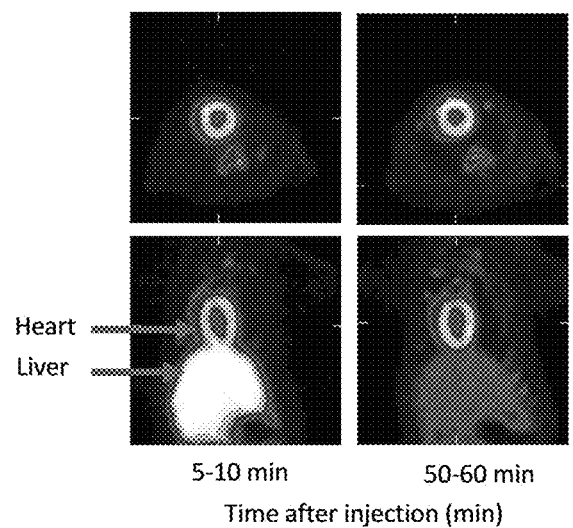
Figure 4:
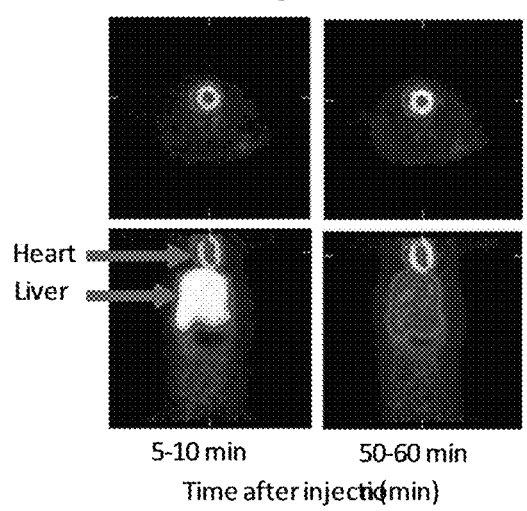
Figure 5:
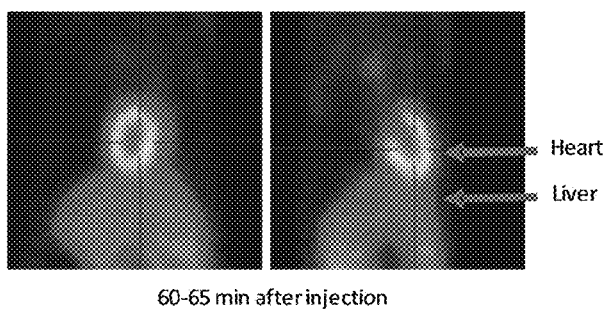
Figure 6:
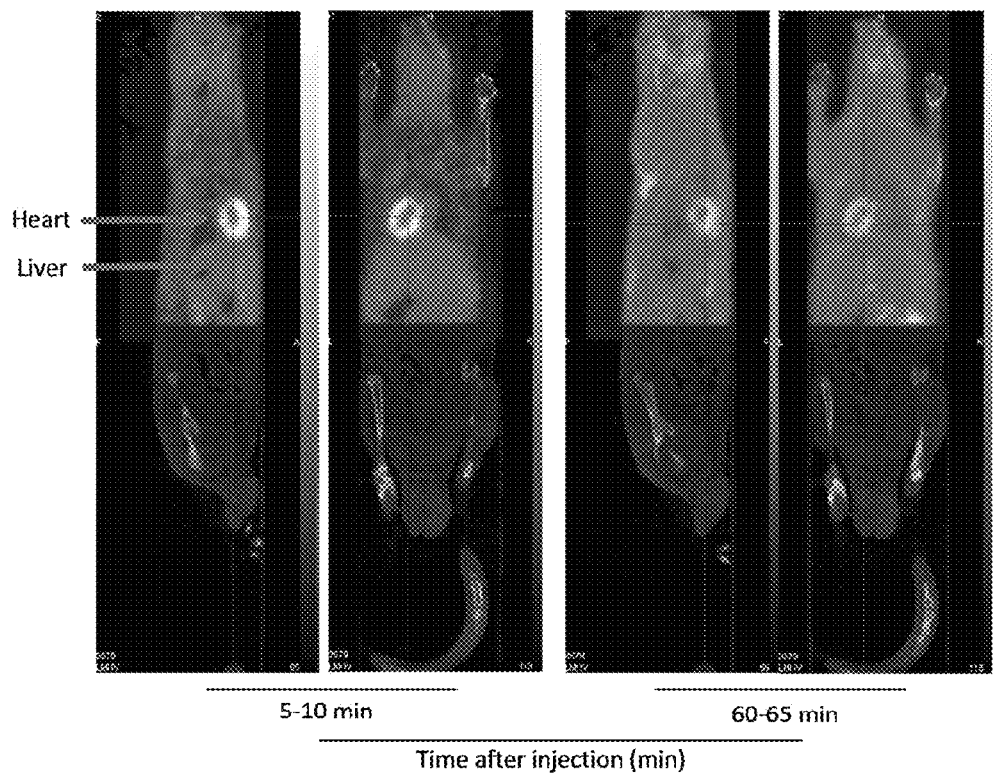
Figure 7:
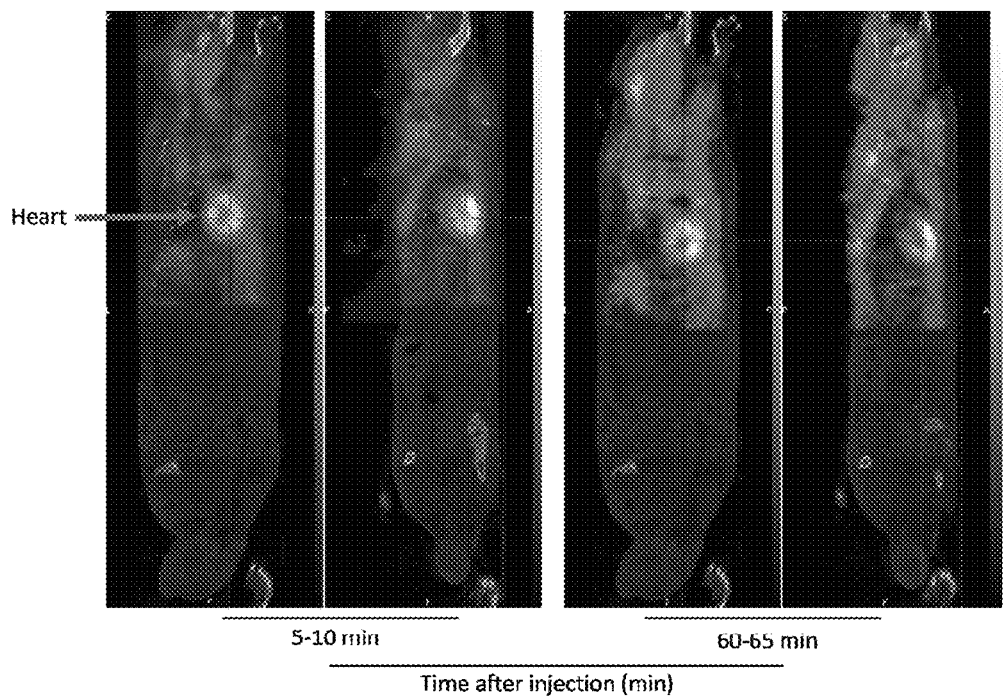
Figure 8:
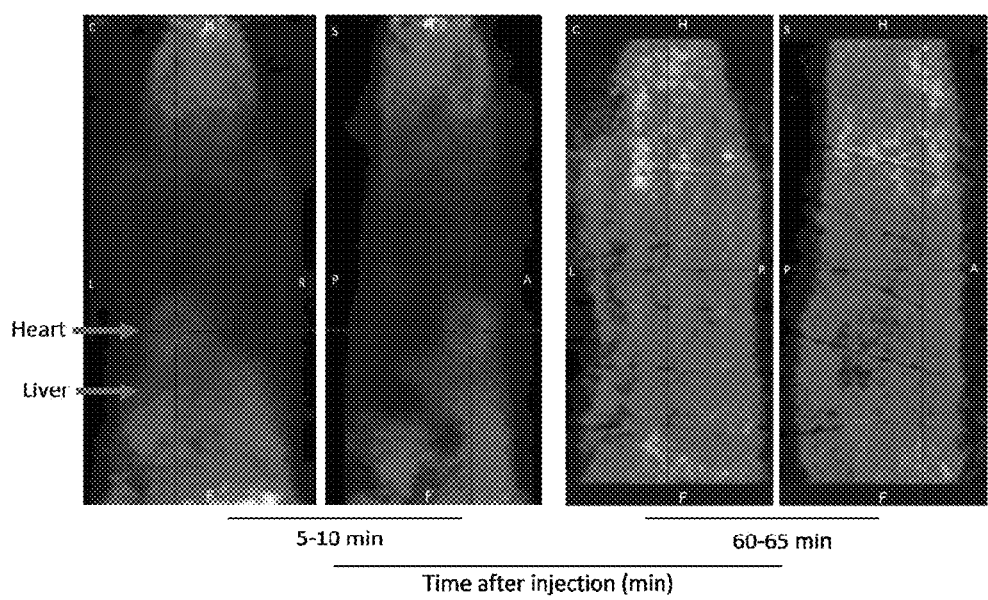
Figure 9:
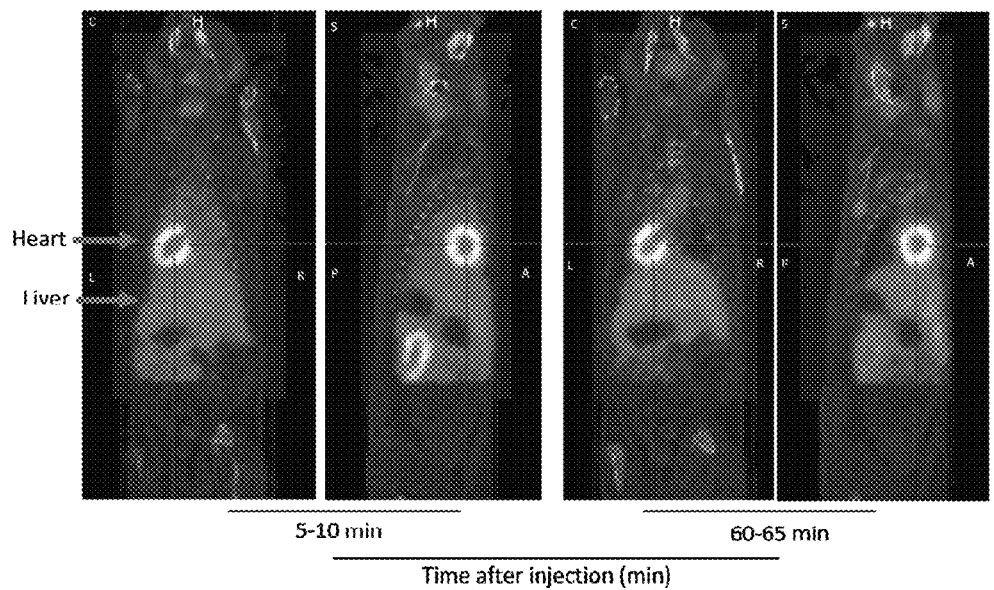
Figure 10:
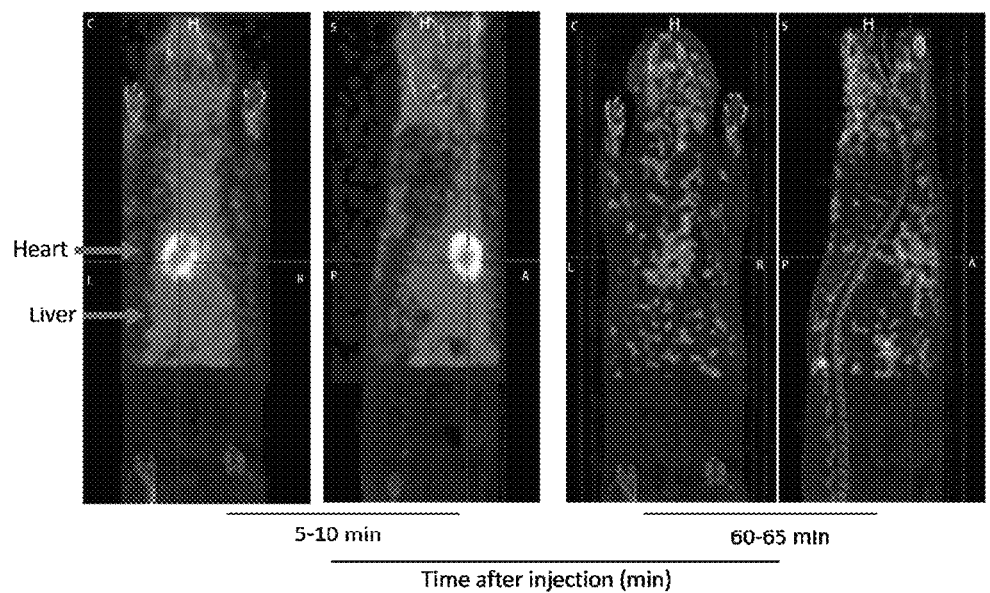
Figure 11:
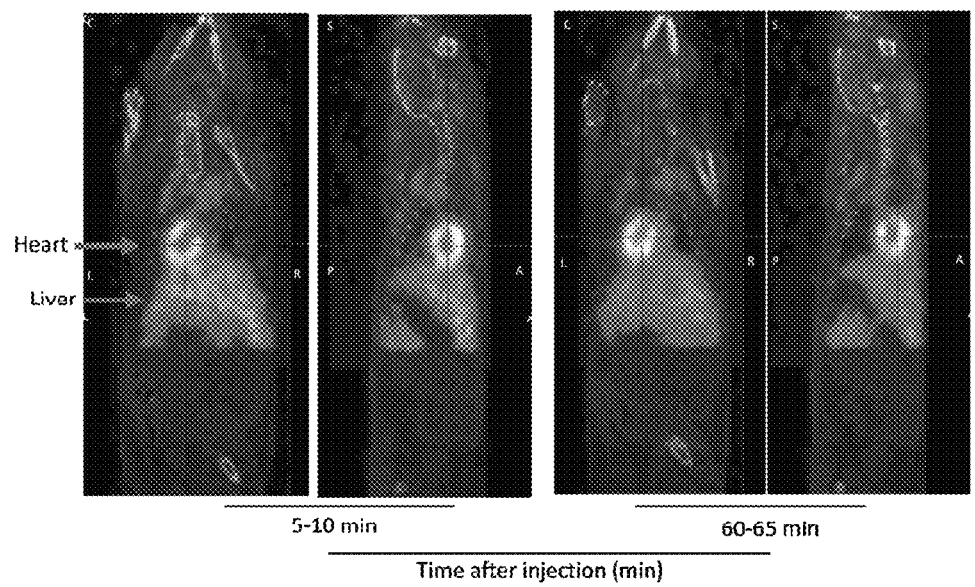
Figure 12:
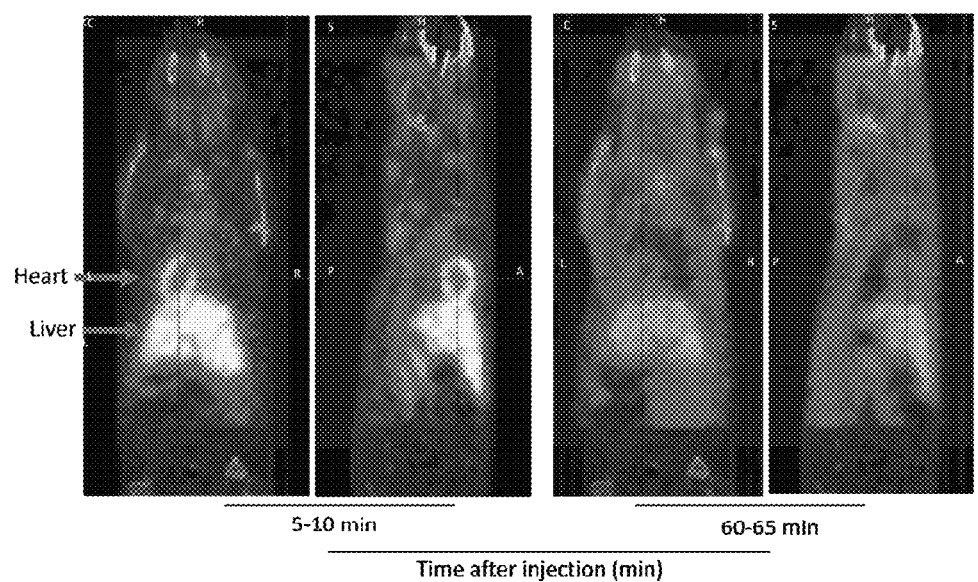
Figure 13:
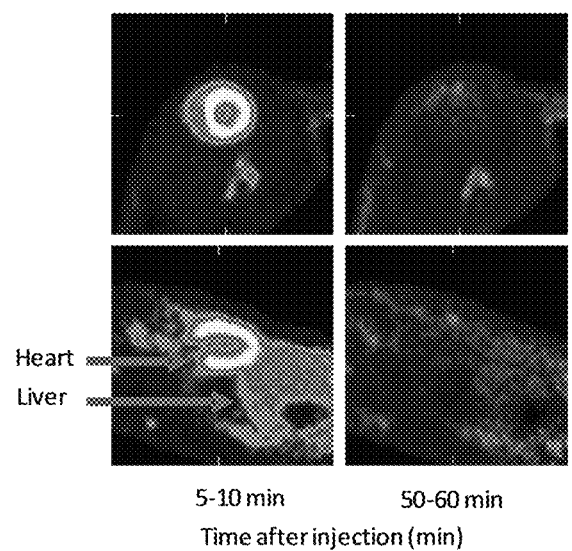
Figure 14:
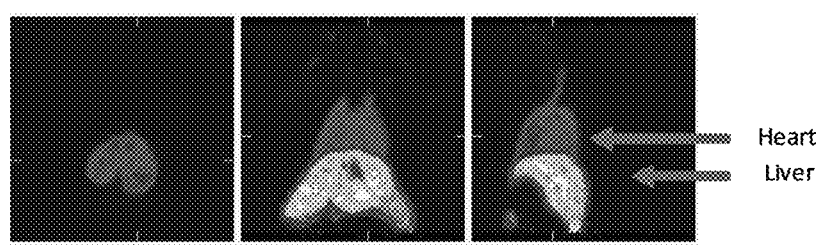
Figure 15:
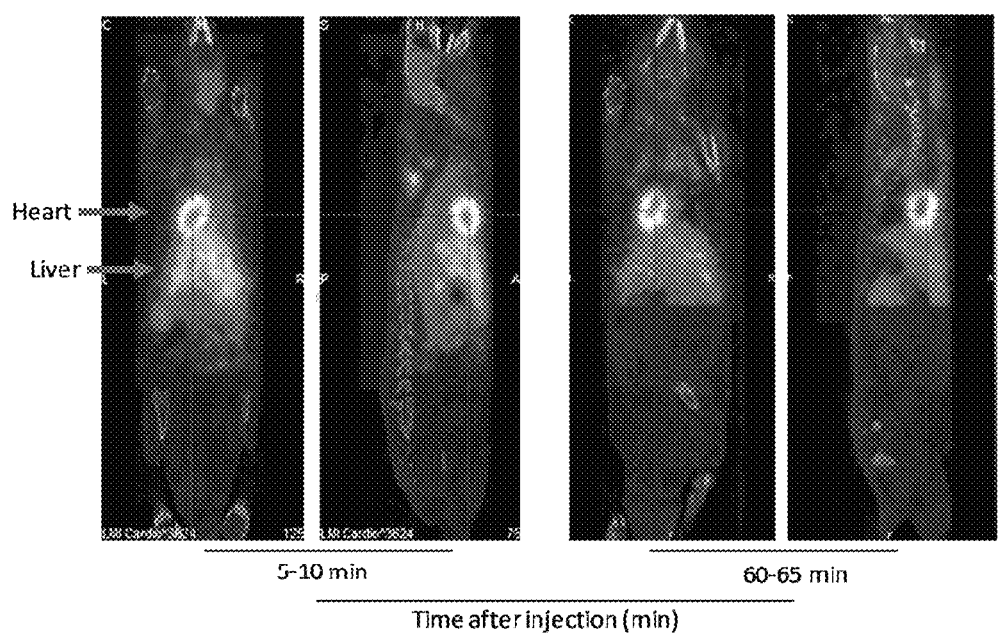

FIG. 1 shows representative images of [$^{18}$F]67A in rat.
FIG. 2 shows representative images of [$^{18}$F]67B in rat.
FIG. 3 shows representative images of [$^{18}$F]67C in rat.
FIG. 4 shows representative images of [$^{18}$F]67D in rat.
FIG. 5 shows representative images of [$^{18}$F]67E in rat.
FIG. 6 shows representative images of [$^{18}$F]67F in rat.
FIG. 7 shows representative images of [$^{18}$F]67G in rat.
FIG. 8 shows representative images of [$^{18}$F]67H in rat.
FIG. 9 shows representative images of [$^{18}$F]67I in rat.
FIG. 10 shows representative images of [$^{18}$F]67J in rat.
FIG. 11 shows representative images of [$^{18}$F]67K in rat.
FIG. 12 shows representative images of [$^{18}$F]67L in rat.
FIG. 13 shows representative images of [$^{18}$F]67M in rat.
FIG. 14 shows representative images of [$^{18}$F]67N in rat.
FIG. 15 shows representative images of [$^{18}$F]67O in rat.

Example 68

Metabolic Profiling of Imaging Agents

Part A—Hepatocyte Preparation

Cryopreserved hepatocytes were purchased from Celsis/In Vitro Technologies, Inc. (Baltimore, Md.) and stored at −150 OC prior to use. Multiple lots of hepatocytes for human (mixed sexes 5-donor pool), primate (male, rhesus monkey), dog (male, beagle), rabbit (male, New Zealand white) and rat (male, Sprague-Dawley) were used. On the day of the study, hepatocytes in cryopreserved vials were vented to release any liquid $N_2$ then placed into a 37° C. water bath for 75-90 seconds to thaw. The hepatocytes were transferred into pre-warmed KHB and centrifuged for 5 min at 50×g. The supernatant was discarded and the hepatocytes re-suspended in KHB at a concentration of 1×10$^6$ cells/mL. Cell viability was confirmed by Trypan blue exclusion.

Part B—Hepatocyte Incubation

Test compounds were incubated in hepatocytes (1×10$^6$ cells/mL; 0.5 mL) were incubated for 0, 15, 30, 60 or 180 min at 37° C./5% $CO_2$ then transferred directly into acetonitrile (1.0 mL), vortexed for 30 s and centrifuged at 2500×g for 20 min. The supernatant was then transferred to a new centrifuge tube, acetonitrile evaporated under a stream of nitrogen in a heating block at 37° C. and, following reconstitution in water, assayed by HPLC with radiodetection.

Part C—HPLC Analysis

Extracted samples and standards were analyzed on an Agilent 1100 HPLC (Agilent Technologies, Burlington, Mass.) using a Phenomenex Luna C18 column (5μ; 4.6×150 mm), maintained at ambient temperature (25° C.), and a flow rate of 1.0 mL/min. Mobile phase A contained 0.1% formic acid in water, and mobile phase B contained 0.1% formic acid in acetonitrile. A linear gradient from 5 to 90% B over 15 min was used for elution. A 5 min post-time of 5% B was used to re-equilibrate the column. Radioactive products were recorded using in-line γ- or β-flow detectors (INUS, Tampa, Fla.).

| Imaging Agent | % Parent Remaining |
|---|---|
| 35 | 30 |
| 25 | 71 |
| 9 | 73 |
| 16 | 20 |
| 1 | 20 |
| 45 | 19 |
| 40 | 34 |
| 57B | 31 |

-continued

| Imaging Agent | % Parent Remaining |
|---|---|
| 43 | 63 |
| 48C | 95 |
| 61G | 6 |
| 62B | 98 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element or a list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A compound comprising the structure:

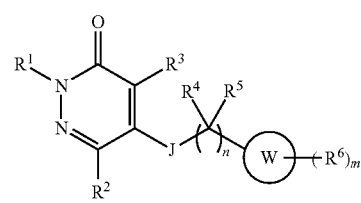

(I)

or a pharmaceutically acceptable salt thereof, wherein:
R$^1$ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, and an imaging moiety;

R² is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, halo, haloalkyl, —NO₂, and an imaging moiety;

R³ is selected from the group consisting of hydrogen, alkyl optionally substituted, heteroalkyl optionally substituted, alkoxy optionally substituted, alkoxyalkyl optionally substituted, aryl optionally substituted, heteroaryl optionally substituted, —CN, —NO₂, and an imaging moiety;

J is selected from the group consisting of N(R⁷), S, O, C(=O), C(=O)O, OC(=O), C(=O)N(R⁷), N(R⁷)C(=O), CH₂O, and a bond;

R⁴ and R⁵ are each independently selected from the group consisting of hydrogen, alkyl optionally substituted, and an imaging moiety, or optionally any two of R⁴ and R⁵ are joined together to form a ring;

n is 0, 1, 2, or 3;

W is heteroaryl, naphthyl, heterocyclyl, or aryl;

each R⁶ is independently selected from the group consisting of hydrogen, alkyl optionally substituted, alkenyl optionally substituted, alkynyl optionally substituted, heteroalkyl optionally substituted, alkoxy optionally substituted, aryloxy optionally substituted, heteroaryloxy optionally substituted, alkoxyalkyl optionally substituted, aryl optionally substituted, heteroaryl optionally substituted, halo, haloalkyl, —N(R⁷)₂, —NO₂, —OH, —C(=O)R⁸, —C(=O)OR⁸, —OC(=O)R⁸, —C(=O)N(R⁷)₂, —N(R⁷)C(=O)R⁸, —CN, —Si(R⁹)₃, —B(R⁹')₃, —OR⁸, and an imaging moiety;

m is 0, 1, 2, 3, 4, 5, 6, or 7;

each R⁷ is independently selected from the group consisting of hydrogen, alkyl optionally substituted, alkenyl optionally substituted, alkynyl optionally substituted, heteroalkyl optionally substituted, alkoxy optionally substituted, alkoxyalkyl optionally substituted, aryl optionally substituted, heteroaryl optionally substituted, halo, haloalkyl, and an imaging moiety, or optionally, any two R⁷ may be joined together to form a ring;

each R⁸ is independently selected from the group consisting of hydrogen, alkyl optionally substituted, heteroalkyl optionally substituted, alkoxyalkyl optionally substituted, aryl optionally substituted, heteroaryl optionally substituted, haloalkyl, and an imaging moiety;

each R⁹ is independently selected from the group consisting of hydrogen, alkyl optionally substituted, aryl optionally substituted, haloalkyl, halogen, and an imaging moiety; and each R⁹' is independently selected from the group consisting of halo, alkyl optionally substituted, aryl optionally substituted, and an imaging moiety, provided that at least one imaging moiety is present in the compound; and provided that when W is aryl, a) R³ is not alkyl, or b) at least one R⁶ is selected from the group consisting of alkynyl optionally substituted, alkenyl optionally substituted, alkyl substituted with —CN, alkyl substituted with —C(=O)OR⁸, alkyl substituted with —C(=O)R⁸, alkyl substituted with —N(R⁷)₂, —CN, —NO₂, —N(R⁷)₂, —C(=O)OR⁸, —OC(=O)R⁸, —C(=O)R⁸, —C(=O)N(R⁷)₂, and —N(R⁷)C(=O)R⁸.

2. A compound, wherein the compound is selected from the group consisting of:

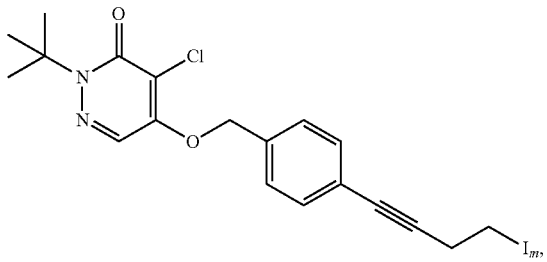

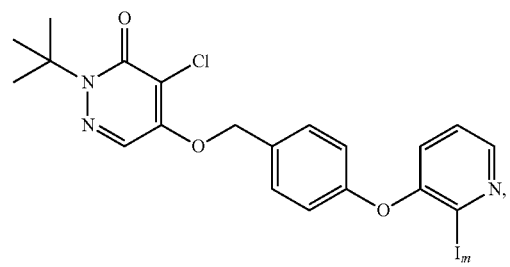

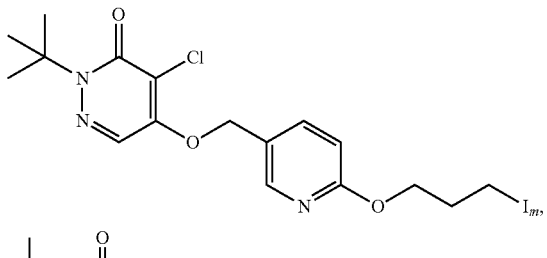

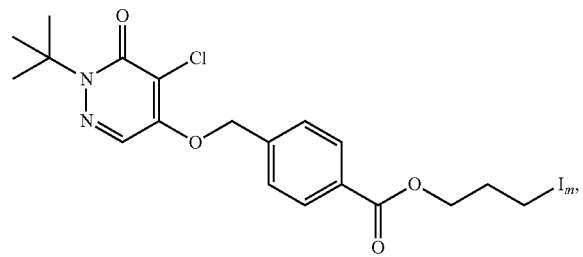

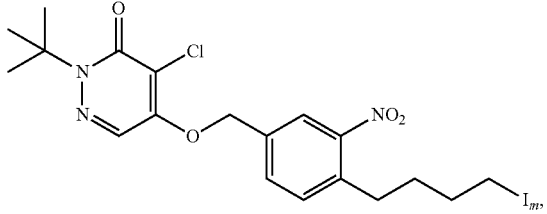

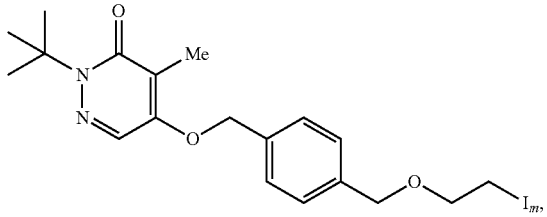

281
-continued
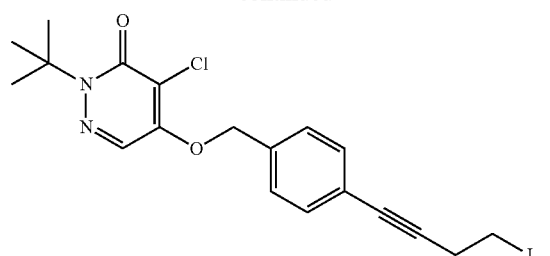
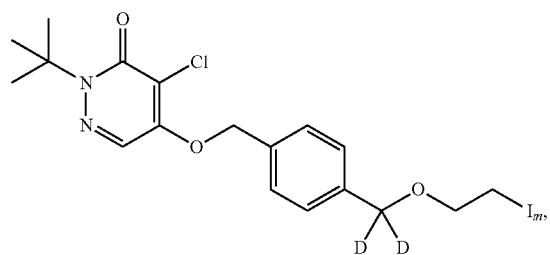
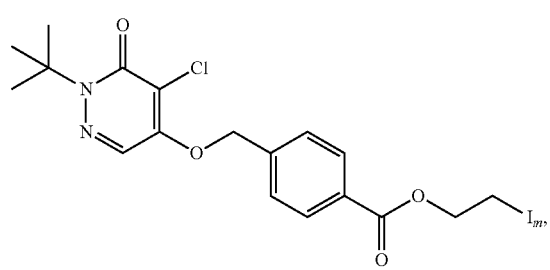
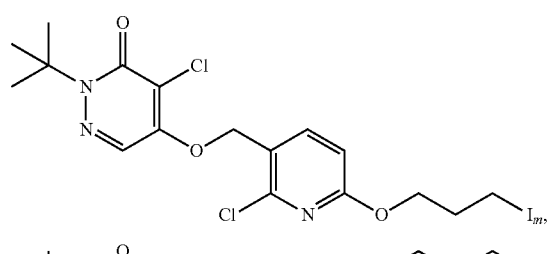
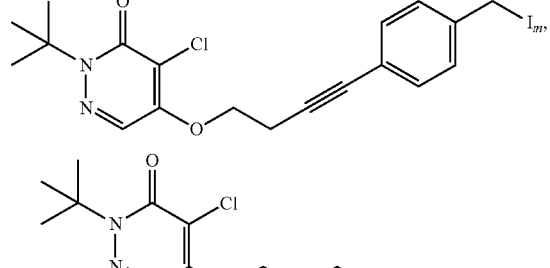
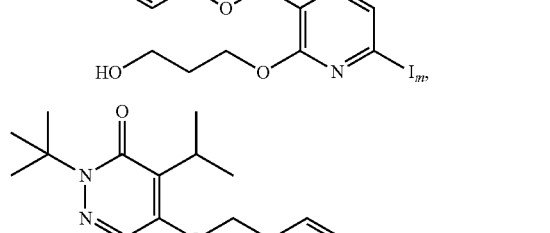
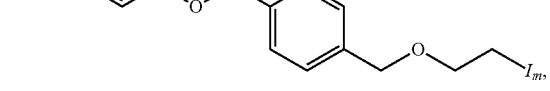
282
-continued
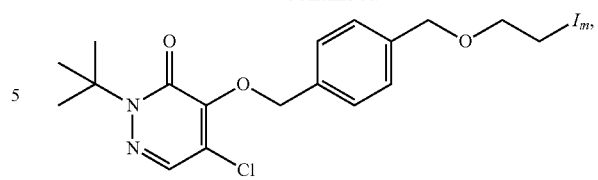
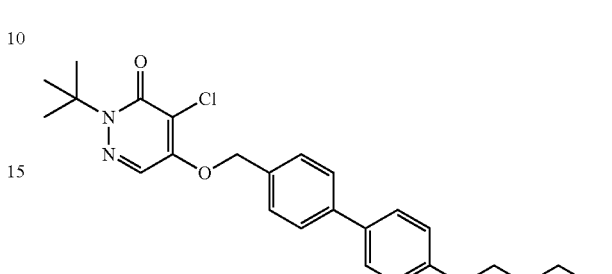
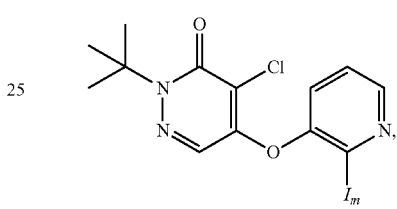
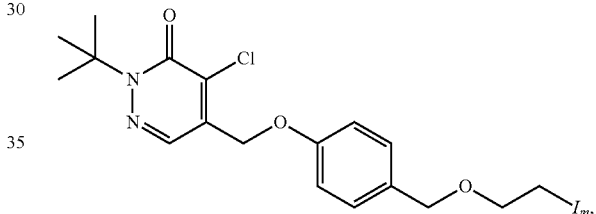
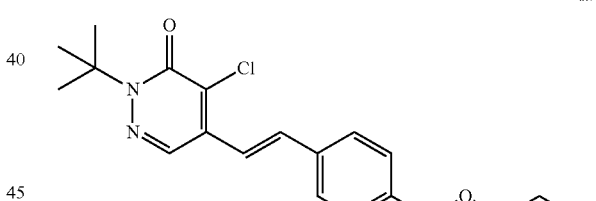
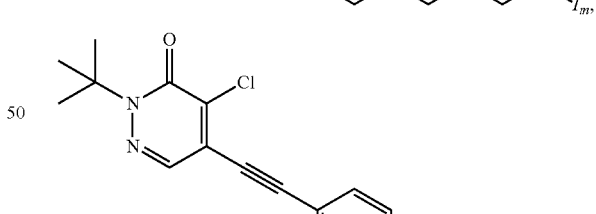
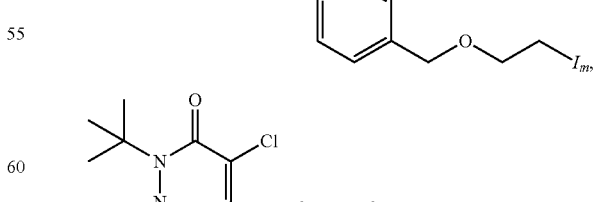
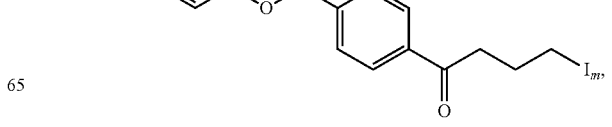

-continued

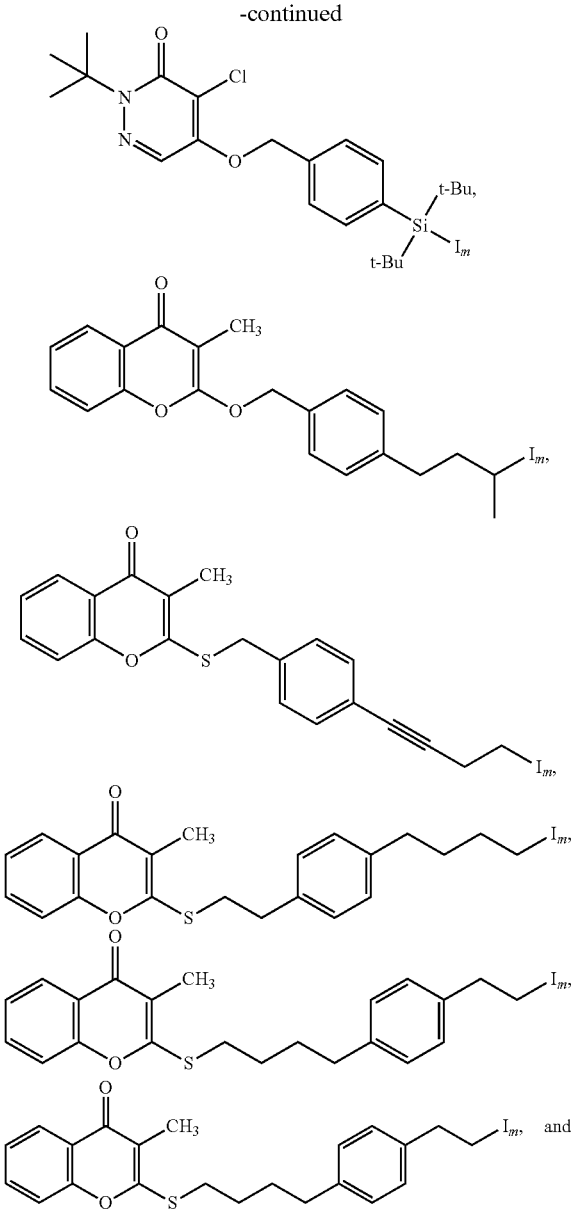

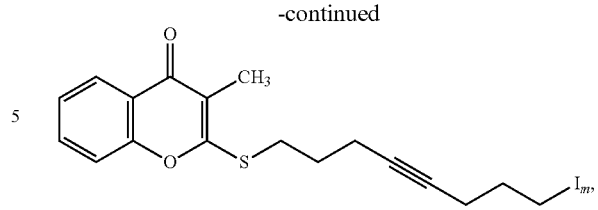

or a pharmaceutically acceptable salt thereof, wherein $I_m$ is an imaging moiety.

3. A pharmaceutical composition comprising a compound or a salt thereof of claim 1, and optionally a pharmaceutically acceptable excipient.

4. A sterile aqueous solution comprising a compound or a salt thereof of claim 1.

5. A method of imaging a portion of a subject, comprising:
   administering to the subject a compound or a salt thereof of claim 1, and
   acquiring at least one image of a portion of the subject.

6. A method of imaging a portion of a subject, comprising:
   administering to a radiolabeled subject a compound or a salt thereof of claim 1,
   detecting radiation emitted by the compound; and
   forming an image therefrom.

7. A diagnostic kit comprising one or more vials containing a precursor to a compound or a salt thereof of claim 1; and optionally other components.

8. A method of imaging myocardial perfusion, comprising:
   administering to a patient a compound or a salt thereof of claim 1, and
   scanning the patient using diagnostic imaging.

9. A method of detecting myocardial perfusion, comprising:
   administering to a patient a compound or a salt thereof of claim 1, and
   scanning the patient using diagnostic imaging.

10. A method of monitoring myocardial perfusion, comprising:
    administering to a patient a compound or a salt thereof of claim 1, and
    scanning the patient using diagnostic imaging.

\* \* \* \* \*